(12) United States Patent
Bronson et al.

(10) Patent No.: US 10,246,469 B2
(45) Date of Patent: *Apr. 2, 2019

(54) BIARYL KINASE INHIBITORS

(71) Applicant: BRISTOL-MYERS SQUIBB COMPANY, Princeton, NJ (US)

(72) Inventors: Joanne J. Bronson, Durham, CT (US); Ling Chen, Doylestown, PA (US); Jonathan L. Ditta, Meriden, CT (US); Carolyn Diane Dzierba, Middletown, CT (US); Prasada Rao Jalagam, Bangalore (IN); Guanglin Luo, Madison, CT (US); John E. Macor, Washington Crossing, PA (US); Tarun Kumar Maishal, Bangalore (IN); Susheel Jethanand Nara, Mumbai (IN); Ramkumar Rajamani, Acton, MA (US); Ramesh Kumar Sistla, Bangalore (IN); Soodamani Thangavel, Hosur (IN)

(73) Assignees: Bristol-Myers Squibb Company, Princeton, NJ (US); Syngene International Limited, Bangalore, Karnataka (IN); Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/763,281

(22) PCT Filed: Sep. 29, 2016

(86) PCT No.: PCT/US2016/054464
§ 371 (c)(1),
(2) Date: Mar. 26, 2018

(87) PCT Pub. No.: WO2017/059080
PCT Pub. Date: Apr. 6, 2017

(65) Prior Publication Data
US 2019/0040080 A1    Feb. 7, 2019

(30) Foreign Application Priority Data

Oct. 1, 2015   (IN) .......................... 3169/DEL/2015

(51) Int. Cl.
| | |
|---|---|
| *C07D 401/04* | (2006.01) |
| *C07D 401/14* | (2006.01) |
| *C07D 403/04* | (2006.01) |
| *C07D 403/14* | (2006.01) |
| *C07D 237/08* | (2006.01) |
| *C07D 239/26* | (2006.01) |
| *C07D 213/34* | (2006.01) |
| *A61K 31/50* | (2006.01) |
| *A61K 31/51* | (2006.01) |
| *A61K 31/505* | (2006.01) |

(Continued)

(52) U.S. Cl.
CPC ............ *C07D 513/04* (2013.01); *A61K 31/44* (2013.01); *A61K 31/4427* (2013.01); *A61K 31/50* (2013.01); *A61K 31/505* (2013.01); *A61K 31/506* (2013.01); *A61K 31/51* (2013.01); *A61P 25/16* (2018.01); *A61P 25/18* (2018.01); *A61P 25/28* (2018.01); *C07D 213/74* (2013.01); *C07D 237/08* (2013.01); *C07D 239/26* (2013.01); *C07D 401/04* (2013.01); *C07D 401/14* (2013.01); *C07D 403/04* (2013.01); *C07D 403/14* (2013.01)

(58) Field of Classification Search
CPC .. C07D 401/04; C07D 401/14; C07D 403/04; C07D 403/14; C07D 213/74; C07D 237/08; C07D 239/26; A61K 31/50; A61K 31/51; A61K 31/505; A61K 31/506; A61K 31/47; A61K 31/44; A61K 31/4427; A61P 25/28
USPC ............... 544/238, 239, 295, 296, 298, 333; 546/113, 152, 255, 257, 261; 514/252.01, 514/252.02, 269, 311, 335, 113, 152, 255, 514/257, 261
See application file for complete search history.

(56) References Cited

U.S. PATENT DOCUMENTS 9,902,722 B2 * 2/2018 Luo ...................... C07D 401/14

FOREIGN PATENT DOCUMENTS

| WO | WO 2004/041810 A1 | 5/2004 |
| WO | WO 2013/134036 A1 | 9/2013 |

(Continued)

OTHER PUBLICATIONS

Kostich et al. J Pharmacol Exp Ther 358:371-386, Sep. 2016.*

(Continued)

*Primary Examiner* — Venkataraman Balasubramanian
(74) *Attorney, Agent, or Firm* — Pamela A. Mingo

(57) ABSTRACT

The present disclosure is directed to biaryl compounds of formula (I) which can inhibit AAK1 (adaptor associated kinase 1), compositions comprising such compounds and their use for treating e.g. pain, Alzheimer's disease, Parkinson's disease and schizophrenia.

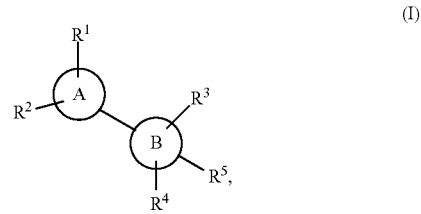

(I)

8 Claims, 1 Drawing Sheet
Specification includes a Sequence Listing.

(51) Int. Cl.
*A61K 31/506* (2006.01)
*A61K 31/44* (2006.01)
*A61K 31/4427* (2006.01)
*A61P 25/28* (2006.01)
*C07D 513/04* (2006.01)
*A61P 25/18* (2006.01)
*A61P 25/16* (2006.01)
*C07D 213/74* (2006.01)

(56) References Cited

FOREIGN PATENT DOCUMENTS

| WO | WO 2013/134336 A2 | 9/2013 |
|----|-------------------|--------|
| WO | WO 2014/022167 A1 | 2/2014 |
| WO | WO 2014/130258 A1 | 8/2014 |
| WO | WO 2015/006100 A1 | 1/2015 |
| WO | WO 2015/038112 A1 | 3/2015 |
| WO | WO 2015/116060 A1 | 8/2015 |
| WO | WO 2015/116492 A1 | 8/2015 |
| WO | WO 2015/153720 A1 | 10/2015 |
| WO | WO 2016/053794 A1 | 4/2016 |
| WO | WO 2016/164295 A2 | 10/2016 |
| WO | WO 2017/059080 A1 | 4/2017 |
| WO | WO 2017/059085 A1 | 4/2017 |

OTHER PUBLICATIONS

Cecil Textbook of Medicine, edited by Bennet, J.C., and Plum F., 20th edition,vol. 1, 1004-1010, 1996.*

Cohen et al., Current Opinion in Chemical Biology, 3,459-465, 1999.*

Freshney et al.,Culture of Animal Cells, A Manual of Basic Technique, Alan R. Liss, Inc., 1983, New York, p. 4.*

Dermer et al., Bio/Technology, 1994, 12:320.*

Buonanno, A., "The neuregulin signaling pathway and schizophrenia: From genes to synapses and neural circuits", Brain Research Bulletin, vol. 83, pp. 122-131 (2010).

Conner, S.D. et al., "AAK-1 Mediated µ2 Phosphorylation is Stimulated by Assembled Clathrin", Traffic, vol. 4, pp. 885-890 (2003).

Conner, S.D. et al., "Identification of an adaptor-associated kinase, AAK1, as a regulator of clathrin-mediated endocytosis", The Journal of Cell Biology, vol. 156, No. 5, pp. 921-929 (2002).

Greenwood, T.A. et al., "Analysis of 94 Candidate Genes and 12 Endophenotypes for Schizophrenia", Am. J. Psychiatry, vol. 168, No. 9, pp. 930-946 (2011).

Henderson, D.M. et al., "A Novel AAK1 Splice Variant Functions at Multiple Steps of the Endocytic Pathway", Molecular Biology of the Cell, vol. 18, pp. 2698-2706 (2007).

Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).

Jackson, A.P. et al., "Clathrin promotes incorporation of cargo into coated pits by activation of the AP2 adaptor µ2 kinase", The Journal of Cell Biology, vol. 163, No. 2, pp. 231-236 (2003).

Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).

Latourelle, J.C. et al., "Genomewide association study for onset age in Parkinson disease", BMC Medical Genetics, 10:98 (2009).

Motley, A.M. et al., Functional Analysis of AP-2 α and µ2 Subunits, Molecular Biology of the Cell, vol. 17, pp. 5298-5308 (2006).

Ricotta, D. et al., "Phosphorylation of the AP2 µ subunit by AAK1 mediates high affinity binding to membrane protein sorting signals", The Journal of Cell Biology, vol. 156, No. 5, pp. 791-795 (2002).

Wen, L. et al., "Neuregulin 1 regulates pyramidal neuron activity via ErbB4 in parvalbumin-positive interneurons", Proc. Natl. Acad. Sci. USA, vol. 107, No. 3, pp. 1211-1216 (2010).

Kostich, W. et al., "Inhibition of AAK1 Kinase as a Novel Therapeutic Approach to Treat Neuropathic Pain," The Journal of Pharmacology and Experimental Therapeutics, 358, pp. 371-386, (Sep. 2016).

* cited by examiner

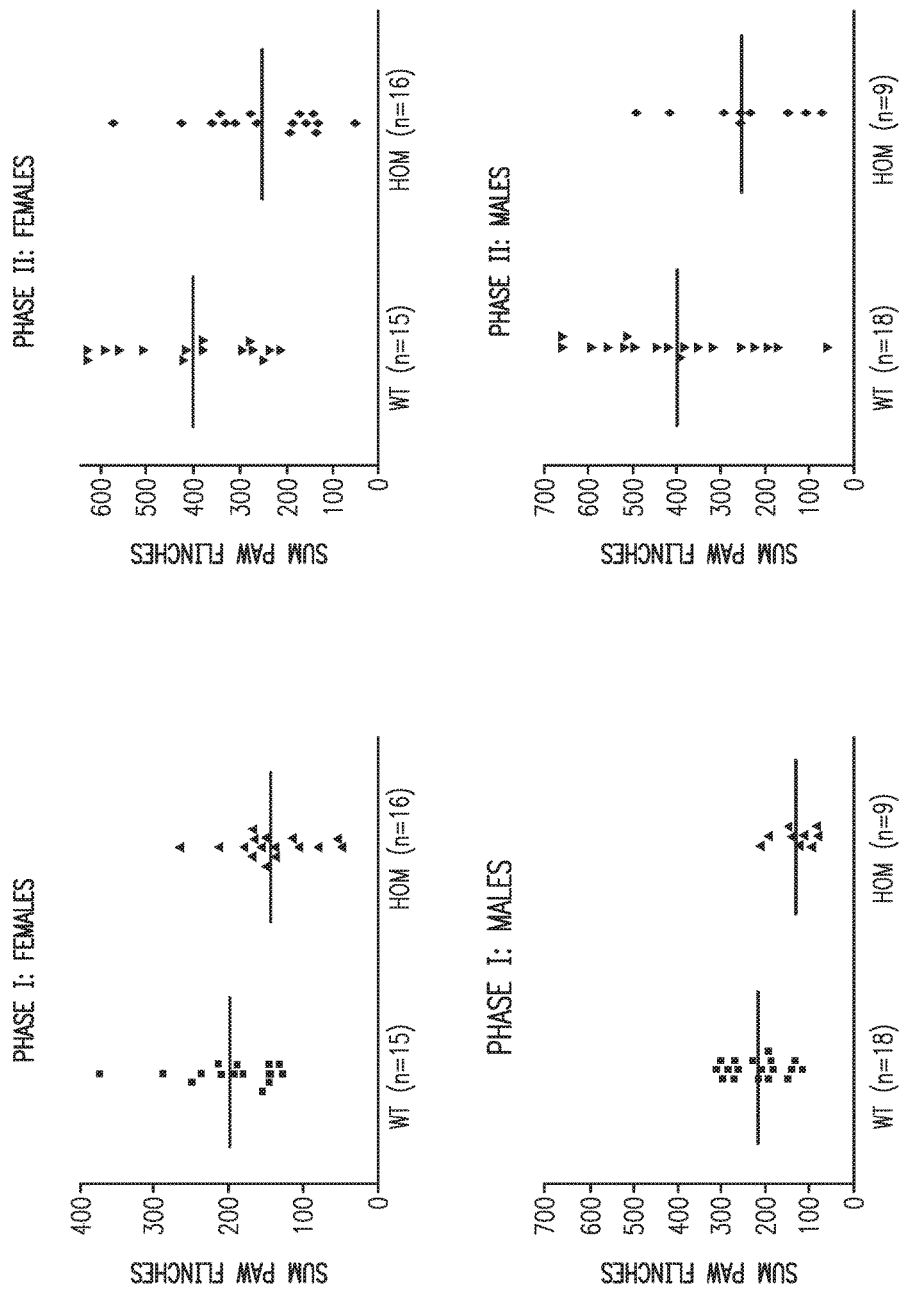

BIARYL KINASE INHIBITORS

CROSS REFERENCE TO RELATED APPLICATION

This application claims the priority of Indian Provisional Application Serial 3169/DEL/15 filed Oct. 1, 2015 which is herein incorporated by reference in its entirety.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., *Proc. Natl. Acad. Sci. USA.* 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In its first aspect the present disclosure provides a compound of formula (I)

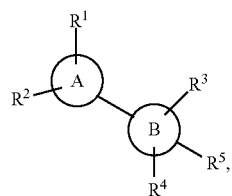

or a pharmaceutically acceptable salt thereof, wherein:

A is selected from

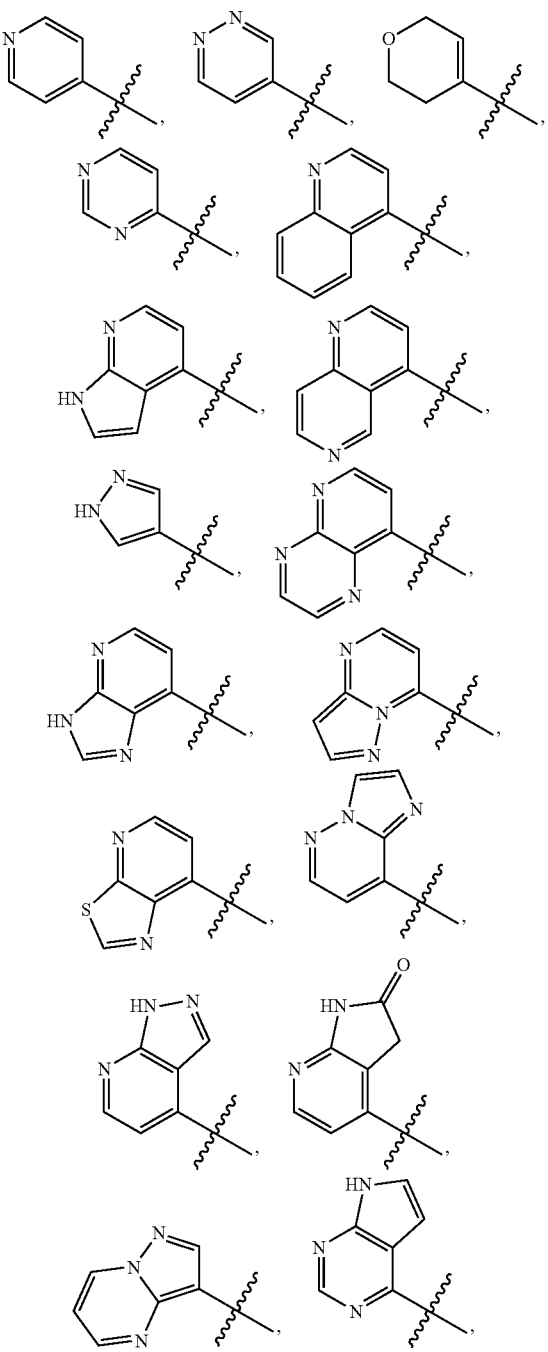

-continued

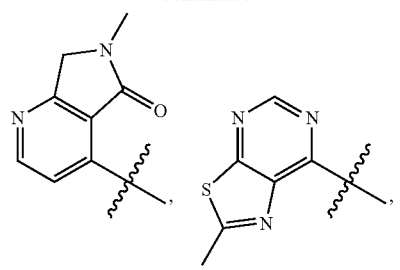

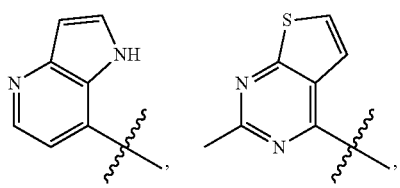

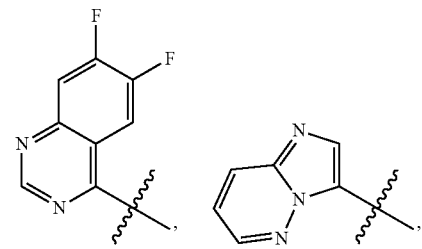

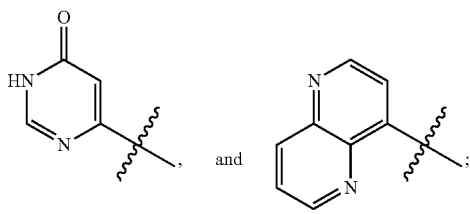

wherein "⌇" denotes the point of attachment to B;
B is selected from

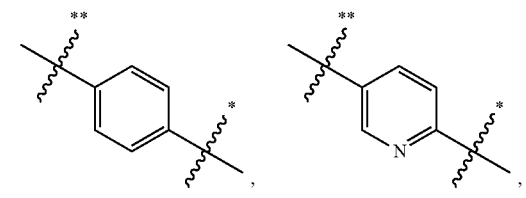

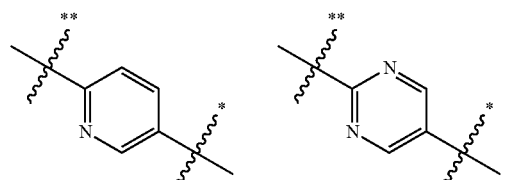

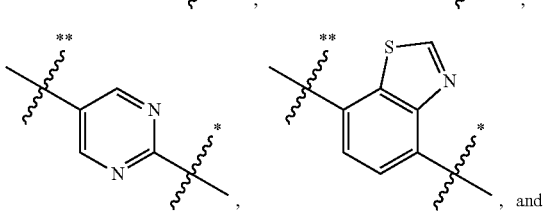

-continued

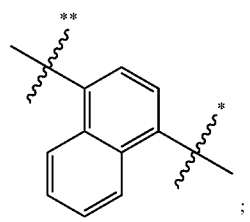

wherein "*" indicates the pint of attachment to R⁵ and "**" indicates the point of attachment to ring A;

R¹ is selected from hydrogen, amino, —CO₂H, cyclopropyl, difluoromethyl, ethyl, halo, hydroxymethyl, methoxy, methoxymethyl, methyl, —NHC(O)CH₃, —NHCO₂CH₃, trifluoromethoxy, trifluromethyl,

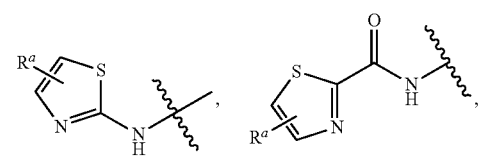

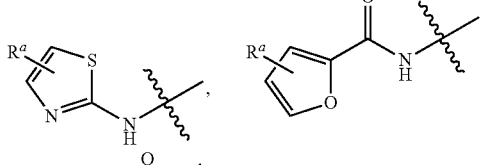

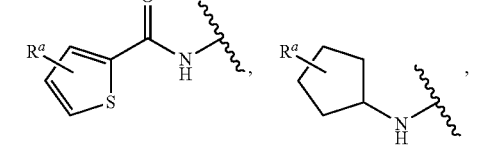

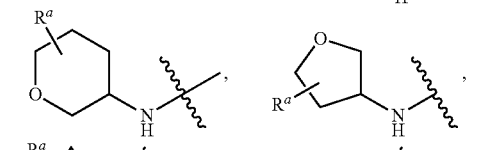

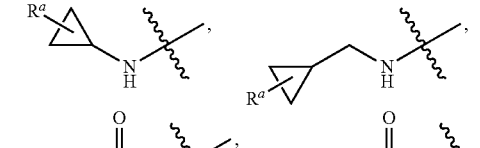

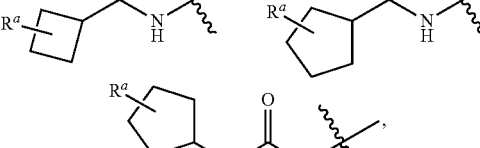

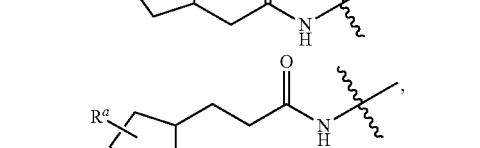

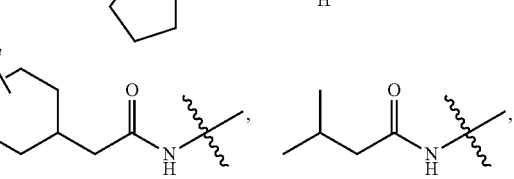

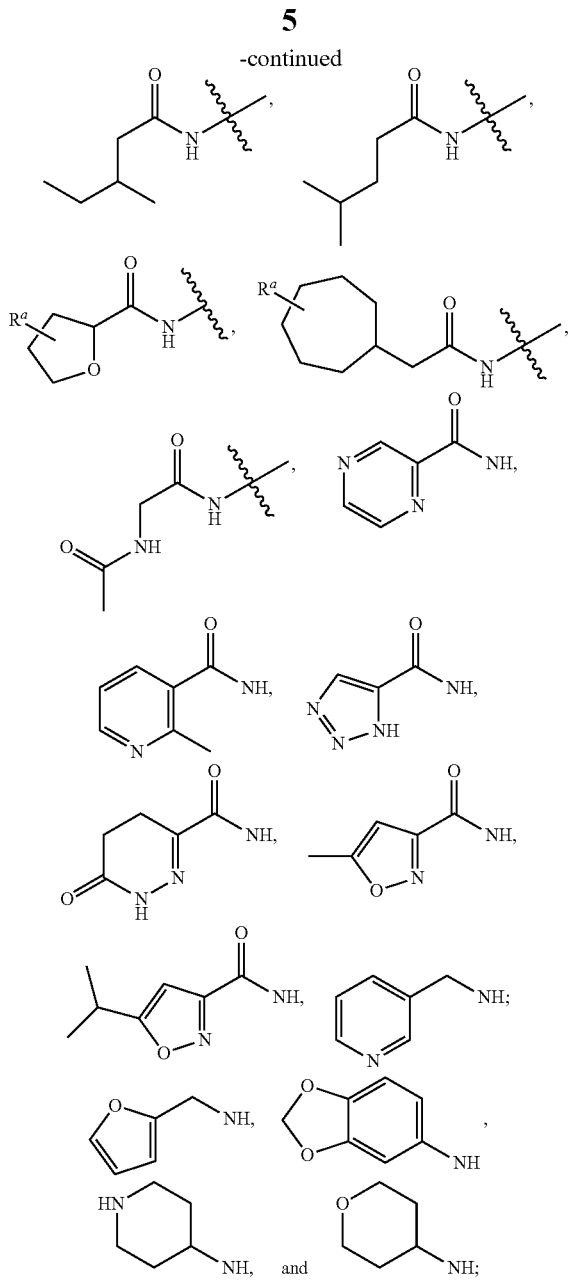

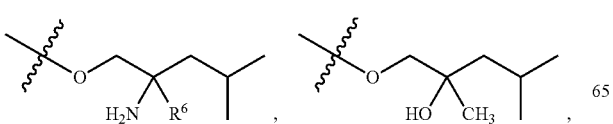

wherein $R^a$ is selected from hydrogen, halo and methyl;

$R^2$ is selected from hydrogen, cyano, —CH$_2$OH, halo, and methyl; $R^3$ is selected from hydrogen, cyano, cyclopropyl, difluoromethyl, fluoromethyl, halo, hydroxymethyl, methoxy, methyl, methylsulfonyl, trifluoromethoxy, trifluoromethyl, —CH$_2$N(CH$_3$)$_2$, and a five-membered aromatic ring containing one, two, or three heteroatoms selected from nitrogen, oxygen, and sulfur;

$R^4$ is selected from hydrogen, halo, and methyl;

$R^5$ is selected from

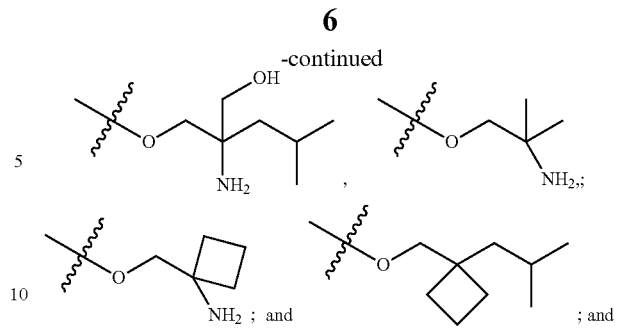

$R^6$ is selected from hydrogen, ethyl, fluoromethyl, difluoromethyl, methyl, and trifluoromethyl;

provided that when A is

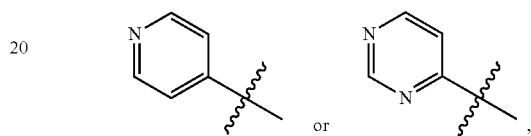

then B is

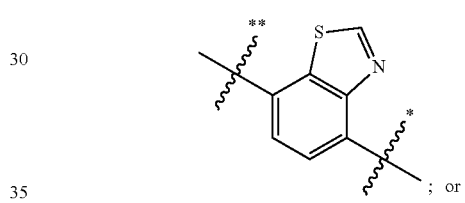

$R^1$ is selected from
cyclopropyl, methoxymethyl,

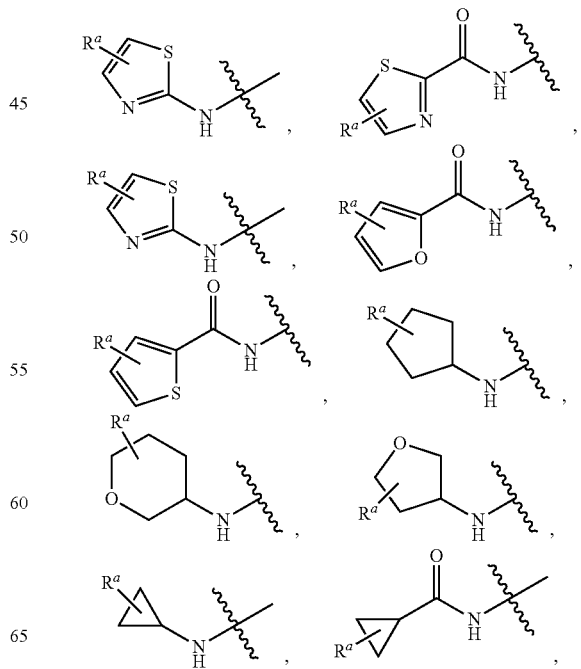

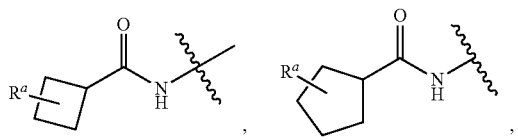

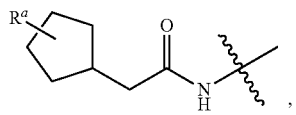

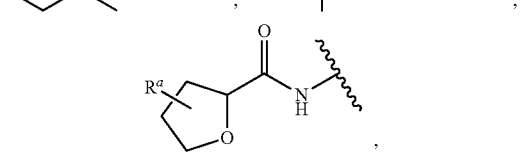

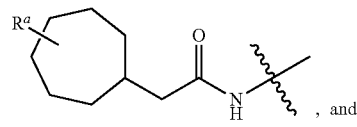

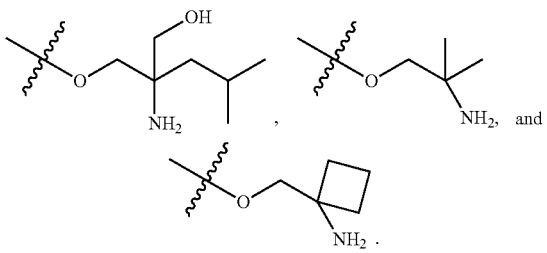

; or $R^5$ is selected from

In a first embodiment of a first aspect the present disclosure provides a compound of formula (I), or a pharmaceutically acceptable salt thereof, wherein A is selected from

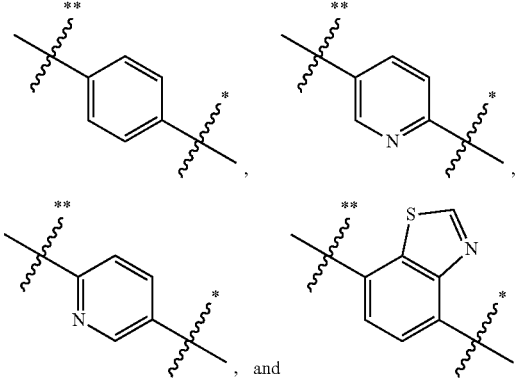

and

In a second embodiment of the first aspect, B is selected from

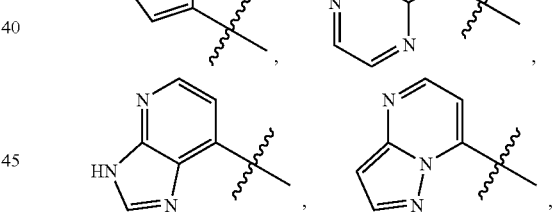

, and

In a third embodiment of the first aspect the present disclosure provides a compound of formula (I), or a pharmaceutically acceptable salt thereof, wherein A is selected from

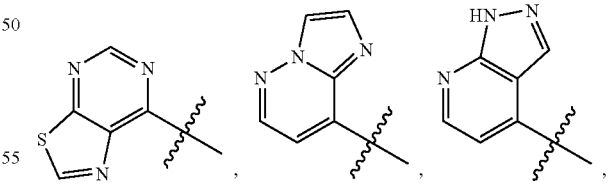

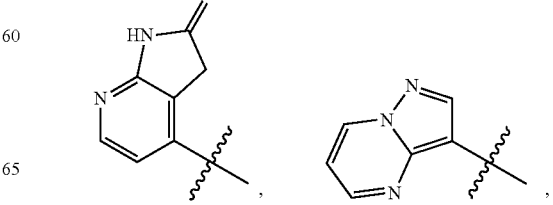

,

-continued

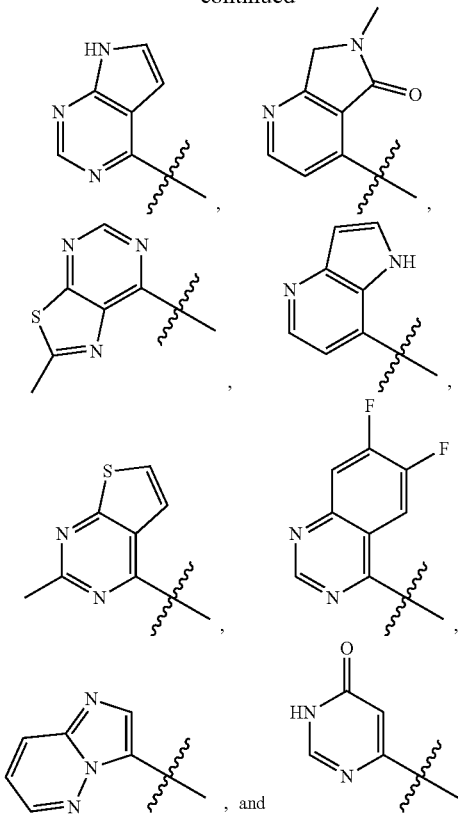

, and .

In a fourth embodiment B is selected from

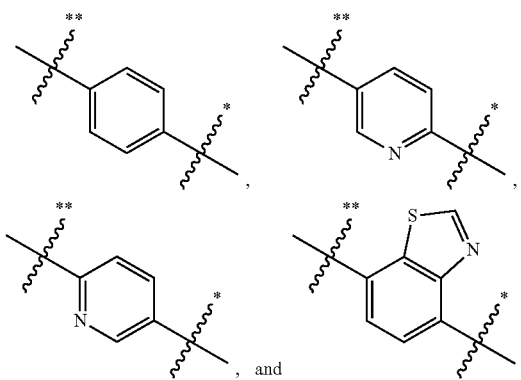

, and .

In a second aspect the present disclosure provides a composition comprising a pharmaceutically acceptable amount of a compound of formula (I), or a pharmaceutically acceptable salt thereof, and a pharmaceutically acceptable carrier.

In a third aspect the present disclosure provides a method of inhibiting adaptor associated kinase 1 (AAK1) activity, comprising contacting AAK1 with a compound of formula (I), or a pharmaceutically acceptable salt thereof.

In a fourth aspect the present disclosure provides a method for treating or managing a disease or a disorder mediated by AAK1 activity, the method comprising administering to a patient in need thereof a therapeutically effective amount of a compound of formula (I), or a pharmaceutically acceptable salt thereof. In a first embodiment of the fourth aspect the disease or disorder is selected from Alzheimer's disease, bipolar disorder, pain, Parkinson's disease, and schizophrenia. In a second embodiment the pain is neuropathic pain. In a third embodiment the neuropathic pain is fibromyalgia or peripheral neuropathy.

Other aspects of the present disclosure may include suitable combinations of embodiments disclosed herein.

Yet other aspects and embodiments may be found in the description provided herein.

BRIEF DESCRIPTION OF THE FIGURES

Aspects of the disclosure are illustrated in FIG. 1, which shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

As used in the present specification, the following terms have the meanings indicated:

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For Example, the term "$C_{1-6}$ alkyl" denotes an alkyl group containing one to six carbon atoms. Where these designations exist they supercede all other definitions contained herein.

The term "halo," as used herein, refers to Br, Cl, F, and/or I.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for Example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general Example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for Example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For Example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional Examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lomoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For Example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for Example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for Example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for Example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for Example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for Example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for Example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For Example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for Example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for Example sealed ampoules and vials, and may be stored in a freeze-dried (lyophilized) condition requiring only the addition of the sterile liquid carrier, for Example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for Example those suitable for oral administration may include flavoring agents.

The term "patient" includes both human and other mammals.

Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following Examples, which include specific embodiments, will illustrate one practice of the present disclosure, it being understood that the Examples are for the purposes of illustration of certain embodiments and are presented to provide what is believed to be the most useful and readily understood description of its procedures and conceptual aspects.

The abbreviations used in the present application, including particularly in the illustrative schemes and Examples which follow, are well-known to those skilled in the art. Some of the abbreviations that may be used are as follows: MeOH for methanol; min for minutes, EtOAc or ETOAC for ethyl acetate; h or hr or hrs for hours; $Ph_3P$ for triphenylphosphine, DIAD for diisopropyl azodicarboxylate; RT or rt or r.t. for room temperature or retention time (context will dictate); $t_R$ for retention time; EtOH for ethanol; DMSO for dimethylsulfoxide; THF for tetrahydrofuran; dppf for diphenylphosphinoferrocene; TFA for trifluoracetic acid; NMP for N-methylpyrrolidine; CBz or Cbz for benzyloxycarbonyl; DCM for dichloromethane; IPA for isopropyl alcohol; DMAP for N,N-dimethylaminopyridine; BOC or Boc for tert-butoxycarbonyl; $(BOC)_2O$ for di-tert-butyl dicarbonate; DMF for N,N-dimethylformamide; OAc for acetate; Cbz for carbobenzyloxy; TMS for trimethylsilane; LDA for lithium diisopropylamide; MOM-Cl for chloromethyl methyl ether; KHMDS for potassium hexamethyldisilazide; KOtBu for potassium tert-butoxide; DAST for diethylaminosulfur trifloride; BuOH for n-butanol; n-BuLi for n-butyllithium; NBS for N-bromosuccinimide; LAH for lithium aluminum hydride; DMF for N,N-dimethylformamide; dppf for 1,1'-bis(diphenylphosphino)ferrocene; TosMIC or TOSMIC for tosylmethyl isocyanide; TEA for triethylamine; PMB for p-methoxybenzyl; Ac for acetyl; DDQ for 2,3-dichloro-5,6-dicyano-1,4-benzoquinone; and AIBN for 2,2'-azoisobutyronitrile.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of Formula Ia can be synthesized following General Scheme I. The two key reactions, Suzuki coupling and ether formation, could alternate as shown depending on the commercially available starting materials. The Suzuki coupling substrates, boronic acids/boronates, were either commercially available or prepared from corresponding halogen intermediates (Cl/Br/I) with various standard literature conditions. The ether formation can be achieved by $SN_{AR}$ when a fluorine intermediate (Formula IV) is available, by Mitsunobu reaction or alkylation with suitable amino alcohol when an OH is available (Formula III/V), and by Buchwald's Pd-catalyzed ether formation reaction when a Cl intermediate (Formula III/V) is available. In cases where $R^5$ is bigger than H, an activated form of the amino alcohol (Formula VII) was used as the OH-alkylating reagent. Sometimes $NH_2$ and OH were protected and deprotected during the reaction sequence.

General Scheme I:

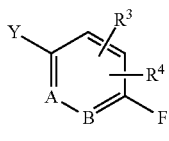

Formula IV

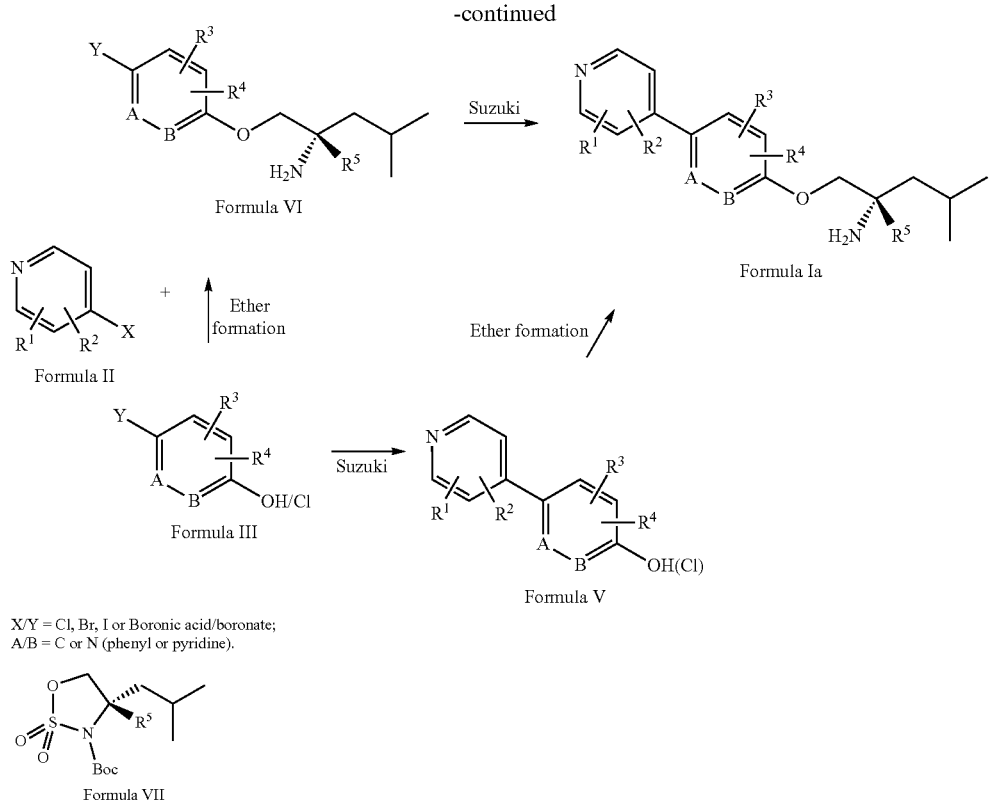

X/Y = Cl, Br, I or Boronic acid/boronate;
A/B = C or N (phenyl or pyridine).

Formula VII

A common activated amino alcohol reagent for ether formation when $R^5$ is not H.

In the following Examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu LC coupled to a Waters Micromass ZQ using at least one of the following methods.
Prep LC/MS methods:
Method A:
Waters Xbridge C18, 19×150 mm, 5 μm; Guard Column: Waters XBridge C18, 19×10 mm, 5 μm; Mobile Phase A=5:95 Acetonitrile:water with 10 mM NH4OAc; Mobile Phase B=95:5 Acetonitrile:water with 10 mM NH4OAc; Gradient: 10-35% B over 25 min, followed by a 10 min hold at 35% B and 5 min hold at 100% B; Flow: 15 mL/min.
Method B:
Waters Xbridge C18, 19×150 mm, 5 m; Guard Column: Waters XBridge C18, 19×10 mm, 5 m; Mobile Phase A=5:95 Acetonitrile:water with 10 mM NH4OAc; Mobile Phase B=95:5 Acetonitrile:water with 10 mM NH4OAc; Gradient: 10-40% B over 25 min, followed by a 10 min hold at 40% B and 5 min hold at 100% B; Flow: 15 mL/min.
Method C:
Waters Xbridge C18, 19×150 mm, 5 m; Guard Column: Waters XBridge C18, 19×10 mm, 5 m; Mobile Phase A=5:95 Methanol:water with 10 mM NH4OAc; Mobile Phase B=95:5 Methanol:water with 10 mM NH4OAc; Gradient: 10-40% B over 25 min, followed by a 10 min hold at 40% B and 5 min hold at 100% B; Flow: 15 mL/min.
Analytical LC/MS Methods:
Method A1:
Ascentis Express $C_{18}$ column (50×2.1 mm-2.7 μm); mobile phase: A=10 mM NH4OAc in Water/ACN (98:2), B=10 mM NH4OAc in Water/ACN (2:98); Run: 0-100% B for 1.7 min, then 100% B over 1.3 min, then 100-0% B over 0.2 min; flow rate=1 mL/min; λ=254 nm.
Method A2:
Phenomenex C18 2×30 mm (3 μm), A=10% MeOH–90% H20-0.1% TFA, B=90% MeOH–10% H20-0.1% TFA; Gradient=0-100% B over 2 min, then hold at 100% B for 1 min; Flow rate=1.0 mL/min
Method B:
Column-ACQUITY UPLC BEH C18 (2.1×50 mm), 1.7 μm; Mobile phase A=0.1% TFA in water; Mobile phase B=Acetonitrile; Gradient=% B: 0-98% B over 1.6 min, then hold at 98% B for 0.65 min; Flow=1 mL/min.
Method C:
Column-ACQUITY UPLC BEH C18 (2.1×50 mm), 1.7 μm; Mobile phase A=0.1% NH4OAc in water; Mobile phase B=Acetonitrile; Gradient=% B: 5-95% B over 1.1 min, then hold at 95% B for 1.4 min; Flow=1 mL/min.
Method C1:
Ascentis Express C18 column (50×4.6 mm-2.7 μm); mobile phase: A=5% ACN, 95% Water, 10 mM NH4OAc, B=95% ACN, 5% Water, 10 mM NH4OAc; Run: 0-100% B over 4 min; flow rate=4 mL/min; oven temp=50° C.; X=254 nm.
Method D:
Ascentis Express C18 column (50×2.1 mm-2.7 μm); mobile phase: A=10 mM NH4OAc in Water, B=ACN; Run: 0-100% B for 1.7 min, then 100% B over 2.3 min; flow rate=1 mL/min.
Method E:
Ascentis Express C18 column (50×2.1 mm-2.7 μm); mobile phase: A=95% Water: 5% Acetonitrile; 0.1% TFA, B=5% Water:95% Acetonitrile; 0.1% TFA; Run: 0-100% B over 3 min, then 100% B over 1.2 min; flow rate=1.1 mL/min; oven temp=50° C.

Method F:
Ascentis Express C18 column (50×2.1 mm-2.7 μm); mobile phase: A=0.1% HCOOH in water; Acetonitrile; Run: 0-100% B over 1.7 min, then 100% B over 2.3 min; flow rate=1.0 mL/min.

Method G:
Column-Kinetex XB-C18 (75λ3 mm-2.6 μm); mobile phase: A=10 mM $NH_4OAc$ in Water/ACN (98:2), B=10 mM $NH_4OAc$ in Water/ACN (2:98); Run: 20-100% B over 4.0 min, then 100% B over 0.6 min, then 100-20% B over 0.1 min; flow rate=1 mL/min.

Method H:
Ascentis Express C18 column (50×2.1 mm-2.7 μm); mobile phase: A=95% Water: 5% Acetonitrile; 10 mM $NH_4OAc$, B=5% Water:95% Acetonitrile; 10 mM $NH_4OAc$; Run: 0-100% B over 3 min, then 100% B over 1.2 min; flow rate=1.1 mL/min; oven temp=50° C.

Method I:
Ascentis Express C18 column (50×2.1 mm-2.7 μm); mobile phase: A=95% Water: 5% Acetonitrile; 0.1% TFA, B=5% Water:95% Acetonitrile; 0.1% TFA; Run: 0-100% B over 3 min, then 100% B over 1.2 min; flow rate=1.1 mL/min; oven temp=50° C.

Method J:
Ascentis Express C18 column (50×4.6 mm-2.7 μm); mobile phase: A=95% Water: 5% Acetonitrile; 0.1% TFA, B=5% Water:95% Acetonitrile; 0.1% TFA; Run: 0-100% B over 4.0 min, then 100% B over 1.1 min; flow rate=4.0 mL/min; oven temp=50° C.

Example 251

(S)-1-(4-(3,5-dimethyl-1H-pyrazol-4-yl)-2-fluorophenoxy)-2,4-dimethylpentan-2-amine

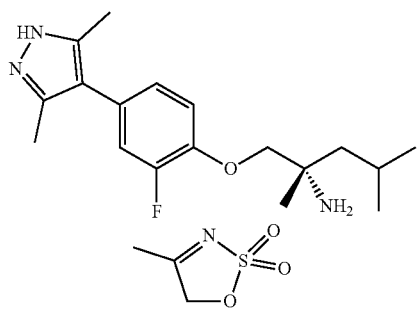

Part A. 4-methyl-5H-1,2,3-oxathiazole 2,2-dioxide

Step 1 Sulfamoyl chloride formation: To a 1000 mL 4 neck round-bottomed flask equipped with a mechanical stirring and an addition funnel, was charged DCM (400 mL) and chlorosulfonyl isocyanate (124 mL, 1430 mmol). Under N2, this solution was cooled to 0° C. Then formic acid (53.9 mL, 1430 mmol) was added to DCM (100 mL) and this solution was transferred to the addition funnel and the solution was added slowly to the vigorously stirring reaction mixture. Gradually a thick slurry formed. A slow exotherm was observed so additional dry ice was added to acetone bath. Once temperature was stabilized, addition of the formic acid was continued. Addition was done in ~25 min. The mixture was allowed to gradually warm to room temperature and was stirred overnight.

Step 2: To a separate 5 L 4 neck reaction flask was charged hydroxyacetone (72.5 mL, 953 mmol), pyridine (116 mL, 1430 mmol), and DCM (2000 mL). This solution was cooled to −5° C. under $N_2$. The sulfamoyl chloride solution was added slowly via Teflon tube over 10 min. After the addition, the reaction was stirred for 15 min then the ice bath was removed and the reaction mixture allowed to warm to room temperature. As the reaction progressed, a gummy material formed. The material was purified via silica gel chromatography (300 g silica gel eluting with DCM). Obtained 4-methyl-5H-1,2,3-oxathiazole 2,2-dioxide (72.4 g, 536 mmol, 56% yield) as a colorless solid. $^1$H NMR (400 MHz, CHLOROFORM-d) δ 5.09 (s, 2H), 2.44 (s, 3H); LCMS (ESI) m/e 136.0 [(M+H)$^+$, calcd for $C_3H_6NO_3S$ 136.0].

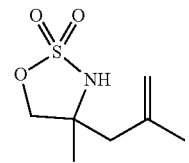

Part B. 2-(tert-butoxycarbonylamino)-1,4-dimethylpentanoic acid 4-methyl-4-(2-methylallyl)-1,2,3-oxathiazolidine 2,2-dioxide A suspension of 4-methyl-5H-1,2,3-oxathiazole 2,2-dioxide (0.541 g, 4 mmol) in methyl tert-butyl ether (30 mL) was cooled below 0° C. with an ice/IPA bath. To the cooled solution was added a solution of (2-methylallyl)magnesium chloride, 0.5 M in THF (9.60 mL, 4.80 mmol). The reaction mixture was allowed to warm to rt overnight. It was then quenched with a saturated solution of $NH_4Cl$ (50 mL) and EtOAc (20 mL) was added. The organic phase was separated, washed with brine (50 mL), dried over $Na_2SO_4$, filtered and concentrated under reduced pressure to give 2-(tert-butoxycarbonylamino)-2,4-dimethylpentanoic acid 4-methyl-4-(2-methylallyl)-1,2,3-oxathiazolidine 2,2-dioxide (0.567 g, 2.96 mmol, 74% yield). $^1$H NMR (400 MHz, CHLOROFORM-d) δ 5.06 (quin, J=1.5 Hz, 1H), 4.87 (dd, J=1.7, 0.8 Hz, 1H), 4.50 (br. s., 1H), 4.40 (d, J=8.6 Hz, 1H), 4.29 (d, J=8.7 Hz, 1H), 2.56 (d, J=13.8 Hz, 1H), 2.40-2.30 (m, 1H), 1.86 (br. s, 3H), 1.49 (s, 3H); LCMS (ESI) m/e 192.1 [(M+H)$^+$, calcd for $C_7H_{14}NO_3S$ 192.1].

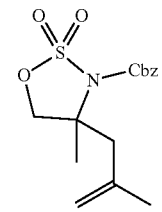 [SMILES: C=C(C)CC1(C)COS(=O)(=O)N1C(=O)OCc1ccccc1]

Part C. benzyl 4-methyl-4-(2-methylallyl)-1,2,3-oxathiazolidine-3-carboxylate 2,2-dioxide To a $N_2$ flushed, 100 mL round-bottomed flask was added a solution of 4-methyl-4-(2-methylallyl)-1,2,3-oxathiazolidine 2,2-dioxide (0.55 g, 2.88 mmol) in THF (10 mL). A solution of potassium tert-butoxide (4.31 mL, 4.31 mmol) in THF was added The temperature rose to 27° C. and the solution became a suspension. The mixture was stirred at room temperature for 1 h. Benzyl carbonochloridate (1.026 mL, 7.19 mmol) was added slowly. The reaction mixture was stirred at room temperature for 2 h. The reaction mixture was then quenched with water (50 mL) and extracted with EtOAc (2×70 mL). The organic extracts were washed with brine (50 mL), dried over $Na_2SO_4$, filtered and concentrated under reduced pressure. The residue was purified by silica gel chromatography (ethyl acetate/hexanes) to give benzyl 4-methyl-4-(2-methylallyl)-1,2,3-oxathiazolidine-3-carboxylate 2,2-dioxide (0.66 g, 2.028 mmol, 71% yield). $^1$H NMR (400 MHz, CHLOROFORM-d) δ 7.58-7.32 (m, 5H), 5.43-5.25 (m, 2H), 5.01 (t, J=1.5 Hz, 1H), 4.81 (d, J=0.9 Hz, 1H), 4.63 (d, J=9.5 Hz, 1H), 4.21 (d, J=9.5 Hz, 1H), 2.87 (d, J=14.1 Hz, 1H), 2.56 (d, J=14.1 Hz, 1H), 1.78 (br. s, 3H), 1.64 (s, 3H); LCMS (ESI) m/e 326.1 [(M+H)$^+$, calcd for $C_{15}H_{20}NO_5S$ 326.1].

The racemic compounds was separated by chiral super critical fluid chromatography (Column: OJ-H (3×25 cm, 5 µm); Mobile Phase: $CO_2$/MeOH (90/10)) to give the two enantiomers.

Analytical super critical fluid chromatography conditions: Column: OJ-H (0.46×25 cm, 5 µm); BPR pressure: 100 bars; Temperature: 35° C.; Flow rate: 3.0 mL/min; Mobile Phase: C02/MeOH (90/10); Detector Wavelength: UV 200-400 nm Enantiomer 1: (S)-benzyl 4-methyl-4-(2-methylallyl)-1,2, 3-oxathiazolidine-3-carboxylate 2,2-dioxide HPLC retention time=2.53 min.

Enantiomer 2: (R)-benzyl 4-methyl-4-(2-methylallyl)-1, 2,3-oxathiazolidine-3-carboxylate 2,2-dioxide HPLC retention time=2.97 min.

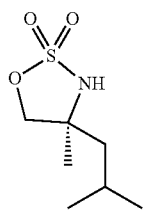

Part D.
(S)-4-isobutyl-4-methyl-1,2,3-oxathiazolidine 2,2-dioxide

To a stirred solution of (S)-benzyl 4-methyl-4-(2-methylallyl)-1,2,3-oxathiazolidine-3-carboxylate 2,2-dioxide (800 mg, 2.459 mmol) in MeOH (20 mL) was added Pd/C (262 mg, 0.246 mmol) under a nitrogen atmosphere. The reaction mixture was stirred under 1 atm hydrogen pressure for 16 h. The reaction mixture was passed through diatomaceous earth pad and the diatomaceous earth pad was washed with EtOAc (15 mL). The organic layer was evaporated under reduced pressure to afford (S)-4-isobutyl-4-methyl-1,2,3-oxathiazolidine 2,2-dioxide (462 mg, 2.39 mmol, 97% yield, 95% purity) as colorless oil. The material was carried forward without further purification. $^1$H NMR (400 MHz, DMSO-d$_6$) δ ppm 7.69 (br, 1H) 4.33 (d, J=8.03 Hz, 1H) 4.17-4.26 (m, 1H) 1.68-1.81 (m, 1H) 1.53-1.63 (m, 1H) 1.43-1.51 (m, 1H) 1.34 (s, 3H) 0.81-1.00 (m, 6H).

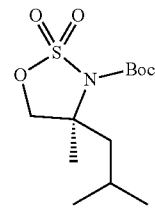 [SMILES: CC(C)C[C@@]1(C)COS(=O)(=O)N1C(=O)OC(C)(C)C]

Part E. (S)-tert-butyl 4-isobutyl-4-methyl-1,2,3-oxathiazolidine-3-carboxylate 2,2-dioxide To a stirred solution of (S)-4-isobutyl-4-methyl-1,2,3-oxathiazolidine 2,2-dioxide (7 g, 15.21 mmol) in DCM (70 mL) cooled to 0° C. was added DMAP (1.858 g, 15.21 mmol) and (BOC)$_2$O (5.30 mL, 22.82 mmol) The reaction mixture was stirred at rt for 12 h. The reaction mixture was transfers to a separating funnel containing water (20 ml) and was extracted with DCM (2×60 ml). The combined organic layers were washed with brine (50 mL), dried over (Na$_2$SO$_4$), and concentrated under reduced pressure. The residue was purified via silica gel chromatography (30% ethyl acetate in pet ether) to afford (S)-tert-butyl 4-isobutyl-4-methyl-1,2,3-oxathiazolidine-3-carboxylate 2,2-dioxide (4.4 g, 14.70 mmol, 97% yield) as a colorless oil. $^1$H NMR (400 MHz, CHLOROFORM-d) δ 4.45 (d, J=9.0 Hz, 1H), 4.20 (d, J=9.0 Hz, 1H), 2.07-1.98 (m, J=8.0 Hz, 1H), 1.83-1.69 (m, 2H), 1.59 (s, 3H), 1.56 (s, 9H), 0.99 (dd, J=8.0, 6.5 Hz, 6H).

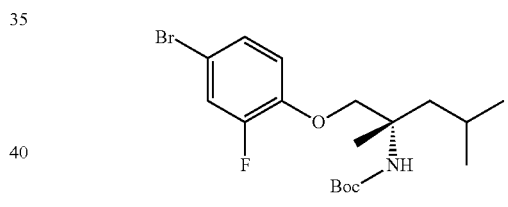

Part F. (S)-tert-butyl (1-(4-bromo-2-fluorophenoxy)-2,4-dimethylpentan-2-yl)carbamate A solution of 4-bromo-2-fluorophenol (0.651 g, 3.41 mmol) in DMF (15 mL) was treated with $Cs_2CO_3$ (2.22 g, 6.82 mmol). The mixture was stirred for 40 min at RT. (S)-tert-butyl 4-isobutyl-4-methyl-1,2,3-oxathiazolidine-3-carboxylate 2,2-dioxide (1 g, 3.41 mmol) was added to the solution and the mixture was heated at 80° C. overnight. It was concentrated, diluted with brine and ethyl acetate. The organic layer was separated, dried over $Na_2SO_4$, filtered, and concentrated to afford an oil. The crude product was purified by silica-gel chromatography (5-20% EtOAc-hexane) to afford (S)-tert-butyl (1-(4-bromo-2-fluorophenoxy)-2,4-dimethylpentan-2-yl)carbamate (1.13 g, 94% yield) as a colorless oil. LCMS (ESI) m/e 304.0 [(M+H-Boc)$^+$, calcd for $C_{18}H_{28}BrFNO_3$ 404.1]; LC/MS retention time (method D): $t_R$=2.81 min. De-Boc mass was detected by LCMS. $^1$H NMR (300 MHz, CDCl$_3$): δ 7.11-7.28 (m, 2H), 6.84-6.93 (m, 1H), 3.96-4.18 (m, 2H), 1.75-1.85 (m, 2H), 1.49-1.55 (m, 1H), 1.39 (s, 3H), 1.31-1.38 (m, 9H), 0.91-1.01 (m, 6H) ppm.

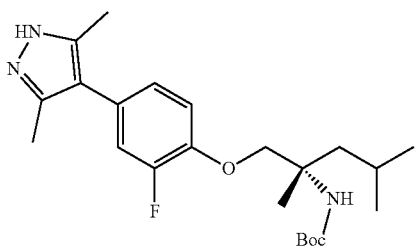 [SMILES: Cc1n[nH]c(C)c1-c1ccc(OC[C@](C)(CC(C)C)NC(=O)OC(C)(C)C)c(F)c1]

Part G: (S)-tert-butyl (1-(4-(3,5-dimethyl-1H-pyrazol-4-yl)-2-fluorophenoxy)-2,4-dimethylpentan-2-yl)carbamate A solution of 3,5-dimethyl-4-(4,4,5,5-tetramethyl-1,3,2-dioxaborolan-2-yl)-1H-pyrazole (100 mg, 0.450 mmol), (S)-tert-butyl (1-(4-bromo-2-fluorophenoxy)-2,4-dimethylpentan-2-yl)carbamate (182 mg, 0.450 mmol), and XPhos 2$^{nd}$ generation precatalyst (333 mg, 0.450 mmol) in tetrahydrofuran (8 mL) was purged with argon for 5 min. A solution of cesium carbonate (293 mg, 0.901 mmol) in water (1 mL) was added and the reaction mixture was stirred at 70° C. for 14 h. The reaction mixture was allowed to cool to room temperature. Water (15 mL) was added and the solution extracted with EtOAc (2×20 mL). The combined organic extracts were washed with brine (25 mL). The organic layer was dried over sodium sulfate, filtered, and concentrated under reduced pressure. The residue was purified by prep. TLC (30% EtOAc in hexanes). The fractions containing product were collected and stirred in DCM (25 mL), passed through diatomaceous earth pad and the diatomaceous earth pad was washed with DCM (20 mL). The combined filtrate was collected and concentrated under reduced pressure to afford (S)-tert-butyl (1-(4-(3,5-dimethyl-1H-pyrazol-4-yl)-2-fluorophenoxy)-2,4-dimethylpentan-2-yl)carbamate (100 mg, 0.231 mmol, 51% yield) as a white solid. LCMS (ESI) m/e 420.2 [(M+H)$^+$, calcd for $C_{23}H_{35}FN_3O_3$, 420.3]; LC/MS retention time (method A1) $t_R$=2.59 min.

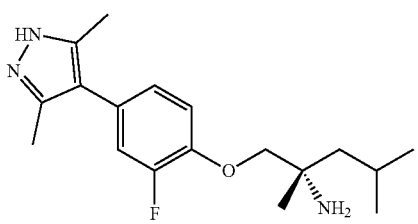 [SMILES: Cc1n[nH]c(C)c1-c1ccc(OC[C@@](C)(N)CC(C)C)c(F)c1]

Part H: (S)-1-(4-(3,5-dimethyl-1H-pyrazol-4-yl)-2-fluorophenoxy)-2,4-dimethylpentan-2-amine To a stirred solution of (S)-tert-butyl (1-(4-(3,5-dimethyl-1H-pyrazol-4-yl)-2-fluorophenoxy)-2,4-dimethylpentan-2-yl)carbamate (100 mg, 0.231 mmol) in DCM (2 mL) cooled to 0° C. was added TFA (0.3 mL, 3.89 mmol) dropwise under a nitrogen atmosphere. The reaction mixture was allowed to warm to room temperature and stirred for 3 h. The solution was concentrated under reduced pressure, residue obtained as yellow oil was purified via preparative LC/MS (method A). Obtained (S)-1-(4-(3,5-dimethyl-1H-pyrazol-4-yl)-2-fluorophenoxy)-2,4-dimethylpentan-2-amine (27 mg, 0.084 mmol, 36% yield) as a pale yellow solid.

$^1$H NMR (300 MHz, METHANOL-d4) δ 7.24 (s, 1H), 7.09 (s, 2H), 4.12 (d, J=15.1 Hz, 2H), 2.24 (s, 6H), 1.91-1.76 (m, 2H), 1.73-1.59 (m, 1H), 1.47 (s, 3H), 1.06 (dd, J=6.6, 7.4 Hz, 6H) ppm. $^{19}$F NMR (300 MHz, METHANOL-d$_4$) δ−135.4. LCMS (ESI) m/e 320.2 [(M+H)$^+$, calcd for $C_{18}H_{27}FN_3O$, 320.2]; LC/MS retention time (method H) $t_R$=1.06 min. LCMS (ESI) m/e 320.0 [(M+H)$^+$, calcd for $C_{18}H_{27}FN_3O$, 320.2]; LC/MS retention time (Method E) $t_R$=0.84 min.

Example 252

(S)-2-((2-amino-2,4-dimethylpentyl)oxy)-5-(2,3-dimethylpyrido[2,3-b]pyrazin-8-yl)benzonitrile

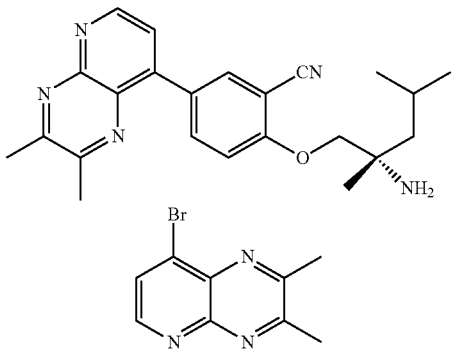

Part A: 8-bromo-2,3-dimethylpyrido[2,3-b]pyrazine

To a stirred solution of biacetyl (68.7 mg, 0.798 mmol) and 4-bromopyridine-2,3-diamine (150 mg, 0.798 mmol) in ethanol (4 mL) was added acetic acid (0.2 mL) under a nitrogen atmosphere. The reaction mixture was heated at 95° C. for 2 h. The reaction mixture was allowed to cool to room temperature and concentrated under reduced pressure. Water (10 mL) was added and the solution extracted with EtOAc (2×10 mL). The combined organic extracts were dried over sodium sulfate, filtered, and concentrated under reduced pressure to afford 8-bromo-2,3-dimethylpyrido[2,3-b]pyrazine (125 mg, 0.525 mmol, 66% yield) as a brown solid. The product was carried forward without further purification. $^1$H NMR (400 MHz, CDCl$_3$): δ 8.16 (d, J=11.20 Hz, 1H), 7.74 (d, J=11.60 Hz, 1H), 2.80 (s, 3H), 2.76 (s, 3H) ppm.

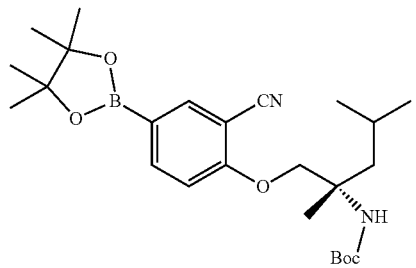 [SMILES: CC(C)C[C@@](C)(COc1ccc(B2OC(C)(C)C(C)(C)O2)cc1C#N)NC(=O)OC(C)(C)C]

Part B: (S)-tert-butyl (1-(2-cyano-4-(4,4,5,5-tetramethyl-1,3,2-dioxaborolan-2-yl)phenoxy)-2,4-dimethylpentan-2-yl)carbamate (S)-tert-butyl (1-(4-bromo-2-cyanophenoxy)-2,4-dimethylpentan-2-yl)carbamate (0.57 g, 1.386 mmol), 4,4,4',4',5,5, 5',5'-octamethyl-2,2'-bi(1,3,2-dioxaborolane) (0.422 g, 1.663 mmol), PdCl$_2$(dppf) (0.051 g, 0.069 mmol), potassium acetate (0.408 g, 4.16 mmol), and dioxane (5 mL) were charged to a pressure rated vial. The vial was purged of oxygen and the mixture stirred under nitrogen at 80° C. overnight. The mixture was cooled to ambient temperature, vacuum filtered, and concentrated under reduced pressure. Obtained (S)-tert-butyl (1-(2-cyano-4-(4,4,5,5-tetramethyl-1,3,2-dioxaborolan-2-yl)phenoxy)-2,4-dimethylpentan-2-yl)carbamate (600 mg, 1.30 mmol, 100% crude yield) as a brown oil that was used without further purification. LCMS (ESI) m/e 481.1 [(M+Na)+, calcd C$_{25}$H$_{39}$BN$_2$NaO$_5$, 481.3]; LC/MS retention time (method A2): t$_R$=2.49 min.

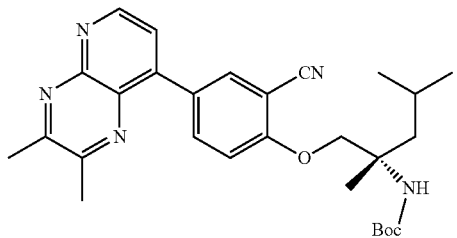 [SMILES: Cc1nc2nccc(-c3ccc(OC[C@](C)(CC(C)C)NC(=O)OC(C)(C)C)c(C#N)c3)c2nc1C]

Part C: (S)-tert-butyl (1-(2-cyano-4-(2,3-dimethyl-pyrido[2,3-b]pyrazin-8-yl)phenoxy)-2,4-dimethylpentan-2-yl)carbamate A stirred solution of 8-bromo-2,3-dimethylpyrido[2,3-b]pyrazine (75 mg, 0.315 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (142 mg, 0.315 mmol) and XPhos 2$^{nd}$ generation precatalyst (12.39 mg, 0.016 mmol) in tetrahydrofuran (8 mL) was purged with nitrogen for 2 min. To this mixture was added a solution of cesium carbonate (205 mg, 0.630 mmol) in water (0.5 mL) and the reaction mixture was stirred at 75° C. under a nitrogen atmosphere for 14 h. Water (30 mL) was added and the solution was extracted with EtOAc (2×15 mL). The combined organic extracts were washed with brine (20 mL). The organic layer was dried over sodium sulfate, filtered, and concentrated under reduced pressure. The residue was purified via prep. TLC (mobile phase of 50% EtOAc in hexanes). Fractions containing the product were collected and stirred in DCM (25 mL), passed through diatomaceous earth pad and the diatomaceous earth pad was washed with DCM (20 mL). The filtrate was collected and concentrated under reduced pressure to afford ((S)-tert-butyl (1-(2-cyano-4-(2,3-dimethylpyrido[2,3-b]pyrazin-8-yl)phenoxy)-2,4-dimethylpentan-2-yl)carbamate (106 mg, 0.149 mmol, 47% yield) as a pale brown solid. LCMS (ESI) m/e 490.2 [(M+H)$^+$, calcd for C$_{28}$H$_{36}$N$_5$O$_3$, 490.3]; LC/MS retention time (Method F) t$_R$=2.38 min

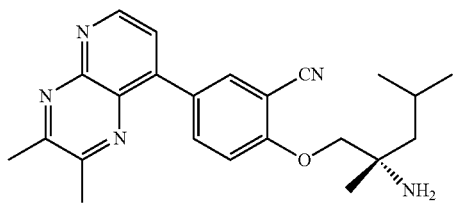 [SMILES: Cc1nc2nccc(-c3ccc(OC[C@@](C)(N)CC(C)C)c(C#N)c3)c2nc1C]

Part D: (S)-2-((2-amino-2,4-dimethylpentyl)oxy)-5-(2,3-dimethylpyrido[2,3-b]pyrazin-8-yl)benzonitrile To a stirred solution of (S)-tert-butyl (1-(2-cyano-4-(2,3-dimethylpyrido[2,3-b]pyrazin-8-yl)phenoxy)-2,4-dimethylpentan-2-yl)carbamate (100 mg, 0.141 mmol) in DCM (5 mL) cooled to 0° C. was added TFA (0.25 mL, 3.24 mmol) dropwise under a nitrogen atmosphere. The reaction mixture was stirred at room temperature for 2 h. The solution was concentrated under reduced pressure to afford a brown oil. The crude material was purified via preparative HPLC using method-B to afford (S)-2-((2-amino-2,4-dimethylpentyl)oxy)-5-(2,3-dimethylpyrido[2,3-b]pyrazin-8-yl)benzonitrile (22 mg, 39%) as a pale yellow solid. $^1$H NMR (400 MHz, METHANOL-d$_4$) δ 8.71-8.60 (m, 2H), 8.56-8.46 (m, 1H), 8.40-8.32 (m, 1H), 7.49 (d, J=9.0 Hz, 1H), 4.36 (d, J=4.0 Hz, 2H), 2.86 (s, 3H), 2.83 (s, 3H), 2.02-1.86 (m, 2H), 1.80-1.71 (m, 1H), 1.58 (s, 3H), 1.10 (m, 6H). LCMS (ESI) m/e 390.0 [(M+H)$^+$, Calcd for C$_{23}$H$_{27}$N$_5$O, 390.2]; LC/MS retention time (Method E) t$_R$=1.15 min.

Example 253

(S)-1-(2-fluoro-4-(pyrido[2,3-b]pyrazin-8-yl)phenoxy)-2,4-dimethylpentan-2-amine

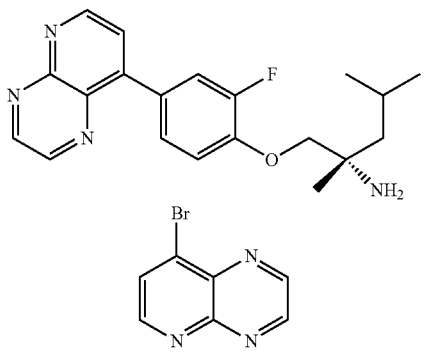

Part A: 8-Bromopyrido[2,3-b]pyrazine

To a stirred solution of 4-bromopyridine-2,3-diamine (100 mg, 0.532 mmol) and oxalaldehyde (30.9 mg, 0.532 mmol) in EtOH (4 mL) was added acetic acid (0.4 mL) under a nitrogen atmosphere. The reaction mixture was heated at 95° C. for 2 h. The reaction mixture was allowed to cool to room temperature, concentrated under reduced pressure and diluted with water (10 mL). The solution was extracted with EtOAc (2×10 mL). The combined organic extracts were dried over sodium sulfate, filtered, and concentrated under reduced pressure to afford 8-bromo-2,3-dimethylpyrido[2,3-b]pyrazine (125 mg, 0.525 mmol, 66% yield) as a brown solid in good purity based on $^1$H NMR. The product was carried forward without further purification. $^1$H NMR (300 MHz, CDCl$_3$): δ 9.08 (d, J=1.8 Hz, 1H), 8.98 (d, J=1.8 Hz, 1H), 8.32 (d, J=8.7 Hz, 1H), 7.89 (d, J=8.7 Hz, 1H) ppm.

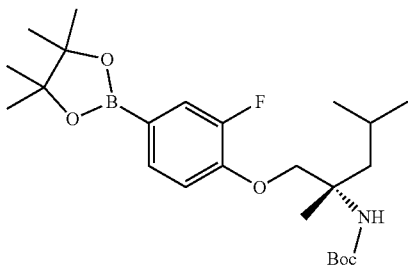 [SMILES: CC(C)C[C@@](C)(COc1ccc(B2OC(C)(C)C(C)(C)O2)cc1F)NC(=O)OC(C)(C)C]

Part B. (S)-tert-butyl (1-(2-fluoro-4-(4,4,5,5-tetramethyl-1,3,2-dioxaborolan-2-yl)phenoxy)-2,4-dimethylpentan-2-yl)carbamate A mixture of (S)-tert-butyl (1-(4-bromo-2-fluorophenoxy)-2,4-dimethylpentan-2-yl)carbamate (1.751 g, 4.33 mmol), 4,4,4',4',5,5,5',5'-octamethyl-2,2'-bi(1,3,2-dioxaborolane) (1.1 g, 4.33 mmol), and potassium acetate (0.850 g, 8.66 mmol) in 1,4-dioxane (20 mL) was heated at 90° C. overnight. The reaction mixture was cooled to room temperature and concentrated under reduced pressure. The residue was diluted with water and ethyl acetate. The ethyl acetate layer was collected, dried over $Na_2SO_4$, filtered, and concentrated under reduced pressure to afford a yellowish semi-solid. The residue was purified by silica gel chromatography (5-10% EtOAc-hexane) to obtain (S)-tert-butyl (1-(2-fluoro-4-(4,4,5,5-tetramethyl-1,3,2-dioxaborolan-2-yl)phenoxy)-2,4-dimethylpentan-2-yl)carbamate as colorless oil (1.7 g, 3.77 mmol, 87% yield). LCMS (ESI) m/e 352.2 [(M+H-Boc)+, calcd for $C_{24}H_{40}BFNO_5$ 452.2]; LC/MS retention time (method B): $t_R$=1.33 min. De-Boc mass was detected by LCMS. $^1$H NMR (400 MHz, $CDCl_3$): δ 7.45-7.49 (m, 2H), 6.94-6.98 (m, 1H), 4.60 (bs, NH, 1H), 4.16 (m, 1H), 4.00 (m, 1H), 1.82 (m, 2H), 1.60 (m, 1H), 1.59 (s, 3H), 1.39 (s, 9H), 1.24 (s, 12H), 0.92-0.99 (m, 6H) ppm.

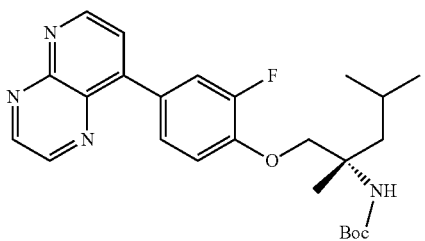 [SMILES: CC(C)C[C@@](C)(COc1ccc(-c2ccnc3nccnc23)cc1F)NC(=O)OC(C)(C)C]

Part C: (S)-tert-butyl (1-(2-fluoro-4-(pyrido[2,3-b]pyrazin-8-yl)phenoxy)-2,4-dimethylpentan-2-yl)carbamate A stirred solution of 8-bromopyrido[2,3-b]pyrazine (75 mg, 0.357 mmol), (S)-tert-butyl (1-(2-fluoro-4-(4,4,5,5-tetramethyl-1,3,2-dioxaborolan-2-yl)phenoxy)-2,4-dimethylpentan-2-yl)carbamate (161 mg, 0.357 mmol) and XPhos $2^{nd}$ generation precatalyst (14.05 mg, 0.018 mmol) in tetrahydrofuran (8 mL) was purged with nitrogen for 2 min. To this mixture, a solution of cesium carbonate (233 mg, 0.714 mmol) in water (0.5 mL) was added and the reaction mixture was stirred at 75° C. under a nitrogen atmosphere for 14 h. Water (30 mL) was added and the solution was extracted with EtOAc (2×15 mL). The combined organic extracts were washed with brine (20 mL). The organic layer was dried over sodium sulfate, filtered, and concentrated under reduced pressure. The residue was purified by prep. TLC (mobile phase of 50% EtOAc in hexanes). Fractions containing the product were collected and stirred in DCM (25 mL), passed through diatomaceous earth pad, and the diatomaceous earth pad was washed with DCM (20 mL). The filtrate was collected and concentrated under reduced pressure to afford (S)-tert-butyl (1-(2-fluoro-4-(pyrido[2,3-b]pyrazin-8-yl)phenoxy)-2,4-dimethylpentan-2-yl)carbamate (110 mg, 0.145 mmol, 41% yield) as a yellow solid. LCMS (ESI) m/e 455.2 [(M+H), calc for $C_{25}H_{32}FN_4O_3$, 455.2]; LC/MS retention time (Method A1): $t_R$=2.40 min.

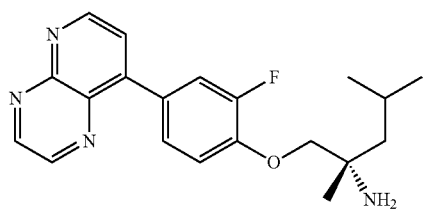 [SMILES: CC(C)C[C@](C)(N)COc1ccc(-c2ccnc3nccnc23)cc1F]

Part D: (S)-1-(2-fluoro-4-(pyrido[2,3-b]pyrazin-8-yl)phenoxy)-2,4-dimethylpentan-2-amine To a stirred solution of (S)-tert-butyl (1-(2-fluoro-4-(pyrido[2,3-b]pyrazin-8-yl)phenoxy)-2,4-dimethylpentan-2-yl)carbamate (100 mg, 0.220 mmol) in DCM (5 mL) cooled to 0° C. was added TFA (1 mL, 12.98 mmol) dropwise under a nitrogen atmosphere. The reaction mixture was allowed to warm to room temperature and stirred for 3 h. The solution was concentrated under reduced pressure to afford a brown oil which was purified via preparative HPLC using method-A. The purification afforded (S)-1-(2-fluoro-4-(pyrido[2,3-b]pyrazin-8-yl)phenoxy)-2,4-dimethylpentan-2-amine (2.7 mg, 7.08 μmol, 3% yield) as a pale yellow solid. $^1$H NMR (400 MHz, METHANOL-$d_4$) δ 9.10 (d, J=1.5 Hz, 1H), 9.00 (d, J=2.0 Hz, 1H), 8.66-8.56 (m, 1H), 8.45 (d, J=8.5 Hz, 1H), 8.22 (dd, J=2.5, 12.5 Hz, 1H), 8.15-8.12 (m, 1H), 7.35 (t, J=8.5 Hz, 1H), 4.04-3.90 (m, 2H), 1.91-1.82 (m, 2H), 1.60 (d, J=5.5 Hz, 1H), 1.34 (s, 3H), 1.04 (m, 6H). LCMS (ESI) m/e 355.0 [(M+H)+, Calcd for $C_{20}H_{24}FN_4O$, 355.1; LC/MS retention time (method H) $t_R$=1.09 min.

Example 254

(S)-2-((2-amino-2,4-dimethylpentyl)oxy)-5-(2-amino-3H-imidazo[4,5-b]pyridin-7-yl)benzonitrile

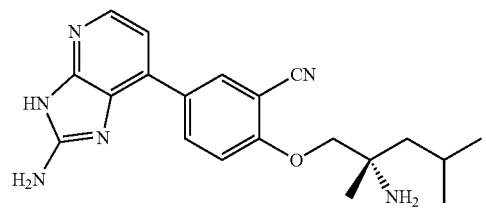

Part A: 4-bromopyridine-2,3-diamine

To a stirred solution of 4-bromo-2-nitropyridin-3-amine (1 g, 4.59 mmol) in a mixture of EtOH (20 mL) and water (5 mL) was added tin(IV) chloride (3.00 g, 11.52 mmol) over a period of 1 min. The reaction mixture was heated to 90° C. and stirred for 2 h. The reaction mixture was allowed to cool to room temperature, then poured into saturated aq. sodium bicarbonate solution (50 mL) and extracted with DCM (2×100 mL). The combined organic extracts were washed with water (100 mL), brine (100 mL), organic layer was dried over sodium sulfate, filtered, and concentrated under reduced pressure to afford 4-bromopyridine-2,3-diamine (460 mg, 2.446 mmol, 53% yield) as a pale brown solid. The compound was taken to the next step without further purification. LCMS (ESI) m/e 187.9 [(M+H)$^+$, calcd for $C_5H_7BrN_3$, 187.9]; LC/MS retention time (Method C) $t_R$=0.52 min.

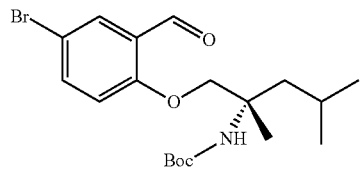 [SMILES: CC(C)C[C@@](C)(COc1ccc(Br)cc1C=O)NC(=O)OC(C)(C)C]

Part B: (S)-tert-butyl (1-(4-bromo-2-formylphenoxy)-2,4-dimethylpentan-2-yl)carbamate To a 20 mL vial was added 5-bromo-2-hydroxybenzaldehyde (81 mg, 0.403 mmol), (S)-tert-butyl 4-isobutyl-4-methyl-1,2,3-oxathiazolidine-3-carboxylate 2,2-dioxide (prepared as described in Example 251, Parts A-E) (107.4 mg, 0.366 mmol), and $K_2CO_3$ (152 mg, 1.098 mmol) in DMF (1.2 mL) to give a white suspension. The vial was sealed and the mixture was heated at 80° C. for 17 h. The reaction mixture was cooled to rt and partitioned between water and EtOAc. The layers were separated. The organic layer was washed with water, brine, dried ($Na_2SO_4$) and concentrated under reduced pressure. The crude residue was purified by silica gel chromatography (up to 40% EtOAc/hexanes) to afford (S)-tert-butyl (1-(4-bromo-2-formylphenoxy)-2,4-dimethylpentan-2-yl)carbamate (115 mg, 0.278 mmol, 76%) as a colorless oil. $^1$H NMR (400 MHz, Chloroform-d) δ 10.43 (s, 1H), 7.89 (d, J=2.6 Hz, 1H), 7.59 (dd, J=8.9, 2.6 Hz, 1H), 6.93 (d, J=8.8 Hz, 1H), 4.58 (s, 1H), 4.29 (d, J=8.8 Hz, 1H), 4.09 (d, J=8.8 Hz, 1H), 1.94-1.74 (m, 2H), 1.48 (dd, J=13.9, 4.8 Hz, 1H), 1.39 (s, 3H), 1.37 (s, 9H), 0.98 (dd, J=6.6, 4.8 Hz, 6H); (ESI) m/e 314.0, 316.0 Br pattern [(M-Boc+H)$^+$, calcd $C_{14}H_{21}BrNO_2$, 414.1]; LC/MS retention time (method A2): $t_R$=2.39 min.

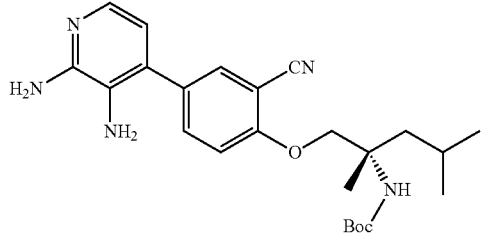 [SMILES: CC(C)C[C@@](C)(COc1ccc(-c2ccnc(N)c2N)cc1C#N)NC(=O)OC(C)(C)C]

Part C. (S)-tert-butyl (1-(2-cyano-4-(2,3-diaminopyridin-4-yl)phenoxy)-2,4-dimethylpentan-2-yl)carbamate To a stirred solution of (S)-tert-butyl (1-(2-cyano-4-(4,4,5,5-tetramethyl-1,3,2-dioxaborolan-2-yl)phenoxy)-2,4-dimethylpentan-2-yl)carbamate (100 mg, 0.218 mmol), 4-bromopyridine-2,3-diamine (41.0 mg, 0.218 mmol) and cesium carbonate (142 mg, 0.436 mmol) in a mixture of 1,4-dioxane (5 mL) and water (0.5 mL) was added XPhos $2^{nd}$ generation precatalyst (17.16 mg, 0.022 mmol) under a nitrogen atmosphere. The reaction mixture was heated at 95° C. for 2 h. The solution was concentrated under reduced pressure, water (20 mL) was added and the solution extracted with EtOAc (2×20 mL). The combined organic extracts were washed with water (50 mL) and brine (20 mL) The organic layer was dried over sodium sulfate, filtered, and concentrated under reduced pressure. The residue was purified by silica gel chromatography (EtOAc in hexanes) to afford (S)-tert-butyl (1-(2-cyano-4-(2,3-diaminopyridin-4-yl)phenoxy)-2,4-dimethylpentan-2-yl)carbamate (92 mg, 0.180 mmol, 83% yield). The product was carried forward without further purification. LCMS (ESI) m/e 384.2 [(M+H)$^+$, calcd for $C_{24}H_{34}N_5O_3$, 440.3]; LC/MS retention time (method B) $t_R$=0.91 min.

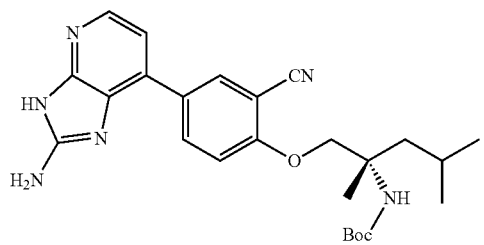 [SMILES: CC(C)C[C@@](C)(COc1ccc(-c2ccnc3[nH]c(N)nc23)cc1C#N)NC(=O)OC(C)(C)C]

Part D. (S)-tert-butyl (1-(4-(2-amino-3H-imidazo[4,5-b]pyridin-7-yl)-2-cyanophenoxy)-2,4-dimethylpentan-2-yl)carbamate To a stirred solution of (S)-tert-butyl (1-(2-cyano-4-(2,3-diaminopyridin-4-yl)phenoxy)-2,4-dimethylpentan-2-yl)carbamate (90 mg, 0.176 mmol) in a mixture of methanol (10 mL) and water (1 mL) was added cyanic bromide (24.25 mg, 0.229 mmol) under nitrogen atmosphere and the reaction mixture was allowed to stirred at room temperature for 12 h. The solution was concentrated under reduced pressure. Water (15 mL) was added and the solution was extracted with EtOAc (2×25 mL). The combined organic extracts were washed with water (20 mL), organic layer was dried over sodium sulfate, filtered, and concentrated under reduced pressure to afford (S)-tert-butyl (1-(4-(2-amino-3H- imidazo[4,5-b]pyridin-7-yl)-2-cyanophenoxy)-2,4-dimethylpentan-2-yl)carbamate (83 mg, 0.168 mmol, 95% yield) as a pale brown solid. The product was carried forward without further purification. LCMS (ESI) m/e 465.3 [(M+H)$^+$ calcd for $C_{25}H_{33}N_6O_3$, 465.3]; LC/MS retention time (method B) $t_R$=0.93 min.

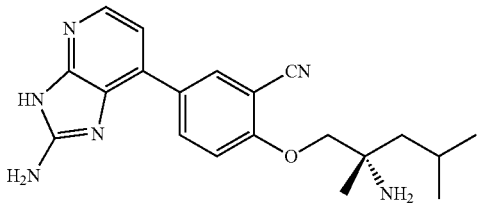

Part E: (S)-2-((2-amino-2,4-dimethylpentyl)oxy)-5-(2-amino-3H-imidazo[4,5-b]pyridin-7-yl)benzonitrile To a stirred solution of (S)-tert-butyl (1-(4-(2-amino-3H-imidazo[4,5-b]pyridin-7-yl)-2-cyanophenoxy)-2,4-dimethylpentan-2-yl)carbamate (82 mg, 0.166 mmol) in $CH_2Cl_2$ (6 mL) cooled to 0° C. was added TFA (0.3 mL, 3.89 mmol). The reaction mixture was allowed to stir at room temperature for 3 h. The solution was concentrated under reduced pressure. The residue was purified via preparative LC/MS (method-A) to afford (S)-2-((2-amino-2,4-dimethylpentyl)oxy)-5-(2-amino-3H-imidazo[4,5-b]pyridin-7-yl)benzonitrile (19 mg, 0.052 mmol, 31% yield) as a pale yellow solid. $^1$H NMR (400 MHz, METHANOL-d$_4$) δ 8.37-8.20 (m, 2H), 7.70-7.43 (m, 2H), 7.31 (d, J=9.0 Hz, 1H), 4.16 (d, J=3.5 Hz, 2H), 1.93-1.77 (m, 2H), 1.70-1.62 (m, 1H), 1.44 (s, 3H), 1.06 (m, 6H). LCMS (ESI) m/e 365.0 [(M+H)$^+$, calcd for $C_{20}H_{25}N_6O$, 365.2]; LC/MS retention time (method H) $t_R$=0.95 min. LCMS (ESI) m/e 365.0 [(M+H)$^+$, calcd for $C_{20}H_{25}N_6O$, 365.2]; LC/MS retention time (Method E) $t_R$=0.78 min.

Example 255

(S)-7-(4-((2-amino-2,4-dimethylpentyl)oxy)-3-(trifluoromethyl)phenyl)-3H-imidazo [4,5-b]pyridin-2-amine

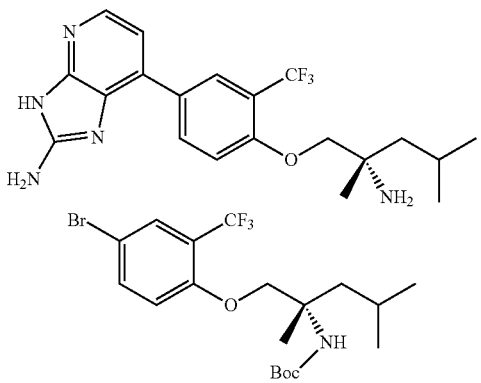

Part A: (S)-Tert-butyl (1-(4-bromo-2-(trifluoromethyl)phenoxy)-2,4-dimethylpentan-2-yl)carbamate To a mixture of 4-bromo-2-(trifluoromethyl) phenol (4 g, 16.60 mmol) in DMF (50 mL) cooled at 0° C., was added $K_2CO_3$ (6.88 g, 49.8 mmol) in portions followed by slow addition of (S)-tert-butyl 4-isobutyl-4-methyl-1,2,3-oxathiazolidine-3-carboxylate 2,2-dioxide (prepared as described in Example 251, Parts A-E) (5.36 g, 18.26 mmol) in 10 mL DMF. The reaction mixture was slowly allowed to warm to room temperature then stirred at 80° C. for 12 h. The reaction mixture was cooled to 0° C. and quenched with aqueous ammonium chloride (100 mL). The reaction mixture was extracted with ethyl acetate (2×100 mL). The organic layer was washed with water (2×50 mL), brine (50 mL), dried over $Na_2SO_4$, and concentrated to afford crude (S)-tert-butyl (1-(4-bromo-2-(trifluoromethyl)phenoxy)-2,4-dimethylpentan-2-yl)carbamate (6.5 g, 13.16 mmol, 79% yield) as a colorless oil which was carried forward without further purification. $^1$H NMR (400 MHz, DMSO-d$_6$): δ 7.74-7.81 (m, 2H), 7.19 (d, J=8.80 Hz, 1H), 6.52 (s, 1H), 4.02-4.24 (m, 2H), 1.69-1.80 (m, 2H), 1.41-1.50 (m, 1H), 1.40 (s, 9H), 1.25 (s, 3H), 0.83-0.96 (m, 6H) ppm.

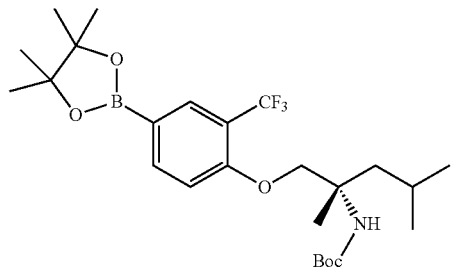 [SMILES: CC(C)C[C@@](C)(COc1ccc(B2OC(C)(C)C(C)(C)O2)cc1C(F)(F)F)NC(=O)OC(C)(C)C]

Part B: (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate A solution of (S)-tert-butyl (1-(4-bromo-2-(trifluoromethyl)phenoxy)-2,4-dimethylpentan-2-yl)carbamate (6.5 g, 14.31 mmol), bis(pinacolato)diboron (7.27 g, 28.6 mmol), potassium acetate (4.21 g, 42.9 mmol) in 1,4-dioxane (100 mL) was purged with argon for 5 min. $PdCl_2$ (dppf)-$CH_2Cl_2$ adduct (1.168 g, 1.431 mmol) was added to the reaction mixture under argon and was heated at 84° C. for 14 h. The reaction mixture was filtered through diatomaceous earth and the diatomaceous earth bed was washed with ethyl acetate (200 mL). The organic layer was washed with water (100 mL). The aqueous layer was re-extracted with ethyl acetate (2×100 mL). The organic layer was collected, washed with brine, dried over $Na_2SO_4$, and concentrated which afforded crude (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate. The crude product was dissolved in 50 mL of DCM, adsorbed on silica gel (60-120), purified silica gel chromatography (0-15% of ethyl acetate/hexane) to give (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (6.01 g, 11.99 mmol, 84% yield) as an off-white semi-solid. $^1$H NMR (400 MHz, DMSO-d$_6$): δ 7.87-7.90 (m, 1H), 7.80 (s, 1H), 7.21 (d, J=8.40 Hz, 1H), 6.53 (s, 1H), 4.07-4.25 (m, 2H), 1.70-1.79

(m, 2H), 1.45-1.50 (m, 1H), 1.26-1.35 (m, 9H), 1.08-1.20 (m, 12H), 0.82-0.91 (m, 6H) ppm.

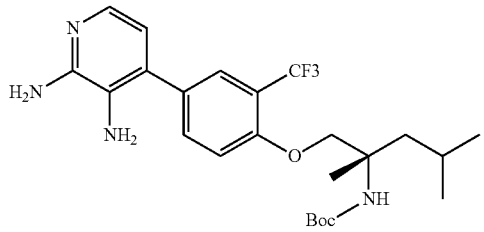

Part C: (S)-tert-butyl (1-(4-(2,3-diaminopyridin-4-yl)-2-(trifluoromethyl)phenoxy)-2,4-dimethylpentan-2-yl) carbamate To a stirred solution of (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (100 mg, 0.199 mmol), 4-bromopyridine-2,3-diamine (37.5 mg, 0.199 mmol) and cesium carbonate (130 mg, 0.399 mmol) in a mixture of 1,4-dioxane (5 mL) and water (0.5 mL) was added XPhos $2^{nd}$ generation precatalyst (15.69 mg, 0.020 mmol) under a nitrogen atmosphere. The reaction mixture was heated at 95° C. for 2 h. The reaction mixture was allowed to cool to room temperature and concentrated under reduced pressure. Water (20 mL) was added and the solution extracted with EtOAc (2×20 mL). The combined organic extracts were washed with water (50 mL) and brine (20 mL). The organic layer was dried over sodium sulfate, filtered, and concentrated under reduced pressure. The residue was purified by silica gel chromatography (EtOAc in hexanes) to afford (S)-tert-butyl (1-(4-(2,3-diaminopyridin-4-yl)-2-(trifluoromethyl)phenoxy)-2,4-dimethylpentan-2-yl)carbamate (71 mg, 0.068 mmol, 34% yield) as a brown oil. LCMS (ESI) m/e 483.2 [(M+H)$^+$, calcd for $C_{24}H_{34}F_3N_4O_3$, 483.2]; LC/MS retention time (method B) $t_R$=0.97 min.

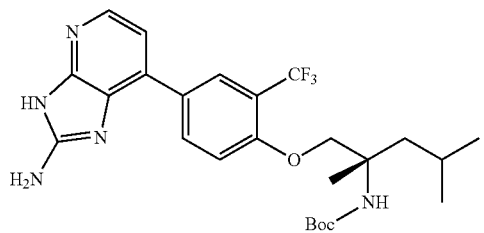

Part D: (S)-tert-butyl (1-(4-(2-amino-3H-imidazo[4,5-b]pyridin-7-yl)-2-(trifluoromethyl)phenoxy)-2,4-dimethylpentan-2-yl)carbamate To a stirred solution of (S)-tert-butyl (1-(4-(2,3-diaminopyridin-4-yl)-2-(trifluoromethyl)phenoxy)-2,4-dimethylpentan-2-yl)carbamate (70 mg, 0.145 mmol) in a mixture of MeOH (4 mL) and water (0.5 mL) was added cyanic bromide (23.05 mg, 0.218 mmol) under a nitrogen atmosphere. The reaction mixture was allowed to stir at room temperature for 12 h. The solution was concentrated under reduced pressure. The brown solid obtained was washed with diethyl ether (2×8 mL). the solid was collected by vacuum filtration and dried under vacuum at room temperature to afford (S)-tert-butyl (1-(4-(2-amino-3H-imidazo[4,5-b]pyridin-7-yl)-2-(trifluoromethyl)phenoxy)-2,4-dimethylpentan-2-yl)carbamate (83 mg, 0.082 mmol, 56% yield) as a brown solid. The product was carried forward without further purification. LCMS (ESI) m/e 508.2 [(M+H)$^+$, calcd for $C25H_{33}F_3N_5O_3$, 508.2]; LC/MS retention time (Method F) $t_R$=2.06 min.

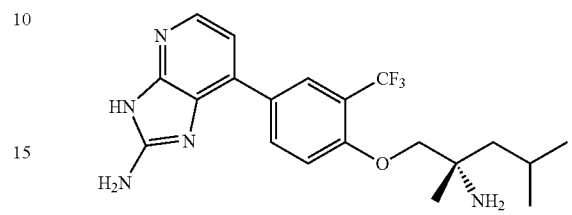

Part E: (S)-7-(4-((2-amino-2,4-dimethylpentyl)oxy)-3-(trifluoromethyl)phenyl)-3H-imidazo[4,5-b]pyridin-2-amine To a stirred solution of (S)-tert-butyl (1-(4-(2-amino-3H-imidazo[4,5-b]pyridin-7-yl)-2-(trifluoromethyl)phenoxy)-2,4-dimethylpentan-2-yl)carbamate (80 mg, 0.079 mmol) in DCM (3 mL) cooled to 0° C. was added TFA (0.25 mL, 3.24 mmol) dropwise under a nitrogen atmosphere. The reaction mixture was allowed to warm to room temperature and stirred for 2 h. The solution was concentrated under reduced pressure. The crude material was purified via preparative LC/MS using method-A to afford (S)-7-(4-((2-amino-2,4-dimethylpentyl)oxy)-3-(trifluoromethyl)phenyl)-3H-imidazo[4,5-b]pyridin-2-amine (5.9 mg, 0.014 mmol, 18% yield) as a pale yellow solid. $^1$H NMR (400 MHz, METHANOL-$d_4$) δ 8.32 (d, J=2.0 Hz, 1H), 8.27-8.18 (m, 1H), 7.59-7.45 (m, 2H), 7.33 (d, J=9.0 Hz, 1H), 4.30-4.13 (m, 2H), 1.98-1.81 (m, 2H), 1.71 (d, J=8.5 Hz, 1H), 1.51 (s, 3H), 1.06 (m, 6H) ppm. LCMS (ESI) m/e 408.2 [(M+H)$^+$, calcd for $C_{20}H_{25}F_3N_5O$, 408.2]; LC/MS retention time (method H) $t_R$=1.23 min. LCMS (ESI) m/e 408.0 [(M+H)$^+$, calcd for $C20H_{25}F_3N_5O$, 408.2]; LC/MS retention time (method I) $t_R$=0.91 min.

Example 256

(S)—N-(4-(4-((2-amino-2,4-dimethylpentyl)oxy)-3-(trifluoromethyl)phenyl)pyridin-2-yl)thiazol-2-amine

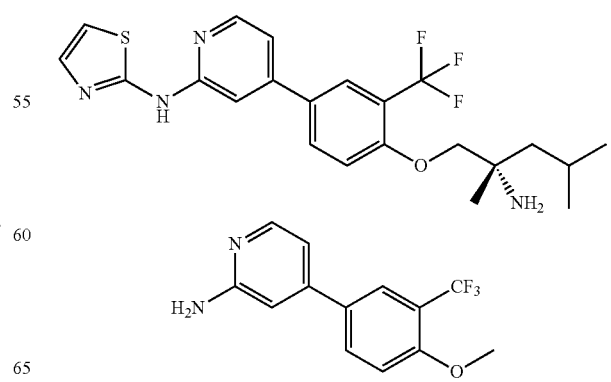

Part A: 4-(4-methoxy-3-(trifluoromethyl)phenyl) pyridin-2-amine

A stirred solution of 4-chloropyridin-2-amine (100 mg, 0.778 mmol) and (4-methoxy-3-(trifluoromethyl)phenyl)boronic acid (171 mg, 0.778 mmol) in a mixture of 1,4-dioxane (5 mL) and water (0.5 mL) was purged with nitrogen for 2 min. To this mixture, XPhos $2^{nd}$ generation precatalyst (61.2 mg, 0.078 mmol) under a nitrogen atmosphere was added and the reaction mixture was heated at 95° C. for 2 h. The reaction mixture was allowed to cool to room temperature Water (15 mL) was added and the solution was extracted with EtOAc (2×20 mL). The combined organic extracts were washed with brine (20 mL). The organic layer was dried over sodium sulfate, filtered, and concentrated under reduced pressure. The residue was purified by silica gel chromatography (EtOAc in hexanes) to afford 4-(4-methoxy-3-(trifluoromethyl)phenyl)pyridin-2-amine (145 mg, 0.492 mmol, 63% yield) as a yellow solid. LCMS (ESI) m/e 269.1 [(M+H)$^+$, calcd for C13H$_{12}$F$_3$N$_2$O, 269.0]; LC/MS retention time $t_R$=0.70 min.

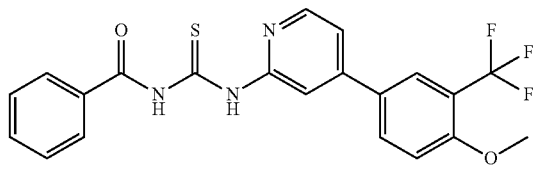 [SMILES: COc1ccc(-c2ccnc(NC(=S)NC(=O)c3ccccc3)c2)cc1C(F)(F)F]

Part B: N-((4-(4-methoxy-3-(trifluoromethyl)phenyl)pyridin-2-yl)carbamothioyl)benzamide To a stirred solution of 4-(4-methoxy-3-(trifluoromethyl)phenyl)pyridin-2-amine (140 mg, 0.522 mmol) in acetone (30 mL) was added benzoyl isothiocyanate (94 mg, 0.574 mmol) dropwise at room temperature under a nitrogen atmosphere. The reaction mixture was heated at 65° C. for 2 h. The reaction mixture was allowed to cool to room temperature and poured in 50 g of ice. The solid obtained was collected by vacuum filtration. The solid was washed with water (2×50 mL) then dried under vacuum at room temperature to afford N-((4-(4-methoxy-3-(trifluoromethyl) phenyl)pyridin-2-yl)carbamothioyl)benzamide (220 mg, 0.408 mmol, 78% yield) as a yellow solid. The product was carried forward without further purification. LCMS (ESI) m/e 430.0 [(M−H)$^−$, Calcd for C$_{21}$H$_{15}$F$_3$N$_3$O$_2$S, 430.1]; LC/MS retention time (method A1) $t_R$=3.20 min.

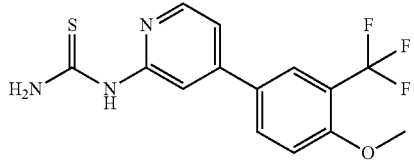 [SMILES: COc1ccc(-c2ccnc(NC(N)=S)c2)cc1C(F)(F)F]

Part C: 1-(4-(4-methoxy-3-(trifluoromethyl)phenyl) pyridin-2-yl) thiourea

To a stirred solution of N-((4-(4-methoxy-3-(trifluoromethyl)phenyl)pyridin-2-yl)carbamothioyl)benzamide (210 mg, 0.487 mmol) in methanol (25 mL) was added a solution of sodium hydroxide (78 mg, 1.947 mmol) in water (5 mL) at room temperature and the reaction mixture was heated to 65° C. for 2 h. The reaction mixture was poured in 40 g of ice and the pH of the mixture was adjusted to pH 7 with (1.5 N aq. HCl solution). The solid obtained was collected by vacuum filtration and dried under vacuum to afford 1-(4-(4-methoxy-3-(trifluoromethyl)phenyl)pyridin-2-yl)thiourea (169 mg, 0.454 mmol, 93% yield) as a pale brown solid. The product was carried forward without further purification. LCMS (ESI) m/e 328.0 [(M+H)$^+$ Calcd for C$_{14}$H$_{13}$F$_3$N$_3$OS, 328.1]; LC/MS retention time (Method F) $t_R$=2.18 min.

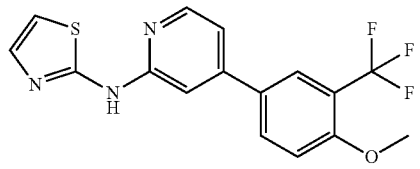 [SMILES: COc1ccc(-c2ccnc(Nc3nccs3)c2)cc1C(F)(F)F]

Part D: N-(4-(4-methoxy-3-(trifluoromethyl)phenyl) pyridin-2-yl) thiazol-2-amine To a stirred solution of 1-(4-(4-methoxy-3-(trifluoromethyl)phenyl)pyridin-2-yl)thiourea (167 mg, 0.449 mmol) in EtOH (20 mL) was added chloroacetaldehyde (50% solution in water) (1.5 mL, 0.449 mmol) dropwise under a nitrogen atmosphere. The reaction mixture was heated at 85° C. for 4 h. The reaction mixture was allowed to cool to room temperature and concentrated under reduced pressure. The mixture was added to 20 g of ice and the solid obtained was collected by vacuum filtration. The solid was washed with water (2×10 mL) then dried under vacuum to afford N-(4-(4-methoxy-3-(trifluoromethyl)phenyl)pyridin-2-yl)thiazol-2-amine (162 mg, 0.424 mmol, 94% yield) as an off white solid. The product was used as is to the next step without further purification. LCMS (ESI) m/e 352.0 [(M+H), calcd for C$_{16}$H$_{13}$F$_3$N$_3$OS, 352.1]; LC/MS retention time (method B) $t_R$=0.84 min.

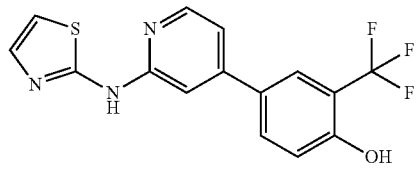 [SMILES: Oc1ccc(-c2ccnc(Nc3nccs3)c2)cc1C(F)(F)F]

Part E: 4-(2-(thiazol-2-ylamino)pyridin-4-yl)-2-(trifluoromethyl)phenol

To a stirred solution of N-(4-(4-methoxy-3-(trifluoromethyl)phenyl)pyridin-2-yl)thiazol-2-amine (160 mg, 0.419 mmol) in dichloromethane (6 mL) cooled to 0° C. was added BBr$_3$ (1M in DCM)) (1.2 mL, 1.200 mmol) dropwise under a nitrogen atmosphere. The reaction mixture was allowed to warm to room temperature and stirred for 2 h. The reaction mixture was cooled to 0° C. and dry MeOH (15 mL) was slowly added. The reaction mixture was then stirred for 10 min. The solution was concentrated under reduced pressure to afford 4-(2-(thiazol-2-ylamino)pyridin-4-yl)-2-(trifluoromethyl)phenol (125 mg, 0.274 mmol, 66% yield) as a pale yellow solid. The product was carried forward without further purification. LCMS (ESI) m/e 338.0 [(M+H)⁺ calcd for C$_{15}$H$_{11}$F$_3$N$_3$OS, 338.1]; LC/MS retention time (Method F) t$_R$=1.99 min.

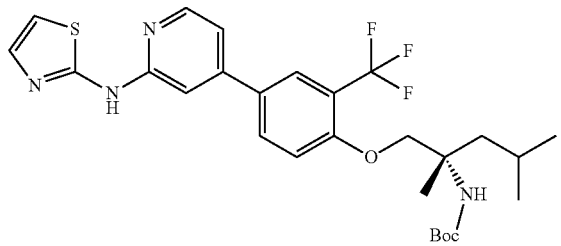 [SMILES: CC(C)C[C@@](C)(COc1ccc(-c2ccnc(Nc3nccs3)c2)cc1C(F)(F)F)NC(=O)OC(C)(C)C]

Part F: (S)-tert-butyl (2,4-dimethyl-1-(4-(2-(thiazol-2-ylamino)pyridin-4-yl)-2-(trifluoromethyl)phenoxy)pentan-2-yl)carbamate To a stirred solution of 4-(2-(thiazol-2-ylamino)pyridin-4-yl)-2-(trifluoromethyl)phenol (120 mg, 0.356 mmol) and potassium carbonate (49.2 mg, 0.356 mmol) in DMF (10 mL) was stirred under a nitrogen atmosphere for 15 min. A solution of (S)-tert-butyl 4-isobutyl-4-methyl-1,2,3-oxathiazolidine-3-carboxylate 2,2-dioxide (prepared as described in Example 251, Parts A-E) (104 mg, 0.356 mmol) in DMF (1 mL) was added and the reaction mixture was heated at 80° C. for 14 h. The solution was concentrated under reduced pressure. Water (50 mL) was added and the solution extracted with EtOAc (2×50 mL). The combined organic extracts were washed with water (50 mL) and brine (50 mL). The organic layer was dried over sodium sulfate, filtered, and concentrated under reduced pressure to afford (S)-tert-butyl (2,4-dimethyl-1-(4-(2-(thiazol-2-ylamino)pyridin-4-yl)-2-(trifluoromethyl)phenoxy)pentan-2-yl)carbamate (110 mg, 0.086 mmol, 24% yield) as a brown solid. The product was carried forward without further purification. LC/MS method L, LCMS (ESI) m/e 551.2 [(M+H)+, calcd for C$_{27}$H$_{34}$F$_3$N$_4$O$_3$S, 551.2]; LC/MS retention time t$_R$=2.72 min.

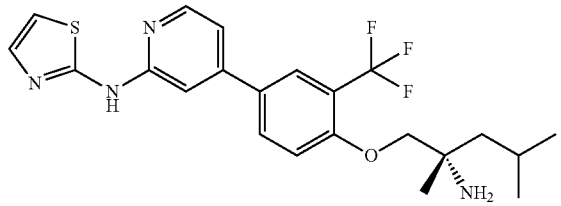 [SMILES: CC(C)C[C@](C)(N)COc1ccc(-c2ccnc(Nc3nccs3)c2)cc1C(F)(F)F]

Part G: (S)—N-(4-(4-((2-amino-2,4-dimethylpentyl)oxy)-3-(trifluoromethyl)phenyl)pyridin-2-yl) thiazol-2-amine A stirred solution of (S)-tert-butyl (2,4-dimethyl-1-(4-(2-(thiazol-2-ylamino)pyridin-4-yl)-2-(trifluoromethyl)phenoxy)pentan-2-yl)carbamate (108 mg, 0.196 mmol) in dichloromethane (3 mL) was cooled to 0° C. under a nitrogen atmosphere was added TFA (0.15 mL, 1.96 mmol) and the reaction mixture was allowed to warm to room temperature and stirred for 2 h. The solution was concentrated under reduced pressure. The crude material was purified via preparative LC/MS using method-A to afford (S)—N-(4-(4-((2-amino-2,4-dimethylpentyl)oxy)-3-(trifluoromethyl)phenyl)thiazol-2-yl)thiazol-2-amine (54.8 mg, 0.114 mmol, 58% yield) as a pale yellow solid. $^1$H NMR (400 MHz, METHANOL-d$_4$) δ=8.38 (d, J=5.5 Hz, 1H), 8.04-7.93 (m, 2H), 7.41-7.31 (m, 2H), 7.29 (d, J=1.0 Hz, 1H), 7.22 (dd, J=1.5, 5.5 Hz, 1H), 6.97-6.93 (m, 1H), 4.08-3.98 (m, 2H), 1.96-1.79 (m, 1H), 1.70-1.53 (m, 2H), 1.32 (s, 3H), 1.02 (m, 6H). LCMS (ESI) m/e 451.0 [(M+H)⁺, calcd for C$_{22}$H$_{26}$F$_3$N$_4$OS, 451.2]; wavelength 220 nm, LC/MS retention time (method H) t$_R$=2.04 min. LCMS (ESI) m/e 451.0 [(M+H)⁺, calcd for C$_{22}$H$_{26}$F$_3$N$_4$OS, 451.2]; wavelength 220 nm, LC/MS retention time (method I) t$_R$=1.18 min.

Example 257

(S)—N-(4-(4-((2-amino-2,4-dimethylpentyl)oxy)-3-chlorophenyl)pyridin-2-yl)thiazol-2-amine

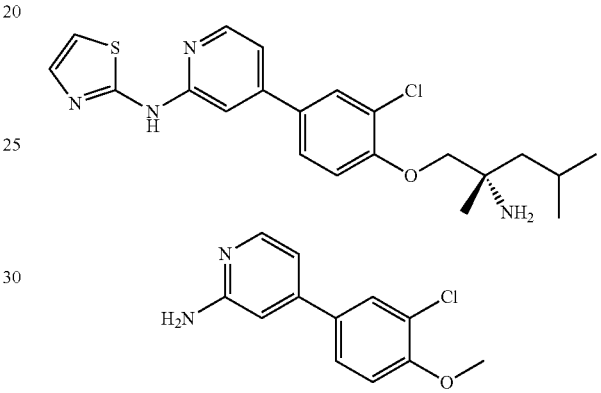

Part A:
4-(3-chloro-4-methoxyphenyl)pyridin-2-amine

A stirred solution of 4-chloropyridin-2-amine (1 g, 7.78 mmol) and (3-chloro-4-methoxyphenyl)boronic acid (1.450 g, 7.78 mmol) in a mixture of 1,4-dioxane (15 mL) and water (3 mL) was purged with nitrogen for 2 min. To this mixture, XPhos 2$^{nd}$ generation precatalyst (0.612 g, 0.778 mmol) was added under a nitrogen atmosphere. The reaction mixture was heated at 95° C. for 2 h. The reaction mixture was allowed to cool to room temperature. Water (100 mL) was added and the solution was extracted with EtOAc (2×120 mL). The combined organic extracts were washed with brine (120 mL). The organic layer was dried over sodium sulfate, filtered, and concentrated under reduced pressure. The residue obtained was purified by silica gel chromatography (EtOAc in hexanes) to afford 4-(3-chloro-4-methoxyphenyl)pyridin-2-amine (1.62 g, 4.62 mmol, 59% yield) as a yellow solid. LCMS (ESI) m/e 235.0 [(M+H)⁺, calcd for C$_{12}$H$_{12}$ClN$_2$O 235.1]; LC/MS retention time (method A1) t$_R$=2.70 min.

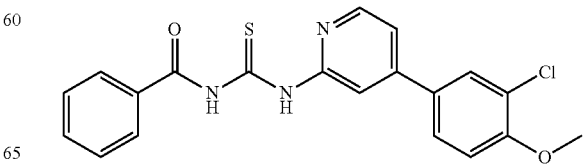

Part B: N-((4-(3-chloro-4-methoxyphenyl)pyridin-2-yl)carbamothioyl)benzamide To a stirred solution of 4-(3-chloro-4-methoxyphenyl) pyridin-2-amine (1.5 g, 6.39 mmol) in acetone (30 mL) was added benzoyl isothiocyanate (1.147 g, 7.03 mmol) dropwise at room temperature under a nitrogen atmosphere. The reaction mixture was heated at 65° C. for 12 h. The reaction mixture was allowed to cool to room temperature and poured in 50 g of ice. The solid was collected by vacuum filtration and washed with water (2×50 mL), then dried under vacuum at room temperature to afford N-((4-(3-chloro-4-methoxyphenyl)pyridin-2-yl)carbamothioyl)benzamide (2.1 g, 2.217 mmol, 35% yield) as a yellow solid. The product was carried forward without further purification. LCMS (ESI) m/e 398.0 [(M+H)$^+$, calcd for C$_{20}$H$_{17}$ClN$_3$O$_2$S, 398.1]; LC/MS retention time (Method F) t$_R$=2.47 min.

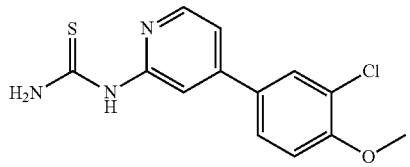 [SMILES: COc1ccc(-c2ccnc(NC(N)=S)c2)cc1Cl]

Part C: 1-(4-(3-chloro-4-methoxyphenyl)pyridin-2-yl) thiourea

To a stirred solution of N-((4-(3-chloro-4-methoxyphenyl)pyridin-2-yl)carbamothioyl)benzamide (2 g, 5.03 mmol) in methanol (25 mL) was added a solution of sodium hydroxide (0.804 g, 20.11 mmol) in water (5 mL) at room temperature. The reaction mixture was heated at 65° C. for 2 h. The reaction mixture was poured in 40 g of ice and the pH of the mixture was adjusted to pH 7 with (1.5 N aq. HCl solution). The solid obtained was collected by vacuum filtration and dried under vacuum to afford 1-(4-(3-chloro-4-methoxyphenyl)pyridin-2-yl)thiourea (700 mg, 1.692 mmol, 34% yield) as a pale brown solid. The product was carried forward without further purification. LCMS (ESI) m/e 294.0 [(M+H) calcd for C$_{13}$H$_{13}$ClN$_3$OS, 294.0]; LC/MS retention time (method B) t$_R$=0.87 min.

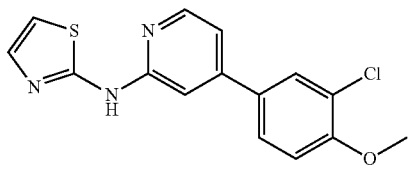 [SMILES: COc1ccc(-c2ccnc(Nc3nccs3)c2)cc1Cl]

Part D: N-(4-(3-chloro-4-methoxyphenyl)pyridin-2-yl) thiazol-2-amine

To a stirred solution of 1-(4-(3-chloro-4-methoxyphenyl) pyridin-2-yl)thiourea (400 mg, 1.362 mmol) in EtOH (20 mL) was added chloroacetaldehyde (50% in water) (1.5 mL, 1.362 mmol) dropwise under a nitrogen atmosphere. The reaction mixture was heated at 85° C. for 4 h. The reaction mixture was allowed to cool to room temperature then concentrated under reduced pressure. To this residue 20 g of ice was added and the solid obtained was collected by vacuum filtration. The solid was washed with water (2×10 mL) and dried under vacuum for afford N-(4-(3-chloro-4-methoxyphenyl)pyridin-2-yl)thiazol-2-amine (210 mg, 0.476 mmol, 35% yield) as an off white solid. The product was used as is for the next step without further purification. LCMS (ESI) m/e 318.0 [(M+H)$^+$, calcd for C$_{15}$H$_{13}$ClN$_3$OS, 318.0]; LC/MS retention time (method B) t$_R$=0.79 min.

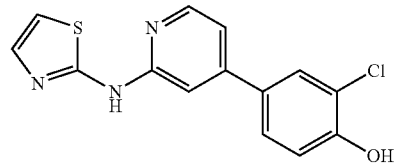 [SMILES: Oc1ccc(-c2ccnc(Nc3nccs3)c2)cc1Cl]

Part E: 2-Chloro-4-(2-(thiazol-2-ylamino)pyridin-4-yl)phenol

To a stirred solution of N-(4-(3-chloro-4-methoxyphenyl) pyridin-2-yl)thiazol-2-amine (200 mg, 0.453 mmol) in DCM (10 mL) cooled to −10° C. was added BBr$_3$ (1 mL, 10.58 mmol) dropwise under a nitrogen atmosphere. The reaction mixture was allowed to warm to room temperature and stirred for 10 h. The reaction mixture was cooled to −10° C., and dry MeOH (25 mL) was added dropwise and the solution stirred for 10 min. The solution was concentrated under reduced pressure. The yellow solid was used as is in the next step without further purification. LCMS (ESI) m/e 304.0 [(M+H)$^+$, calcd for C$_{14}$H$_{11}$ClN$_3$OS, 304.0]; LC/MS retention time (method B) t$_R$=0.68 min.

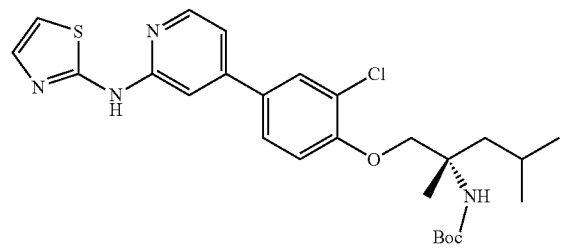 [SMILES: CC(C)C[C@@](C)(COc1ccc(-c2ccnc(Nc3nccs3)c2)cc1Cl)NC(=O)OC(C)(C)C]

Part F: (S)-tert-butyl (1-(2-chloro-4-(2-(thiazol-2-ylamino)pyridin-4-yl)phenoxy)-2,4-dimethylpentan-2-yl) carbamate A solution of 2-chloro-4-(2-(thiazol-2-ylamino)pyridin-4-yl)phenol (120 mg, 0.261 mmol) and potassium carbonate (36.0 mg, 0.261 mmol) in DMF (10 mL) was stirred under a nitrogen atmosphere for 15 min. To this mixture, a solution of (S)-tert-butyl 4-isobutyl-4-methyl-1,2,3-oxathiazolidine-3-carboxylate 2,2-dioxide (prepared as described in Example 251, Parts A-E) (76 mg, 0.261 mmol) in (1 mL of DMF) was added and the reaction mixture was heated at 80° C. for 14 h. The solution was concentrated under reduced pressure. Water (50 mL) was added and the solution was extracted with EtOAc (2×50 mL). The combined organic extracts were washed with water (50 mL), brine (50 mL), dried over sodium sulfate, filtered, and concentrated under reduced pressure. The residue was purified by silica gel chromatography (EtOAc in hexanes) to afford (S)-tert-butyl (1-(2-chloro-4-(2-(thiazol-2-ylamino)pyridin-4-yl)phenoxy)-2,4-dimethylpentan-2-yl)carbamate (60 mg, 0.078 mmol, 30% yield) as colorless oil. The product was carried forward without further purification. LCMS (ESI) m/e 517.3 [(M+H)+, calcd for $C_{26}H_{34}ClN_4O_3S$, 517.2]; LC/MS retention time (method B) $t_R$=1.09 min.

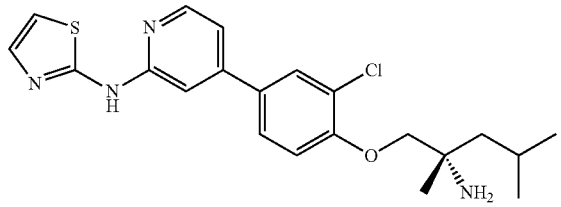 [SMILES: CC(C)C[C@](C)(N)COc1ccc(-c2ccnc(Nc3nccs3)c2)cc1Cl]

Part G. (S)—N-(4-(4-((2-amino-2,4-dimethylpentyl) oxy)-3-chlorophenyl)pyridin-2-yl) thiazol-2-amine To a stirred solution of (S)-tert-butyl (1-(2-chloro-4-(2-(thiazol-2-ylamino)pyridin-4-yl)phenoxy)-2,4-dimethyl-pentan-2-yl)carbamate (55 mg, 0.071 mmol) in DCM cooled to 0° C. was added TFA (0.2 mL, 2.60 mmol) dropwise under a nitrogen atmosphere. The reaction mixture was allowed to warm to room temperature and stirred for 2 h. The solution was concentrated under reduced pressure. The crude material was purified via preparative LC/MS using method-A to afford (S)—N-(4-(4-((2-amino-2,4-dimethyl-pentyl)oxy)-3-chlorophenyl)pyridin-2-yl)thiazol-2-amine (7.2 mg, 0.017 mmol, 24% yield) as a pale yellow solid. 1H NMR (400 MHz, METHANOL-$d_4$) δ=8.39-8.31 (m, 1H), 7.86-7.77 (m, 1H), 7.73-7.67 (m, 1H), 7.37 (s, 1H), 7.28-7.23 (m, 2H), 7.21-7.17 (m, 1H), 6.95 (s, 1H), 4.07-3.98 (m, 2H), 1.91-1.82 (m, 1H), 1.78-1.68 (m, 1H), 1.65-1.56 (m, 1H), 1.37 (s, 3H), 1.03 (m, 6H) ppm. LCMS (ESI) m/e 417.0 [(M+H)+, calcd for $C_{21}H_{26}ClN_4OS$ 417.1]; LC/MS retention time (method H) $t_R$=1.84 min. LCMS (ESI) m/e 417.0 [(M+H)+, calcd for $C_{21}H_{26}ClN_4OS$ 417.1]; LC/MS retention time (method I) $t_R$=1.12 min.

Example 258

(S)—N-(4-(4-((2-amino-2,4-dimethylpentyl)oxy)-3-(trifluoromethyl)phenyl)pyridin-2-yl)thiazole-2-carboxamide

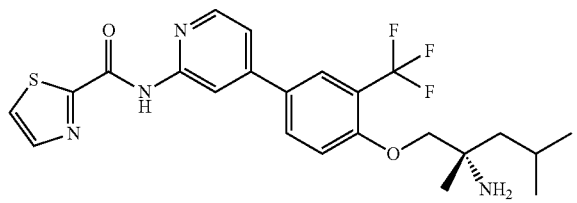

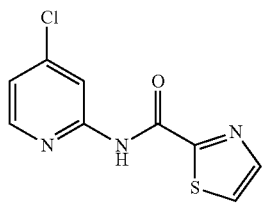

Part A: N-(4-chloropyridin-2-yl) thiazole-2-carboxamide

A solution of 4-chloropyridin-2-amine (200 mg, 1.556 mmol), thiazole-2-carbaldehyde (197 mg, 1.742 mmol) and copper(I) iodide (89 mg, 0.467 mmol) in DMF (3 mL) was heated at 80° C. for 24 h. The reaction mixture was allowed to cool to room temperature. Water (30 mL) was added and the solution was extracted with EtOAc (2×30 mL). The combined organic extracts were washed with brine (20 mL), dried over sodium sulfate, filtered, and concentrated under reduced pressure. The residue was washed with diethyl ether and the solid was collected by vacuum filteration and dried under vacuum at room temperature to afford N-(4-chloro-pyridin-2-yl)thiazole-2-carboxamide (240 mg, 0.861 mmol, 55% yield) as a pale brown solid. LCMS (ESI) m/e 240.0 [(M+H)+, calcd for $C_9H_7ClN_3OS$, 239.9]; LC/MS retention time (Method F) $t_R$=2.15 min.

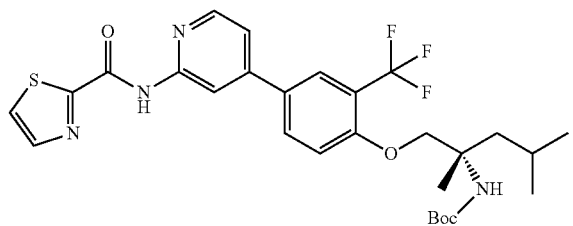 [SMILES: CC(C)C[C@@](C)(COc1ccc(-c2ccnc(NC(=O)c3nccs3)c2)cc1C(F)(F)F)NC(=O)OC(C)(C)C]

Part B: (S)-Tert-butyl (2,4-dimethyl-1-(4-(2-(thiazole-2-carboxamido)pyridin-4-yl)-2-(trifluoromethyl) phenoxy)pentan-2-yl)carbamate To a stirred solution of (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (105 mg, 0.209 mmol) (prepared as described in Example 255, Part B), N-(4-chloropyridin-2-yl)thiazole-2-carboxamide (50 mg, 0.209 mmol), cesium carbonate (136 mg, 0.417 mmol) in a mixture of 1,4-dioxane (5 mL) and water (0.5 mL) was bubbled nitrogen gas. Added XPhos 2$^{nd}$ generation precatalyst (24.62 mg, 0.031 mmol) in one portion and the reaction mixture was heated at 85° C. for 2 h. The solution was concentrated under reduced pressure. Water (30 mL) was added and the solution was extracted with EtOAc (2×50 mL). The combined organic extracts were washed with water (50 mL), brine (50 mL), dried over sodium sulfate, filtered, and concentrated under reduced pressure. The residue was purified by silica gel chromatography (EtOAc in hexanes) to afford (S)-tert-butyl (2,4-dimethyl-1-(4-(2-(thi-azole-2-carboxamido)pyridin-4-yl)-2-(trifluoromethyl)phe-noxy)pentan-2-yl)carbamate (62 mg, 0.064 mmol, 31% yield) as yellow oil. LCMS (ESI) m/e 579.2 [(M+H)+, calcd for $C_{28}H_{34}F_3N_4O_4S$, 579.2]; LC/MS retention time (method B) $t_R$=1.22 min.

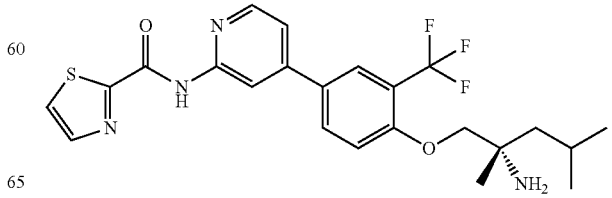

Part C: (S)—N-(4-(4-((2-amino-2,4-dimethylpentyl)oxy)-3-(trifluoromethyl)phenyl)pyridin-2-yl) thiazole-2-carboxamide To a stirred solution of (S)-tert-butyl (2,4-dimethyl-1-(4-(2-(thiazole-2-carboxamido)pyridin-4-yl)-2-(trifluoromethyl)phenoxy)pentan-2-yl)carbamate (60 mg, 0.062 mmol) in DCM (3 mL) was added TFA (0.21 mL, 2.73 mmol) dropwise under a nitrogen atmosphere. The reaction mixture was stirred at room temperature for 4 h. The solution was concentrated under reduced pressure. The residue was purified via preparative LC/MS using method-A to afford (S)—N-(4-(4-((2-amino-2,4-dimethylpentyl)oxy)-3-(trifluoromethyl)phenyl)pyridin-2-yl)thiazole-2-carboxamide (7.4 mg, 0.015 mmol, 24% yield) as a pale yellow solid. $^1$H NMR (400 MHz, METHANOL-$d_4$) δ 8.55 (s, 1H), 8.44 (d, J=6.0 Hz, 1H), 8.03-8.06 (m, 3H), 7.99 (d, J=3.2 Hz, 1H), 7.5 (d, J=1.6 Hz, 1H), 7.44 (d, J=8.5 Hz, 1H), 4.26-4.15 (m, 2H), 1.94-1.77 (m, 2H), 1.74-1.63 (m, 1H), 1.48 (s, 3H), 1.05 (m, 6H) ppm. LCMS (ESI) m/e 479.0 [(M+H)$^+$, calcd for $C_{23}H_{26}F_3N_4O_2S$, 479.2]; LC/MS retention time (method H) $t_R$=2.06 min. LCMS (ESI) m/e 479.0 [(M+H)$^+$, calcd for $C_{23}H_{26}F_3N_4O_2S$, 479.2]; LC/MS retention time (method I) $t_R$=1.45 min.

Example 259

(S)-7-(4-((2-amino-2,4-dimethylpentyl)oxy)-3-methylphenyl)-3H-imidazo[4,5-b]pyridin-2-amine

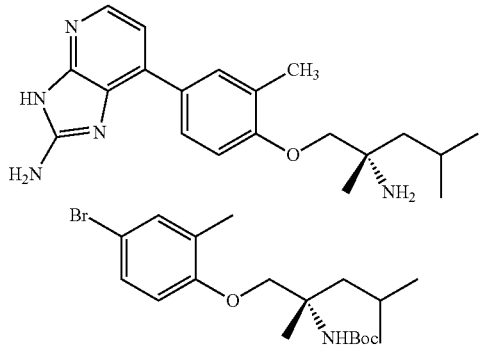

Part A. (S)-tert-butyl (1-(4-bromo-2-methylphenoxy)-2,4-dimethylpentan-2-yl)carbamate A mixture of 4-bromo-2-methylphenol (0.2 g, 1.069 mmol), $K_2CO_3$ (0.443 g, 3.21 mmol) and (S)-tert-butyl 4-isobutyl-4-methyl-1,2,3-oxathiazolidine-3-carboxylate 2,2-dioxide (prepared as described in Example 251, Parts A-E) (0.376 g, 1.283 mmol) in DMF (5 mL) was heated at 80° C. overnight. The reaction mixture was cooled to 0° C. and quenched with aqueous ammonium chloride (50 mL). The reaction mixture was extracted with ethyl acetate (2×50 mL). The organic layer was washed with water (2×50 mL), brine (50 mL), dried over $Na_2SO_4$, and concentrated to afford (S)-tert-butyl (1-(4-bromo-2-methylphenoxy)-2,4-dimethylpentan-2-yl)carbamate (0.3 g, 0.749 mmol, 70% yield). The material was carried forward without further purification. LCMS (ESI) m/e 346.0 [(M+H-$^t$Bu)$^+$, calcd for $C_{19}H_{31}BrNO_3$ 400.1]; LC/MS retention time (method D): $t_R$=3.27 min.

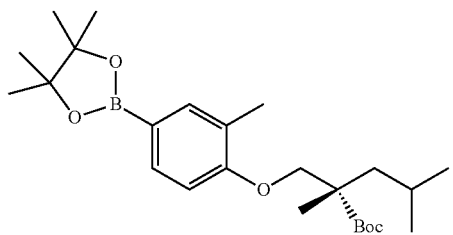

Part B. (S)-tert-butyl (2,4-dimethyl-1-(2-methyl-4-(4,4,5,5-tetramethyl-1,3,2-dioxaborolan-2-yl)phenoxy)pentan-2-yl)carbamate A mixture of (S)-tert-butyl (1-(4-bromo-2-methylphenoxy)-2,4-dimethylpentan-2-yl)carbamate (0.3 g, 0.749 mmol), bis(pinacolato)diboron (0.209 g, 0.824 mmol), potassium acetate (0.221 g, 2.248 mmol) and $PdCl_2$ (dppf)-$CH_2Cl_2$ adduct (0.031 g, 0.037 mmol) in 1,4-dioxane (25 mL) was heated at 90° C. overnight. The reaction mixture was filtered through diatomaceous earth and the diatomaceous earth bed was washed with ethyl acetate (100 mL). The organic layer was washed with water (50 mL). The aqueous layer was re-extracted with ethyl acetate (2×50 mL). The organic layer was collected, washed with brine, dried over $Na_2SO_4$, and concentrated under reduced pressure to afford crude (S)-tert-butyl (2,4-dimethyl-1-(2-methyl-4-(4,4,5,5-tetramethyl-1,3,2-dioxaborolan-2-yl)phenoxy)pentan-2-yl)carbamate (0.2 g, 0.447 mmol, 60% yield). $^1$H NMR (400 MHz, $CDCl_3$): δ 7.61 (t, J=14.40 Hz, 2H), 6.81 (d, J=10.80 Hz, 1H), 4.61 (bs, 1H), 4.08 (d, J=11.60 Hz, 1H), 3.94 (d, J=11.60 Hz, 1H), 2.24 (s, 3H), 1.76-1.84 (m, 2H), 1.61-1.66 (m, 1H), 1.51 (s, 3H), 1.33-1.43 (m, 12H), 0.95-0.98 (m, 6H) ppm.

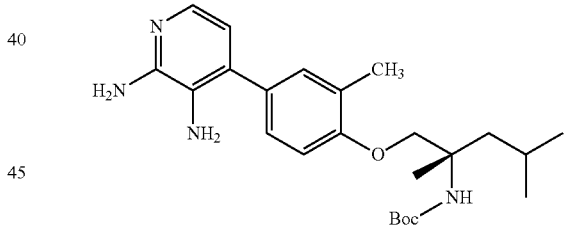

Part C: (S)-tert-butyl (1-(4-(2,3-diaminopyridin-4-yl)-2-methylphenoxy)-2,4-dimethylpentan-2-yl)carbamate To a stirred solution of (S)-tert-butyl (2,4-dimethyl-1-(2-methyl-4-(4,4,5,5-tetramethyl-1,3,2-dioxaborolan-2-yl)phenoxy)pentan-2-yl)carbamate (150 mg, 0.335 mmol), 4-bromopyridine-2,3-diamine (63.0 mg, 0.335 mmol) and cesium carbonate (218 mg, 0.671 mmol) in a mixture of 1,4-dioxane (5 mL) and water (0.5 mL) was added XPhos 2$^{nd}$ generation precatalyst (26.4 mg, 0.034 mmol) under a nitrogen atmosphere. The reaction mixture was heated at 95° C. for 2 h. The reaction mixture was allowed to cool to room temperature and concentrated under reduced pressure. Water (20 mL) was added and the solution was extracted with EtOAc (2×20 mL). The combined organic extracts were washed with water (50 mL), brine (20 mL), dried over sodium sulfate, filtered, and concentrated under reduced pressure.

The residue obtained was purified by silica gel chromatography (EtOAc in hexanes) to afford (S)-tert-butyl (1-(4-bromo-2-methylphenoxy)-2,4-dimethylpentan-2-yl)carbamate (0.3 g, 0.749 mmol, 70% yield) as a pale yellow semi-solid. LCMS (ESI) m/e 429.2 [(M+H)$^+$, calcd for C$_{24}$H$_{37}$N$_4$O$_3$; 429.2]; LC/MS retention time (method A2) t$_R$=2.11 min.

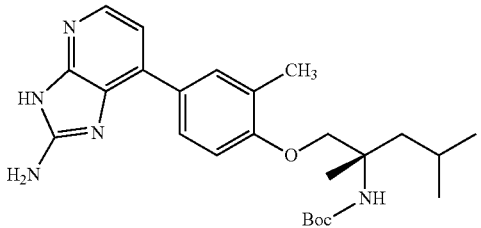 [SMILES: Cc1cc(-c2ccnc3[nH]c(N)nc23)ccc1OC[C@](C)(CC(C)C)NC(=O)OC(C)(C)C]

Part D: (S)-tert-butyl (1-(4-(2-amino-3H-imidazo[4,5-b]pyridin-7-yl)-2-methylphenoxy)-2,4-dimethylpentan-2-yl)carbamate To a stirred solution of (S)-tert-butyl (1-(4-(2,3-diaminopyridin-4-yl)-2-methylphenoxy)-2,4-dimethylpentan-2-yl)carbamate (70 mg, 0.101 mmol) in a mixture of MeOH (4 mL) and water (0.5 mL) was added cyanic bromide (16.09 mg, 0.152 mmol) under a nitrogen atmosphere. The reaction mixture was allowed to stir at room temperature for 12h. The solution was concentrated under reduced pressure. The brown solid obtained was washed with diethyl ether (2×8 mL), collected by vacuum filtration, and dried under vacuum at room temperature to afford (S)-tert-butyl (1-(4-(2-amino-3H-imidazo[4,5-b]pyridin-7-yl)-2-methylphenoxy)-2,4-dimethylpentan-2-yl)carbamate (58 mg, 0.081 mmol, 80% yield) as a brown solid. The product was carried forward without further purification. LCMS (ESI) m/e 454.4 [(M+H)$^+$, calcd for C$_{25}$H$_{36}$N$_5$O$_3$; 454.2] LC/MS retention time (method B) t$_R$=0.97 min.

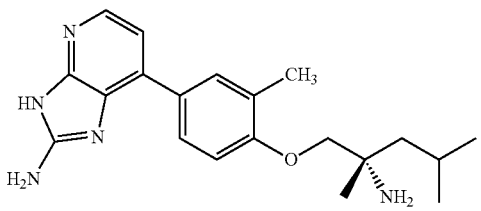 [SMILES: Cc1cc(-c2ccnc3[nH]c(N)nc23)ccc1OC[C@@](C)(N)CC(C)C]

Part E: (S)-7-(4-((2-amino-2,4-dimethylpentyl)oxy)-3-methylphenyl)-3H-imidazo[4,5-b]pyridin-2-amine To a stirred solution of (S)-tert-butyl (1-(4-(2-amino-3H-imidazo[4,5-b]pyridin-7-yl)-2-methylphenoxy)-2,4-dimethylpentan-2-yl)carbamate (55 mg, 0.076 mmol) in dichloromethane (3 mL) was cooled to 0° C. was added TFA (0.25 mL, 3.24 mmol) dropwise under a nitrogen atmosphere. The reaction mixture was allowed to warm to room temperature and was stirred for 2h. The solution was concentrated under reduced pressure. The crude material was purified via preparative LC/MS using method-C to afford (S)-7-(4-((2-amino-2,4-dimethylpentyl)oxy)-3-methylphenyl)-3H-imidazo[4,5-b]pyridin-2-amine (6.9 mg, 0.019 mmol, 25% yield) as a pale yellow solid. $^1$H NMR (400 MHz, METHANOL-d$_4$) δ 7.87-7.71 (m, 2H), 7.58-7.47 (m, 1H), 7.45-7.36 (m, 1H), 7.04 (d, J=8.5 Hz, 1H), 4.19-3.99 (m, 2H), 2.40 (s, 3H), 1.89 (d, J=11.0 Hz, 2H), 1.70 (d, J=9.0 Hz, 1H), 1.51 (s, 3H), 1.07 (m, 6H) ppm. LCMS (ESI) m/e 354.0 [(M+H)$^+$, Calcd for C$_{20}$H$_{28}$N$_5$O, 354.2]; LC/MS retention time (method H) t$_R$=0.99 min. LCMS (ESI) m/e 354.0 [(M+H)$^+$, Calcd for C$_{20}$H$_{28}$N$_5$O, 354.2]; LC/MS retention time (method I) t$_R$=0.85 min.

Example 260

(S)—N-(4-(4-((2-amino-2,4-dimethylpentyl)oxy)-3-chlorophenyl)pyridin-2-yl)thiazole-2-carboxamide

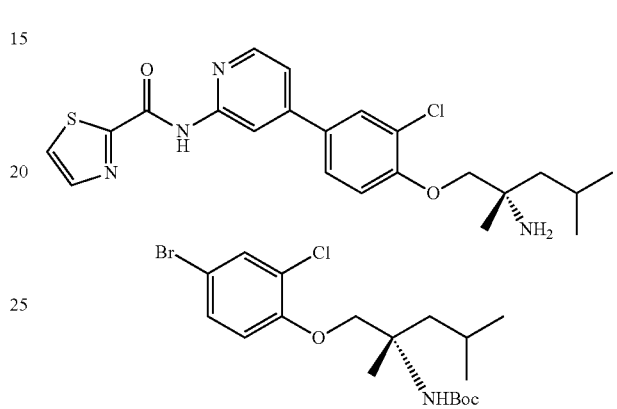

Part A. (S)-tert-butyl (1-(4-bromo-2-chlorophenoxy)-2,4-dimethylpentan-2-yl)carbamate A mixture of 4-bromo-2-chlorophenol (1.2 g, 5.78 mmol), K$_2$CO$_3$ (2.398 g, 17.35 mmol) and (S)-tert-butyl 4-isobutyl-4-methyl-1,2,3-oxathiazolidine-3-carboxylate 2,2-dioxide (prepared as described in Example 251, Parts A-E) (2.036 g, 6.94 mmol) in DMF (20 mL) was heated at 80° C. overnight. The reaction mixture was cooled to 0° C. and quenched with aqueous ammonium chloride (50 mL). The reaction mixture was extracted with ethyl acetate (2×50 mL). The organic layer was washed with water (2×50 mL), brine (50 mL), dried over Na$_2$SO$_4$, and concentrated to afford (S)-tert-butyl (1-(4-bromo-2-chlorophenoxy)-2,4-dimethylpentan-2-yl)carbamate (1.5 g, 3.45 mmol, 60% yield) as a pale yellowish semi-solid. LCMS (ESI) m/e=366.0 [(M+H-$^t$Bu)$^+$, calcd for C$_{18}$H$_{28}$BrClNO$_3$ 420.1]; LC/MS retention time (method A2): t$_R$=2.51 min.

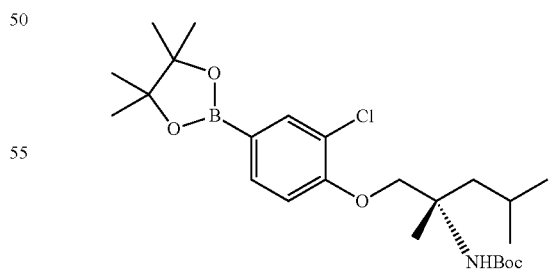

Part B. (S)-tert-butyl (1-(2-chloro-4-(4,4,5,5-tetramethyl-1,3,2-dioxaborolan-2-yl)phenoxy)-2,4-dimethylpentan-2-yl)carbamate A mixture of (S)-tert-butyl (1-(4-bromo-2-chlorophenoxy)-2,4-dimethylpentan-2-yl)carbamate (1.2 g, 2.85 mmol), bis(pinacolato)diboron (0.797 g, 3.14 mmol), potassium acetate (0.840 g, 8.56 mmol and PdCl₂ (dppf)-CH₂Cl₂ adduct (0.116 g, 0.143 mmol) in 1,4-dioxane (20 mL) was heated at 90° C. overnight. The reaction mixture was filtered through diatomaceous earth and the diatomaceous earth bed was washed with ethyl acetate (100 mL). The organic layer was washed with water (50 mL). The aqueous layer was re-extracted with ethyl acetate (2×50 mL).

The organic layer was collected, washed with brine, dried over Na₂SO₄, and concentrated under reduced pressure to afford (S)-tert-butyl (1-(2-chloro-4-(4,4,5,5-tetramethyl-1,3,2-dioxaborolan-2-yl)phenoxy)-2,4-dimethylpentan-2-yl)carbamate (1.2 g, 2.57 mmol, 90% yield) as colorless liquid. 1H NMR (400 MHz, CDCl3): δ 7.78 (d, J=1.60 Hz, 1H), 7.61-7.63 (m, 1H), 6.91 (d, J=8.00 Hz, 1H), 4.10-4.19 (m, 1H), 4.63 (s, 1H), 4.02 (d, J=8.80 Hz, 1H), 1.79-1.87 (m, 2H), 1.57-1.62 (m, 1H), 1.51 (s, 3H), 1.33-1.41 (m, 12H), 0.96-0.98 (m, 6H) ppm.

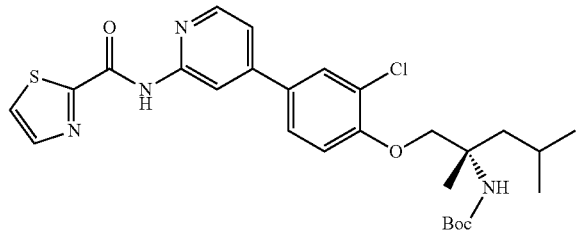 [SMILES: CC(C)C[C@@](C)(COc1ccc(-c2ccnc(NC(=O)c3nccs3)c2)cc1Cl)NC(=O)OC(C)(C)C]

Part C: (S)-tert-butyl (1-(2-chloro-4-(2-(thiazole-2-carboxamido)pyridin-4-yl)phenoxy)-2,4-dimethylpentan-2-yl)carbamate A stirred solution of (S)-tert-butyl (1-(2-chloro-4-(4,4,5,5-tetramethyl-1,3,2-dioxaborolan-2-yl)phenoxy)-2,4-dimethylpentan-2-yl)carbamate (98 mg, 0.209 mmol), N-(4-chloropyridin-2-yl)thiazole-2-carboxamide (50 mg, 0.209 mmol), cesium carbonate (136 mg, 0.417 mmol) in a mixture of 1,4-dioxane (5 mL) and water (0.5 mL) was purged with nitrogen gas for 10 min. XPhos 2$^{nd}$ generation precatalyst (24.62 mg, 0.031 mmol) was added in one portion and the reaction mixture was heated at 85° C. for 2 h. The solution was concentrated under reduced pressure. Water (50 mL) was added and the solution was extracted with EtOAc (2×50 mL). The combined organic extracts were washed with water (50 mL) and brine (50 mL), dried over sodium sulfate, filtered, and concentrated under reduced pressure. The residue was purified by silica gel chromatography (EtOAc in hexanes) to afford (S)-tert-butyl (1-(2-chloro-4-(2-(thiazole-2-carboxamido)pyridin-4-yl)phenoxy)-2,4-dimethylpentan-2-yl)carbamate (80 mg, 0.076 mmol, 37% yield) as a pale brown oil. The product was carried forward without further purification. LCMS (ESI) m/e 545.2 [(M+H)⁺, calcd for C₂₇H₃₄ClN₄O₄S, 545.2]; LC/MS retention time (Method F) t$_R$=2.89 min.

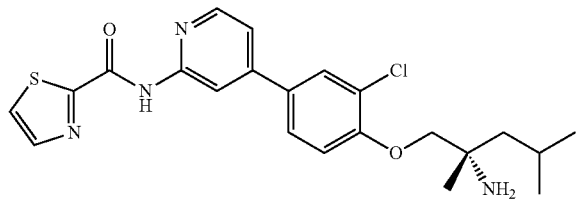 [SMILES: CC(C)C[C@](C)(N)COc1ccc(-c2ccnc(NC(=O)c3nccs3)c2)cc1Cl]

Part D: (S)—N-(4-(4-((2-amino-2,4-dimethylpentyl)oxy)-3-chlorophenyl)pyridin-2-yl) thiazole-2-carboxamide To a stirred solution of (S)-tert-butyl (1-(2-chloro-4-(2-(thiazole-2-carboxamido)pyridin-4-yl)phenoxy)-2,4-dimethylpentan-2-yl)carbamate (78 mg, 0.074 mmol) in DCM (2 mL) cooled to 0° C. was added TFA (0.2 mL, 2.60 mmol) dropwise under a nitrogen atmosphere. The reaction mixture was allowed to warm to room temperature and stirred for 3 h. The solution was concentrated under reduced pressure. The crude material was purified via preparative LC/MS using method-A to afford (S)—N-(4-(4-((2-amino-2,4-dimethylpentyl)oxy)-3-chlorophenyl)pyridin-2-yl)thiazole-2-carboxamide (7 mg, 0.015 mmol, 20% yield) as a pale yellow solid. LCMS (ESI) m/e 445.0 [(M+H)⁺, calcd for C₂₂H₂₆ClN₄O₂S, 445.1]; LC/MS retention time (method H) t$_R$=1.85 min. LCMS (ESI) m/e 445.0 [(M+H)⁺, calcd for C₂₂H₂₆ClN₄O₂S, 445.1]; LC/MS retention time (method I) t$_R$=1.36 min. ¹H NMR (400 MHz, METHANOL-d₄) δ=8.54 (d, J=1.0 Hz, 1H), 8.42 (d, J=5.0 Hz, 1H), 8.08 (d, J=3.0 Hz, 1H), 8.00 (d, J=3.0 Hz, 1H), 7.88 (d, J=2.5 Hz, 1H), 7.76 (dd, J=2.0, 8.5 Hz, 1H), 7.48 (dd, J=1.8, 5.3 Hz, 1H), 7.30 (d, J=8.5 Hz, 1H), 3.8 (m, 2H), 1.7-1.9 (m, 2H), 1.5-1.6 (m, 1H), 1.31 (s, 3H), 0.90-0.95 (m, 6H) ppm.

Example 261

(S)—N-(4-(4-((2-amino-2,4-dimethylpentyl)oxy)-3-cyanophenyl)pyridin-2-yl)thiazole-2-carboxamide

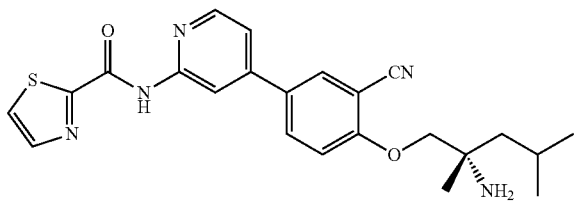

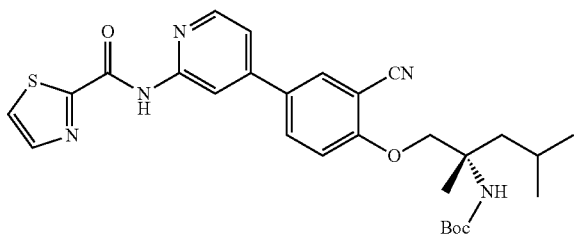 [SMILES: CC(C)C[C@@](C)(COc1ccc(-c2ccnc(NC(=O)c3nccs3)c2)cc1C#N)NC(=O)OC(C)(C)C]

Part A: (S)-tert-butyl (1-(2-cyano-4-(2-(thiazole-2-carboxamido)pyridin-4-yl)phenoxy)-2,4-dimethylpentan-2-yl)carbamate To a stirred solution of (S)-tert-butyl (1-(2-cyano-4-(4,5,5-tetramethyl-1,3,2-dioxaborolan-2-yl)phenoxy)-2,4-dimethylpentan-2-yl)carbamate (96 mg, 0.209 mmol) (prepared as in Example 254, Part B-G), N-(4-chloropyridin-2-yl)thiazole-2-carboxamide (50 mg, 0.209 mmol), cesium carbonate (136 mg, 0.417 mmol) in a mixture of 1,4-dioxane (5 mL) and water (0.5 mL) was bubbled nitrogen gas for 5 min. To this mixture was added XPhos 2$^{nd}$ generation precatalyst (24.62 mg, 0.031 mmol) in one portion and the reaction mixture was heated to 85° C. and stirred for 2 h. The reaction mixture was allowed to cool to room temperature, then concentrated under reduced pressure. Water (50 mL) was added and the solution was extracted with EtOAc (2×50 mL). The combined organic extracts were washed with water (50 mL) and brine (50 mL), dried over sodium sulfate, filtered, and concentrated under reduced pressure. The residue was purified by silica gel chromatography (EtOAc in hexanes) to afford (S)-tert-butyl (1-(2-cyano-4-(2-(thiazole-2-carboxamido)pyridin-4-yl)phenoxy)-2,4-dimethylpentan-2-yl)carbamate (57 mg, 0.095 mmol, 45% yield) as a pale brown oil in 89% purity based on UV from LCMS. LCMS (ESI) m/e 536.2 [(M+H)+ calcd for $C_{28}H_{34}N_5O_4S$, 536.2]; LC/MS retention time (Method F) $t_R$=2.63 min.

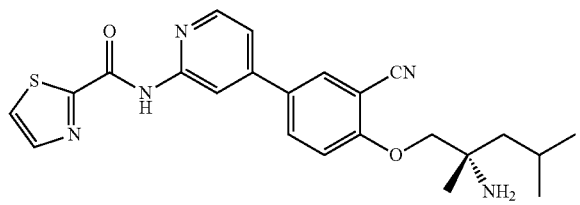 [SMILES: CC(C)C[C@](C)(N)COc1ccc(-c2ccnc(NC(=O)c3nccs3)c2)cc1C#N]

Part B: (S)—N-(4-(4-((2-amino-2,4-dimethylpentyl)oxy)-3-cyanophenyl)pyridin-2-yl) thiazole-2-carboxamide To a stirred solution of (S)-tert-butyl (1-(2-cyano-4-(2-(thiazole-2-carboxamido)pyridin-4-yl)phenoxy)-2,4-dimethylpentan-2-yl)carbamate (55 mg, 0.091 mmol) in DCM (2 mL) cooled to 0° C. was added TFA (0.2 mL, 2.60 mmol) dropwise under a nitrogen atmosphere. The reaction mixture was allowed to warm to room temperature and stirred for 3 h. The solution was concentrated under reduced pressure. The crude material was purified via preparative LC/MS using method-A to afford (S)—N-(4-(4-((2-amino-2,4-dimethylpentyl)oxy)-3-cyanophenyl)pyridin-2-yl)thiazole-2-carboxamide (13 mg, 0.029 mmol, 32% yield) as a pale yellow solid. $^1$H NMR (400 MHz, METHANOL-$d_4$) δ 8.54 (d, J=1.0 Hz, 1H), 8.44 (d, J=5.5 Hz, 1H), 8.13 (d, J=2.0 Hz, 1H), 8.11-8.06 (m, 2H), 8.00 (d, J=3.0 Hz, 1H), 7.50 (dd, J=1.8, 5.3 Hz, 1H), 7.38 (d, J=8.5 Hz, 1H), 4.08 (d, J=2.0 Hz, 2H), 1.88 (s, 1H), 1.71-1.52 (m, 2H), 1.35 (s, 3H), 1.03 (m, 6H) ppm. LCMS (ESI) m/e 436.0 [(M+H)+, calcd for $C_{23}H_{26}N_5O_2S$, 436.2]; LC/MS retention time (method H) $t_R$=1.62 min. LCMS (ESI) m/e 436.0 [(M+H)+, calcd for $C_{23}H_{26}N_5O_2S$, 436.2]; LC/MS retention time (method I) $t_R$=1.26 min.

Example 262

(S)—N-(4-(4-((2-amino-2,4-dimethylpentyl)oxy)-3-chlorophenyl)pyridin-2-yl)-4-methylthiazol-2-amine

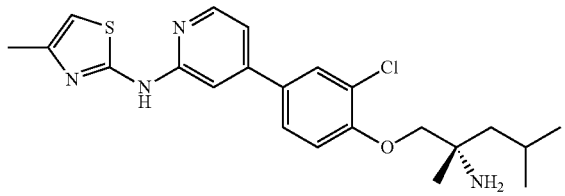

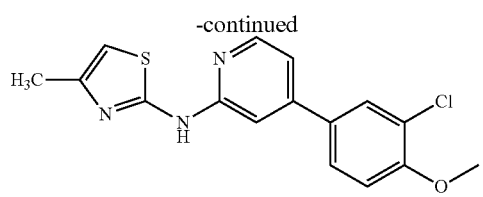

Part A. N-(4-(3-chloro-4-methoxyphenyl)pyridin-2-yl)-4-methylthiazol-2-amine

To a stirred solution of 1-(4-(3-chloro-4-methoxyphenyl)pyridin-2-yl)thiourea (400 mg, 0.967 mmol) (prepared as described in Example 257, Part C) in EtOH (20 mL) was added 1-chloropropan-2-one (1.5 mL, 0.967 mmol) dropwise under a nitrogen atmosphere. The reaction mixture was heated at 85° C. for 4 h. The reaction mixture was allowed to cool to room temperature then concentrated under reduced pressure. To the residue 20 g of ice was added and the solid was collected by vacuum filtration. The solid was washed with water (2×10 mL) and dried under vacuum to afford N-(4-(3-chloro-4-methoxyphenyl)pyridin-2-yl)-4-methylthiazol-2-amine (130 mg, 0.157 mmol, 16% yield) as an off white solid. The product was carried forward without further purification. LCMS (ESI) m/e 332.0 [(M+H), calcd for $C_{16}H_{15}ClN_3OS$, 332.0]; LC/MS retention time (method B) $t_R$=0.84 min.

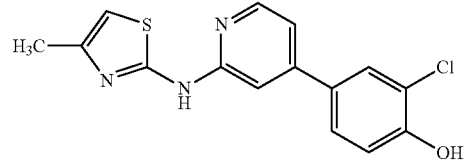 [SMILES: Cc1csc(Nc2cc(-c3ccc(O)c(Cl)c3)ccn2)n1]

Part B: 2-Chloro-4-(2-((4-methylthiazol-2-yl)amino)pyridin-4-yl)phenol

To a stirred solution of N-(4-(3-chloro-4-methoxyphenyl)pyridin-2-yl)-4-methylthiazol-2-amine (125 mg, 0.151 mmol) in DCM (10 mL) cooled to −10° C. was added BBr$_3$ (1.00 mL, 10.58 mmol) dropwise under a nitrogen atmosphere. The reaction mixture was allowed to warm to room temperature and stirred for 2 h. The reaction mixture was cooled to 0° C., and dry MeOH (20 mL) was added dropwise and the reaction mixture was stirred for 15 min. The solution was concentrated under reduced pressure. The residue was washed with diethyl ether (15 mL) and the solid obtained was collected by vacuum filtration and dried under vacuum to afford 2-chloro-4-(2-((4-methylthiazol-2-yl)amino)pyridin-4-yl)phenol (62 mg, 0.137 mmol, 91% yield). The product was carried forward without further purification. LCMS (ESI) m/e 318.0 [(M+H)+, calcd for $C_{15}H_{13}ClN_3OS$, 318.0]; LC/MS retention time (Method F) $t_R$=2.02 min.

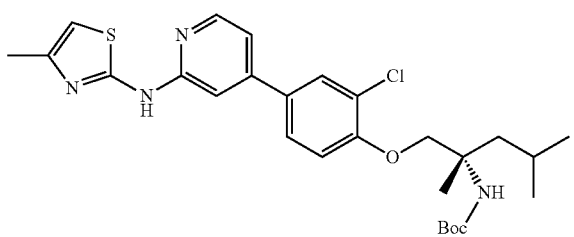 [SMILES: Cc1csc(Nc2cc(-c3ccc(OC[C@](C)(CC(C)C)NC(=O)OC(C)(C)C)c(Cl)c3)ccn2)n1]

Part C: (S)-tert-butyl (1-(2-chloro-4-(2-((4-methyl-thiazol-2-yl)amino)pyridin-4-yl)phenoxy)-2,4-dimethylpentan-2-yl)carbamate A stirred solution of 2-chloro-4-(2-((4-methylthiazol-2-yl)amino)pyridin-4-yl)phenol (102 mg, 0.321 mmol) and potassium carbonate (444 mg, 3.21 mmol) in DMF (10 mL) was stirred under a nitrogen atmosphere for 15 min. To this mixture was added a solution of (S)-tert-butyl 4-isobutyl-4-methyl-1,2,3-oxathiazolidine-3-carboxylate 2,2-dioxide (prepared as described in Example 251, Parts A-E) (122 mg, 0.417 mmol) in (1 mL of DMF) and the reaction mixture was heated at 80° C. for 14 h. The solution was concentrated under reduced pressure. Water (50 mL) was added and the solution was extracted with EtOAc (2×50 mL). The combined organic extracts were washed with water (50 mL) and brine (50 mL). The organic layer was dried over sodium sulfate, filtered, and concentrated under reduced pressure. The residue was purified by silica gel chromatography (EtOAc in hexanes) to afford (S)-tert-butyl (1-(2-chloro-4-(2-((4-methylthiazol-2-yl)amino)pyridin-4-yl)phenoxy)-2,4-dimethylpentan-2-yl)carbamate (92 mg, 0.071 mmol, 22% yield) as colorless oil. LCMS (ESI) m/e 531.2 [(M+H)$^+$, calcd for $C_{27}H_{36}ClN_4O_3S$, 531.2]; LC/MS retention time (Method F) $t_R$=2.73 min.

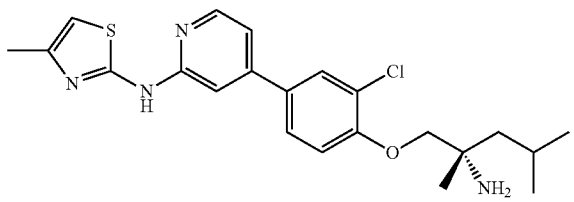 [SMILES: Cc1csc(Nc2cc(-c3ccc(OC[C@@](C)(N)CC(C)C)c(Cl)c3)ccn2)n1]

Part D: (S)—N-(4-(4-((2-amino-2,4-dimethylpentyl)oxy)-3-chlorophenyl)pyridin-2-yl)-4-methylthiazol-2-amine To a stirred solution of (S)-tert-butyl (1-(2-chloro-4-(2-((4-methylthiazol-2-yl)amino)pyridin-4-yl)phenoxy)-2,4-dimethylpentan-2-yl)carbamate (90 mg, 0.069 mmol) in DCM (4 mL) cooled to 0° C. was added TFA (0.36 mL, 4.67 mmol) dropwise under a nitrogen atmosphere. The reaction mixture was allowed to warm to room temperature and stirred for 3 h. The solution was concentrated under reduced pressure. The crude material was purified via preparative LC/MS using method-B to afford (S)—N-(4-(4-((2-amino-2,4-dimethylpentyl)oxy)-3-chlorophenyl)pyridin-2-yl)-4-methylthiazol-2-amine (1.1 mg, 2.53 µmol, 4% yield) as a pale yellow solid. $^1$H NMR (400 MHz, DMSO-$d_6$) δ 8.40-8.28 (m, 1H), 7.84-7.77 (m, 1H), 7.72-7.62 (m, 1H), 7.40 (s, 1H), 7.31 (s, 2H), 7.26-7.22 (m, 1H), 7.02 (s, 1H), 3.89-3.85 (m, 2H), 3.34-3.30 (m, 2H), 3.14-3.12 (m, 3H), 1.48-1.42 (m, 2H), 1.27-1.23 (m, 1H), 1.18 (s, 3H), 0.94 (m, 6H). LCMS (ESI) m/e 431.0 [(M+H)$^+$, calcd for $C_{22}H_{28}ClN_4OS$, 431.2]; LC/MS retention time (method H) $t_R$=1.89 min. LCMS (ESI) m/e 431.0 [(M+H)$^+$, calcd for $C_{22}H_{28}ClN_4OS$, 431.2]; LC/MS retention time (method I) $t_R$=1.20 min.

Example 264

(R)-2,4-dimethyl-1-((3-methyl-5-(pyrazolo[1,5-a]pyrimidin-7-yl)pyridin-2-yl)oxy)pentan-2-amine

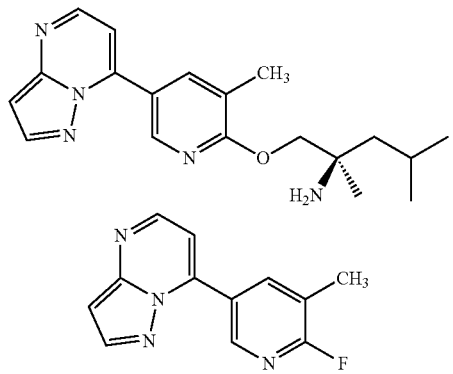

Part A: 7-(6-fluoro-5-methylpyridin-3-yl)pyrazolo[1,5-a]pyrimidine

A stirred solution of 7-chloropyrazolo[1,5-a]pyrimidine (50 mg, 0.326 mmol), (6-fluoro-5-methylpyridin-3-yl)boronic acid (50.4 mg, 0.326 mmol), and cesium carbonate (212 mg, 0.651 mmol) in a mixture of 1,4-dioxane (5 mL) and water (0.5 mL) was purged with nitrogen. XPhos 2$^{nd}$ generation precatalyst (38.4 mg, 0.049 mmol) was added in one portion and the reaction mixture was heated to 85° C. and stirred for 2 h. The solution was concentrated under reduced pressure. Water (50 mL) was added and the solution was extracted with EtOAc (2×50 mL). The combined organic extracts were washed with water (50 mL) and brine (50 mL), dried over sodium sulfate, filtered, and concentrated under reduced pressure. The residue was purified by silica gel chromatography (EtOAc in hexanes) to afford 7-(6-fluoro-5-methylpyridin-3-yl)pyrazolo[1,5-a]pyrimidine (38 mg, 0.165 mmol, 51% yield). LCMS (ESI) m/e 229.2 [(M+H)$^+$, calcd for $C_{12}H_{10}FN_4$, 229.1]; LC/MS retention time (method D) $t_R$=1.86 min.

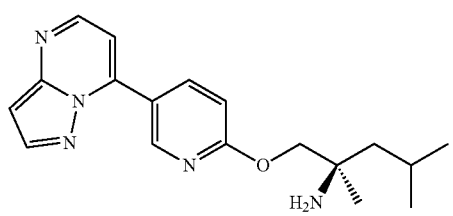 [SMILES: CC(C)C[C@@](C)(N)COc1ccc(-c2ccnc3ccnn23)cn1]

Part B: (R)-2,4-dimethyl-1-((3-methyl-5-(pyrazolo[1,5-a]pyrimidin-7-yl)pyridin-2-yl)oxy)pentan-2-amine To a stirred solution of (R)-2,4-dimethyl-1-((3-methyl-5-(pyrazolo[1,5-a]pyrimidin-7-yl)pyridin-2-yl)oxy)pentan-2- amine (5 mg, 0.013 mmol) and (R)-2-amino-2,4-dimethylpentan-1-ol (27.4 mg, 0.209 mmol) in DMF (2 mL) was added cesium carbonate (52.3 mg, 0.160 mmol) under a nitrogen atmosphere. The reaction mixture was heated at 85° C. for 6 h. The reaction mixture was passed through diatomaceous earth and the diatomaceous earth pad was washed with MeOH (5 mL). The filtrate was concentrated under reduced pressure. The crude material was purified via preparative LC/MS using method-A to afford (R)-2,4-dimethyl-1-((3-methyl-5-(pyrazolo[1,5-a]pyrimidin-7-yl)pyridin-2-yl)oxy)pentan-2-amine (5 mg, 0.013 mmol, 8% yield) as a pale yellow solid. $^1$H NMR (400 MHz, METHANOL-d$_4$) δ 8.82 (d, J=1.5 Hz, 1H), 8.57 (d, J=4.5 Hz, 1H), 8.37 (dd, J=1.0, 2.5 Hz, 1H), 8.24 (d, J=2.5 Hz, 1H), 7.19 (d, J=4.5 Hz, 1H), 6.81 (d, J=2.5 Hz, 1H), 4.49 (s, 2H), 2.42 (s, 3H), 1.93-1.78 (m, 2H), 1.67 (dd, J=5.5, 14.1 Hz, 1H), 1.46 (s, 3H), 1.07 (m, 6H). LCMS (ESI) m/e 340.2 [(M+H)$^+$, calcd for C$_{19}$H$_{26}$N$_5$O, 340.2]; LC/MS retention time (method J) t$_R$=1.68 min. LCMS (ESI) m/e 340.2 [(M+H)$^+$, calcd for C$_{19}$H$_{26}$N$_5$O, 340.2]; LC/MS retention time (method H) t$_R$=1.86 min.

Example 265

(R)-1-((3-chloro-5-(pyrazolo[1,5-a]pyrimidin-7-yl)pyridin-2-yl)oxy)-2,4-dimethylpentan-2-amine

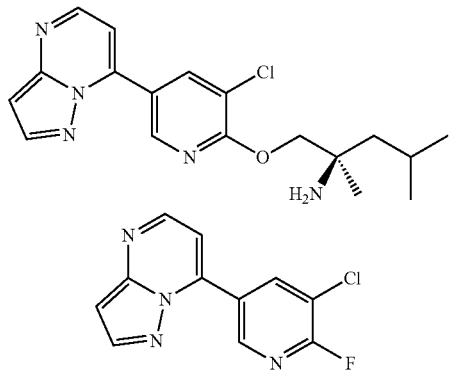

Part A: 7-(5-chloro-6-fluoropyridin-3-yl)pyrazolo[1,5-a]pyrimidine

A stirred solution of 7-chloropyrazolo[1,5-a]pyrimidine (100 mg, 0.651 mmol), (5-chloro-6-fluoropyridin-3-yl)boronic acid (114 mg, 0.651 mmol), and cesium carbonate (424 mg, 1.302 mmol) in a mixture of 1,4-dioxane (5 mL) and water (0.5 mL) was purged with nitrogen. PdCl$_2$(dppf)-CH$_2$Cl$_2$ adduct (80 mg, 0.098 mmol) was added in one portion and the reaction mixture was heated to 85° C. and stirred for 2 h. The solution cooled to room temperature and was concentrated under reduced pressure. Water (50 mL) was added and the solution was extracted with EtOAc (2×50 mL). The combined organic extracts were washed with water (50 mL) and brine (50 mL), dried over sodium sulfate, filtered, and concentrated under reduced pressure. The residue was purified by silica gel chromatography (EtOAc in hexanes) to afford 7-(5-chloro-6-fluoropyridin-3-yl)pyrazolo[1,5-a]pyrimidine (56 mg, 0.122 mmol, 19% yield). LCMS (ESI) m/e 249.0 [(M+H)$^+$, calcd for C$_{11}$H$_7$ClFN$_4$, 249.0]; LC/MS retention time (method B) t$_R$=0.95 min.

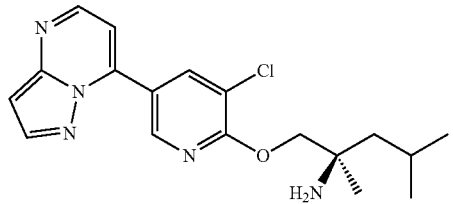 [SMILES: CC(C)C[C@@](C)(N)COc1ncc(-c2ccnc3ccnn23)cc1Cl]

Part B: (R)-1-((3-chloro-5-(pyrazolo[1,5-a]pyrimidin-7-yl)pyridin-2-yl)oxy)-2,4-dimethylpentan-2-amine To a stirred solution of (R)-2-amino-2,4-dimethylpentan-1-ol (15.39 mg, 0.117 mmol) and 7-(5-chloro-6-fluoropyridin-3-yl)pyrazolo[1,5-a]pyrimidine (54 mg, 0.117 mmol) in DMF (5 mL) was added cesium carbonate (38.2 mg, 0.117 mmol) under a nitrogen atmosphere. The reaction mixture was heated at 80° C. and stirred for 12 h. The solution was concentrated under reduced pressure. The crude material was purified via preparative LC/MS using method-A to afford (R)-1-((3-chloro-5-(pyrazolo[1,5-a]pyrimidin-7-yl)pyridin-2-yl)oxy)-2,4-dimethylpentan-2-amine (2 mg, 5.28 µmol, 5% yield) as a pale yellow solid. $^1$H NMR (400 MHz, METHANOL-d$_4$) δ=8.98-8.86 (m, 1H), 8.79-8.72 (m, 1H), 8.60 (d, J=4.5 Hz, 1H), 8.25 (d, J=2.5 Hz, 1H), 7.24 (d, J=4.5 Hz, 1H), 6.83 (d, J=2.5 Hz, 1H), 4.68-4.58 (m, 2H), 1.99-1.85 (m, 2H), 1.72 (d, J=9.0 Hz, 1H), 1.54 (s, 3H), 1.08 (m, 6H) ppm. LCMS (ESI) m/e 360.2, [(M+H)$^+$, calcd for C$_{18}$H$_{23}$ClN$_5$O, 360.1]; LC/MS retention time (method I) t$_R$=1.12 min. LCMS (ESI) m/e 360.2 [(M+H)$^+$, calcd for C$_{18}$H$_{23}$ClN$_5$O, 360.1]; LC/MS retention time (method H) t$_R$=1.50 min.

Example 266

(R)-1-((5-(2-cyclopropylpyrazolo[1,5-a]pyrimidin-7-yl)-3-methylpyridin-2-yl)oxy)-2,4-dimethylpentan-2-amine

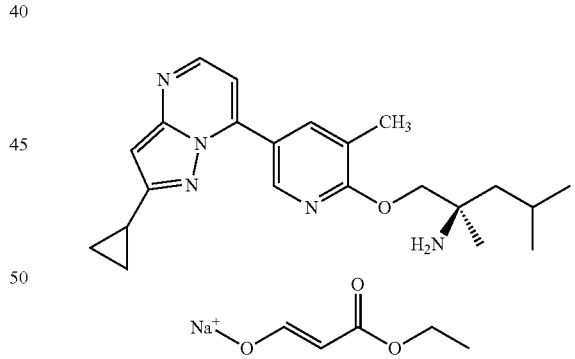

Part A: Sodium (E)-3-ethoxy-3-oxoprop-1-en-1-olate

Ethyl acetate (5 g, 56.8 mmol) was added to a solution of NaH (60%) (3.40 g, 142 mmol) in THF (50 mL) at room temperature. The internal temperature of the reaction mixture was adjusted to 40° C. and ethyl formate (8.41 g, 114 mmol) was added dropwise to maintain the internal temperature between 40-42° C. The reaction mixture was stirred at room temperature for 16 h. The reaction mixture was filtered under argon and the white solid obtained was washed with hexane. The resulting white solid was dried to afford sodium (E)-3-ethoxy-3-oxoprop-1-en-1-olate (4.8 g, 34.8 mmol, 61% yield). The product was taken to next step without further purification. $^1$H NMR (400 MHz, DMSO-d$_6$): δ 8.06 (d, J=5.60 Hz, 1H), 4.06 (d, J=5.60 Hz, 1H), 3.76-3.88 (m, 2H), 1.03-1.12 (m, 3H) ppm.

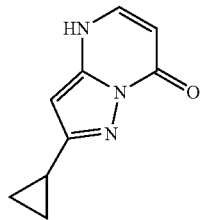 [SMILES: O=c1cc[nH]c2cc(C3CC3)nn12]

Part B: 2-Cyclopropylpyrazolo[1,5-a]pyrimidin-7(4H)-one

To a solution of 5-cyclopropyl-1H-pyrazol-3-amine (1 g, 8.12 mmol) in ethanol (10 mL) was added sodium (E)-3-ethoxy-3-oxoprop-1-en-1-olate (1.121 g, 8.12 mmol) portionwise and the mixture stirred for 5 min. The reaction mixture was heated at 88° C. for 14 h. The reaction mixture was concentrated under reduced pressure. Dichloromethane was added to the residue and the mixture stirred for 20 min. An off-white solid formed and was collected by vacuum filtration and dried to afford 2-cyclopropylpyrazolo [1,5-a]pyrimidin-7(4H)-one (0.8 g, 4.57 mmol, 56% yield) which was carried forward without further purification. LCMS (ESI) m/e 176.2 [(M+H)$^+$, calcd for C$_9$H$_{10}$N$_3$O 176.1]; LC/MS retention time (method A1): t$_R$=1.43 min.

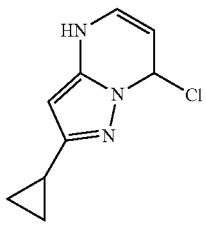 [SMILES: ClC1C=CNc2cc(C3CC3)nn21]

Part C: 7-Chloro-2-cyclopropylpyrazolo[1,5-a]pyrimidine

2-Cyclopropylpyrazolo [1,5-a]pyrimidin-7-ol (0.5 g, 2.85 mmol) was cooled to 0° C. in a 100 mL round bottom flask. POCl$_3$ (1.330 mL, 14.27 mmol) was added dropwise followed by slow addition of DIPEA (0.748 mL, 4.28 mmol) to the reaction mixture and stirred for 5 min at 0° C. The reaction mixture was allowed to warm to room temperature and heated at 105° C. for 12 h. The reaction mixture was concentrated under reduced pressure. The brown residue obtained was diluted with ice-water and basified with saturated sodium carbonate solution and extracted with ethyl acetate (3×25 mL). The ethyl acetate layer was dried over Na$_2$SO$_4$, filtered, and concentrated to afford the crude 7-chloro-2-cyclopropylpyrazolo [1,5-a]pyrimidine (crude yield) (0.48 g, 2.479 mmol, 87% yield) as a brown solid which was carried forward without further purification. LCMS (ESI) m/e 194.2 [(M+H)$^+$, calcd for C$_9$H$_9$ClN$_3$ 194.0]; LC/MS retention time (method A1): t$_R$=1.95 min.

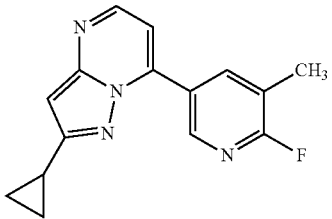 [SMILES: Cc1cc(-c2ccnc3cc(C4CC4)nn23)cnc1F]

Part D: 2-cyclopropyl-7-(6-fluoro-5-methylpyridin-3-yl)pyrazolo[1,5-a]pyrimidine To a stirred solution of 7-chloro-2-cyclopropylpyrazolo [1,5-a]pyrimidine (100 mg, 0.516 mmol), (6-fluoro-5-methylpyridin-3-yl)boronic acid (80 mg, 0.516 mmol), and cesium carbonate (337 mg, 1.033 mmol) in a mixture of 1,4-dioxane (5 mL) and water (0.5 mL) was purged with nitrogen. XPhos 2$^{nd}$ generation precatalyst (61.0 mg, 0.077 mmol) was added in one portion and the reaction mixture was heated to 85° C. and stirred for 2 h. The reaction mixture was allowed to cool to room temperature. Water (50 mL) was added and the solution was extracted with EtOAc (2×50 mL). The combined organic extracts were washed with water (50 mL) and brine (50 mL), dried over sodium sulfate, filtered, and concentrated under reduced pressure. The residue was purified by silica gel chromatography (EtOAc in hexanes) to afford 2-cyclopropyl-7-(6-fluoro-5-methylpyridin-3-yl)pyrazolo[1,5-a]pyrimidine (52 mg, 0.081 mmol, 16% yield). The product was carried forward without further purification. LCMS (ESI) m/e 269.2 [(M+H)$^+$, calcd for C$_{15}$H$_{14}$FN$_4$, 269.1]; LC/MS retention time (method H) t$_R$=2.31 min.

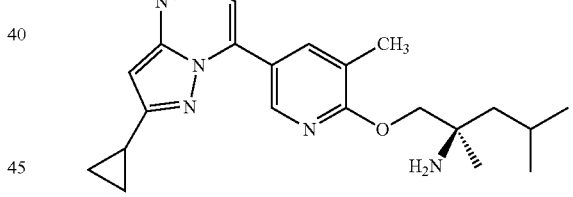

Part E: (R)-1-((5-(2-cyclopropylpyrazolo[1,5-a]pyrimidin-7-yl)-3-methylpyridin-2-yl)oxy)-2,4-dimethylpentan-2-amine To a stirred solution of (R)-1-((5-(2-cyclopropylpyrazolo [1,5-a]pyrimidin-7-yl)-3-methylpyridin-2-yl)oxy)-2,4-dimethylpentan-2-amine (3 mg, 7.67 µmol) and (R)-2-amino-2,4-dimethylpentan-1-ol (22.25 mg, 0.170 mmol) in THF (2 mL) was added potassium tert-butoxide (1M in THF) (0.130 mL, 0.130 mmol) under a nitrogen atmosphere. The reaction mixture was stirred at rt for 12 h. The solution was concentrated under reduced pressure. Water (50 mL) was added and the solution was extracted with EtOAc (2×50 mL). The combined organic extracts were washed with water (30 mL) and brine (30 mL), dried over sodium sulfate, filtered, and concentrated under reduced pressure. The crude material was purified via preparative LC/MS using method-A to afford (R)-1-((5-(2-cyclopropylpyrazolo[1,5-a]pyrimidin-7-yl)-3-methylpyridin-2-yl)oxy)-2,4-dimethylpentan-2-amine (3 mg, 7.67 μmol, 6% yield) as a pale yellow solid. ¹H NMR (400 MHz, METHANOL-d₄) δ 8.86 (d, J=3.0 Hz, 1H), 8.45 (d, J=4.5 Hz, 1H), 8.38-8.32 (m, 1H), 7.07 (d, J=4.5 Hz, 1H), 6.46 (s, 1H), 4.50 (s, 2H), 2.42 (s, 3H), 2.22-2.11 (m, 1H), 1.93-1.79 (m, 2H), 1.67 (dd, J=5.5, 14.1 Hz, 1H), 1.47 (s, 3H), 1.13-1.04 (m, 8H), 0.97-0.92 (m, 2H) ppm. LCMS (ESI) m/e 380.2 [(M+H)⁺, calcd for $C_{22}H_{30}N_5O$, 380.2]; LC/MS retention time (method I) $t_R$=1.98 min. LCMS (ESI) m/e 380.2 [(M+H)⁺, calcd for $C_{22}H_{30}N_5O$, 380.2]; LC/MS retention time (method H) $t_R$=2.30 min.

Example 267

(S)-2,4-dimethyl-1-((7-(2-methylpyridin-4-yl)benzo[d]thiazol-4-yl)oxy)pentan-2-amine

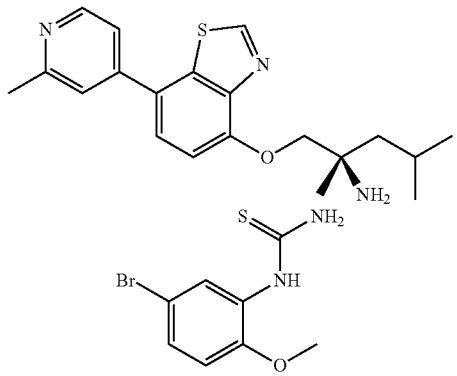

Part A: 1-(5-bromo-2-methoxyphenyl) thiourea

To a stirred solution of 5-bromo-2-methoxyaniline (1 g, 4.95 mmol) in conc. HCl (5 mL) and water (20 mL) was added potassium thiocyanate (0.481 g, 4.95 mmol) and the reaction mixture was heated at 100° C. for 24 h. The reaction mixture was allowed to cool to room temperature. Water (150 mL) was added and the solution was extracted with CHCl₃ (3×80 mL). The combined organic extracts were washed with brine (150 mL), dried over sodium sulfate, filtered, and concentrated under reduced pressure. The residue was purified by silica gel chromatography (EtOAc in hexanes) to afford 1-(5-bromo-2-methoxyphenyl)thiourea (960 mg, 2.94 mmol, 59% yield) as a white solid. LCMS (ESI) m/e 261.0 [(M+2H)⁺, calcd for $C_8H_{10}BrN_2OS$, 260.9]; LC/MS retention time (method A1) $t_R$=2.09 min.

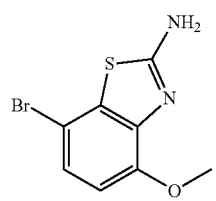

Part B:
7-Bromo-4-methoxybenzo[d]thiazol-2-amine

To a stirred solution of 1-(5-bromo-2-methoxyphenyl) thiourea (960 mg, 2.94 mmol) in CHCl₃ (25 mL) cooled to 0° C. was added bromine (0.303 mL, 5.88 mmol) dropwise over a period of 3 min under a nitrogen atmosphere. The reaction mixture was stirred at ambient temperature for 30 min, then heated to reflux at 70° C. for 1 h. The reaction mixture was allowed to cool to room temperature. The solid obtained was collected by vacuum filtration. The solid was dried under vacuum at room temperature to afford 7-bromo-4-methoxybenzo[d]thiazol-2-amine (940 mg, 2.79 mmol, 95% yield) as a pale yellow solid. The product was carried forward without further purification. LCMS (ESI) m/e 259.0 [(M+H)⁺, calcd for $C_8H_8BrN_2OS$, 258.9]; LC/MS retention time (method A1) $t_R$=1.78 min.

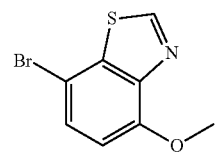

Part C: 7-bromo-4-methoxybenzo[d]thiazole

To a stirred solution of 7-bromo-4-methoxybenzo[d]thiazol-2-amine (100 mg, 0.386 mmol) in tetrahydrofuran (6 mL) was added tert-butyl nitrite (0.25 mL, 2.085 mmol) dropwise under a nitrogen atmosphere. The reaction mixture was heated at 55° C. for 14 h. The reaction mixture was allowed to cool to room temperature. Water 10 mL was added and the solution extracted with EtOAc (2×15 mL). The combined organic extracts were washed with brine (10 mL), dried over sodium sulfate, filtered, and concentrated under reduced pressure. The residue was purified by silica gel chromatography (EtOAc in hexanes) to afford 7-bromo-4-methoxybenzo[d]thiazole (89 mg, 0.350 mmol, 91% yield) as an off-white solid. ¹H NMR (400 MHz, METHANOL-d₄) δ 9.22 (s, 1H), 7.61 (d, J=8.40 Hz, 1H), 7.07 (d, J=8.40 Hz, 1H), 4.06 (s, 3H) ppm. LCMS (ESI) m/e 244.0 [(M+H)⁺, calcd for $C_8H_7BrNOS$, 244.0]; LC/MS retention time (method A1) $t_R$=2.17 min.

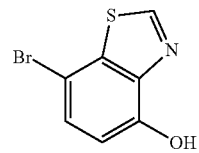 [SMILES: Oc1ccc(Br)c2scnc12]

Part D: 7-bromobenzo[d]thiazol-4-ol

To a stirred solution of 7-bromo-4-methoxybenzo[d]thiazole (80 mg, 0.315 mmol) in DCM (5 mL) cooled to 0° C. was added BBr₃ 1M in DCM (0.629 mL, 0.629 mmol) dropwise under nitrogen atmosphere. The reaction mixture was allowed to warm to room temperature and stirred for 50 min. The reaction mixture was cooled to 0° C., quenched slowly with dry MeOH (15 mL) then stirred for 10 min. the solution was concentrated under reduced pressure. Obtained 7-bromobenzo[d]thiazol-4-ol (78 mg, 0.312 mmol, 99% yield) as a brown solid. The solid was used as is to the next step without further purification. LCMS (ESI) m/e 229.8 [(M+H)⁺, Calcd for $C_7H_5BrNOS$, 229.9]; LC/MS retention time (method A1) $t_R$=2.09 min.

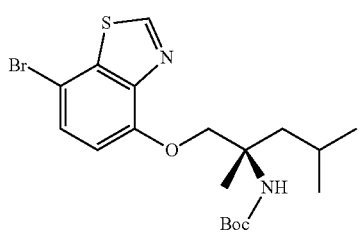 [SMILES: CC(C)C[C@@](C)(COc1ccc(Br)c2scnc12)NC(=O)OC(C)(C)C]

Part E: (S)-tert-butyl (1-((7-bromobenzo[d]thiazol-4-yl)oxy)-2,4-dimethylpentan-2-yl)carbamate To a stirred solution of 7-bromobenzo[d]thiazol-4-ol (75 mg, 0.300 mmol) in DMF (5 mL) was added potassium carbonate (166 mg, 1.200 mmol) and the reaction mixture was stirred at room temperature for 10 min. A solution of (S)-tert-butyl 4-isobutyl-4-methyl-1,2,3-oxathiazolidine-3-carboxylate 2,2-dioxide (prepared as described in Example 251, Parts A-E) (88 mg, 0.300 mmol) in 0.5 mL of DMF was added. The reaction mixture was heated at 80° C. and stirred for 14 h. The reaction mixture was allowed to cool to room temperature, then was concentrated under reduced pressure. Water (15 mL) was added and the solution was extracted with EtOAc (2×15 mL). The combined organic extracts were washed with water (10 mL) and brine (10 mL), dried over sodium sulfate, filtered, and concentrated under reduced pressure. Obtained (S)-tert-butyl (1-((7-bromobenzo[d]thiazol-4-yl)oxy)-2,4-dimethylpentan-2-yl)carbamate (105 mg, 0.156 mmol, 52% yield). The material was used as is in the next step without further purification. LCMS (ESI) m/e 443.0 [(M+H)$^+$, calcd for $C_{19}H_{28}BrN_2O_3S$, 443.1]; LC/MS retention time (method A1) $t_R$=2.56 min.

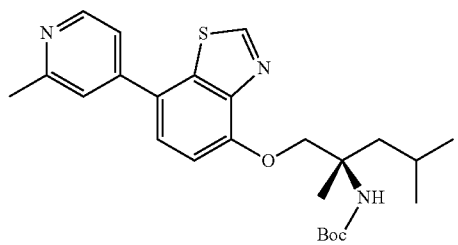 [SMILES: Cc1cc(-c2ccc(OC[C@](C)(CC(C)C)NC(=O)OC(C)(C)C)c3ncsc23)ccn1]

Part F: (S)-tert-butyl (2,4-dimethyl-1-((7-(2-methylpyridin-4-yl)benzo[d]thiazol-4-yl) oxy)pentan-2-yl) carbamate A stirred solution of (S)-tert-butyl (1-((7-bromobenzo[d]thiazol-4-yl)oxy)-2,4-dimethylpentan-2-yl)carbamate (40 mg, 0.060 mmol), (2-methylpyridin-4-yl)boronic acid (8.15 mg, 0.060 mmol) and cesium carbonate (38.8 mg, 0.119 mmol) in a mixture of 1,4-dioxane (10 mL) and water (2 mL) was purged argon for 2 min. $PdCl_2(dppf)-CH_2Cl_2$ adduct (2.431 mg, 2.98 μmol) was added in one portion and the reaction mixture was heated at 85° C. for 12 h.

The reaction mixture was allowed to cool to room temperature. Water (50 mL) was added and the solution was extracted with EtOAc (2×50 mL). The combined organic extracts were washed with water (100 mL) and brine (100 mL). The organic layer was dried over sodium sulfate, filtered, and concentrated under reduced pressure. The residue obtained was purified by silica gel chromatography (EtOAc in hexanes) to afford (S)-tert-butyl (2,4-dimethyl-1-((7-(2-methylpyridin-4-yl)benzo[d]thiazol-4-yl)oxy)pentan-2-yl)carbamate (26 mg, 0.055 mmol, 93% yield) in 97% purity based on UV from LCMS. LCMS (ESI) m/e 456.2 [(M+H)$^+$, calcd for $C_{25}H_{34}N_3O_3S$, 456.2]; LC/MS retention time (method A1) $t_R$=2.58 min.

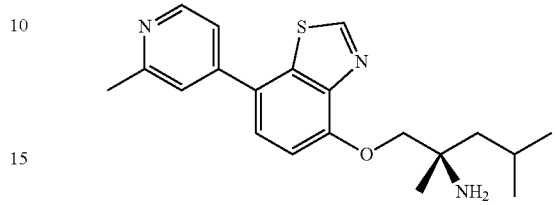

Part G: (S)-2,4-dimethyl-1-((7-(2-methylpyridin-4-yl)benzo[d]thiazol-4-yl)oxy)pentan-2-amine To a stirred solution of (S)-tert-butyl (2,4-dimethyl-1-((7-(2-methylpyridin-4-yl)benzo[d]thiazol-4-yl)oxy)pentan-2-yl)carbamate (25 mg, 0.053 mmol) in DCM (5 mL) was added TFA (4.10 μl, 0.053 mmol) dropwise under a nitrogen atmosphere at room temperature. The reaction mixture was stirred at room temperature for 12 h. The solution was concentrated under reduced pressure. The crude material was purified via preparative LC/MS using method-B to afford (S)-2,4-dimethyl-1-((7-(2-methylpyridin-4-yl)benzo[d]thiazol-4-yl)oxy)pentan-2-amine (5 mg, 8.48 μmol, 16% yield) as a pale yellow solid. $^1$H NMR (400 MHz, METHANOL-$d_4$) δ 9.52 (s, 1H), 8.76 (d, J=6.0 Hz, 1H), 8.19-8.07 (m, 2H), 7.95 (d, J=8.5 Hz, 1H), 7.43 (d, J=8.5 Hz, 1H), 4.54-4.36 (m, 2H), 2.85 (s, 3H), 2.00-1.88 (m, 2H), 1.79 (d, J=9.0 Hz, 1H), 1.59 (s, 3H), 1.14-0.97 (m, 6H) ppm. LCMS (ESI) m/e 356.2 [(M+H)$^+$, calcd for $C_{20}H_{26}N_3OS$, 356.2]; LC/MS retention time (method H) $t_R$=1.89 min. LCMS (ESI) m/e 356.2 [(M+H)$^+$, calcd for $C_{20}H_{26}N_3OS$, 356.2]; LC/MS retention time (method I) $t_R$=1.35 min.

Example 269

(S)-methyl (4-(4-((2-amino-2,4-dimethylpentyl)oxy)benzo[d]thiazol-7-yl)pyridin-2-yl)carbamate

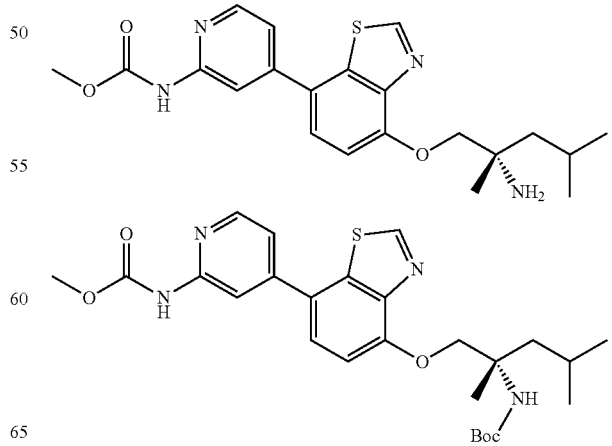

Part A: (S)-methyl (4-(4-((2-(Boc-amino)-2,4-dimethylpentyl)oxy)benzo[d]thiazol-7-yl)pyridin-2-yl)carbamate To a stirred solution of (S)-tert-butyl (1-((7-bromobenzo[d]thiazol-4-yl)oxy)-2,4-dimethylpentan-2-yl)carbamate (40 mg, 0.060 mmol) (prepared as described in Example 267, Parts A-E), methyl (4-(4,4,5,5-tetramethyl-1,3,2-dioxaborolan-2-yl)pyridin-2-yl)carbamate (16.56 mg, 0.060 mmol) and cesium carbonate (38.8 mg, 0.119 mmol) in a mixture of 1,4-dioxane (10 mL) and water (2 mL) was purged argon for 2 min. PdCl$_2$(dppf)-CH$_2$Cl$_2$ adduct (2.431 mg, 2.98 μmol) was added in one portion and the reaction mixture was heated at 85° C. for 10 h. The reaction mixture was allowed to cool to room temperature and concentrated under reduced pressure. Water (50 mL) was added and the solution was extracted with EtOAc (2×50 mL). The combined organic extracts were washed with water (100 mL) and brine (100 mL), dried over sodium sulfate, filtered, and concentrated under reduced pressure. The residue was purified by silica gel chromatography (EtOAc in hexanes) to afford (S)-methyl (4-(4-((2-(Boc-amino)-2,4-dimethylpentyl)oxy)benzo[d]thiazol-7-yl)pyridin-2-yl)carbamate (96 mg, 0.039 mmol, 66% yield). The product was carried forward without further purification. LCMS (ESI) m/e 515.2 [(M+H)$^+$, calcd for C$_{26}$H$_{35}$N$_4$O$_5$S, 515.2]; LC/MS retention time (method A1) $t_R$=2.57 min.

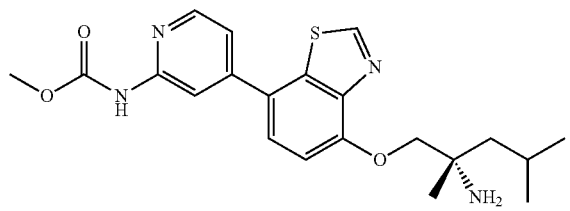 [SMILES: COC(=O)Nc1cc(-c2ccc(OC[C@@](C)(N)CC(C)C)c3ncsc23)ccn1]

Part B: (S)-methyl (4-(4-((2-amino-2,4-dimethylpentyl)oxy)benzo[d]thiazol-7-yl)pyridin-2-yl)carbamate To a stirred solution of (S)-methyl (4-(4-((2-(Boc-amino)-2,4-dimethylpentyl)oxy)benzo[d]thiazol-7-yl)pyridin-2-yl)carbamate (96 mg, 0.039 mmol) in DCM (2 mL) was added TFA (0.15 mL, 1.947 mmol) dropwise under a nitrogen atmosphere. The reaction mixture was allowed to stir at ambient temperature for 3 h. The solution was concentrated under reduced pressure. The residue was purified via preparative LC/MS using method-B to afford (S)-methyl (4-(4-((2-amino-2,4-dimethylpentyl)oxy)benzo[d]thiazol-7-yl)pyridin-2-yl)carbamate (7 mg, 10.57 μmol, 28% yield) as a pale yellow solid. $^1$H NMR (400 MHz, METHANOL-d$_4$) δ 9.44 (s, 1H), 8.39 (d, J=5.5 Hz, 1H), 8.29 (d, J=1.0 Hz, 1H), 7.78 (d, J=8.5 Hz, 1H), 7.43 (dd, J=1.8, 5.3 Hz, 1H), 7.35 (d, J=8.0 Hz, 1H), 4.45 (d, J=10.0 Hz, 1H), 4.31 (d, J=10.5 Hz, 1H), 3.83 (s, 3H), 1.91 (s, 2H), 1.83-1.73 (m, 1H), 1.58 (s, 3H), 1.15-0.98 (m, 6H) ppm. LCMS (ESI) me 415.2 [M+H)$^+$, calcd for C$_{21}$H$_{27}$N$_4$O$_3$S, 415.2]; LC/MS retention time (method H) $t_R$=1.87 min. LCMS (ESI) m/e 415.2 [M+H)$^+$, calcd for C$_{21}$H$_{27}$N$_4$O$_3$S, 415.2]; LC/MS retention time (method I) $t_R$=1.60 min.

Example 270

(S)-2,4-dimethyl-1-(4-(2-methylthiazolo[5,4-d]pyrimidin-7-yl)-2-(trifluoromethyl)phenoxy)pentan-2-amine

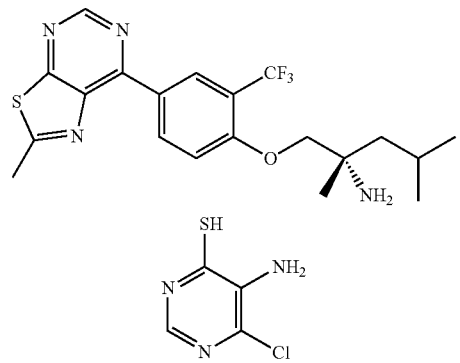

Part A: 5-amino-6-chloropyrimidine-4-thiol

To a solution of 4,6-dichloropyrimidin-5-amine (250 mg, 1.524 mmol) in methanol (15 mL) was added sodium hydrosulfide hydrate (113 mg, 1.524 mmol) under a nitrogen atmosphere. The reaction mixture was heated to 75° C. for 1 h. The reaction mixture was concentrated under reduced pressure and 10% aqueous sodium hydroxide solution was added. The pH was adjusted to pH 5 by adding acetic acid. The solution was extracted with ethyl acetate (2×50 mL). The ethyl acetate layer was dried over Na$_2$SO$_4$, filtered, and concentrated under reduced pressure to afford 5-amino-6-chloropyrimidine-4-thiol (270 mg, 1.186 mmol, 78% yield) as a pale brown solid which was taken to next step without further purification. LCMS (ESI) m/e 162.4 [(M+H)$^+$, calcd for C$_4$H$_5$ClN$_3$S 162.0]; LC/MS retention time (method B): $t_R$=0.55 min.

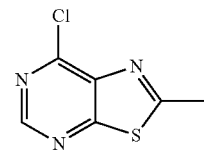

Part B: 7-chloro-2-methylthiazolo[5,4-d]pyrimidine

A mixture of 5-amino-6-chloropyrimidine-4-thiol (200 mg, 1.238 mmol) and triethylorthoacetate (5 mL, 27.1 mmol) was stirred at 130° C. for 3 h. The reaction mixture was allowed to cool to room temperature and concentrated under reduced pressure. The residue was purified by silica gel column chromatography eluting pet ether/ethyl acetate (0-25%) to afford 7-chloro-2-methylthiazolo[5,4-d]pyrimidine (65 mg, 0.350 mmol, 28% yield) as a brown solid. LCMS (ESI) m/e 186.4 [(M+H)$^+$, calcd for C$_6$H$_5$ClN$_3$S 185.98]; LC/MS retention time (method B): $t_R$=0.72 min.

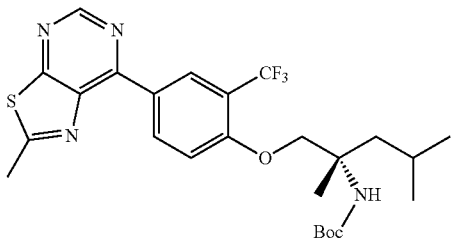 [SMILES: Cc1nc2c(-c3ccc(OC[C@](C)(CC(C)C)NC(=O)OC(C)(C)C)c(C(F)(F)F)c3)ncnc2s1]

Part C: (S)-tert-butyl (2,4-dimethyl-1-(4-(2-methyl-thiazolo[5,4-d]pyrimidin-7-yl)-2-(trifluoromethyl)phenoxy)pentan-2-yl)carbamate A solution 7-chloro-2-methylthiazolo[5,4-d]pyrimidine (40 mg, 0.215 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (108 mg, 0.215 mmol), cesium carbonate (140 mg, 0.431 mmol) in 1,4-dioxane (4 mL) and water (1 mL) was purged with nitrogen gas for 5 min. PdCl$_2$(dppf)-CH$_2$Cl$_2$ adduct (8.80 mg, 10.77 μmol) was added to the reaction mixture and reaction mixture was heated at 85° C. for 12 h. The reaction mixture was concentrated and to the residue was added water (50 mL) and the solution was extracted with ethyl acetate (2×30 mL). The organic layer was separated, washed with water (50 mL) and brine (50 mL), dried over Na$_2$SO$_4$, filtered, and concentrated under reduced pressure. The crude product was purified by Preparative TLC using 30% ethyl acetate in hexanes. The required spot was collected, dissolved in dichloromethane (25 mL), filtered and concentrated under reduced pressure to afford (S)-tert-butyl (2,4-dimethyl-1-(4-(2-methylthiazolo[5,4-d]pyrimidin-7-yl)-2-(trifluoromethyl)phenoxy)pentan-2-yl)carbamate (56 mg, 0.049 mmol, 23% yield) as yellow oil. LCMS (ESI) m/e 525.6 [(M+H)$^+$, calcd for C$_{25}$H$_{32}$F$_3$N$_4$O$_3$S 525.2]; LC/MS retention time (method B): $t_R$=1.42 min.

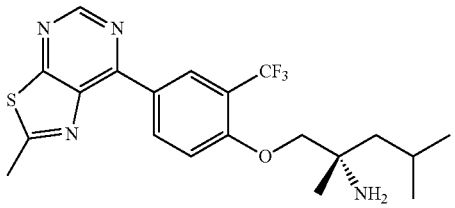 [SMILES: Cc1nc2c(-c3ccc(OC[C@@](C)(N)CC(C)C)c(C(F)(F)F)c3)ncnc2s1]

Part D: (S)-2,4-dimethyl-1-(4-(2-methylthiazolo[5,4-d]pyrimidin-7-yl)-2-(trifluoromethyl)phenoxy)pentan-2-amine To a solution of (S)-tert-butyl (2,4-dimethyl-1-(4-(2-methylthiazolo[5,4-d]pyrimidin-7-yl)-2-(trifluoromethyl)phenoxy)pentan-2-yl)carbamate (50 mg, 0.044 mmol) in dichloromethane (2 mL), was added TFA (0.3 mL, 3.89 mmol). The reaction mixture was allowed to stir for 2 h at room temperature, then concentrated under reduced pressure. The crude material was purified by prep LC/MS (method A) to afford (S)-2,4-dimethyl-1-(4-(2-methylthiazolo[5,4-d]pyrimidin-7-yl)-2-(trifluoromethyl)phenoxy)pentan-2-amine (5 mg. 0.012 mmol, 26% yield) as a pale yellow solid. LCMS (ESI) m/e 425.2 [(M+H)$^+$, calcd for C$_{20}$H$_{24}$F$_3$N$_4$OS 425.2]; LC/MS retention time (method H): $t_R$=2.96 min; LC/MS retention time (method I): $t_R$=2.29 min. $^1$H NMR (400 MHz, Methanol-d$_4$): δ 9.18 (d, J=2.01 Hz, 1H), 9.11-9.16 (m, 1H), 9.06 (s, 1H), 7.41 (d, J=8.53 Hz, 1H), 4.10 (d, J=6.02 Hz, 2H), 2.98 (s, 3H), 1.83-1.91 (m, 1H), 1.64 (m, 2H), 1.35 (s, 3H), 1.03 (m 6H) ppm.

Example 271

(S)-2-((2-amino-2,4-dimethylpentyl)oxy)-5-(2-methylthiazolo[5,4-d]pyrimidin-7-yl)benzonitrile

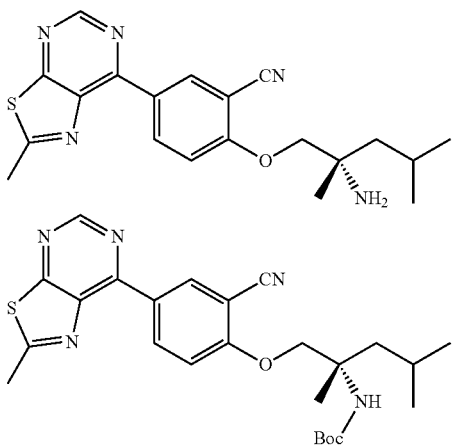

Part A: (S)-tert-butyl (1-(2-cyano-4-(2-methylthiazolo[5,4-d]pyrimidin-7-yl)phenoxy)-2,4-dimethyl-pentan-2-yl)carbamate A solution 7-chloro-2-methylthiazolo[5,4-d]pyrimidine (prepared as described in Example 270) (40 mg, 0.215 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (99 mg, 0.215 mmol), cesium carbonate (140 mg, 0.431 mmol) in 1,4-dioxane (4 mL) and water (1 mL) was purged with nitrogen gas for 5 min. PdCl$_2$(dppf)-CH$_2$Cl$_2$ adduct (8.80 mg, 10.77 μmol) was added to the reaction mixture and reaction mixture was heated at 85° C. for 12 h. The reaction mixture was concentrated and to the residue was added water (50 mL) and the solution was extracted with ethyl acetate (2×50 mL). The organic layer was separated, washed with water (30 mL) and brine (30 mL), dried over Na$_2$SO$_4$, and concentrated under reduced pressure. The crude product was purified by preparative TLC using 30% ethyl acetate in hexanes. The required spot was collected, dissolved in dichloromethane (25 mL), filtered and concentrated under reduced pressure to afford (S)-tert-butyl (1-(2-cyano-4-(2-methylthiazolo[5,4-d]pyrimidin-7-yl)phenoxy)-2,4-dimethylpentan-2-yl)carbamate (82 mg, 0.095 mmol, 44% yield) as colorless oil. LCMS (ESI) m/e 482.6 [(M+H)$^+$, calcd for C$_{25}$H$_{32}$N$_5$O$_3$S 482.2]; LC/MS retention time (method B): $t_R$=1.33 min.

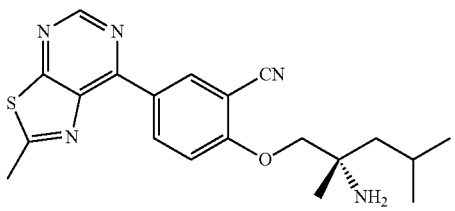

Part B: (S)-2-((2-amino-2,4-dimethylpentyl)oxy)-5-(2-methylthiazolo[5,4-d]pyrimidin-7-yl)benzonitrile To a solution of (S)-tert-butyl (1-(2-cyano-4-(2-methylthiazolo[5,4-d]pyrimidin-7-yl)phenoxy)-2,4-dimethylpentan-2-yl)carbamate (80 mg, 0.086 mmol) in dichloromethane (5 mL) was added TFA (6.65 µl, 0.086 mmol). The reaction mixture was allowed to stir for 3 h at room temperature and then was concentrated under reduced pressure. The crude material was purified by prep LC/MS (method B) which afforded (S)-2-((2-amino-2,4-dimethylpentyl)oxy)-5-(2-methylthiazolo[5,4-d]pyrimidin-7-yl)benzonitrile (15 mg, 0.038 mmol, 44% yield) as a pale yellow solid. LCMS (ESI) m/e 382.2 [(M+H)$^+$, calcd for $C_{20}H_{24}N_5OS$ 382.2]; LC/MS retention time (method H): $t_R$=2.56 min; LC/MS retention time (method I): $t_R$=2.17 min. $^1$H NMR (400 MHz, Methanol-d4): δ 9.20 (d, J=2.01 Hz, 1H), 9.14 (dd, J=9.04, 2.01 Hz, 1H), 9.08 (s, 1H), 7.49 (d, J=9.04 Hz, 1H), 4.38 (d, J=2.01 Hz, 2H), 2.99 (s, 3H), 1.96-1.86 (m, 2H), 1.77 (d, J=5.02 Hz, 1H), 1.58 (s, 3H), 1.09 (m, 6H) ppm.

Example 272

(S)-1-((3-chloro-5-(pyrazolo[1,5-a]pyrimidin-7-yl)pyridin-2-yl)oxy)-2,4-dimethylpentan-2-amine

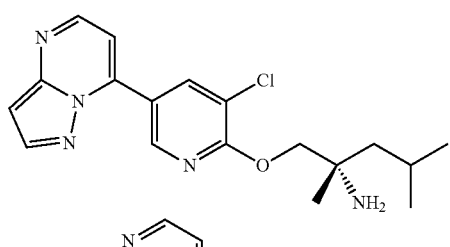

Part A: 7-(5-chloro-6-fluoropyridin-3-yl)pyrazolo[1,5-a]pyrimidine

A solution 7-chloropyrazolo[1,5-a]pyrimidine (65 mg, 0.423 mmol), (5-chloro-6-fluoropyridin-3-yl)boronic acid (74.2 mg, 0.423 mmol), cesium carbonate (276 mg, 0.847 mmol) in a mixture in 1,4-dioxane (5 mL) and water (0.5 mL) was purged with nitrogen gas for 5 min. PdCl$_2$(dppf)-CH$_2$Cl$_2$ adduct (17.28 mg, 0.021 mmol) was added to the reaction mixture and reaction mixture was heated at 85° C. for 90 min. The reaction mixture was concentrated and to the residue was added water (15 mL) and the solution was extracted with ethyl acetate (2×15 mL). The organic layer was separated, washed with water (20 mL) and brine (20 mL), dried over Na$_2$SO$_4$, and concentrated under reduced pressure to afford crude 7-(5-chloro-6-fluoropyridin-3-yl)pyrazolo[1,5-a]pyrimidine (95 mg, 0.191 mmol, 45% yield) as a pale yellow solid which was taken to next step without any further purification. LCMS (ESI) m/e 249.5 [(M+H)$^+$, calcd for $C_{11}H_7ClFN_4$ 249.0]; LC/MS retention time (method B): $t_R$=0.89 min.

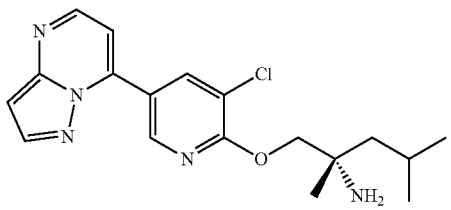 [SMILES: CC(C)C[C@](C)(N)COc1ncc(-c2ccnc3ccnn23)cc1Cl]

Part B: (S)-1-((3-chloro-5-(pyrazolo[1,5-a]pyrimidin-7-yl)pyridin-2-yl)oxy)-2,4-dimethylpentan-2-amine To a solution of 7-(5-chloro-6-fluoropyridin-3-yl)pyrazolo[1,5-a]pyrimidine (40 mg, 0.161 mmol) and (S)-2-amino-2,4-dimethylpentan-1-ol (21.11 mg, 0.161 mmol) in tetrahydrofuran (3 mL) was added potassium tert-butoxide (1M in THF) (0.161 mL, 0.161 mmol) under a nitrogen atmosphere. The reaction mixture was allowed to stir for 2 h at room temperature, then concentrated under reduced pressure. The crude material was purified by prep LC/MS (method A) which afforded (S)-1-((3-chloro-5-(pyrazolo[1,5-a]pyrimidin-7-yl)pyridin-2-yl)oxy)-2,4-dimethylpentan-2-amine, TFA (10 mg, 0.021 mmol, 13% yield) as a pale yellow solid. LCMS (ESI) m/e 360.2 [(M+H)$^+$, calcd for $C_{18}H_{23}ClN_5O$ TFA 360.2]; LC/MS retention time (method H): $t_R$=2.14 min; LC/MS retention time (method I): $t_R$=1.94 min. $^1$H NMR (400 MHz, Methanol-d4): δ 8.87-8.94 (m, 1H), 8.75 (d, J=2.51 Hz, 1H), 8.59 (d, J=4.52 Hz, 1H), 8.25 (d, J=2.51 Hz, 1H), 7.24 (d, J=4.52 Hz, 1H), 6.83 (d, J=2.01 Hz, 1H), 4.64 (d, J=4.02 Hz, 2H), 1.89-1.96 (m, 2H), 1.73 (d, J=8.53 Hz, 1H), 1.55 (s, 3H), 1.08 (m, 6H) ppm.

Example 275

(S)-2,4-dimethyl-1-((3-methyl-5-(pyrazolo[1,5-a]pyrimidin-7-yl)pyridin-2-yl)oxy)pentan-2-amine

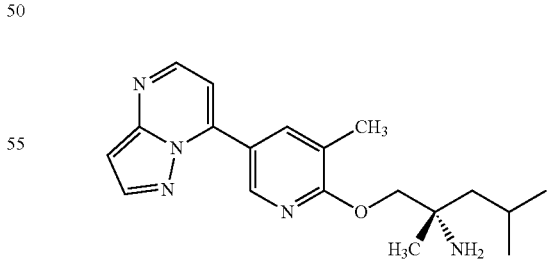

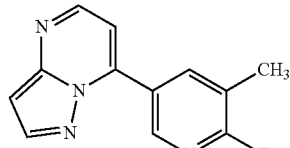

Part A: 7-(6-Fluoro-5-methylpyridin-3-yl)pyrazolo[1,5-a]pyrimidine

A stirred solution of 7-chloropyrazolo[1,5-a]pyrimidine (65 mg, 0.423 mmol), (6-fluoro-5-methylpyridin-3-yl)boronic acid (65.6 mg, 0.423 mmol), cesium carbonate (276 mg, 0.847 mmol) in a mixture of 1,4-dioxane (5 mL) and water (0.5 mL) was purged with nitrogen for 5 min. $PdCl_2$(dppf)-$CH_2Cl_2$ adduct (17.28 mg, 0.021 mmol) was added in one portion and the reaction mixture was heated at 85° C. and stirred for 2 h. The reaction mixture was allowed to cool to room temperature. Water (50 mL) was added and the solution was extracted with EtOAc (2×30 mL). The combined organic extracts were washed with water (70 mL) and brine (50 mL). The organic layer was dried over sodium sulfate, filtered, and concentrated under reduced pressure. The residue was purified by silica gel chromatography (EtOAc in hexanes) to afford 7-(6-fluoro-5-methylpyridin-3-yl)pyrazolo [1,5-a]pyrimidine (79 mg, 0.211 mmol, 50% yield). LCMS (ESI) m/e 229.2 [(M+H)$^+$, calcd for $C_{12}H_{10}FN_4$, 229.0]; LC/MS retention time (method A1) $t_R$=1.70 min.

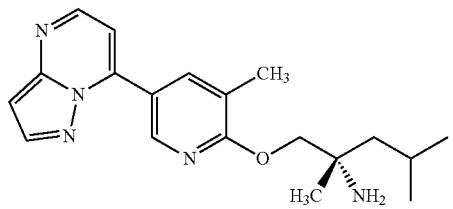 [SMILES: Cc1cc(-c2ccnc3ccnn23)cnc1OC[C@@](C)(N)CC(C)C]

Part B: (S)-2,4-dimethyl-1-((3-methyl-5-(pyrazolo[1,5-a]pyrimidin-7-yl)pyridin-2-yl)oxy)pentan-2-amine To a stirred solution of 7-(6-fluoro-5-methylpyridin-3-yl)pyrazolo[1,5-a]pyrimidine (40 mg, 0.107 mmol) and (S)-2-amino-2,4-dimethylpentan-1-ol (14.03 mg, 0.107 mmol) in tetrahydrofuran (3 mL) was added potassium tert-butoxide (1M in THF) (0.267 mL, 0.267 mmol) under a nitrogen atmosphere at ambient temperature. The reaction mixture was allowed to stir for 2 h. MeOH (2 mL) was added to the reaction mixture and the reaction mixture was filtered. The filtrate was concentrated under reduced pressure and purified via preparative LC/MS using method-A to afford (S)-2,4-dimethyl-1-((3-methyl-5-(pyrazolo[1,5-a]pyrimidin-7-yl)pyridin-2-yl)oxy)pentan-2-amine (25 mg, 0.072 mmol, 68% yield) as a pale yellow solid. $^1$H NMR (400 MHz, METHANOL-$d_4$) δ 8.73-8.95 (m, 1H), 8.53-8.66 (m, 1H), 8.31-8.46 (m, 1H), 8.18-8.30 (m, 1H), 7.12-7.27 (m, 1H), 6.67-6.87 (m, 1H), 4.51-4.66 (m, 2H), 2.51 (s, 3H), 1.82-2.03 (m, 2H), 1.61-1.77 (m, 1H), 1.54 (s, 3H), 0.94 (m, 6H) ppm. LCMS (ESI) m/e 340.2 [(M+H)$^+$, calcd for $C_{19}H_{26}N_5O$, 340.2]; LC/MS retention time (method H) $t_R$=2.15 min. LCMS (ESI) m/e 340.2 [(M+H)$^+$, calcd for $C_{19}H_{26}N_5O$, 340.2]; LC/MS retention time (method I): $t_R$=1.97 min.

Example 276

(S)-1-((2-(fluoromethyl)-6-(pyrazolo[1,5-a]pyrimidin-7-yl)pyridin-3-yl)oxy)-2,4-dimethylpentan-2-amine

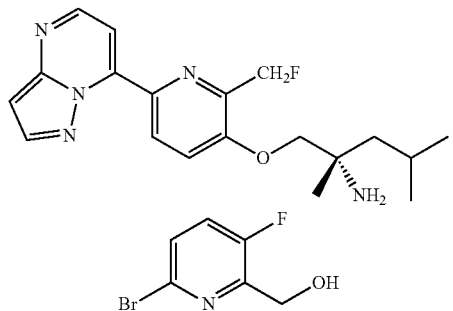

Part A: (6-bromo-3-fluoropyridin-2-yl)methanol

A solution of 6-bromo-3-fluoropicolinaldehyde (250 mg, 1.226 mmol) in methanol (3 mL) and tetrahydrofuran (5 mL) was cooled to 0° C. then sodium borohydride (46.4 mg, 1.226 mmol) was added in two portions. The reaction mixture was stirred for 30 min. The reaction mixture was concentrated under reduced pressure. Water (15 mL) was added to the reaction mixture and the solution was extracted with ethyl acetate (2×15 mL). The combined organic extracts were washed with water (30 mL) and brine (30 mL), dried over $Na_2SO_4$, filtered, and concentrated under reduced pressure to afford crude (6-bromo-3-fluoropyridin-2-yl)methanol (236 mg, 1.100 mmol, 90% yield). LCMS (ESI) m/e 206.0 (bromo pattern) [(M+H)$^+$, calcd for $C_6H_6BrFNO$ 205.9]; LC/MS retention time (Method G) $t_R$=1.17 min.

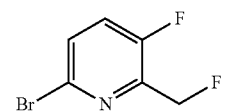

Part B: 6-bromo-3-fluoro-2-(fluoromethyl)pyridine

A solution of (6-bromo-3-fluoropyridin-2-yl)methanol (230 mg, 1.072 mmol) in dichloromethane (8 mL) was cooled to −20° C. and DAST (0.142 mL, 1.072 mmol) was added under a nitrogen atmosphere. The reaction mixture was allowed to stir at room temperature for 12 h. The reaction mixture was cooled to 0° C., quenched with 10% aqueous sodium bicarbonate solution (15 mL) and extracted with ethyl acetate (2×15 mL). The organic layer was washed with water (20 mL) and brine (20 mL), dried over $Na_2SO_4$, filtered, and concentrated under reduced pressure to afford crude 6-bromo-3-fluoro-2-(fluoromethyl)pyridine (170 mg, 0.662 mmol, 62% yield) as brown oil. The product was taken to next step without further purification. LCMS (ESI) m/e 208.0, 210.0 (bromo pattern) [(M+H)$^+$, calcd for $C_6H_5BrF_2N$ 208.0]; LC/MS retention time (method B): $t_R$=0.81 min.

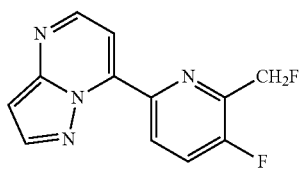

Part C: 7-(5-fluoro-6-(fluoromethyl)pyridin-2-yl) pyrazolo[1, 5-a]pyrimidine

A solution 7-chloropyrazolo[1,5-a]pyrimidine (75 mg, 0.488 mmol), 6-bromo-3-fluoro-2-(fluoromethyl)pyridine (102 mg, 0.488 mmol), tetrakis(triphenylphosphine)palladium (0) (28.2 mg, 0.024 mmol) and hexamethylditin (0.101 mL, 0.488 mmol) in 1,4-dioxane (2 mL) was purged with nitrogen gas for 2 min and irradiated at 130° C. in a microwave for 90 min. The reaction mixture was concentrated under reduced pressure. Water (10 mL) was added and the solution was extracted with ethyl acetate (2×10 mL). The organic layer was separated, washed with water (10 mL) and brine (10 mL), dried over $Na_2SO_4$, filtered, and concentrated under reduced pressure. The residue was purified by silica gel column chromatography (ethyl acetate in hexanes) to afford 7-(5-fluoro-6-(fluoromethyl)pyridin-2-yl)pyrazolo [1,5-a]pyrimidine (72 mg, 0.120 mmol, 25% yield) as a yellow solid. LCMS (ESI) m/e 247.0 [(M+H)$^+$, calcd for $C_{12}H_9F_2N_4$ 247.1]; LC/MS retention time (Method C): $t_R$=0.79 min.

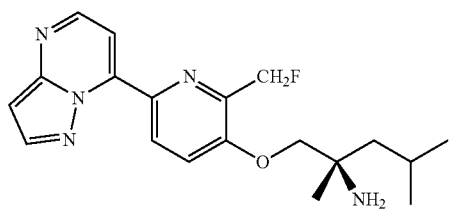

Part D: (S)-1-((2-(fluoromethyl)-6-(pyrazolo[1,5-a] pyrimidin-7-yl)pyridin-3-yl)oxy)-2,4-dimethylpentan-2-amine To a solution of (S)-2-amino-2,4-dimethylpentan-1-ol (27.7 mg, 0.211 mmol) and 7-(5-fluoro-6-(fluoromethyl) pyridin-2-yl)pyrazolo[1,5-a]pyrimidine (52 mg, 0.211 mmol) in tetrahydrofuran (5 mL) was added potassium tert-butoxide (0.317 mL, 0.317 mmol) under a nitrogen atmosphere. The reaction mixture was allowed to stir for 12 h at room temperature then was concentrated under reduced pressure. The crude material was purified by prep LC/MS (method B) which afforded (S)-1-((2-(fluoromethyl)-6-(pyrazolo[1,5-a]pyrimidin-7-yl)pyridin-3-yl)oxy)-2,4-dimethylpentan-2-amine (6 mg, 0.017 mmol, 8% yield) as a pale yellow solid. LCMS (ESI) m/e 358.3 [(M+H)$^+$, calcd for $C_{19}H_{25}FN_5O$ 358.2]; LC/MS retention time (method H): $t_R$=1.26 min; LC/MS retention time (method I): $t_R$=1.08 min. $^1$H NMR (400 MHz, Methanol-d4): δ 9.29-9.35 (m, 1H), 8.63-8.67 (m, 1H), 8.25-8.34 (m, 1H), 7.82-7.87 (m, 1H), 7.76-7.82 (m, 1H), 6.83-6.88 (m, 1H), 5.59-5.87 (m, 2H), 4.34-4.41 (m, 1H), 4.24-4.32 (m, 1H), 1.85-1.99 (m, 2H), 1.69-1.78 (m, 1H) 1.57 (s, 3H) 1.10 (m, 6H) ppm.

Example 277

2-amino-2-(((2',4-bis(difluoromethyl)-[2,4'-bipyridin]-5-yl)oxy)methyl)-4-methylpentan-1-ol

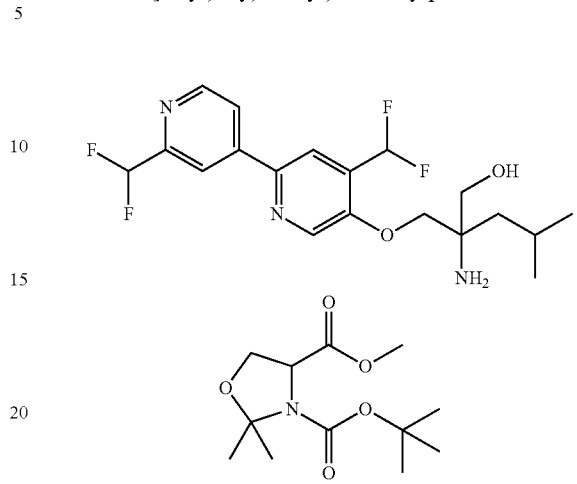

Part A: 3-tert-butyl 4-methyl 2,2-dimethyloxazolidine-3,4-dicarboxylate

To a solution of methyl 2-((tert-butoxycarbonyl)amino)-3-hydroxypropanoate (2 g, 9.12 mmol) in acetone (50 mL) and 2,2-dimethoxypropane (10 mL, 9.12 mmol) was added $BF_3$.$OEt_2$ (0.2 mL, 1.578 mmol) at room temperature under a nitrogen atmosphere. The reaction mixture was stirred for 2 h. The reaction mixture was concentrated under reduced pressure. Water (150 mL) was added to the residue and the solution was extracted with ethyl acetate (2×100 mL). The ethyl acetate layer was washed with water (100 mL) and brine (100 mL), dried over $Na_2SO_4$, filtered, and concentrated under reduced pressure. The residue was purified by silica gel chromatography (ethyl acetate in hexanes) to afford 3-tert-butyl 4-methyl 2,2-dimethyloxazolidine-3,4-dicarboxylate (1.92 g, 7.40 mmol, 81% yield) as yellow oil. $^1$H NMR (400 MHz, CDCl$_3$): δ 4.50-4.35 (m, 1H), 4.20-4.10 (m, 1H), 4.10-4.00 (m, 1H), 3.76 (s, 3H), 1.62 (s, 3H), 1.52 (s, 3H), 1.44 (s, 9H) ppm.

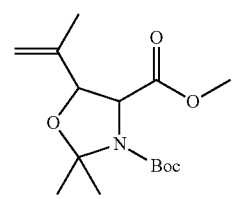 [SMILES: C=C(C)C1OC(C)(C)N(C(=O)OC(C)(C)C)C1C(=O)OC]

Part B: 3-tert-butyl 4-methyl 2,2-dimethyl-4-(2-methylallyl)oxazolidine-3,4-dicarboxylate A solution of LHMDS (1M in THF) (5.37 mL, 5.37 mmol) in THF (5 mL) was cooled to −80° C. and 3-tert-butyl 4-methyl 2,2-dimethyloxazolidine-3,4-dicarboxylate (0.87 g, 3.36 mmol) in THF (4 mL) was added. The reaction mixture was stirred for 30 min at room temperature. The reaction mixture was cooled to at −80° C. and 3-bromo-2-methylprop-1-ene (1.409 g, 10.43 mmol) was added under a nitrogen atmosphere. The reaction was stirred at −80° C. for 2 h and at room temperature for 14 h. The reaction mixture was quenched with saturated aqueous ammonium chloride and extracted with ethyl acetate (2×50 mL). The ethyl acetate layer was washed with water (100 mL) and brine (100 mL), dried over Na$_2$SO$_4$, filtered, and concentrated under reduced pressure to afford crude product which was purified by silica gel chromatography (ethyl acetate in hexanes) to afford 3-tert-butyl 4-methyl 2,2-dimethyl-4-(2-methylallyl)oxazolidine-3,4-dicarboxylate (400 mg, 1.276 mmol, 38% yield) as colorless oil. $^1$H NMR (300 MHz, CDCl$_3$): δ 5.00 (m, 1H), 4.78 (m, 1H), 4.15-4.10 (m, 2H), 3.76 (s, 3H), 3.19-2.93 (dd, J=14.1 Hz, 1H), 2.56 (m, 1H), 1.83 (m, 3H), 1.62 (s, 3H), 1.57 (s, 3H), 1.44 (s, 9H) ppm.

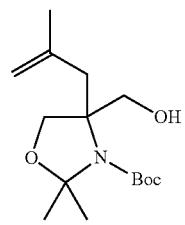 [SMILES: C=C(C)CC1(CO)COC(C)(C)N1C(=O)OC(C)(C)C]

Part C: Tert-butyl 4-(hydroxymethyl)-2,2-dimethyl-4-(2-methylallyl)oxazolidine-3-carboxylate A solution of 3-tert-butyl 4-methyl 2,2-dimethyl-4-(2-methylallyl)oxazolidine-3,4-dicarboxylate (560 mg, 1.787 mmol) in tetrahydrofuran (15 mL) was cooled to 0° C. then LAH (1M in THF) (2.5 mL, 2.500 mmol) was added dropwise under a nitrogen atmosphere. The reaction mixture was stirred at 0° C. for 20 min. The reaction mixture was quenched carefully by dropwise addition of water (25 mL) and extracted with ethyl acetate (2×50 mL). The ethyl acetate layer was washed with water (100 mL) and brine (100 mL), dried over Na$_2$SO$_4$, filtered, and concentrated under reduced pressure to afford crude tert-butyl 4-(hydroxymethyl)-2,2-dimethyl-4-(2-methylallyl)oxazolidine-3-carboxylate (320 mg, 1.121 mmol, 63% yield) as colorless oil. $^1$H NMR (400 MHz, DMSO-d$_6$): δ 4.95-4.85 (m, 2H), 4.75-4.65 (d, J=11.6 Hz, 1H), 3.97-3.90 (m, 1H), 3.85-3.75 (m, 1H), 3.60-3.40 (m, 2H), 2.22-2.10 (m, 1H), 1.80-1.70 (d, J=6.8 Hz, 3H), 1.45-1.35 (s, 15H) ppm.

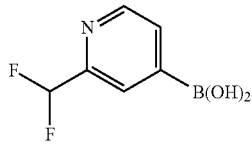 [SMILES: OB(O)c1ccnc(C(F)F)c1]

Part D: (2-(difluoromethyl)pyridin-4-yl)boronic acid

A solution of hypodiboric acid (576 mg, 6.42 mmol), potassium acetate (1260 mg, 12.84 mmol), and 2-(dicyclohexylphosphino)-2',4',6'-triisopropylbiphenyl (204 mg, 0.428 mmol) in ethanol (20 ml) was purged with nitrogen for 5 min. XPhos 2$^{nd}$ generation precatalyst (168 mg, 0.214 mmol) was added under nitrogen atmosphere to give a suspension and the reaction mixture was purged under nitrogen for 5 min. 4-Chloro-2-(difluoromethyl)pyridine (700 mg, 4.28 mmol) was added and the reaction mixture was heated at 80° C. for 3 h. The reaction mixture was passed through diatomaceous earth and the diatomaceous earth pad was washed with EtOAc (50 mL). The filtrate was evaporated to dryness under reduced pressure. Obtained (2-(difluoromethyl)pyridin-4-yl)boronic acid (740 mg, 4.28 mmol, quantitative crude yield). Carried on without further purification. LCMS (ESI) m/e 174.0 [(M+H)$^+$, calcd for C$_6$H$_7$BF$_2$NO$_2$ 174.0]; LC/MS retention time (Method C): t$_R$=0.43 min.

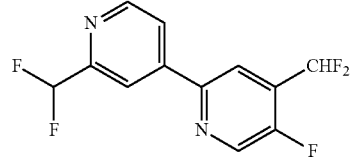 [SMILES: Fc1cnc(-c2ccnc(C(F)F)c2)cc1C(F)F]

Part E: 4-bromo-2-(difluoromethyl)pyridine

A solution of (2-(difluoromethyl)pyridin-4-yl)boronic acid (4.59 g, 26.5 mmol), 2-bromo-4-(difluoromethyl)-5-fluoropyridine (3 g, 13.27 mmol), tripotassium phosphate (2 M in water) (19.91 mL, 39.8 mmol) and XPhos 2$^{nd}$ generation precatalyst (0.313 g, 0.398 mmol) in THF (12 mL) was purged with nitrogen for 5 minutes. The solution was then heated at 80° C. for 14 h. The reaction mixture was allowed to cool to room temperature, diluted with EtOAc (100 mL) and stirred for 10 min. The reaction mixture was passed through diatomaceous earth and the diatomaceous earth pad was washed with EtOAc (50 mL). The filtrate was evaporated to dryness under reduced pressure. The residue was dissolved in EtOAc (200 mL) and washed with water (120 mL) and brine (200 mL). The organic layer was dried over sodium sulfate, filtered, and concentrated under reduced pressure. The residue was purified by silica gel chromatography (EtOAc in hexanes) to afford 2',4-bis(difluoromethyl)-5-fluoro-2,4'-bipyridine (2.5 g, 7.39 mmol, 55.6% yield) as pale brown solid. LCMS (ESI) m/e 275.0 [(M+H)$^+$, calcd for C$_{12}$H$_7$F$_5$N$_2$ 275.2]; LC/MS retention time (method B): t$_R$=1.59 min.

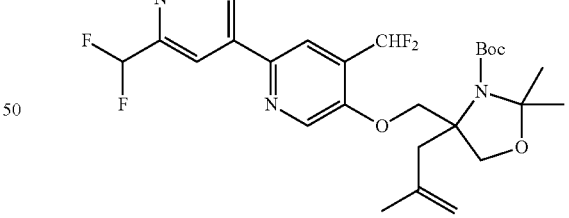

Part F: Tert-butyl 4-(((2',4-bis(difluoromethyl)-[2,4'-bipyridin]-5-yl)oxy)methyl)-2,2-dimethyl-4-(2-methylallyl)oxazolidine-3-carboxylate To a solution of 2',4-bis(difluoromethyl)-5-fluoro-2,4'-bipyridine (45 mg, 0.164 mmol) and tert-butyl 4-(hydroxymethyl)-2,2-dimethyl-4-(2-methylallyl)oxazolidine-3-carboxylate (46.8 mg, 0.164 mmol) in tetrahydrofuran was added potassium tert-butoxide (1 M in THF) (0.7 mL, 0.700 mmol) under a nitrogen atmosphere. The reaction mixture was stirred for 1 h. The reaction mixture was concentrated under reduced pressure. Water (10 mL) was added and extracted with ethyl acetate (2×15 mL). The ethyl acetate layer was washed with water (20 mL) and brine (20 mL), dried over Na$_2$SO$_4$, filtered, and concentrated under reduced pressure to afford crude product tert-butyl 4-(((2',4-bis(difluoromethyl)-[2,4'-bipyridin]-5-yl)oxy)methyl)-2,2-dimethyl-4-(2-methylallyl)oxazolidine-3-carboxylate (75 mg, 0.093 mmol, 57% yield) as yellow oil which was taken to next step without purification. LCMS (ESI) m/e 540.2 [(M+H)$^+$, calcd for C$_{27}$H$_{34}$F$_4$N$_3$O$_4$ 540.2]; LC/MS retention time (Method G): t$_R$=4.09 min.

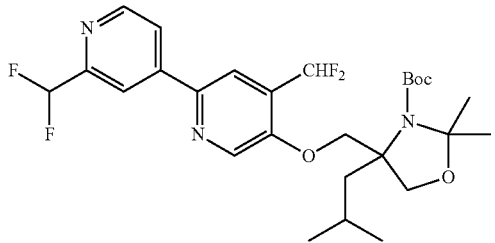 [SMILES: CC(C)CC1(COc2cnc(-c3ccnc(C(F)F)c3)cc2C(F)F)COC(C)(C)N1C(=O)OC(C)(C)C]

Part G: Tert-butyl 4-(((2',4-bis(difluoromethyl)-[2,4'-bipyridin]-5-yl)oxy)methyl)-4-isobutyl-2,2-dimethyloxazolidine-3-carboxylate To a solution of tert-butyl 4-(((2',4-bis(difluoromethyl)-[2,4'-bipyridin]-5-yl)oxy)methyl)-2,2-dimethyl-4-(2-methylallyl)oxazolidine-3-carboxylate (62 mg, 0.077 mmol) in methanol (5 mL) was added palladium on carbon (15 mg, 0.014 mmol) under a nitrogen atmosphere. The reaction mixture was stirred under 1 atm of hydrogen gas for 18 h. The reaction mixture was filtered through diatomaceous earth and the diatomaceous earth bed was washed with methanol (15 mL). The filtrate was concentrated under reduced pressure to afford tert-butyl 4-(((2',4-bis(difluoromethyl)-[2,4'-bipyridin]-5-yl)oxy)methyl)-4-isobutyl-2,2-dimethyloxazolidine-3-carboxylate (73 mg, 0.047 mmol, 61% yield). LCMS (ESI) m/e 542.3 [(M+H)$^+$, calcd for C$_{27}$H$_{36}$F$_4$N$_3$O$_4$ 542.3]; LC/MS retention time (method B): t$_R$=1.24 min.

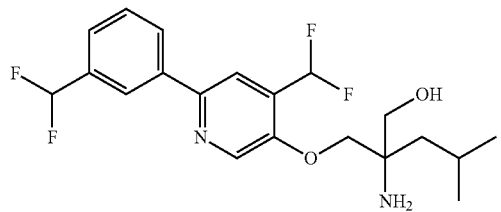 [SMILES: CC(C)CC(N)(CO)COc1cnc(-c2cccc(C(F)F)c2)cc1C(F)F]

Part H: 2-amino-2-(((2',4-bis(difluoromethyl)-[2,4'-bipyridin]-5-yl)oxy)methyl)-4-methylpentan-1-ol A solution of tert-butyl 4-(((2',4-bis(difluoromethyl)-[2,4'-bipyridin]-5-yl)oxy)methyl)-4-isobutyl-2,2-dimethyloxazolidine-3-carboxylate (72 mg, 0.047 mmol) in 1,4-dioxane (4 mL) and 6N HCl (4 mL) was heated at 90° C. for 2 h. The reaction mixture was cooled to room temperature then was concentrated under reduced pressure. The crude material was purified by prep LC/MS (method A) to afford 2-amino-2-(((2',4-bis(difluoromethyl)-[2,4'-bipyridin]-5-yl)oxy) methyl)-4-methylpentan-1-ol (1.5 mg, 3.62 μmol, 8% yield) as a pale yellow solid. LCMS (ESI) m/e 402.2 [(M+H)$^+$, calcd for C$_{19}$H$_{24}$F$_4$N$_3$O$_2$ 402.2]; LC/MS retention time (method H): t$_R$=1.47 min; LC/MS retention time (method I): t$_R$=1.16 min. $^1$H NMR (400 MHz, Methanol-d$_4$): δ 8.75 (d, J=5.5 Hz, 1H), 8.70 (s, 1H), 8.37 (s, 1H), 8.23 (s, 1H), 8.21-8.16 (m, 1H), 7.33-6.67 (m, 2H), 4.28 (d, J=1.0 Hz, 2H), 3.71 (d, J=11.0 Hz, 1H), 3.58 (d, J=11.0 Hz, 1H), 1.91 (s, 1H), 1.59 (t, J=5.8 Hz, 2H), 1.02 (t, J=6.5 Hz, 6H) ppm.

Example 281

(S)-1-(4-(imidazo[1,2-b]pyridazin-8-yl)phenoxy)-2,4-dimethylpentan-2-amine

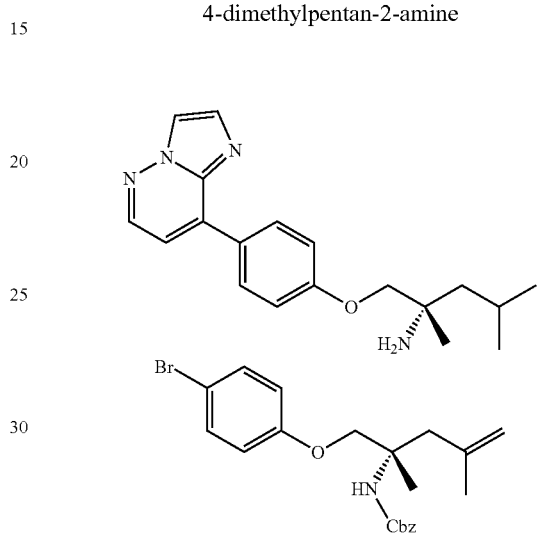

Part A: (S)-benzyl (1-(4-bromophenoxy)-2,4-dimethylpent-4-en-2-yl)carbamate

A mixture of 4-bromophenol (0.3 g, 1.734 mmol), (S)-benzyl 4-methyl-4-(2-methylallyl)-1,2,3-oxathiazolidine-3-carboxylate 2,2-dioxide (0.733 g, 2.254 mmol), K$_2$CO$_3$ (0.599 g, 4.34 mmol) in DMF (6.94 mL) was heated at 80° C. overnight under nitrogen. The reaction mixture was extracted with ethyl acetate (2×100 mL), washed with water (75 mL), brine (75 mL), dried over Na$_2$SO$_4$, and concentrated under reduced pressure. The residue was purified by silica gel chromatography (0-20% of ethyl acetate/hexane) to afford (S)-benzyl (1-(4-bromophenoxy)-2,4-dimethylpent-4-en-2-yl)carbamate (0.8 g, 1.683 mmol, 97% yield). LCMS (ESI) m/e 418.3; 420.3 (bromo pattern) [(M+H)$^+$, calcd for C$_{21}$H$_{26}$BrNO$_3$ 418.1]; LC/MS retention time (method B): t$_R$=1.22 min.

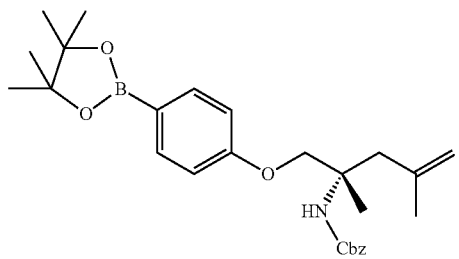 [SMILES: C=C(C)C[C@@](C)(COc1ccc(B2OC(C)(C)C(C)(C)O2)cc1)NC(=O)OCc1ccccc1]

Part B: (S)-benzyl (2,4-dimethyl-1-(4-(4,4,5,5-tetramethyl-1,3,2-dioxaborolan-2-yl)phenoxy)pent-4-en-2-yl)carbamate A solution of (S)-benzyl (1-(4-bromophenoxy)-2,4-dimethylpent-4-en-2-yl)carbamate (0.2 g, 0.478 mmol), bis(pinacolato)diboron (0.182 g, 0.717 mmol), and potassium acetate (0.141 g, 1.434 mmol) in 1,4-dioxane (2.39 mL) was purged with argon for 5 min. PdCl$_2$(dppf)-CH$_2$Cl$_2$ adduct (0.039 g, 0.048 mmol) was added to the reaction mixture was heated under argon at 80° C. overnight. The reaction mixture was extracted with ethyl acetate (2×50 mL). The ethyl acetate layer was washed with water (20 mL) and brine (20 mL), dried over Na$_2$SO$_4$, filtered, and concentrated under reduced pressure. The residue was purified by silica gel chromatography (0-15% of ethyl acetate/hexane) to afford (S)-benzyl (2,4-dimethyl-1-(4-(4,4,5,5-tetramethyl-1,3,2-dioxaborolan-2-yl)phenoxy)pent-4-en-2-yl)carbamate (0.13 g, 0.263 mmol, 55% yield) as gummy liquid. LCMS (ESI) m/e 466.2 [(M+H)$^+$, calcd for C$_{27}$H$_{37}$BNO$_5$ 466.3]; LC/MS retention time (Method F): t$_R$=2.55 min.

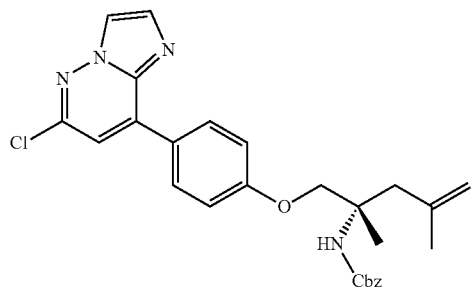 [SMILES: C=C(C)C[C@@](C)(COc1ccc(-c2cc(Cl)nn3ccnc23)cc1)NC(=O)OCc1ccccc1]

Part C: (S)-benzyl (1-(4-(6-chloroimidazo[1,2-b]pyridazin-8-yl)phenoxy)-2,4-dimethylpent-4-en-2-yl)carbamate A solution of 8-bromo-6-chloroimidazo[1,2-b]pyridazine (0.05 g, 0.215 mmol), (S)-benzyl (2,4-dimethyl-1-(4-(4,4,5,5-tetramethyl-1,3,2-dioxaborolan-2-yl)phenoxy)pent-4-en-2-yl)carbamate (0.110 g, 0.237 mmol), and potassium phosphate tribasic (2M in water) (0.323 mL, 0.645 mmol) in 1,4-dioxane (1.075 mL) was purged with argon for 5 min. Tetrakis(triphenylphosphine)palladium (0) (triphenylphosphine)palladium(0) (0.012 g, 10.75 µmol) was added to the reaction mixture under argon and the mixture was heated to 100° C. overnight. The reaction mixture was diluted with water (20 mL) and extracted with ethyl acetate (2×30 mL). The ethyl acetate layer was washed with water (20 mL), brine, dried over Na$_2$SO$_4$, filtered, and concentrated under reduced pressure. The residue was purified by silica gel chromatography (0-60% of ethyl acetate/hexane) to afford (S)-benzyl (1-(4-(6-chloroimidazo[1,2-b]pyridazin-8-yl)phenoxy)-2,4-dimethylpent-4-en-2-yl)carbamate (0.05 g, 0.092 mmol, 43% yield) as a gummy liquid. LCMS (ESI) m/e 491.2 [(M+H)$^+$, calcd for C$_{27}$H$_{28}$ClN$_4$O$_3$ 491.2]; LC/MS retention time (method A1): t$_R$=2.88 min.

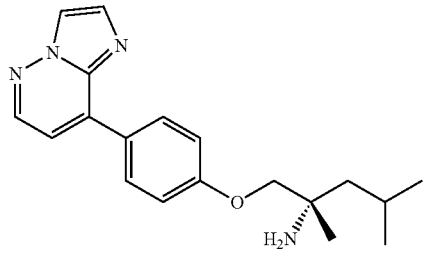 [SMILES: CC(C)C[C@](C)(N)COc1ccc(-c2ccnn3ccnc23)cc1]

Part D: (S)-1-(4-(imidazo[1,2-b]pyridazin-8-yl)phenoxy)-2,4-dimethylpentan-2-amine To a solution of (S)-benzyl (1-(4-(6-chloroimidazo[1,2-b]pyridazin-8-yl)phenoxy)-2,4-dimethylpent-4-en-2-yl)carbamate (0.055 g, 0.100 mmol) in ethyl acetate (2 mL) was added palladium on carbon (0.027 g, 0.025 mmol). The reaction mixture was stirred under hydrogen at 1 atm overnight at room temperature. The reaction mixture was filtered through diatomaceous earth and the diatomaceous earth pad was washed with methanol (50 mL). The filtrate was concentrated under reduced pressure to give (S)-1-(4-(imidazo[1,2-b]pyridazin-8-yl)phenoxy)-2,4-dimethylpentan-2-amine (0.024 g, 0.070 mmol, 70% yield) as brown gummy liquid. LCMS (ESI) m/e 325.2 [(M+H)$^+$, calcd for C$_{19}$H$_{25}$N$_4$O 325.2]; LC/MS retention time (Method A1): t$_R$=1.80 min. $^1$H NMR (400 MHz, Methanol-d$_4$): δ 8.48 (d, J=4.8 Hz, 1H), 8.22-8.19 (m, 1H), 8.18-8.13 (m, 2H), 7.80 (d, J=1.3 Hz, 1H), 7.34 (d, J=4.8 Hz, 1H), 7.26-7.22 (m, 2H), 4.22 (d, J=10.3 Hz, 1H), 4.13 (d, J=10.3 Hz, 1H), 1.94-1.81 (m, 2H), 1.75-1.66 (m, 1H), 1.52 (s, 3H), 1.09 (d, J=6.5 Hz, 3H), 1.05 (d, J=6.3 Hz, 3H) ppm.

Example 282

(S)-1-(2-chloro-4-(2-methyl-3H-imidazo[4,5-b]pyridin-7-yl)phenoxy)-2,4-dimethylpentan-2-amine

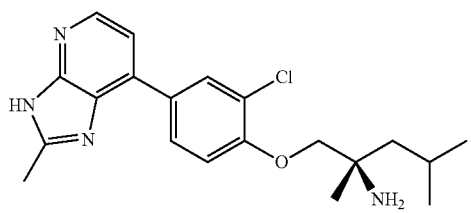

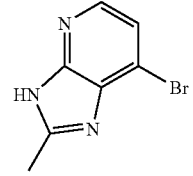

Part A: 7-bromo-2-methyl-3H-imidazo[4,5-b]pyridine

A mixture of 4-bromopyridine-2,3-diamine (0.15 g, 0.798 mmol), AcOH (0.069 mL, 1.197 mmol), and PPA (0.340 mL, 0.798 mmol) was heated at 150° C. for 2 h. The reaction mixture was diluted with water and the pH was adjusted to 13 with aqueous NaOH (10%). The solution was extracted with ethyl acetate (2×100 mL). The ethyl acetate layers were washed with water, brine, dried over Na$_2$SO$_4$, filtered, and concentrated under reduced pressure to afford 7-bromo-2-methyl-3H-imidazo[4,5-b]pyridine (0.130 g, 0.460 mmol, 58% yield). LCMS (ESI) m/e 212.0 [(M+H)$^+$, calcd for C$_7$H$_7$BrN$_3$ 212.0]; LC/MS retention time (method B): t$_R$=0.49 min.

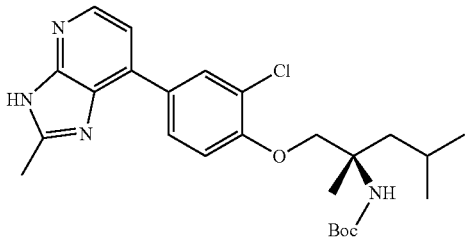 [SMILES: Cc1nc2c(-c3ccc(OC[C@](C)(CC(C)C)NC(=O)OC(C)(C)C)c(Cl)c3)ccnc2[nH]1]

Part B: (S)-tert-butyl (1-(2-chloro-4-(2-methyl-3H-imidazo[4,5-b]pyridin-7-yl)phenoxy)-2,4-dimethylpentan-2-yl)carbamate A solution of 7-bromo-2-methyl-3H-imidazo[4,5-b]pyridine (0.1 g, 0.472 mmol), (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (0.265 g, 0.566 mmol), and K$_2$CO$_3$ (0.196 g, 1.415 mmol) in 1,4-dioxane (4 mL) and water (1 mL) was purged with argon for 5 min. PdCl$_2$(dppf)-CH$_2$Cl$_2$ adduct (0.019 g, 0.024 mmol) was added to the reaction mixture under argon and the mixture was heated to 100° C. overnight. The reaction mixture was extracted with ethyl acetate (2×30 mL). The ethyl acetate layer was washed with water (20 mL) and brine (20 mL), dried over Na$_2$SO$_4$, filtered, and concentrated under reduced pressure. The crude product which was purified by silica gel chromatography (0-10% of CHCl$_3$/MeOH) to afford (S)-tert-butyl (1-(2-chloro-4-(2-methyl-3H-imidazo[4,5-b]pyridin-7-yl)phenoxy)-2,4-dimethylpentan-2-yl)carbamate (0.08 g, 0.169 mmol, 36% yield) as a brown solid. LCMS (ESI) m/e 473.2 [(M+H)$^+$, calcd for C$_{25}$H$_{34}$ClN$_4$O$_3$ 473.2]; LC/MS retention time (method B): t$_R$=0.98 min.

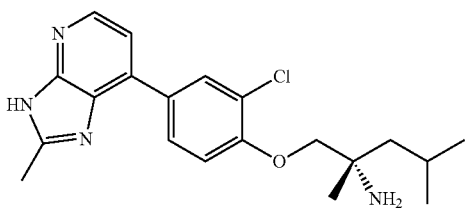 [SMILES: Cc1nc2c(-c3ccc(OC[C@@](C)(N)CC(C)C)c(Cl)c3)ccnc2[nH]1]

Part C: (S)-1-(2-chloro-4-(2-methyl-3H-imidazo[4,5-b]pyridin-7-yl)phenoxy)-2,4-dimethylpentan-2-amine To a solution of (S)-tert-butyl (1-(2-chloro-4-(2-methyl-3H-imidazo[4,5-b]pyridin-7-yl)phenoxy)-2,4-dimethylpentan-2-yl)carbamate (0.05 g, 0.106 mmol) in dichloromethane (0.5 mL) cooled to 0° C. was added 4N HCl in 1,4-dioxane (0.661 mL, 2.64 mmol) under nitrogen. The reaction mixture was stirred at room temperature for 1 h, then was concentrated under reduced pressure. The crude material was purified by preparative LC/MS (method A) to afford (S)-1-(2-chloro-4-(2-methyl-3H-imidazo [4,5-b]pyridin-7-yl)phenoxy)-2,4-dimethylpentan-2-amine, 2 TFA (0.017 g, 0.029 mmol, 27% yield) as a pale yellow solid. LCMS (ESI) m/e 373.0 [(M+H)$^+$, calcd for C$_{20}$H$_{26}$ClN$_4$O 373.2]; LC/MS retention time (method H): t$_R$=0.83 min; LC/MS retention time (method I): t$_R$=0.92 min. $^1$H NMR (400 MHz, Methanol-d$_4$): δ 8.19 (d, J=2.2 Hz, 1H), 8.02 (dd, J=2.3, 8.6 Hz, 1H), 7.94 (d, J=8.3 Hz, 1H), 7.73 (d, J=8.4 Hz, 1H), 7.27 (d, J=8.7 Hz, 1H), 4.23 (d, J=10.2 Hz, 1H), 4.17 (d, J=10.2 Hz, 1H), 2.65 (s, 3H), 1.97-1.85 (m, 2H), 1.77-1.68 (m, 1H), 1.53 (s, 3H), 1.09 (d, J=6.5 Hz, 3H), 1.06 (d, J=6.5 Hz, 3H) ppm.

Example 283

(S)-1-(4-(imidazo[1,2-b]pyridazin-8-yl)-2-(trifluoromethyl)phenoxy)-2,4-dimethylpentan-2-amine

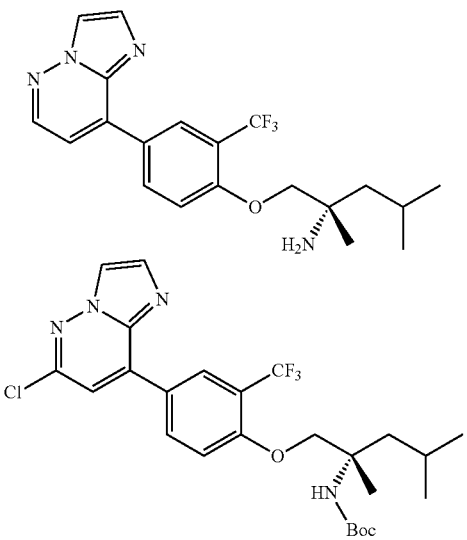

Part A: (S)-tert-butyl (1-(4-(6-chloroimidazo[1,2-b]pyridazin-8-yl)-2-(trifluoromethyl)phenoxy)-2,4-dimethylpentan-2-yl)carbamate A solution of 8-bromo-6-chloroimidazo[1,2-b]pyridazine (0.03 g, 0.129 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.065 g, 0.129 mmol), and potassium phosphate tribasic (2m in water) (0.194 mL, 0.387 mmol) in 1,4-dioxane (0.645 mL) was purged with argon for 10 min. Tetrakis(triphenylphosphine) palladium (0) (7.46 mg, 6.45 μmol) was added to the reaction mixture under argon and the mixture was heated to 100° C. overnight. The reaction mixture was diluted with water (20 mL) and extracted with ethyl acetate (2×30 mL). The ethyl acetate layer was washed with brine, dried over Na$_2$SO$_4$, filtered, and concentrated under reduced pressure. The crude product was purified by silica gel chromatography (0-20% of ethyl acetate/hexane) to give (S)-tert-butyl (1-(4-(6-chloroimidazo[1,2-b]pyridazin-8-yl)-2-(trifluoromethyl)

phenoxy)-2,4-dimethylpentan-2-yl)carbamate (0.042 g, 0.073 mmol, 57% yield). LCMS (ESI) m/e 527.2 [(M+H)+, calcd for $C_{25}H_{31}ClF_3N_4O_3$ 527.2]; LC/MS retention time (method A2): $t_R$=1.28 min.

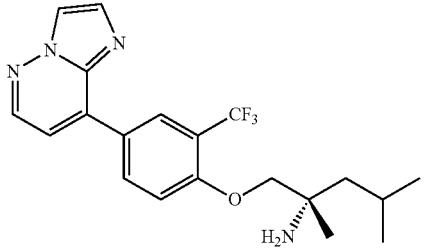 [SMILES: CC(C)C[C@](C)(N)COc1ccc(-c2ccnn3ccnc23)cc1C(F)(F)F]

Part B: (S)-1-(4-(imidazo[1,2-b]pyridazin-8-yl)-2-(trifluoromethyl)phenoxy)-2,4-dimethylpentan-2-amine To a solution of (S)-tert-butyl (1-(4-(6-chloroimidazo[1,2-b]pyridazin-8-yl)-2-(trifluoromethyl)phenoxy)-2,4-dimethylpentan-2-yl)carbamate (0.04 g, 0.076 mmol) in methanol (3 mL) was added palladium on carbon (0.020 g, 0.019 mmol). The reaction mixture was hydrogenated under 1 atm $H_2$ for 1 h. The reaction mixture was filtered through diatomaceous earth and the diatomaceous earth bed was washed with methanol (20 mL). The filtrate concentrated under reduced pressure. The crude product was dissolved in dichloromethane (2 mL), cooled to 0° C. and TFA (0.088 mL, 1.139 mmol) was added under nitrogen. The reaction mixture was stirred at room temperature for 1 h. The solvent was removed under reduced pressure and the crude compound was purified by RP-HPLC (TFA in water and acetonitrile) to afford (S)-1-(4-(imidazo[1,2-b]pyridazin-8-yl)-2-(trifluoromethyl)phenoxy)-2,4-dimethylpentan-2-amine, TFA (0.030 g, 0.055 mmol, 72% yield) as an off-white solid. LCMS (ESI) m/e 393.2 [(M+H)+, calcd for $C_{20}H_{24}F_3N_4O$, 393.2]; LC/MS retention time (Method A1): $t_R$=2.02 min. 1H NMR (400 MHz, Methanol-d4): δ 8.57 (d, J=4.8 Hz, 1H), 8.50 (d, J=2.0 Hz, 1H), 8.42 (dd, J=2.2, 8.8 Hz, 1H), 8.28 (d, J=1.4 Hz, 1H), 7.88 (d, J=1.4 Hz, 1H), 7.49 (d, J=8.8 Hz, 1H), 7.47 (d, J=4.8 Hz, 1H), 4.35 (d, J=10.2 Hz, 1H), 4.29 (d, J=10.2 Hz, 1H), 1.95-1.85 (m, 2H), 1.79-1.70 (m, 1H), 1.56 (s, 3H), 1.09 (d, J=6.5 Hz, 3H), 1.05 (d, J=6.4 Hz, 3H) ppm.

Example 284

(S)-1-(2-chloro-4-(1H-pyrazolo[3,4-b]pyridin-4-yl)phenoxy)-2,4-dimethylpentan-2-amine

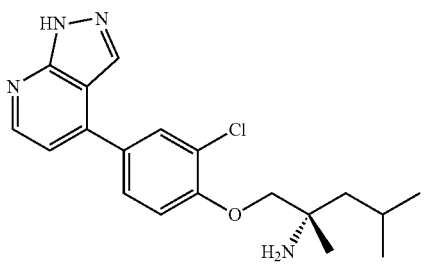

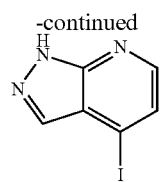

Part A: 4-iodo-1H-pyrazolo[3,4-b]pyridine

To a solution of 2-fluoro-4-iodonicotinaldehyde (0.2 g, 0.797 mmol) in 2-propanol (2 mL) was added hydrazine monohydrate (0.2 mL, 6.37 mmol) and the reaction mixture was heated to 60° C. for 3 h. The reaction mixture was concentrated under reduced pressure. To the residue was added water and ethyl acetate (8 mL). The ethyl acetate layer was separated. The aqueous layer was washed ethyl acetate (2×6 mL). The combined The ethyl acetate layer was washed with brine, dried over $Na_2SO_4$, filtered, and concentrated under reduced pressure to afford 4-iodo-1H-pyrazolo[3,4-b]pyridine (0.150 g, 0.612 mmol, 77% yield) as a off white solid which was taken to next step without purification. LCMS (ESI) m/e 246.0 [(M+H)+, calcd for $C_6H_5IN_3$ 246.0]; LC/MS retention time (method A2): $t_R$=1.65 min.

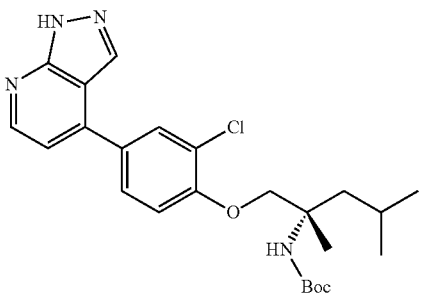 [SMILES: CC(C)C[C@@](C)(COc1ccc(-c2ccnc3[nH]ncc23)cc1Cl)NC(=O)OC(C)(C)C]

Part B: (S)-tert-butyl (1-(2-chloro-4-(1H-pyrazolo[3,4-b]pyridin-4-yl)phenoxy)-2,4-dimethylpentan-2-yl)carbamate A solution of 4-iodo-1H-pyrazolo[3,4-b]pyridine (0.030 g, 0.122 mmol), (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (0.057 g, 0.122 mmol) and potassium phosphate, dibasic (0.043 g, 0.245 mmol) in 1,4-dioxane (6 mL) and water (2 mL) was purged with argon for 10 min. $PdCl_2(dppf)$-$CH_2Cl_2$ adduct (10.00 mg, 0.012 mmol) was added to the reaction mixture under argon and heated to 60° C. for 3 h. The reaction mixture was diluted with ethyl acetate and the organic layer was separated. The aqueous layer was extracted with ethyl acetate (2×5 mL). The ethyl acetate layer was washed with brine, dried over $Na_2SO_4$, filtered, and concentrated under reduced pressure. The crude product was purified by Prep TLC using 40% ethyl acetate in hexane. The required spot was collected, dissolved in 10% methanol in dichloromethane (20 mL), filtered and concentrated under reduced pressure to afford (S)-tert-butyl (1-(2-chloro-4-(1H-pyrazolo[3,4-b]pyridin-4-yl)phenoxy)-2,4-dimethylpentan-2-yl)carbamate (0.032 g, 0.063 mmol, 52% yield) as a pale yellow solid. LCMS (ESI) m/e 459.2

[(M+H)⁺, calcd for $C_{24}H_{32}ClN_4O_3$ 459.2]; LC/MS retention time (method A2): $t_R$=2.16 min.

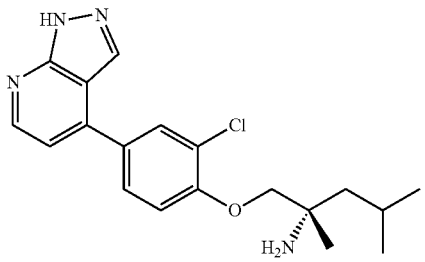

Part C: (S)-1-(2-chloro-4-(1H-pyrazolo[3,4-b]pyridin-4-yl)phenoxy)-2,4-dimethylpentan-2-amine To a solution of (S)-tert-butyl (1-(2-chloro-4-(1H-pyrazolo[3,4-b]pyridin-4-yl)phenoxy)-2,4-dimethylpentan-2-yl)carbamate (0.032 g, 0.063 mmol) in dichloromethane (0.5 mL) cooled to 0° C. was added HCl in 1,4-dioxane (4M) (0.016 mL, 0.063 mmol) and the mixture stirred at 0° C. for 10 min. The reaction mixture was warmed to room temperature and stirred for 3 h. The mixture was concentrated under reduced pressure and to the residue diethyl ether (5 mL) was added and stirred for 30 min. The solvent was separated and the solid was dried under high vacuum to afford (S)-1-(2-chloro-4-(1H-pyrazolo[3,4-b]pyridin-4-yl)phenoxy)-2,4-dimethylpentan-2-amine, 0.5 HCl (0.023 g, 0.059 mmol, 93% yield) as a pale yellow solid. LCMS (ESI) m/e 359.2 [(M+H)⁺, calcd for $C_{19}H_{24}ClN_4O$, 359.2]; LC/MS retention time (Method A1): $t_R$=1.91 min. ¹H NMR (400 MHz, Methanol-d₄): δ 8.67 (d, J=5.2 Hz, 1H), 8.55 (s, 1H), 8.04 (d, J=2.4 Hz, 1H), 7.92 (dd, J=8.4, 2.0 Hz, 1H), 7.51 (d, J=8.6 Hz, 1H), 7.42 (d, J=8.4 Hz, 1H), 4.31-4.23 (m, 2H), 1.98-1.85 (m, 2H), 1.75-1.70 (m, 1H), 1.55 (s, 3H), 1.08-1.03 (m, 6H) ppm.

Example 286

(S)-2-((2-amino-2,4-dimethylpentyl)oxy)-5-(6-chloroimidazo[1,2-b]pyridazin-8-yl)benzonitrile

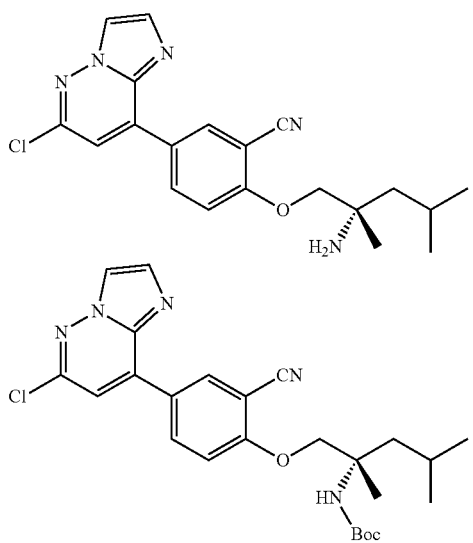

Part A: (S)-tert-butyl (1-(4-(6-chloroimidazo[1,2-b]pyridazin-8-yl)-2-cyanophenoxy)-2,4-dimethylpentan-2-yl)carbamate A solution of 8-bromo-6-chloroimidazo[1,2-b]pyridazine (0.04 g, 0.172 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as described in Example 285) (0.079 g, 0.172 mmol), and potassium phosphate tribasic (2M in water) (0.258 mL, 0.516 mmol) in 1,4-dioxane (0.860 mL) was purged with argon for 5 min. Tetrakis(triphenylphosphine)palladium(0) (9.94 mg, 8.60 μmol) was added to the reaction mixture under argon and the mixture was heated to 100° C. overnight. The reaction mixture was diluted with water (20 mL) and extracted with ethyl acetate (2×30 mL). The ethyl acetate layer was washed with brine, dried over Na₂SO₄, filtered, and concentrated under reduced pressure. The crude product was purified by silica gel chromatography (0-20% of ethyl acetate/hexane) to give (S)-tert-butyl (1-(4-(6-chloroimidazo[1,2-b]pyridazin-8-yl)-2-cyanophenoxy)-2,4-dimethylpentan-2-yl)carbamate (0.055 g, 0.091 mmol, 53% yield) as a yellow solid. LCMS (ESI) m/e 484.2 [(M+H)⁺, calcd for $C_{25}H_{31}ClN_5O_3$ 484.2]; LC/MS retention time (method B): $t_R$=1.18 min.

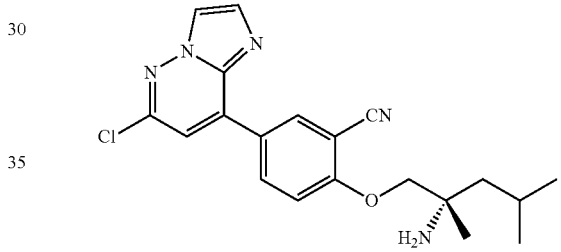

Part B: (S)-2-((2-amino-2,4-dimethylpentyl)oxy)-5-(6-chloroimidazo[1,2-b]pyridazin-8-yl)benzonitrile To a solution of (S)-tert-butyl (1-(4-(6-chloroimidazo[1,2-b]pyridazin-8-yl)-2-cyanophenoxy)-2,4-dimethylpentan-2-yl)carbamate (0.015 g, 0.031 mmol) in dichloromethane (1 mL) cooled to 0° C. was added TFA (0.048 mL, 0.620 mmol). The reaction mixture was allowed to stir for 2 h at room temperature. The mixture was concentrated under reduced pressure. Toluene (3 mL) was added and the mixture concentrated under reduced pressure (repeated 2 more times). The crude material was purified by prep LC/MS (method A) to afford (S)-2-((2-amino-2,4-dimethylpentyl)oxy)-5-(6-chloroimidazo[1,2-b]pyridazin-8-yl)benzonitrile (7.8 mg, 0.020 mmol, 66% yield) as a pale yellow solid. LCMS (ESI) m/e 384.0 [(M+H)⁺, calcd for $C_{20}H_{23}ClN_5O$ 384.2]; LC/MS retention time (method H): $t_R$=1.63 min; LC/MS retention time (method I): $t_R$=1.29 min. ¹H NMR (400 MHz, Methanol-d4): δ 8.66 (d, J=2.3 Hz, 1H), 8.58-8.49 (m, 1H), 8.22 (d, J=1.3 Hz, 1H), 7.87 (d, J=1.3 Hz, 1H), 7.58-7.53 (m, 1H), 7.45 (d, J=8.9 Hz, 1H), 4.27-4.19 (m, 2H), 1.94-1.78 (m, 2H), 1.71-1.63 (m, 1H), 1.45 (s, 3H), 1.10-1.02 (m, 6H) ppm.

Example 287

(S)-2-((2-amino-2,4-dimethylpentyl)oxy)-5-(imidazo[1,2-b]pyridazin-8-yl)benzonitrile

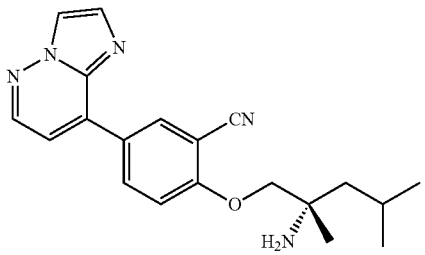 [SMILES: CC(C)C[C@](C)(N)COc1ccc(-c2ccnn3ccnc23)cc1C#N]

To a stirred solution of (S)-tert-butyl (1-(4-(6-chloroimidazo[1,2-b]pyridazin-8-yl)-2-cyanophenoxy)-2,4-dimethylpentan-2-yl)carbamate (prepared as described in Example 286) (0.035 g, 0.072 mmol) in methanol (6 mL) was added palladium on carbon (0.019 g, 0.018 mmol). The mixture was stirred under 1 atm hydrogen gas for 1 h. The reaction mixture was filtered through diatomaceous earth and the diatomaceous earth bed was washed with methanol (25 mL). The filtrate was concentrated under reduced pressure. The crude product was dissolved in dichloromethane (3 mL) and cooled to 0° C. TFA (0.111 mL, 1.446 mmol) was added at 0° C. The reaction mixture was allowed to stir for 4 h at room temperature. The mixture was concentrated under reduced pressure. The crude material was purified by prep LC/MS (method A) to afford (S)-2-((2-amino-2,4-dimethylpentyl)oxy)-5-(imidazo[1,2-b]pyridazin-8-yl)benzonitrile (13 mg, 0.037 mmol, 51% yield) as a pale yellow gummy liquid. LCMS (ESI) m/e 350.2 [(M+H)$^+$, calcd for $C_{20}H_{24}N_5O$ 350.2]; LC/MS retention time (Method F): $t_R$=1.70 min. $^1$H NMR (400 MHz, Methanol-d4): δ 8.57 (d, J=2.3 Hz, 1H), 8.52 (d, J=4.8 Hz, 1H), 8.46 (dd, J=2.4, 8.9 Hz, 1H), 8.23 (d, J=1.3 Hz, 1H), 7.83 (d, J=1.3 Hz, 1H), 7.43-7.39 (m, 2H), 4.13-4.07 (m, 2H), 1.92-1.84 (m, 1H), 1.73-1.57 (m, 2H), 1.35 (s, 3H), 1.06-1.01 (m, 6H) ppm.

Example 288

(S)-1-(2-fluoro-4-(1H-pyrazolo[3,4-b]pyridin-4-yl)phenoxy)-2,4-dimethylpentan-2-amine

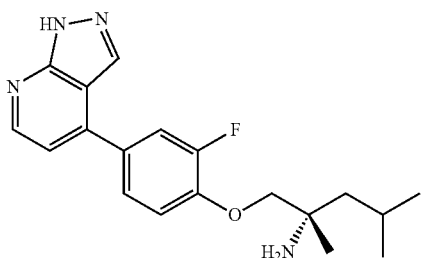

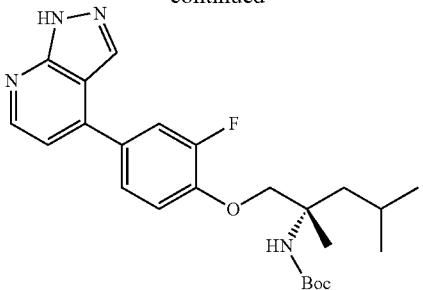

Part A: (S)-Tert-butyl (1-(2-fluoro-4-(1H-pyrazolo[3,4-b]pyridin-4-yl)phenoxy)-2,4-dimethylpentan-2-yl)carbamate To a solution of 4-iodo-1H-pyrazolo[3,4-b]pyridine (prepared as described in Example 284) (0.030 g, 0.122 mmol) in 1,4-dioxane (6 mL) and water (2 mL) was added (S)-tert-butyl (1-(2-fluoro-4-(4,4,5,5-tetramethyl-1,3,2-dioxaborolan-2-yl)phenoxy)-2,4-dimethylpentan-2-yl)carbamate (prepared as in Example 253, Part B) (0.055 g, 0.122 mmol) and potassium phosphate, dibasic (0.043 g, 0.245 mmol). The reaction mixture was purged with argon for 10 min and PdCl$_2$(dppf)-CH$_2$Cl$_2$ adduct (10.00 mg, 0.012 mmol) was added. The reaction mixture was again purged with argon for 10 min and heated for 3 h at 60° C. The reaction mixture was diluted with ethyl acetate and the organic layer was separated. The aqueous layer was extracted with ethyl acetate (2×5 mL). The ethyl acetate layer was washed with water, brine, dried over Na$_2$SO$_4$, filtered, and concentrated under reduced pressure. The crude product was purified by Preparative TLC using 40% EtOAc in hexane. The required spot was collected, dissolved in 10% MeOH in DCM (20 mL), filtered and concentrated under reduced pressure to afford (S)-tert-butyl (1-(2-fluoro-4-(1H-pyrazolo[3,4-b]pyridin-4-yl)phenoxy)-2,4-dimethylpentan-2-yl)carbamate (0.038 g, 0.086 mmol, 70% yield) as a pale yellow solid. LCMS (ESI) m/e 443.2 [(M+H)$^+$, calcd for $C_{24}H_{32}FN_4O_3$ 443.2]; LC/MS retention time (method D): $t_R$=2.13 min.

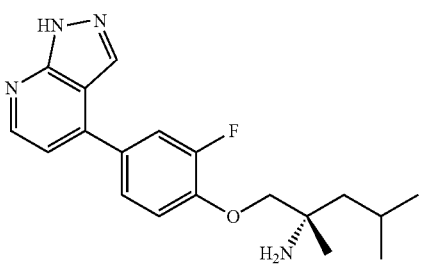 [SMILES: CC(C)C[C@](C)(N)COc1ccc(-c2ccnc3[nH]ncc23)cc1F]

Part B: (S)-1-(2-fluoro-4-(1H-pyrazolo[3,4-b]pyridin-4-yl)phenoxy)-2,4-dimethylpentan-2-amine A solution of (S)-tert-butyl (1-(2-fluoro-4-(1H-pyrazolo[3,4-b]pyridin-4-yl)phenoxy)-2,4-dimethylpentan-2-yl)carbamate (0.038 g, 0.086 mmol) in dichloromethane (0.5 mL) was cooled to 0° C. and HCl in 1,4-dioxane (4M) (0.5 mL, 2.00 mmol) was added. The reaction mixture was stirred at room temperature for 3 h. The reaction mixture was concentrated under reduced pressure. To the residue was added diethyl ether (5 mL) and the mixture stirred for 30 min. The solid formed was collected by vacuum filtration and dried under high vacuum to afford (S)-1-(2-fluoro-4-(1H-pyrazolo[3,4-b]pyridin-4-yl)phenoxy)-2,4-dimethylpentan-2-amine, 1.2 HCl (0.031 g, 0.076 mmol, 88% yield) as a colorless solid. LCMS (ESI) m/e 343.2 [(M+H)+, calcd for $C_{19}H_{24}FN_4O$ 343.2]; LC/MS retention time (method H): $t_R$=1.84 min. $^1$H NMR (400 MHz, METHANOL-$d_4$): δ 8.66 (d, J=5.2 Hz, 1H), 8.51 (s, 1H), 7.81-7.76 (m, 2H), 7.49-7.42 (m, 2H), 4.31-4.20 (m, 2H), 1.91-1.84 (m, 2H), 1.74-1.70 (m, 1H), 1.52 (s, 3H) 1.08-1.04 (m, 6H) ppm.

Example 289

(S)-1-(2-fluoro-4-(1-methyl-1H-pyrazolo[3,4-b]pyridin-4-yl)phenoxy)-2,4-dimethylpentan-2-amine

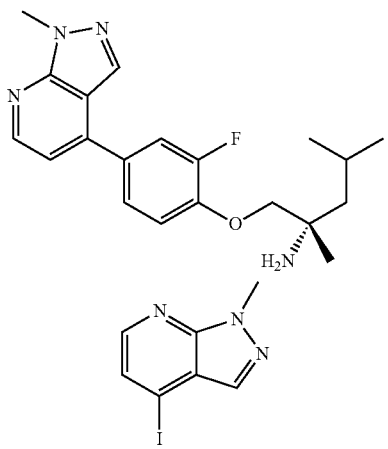

Part A: 4-iodo-1-methyl-1H-pyrazolo[3,4-b]pyridine

A solution of 4-iodo-1H-pyrazolo[3,4-b]pyridine, prepared as described in Example 284 (0.050 g, 0.204 mmol) in DMF (0.5 mL) was cooled to 0° C. and NaH (8.16 mg, 0.204 mmol) was added. The reaction mixture was stirred for 30 min at 0° C. and iodomethane (0.029 g, 0.204 mmol) was added. The reaction mixture was stirred for 10 min at 0° C. and at room temperature for 1 h. The reaction mixture was quenched with ice and diluted with ethyl acetate (5 mL). The organic layer was separated. The aqueous layer was again extracted with ethyl acetate (2×5 mL). The ethyl acetate layer was washed with brine, dried over $Na_2SO_4$, filtered, and concentrated under reduced pressure. The crude material was purified via silica gel chromatography (30% ethyl acetate in hexanes) to afford 4-iodo-1-methyl-1H-pyrazolo[3,4-b]pyridine (0.030 g, 0.114 mmol, 56% yield) as a brown solid. LCMS (ESI) m/e 259.9 [(M+H)+, calcd for $C_7H_7IN_3$ 259.9]; LC/MS retention time (Method C): $t_R$=0.87 min.

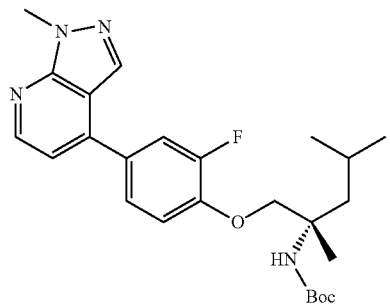 [SMILES: CC(C)C[C@@](C)(COc1ccc(-c2ccnc3c2cnn3C)cc1F)NC(=O)OC(C)(C)C]

Part B: (S)-tert-butyl (1-(2-fluoro-4-(1-methyl-1H-pyrazolo[3,4-b]pyridin-4-yl)phenoxy)-2,4-dimethylpentan-2-yl)carbamate To a solution of 4-iodo-1-methyl-1H-pyrazolo[3,4-b]pyridine (0.030 g, 0.114 mmol) in 1,4-dioxane (6 mL) and water (2 mL) was added (S)-tert-butyl (1-(2-fluoro-4-(4,4,5,5-tetramethyl-1,3,2-dioxaborolan-2-yl)phenoxy)-2,4-dimethylpentan-2-yl)carbamate (prepared as described in Example 285) (0.052 g, 0.114 mmol) and potassium phosphate, dibasic (0.040 g, 0.229 mmol). The reaction mixture was purged with argon for 10 min and $PdCl_2$(dppf)-$CH_2Cl_2$ adduct (9.33 mg, 0.011 mmol) was added. The reaction mixture was again purged with argon for 10 min and heated for 3 h at 60° C. The reaction mixture was filtered through diatomaceous earth and the diatomaceous earth bed was washed with ethyl acetate (2×5 mL). The reaction mixture was purified by Preparative TLC by (30% ethyl acetate in hexanes). The required spot was collected, dissolved in 10% Methanol in DCM (20 mL), filtered and concentrated under reduced pressure to afford (S)-tert-butyl (1-(2-fluoro-4-(1-methyl-1H-pyrazolo[3,4-b]pyridin-4-yl)phenoxy)-2,4-dimethylpentan-2-yl)carbamate (0.042 g, 0.090 mmol, 79% yield) as an off-white solid. LCMS (ESI) m/e 457.2 [(M+H)+, calcd for $C_{25}H_{34}FN_4O_3$ 457.2]; LC/MS retention time (method A2): $t_R$=2.31 min.

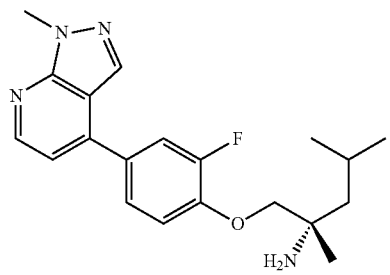 [SMILES: CC(C)C[C@](C)(N)COc1ccc(-c2ccnc3c2cnn3C)cc1F]

Part C: (S)-1-(2-fluoro-4-(1-methyl-1H-pyrazolo[3,4-b]pyridin-4-yl)phenoxy)-2,4-dimethylpentan-2-amine To a solution (S)-tert-butyl (1-(2-fluoro-4-(1-methyl-1H-pyrazolo[3,4-b]pyridin-4-yl)phenoxy)-2,4-dimethylpentan-2-yl)carbamate (0.040 g, 0.086 mmol) in DCM (0.5 mL) at 0° C. was added HCl in 1,4-dioxane (0.6 mL, 19.75 mmol). The reaction mixture was allowed to stir for 1.5 h at room temperature, then was concentrated under reduced pressure. The solid was washed with diethyl ether (5 mL) and lyophilized over 16 h. The crude material was purified by prep LC/MS (method B) to afford (S)-1-(2-fluoro-4-(1-methyl-1H-pyrazolo[3,4-b]pyridin-4-yl)phenoxy)-2,4-dimethylpentan-2-amine (0.0202 g, 0.057 mmol, 66% yield) as a pale yellow solid. LCMS (ESI) m/e 357.2 [(M+H)+, calcd for $C_{20}H_{26}FN_4O$ 357.2]; LC/MS retention time (method H): $t_R$=1.16 min; LC/MS retention time (method I): $t_R$=0.99 min. $^1H$ NMR (400 MHz, METHANOL-$d_4$): δ 8.59 (m, 1H), 8.25 (s, 1H), 7.73-7.68 (m, 2H), 7.42-7.35 (m, 2H), 4.29-4.26 (m, 1H), 4.20-4.24 (m, 1H), 4.18 (s, 3H), 1.86-1.94 (m, 2H), 1.69-1.77 (m, 1H), 1.54 (s, 3H) 1.05 (m, 6H) ppm.

Example 291

2,4-dimethyl-1-(4-(2-methyl-3H-imidazo[4,5-b]pyridin-7-yl)-2-(trifluoromethyl)phenoxy)pentan-2-amine

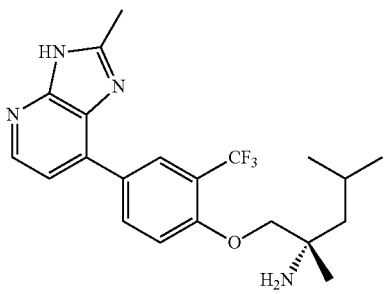

Part A: 7-bromo-2-methyl-3H-imidazo[4,5-b]pyridine

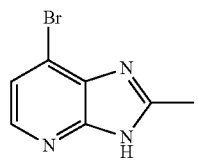

A solution of 4-bromopyridine-2,3-diamine (0.2 g, 1.064 mmol), PPA (0.680 mL, 1.064 mmol) and AcOH (0.061 mL, 1.064 mmol) was heated at 150° C. for 3 h. The reaction mixture was quenched with 10% NaOH solution (18 mL) to maintain pH-14 and extracted with ethyl acetate (15 mL). The ethyl acetate layer was washed with sat $K_2CO_3$ solution (5 mL), brine, dried over $Na_2SO_4$, filtered, and concentrated under reduced pressure to afford 7-bromo-2-methyl-3H-imidazo[4,5-b]pyridine (0.170 g, 0.801 mmol, 75% yield) as a pale yellow solid. LCMS (ESI) m/e 212.0 (bromo pattern) [(M+H)+, calcd for $C_7H_7BrN_3$ 212.0]; LC/MS retention time (method A2): $t_R$=1.35 min.

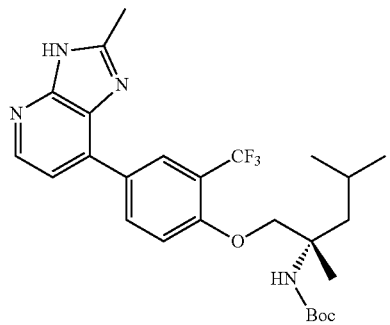 [SMILES: Cc1nc2c(-c3ccc(OC[C@](C)(CC(C)C)NC(=O)OC(C)(C)C)c(C(F)(F)F)c3)ccnc2[nH]1]

Part B. (S)-tert-butyl (2,4-dimethyl-1-(4-(2-methyl-3H-imidazo[4,5-b]pyridin-7-yl)-2-(trifluoromethyl)phenoxy)pentan-2-yl)carbamate A solution of 7-bromo-2-methyl-3H-imidazo[4,5-b]pyridine (0.030 g, 0.141 mmol), (S)-tert-butyl(2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 290) (0.071 g, 0.141 mmol) and potassium phosphate, dibasic (0.049 g, 0.283 mmol) in 1,4-dioxane (6 mL) and water (2 mL) was purged with argon for 20 min and $PdCl_2$(dppf)-$CH_2Cl_2$ adduct (0.012 g, 0.014 mmol) was added. The reaction mixture was again purged with argon for 10 min and heated for 19 h at 60° C. The reaction mixture was cooled to room temperature and was diluted with ethyl acetate (10 mL) The organic layer was separated the aqueous layer was extracted with ethyl acetate (2×4 mL). The combined organic layers were washed with brine, dried over $Na_2SO_4$, filtered, and concentrated under reduced pressure. The residue was purified by Preparative TLC using 3% methanol in dichloromethane. The required spot was collected, dissolved 15% methanol in dichloromethane (30 mL), filtered and concentrated under reduced pressure to afford (S)-tert-butyl (2,4-dimethyl-1-(4-(2-methyl-3H-imidazo[4,5-b]pyridin-7-yl)-2-(trifluoromethyl)phenoxy)pentan-2-yl)carbamate (0.035 g, 0.039 mmol, 27% yield) as a yellow solid. LCMS (ESI) m/e 507.2 [(M+H)+, calcd for $C_{26}H_{34}F_3N_4O_3$ 507.2]; LC/MS retention time (method B): $t_R$=1.01 min.

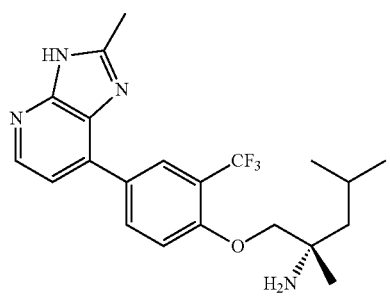 [SMILES: Cc1nc2c(-c3ccc(OC[C@@](C)(N)CC(C)C)c(C(F)(F)F)c3)ccnc2[nH]1]

Part C. (S)-2,4-dimethyl-1-(4-(2-methyl-3H-imidazo[4,5-b]pyridin-7-yl)-2-(trifluoromethyl)phenoxy)pentan-2-amine To a solution (S)-tert-butyl (2,4-dimethyl-1-(4-(2-methyl-3H-imidazo[4,5-b]pyridin-7-yl)-2-(trifluoromethyl)phenoxy)pentan-2-yl)carbamate (0.030 g, 0.033 mmol) in dichloromethane (0.5 mL) at 0° C. was added HCl in 1,4-dioxane (4M) (0.5 mL, 2.000 mmol) and the reaction mixture was allowed to stir at 0° C. for 10 min. The reaction mixture was allowed to stir for 1 h at room temperature, then was concentrated under reduced pressure. The crude material was purified by prep LC/MS (method B) to afford (S)-2,4-dimethyl-1-(4-(2-methyl-3H-imidazo[4,5-b]pyridin-7-yl)-2-(trifluoromethyl)phenoxy)pentan-2-amine (0.0045 g, 10.98 μmol, 33% yield) as a pale yellow solid. LCMS (ESI) m/e 407.0 [(M+H)$^+$, calcd for $C_{21}H_{26}F_3N_4O$ 407.2]; LC/MS retention time (method H): $t_R$=1.37 min; LC/MS retention time (method I): $t_R$=0.93 min. $^1$H NMR (400 MHz, MeOD): δ 8.44 (d, J=2.00 Hz, 1H), 8.36 (m, 1H), 8.07 (d, J=8.80 Hz, 1H), 7.92 (d, J=8.40 Hz, 1H), 7.39 (d, J=8.40 Hz, 1H), 4.26 (m, 2H), 2.75 (s, 3H), 1.86-1.90 (m, 2H), 1.71-1.75 (m, 1H), 1.53 (s, 3H), 1.06 (d, J=6.40 Hz, 3H), 1.02 (d, J=6.00 Hz, 3H) ppm.

Example 292

(S)-1-(4-(1H-pyrazolo[3,4-b]pyridin-4-yl)-2-(trifluoromethyl)phenoxy)-2,4-dimethylpentan-2-amine

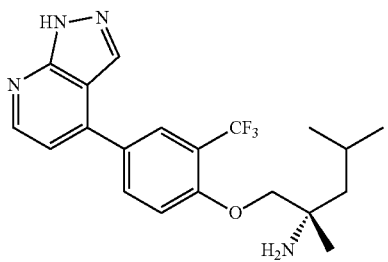 [SMILES: CC(C)C[C@](C)(N)COc1ccc(-c2ccnc3[nH]ncc23)cc1C(F)(F)F]

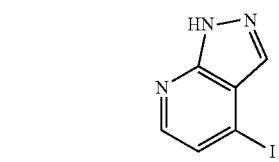

Part A: 4-iodo-1H-pyrazolo[3,4-b]pyridine

To a solution of 2-fluoro-4-iodonicotinaldehyde (0.2 g, 0.797 mmol) in 2-propanol (2 mL), hydrazine monohydrate (0.2 mL, 6.37 mmol) was added and the reaction mixture was heated at 60° C. for 3 h. The reaction mixture was concentrated under reduced pressure and the residue was diluted with ethyl acetate (8 mL) and water. The ethyl acetate layer was separated and the aqueous layer was again extracted with ethyl acetate (2×6 mL). The ethyl acetate layer was washed with brine, dried over Na$_2$SO$_4$, filtered, and concentrated under reduced pressure to afford 4-iodo-1H-pyrazolo[3,4-b]pyridine (0.117 g, 0.478 mmol, 60% yield) as an off-white solid. LCMS (ESI) m/e 246.0 [(M+H)$^+$, calcd for $C_6H_5IN_3$ 246.0]; LC/MS retention time (Method A1): $t_R$=1.56 min.

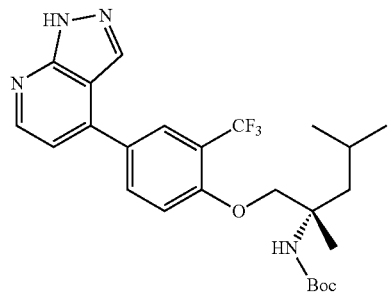 [SMILES: CC(C)C[C@@](C)(COc1ccc(-c2ccnc3[nH]ncc23)cc1C(F)(F)F)NC(=O)OC(C)(C)C]

Part B: (S)-tert-butyl (1-(4-(1H-pyrazolo[3,4-b]pyridin-4-yl)-2-(trifluoromethyl)phenoxy)-2,4-dimethylpentan-2-yl)carbamate To a solution of 4-iodo-1H-pyrazolo[3,4-b]pyridine (0.030 g, 0.122 mmol) in 1,4-dioxane (6 mL) and water (2 mL), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.061 g, 0.122 mmol) and potassium phosphate, dibasic (0.043 g, 0.244 mmol) was added. The reaction mixture was purged with argon for 10 min and PdCl$_2$(dppf)-CH$_2$Cl$_2$ adduct (9.98 mg, 0.012 mmol) was added. The reaction mixture was again purged with argon for 10 min and heated for 4 h at 60° C. The reaction mixture was diluted with ethyl acetate (10 mL) and the aqueous layer was washed with ethyl acetate (2×8 mL). The ethyl acetate layer was washed with brine, dried over Na$_2$SO$_4$, filtered, and concentrated under reduced pressure. The reaction mixture was purified by Preparative TLC by 70% ethyl acetate in hexanes. The required spot was collected, dissolved 15% MeOH in DCM (20 mL), filtered and concentrated under reduced pressure to afford (S)-tert-butyl (1-(4-(1H-pyrazolo[3,4-b]pyridin-4-yl)-2-(trifluoromethyl)phenoxy)-2,4-dimethylpentan-2-yl)carbamate (0.031 g, 0.058 mmol, 47% yield) as an off-white solid. LCMS (ESI) m/e 493.2 [(M+H)$^+$, calcd for $C_{25}H_{32}F_3N_4O_3$ 493.2]; LC/MS retention time (method B): $t_R$=1.11 min.

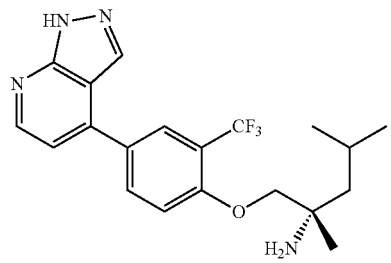

Part C: (S)-1-(4-(1H-pyrazolo[3,4-b]pyridin-4-yl)-2-(trifluoromethyl)phenoxy)-2,4-dimethylpentan-2-amine To a solution (S)-tert-butyl (1-(4-(1H-pyrazolo[3,4-b]pyridin-4-yl)-2-(trifluoromethyl)phenoxy)-2,4-dimethylpentan-2-yl)carbamate (0.030 g, 0.056 mmol) in DCM (0.5 mL) at 0° C. was added HCl in 1,4-dioxane (0.5 μL, 0.016 mmol) and the reaction mixture was allowed to stir at 0° C. for 10 min. The reaction mixture was allowed to stir for 1 h at room temperature, then was concentrated under reduced pressure. The crude material was purified by prep LC/MS (method A) to afford (S)-1-(4-(1H-pyrazolo[3,4-b]pyridin-4-yl)-2-(trifluoromethyl)phenoxy)-2,4-dimethylpentan-2-amine (0.0055 g, 0.013 mmol, 24% yield). LCMS (ESI) m/e 393.0 [(M+H)+, calcd for $C_{20}H_{24}F_3N_4O$ 393.2]; LC/MS retention time (method H): $t_R$=1.43 min; LC/MS retention time (method I): $t_R$=1.06 min. $^1$H NMR (400 MHz, MeOD): δ 8.58 (d, J=4.80 Hz, 1H), 8.27 (s, 1H), 8.13 (m, 1H), 8.07 (d, J=2.00 Hz, 1H), 7.42 (d, J=8.80 Hz, 1H), 7.38 (d, J=4.80 Hz, 1H), 4.04 (m, 2H), 1.81-1.91 (m, 1H), 1.54-1.66 (m, 2H), 1.31 (s, 3H), 1.01 (m, 6H) ppm.

Example 293

(S)-2-((2-amino-2,4-dimethylpentyl)oxy)-5-(2-methyl-3H-imidazo[4,5-b]pyridin-7-yl)benzonitrile

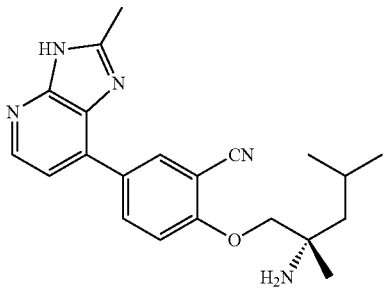

Part A. 7-bromo-2-methyl-3H-imidazo[4,5-b]pyridine

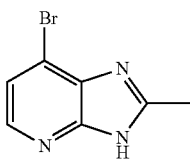

A solution of 4-bromopyridine-2,3-diamine (0.2 g, 1.064 mmol), PPA (0.680 mL, 1.064 mmol) and AcOH (0.061 mL, 1.064 mmol) was heated at 150° C. for 3 h. The reaction mixture was quenched with 10% NaOH solution (18 mL) to maintain pH-14 and extracted with ethyl acetate (15 mL). The ethyl acetate layer was washed with saturated $K_2CO_3$ solution (5 mL), brine, dried over $Na_2SO_4$, filtered, and concentrated under reduced pressure to afford 7-bromo-2-methyl-3H-imidazo[4,5-b]pyridine (0.170 g, 0.801 mmol, 75% yield) as a pale yellow solid. LCMS (ESI) m/e 212.0 (bromo pattern) [(M+H)+, calcd for $C_7H_7BrN_3$ 212.0]; LC/MS retention time (method A2): $t_R$=1.35 min.

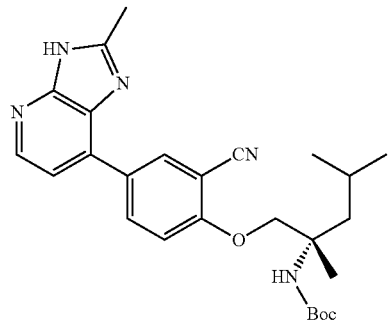 [SMILES: Cc1nc2c(-c3ccc(OC[C@](C)(CC(C)C)NC(=O)OC(C)(C)C)c(C#N)c3)ccnc2[nH]1]

Part B. (S)-tert-butyl (1-(2-cyano-4-(2-methyl-3H-imidazo[4,5-b]pyridin-7-yl)phenoxy)-2,4-dimethylpentan-2-yl)carbamate To a solution of 7-bromo-2-methyl-3H-imidazo[4,5-b]pyridine (0.030 g, 0.141 mmol) in 1,4-dioxane (6 mL) and water (2 mL) was added (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as described in Example 285) (0.065 g, 0.141 mmol) and potassium phosphate, dibasic (0.049 g, 0.283 mmol). The reaction mixture was purged with argon for 30 min and $PdCl_2(dppf)$-$CH_2Cl_2$ adduct (0.012 g, 0.014 mmol) was added. The reaction mixture was again purged with argon for 10 min and heated for 16 h at 100° C. The reaction mixture was diluted with ethyl acetate (10 mL) and the organic layer was separated. The aqueous layer was again extracted with ethyl acetate (2×8 mL). The combined ethyl acetate layers were washed with brine, dried over $Na_2SO_4$, filtered, and concentrated under reduced pressure. The crude product was purified by Preparative TLC by (70% ethyl acetate in hexanes). The required spot was collected, dissolved in 15% Methanol in dichloromethane (20 mL), filtered, and concentrated under reduced pressure to afford the (S)-tert-butyl (1-(2-cyano-4-(2-methyl-3H-imidazo[4,5-b]pyridin-7-yl)phenoxy)-2,4-dimethylpentan-2-yl)carbamate (0.040 g, 0.081 mmol, 57% yield) as a pale yellow solid. LCMS (ESI) m/e 464.3 [(M+H)+, calcd for $C_{26}H_{34}N_5O_3$ 464.3]; LC/MS retention time (method B): $t_R$=0.95 min.

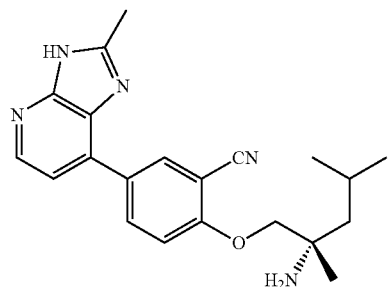

Part C: (S)-2-((2-amino-2,4-dimethylpentyl)oxy)-5-(2-methyl-3H-imidazo[4,5-b]pyridin-7-yl)benzonitrile To a solution of (S)-tert-butyl (1-(2-cyano-4-(2-methyl-3H-imidazo[4,5-b]pyridin-7-yl)phenoxy)-2,4-dimethylpentan-2-yl)carbamate (0.040 g, 0.081 mmol) in DCM (1 mL)

at 0° C. was added HCl in 1,4-dioxane (0.8 mL, 3.20 mmol). The reaction mixture was allowed to stir for 1 h at room temperature, then concentrated under reduced pressure. The solid residue was washed with diethyl ether (5 mL) and dried under vacuum to afford (S)-2-((2-amino-2,4-dimethylpentyl)oxy)-5-(2-methyl-3H-imidazo[4,5-b]pyridin-7-yl)benzonitrile, 1.5 HCl (0.032 g, 0.074 mmol, 91% yield) as a brown solid. LCMS (ESI) m/e 364.2 [(M+H)$^+$, calcd for $C_{21}H_{26}N_5O$ 364.2]; LC/MS retention time (Method A1): $t_R$=2.28 min. $^1$H NMR (300 MHz, MeOD): δ 8.51-8.45 (m, 2H), 8.20 (d, J=8.7 Hz, 1H), 8.08 (d, J=8.7 Hz, 1H), 7.43 (d, J=8.7 Hz, 1H), 4.32 (m, 2H), 2.87 (s, 3H), 1.87-1.99 (m, 2H), 1.70-1.76 (m, 1H), 1.29 (s, 3H), 1.05 (m, 6H) ppm.

Example 294

(S)-2,4-dimethyl-1-(2-methyl-4-(2-methyl-3H-imidazo[4,5-b]pyridin-7-yl)phenoxy)pentan-2-amine

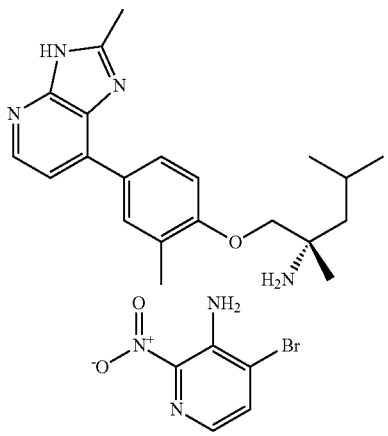

Part A. 4-bromo-2-nitropyridin-3-amine

To a solution of 2-nitropyridin-3-amine (4 g, 28.8 mmol) in AcOH (40 mL) was added potassium acetate (2.82 g, 28.8 mmol) and the mixture stirred for 1 h at room temperature. Br$_2$ (1.481 mL, 28.8 mmol) was added slowly to the reaction mixture and the mixture stirred at room temperature for 16 h. The solid formed was collected by vacuum filtration, washed with diethyl ether (2×10 mL) and dried under high vacuum to afford 4-bromo-2-nitropyridin-3-amine (6 g, 27.5 mmol, 96% yield) as a yellow solid. LCMS (ESI) m/e 218.0 [(M+H)$^+$, calcd for $C_5H_5BrN_3O_2$ 218.0]; LC/MS retention time (method B): $t_R$=0.61 min.

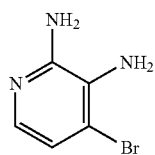

Part B: 4-bromopyridine-2,3-diamine

To a solution of 4-bromo-2-nitropyridin-3-amine (2 g, 9.16 mmol) in ethanol (60 mL) and water (25 mL) was added tin (II) chloride (8.69 g, 45.8 mmol) and the reaction mixture was heated at 80° C. for 4.5 h. The reaction mixture was concentrated under reduced pressure, diluted with ethyl acetate (25 mL) and filtered through diatomaceous earth to remove the emulsion. The ethyl acetate layer was separated and the aqueous layer was again extracted with ethyl acetate (2×15 mL). The combined organic extracts were washed with brine, dried over Na$_2$SO$_4$, filtered, and concentrated under reduced pressure. The residue was washed with n-hexane(15 mL) to remove the color impurities to afford 4-bromopyridine-2,3-diamine (0.9 g, 4.44 mmol, 49% yield) as a black solid. LCMS (ESI) m/e 188.0 (bromo pattern) [(M+H)$^+$, calcd for $C_5H_7BrN_3$ 188.0]; LC/MS retention time (Method A1): $t_R$=1.90 min.

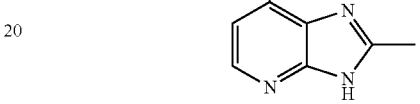

Part C: 7-bromo-2-methyl-3H-imidazo[4,5-b]pyridine

A mixture of 4-bromopyridine-2,3-diamine (0.9 g, 4.44 mmol), PPA (0.680 mL, 4.44 mmol) in AcOH (0.254 mL, 4.44 mmol) was heated at 150° C. for 3 h. At room temperature the reaction mixture was basified with 10% NaOH solution(20 mL) and extracted with ethyl acetate. The ethyl acetate layer was washed with saturated K$_2$CO$_3$(10 mL) solution, brine, dried over Na$_2$SO$_4$, filtered, and concentrated under reduced pressure to afford a solid. The solid was washed with n-hexane(15 mL) and dried the solid under high vacuum to afford 7-bromo-2-methyl-3H-imidazo[4,5-b]pyridine (0.540 g, 2.53 mmol, 57% yield) as a pale yellow color solid. LCMS (ESI) m/e 212.0 (bromo pattern) [(M+H)$^+$, calcd for $C_7H_7BrN_3$ 212.0]; LC/MS retention time (Method A1): $t_R$=2.07 min.

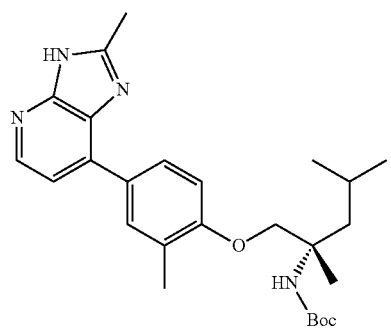 [SMILES: Cc1nc2c(-c3ccc(OC[C@](C)(CC(C)C)NC(=O)OC(C)(C)C)c(C)c3)ccnc2[nH]1]

Part D: (S)-tert-butyl (2,4-dimethyl-1-(2-methyl-4-(2-methyl-3H-imidazo[4,5-b]pyridin-7-yl)phenoxy)pentan-2-yl)carbamate To a solution of 7-bromo-2-methyl-3H-imidazo[4,5-b]pyridine (0.030 g, 0.140 mmol) in 1,4-dioxane (6 mL) and water(2 mL) was added (S)-tert-butyl(2,4-dimethyl-1-(2-methyl-4-(4,4,5,5-tetramethyl-1,3,2-dioxaborolan-2-yl)phenoxy)pentan-2-yl)carbamate (prepared as described in Example 285) (0.069 g, 0.154 mmol) and potassium phosphate, dibasic (0.073 g, 0.421 mmol). The reaction mixture was purged with argon for 30 min and PdCl₂(dppf)-CH₂Cl₂ adduct (0.011 g, 0.014 mmol) was added. The reaction mixture was again purged with argon for 10 min and heated for 3 h at 100° C. The reaction mixture was diluted with ethyl acetate (8 mL) and the organic layer was separated. The aqueous layer was again extracted with ethyl acetate (2×5 mL). The ethyl acetate layer was washed with brine, dried over Na₂SO₄, filtered, and concentrated under reduced pressure. The crude product was purified by Preparative TLC by (70% ethyl acetate in hexanes). The required spot was collected, dissolved in 15% methanol in dichloromethane (30 mL), filtered and concentrated under reduced pressure. The residue was washed with diethyl ether (4 mL) and dried under high vacuum to afford (S)-tert-butyl (2,4-dimethyl-1-(2-methyl-4-(2-methyl-3H-imidazo[4,5-b]pyridin-7-yl)phenoxy)pentan-2-yl)carbamate (0.040 g, 0.066 mmol, 47% yield) as a colorless solid. LCMS (ESI) m/e 453.3 [(M+H)⁺, calcd for $C_{26}H_{37}N_4O_3$ 453.3]; LC/MS retention time (method B): $t_R$=0.98 min.

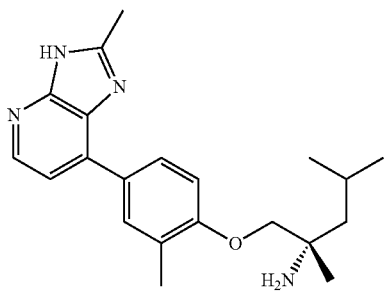 [SMILES: Cc1nc2c(-c3ccc(OC[C@@](C)(N)CC(C)C)c(C)c3)ccnc2[nH]1]

Part E: (S)-2,4-dimethyl-1-(2-methyl-4-(2-methyl-3H-imidazo[4,5-b]pyridin-7-yl)phenoxy)pentan-2-amine To a solution of (S)-tert-butyl (2,4-dimethyl-1-(2-methyl-4-(2-methyl-3H-imidazo[4,5-b]pyridin-7-yl)phenoxy)pentan-2-yl)carbamate (0.040 g, 0.066 mmol) in dichloromethane (0.8 mL) at 0° C. was added HCl in 1,4-dioxane (0.8 mL, 3.20 mmol) and stirred at 0° C. for 5 min. The reaction mixture was allowed to stir for 1 h at room temperature, then was concentrated under reduced pressure. The crude material was purified by prep LC/MS (method B) to afford (S)-2,4-dimethyl-1-(2-methyl-4-(2-methyl-3H-imidazo[4,5-b]pyridin-7-yl)phenoxy)pentan-2-amine, 2 TFA (0.015 g, 0.028 mmol, 42% yield) as a pale yellow solid. LCMS (ESI) m/e 353.2 [(M+H)⁺, calcd for $C_{21}H_{29}N_4O$ 353.2]; LC/MS retention time (method H): $t_R$=1.08 min; LC/MS retention time (method I): $t_R$=0.83 min. ¹H NMR (400 MHz, MeOD): δ 8.09 (d, J=8.40 Hz, 1H), 7.91-7.96 (m, 3H), 7.10 (d, J=8.40 Hz, 1H), 4.18 (m, J=10.40 Hz, 1H), 4.11 (d, J=10.40 Hz, 1H), 2.80 (s, 3H), 2.41 (s, 3H), 1.86-1.94 (m, 2H), 1.68-1.73 (m, 1H), 1.53 (s, 3H), 1.07 (d, J=6.40 Hz, 3H), 1.03 (d, J=6.40 Hz, 3H) ppm.

Example 295

(S)-1-(4-(2-(methoxymethyl)-3H-imidazo[4,5-b]pyridin-7-yl)-2-(trifluoromethyl)phenoxy)-2,4-dimethylpentan-2-amine

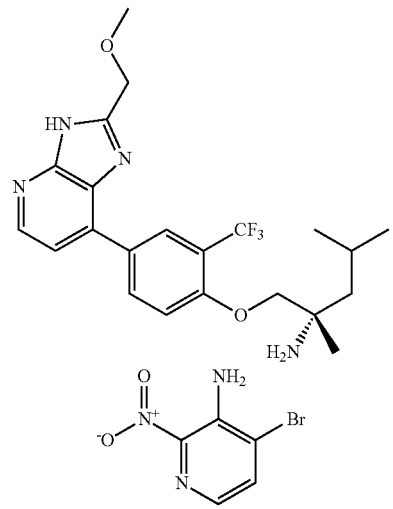

Part A. 4-bromo-2-nitropyridin-3-amine

To a solution of 2-nitropyridin-3-amine (4 g, 28.8 mmol) in AcOH (40 mL) was added potassium acetate (2.82 g, 28.8 mmol) and stirred for 1 h at room temperature. Br₂ (1.481 mL, 28.8 mmol) was added slowly to the reaction mixture and stirred at room temperature for 16 h. The solid formed was filtered, washed with diethyl ether (2×10 mL) and dried under high vacuum to afford 4-bromo-2-nitropyridin-3-amine (6 g, 27.5 mmol, 96% yield) as a yellow solid. LCMS (ESI) m/e 217.9 [(M+H)⁺, calcd for $C_5H_5BrN_3O_2$ 217.9]; LC/MS retention time (method B): $t_R$=0.67 min.

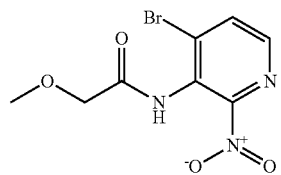

Part B.
N-(4-bromo-2-nitropyridin-3-yl)-2-methoxyacetamide

A solution of 4-bromo-2-nitropyridin-3-amine (0.550 g, 2.52 mmol) in Pyridine (1 mL) was cooled to 0° C. 2-methoxyacetyl chloride (0.410 g, 3.78 mmol) was added to the reaction mixture and the mixture stirred for 15 min at 0° C. The reaction mixture was stirred at room temperature for 6 h. The reaction mixture was concentrated under reduced pressure. The residue was diluted with water (10 mL) and ethyl acetate (1 mL). The organic layer was separated. The aqueous layer was extracted with ethyl acetate (2×8 mL). The combined ethyl acetate layers were washed with brine, dried over Na₂SO₄, filtered, and concentrated under reduced pressure. The crude product was purified via silica gel chromatography (100% ethyl acetate in hexane) to N-(4-bromo-2-nitropyridin-3-yl)-2-methoxyacetamide (0.3 g, 1.013 mmol, 40% yield) as a yellow color solid. LCMS (ESI) m/e 290.0 (bromo pattern) [(M+H)+, calcd for $C_8H_9BrN_3O_4$ 290.0]; LC/MS retention time (Method A1): $t_R$=2.35 min.

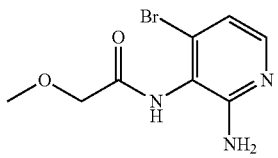

Part C: N-(2-amino-4-bromopyridin-3-yl)-2-methoxyacetamide

To a solution of N-(4-bromo-2-nitropyridin-3-yl)-2-methoxyacetamide (0.050 g, 0.169 mmol) in methanol (1.5 mL), water (0.5 mL) mixture, iron (0.075 g, 1.350 mmol) was added followed by ammonium chloride (0.090 g, 1.688 mmol) and the reaction mixture was stirred at 80° C. for 4 h. The reaction mixture was filtered through diatomaceous earth and the diatomaceous earth bed was washed with 10% methanol in dichloromethane (10 mL). The filtrate was concentrated under reduced pressure and water (10 mL) was added to the residue. The compound was extracted with ethyl acetate (2×8 mL). The ethyl acetate layer was washed with brine, dried over $Na_2SO_4$, filtered, and concentrated under reduced pressure. The solid obtained was washed with diethyl ether (5 mL) to afford N-(2-amino-4-bromopyridin-3-yl)-2-methoxyacetamide (0.030 g, 0.115 mmol, 68% yield) as a brown solid LCMS (ESI) m/e 260.0 (bromo pattern) [(M+H)+, calcd for $C_8H_{11}BrN_3O_2$ 260.0]; LC/MS retention time (Method A1): $t_R$=1.49 min.

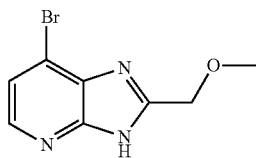

Part D: 7-bromo-2-(methoxymethyl)-3H-imidazo[4,5-b]pyridine

A mixture of N-(2-amino-4-bromopyridin-3-yl)-2-methoxyacetamide (0.165 g, 0.621 mmol) CsF (0.9 g, 5.92 mmol) and N,N-dimethylformamide (15 mL) was taken in a sealed tube and heated at 130° C. for 16 h. The reaction mixture was quenched with chilled water (15 mL) and extracted with ethyl acetate (15 mL). The organic layer was separated and the aqueous layer was again extracted with ethyl acetate (2×10 mL). The combined ethyl acetate layers were washed with water (20 mL), brine, dried over $Na_2SO_4$, filtered, and concentrated under reduced pressure. The solid was washed with hexane (2×5 mL) to afford 7-bromo-2-(methoxymethyl)-3H-imidazo[4,5-b]pyridine (0.1 g, 0.397 mmol, 64% yield) as a brown solid. LCMS (ESI) m/e 242.0 [(M+H)+, calcd for $C_8H_9BrN_3O$ 242.0]; LC/MS retention time (method B): $t_R$=0.52 min.

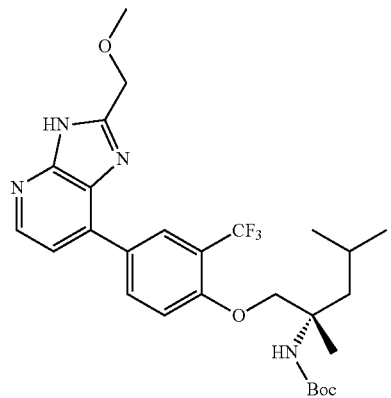 [SMILES: COCc1nc2c(-c3ccc(OC[C@](C)(CC(C)C)NC(=O)OC(C)(C)C)c(C(F)(F)F)c3)ccnc2[nH]1]

Part E: (S)-tert-butyl (1-(4-(2-(methoxymethyl)-3H-imidazo[4,5-b]pyridin-7-yl)-2-(trifluoromethyl)phenoxy)-2,4-dimethylpentan-2-yl)carbamate To a solution of 7-bromo-2-(methoxymethyl)-3H-imidazo[4,5-b]pyridine (0.025 g, 0.099 mmol) in 1,4-dioxane (6 mL) and water (2 mL) was added (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.055 g, 0.109 mmol) and potassium phosphate, dibasic (0.052 g, 0.298 mmol). The reaction mixture was purged with argon for 30 min and $PdCl_2(dppf)-CH_2Cl_2$ adduct (8.10 mg, 9.92 µmol) was added. The reaction mixture was again purged with argon for 10 min and heated for 16 h at 100° C. The reaction mixture was diluted with ethyl acetate (8 mL) and the organic layer was separated. The aqueous layer was again extracted with ethyl acetate (2×5 mL). The combined ethyl acetate layers were washed with brine, dried over $Na_2SO_4$, filtered, and concentrated under reduced pressure. The crude product was purified by Prep TLC (70% ethyl acetate in hexanes). The required spot was collected, dissolved in 15% methanol in dichloromethane (30 mL), filtered and concentrated under reduced pressure. The residue was washed with diethyl ether (4 mL) and dried under high vacuum to afford (S)-tert-butyl (1-(4-(2-(methoxymethyl)-3H-imidazo[4,5-b]pyridin-7-yl)-2-(trifluoromethyl)phenoxy)-2,4-dimethylpentan-2-yl)carbamate (0.030 g, 0.056 mmol, 56% yield) as an off-white solid. LCMS (ESI) m/e 537.3 [(M+H)+, calcd for $C_{27}H_{36}F_3N_4O_4$ 537.3]; LC/MS retention time (method B): $t_R$=1.05 min.

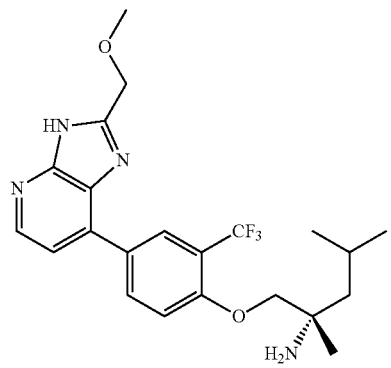 [SMILES: COCc1nc2c(-c3ccc(OC[C@@](C)(N)CC(C)C)c(C(F)(F)F)c3)ccnc2[nH]1]

Part F: (S)-1-(4-(2-(methoxymethyl)-3H-imidazo[4,5-b]pyridin-7-yl)-2-(trifluoromethyl)phenoxy)-2,4-dimethylpentan-2-amine To a solution of (S)-tert-butyl (1-(4-(2-(methoxymethyl)-3H-imidazo[4,5-b]pyridin-7-yl)-2-(trifluoromethyl)phenoxy)-2,4-dimethylpentan-2-yl)carbamate (0.030 g, 0.056 mmol) in dichloromethane (1 mL) at 0° C. was added TFA (0.6 mL, 7.79 mmol). The reaction mixture was allowed to stir for 2 h at room temperature, then was concentrated under reduced pressure. To the residue was added water (2 mL). The solution was cooled to 0° C. then basified with saturated NaHCO$_3$ solution (8 mL) and extracted with ethyl acetate (2×6 mL). The ethyl acetate layer was washed with water, brine, dried over Na$_2$SO$_4$, filtered, and concentrated under reduced pressure to afford the crude product. The crude product was washed with diethyl ether (2 mL) to afford (S)-1-(4-(2-(methoxymethyl)-3H-imidazo[4,5-b]pyridin-7-yl)-2-(trifluoromethyl)phenoxy)-2,4-dimethylpentan-2-amine (0.020 g, 0.046 mmol, 82% yield) as an off-white solid. LCMS (ESI) m/e 437.2 [(M+H)$^+$, calcd for C$_{22}$H$_{28}$F$_3$N$_4$O$_2$ 437.2]; LC/MS retention time (Method A1): t$_R$=2.13 min. $^1$H NMR (400 MHz, METHANOL-d$_4$): δ 8.40 (d, J=2.01 Hz, 1H), 8.30 (dd, J=8.78, 2.26 Hz, 1H) 8.03 (d, J=8.53 Hz, 1H), 7.81 (d, J=8.53 Hz, 1H), 7.29 (d, J=8.53 Hz, 1H), 4.76 (s, 2H), 3.94-4.01 (m, 2H), 3.53 (s, 3H), 1.85 (dt, J=12.80, 6.15 Hz, 1H), 1.51-1.63 (m, 2H), 1.28 (s, 3H), 1.01 (m, 6H) ppm.

Example 296

(S)-1-(4-(2-(methoxymethyl)-3H-imidazo[4,5-b]pyridin-7-yl)-2-methylphenoxy)-2,4-dimethylpentan-2-amine

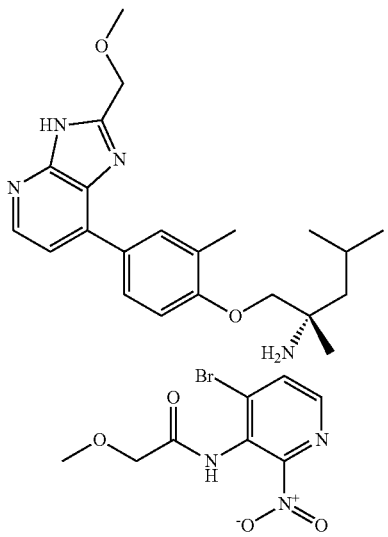

Part A:
N-(4-bromo-2-nitropyridin-3-yl)-2-methoxyacetamide

A solution of 4-bromo-2-nitropyridin-3-amine (0.550 g, 2.52 mmol) in pyridine (1 mL) was cooled to 0° C. and 2-methoxyacetyl chloride (0.410 g, 3.78 mmol) was added. The reaction mixture was stirred for 15 min at 0° C. and at room temperature for 6 h. The reaction mixture was concentrated by high vacuum and the residue was diluted with water (10 mL) and ethyl acetate (1 mL). The organic layer was separated and the aqueous layer was again extracted with ethyl acetate (2×8 mL). The ethyl acetate layer was washed with brine, dried over Na$_2$SO$_4$, filtered, and concentrated under reduced pressure. The crude product was purified via silica gel chromatography (100% ethyl acetate in hexane) to afford N-(4-bromo-2-nitropyridin-3-yl)-2-methoxyacetamide (0.3 g, 1.013 mmol, 40% yield) as a yellow solid. LCMS (ESI) m/e 290.0 (bromo pattern) [(M+H)$^+$, calcd for C$_8$H$_9$BrN$_3$O$_4$ 290.0]; LC/MS retention time (Method A1): t$_R$=2.35 min.

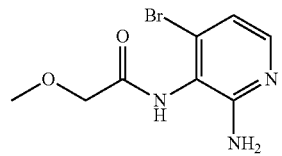

Part B:
N-(2-amino-4-bromopyridin-3-yl)-2-methoxyacetamide

To a solution of N-(4-bromo-2-nitropyridin-3-yl)-2-methoxyacetamide (0.050 g, 0.169 mmol) in methanol (1.5 mL) water (0.5 mL) mixture was added iron (0.075 g, 1.350 mmol) followed by ammonium chloride (0.090 g, 1.688 mmol) and the reaction mixture was stirred at 80° C. for 4 h. The reaction mixture was filtered through diatomaceous earth and the diatomaceous earth bed was washed with 10% methanol in dichloromethane (10 mL). The filtrate was concentrated under reduced pressure and water (10 mL) was added to the residue. The compound was extracted with ethyl acetate (2×8 mL). The ethyl acetate layer was washed with brine, dried over Na$_2$SO$_4$, filtered, and concentrated under reduced pressure. The solid obtained was washed with diethyl ether (5 mL) to afford N-(2-amino-4-bromopyridin-3-yl)-2-methoxyacetamide (0.030 g, 0.115 mmol, 68% yield) as a brown solid. LCMS (ESI) m/e 260.0 (bromo pattern) [(M+H)$^+$, calcd for C$_8$H$_{11}$BrN$_3$O$_2$ 260.0]; LC/MS retention time (Method A1): t$_R$=1.49 min.

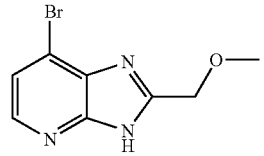

Part C: 7-bromo-2-(methoxymethyl)-3H-imidazo[4,5-b]pyridine

A mixture of N-(2-amino-4-bromopyridin-3-yl)-2-methoxyacetamide (0.165 g, 0.621 mmol), CsF (0.9 g, 5.92 mmol) and N,N-dimethylformamide (15 mL) was taken in a sealed tube and heated at 130° C. for 16 h. The reaction mixture was quenched with chilled water (15 mL) and then diluted with ethyl acetate (15 mL). Then organic layer was separated and the aqueous layer was washed with ethyl acetate (2×10 mL). The ethyl acetate layer was washed with water (20 mL), brine, dried over Na$_2$SO$_4$, filtered, and concentrated under reduced pressure. The solid was washed with hexane (2×5 mL) to afford 7-bromo-2-(methoxymethyl)-3H-imidazo[4,5-b]pyridine (0.1 g, 0.397 mmol, 64% yield) as a brown solid. LCMS (ESI) m/e 242.0 (bromo pattern) [(M+H)$^+$, calcd for C$_8$H$_9$BrN$_3$O 242.0]; LC/MS retention time (method B): t$_R$=0.52 min.

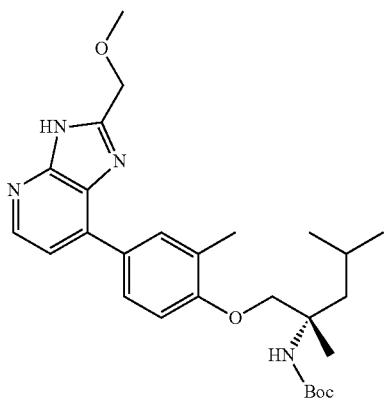 [SMILES: COCc1nc2c(-c3ccc(OC[C@](C)(CC(C)C)NC(=O)OC(C)(C)C)c(C)c3)ccnc2[nH]1]

Part D: (S)-tert-butyl (1-(4-(2-(methoxymethyl)-3H-imidazo[4,5-b]pyridin-7-yl)-2-methylphenoxy)-2,4-dimethylpentan-2-yl)carbamate To a solution of 7-bromo-2-(methoxymethyl)-3H-imidazo[4,5-b]pyridine (0.030 g, 0.119 mmol) in 1,4-dioxane (6 mL) water (2 mL) mixture was added (S)-tert-butyl (2,4-dimethyl-1-(2-methyl-4-(4,4,5,5-tetramethyl-1,3,2-dioxaborolan-2-yl)phenoxy)pentan-2-yl)carbamate (prepared as described in Example 259, Part A and B) (0.059 g, 0.131 mmol) and potassium phosphate, dibasic (0.062 g, 0.357 mmol). The reaction mixture was purged with argon for 30 min and PdCl$_2$(dppf)-CH$_2$Cl$_2$ adduct (9.72 mg, 0.012 mmol) was added. The reaction mixture was again purged with argon for 10 min and heated for 16 h at 100° C. The reaction mixture was diluted with ethyl acetate (8 mL) The organic layer was separated and the aqueous layer was washed with ethyl acetate (2×5 mL). The combined ethyl acetate layers were washed with brine, dried over Na$_2$SO$_4$, filtered, and concentrated under reduced pressure. The reaction mixture was purified by Preparative TLC using 70% ethyl acetate in hexanes. The required spot was collected, dissolved 15% methanol in dichloromethane (30 mL), filtered and concentrated under reduced pressure to afford (S)-tert-butyl (1-(4-(2-(methoxymethyl)-3H-imidazo[4,5-b]pyridin-7-yl)-2-methylphenoxy)-2,4-dimethylpentan-2-yl)carbamate (0.035 g, 0.056 mmol, 47% yield) as an off white-solid. LCMS (ESI) m/e 483.3 [(M+H)$^+$, calcd for C$_{27}$H$_{39}$N$_4$O$_4$ 483.3]; LC/MS retention time (method B): t$_R$=1.00 min.

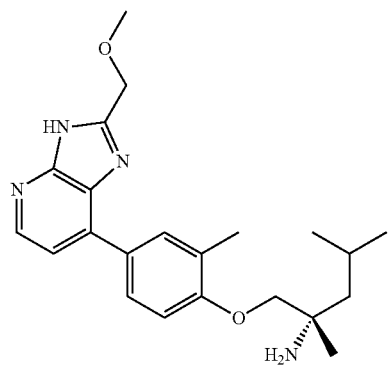 [SMILES: COCc1nc2c(-c3ccc(OC[C@@](C)(N)CC(C)C)c(C)c3)ccnc2[nH]1]

Part E: (S)-1-(4-(2-(methoxymethyl)-3H-imidazo[4,5-b]pyridin-7-yl)-2-methylphenoxy)-2,4-dimethylpentan-2-amine To a solution (S)-tert-butyl (1-(4-(2-(methoxymethyl)-3H-imidazo[4,5-b]pyridin-7-yl)-2-methylphenoxy)-2,4-dimethylpentan-2-yl)carbamate (0.030 g, 0.048 mmol) in dichloromethane (1 mL) at 0° C. was added TFA (0.6 mL, 7.79 mmol) and the reaction mixture was allowed to stir for 2 h at room temperature, then was concentrated under reduced pressure. The crude material was purified by prep LC/MS (method A) to afford (S)-1-(4-(2-(methoxymethyl)-3H-imidazo[4,5-b]pyridin-7-yl)-2-methylphenoxy)-2,4-dimethylpentan-2-amine (0.0055 g, 0.014 mmol, 29% yield) as a pale yellow solid. LCMS (ESI) m/e 383.2 [(M+H)$^+$, calcd for C$_{22}$H$_{31}$N$_4$O$_2$ 383.2]; LC/MS retention time (method H): t$_R$=1.11 min; LC/MS retention time (method I): t$_R$=1.00 min. $^1$H NMR (400 MHz, MeOD): δ 7.97 (d, J=8.40 Hz, 1H), 7.89 (d, J=4.40 Hz, 1H), 7.86 (d, J=2.00 Hz, 1H), 7.72 (d, J=8.40 Hz, 1H), 7.04 (d, J=8.40 Hz, 1H), 4.74 (s, 2H), 4.04 (d, J=10.00 Hz, 1H), 3.99 (d, J 9.60 Hz, 1H), 3.51 (s, 3H), 2.38 (s, 3H), 1.82-1.86 (m, 2H), 1.61-1.66 (m, 1H), 1.43 (s, 3H), 1.05 (d, J=6.40 Hz, 3H), 1.01 (d, J=6.40 Hz, 3H) ppm.

Example 302

(S)-2-((2-amino-2,4-dimethylpentyl)oxy)-5-(2-oxo-2,3-dihydro-1H-pyrrolo[2,3-b]pyridin-4-yl)benzonitrile

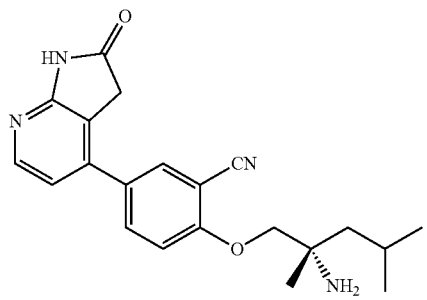 [SMILES: CC(C)C[C@](C)(N)COc1ccc(-c2ccnc3c2CC(=O)N3)cc1C#N]

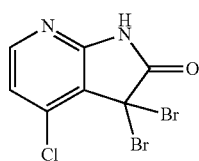 [SMILES: O=C1Nc2nccc(Cl)c2C1(Br)Br]

Part A. 3,3-dibromo-4-chloro-1H-pyrrolo[2,3-b]pyridin-2(3H)-one

To a solution of 4-chloro-1H-pyrrolo[2,3-b]pyridine (1 g, 6.55 mmol) in t-BuOH (60 mL) was added pyridinium tribromide (5.24 g, 16.38 mmol) portionwise. The reaction mixture was stirred at room temperature overnight. The reaction mixture was concentrated, diluted with water and ethyl acetate. The organic layer was separated, dried over Na$_2$SO$_4$, filtered, and concentrated to afford 3,3-dibromo-4-chloro-1H-pyrrolo[2,3-b]pyridin-2(3H)-one (2.1 g, 5.79 mmol, 88% yield) as an off-white solid which was carried forward without further purification. LCMS (ESI) m/e 324.8 Br pattern [(M+H)$^+$, calcd for C$_7$H$_4$Br$_2$ClN$_2$O, 324.8]; LC/MS retention time (method B): t$_R$=0.82 min.

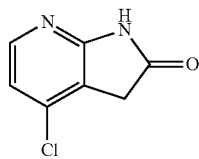 [SMILES: O=C1Cc2c(Cl)ccnc2N1]

Part B. 4-chloro-H-pyrrolo[2,3-b]pyridin-2(3H)-one

To a solution of 3,3-dibromo-4-chloro-1H-pyrrolo[2,3-b]pyridin-2(3H)-one (350 mg, 1.072 mmol) in MeOH (5 mL) was added acetic acid (5 mL) then zinc dust (351 mg, 5.36 mmol) in portions. The mixture was stirred at room temperature for 1 h. The reaction mixture was diluted with ethyl acetate (50 mL), filtered through diatomaceous earth and the filtrate neutralized with 10% aq. NaHCO$_3$ solution. The organic layer was separated out, dried over Na$_2$SO$_4$, filtered, and concentrated to afford a brownish solid. The solid was washed with hexane (2×20 mL) to afford 4-chloro-1H-pyrrolo[2,3-b]pyridin-2(3H)-one (164 mg, 0.973 mmol, 91% yield) as an off white solid. LCMS (ESI) m/e 168.9 [(M+H)$^+$, calcd for C$_7$H$_6$ClN$_2$O, 169.0]; LC/MS retention time (method B): t$_R$=0.58 min.

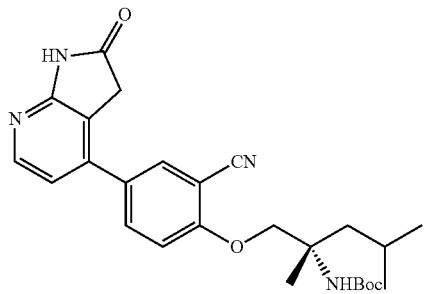 [SMILES: CC(C)C[C@@](C)(COc1ccc(-c2ccnc3c2CC(=O)N3)cc1C#N)NC(=O)OC(C)(C)C]

Part C. (S)-tert-butyl (1-(2-cyano-4-(2-oxo-2,3-dihydro-1H-pyrrolo[2,3-b]pyridin-4-yl)phenoxy)-2,4-dimethylpentan-2-yl)carbamate A solution of 4-chloro-1H-pyrrolo[2,3-b]pyridin-2(3H)-one (0.05 g, 0.297 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (0.136 g, 0.297 mmol), PdCl$_2$(dppf) (10.85 mg, 0.015 mmol) and Cs$_2$CO$_3$ (0.290 g, 0.890 mmol) were taken in 1,4-dioxane (2 mL) and water (0.4 mL) heated at 90° C. overnight. The reaction mixture was concentrated, diluted with brine and ethyl acetate. The organic layer was separated, dried over Na$_2$SO$_4$, filtered, and concentrated. The brown solid was washed with hexane and dried under vacuum to afford (S)-tert-butyl (1-(2-cyano-4-(2-oxo-2,3-dihydro-1H-pyrrolo[2,3-b]pyridin-4-yl)phenoxy)-2,4-dimethylpentan-2-yl)carbamate (120 mg, 0.258 mmol, 87% yield) as a pale solid. LCMS (ESI) m/e 465.2 [(M+H)$^+$, calcd for C$_{26}$H$_{33}$N$_4$O$_4$ 465.2]; LC/MS retention time (method B): t$_R$=1.00 min.

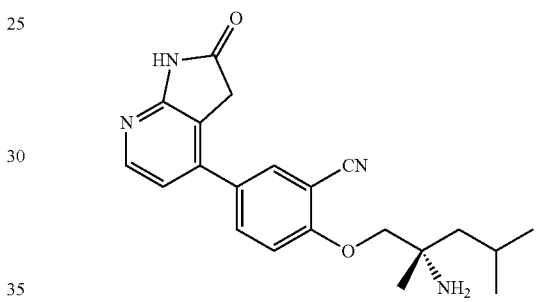

Part D. (S)-2-((2-amino-2,4-dimethylpentyl)oxy)-5-(2-oxo-2,3-dihydro-1H-pyrrolo[2,3-b]pyridin-4-yl)benzonitrile To a solution of (S)-tert-butyl (1-(2-cyano-4-(2-oxo-2,3-dihydro-1H-pyrrolo[2,3-b]pyridin-4-yl)phenoxy)-2,4-dimethylpentan-2-yl)carbamate (0.12 g, 0.258 mmol) in dichloromethane (2 mL) was added hydrogen chloride in 1,4-dioxane (0.646 mL, 2.58 mmol) and the mixture stirred at room temperature for 3 h. The reaction mixture was concentrated, neutralized with 10% aq. NaHCO$_3$ solution and diluted with ethyl acetate. The organic layer was separated, dried over Na$_2$SO$_4$, filtered, and concentrated under reduced pressure. The crude material was purified by prep LC/MS (method A) to afford (S)-2-((2-amino-2,4-dimethylpentyl)oxy)-5-(2-oxo-2,3-dihydro-1H-pyrrolo[2,3-b]pyridin-4-yl)benzonitrile (6 mg, 0.015 mmol, 6% yield) as a pale yellow solid. LCMS (ESI) m/e 365.0 [(M+H)$^+$, calcd for C$_{21}$H$_{25}$N$_4$O$_2$ 365.2]; LC/MS retention time (method H): t$_R$=1.00 min; LC/MS retention time (method I): t$_R$=0.97 min. $^1$H NMR (400 MHz, methanol-d$_4$): δ 8.14-8.16 (d, J=5.6 Hz, 1H), 8.02 (s, 1H), 7.94-7.97 (m, 1H), 7.39-7.42 (d, J=8.8 Hz, 1H), 7.11-7.12 (d, J 5.6 Hz, 1H), 4.29-4.33 (m, 2H), 3.3 (s, 2H), 1.88-1.98 (m, 2H), 1.69-1.74 (m, 1H), 1.54 (s, 3H), 1.01-1.09 (m, 6H) ppm.

Example 303

(S)-4-(4-((2-amino-2,4-dimethylpentyl)oxy)-3-(trifluoromethyl)phenyl)-1H-pyrrolo[2,3-b]pyridin-2(3H)-one

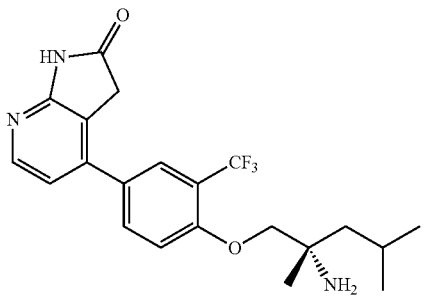

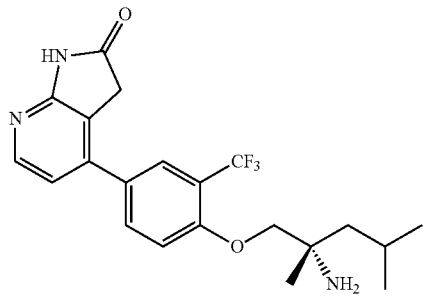 [SMILES: CC(C)C[C@](C)(N)COc1ccc(-c2ccnc3c2CC(=O)N3)cc1C#N]

Part B. (S)-4-(4-((2-amino-2,4-dimethylpentyl)oxy)-3-(trifluoromethyl)phenyl)-1H-pyrrolo[2,3-b]pyridin-2(3H)-one To a solution of (S)-tert-butyl (2,4-dimethyl-1-(4-(2-oxo-2,3-dihydro-1H-pyrrolo[2,3-b]pyridin-4-yl)-2-(trifluoromethyl)phenoxy)pentan-2-yl)carbamate (0.12 g, 0.236 mmol) in dichloromethane (3 mL) at 0° C. was added hydrogen chloride in 1,4-dioxane (0.591 mL, 2.364 mmol). The mixture was stirred at room temperature overnight, then was concentrated under reduced pressure, diluted with aq. NaHCO$_3$ solution and ethyl acetate. The organic layer was separated, dried over Na$_2$SO$_4$, filtered, and concentrated which afforded off-white solid as crude product. The crude material was purified by prep LC/MS (method A) to afford (S)-4-(4-((2-amino-2,4-dimethylpentyl)oxy)-3-(trifluoromethyl)phenyl)-1H-pyrrolo[2,3-b]pyridin-2(3H)-one (6 mg, 0.014 mmol, 6% yield) as a pale yellow solid. LCMS (ESI) m/e 408.0 [(M+H)$^+$, calcd for C$_{21}$H$_{25}$F$_3$N$_3$O$_2$ 408.2]; LC/MS retention time (method H): t$_R$=1.38 min; LC/MS retention time (method I): t$_R$=1.05 min. $^1$H NMR (400 MHz, methanol-d$_4$): δ 8.17-8.18 (d, J=5.6 Hz, 1H), 7.92-7.96 (m, 2H), 7.42-7.44 (d, J=8.0 Hz, 1H), 7.14-7.16 (d, J=5.6 Hz, 1H), 4.22-4.31 (m, 2H), 3.3 (s, 2H), 1.87-1.92 (m, 2H), 1.71-1.76 (m, 1H), 1.54 (s, 3H), 1.02-1.08 (m, 6H) ppm.

Example 321

2-methyl-1-((2-methyl-6-(2-methylpyrimidin-4-yl)pyridin-3-yl)oxy)propan-2-amine

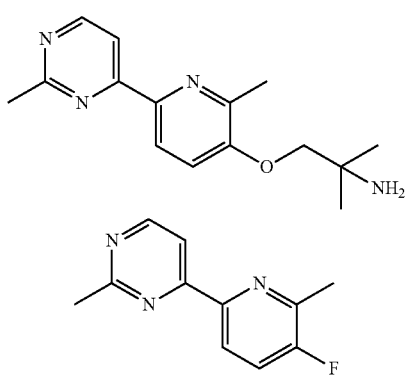

Part A. 4-(5-fluoro-6-methylpyridin-2-yl)-2-methylpyrimidine

In a microwave tube 4-chloro-2-methylpyrimidine (50 mg, 0.389 mmol), 6-bromo-3-fluoro-2-methylpyridine (73.9

Part A. (S)-Tert-butyl (2,4-dimethyl-1-(4-(2-oxo-2,3-dihydro-1H-pyrrolo[2,3-b]pyridin-4-yl)-2-(trifluoromethyl)phenoxy)pentan-2-yl)carbamate A solution of 4-chloro-1H-pyrrolo[2,3-b]pyridin-2(3H)-one (0.05 g, 0.297 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.178 g, 0.356 mmol), Cs$_2$CO$_3$ (0.193 g, 0.593 mmol) and PdCl$_2$(dppf) (10.85 mg, 0.015 mmol) in 1,4-dioxane (3 mL) and water (0.5 mL) mixture was heated at 80° C. overnight. The reaction mixture was concentrated, diluted with brine and ethyl acetate. The organic layer was separated, dried over Na$_2$SO$_4$, filtered, and concentrated to afford a brown solid which was dissolved in ethyl acetate, passed through pad of silica-gel and the filtrate concentrated to afford (S)-tert-butyl (2,4-dimethyl-1-(4-(2-oxo-2,3-dihydro-1H-pyrrolo[2,3-b]pyridin-4-yl)-2-(trifluoromethyl)phenoxy)pentan-2-yl)carbamate (120 mg, 0.236 mmol, 79% yield) as an off-white solid. LCMS (ESI) m/e 508.2 [(M+H)$^+$, calcd for C$_{26}$H$_{33}$F$_3$N$_3$O$_4$ 508.2]; LC/MS retention time (method B): t$_R$=1.17 min.

mg, 0.389 mmol), 1,1,1,2,2,2-hexamethyldistannane (127 mg, 0.389 mmol) and Pd(Ph₃P)₄ (22.47 mg, 0.019 mmol) were taken in DMF (4 mL). The reaction mixture was purged with nitrogen and heated at 160° C. under microwave for 1 h. The reaction mixture was concentrated, diluted with brine and ethyl acetate. The organic layer was separated, dried over Na₂SO₄, filtered, and concentrated which afforded brownish oil. The crude product was purified by silica gel chromatography (20-40% ethyl acetate-hexane) to afford 4-(5-fluoro-6-methylpyridin-2-yl)-2-methylpyrimidine (72 mg, 0.354 mmol, 91% yield). LCMS (ESI) m/e 204.5 [(M+H)⁺, calcd for $C_{11}H_{11}FN_3$ 204.1]; LC/MS retention time (method B): $t_R$=0.75 min.

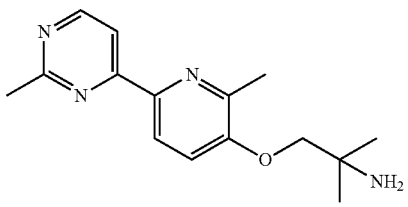 [SMILES: Cc1nccc(-c2ccc(OCC(C)(C)N)c(C)n2)n1]

Part B. 2-methyl-1-((2-methyl-(2-methylpyrimidin-4-yl)pyridin-3-yl)oxy)propan-2-amine To a solution of 2-amino-2-methylpropan-1-ol (8.77 mg, 0.098 mmol) in tetrahydrofuran (2 mL) was added NaH (2.362 mg, 0.098 mmol). The mixture was stirred for 10 min and then 4-(5-fluoro-6-methylpyridin-2-yl)-2-methylpyrimidine (20 mg, 0.098 mmol) were added to the solution. The reaction mixture was stirred overnight at room temperature. The reaction mixture was quenched with water, diluted with brine and ethyl acetate. The organic layer was separated, dried over anhydrous Na₂SO₄, and concentrated under reduced pressure. The crude material was purified by prep LC/MS (method A) to afford 2-methyl-1-((2-methyl-6-(2-methylpyrimidin-4-yl)pyridin-3-yl)oxy)propan-2-amine (11 mg, 0.040 mmol, 41% yield) as a pale yellow solid. LCMS (ESI) m/e 273.3 [(M+H)⁺, calcd for $C_{15}H_{21}N_4O$ 273.2]; LC/MS retention time (method H): $t_R$=0.76 min; LC/MS retention time (method I): $t_R$=0.56 min. ¹H NMR (400 MHz, methanol-d₄): δ 8.74 (d, J=5.2 Hz, 1H), 8.28 (d, J=8.8 Hz, 1H), 8.05 (d, J=5.2 Hz, 1H), 7.47 (d, J=8.4 Hz, 1H), 3.82 (s, 2H), 2.67 (s, 3H), 2.50 (s, 3H), 1.19 (s, 6H) ppm.

Example 322

(S)-1-((2-(difluoromethyl)-6-(pyrazolo [1,5-a]pyrimidin-7-yl)pyridin-3-yl)oxy)-2,4-dimethylpentan-2-amine

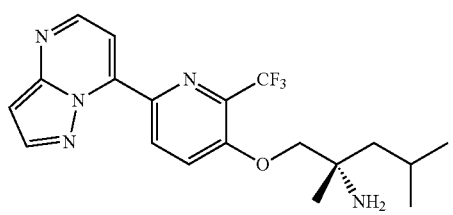

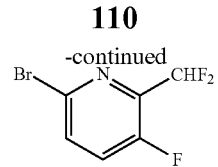

Part A: 6-bromo-2-(difluoromethyl)-3-fluoropyridine

A solution of 6-bromo-3-fluoropicolinaldehyde (2 g, 9.80 mmol) in DCM (10 mL) was cooled to 0° C. DAST (1.295 mL, 9.80 mmol) was added dropwise and the mixture stirred for 5 min at 0° C. The reaction mixture was warmed to room temperature and stirred for 12 h. The reaction mixture was diluted with DCM (50 mL) and washed with saturated sodium bicarbonate solution (20 mL), water (2×20 mL), brine (1×20 mL), dried over Na₂SO₄, filtered, and concentrated under reduced pressure to afford crude 6-bromo-2-(difluoromethyl)-3-fluoropyridine (1.2 g, 5.31 mmol, 54% yield) as a light yellow solid which was carried forward without further purification. LCMS (ESI) m/e 225.9 [(M+H)⁺, calcd for $C_6H_4BrF_3N$ 225.9]; LC/MS retention time (Method A1): $t_R$=2.73 min.

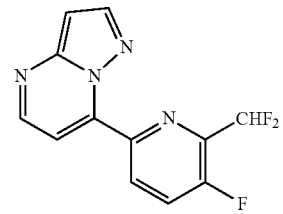 [SMILES: Fc1ccc(-c2ccnc3ccnn23)nc1C(F)F]

Part B: 7-(6-(difluoromethyl)-5-fluoropyridin-2-yl)pyrazolo [1,5-a]pyrimidine

A solution of 7-chloropyrazolo[1,5-a]pyrimidine (0.1 g, 0.651 mmol), 6-bromo-2-(difluoromethyl)-3-fluoropyridine (0.162 g, 0.716 mmol) and 1,1,1,2,2,2-hexamethyldistannane (0.235 g, 0.716 mmol) in 1,4-dioxane (2 mL) was purged with nitrogen gas for 10 min. Pd(Ph₃P)₄ (0.075 g, 0.065 mmol) was added to the reaction mixture and the solution was purged with nitrogen gas for another 10 min. The reaction mixture was heated at 150° C. for 1.5 h. The reaction mixture was cooled to room temperature and concentrated under reduced pressure. The residue was purified by silica-gel chromatography (pet ether/ethyl acetate (0-40%)) to afford 7-(6-(difluoromethyl)-5-fluoropyridin-2-yl) pyrazolo [1,5-a]pyrimidine (40 mg, 0.151 mmol, 23% yield) as a yellow solid. LCMS (ESI) m/e 265.0 [(M+H)⁺, calcd for $C_{12}H_8F_3N_4$ 265.1]; LC/MS retention time (Method A1): $t_R$=2.08 min.

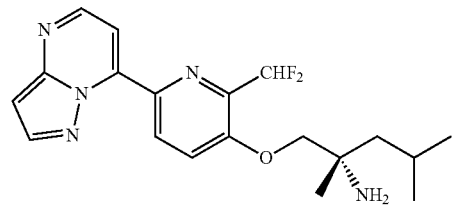

Part C: (S)-1-((2-(difluoromethyl)-6-(pyrazolo[1,5-a]pyrimidin-7-yl)pyridin-3-yl)oxy)-2,4-dimethylpentan-2-amine A solution of (S)-2-amino-2,4-dimethylpentan-1-ol (0.016 g, 0.125 mmol) in DMF (4 mL) was cooled to 0° C. NaH (3.00 mg, 0.125 mmol) was added followed by slow addition of 7-(6-(difluoromethyl)-5-fluoropyridin-2-yl)pyrazolo[1,5-a]pyrimidine (0.033 g, 0.125 mmol) and stirred for 5 min at 0° C. The reaction mixture was heated at 60° C. for 2 h. The reaction mixture was quenched with water (20 mL) and extracted with ethyl acetate (20 mL) and the organic layer was separated out. The ethyl acetate layer was dried over $Na_2SO_4$, and concentrated under reduced pressure. The crude material was purified by prep LC/MS (method C) to afford (S)-1-((2-(difluoromethyl)-6-(pyrazolo[1,5-a]pyrimidin-7-yl)pyridin-3-yl)oxy)-2,4-dimethylpentan-2-amine (4 mg. 10.23 μmol, 8% yield) as a pale yellow solid. LCMS (ESI) m/e 376.2 [(M+H)+, calcd for $C_{19}H_{24}F_2N_5O$ 376.2]; LC/MS retention time (method H): $t_R$=2.21 min; LC/MS retention time (method I): $t_R$=1.77 min. $^1$H NMR (400 MHz, DMSO-$d_6$): δ 9.31 (d, J=8.80 Hz, 1H), 8.72 (d, J=4.40 Hz, 1H), 8.40 (d, J=2.40 Hz, 1H), 7.94 (d, J=8.80 Hz, 1H), 7.76 (d, J=4.40 Hz, 1H), 7.20-7.47 (m, 1H), 6.92 (d, J=2.80 Hz, 1H), 4.01 (s, 2H), 1.80-1.85 (m, 1H), 1.41-1.52 (m, 2H), 1.20 (s, 3H), 0.92-0.97 (m, 6H) ppm.

Example 332

(S)-1-(2-chloro-4-(pyrazolo[1,5-a]pyridin-3-yl)phenoxy)-2,4-dimethylpentan-2-amine

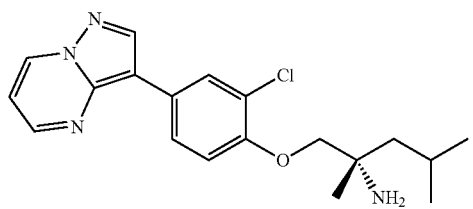

Prepared as described in Example 282 using (S)-tert-butyl (1-(2-chloro-4-(pyrazolo[1,5-a]pyrimidin-3-yl)phenoxy)-2,4-dimethylpentan-2-yl)carbamate (0.04 g, 0.031 mmol) in the final step to afford crude product. The crude material was purified by prep HPLC (method B) to afford (S)-1-(2-chloro-4-(pyrazolo[1,5-a]pyridin-3-yl)phenoxy)-2,4-dimethylpentan-2-amine, TFA (11 mg, 0.031 mmol, 89% yield) as a pale yellow solid. LCMS (ESI) m/e 359.1 [(M+H)+, calcd for $C_{19}H_{24}ClN_4O$, 359.1]; LC/MS retention time (method D); $t_R$=2.14 min. LC/MS retention time (Method E); $t_R$=1.84 min. $^1$H NMR (400 MHz, METHANOL-$d_4$): δ 8.95 (dd, J=1.60, 7.20 Hz, 1H), 8.65 (dd, J=1.60, 4.00 Hz, 1H), 8.56 (s, 1H), 8.29 (d, J=2.40 Hz, 1H), 8.04 (dd, J=2.40, 8.60 Hz, 1H), 7.25 (d, J=8.80 Hz, 1H), 7.07 (dd, J=4.00, 7.20 Hz, 1H), 4.21 (d, J=10.00 Hz, 1H), 4.15 (d, J=10.00 Hz, 1H), 1.89-1.98 (m, 2H), 1.70-1.75 (m, 1H), 1.55 (s, 3H), 1.06-1.10 (m, 6H) ppm.

Example 333

(S)-2,4-dimethyl-1-(2-methyl-4-(pyrazolo[1,5-a]pyridin-3-yl)phenoxy)pentan-2-amine

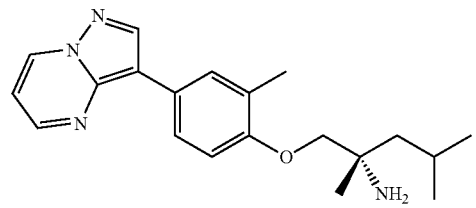 [SMILES: Cc1cc(-c2cnn3cccnc23)ccc1OC[C@@](C)(N)CC(C)C]

Prepared as described in Example 282 using (S)-tert-butyl (2,4-dimethyl-1-(2-methyl-4-(pyrazolo[1,5-a]pyrimidin-3-yl)phenoxy)pentan-2-yl)carbamate (0.04 g, 0.082 mmol) to afford crude product. The crude material was purified by prep HPLC (method B) to afford (S)-2,4-dimethyl-1-(2-methyl-4-(pyrazolo[1,5-a]pyridin-3-yl)phenoxy)pentan-2-amine 2. TFA (17 mg, 0.082 mmol, 37% yield) as a pale yellow solid. LCMS (ESI) m/e 339.2 [(M+H)+, calcd for $C_{20}H_{27}N_4O$, 339.2]; LC/MS retention time (method D); $t_R$=1.96. LC/MS retention time (Method E); $t_R$=1.99 min. $^1$H NMR (400 MHz, METHANOL-$d_4$): δ 8.92 (dd, J=1.60, 7.20 Hz, 1H), 8.60 (dd, J=1.60, 4.00 Hz, 1H), 8.50 (s, 1H), 7.90-7.90 (m, 2H), 7.02-7.07 (m, 2H), 4.15 (d, J=10.40 Hz, 1H), 4.09 (d, J=10.00 Hz, 1H), 2.41 (s, 3H), 1.87-1.96 (m, 2H), 1.70-1.75 (m, 1H), 1.54 (s, 3H), 1.04-1.10 (m, 6H) ppm.

Example 334

4-(4-(((S)-2-amino-2,4-dimethylpentyl)oxy)-3-chlorophenyl)-N-(3-fluorocyclopentyl)pyridin-2-amine

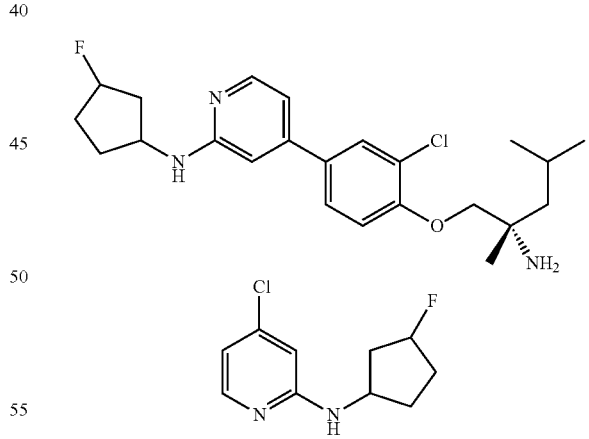

Part A:
4-Chloro-N-(3-fluorocyclopentyl)pyridin-2-amine

The solution of 3-fluorocyclopentanamine, TFA (Synthesis described in Patent: WO2009/63244 A1, 2009) (0.066 g, 0.304 mmol) in DMSO (1 mL) cooled to 0° C. under a nitrogen atmosphere was stirred at 0° C. for 5 min. To this solution, $Cs_2CO_3$ (0.198 g, 0.608 mmol) was added and stirred for 5 min. 4-Chloro-2-fluoropyridine (0.05 g, 0.304 mmol) was added and the mixture heated at 90° C. for 14 h. The reaction mixture was cooled to room temperature and diluted with water (20 mL) and extracted with ethyl acetate (3×10 mL). The combined organic layers were washed with water (2×10 mL). The organic layers were dried over sodium sulfate and concentrated under reduced pressure. The residue was purified via silica gel chromatography (ethyl acetate and pet ether) to afford 4-chloro-N-(3-fluorocyclopentyl)pyridin-2-amine (0.02 g, 0.078 mmol, 26% yield) as a yellow oil. LCMS (ESI) m/e 215.2 [(M+H)+, calcd for $C_{10}H_{13}ClFN_2$, 215.0]; LC/MS retention time (method A1); $t_R$=1.91 min.

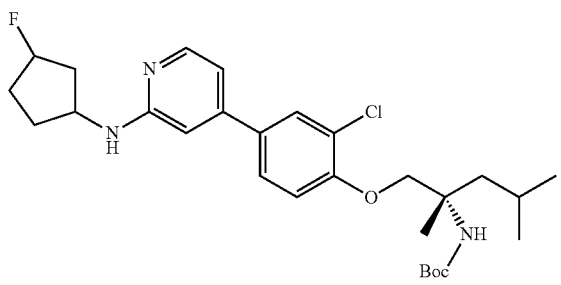 [SMILES: CC(C)C[C@@](C)(COc1ccc(-c2ccnc(NC3CCC(F)C3)c2)cc1Cl)NC(=O)OC(C)(C)C]

Part B: tert-butyl ((2S)-1-(2-chloro-4-(2-((3-fluorocyclopentyl)amino)pyridin-4-yl)phenoxy)-2,4-dimethylpentan-2-yl)carbamate A mixture of (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in 285) (0.037 g, 0.078 mmol), 4-chloro-N-(3-fluorocyclopentyl)pyridin-2-amine (0.02 g, 0.078 mmol), and tripotassium phosphate (2M Solution) (0.4 mL, 0.800 mmol) in THF (2 mL) was purged with nitrogen for 15 min. XPhos $2^{nd}$ generation precatalyst (9.24 mg, 0.012 mmol) was added and the mixture purged for a further 5 min with nitrogen. The reaction mixture was then stirred at 80° C. for 12 h. The reaction mixture was cooled to room temperature and diluted with THF (20 mL) and filtered through diatomaceous earth. The diatomaceous earth bed was washed with excess of THF. The filtrate was concentrated under reduced pressure. The residue was purified via silica gel chromatography (ethyl acetate and pet ether) to afford tert-butyl ((2S)-1-(2-chloro-4-(2-((3-fluorocyclopentyl)amino)pyridin-4-yl)phenoxy)-2,4-dimethylpentan-2-yl)carbamate (0.013 g, 0.015 mmol, 19% yield) as a yellow oil. LCMS (ESI) m/e 520.2 [(M+H)+, calcd for $C_{28}H_{40}ClFN_3O_3$, 520.2]; LC/MS retention time (method D); $t_R$=3.14.

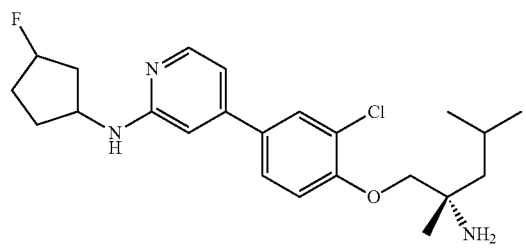 [SMILES: CC(C)C[C@](C)(N)COc1ccc(-c2ccnc(NC3CCC(F)C3)c2)cc1Cl]

Part C: 4-(4-(((S)-2-amino-2,4-dimethylpentyl)oxy)-3-chlorophenyl)-N-(3-fluorocyclopentyl)pyridin-2-amine To a solution of tert-butyl ((2S)-1-(2-chloro-4-(2-((3-fluorocyclopentyl)amino)pyridin-4-yl)phenoxy)-2,4-dimethylpentan-2-yl)carbamate (0.013 g, 0.015 mmol) in DCM (0.8 mL) cooled to 0° C. under nitrogen atmosphere was added TFA (2.5 mL, 32.4 mmol) dropwise over a period of 1 min. The mixture was warmed to room temperature and stirred for 2.5 h. The reaction mixture was concentrated under reduced pressure at lower temperature (28° C.). The residue was washed with diethyl ether (2×10 mL) then purified by prep HPLC (method B) to afford 4-(4-(((S)-2-amino-2,4-dimethylpentyl)oxy)-3-chlorophenyl)-N-(3-fluorocyclopentyl)pyridin-2-amine (1 mg, 1.073 µmol, 7% yield) as a pale yellow solid. LCMS (ESI) m/e 420.2 [(M+H)+, calcd for $C_{23}H_{30}ClFN_3$, 420.2]; LC/MS retention time (method D); $t_R$=2.49. LC/MS retention time (Method E); $t_R$=1.59 min. $^1$H NMR (400 MHz, METHANOL-$d_4$): δ 7.77-7.81 (m, 2H), 7.66 (dd, J=2.40, 8.40 Hz, 1H), 7.23 (d, J=8.40 Hz, 1H), 7.03-7.05 (m, 2H), 5.09-5.25 (m, 1H), 4.24-4.27 (m, 1H), 4.15 (d, J=10.40 Hz, 1H), 4.10 (d, J=10.40 Hz, 1H), 2.25-2.41 (m, 2H), 1.75-2.00 (m, 5H), 1.58-1.63 (m, 2H), 1.43 (s, 3H), 0.78-0.97 (m, 6H) ppm.

Example 335

(S)-1-(2-fluoro-4-(2-(trifluoromethyl) pyrazolo[1,5-a]pyrimidin-7-yl)phenoxy)-2,4-dimethylpentan-2-amine

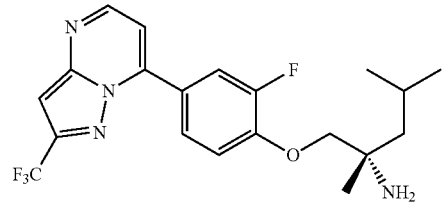 [SMILES: CC(C)C[C@](C)(N)COc1ccc(-c2ccnc3cc(C(F)(F)F)nn23)cc1F]

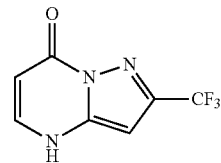 [SMILES: O=c1cc[nH]c2cc(C(F)(F)F)nn12]

Part A: 2-(trifluoromethyl)pyrazolo[1,5-a]pyrimidin-7(4H)-one

To a stirred solution of 5-(trifluoromethyl)-1H-pyrazol-3-amine (1.5 g, 9.93 mmol) in ethanol (20 mL) was added sodium (E)-3-ethoxy-3-oxoprop-1-en-1-olate (prepared as described in Example 266) (1.508 g, 10.92 mmol) in portions and the mixture stirred for 5 min. The reaction mixture was heated at 90° C. for 14 h. The reaction mixture was allowed to cool to room temperature and concentrated under reduced pressure. The reaction mixture was acidified with saturated citric acid solution (40 mL). The solid that formed was filtered through a sintered glass funnel and was washed with hexanes and water, then dried under vacuum for 2 h to afford 2-(trifluoromethyl)pyrazolo[1,5-a]pyrimidin-7(4H)-one (1 g, 4.58 mmol, 43% yield). LCMS (ESI) m/e 204.0 [(M+H)+, calcd for $C_7H_5F_3N_3O$, 204.1]; LC/MS retention time (Method A1); $t_R$=1.45 min.

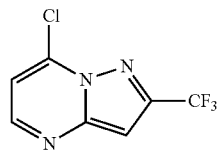 [SMILES: FC(F)(F)c1cc2nccc(Cl)n2n1]

Part B: 7-chloro-2-(trifluoromethyl)pyrazolo[1,5-a]pyrimidine

A suspension of 2-(trifluoromethyl)pyrazolo[1,5-a]pyrimidin-7(4H)-one (1 g, 4.58 mmol) in $POCl_3$ (12 mL, 129 mmol) was heated to 108° C. for 16 h. The reaction mixture was then cooled to room temperature and was concentrated under reduced pressure. The residue was added to stirred mixture of ice cold saturated solution of sodium bicarbonate (60 mL) and ethyl acetate (100 mL), keeping the temperature at 0° C. for 20 min. The aqueous layer was extracted with ethyl acetate (5×100 mL). The combined organic layers washed with brine solution (100 mL), dried over sodium sulfate, and concentrated under reduced pressure to afford 7-chloro-2-(trifluoromethyl) pyrazolo[1,5-a]pyrimidine (0.8 g, 3.03 mmol, 66% yield) as a brown solid. The crude product was used as is for the next step without further purification. LCMS (ESI) m/e 222.0 [(M+H)+, calcd for $C_7H_4ClF_3N_3$, 222.0]; LC/MS retention time (method A2); $t_R$=4.35 min.

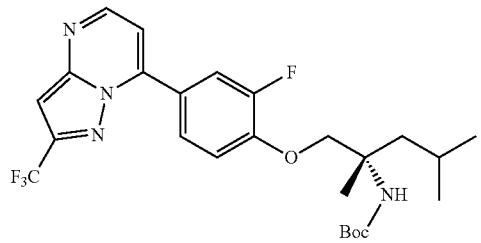 [SMILES: CC(C)C[C@@](C)(COc1ccc(-c2ccnc3cc(C(F)(F)F)nn23)cc1F)NC(=O)OC(C)(C)C]

Part C: (S)-tert-butyl (1-(2-fluoro-4-(2-(trifluoromethyl)pyrazolo [1,5-a]pyrimidin-7-yl)phenoxy)-2,4-dimethylpentan-2-yl)carbamate A mixture of 7-chloro-2-(trifluoromethyl)pyrazolo[1,5-a] pyrimidine (0.02 g, 0.076 mmol), (S)-tert-butyl (1-(2-fluoro-4-(4,4,5,5-tetramethyl-1,3,2-dioxaborolan-2-yl)phenoxy)-2,4-dimethylpentan-2-yl)carbamate (prepared as in Example 253, Part B) (0.034 g, 0.076 mmol), and $Cs_2CO_3$ (0.049 g, 0.152 mmol) in THF (2 mL) and water (0.667 mL) was purged with nitrogen for 15 min. XPhos $2^{nd}$ generation precatalyst (8.95 mg, 0.011 mmol) was added, purged for a further 5 min then reaction mixture was stirred at 65° C. for 14h. The reaction mixture was cooled to room temperature and diluted with THF (10 mL) then filtered through diatomaceous earth. The diatomaceous earth bed was washed with 20 mL of THF. The filtrate was concentrated under reduced pressure. The crude was purified through silica gel chromatography (ethyl acetate and pet ether) to afford (S)-tert-butyl (1-(2-fluoro-4-(2-(trifluoromethyl)pyrazolo[1,5-a]pyrimidin-7-yl)phenoxy)-2,4-dimethylpentan-2-yl)carbamate (0.02 g, 0.021 mmol, 27% yield) as yellow semi-solid. LCMS (ESI) m/e 511.2 [(M+H)+, calcd for $C_{25}H_{31}F_4N_4O_3$, 511.2]; LC/MS retention time (method H); $t_R$=2.78 min.

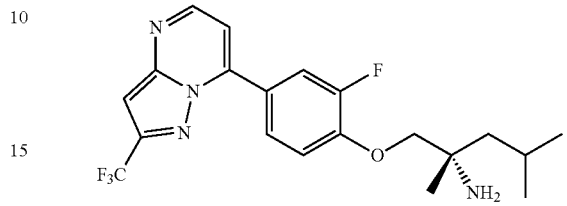

Part D: (S)-1-(2-fluoro-4-(2-(trifluoromethyl)pyrazolo[1,5-a]pyrimidin-7-yl)phenoxy)-2,4-dimethylpentan-2-amine A solution of (S)-tert-butyl (1-(2-fluoro-4-(2-(trifluoromethyl)pyrazolo[1,5-a]pyrimidin-7-yl)phenoxy)-2,4-dimethylpentan-2-yl)carbamate (0.02 g, 0.021 mmol) in MeOH (1.5 mL) cooled to 0° C. under nitrogen atmosphere was added TFA (1.5 mL, 19.47 mmol) dropwise over a period of 1 min. The mixture was then warmed to room temperature and allowed to stir for 4 h. The reaction mixture was concentrated under reduced pressure at lower temperature (28° C.). The crude material was purified by prep HPLC (method B) to afford (S)-1-(2-fluoro-4-(2-(trifluoromethyl)pyrazolo[1,5-a]pyrimidin-7-yl)phenoxy)-2,4-dimethylpentan-2-amine, TFA (1 mg, 0.021 mmol, 8% yield) as a pale yellow solid. LCMS (ESI) m/e 411.2 [(M+H)+, calcd for $C_{20}H_{23}F_4N_4O$, 411.1]; LC/MS retention time (method D); $t_R$=2.56. LC/MS retention time (Method E); $t_R$=2.11 min. $^1H$ NMR (400 MHz, METHANOL-$d_4$): δ 8.71 (d, J=4.40 Hz, 1H), 8.14 (dd, J=2.40, 12.40 Hz, 1H), 8.04-8.07 (m, 1H), 7.44 (t, J=8.80 Hz, 1H), 7.39 (d, J=4.40 Hz, 1H), δ 7.14 (s, 1H), 4.25 (d, J=10.40 Hz, 1H), 4.33 (d, J=10.40 Hz, 1H), 1.87-1.93 (m, 2H), 1.70-1.76 (m, 1H), 1.70 (s, 3H), 1.05-1.10 (m, 6H) ppm.

Example 336

(S)-1-(2-chloro-4-(2-(trifluoromethyl)pyrazolo[1,5-a]pyrimidin-7-yl)phenoxy)-2,4-dimethylpentan-2-amine

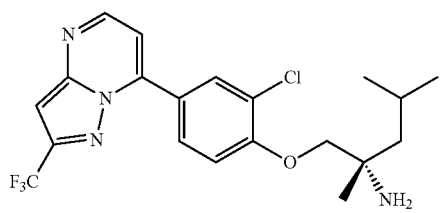

Prepared as described in Example 282 to afford (S)-1-(2-chloro-4-(2-(trifluoromethyl)pyrazolo[1,5-a]pyrimidin-7-yl)phenoxy)-2,4-dimethylpentan-2-amine, TFA (1 mg, 0.039 mmol, 4% yield) as a pale yellow solid. LCMS (ESI) m/e 427.0 [(M+H)+, calcd for $C_{20}H_{23}ClF_3N_4O$, 427.1];

LC/MS retention time (method D); $t_R$=2.75 min. LC/MS retention time (Method E); $t_R$=2.19 min. $^1$H NMR (400 MHz, METHANOL-$d_4$): δ 8.59 (d, J=4.80 Hz, 1H), 8.22 (d, J=2.40 Hz, 1H), 8.09 (dd, J=2.00, 8.60 Hz, 1H), 7.26-7.26 (m, 2H), 7.02 (s, 1H), 4.07-4.09 (m, 2H), 1.75-1.80 (m, 2H), 1.57-1.60 (m, 1H), 1.38 (s, 3H), 0.88-0.95 (m, 6H) ppm.

Example 338

4-(4-(((S)-2-amino-2,4-dimethylpentyl)oxy)-3-chlorophenyl)-N-(tetrahydro-2H-pyran-3-yl)pyridin-2-amine

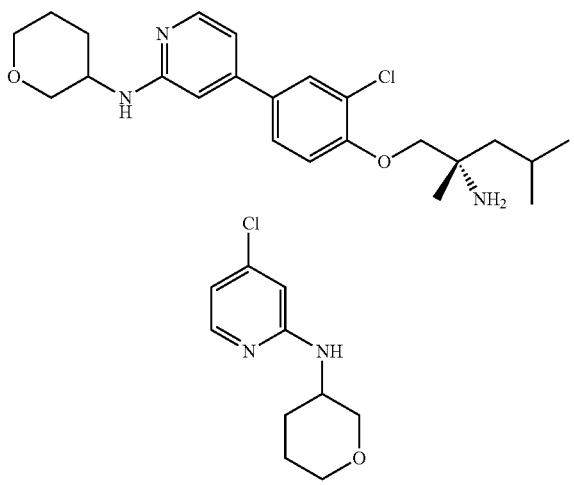

Part A: 4-chloro-N-(tetrahydro-2H-pyran-3-yl)pyridin-2-amine

To a stirred solution of 4-chloro-2-fluoropyridine (1 g, 6.08 mmol) in DMSO (10 mL) cooled to 0° C. under a nitrogen atmosphere was added $Cs_2CO_3$ (3.96 g, 12.16 mmol). The mixture was stirred for 5 min. Tetrahydro-2H-pyran-3-amine (0.677 g, 6.69 mmol) was added and the mixture heated to 90° C. for 14 h. Water was added and the solution was extracted with ethyl acetate (5×50 mL). The combined organic layers were washed with water (2×50 mL). The organic layers were dried over sodium sulfate and concentrated under reduced pressure. The crude material was purified via silica gel chromatography (ethyl acetate and pet ether) to afford 4-chloro-N-(tetrahydro-2H-pyran-3-yl)pyridin-2-amine (0.58 g, 2.509 mmol, 41% yield) as a yellow oil. LCMS (ESI) m/e 213.2 [(M+H)$^+$, calcd for $C_{10}H_{14}ClN_2O$, 213.0]; LC/MS retention time (method D); $t_R$=1.79 min.

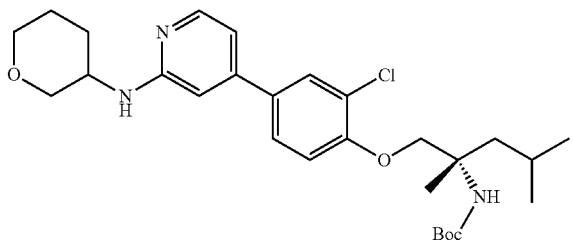 [SMILES: CC(C)C[C@@](C)(COc1ccc(-c2ccnc(NC3CCCOC3)c2)cc1Cl)NC(=O)OC(C)(C)C]

Part B: tert-butyl ((2S)-1-(2-chloro-4-(2-((tetrahydro-2H-pyran-3-yl)amino)pyridin-4-yl)phenoxy)-2,4-dimethylpentan-2-yl)carbamate A mixture of (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 285) (0.121 g, 0.260 mmol), 4-chloro-N-(tetrahydro-2H-pyran-3-yl)pyridin-2-amine (0.05 g, 0.216 mmol), and tripotassium phosphate (2M Solution) (0.324 mL, 0.649 mmol) in 1,4-dioxane (2 mL) was purged with nitrogen for 15 min. XPhos $2^{nd}$ generation precatalyst (0.026 g, 0.032 mmol) was added and the mixture purged for a further 5 min then stirred at 80° C. for 12 h. The reaction mixture was cooled to room temperature and diluted with ethyl acetate (20 mL) and filtered through diatomaceous earth. The diatomaceous earth bed was washed with 15 mL of ethyl acetate. The filtrate was concentrated under reduced pressure. The crude was purified via reverse phase HPLC. The desired fractions were concentrated under reduced pressure to afford racemic tert-butyl ((2S)-1-(2-chloro-4-(2-((tetrahydro-2H-pyran-3-yl)amino)pyridin-4-yl)phenoxy)-2,4-dimethylpentan-2-yl)carbamate (55 mg, 0.106 mmol, 49% yield) as a pale yellow solid. LCMS (ESI) m/e 518.2 [(M+H)$^+$, calcd for $C_{28}H_{41}ClN_3O_4$, 518.2]; LC/MS retention time (method H); $t_R$=2.28 min.

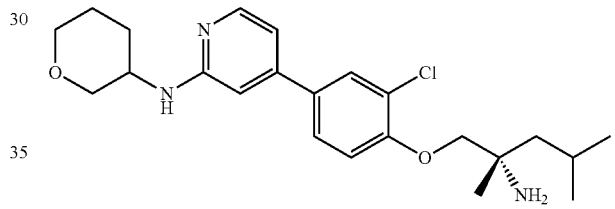

Part C: 4-(4-(((S)-2-amino-2,4-dimethylpentyl)oxy)-3-chlorophenyl)-N-(tetrahydro-2H-pyran-3-yl)pyridin-2-amine A solution of tert-butyl ((2S)-1-(2-chloro-4-(2-((tetrahydro-2H-pyran-3-yl)amino)pyridin-4-yl)phenoxy)-2,4-dimethylpentan-2-yl)carbamate (0.01 g, 0.019 mmol) in methanol (0.5 mL) was cooled to 0° C. under a nitrogen atmosphere. The solution was stirred at 0° C. for 10 min. TFA (1.5 mL, 19.47 mmol) was added dropwise over a period of 1 min and the mixture was warmed to room temperature and allowed to stir for 2 h. The reaction mixture was concentrated under reduced pressure at lower temperature (28° C.). The residue was washed with diethyl ether (2×10 mL) and dried under vacuum for 10 min. Water was added to the reaction mixture was frozen in a −78° C. dry ice bath then lyophilized to afford 4-(4-(((S)-2-amino-2,4-dimethylpentyl)oxy)-3-chlorophenyl)-N-(tetrahydro-2H-pyran-3-yl)pyridin-2-amine, TFA (0.009 g, 0.016 mmol, 85% yield) as a pale yellow solid and as a mixture of diastereomers. LCMS (ESI) m/e 418.2 [(M+H)$^+$, calcd for $C_{23}H_{33}ClN_3O_2$, 418.2]; LC/MS retention time (method A1); $t_R$=1.84 min. $^1$H NMR (400 MHz, METHANOL-$d_4$) δ 7.93 (d, J=2.51 Hz, 1H), 7.87 (d, J=7.03 Hz, 1H), 7.76-7.80 (m, 1H), 7.34 (d, J=8.53 Hz, 1H), 7.26 (d, J=1.00 Hz, 1H), 7.20 (dd, J=6.78, 1.76 Hz, 1H), 4.19-4.28 (m, 2H), 3.75-3.97 (m, 3H), 3.61-3.68 (m, 1H), 3.47-3.54 (m, 1H), 2.1-2.2 (m, 1H), 1.66-1.96 (m, 6H), 1.53 (s, 3H), 1.00-1.06 (m, 6H) ppm.

Example 339

4-(4-(((S)-2-amino-2,4-dimethylpentyl)oxy)-3-chlorophenyl)-N-(tetrahydro-2H-pyran-3-yl)pyridin-2-amine

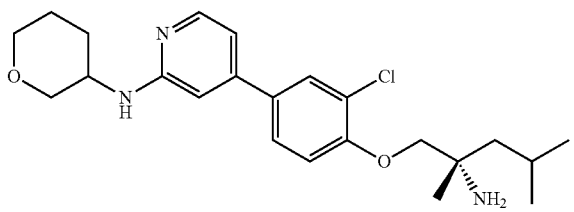

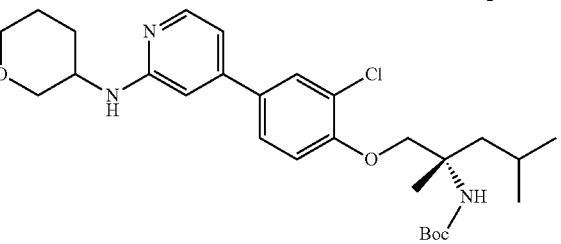

Part A: tert-butyl ((2S)-1-(2-chloro-4-(2-((tetrahydro-2H-pyran-3-yl)amino)pyridin-4-yl)phenoxy)-2,4-dimethylpentan-2-yl)carbamate diastereomer 1

Racemic tert-butyl ((2S)-1-(2-chloro-4-(2-((tetrahydro-2H-pyran-3-yl)amino)pyridin-4-yl)phenoxy)-2,4-dimethylpentan-2-yl)carbamate (prepared in Example 338, Parts A and B) (40 mg, 0.077 mmol) was resolved into the two diastereomers by chiral SFC (Method: Column/dimensions: Luxcellulose-4 (250×21.5) mm, 5u, % CO2: 70%, % Co solvent: 30% (0.25% DEA in Methanol, Total Flow: 60 g/min, Back Pressure: 100 bar, Temperature: 25° C., UV: 257 nm).

Isomer 1 was concentrated under reduced pressure to afford tert-butyl ((2S)-1-(2-chloro-4-(2-((tetrahydro-2H-pyran-3-yl)amino)pyridin-4-yl)phenoxy)-2,4-dimethylpentan-2-yl)carbamate (0.015 g, 0.029 mmol, 14% yield) as a yellow semi-solid. LCMS (ESI) m/e 518.2 [(M+H)$^+$, calcd for $C_{28}H_{41}ClN_3O_4$, 518.2]; LC/MS retention time (method H); $t_R$=2.28 min.

Isomer 2 was concentrated under reduced pressure to afford tert-butyl ((2S)-1-(2-chloro-4-(2-((tetrahydro-2H-pyran-3-yl)amino)pyridin-4-yl)phenoxy)-2,4-dimethylpentan-2-yl)carbamate (0.012 g, 0.023 mmol, 10% yield) as a yellow semi-solid. LCMS (ESI) m/e 518.2 [(M+H)$^+$, calcd for $C_{28}H_{41}ClN_3O_4$, 518.2]; LC/MS retention time (method H); $t_R$=2.29 min.

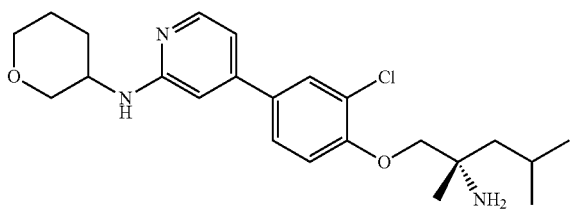

Part B: 4-(4-(((S)-2-amino-2,4-dimethylpentyl)oxy)-3-chlorophenyl)-N-(tetrahydro-2H-pyran-3-yl)pyridin-2-amine A solution of tert-butyl ((2S)-1-(2-chloro-4-(2-((tetrahydro-2H-pyran-3-yl)amino)pyridin-4-yl)phenoxy)-2,4-dimethylpentan-2-yl)carbamate, isomer 1 (0.015 g, 0.028 mmol) in methanol (0.5 mL) was cooled to 0° C. under a nitrogen atmosphere. The solution was stirred at 0° C. for 10 min. TFA (1.5 mL, 19.47 mmol) was added dropwise over a period of 1 min and the mixture was warmed to room temperature and allowed to stir for 2 h. The reaction mixture was concentrated under reduced pressure at lower temperature (28° C.). The residue was washed with diethyl ether (2×10 mL) and dried under vacuum for 10 min. Water was added to the reaction mixture was frozen in a −78° C. dry ice bath then lyophilized to afford 4-(4-(((S)-2-amino-2,4-dimethylpentyl)oxy)-3-chlorophenyl)-N-(tetrahydro-2H-pyran-3-yl)pyridin-2-amine, TFA (0.012 g, 0.012 mmol, 79% yield) as a pale yellow solid and as a single diastereomer. The absolute stereochemistry of pyran linkage is unassigned. LCMS (ESI) m/e 418.2 [(M+H)$^+$, calcd for $C_{23}H_{33}ClN_3O_2$ 418.2]; LC/MS retention time (method H): $t_R$=2.53 min; LC/MS retention time (method I): $t_R$=1.81 min. $^1$H NMR (400 MHz, METHANOL-$d_4$) δ=7.92 (d, J=2.5 Hz, 1H), 7.88 (d, J=7.0 Hz, 1H), 7.77 (dd, J=8.5, 2.5 Hz, 1H), 7.34 (d, J=9.0 Hz, 1H), 7.23 (d, J=1.5 Hz, 1H), 7.18 (dd, J=6.8, 1.8 Hz, 1H), 4.28-4.19 (m, 2H), 3.98-3.93 (m, 1H), 3.89-3.76 (m, 2H), 3.76-3.60 (m, 1H), 3.53-3.42 (m, 1H), 2.13 (dd, J=12.5, 3.5 Hz, 1H), 1.97-1.82 (m, 3H), 1.79-1.67 (m, 3H), 1.53 (s, 3H), 1.07-1.01 (m, 6H) ppm.

Example 340

4-(4-(((S)-2-amino-2,4-dimethylpentyl)oxy)-3-chlorophenyl)-N-(tetrahydro-2H-pyran-3-yl)pyridin-2-amine

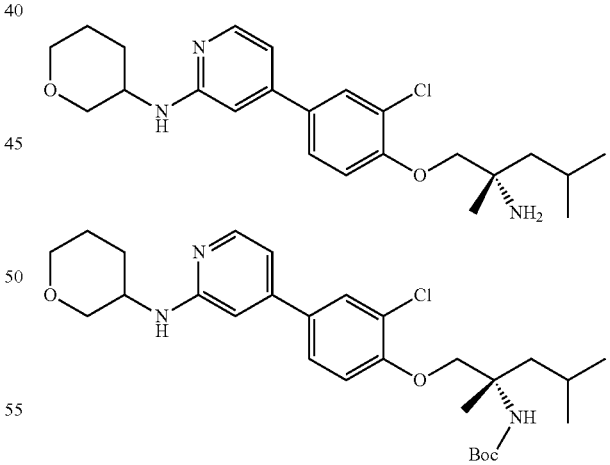

Part A: tert-butyl ((2S)-1-(2-chloro-4-(2-((tetrahydro-2H-pyran-3-yl)amino)pyridin-4-yl)phenoxy)-2,4-dimethylpentan-2-yl)carbamate diastereomer 1

Racemic tert-butyl ((2S)-1-(2-chloro-4-(2-((tetrahydro-2H-pyran-3-yl)amino)pyridin-4-yl)phenoxy)-2,4-dimethylpentan-2-yl)carbamate (prepared in Example 338, Parts A and B) (40 mg, 0.077 mmol) was resolved into the two diastereomers by chiral SFC (Method: Column/dimensions: Luxcellulose-4 (250×21.5) mm, 5u, % CO2: 70%, % Co solvent: 30% (0.25% DEA in Methanol, Total Flow: 60 g/min, Back Pressure: 100 bar, Temperature: 25° C., UV: 257 nm).

Isomer 1 was concentrated under reduced pressure to afford tert-butyl ((2S)-1-(2-chloro-4-(2-((tetrahydro-2H-pyran-3-yl)amino)pyridin-4-yl)phenoxy)-2,4-dimethylpentan-2-yl)carbamate (0.015 g, 0.029 mmol, 14% yield) as a yellow semi-solid. LCMS (ESI) m/e 518.2 [(M+H)$^+$, calcd for $C_{28}H_{41}ClN_3O_4$, 518.2]; LC/MS retention time (method H); $t_R$=2.28 min.

Isomer 2 was concentrated under reduced pressure to afford tert-butyl ((2S)-1-(2-chloro-4-(2-((tetrahydro-2H-pyran-3-yl)amino)pyridin-4-yl)phenoxy)-2,4-dimethylpentan-2-yl)carbamate (0.012 g, 0.023 mmol, 10% yield) as a yellow semi-solid. LCMS (ESI) m/e 518.2 [(M+H)$^+$, calcd for $C_{28}H_{41}ClN_3O_4$, 518.2]; LC/MS retention time (method H); $t_R$=2.29 min.

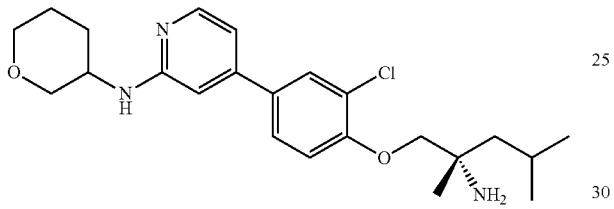

Part B: 4-(4-(((S)-2-amino-2,4-dimethylpentyl)oxy)-3-chlorophenyl)-N-(tetrahydro-2H-pyran-3-yl)pyridin-2-amine A solution of tert-butyl ((2S)-1-(2-chloro-4-(2-((tetrahydro-2H-pyran-3-yl)amino)pyridin-4-yl)phenoxy)-2,4-dimethylpentan-2-yl)carbamate, isomer 2 (0.01 g, 0.019 mmol) (0.012 g, 0.023 mmol) in methanol (0.5 mL) was cooled to 0° C. under a nitrogen atmosphere. The solution was stirred at 0° C. for 10 min. TFA (1.5 mL, 19.47 mmol) was added dropwise over a period of 1 min and the mixture was warmed to room temperature and allowed to stir for 2 h. The reaction mixture was concentrated under reduced pressure at lower temperature (28° C.). The residue was washed with diethyl ether (2×10 mL) and dried under vacuum for 10 min. Water was added to the reaction mixture was frozen in a −78° C. dry ice bath then lyophilized to afford 4-(4-(((S)-2-amino-2,4-dimethylpentyl)oxy)-3-chlorophenyl)-N-(tetrahydro-2H-pyran-3-yl)pyridin-2-amine, TFA (0.007 g, 0.013 mmol, 57% yield) as a pale yellow solid and as a single diastereomer. The absolute stereochemistry of pyran linkage is unassigned. LCMS (ESI) m/e 418.2 [(M+H)$^+$, calcd for $C_{23}H_{33}ClN_3O_2$ 418.2]; LC/MS retention time (method H): $t_R$=2.55 min; LC/MS retention time (method I): $t_R$=1.80 min. $^1$H NMR (400 MHz, METHANOL-d$_4$) δ=7.93 (d, J=2.0 Hz, 1H), 7.88 (d, J=7.5 Hz, 1H), 7.78 (dd, J=8.5, 2.5 Hz, 1H), 7.36-7.33 (m, 1H), 7.25 (d, J=1.0 Hz, 1H), 7.19 (dd, J=6.8, 1.8 Hz, 1H), 4.28-4.20 (m, 2H), 4.00-3.93 (m, 1H), 3.89-3.84 (m, 1H), 3.82-3.68 (m, 1H), 3.67-3.57 (m, 1H), 3.54-3.40 (m, 1H), 2.17-2.09 (m, 1H), 1.98-1.80 (m, 3H), 1.79-1.64 (m, 3H), 1.53 (s, 3H), 1.07-1.04 (m, 6H) ppm.

Example 341

(S)-2,4-dimethyl-1-((7-(pyrazolo[1,5-a]pyrimidin-7-yl)benzo[d]thiazol-4-yl)oxy)pentan-2-amine

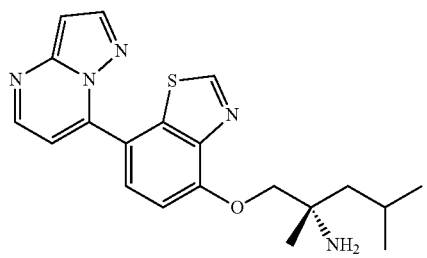

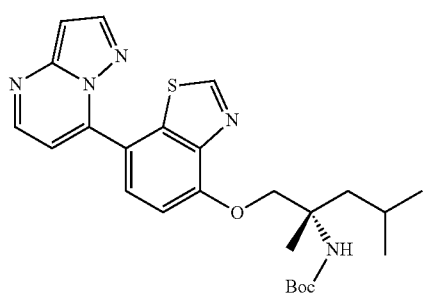

Part A: (S)-tert-butyl (2,4-dimethyl-1-((7-(pyrazolo[1,5-a]pyrimidin-7-yl) benzo[d]thiazol-4-yl)oxy) pentan-2-yl)carbamate A mixture of 7-chloropyrazolo[1,5-a]pyrimidine (0.02 g, 0.130 mmol), (S)-tert-butyl (2,4-dimethyl-1-((7-(4,4,5,5-tetramethyl-1,3,2-dioxaborolan-2-yl)benzo[d]thiazol-4-yl) oxy)pentan-2-yl)carbamate (prepared as described in Example 267) (0.077 g, 0.156 mmol), triphenylphosphine (6.83 mg, 0.026 mmol), and tripotassium phosphate (0.055 g, 0.260 mmol) in 1,4-dioxane (2 mL) and water (4.69 μL, 0.260 mmol) was purged with nitrogen for 15 min. Palladium(II) acetate (2.92 mg, 0.013 mmol) was added and the mixture was purged for a further 5 min, then the reaction mixture was heated to 100° C. for 45 min. The reaction mixture was cooled to room temperature and diluted with 1,4-dioxane (10 mL) and filtered through diatomaceous earth. The diatomaceous earth bed was washed with 15 mL of ethyl acetate. The filtrate was concentrated under reduced pressure. The crude was purified via reverse phase HPLC. The desired fractions were concentrated under reduced pressure to afford (S)-tert-butyl (2,4-dimethyl-1-((7-(pyrazolo[1,5-a]pyrimidin-7-yl)benzo[d]thiazol-4-yl)oxy)pentan-2-yl)carbamate (0.025 g, 0.051 mmol, 31% yield) as a yellow semi-solid. LCMS (ESI) m/e 482.2 [(M+H)$^+$, calcd for $C_{25}H_{32}N_5O_3S$, 482.2]; LC/MS retention time (Method A1); $t_R$=2.81 min.

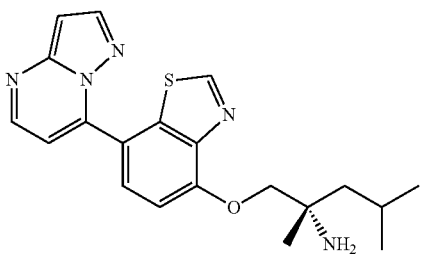 [SMILES: CC(C)C[C@](C)(N)COc1ccc(-c2ccnc3ccnn23)c2scnc12]

Part B: (S)-2,4-dimethyl-1-((7-(pyrazolo[1,5-a]py-rimidin-7-yl)benzo[d]thiazol-4-yl)oxy)pentan-2-amine To a solution of (S)-tert-butyl (2,4-dimethyl-1-((7-(pyrazolo[1,5-a]pyrimidin-7-yl)benzo[d]thiazol-4-yl)oxy)pentan-2-yl)carbamate (0.025 g, 0.051 mmol) in MeOH (0.5 mL) cooled to 0° C. under a nitrogen atmosphere was added TFA (1.5 mL, 19.47 mmol) dropwise over a period of 1 min. The reaction mixture was warmed to room temperature and allowed to stir for 2 h. The reaction mixture was concentrated under reduced pressure at lower temperature (28° C.). The residue was washed with diethyl ether (2×10 mL) and dried under vacuum for 10 min. Water was added to the reaction mixture and it was frozen in a −78° C. dry ice bath then lyophilized to afford (S)-2,4-dimethyl-1-((7-(pyrazolo[1,5-a]pyrimidin-7-yl)benzo[d]thiazol-4-yl)oxy)pentan-2-amine, TFA (17.24 mg, 0.038 mmol, 75% yield) as a pale yellow solid. LCMS (ESI) m/e 382.2 [(M+H)$^+$, calcd for $C_{20}H_{24}N_5OS$, 382.1]; LC/MS retention time (method A1); $t_R$=1.73 min. $^1$H NMR (400 MHz, METHANOL-$d_4$): δ 9.42 (s, 1H), 8.65 (d, J=4.52 Hz, 1H), 8.21 (d, J=2.51 Hz, 1H), 8.10 (d, J=8.03 Hz, 1H), 7.39 (d, J=8.03 Hz, 1H), 7.27 (d, J=4.02 Hz, 1H), 6.87 (d, J=2.51 Hz, 1H), 4.49 (d, J=10.04 Hz, 1H), 4.36 (d, J=10.54 Hz, 1H), 1.89-1.96 (m, 2H), 1.75-1.82 (m, 1H), 1.58 (s, 3H), 1.01-1.11 (m, 6H) ppm.

Example 342

(S)-2,4-dimethyl-1-((7-(2-methylpyrimidin-4-yl)benzo[d]thiazol-4-yl)oxy)pentan-2-amine

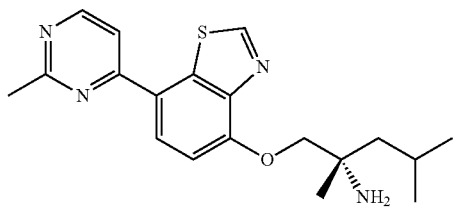 [SMILES: Cc1nccc(-c2ccc(OC[C@@](C)(N)CC(C)C)c3ncsc23)n1]

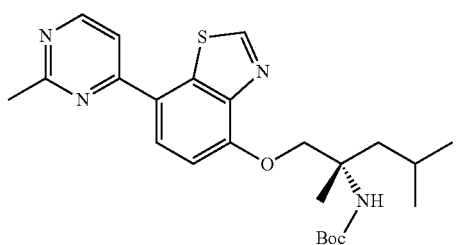 [SMILES: Cc1nccc(-c2ccc(OC[C@](C)(CC(C)C)NC(=O)OC(C)(C)C)c3ncsc23)n1]

Part A: (S)-tert-butyl (2,4-dimethyl-1-((7-(2-methyl-pyrimidin-4-yl)benzo[d]thiazol-4-yl)oxy)pentan-2-yl)carbamate A mixture of 4-chloro-2-methylpyrimidine (0.018 g, 0.140 mmol), (S)-tert-butyl (2,4-dimethyl-1-((7-(4,4,5,5-tetramethyl-1,3,2-dioxaborolan-2-yl)benzo[d]thiazol-4-yl)oxy)pentan-2-yl)carbamate (0.069 g, 0.140 mmol) (prepared as described in Example 267), triphenylphosphine (7.34 mg, 0.028 mmol), and tripotassium phosphate (0.059 g, 0.280 mmol) in 1,4-dioxane (1.5 mL) and water (5.04 µL, 0.280 mmol) was purged with nitrogen for 15 min. Palladium(II) acetate (3.14 mg, 0.014 mmol) was added and the mixture purged for a further 5 min. The reaction mixture was heated at 100° C. for 45 min. The reaction mixture was cooled to room temperature and diluted with 1,4-dioxane (10 mL) and filtered through diatomaceous earth. The diatomaceous earth bed was washed with 15 mL of ethyl acetate. The filtrate was concentrated under reduced pressure. The crude purified through reverse phase HPLC (10 mM ammonium acetate). The desired fractions were concentrated under reduced pressure to afford (S)-tert-butyl (2,4-dimethyl-1-((7-(2-methylpyrimidin-4-yl)benzo [d]thiazol-4-yl)oxy)pentan-2-yl)carbamate (0.024 g, 0.050 mmol, 35% yield) as a yellow semi-solid. LCMS (ESI) m/e 457.2 [(M+H)$^+$, calcd for $C_{24}H_{33}N_4O_3S$, 457.2]; LC/MS retention time (Method A1); $t_R$=2.89.

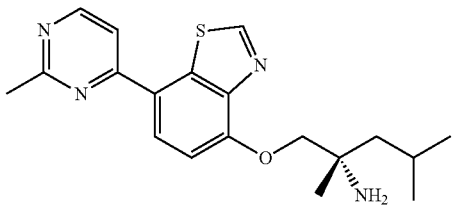 [SMILES: Cc1nccc(-c2ccc(OC[C@@](C)(N)CC(C)C)c3ncsc23)n1]

Part B: (S)-2,4-dimethyl-1-((7-(2-methylpyrimidin-4-yl)benzo[d]thiazol-4-yl)oxy)pentan-2-amine To a solution of (S)-tert-butyl (2,4-dimethyl-1-((7-(2-methylpyrimidin-4-yl)benzo[d]thiazol-4-yl)oxy)pentan-2-yl)carbamate (0.024 g, 0.050 mmol) in MeOH (0.5 mL) cooled to 0° C. under a nitrogen atmosphere was added TFA (1.5 mL, 19.47 mmol) dropwise over a period of 1 min and warmed to room temperature. The reaction mixture was allowed to stir for 2 h. Solvent was concentrated under reduced pressure at lower temperature (28° C.). The residue was washed with diethyl ether (2×15 mL) and dried under vacuum for 10 min. Water was added to the reaction mixture was frozen in a −78° C. dry ice bath then lyophilized to afford (S)-2,4-dimethyl-1-((7-(2-methylpyrimidin-4-yl)benzo[d]thiazol-4-yl)oxy)pentan-2-amine, TFA (0.023 g, 0.045 mmol, 91% yield) as a pale yellow solid. LCMS (ESI) m/e 357.2 [(M+H)$^+$, calcd for $C_{19}H_{25}N_4OS$, 357.0]; LC/MS retention time (method H); $t_R$=2.02 min. $^1$H NMR (400 MHz, METHANOL-$d_4$): δ 9.45 (s, 1H), 8.74 (d, J=5.52 Hz, 1H), 8.42 (d, J=8.53 Hz, 1H), 8.06 (d, J=5.52 Hz, 1H), 7.35 (d, J=8.53 Hz, 1H), 4.47 (d, J=10.04 Hz, 1H), 4.34 (d, J=10.54 Hz, 1H), 2.86 (s, 3H), 1.86-1.96 (m, 2H), 1.72-1.81 (m, 1H), 1.57 (s, 3H), 0.98-1.11 (m, 6H) ppm.

Example 345

4-(4-(((S)-2-amino-2,4-dimethylpentyl)oxy)-3-chlorophenyl)-N-(tetrahydrofuran-3-yl)pyridin-2-amine

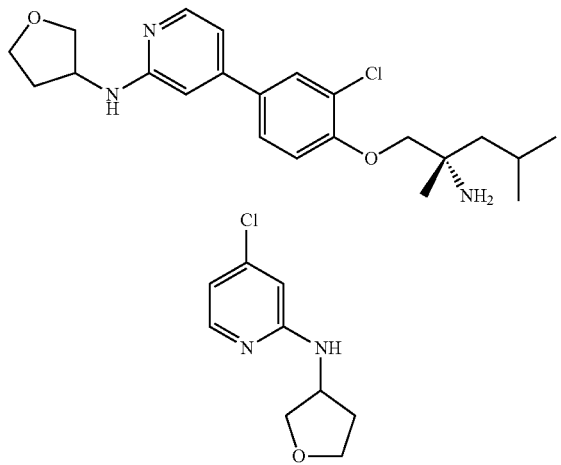

Part A: 4-chloro-N-(tetrahydrofuran-3-y pyri in-2-amine

To a stirred solution of 4-chloro-2-fluoropyridine (0.094 g, 0.574 mmol) in DMSO (2 mL) cooled to 0° C. under a nitrogen atmosphere was added $Cs_2CO_3$ (0.374 g, 1.148 mmol) and the mixture was stirred for 5 min. Tetrahydrofuran-3-amine (0.05 g, 0.574 mmol) was added and the mixture heated to 90° C. for 14 h. Water was added and the solution was extracted with ethyl acetate (2×20 mL). The combined organic layers were washed with water (2×20 mL). The organic layers were dried over sodium sulfate and concentrated under reduced pressure. The residue was purified via silica gel chromatography (ethyl acetate and pet ether) to afford 4-chloro-N-(tetrahydrofuran-3-yl)pyridin-2-amine (0.05 g, 0.209 mmol, 36% yield) as a yellow oil. LCMS (ESI) m/e 199.2 [(M+H)$^+$, calcd for $C_9H_{12}ClN_2O$, 199.0]; LC/MS retention time (method A1); $t_R$=1.73 min.

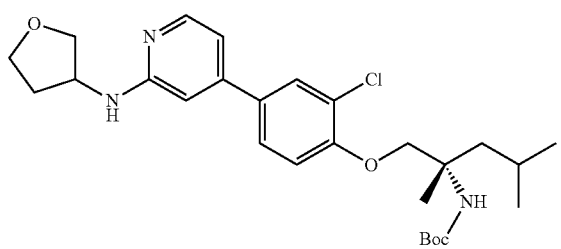 [SMILES: CC(C)C[C@@](C)(COc1ccc(-c2ccnc(NC3CCOC3)c2)cc1Cl)NC(=O)OC(C)(C)C]

Part B: tert-butyl ((2S)-1-(2-chloro-4-(2-((tetrahydrofuran-3-yl)amino)pyridin-4-yl)phenoxy)-2,4-dimethylpentan-2-yl)carbamate A mixture of (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (0.113 g, 0.242 mmol), 4-chloro-N-(tetrahydrofuran-3-yl)pyridin-2-amine (0.04 g, 0.201 mmol), and tripotassium phosphate (2M Solution) (0.302 mL, 0.604 mmol) in 1,4-dioxane (2 mL) was purged with nitrogen for 15 min. XPhos 2$^{nd}$ generation precatalyst (0.024 g, 0.030 mmol) was added and the mixture was purged for a further 5 min then stirred at 80° C. for 12 h. The reaction mixture was cooled to room temperature and diluted with ethyl acetate (20 mL) and filtered through diatomaceous earth. The diatomaceous earth bed was washed with 10 mL of ethyl acetate. The filtrate was concentrated under reduced pressure. The residue was purified via reverse phase HPLC (Method B) to afford tert-butyl ((2S)-1-(2-chloro-4-(2-((tetrahydrofuran-3-yl)amino)pyridin-4-yl)phenoxy)-2,4-dimethylpentan-2-yl)carbamate (30 mg, 0.060 mmol, 29% yield) as a yellow semi-solid. LCMS (ESI) m/e 504.6 [(M+H)$^+$, calcd for $C_{27}H_{39}ClN_3O_4$, 504.2]; LC/MS retention time (method D); $t_R$=1.11 min.

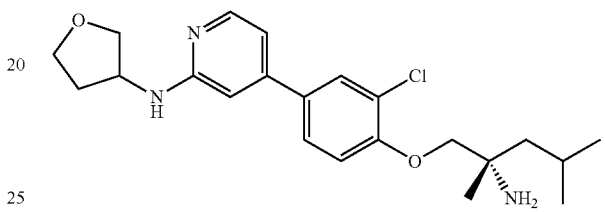

Part C: 4-(4-(((S)-2-amino-2,4-dimethylpentyl)oxy)-3-chlorophenyl)-N-(tetrahydrofuran-3-yl)pyridin-2-amine To a solution of tert-butyl ((2S)-1-(2-chloro-4-(2-((tetrahydrofuran-3-yl)amino)pyridin-4-yl)phenoxy)-2,4-dimethylpentan-2-yl)carbamate (0.03 g, 0.060 mmol) in MeOH (0.5 mL) cooled to 0° C. under a nitrogen atmosphere was added TFA (1.5 mL, 19.47 mmol) dropwise over a period of 1 min and the mixture was warmed to room temperature and allowed to stir for 2 h. The reaction mixture was concentrated under reduced pressure at lower temperature (28° C.). The crude material was purified by prep HPLC (method A) to afford LCMS (ESI) m/e 404.3 [(M+H)$^+$, calcd for $C_{22}H_{31}ClN_3O_2$, 404.2]; LC/MS retention time (method D); $t_R$=1.51 min. LC/MS retention time (Method E); $t_R$=0.83 min. $^1$H NMR (400 MHz, METHANOL-$d_4$): δ 7.89-7.95 (m, 2H), 7.78 (dd, J=8.78, 2.26 Hz, 1H), 7.32-7.37 (m, 1H), 7.20-7.24 (m, 2H), 4.39-4.41 (m, 1H), 4.19-4.28 (m, 2H), 3.83-4.06 (m, 4H), 2.38-2.48 (m, 1H), 2.03-2.04 (m, 1H), 1.81-1.97 (m, 2H), 1.68-1.75 (m, 1H), 1.53 (s, 3H), 1.00-1.14 (m, 6H) ppm.

Example 346

4-(4-(((S)-2-amino-2,4-dimethylpentyl)oxy)-3-methylphenyl)-N-(tetrahydrofuran-3-yl)pyridin-2-amine

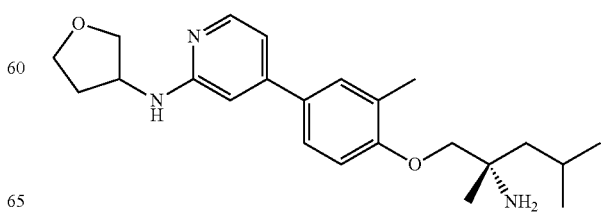

Prepared as described in Example 345 to afford 4-(4-(((S)-2-amino-2,4-dimethylpentyl)oxy)-3-methylphenyl)-N-(tetrahydrofuran-3-yl)pyridin-2-amine, TFA as a pale yellow solid. LCMS (ESI) m/e 384.2 [(M+H)$^+$, calcd for C$_{23}$H$_{34}$N$_3$O$_2$, 384.2]; LC/MS retention time (method D); t$_R$=2.27 min. LC/MS retention time (Method E); t$_R$=1.77 min. $^1$H NMR (400 MHz, METHANOL-d$_4$): δ 7.87 (d, J=7.03 Hz, 1H), 7.64-7.69 (m, 2H), 7.12-7.23 (m, 3H), 4.3-4.39 (m, 1H), 4.10-4.21 (m, 2H), 3.68-4.06 (m, 4H), 2.33-2.48 (m, 4H), 1.97-2.06 (m, 1H), 1.80-1.93 (m, 2H), 1.67-1.73 (m, 1H), 1.52 (s, 3H), 0.98-1.08 (m, 6H) ppm.

Example 347

1-(((3-methyl-5-(2-methylpyrimidin-4-yl)pyridin-2-yl)oxy)methyl)cyclobutanamine

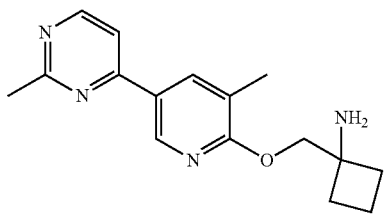 [SMILES: Cc1nccc(-c2cnc(OCC3(N)CCC3)c(C)c2)n1]

Prepared as described in Example 263. 1-(((3-methyl-5-(2-methylpyrimidin-4-yl)pyridin-2-yl)oxy)methyl)cyclobutanamine, TFA (0.018 g, 0.045 mmol, 51% yield) as a pale yellow solid. LCMS (ESI) m/e 285.2 [(M+H)$^+$, calcd for C$_{16}$H$_{21}$N$_4$O 285.2]; LC/MS retention time (method H): t$_R$=0.92 min; LC/MS retention time (method I): t$_R$=0.70 min. $^1$H NMR (400 MHz, MeOD): δ 8.84 (d, J=2.51 Hz, 1H), 8.69 (d, J=5.52 Hz, 1H), 8.33-8.37 (m, 1H), 7.84 (d, J=5.52 Hz, 1H), 4.72 (s, 2H), 2.76 (s, 3H), 2.33-2.44 (m, 7H), 2.05-2.15 (m, 2H) ppm.

Example 351

(S)-1-(2-(difluoromethyl)-4-(pyrazolo [1,5-a]pyrimidin-7-yl)phenoxy)-2,4-dimethylpentan-2-amine

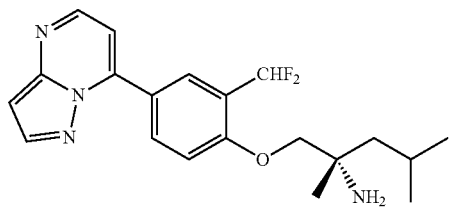 [SMILES: CC(C)C[C@](C)(N)COc1ccc(-c2ccnc3ccnn23)cc1C(F)F]

Prepared as described in Example 351. The crude final product was purified by prep HPLC (method B) to afford (S)-1-(2-(difluoromethyl)-4-(pyrazolo[1,5-a]pyrimidin-7-yl)phenoxy)-2,4-dimethylpentan-2-amine, TFA (0.028 g, 0.056 mmol, 30% yield for the final two steps) as a pale yellow solid. LCMS (ESI) m/e 375.3 [(M+H)$^+$, calcd for C$_{20}$H$_{25}$F$_2$N$_4$O 375.2]; LC/MS retention time (method H): t$_R$=1.46 min; LC/MS retention time (method I): t$_R$=1.20 min. $^1$H NMR (400 MHz, MeOD): δ 8.56 (d, J=4.52 Hz, 1H) 8.42 (d, J=1.00 Hz, 1H) 8.34 (dd, J=8.53, 2.51 Hz, 1H) 8.22 (d, J=2.51 Hz, 1H) 7.12-7.42 (m, 3H) 6.79 (d, J=2.01 Hz, 1H) 4.33 (d, J=10.1 Hz 1H) 4.25 (d, J=10 Hz, 1H) 1.80-1.92 (m, 2H) 1.66-1.74 (m, 1H) 1.53 (s, 3H) 0.99-1.10 (m, 6H) ppm.

Example 353

(S)-1-(2-(fluoromethyl)-4-(pyrazolo[1,5-a]pyrimidin-7-yl)phenoxy)-2,4-dimethylpentan-2amine

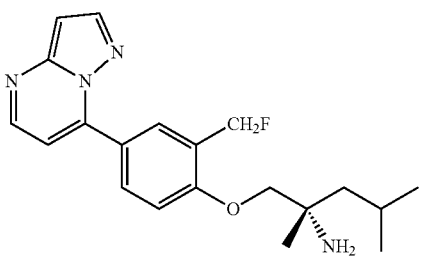

Prepared as described in Example 290. The crude final product was purified by prep HPLC (method B) to afford (S)-1-(2-(fluoromethyl)-4-(pyrazolo[1,5-a]pyrimidin-7-yl)phenoxy)-2,4-dimethylpentan-2-amine, TFA (0.001 g, 0.0002 mmol, 2% yield for the final two steps) as a pale yellow solid. LCMS (ESI) m/e 357.3 [(M+H)$^+$, calcd for C$_{20}$H$_{26}$FN$_4$O 357.2]; LC/MS retention time (method H): t$_R$=1.26 min; LC/MS retention time (method I): t$_R$=1.29 min. $^1$H NMR (400 MHz, MeOD): δ 8.57 (d, J=4.52 Hz, 1H) 8.21-8.29 (m, 3H) 7.32 (d, J=9.54 Hz, 1H) 7.16 (d, J=4.52 Hz, 1H) 6.80 (d, J=2.51 Hz, 1H) 5.67-5.77 (m, 1H) 5.55-5.65 (m, 1H) 4.30 (d, J=10.2 Hz, 1H) 4.22 (d, J=10.1 Hz, 1H) 1.82-1.96 (m, 2H) 1.68-1.77 (m, 1H) 1.55 (s, 3H) 1.01-1.12 (m, 6H) ppm.

Example 357

(S)-2,4-dimethyl-1-(5-methyl-2-(pyridin-4-yl)thiazol-4-yloxy)pentan-2-amine

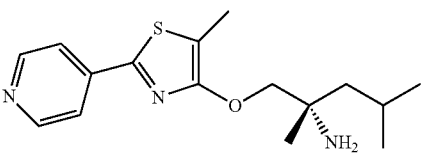

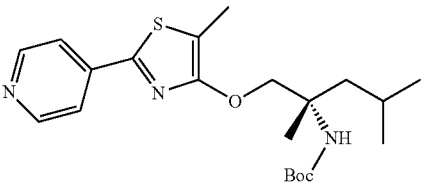

Part A: (S)-tert-butyl (2,4-dimethyl-1-((5-methyl-2-(pyridin-4-yl) thiazol-4-yl) oxy) pentan-2-yl) carbamate A solution of ethyl 5-methyl-2-(pyridin-4-yl) thiazol-4-ol (0.08 g, 0.416 mmol) in DMF (5 mL) was cooled to 0° C. K$_2$CO$_3$ (0.173 g, 1.248 mmol) was added in portions to the reaction mixture followed by slow addition of (S)-tert-butyl 4-isobutyl-4-methyl-1,2,3-oxathiazolidine-3-carboxylate 2,2-dioxide (prepared as described in Example 251, Parts A-E) (0.147 g, 0.499 mmol) in 1 mL DMF at 0° C. The reaction mixture was slowly allowed to warm to room temperature and heated at 88° C. for 12 h. The reaction mixture was cooled to 0° C. and quenched with aqueous ammonium chloride solution (10 mL). The reaction mixture was extracted with ethyl acetate (2×20 mL). The organic layer was washed with water (2×20 mL) and brine(10 mL), dried over $Na_2SO_4$, filtered, and concentrated under reduced pressure to afford (S)-tert-butyl (2,4-dimethyl-1-((5-methyl-2-(pyridin-4-yl) thiazol-4-yl) oxy) pentan-2-yl) carbamate (0.11 g, 0.271 mmol, 65% yield) as a brown color semi-solid. The brown solid was carried forward without further purification. LCMS (ESI) m/e 406.2 [(M+H)$^+$, calcd for $C_{21}H_{32}N_3O_3S$ 406.2]; LC/MS retention time (Method A1): $t_R$=1.55 min.

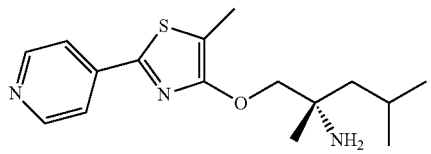 [SMILES: Cc1sc(-c2ccncc2)nc1OC[C@@](C)(N)CC(C)C]

Part B: (S)-2,4-dimethyl-1-(5-methyl-2-(pyridin-4-yl) thiazol-4-yloxy)pentan-2-amine To a solution of (S)-tert-butyl (2,4-dimethyl-1-((5-methyl-2-(pyridin-4-yl)thiazol-4-yl)oxy)pentan-2-yl)carbamate (0.11 g, 0.271 mmol) in dichloromethane (2 mL) at 0° C. was added TFA (0.418 mL, 5.42 mmol). The reaction mixture was allowed to stir for 4 h at room temperature, then was concentrated under reduced pressure. The residue was purified by preparative LC/MS (method B) to afford (S)-2, 4-dimethyl-1-(5-methyl-2-(pyridin-4-yl)thiazol-4-yloxy) pentan-2-amine (76 mg, 0.178 mmol, 66% yield) as a pale yellow solid. LCMS (ESI) m/e 306.0 [(M+H)$^+$, calcd for $C_{16}H_{24}N_3OS$ 306.2]; LC/MS retention time (method H): $t_R$=1.21 min; LC/MS retention time (method I): $t_R$=0.70 min. $^1$H NMR (400 MHz, Methanol-$d_4$): δ 8.72-8.74 (m, 2H), 8.18-8.19 (m, 2H), 4.44-4.54 (m, 2H), 2.47 (s, 3H), 1.83-1.91 (m, 2H), 1.66-1.71 (m, 1H), 1.50 (s, 3H), 1.03-1.08 (m, 6H) ppm.

Example 358

6-(4-(((S)-2-amino-2,4-dimethylpentyl)oxy)-3-(trifluoromethyl)phenyl)-N-(tetrahydro-2H-pyran-3-yl) pyrimidin-4-amine

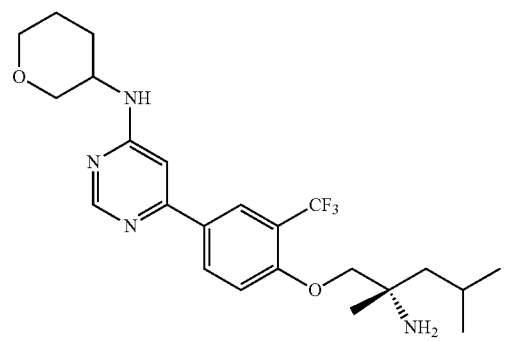

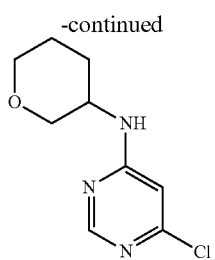

Part A. 6-chloro-N-(tetrahydro-2H-pyran-3-yl)pyrimidin-4-amine

To a stirred solution of 4,6-dichloropyrimidine (0.35 g, 2.349 mmol) in DMF (10 mL) at 0° C. was added NaH (0.282 g, 7.05 mmol). It was stirred for 5 min and tetrahydro-2H-pyran-3-amine (0.238 g, 2.349 mmol) was added. The mixture was then stirred at RT overnight. The mixture was diluted with water (10 mL) and extracted with ethyl acetate (2×50 mL). The EtOAc layer was collected, dried over $Na_2SO_4$, filtered, and concentrated under reduced pressure to afford 6-chloro-N-(tetrahydro-2H-pyran-3-yl)pyrimidin-4-amine (0.22 g, 0.634 mmol, 27% yield) as a gummy residue which was carried forward without further purification. LCMS (ESI) m/e 214.0 [(M+H)$^+$, calcd for $C_9H_{13}ClN_3O$ 214.1]; LC/MS retention time (Method A1): $t_R$=1.64 min.

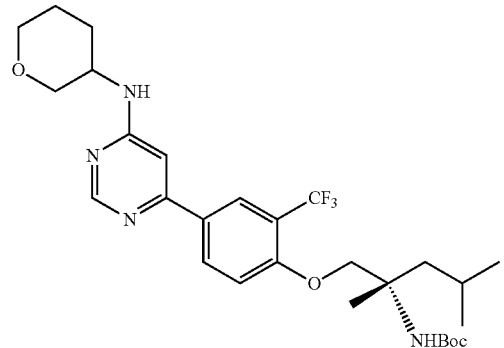 [SMILES: CC(C)C[C@@](C)(COc1ccc(-c2cc(NC3CCCOC3)ncn2)cc1C(F)(F)F)NC(=O)OC(C)(C)C]

Part B. tert-butyl ((2S)-2,4-dimethyl-1-(4-(6-((tetrahydro-2H-pyran-3-yl)amino)pyrimidin-4-yl)-2-(trifluoromethyl)phenoxy)pentan-2-yl)carbamate A mixture of 6-chloro-N-(tetrahydro-2H-pyran-3-yl)pyrimidin-4-amine (0.05 g, 0.143 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.072 g, 0.143 mmol), Pd(Ph$_3$P)$_4$ (0.016 g, 0.014 mmol), and potassium phosphate (0.214 mL, 0.428 mmol) in 1,4-dioxane (5 mL) was heated at 100° C. for 3 h. After cooling, the reaction mixture was concentrated, diluted with water and extracted with ethyl acetate. The ethyl acetate layer was collected, dried over $Na_2SO_4$, filtered, and concentrated under reduced pressure to afford tert-butyl ((2S)-2,4-dimethyl-1-(4-(6-((tetrahydro-2H-pyran-3-yl)amino)pyrimidin-4-yl)-2-(trifluoromethyl)phenoxy)pentan-2-yl)carbamate (0.05 g, 0.053 mmol, 37% yield) as a yellowish semi-solid which was carried forward without further purification.

LCMS (ESI) m/e 553.2 [(M+H)$^+$, calcd for $C_{28}H_{40}F_3N_4O_4$ 553.3]; LC/MS retention time (Method A1): $t_R$=2.77 min.

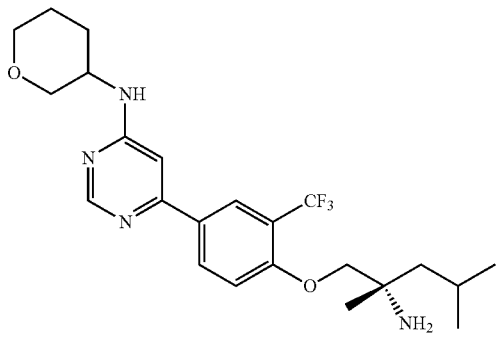 [SMILES: CC(C)C[C@](C)(N)COc1ccc(-c2cc(NC3CCCOC3)ncn2)cc1C(F)(F)F]

Part C. 6-(4-(((S)-2-amino-2,4-dimethylpentyl)oxy)-3-(trifluoromethyl)phenyl)-N-(tetrahydro-2H-pyran-3-yl)pyrimidin-4-amine To a solution of tert-butyl ((2S)-2,4-dimethyl-1-(4-(6-((tetrahydro-2H-pyran-3-yl)amino)pyrimidin-4-yl)-2-(trifluoromethyl)phenoxy)pentan-2-yl)carbamate (0.1 g, 0.181 mmol) in MeOH (2 mL) at 0° C. was added 4N HCl in 1,4-dioxane (0.452 mL, 1.810 mmol) and stirred at RT for 2 h. The reaction mixture was concentrated under reduced pressure. The residue was purified by preparative LC/MS (method B) to afford 6-(4-(((S)-2-amino-2,4-dimethylpentyl)oxy)-3-(trifluoromethyl)phenyl)-N-(tetrahydro-2H-pyran-3-yl)pyrimidin-4-amine (0.01 g, 0.021 mmol, 12% yield) as a yellow solid. LCMS (ESI) m/e 453.2 [(M+H)$^+$, calcd for $C_{23}H_{32}F_3N_4O_2$ 453.2]; LC/MS retention time (Method E): $t_R$=1.54 min; LCMS retention time (method F): $t_R$=2.40 min; $^1$H NMR (400 MHz, METHANOL-d$_4$): δ 8.66 (s, 1H) 8.19 (bs, 2H), 7.52 (d, J=9.04 Hz, 1H), 6.97-7.07 (m, 1H), 4.23-4.38 (m, 3H), 3.96 (dd, J=11.04, 2.51 Hz, 1H), 3.74-3.86 (m, 1H), 3.57-3.69 (m, 1H), 3.43-3.52 (m, 1H), 2.05 (s, 1H), 1.64-1.94 (m, 6H), 1.54 (s, 3H), 1.04 (m, 6H) ppm.

Example 361

(S)-1-(2-chloro-4-(7H-pyrrolo[2,3-d]pyrimidin-4-yl)phenoxy)-2,4-dimethylpentan-2-amine

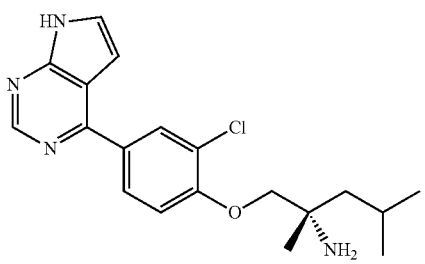

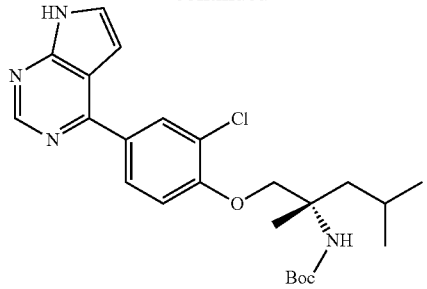

Part A: (S)-tert-butyl (1-(2-chloro-4-(7H-pyrrolo[2,3-d]pyrimidin-4-yl)phenoxy)-2,4-dimethylpentan-2-yl)carbamate A mixture of (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (168 mg, 0.358 mmol), 4-chloro-7H-pyrrolo[2,3-d]pyrimidine (50 mg, 0.326 mmol), Pd(Ph$_3$P)$_4$ (18.81 mg, 0.016 mmol) and 2M aq. solution of potassium phosphate (0.488 mL, 0.977 mmol) in 1,4-dioxane (4 mL) was purged with nitrogen and heated at 100° C. for 12 h. The reaction mixture was diluted with ethyl acetate (25 mL) and filtered through diatomaceous earth. The filtrate was concentrated under reduced pressure to afford a brown residue. The residue was purified by silica gel chromatography (15% ethyl acetate-hexane) to afford (S)-tert-butyl (1-(2-chloro-4-(7H-pyrrolo[2,3-d]pyrimidin-4-yl)phenoxy)-2,4-dimethylpentan-2-yl)carbamate (75 mg, 0.042 mmol, 13% yield) as a blackish gummy solid. LCMS (ESI) m/e 459.2 [(M+H)$^+$, calcd for $C_{24}H_{32}ClN_4O_3$ 459.2]; LC/MS retention time (method B): $t_R$=0.98 min.

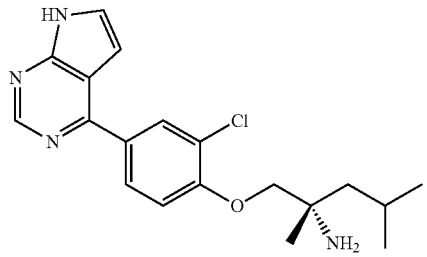 [SMILES: CC(C)C[C@](C)(N)COc1ccc(-c2ncnc3[nH]ccc23)cc1Cl]

Part B: (S)-1-(2-chloro-4-(7H-pyrrolo[2,3-d]pyrimidin-4-yl)phenoxy)-2,4-dimethylpentan-2-amine To a stirred solution of (S)-tert-butyl (1-(2-chloro-4-(7H-pyrrolo[2,3-d]pyrimidin-4-yl)phenoxy)-2,4-dimethylpentan-2-yl)carbamate (60 mg, 0.131 mmol) in DCM (2 mL) at 0° C. was added 4N HCl in 1,4-dioxane (2 mL, 65.8 mmol) and stirred the mixture was stirred for 30 min. The reaction mixture was concentrated under reduced pressure. The crude material was purified by prep HPLC (method B) to afford to afford (S)-1-(2-chloro-4-(7H-pyrrolo[2,3-d]pyrimidin-4-yl)phenoxy)-2,4-dimethylpentan-2-amine (13.7 mg, 0.038 mmol, 29% yield) as a pale-yellow solid. LCMS (ESI) m/e 359.0 [(M+H)$^+$, calcd for $C_{19}H_{24}ClN_4O$ 359.2]; LC/MS retention time (method D): $t_R$=1.25 min. $^1$H NMR (400 MHz, METHANOL-d$_4$): δ 8.79 (s, 1H), 8.21 (d, J=2.20 Hz, 1H), 8.11 (dd, J=8.60, 2.20 Hz, 1H), 7.58 (d, J=3.64 Hz, 1H), 7.35 (d, J=8.66 Hz, 1H), 6.89 (d, J=3.64 Hz, 1H), 4.10-4.19 (m, 2H), 1.79-1.92 (m, 2H), 1.64-1.71 (m, 1H), 1.45 (s, 3H), δ 1.03-1.08 (m, 6H) ppm.

Example 362

(S)-2-((2-amino-2,4-dimethylpentyl)oxy)-5-(7H-pyrrolo[2,3-d]pyrimidin-4-yl)benzonitrile

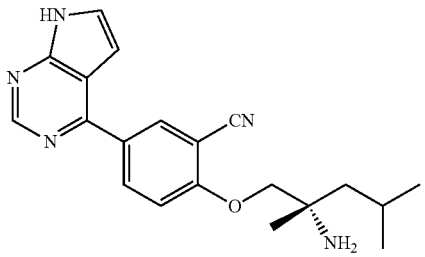 [SMILES: CC(C)C[C@](C)(N)COc1ccc(-c2ncnc3[nH]ccc23)cc1C#N]

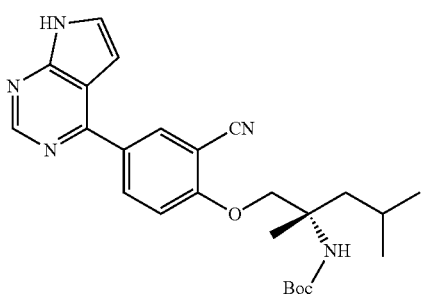 [SMILES: CC(C)C[C@@](C)(COc1ccc(-c2ncnc3[nH]ccc23)cc1C#N)NC(=O)OC(C)(C)C]

Part A: (S)-tert-butyl (1-(2-cyano-4-(7H-pyrrolo[2,3-d]pyrimidin-4-yl)phenoxy)-2,4-dimethylpentan-2-yl)carbamate A mixture of (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (90 mg, 0.195 mmol), 4-chloro-7H-pyrrolo[2,3-d]pyrimidine (30 mg, 0.195 mmol), Pd(Ph₃P)₄ (11.29 mg, 9.77 μmol) and 2M aq. potassium phosphate (0.293 mL, 0.586 mmol) in 1,4-dioxane (4 mL) was purged with nitrogen and heated at 100° C. for 12h. The reaction mixture was diluted with ethyl acetate (25 mL) and filtered through diatomaceous earth. The filtrate was concentrated under reduced pressure to afford a brown residue. The residue was purified by silica gel chromatography (15% ethyl acetate-hexane) to afford (S)-tert-butyl (1-(2-cyano-4-(7H-pyrrolo[2,3-d]pyrimidin-4-yl)phenoxy)-2,4-dimethylpentan-2-yl)carbamate (45 mg, 0.047 mmol, 24% yield) as brown gummy solid. LCMS (ESI) m/e 450.2 [(M+H)⁺, calcd for $C_{25}H_{32}N_5O_3$ 450.2]; LC/MS retention time (method B): $t_R$=0.94 min.

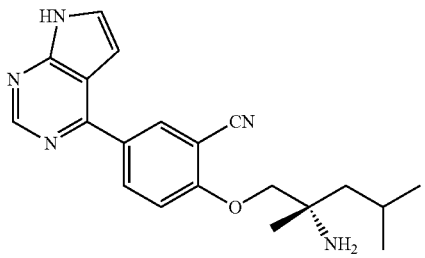

Part B (S)-2-((2-amino-2,4-dimethylpentyl)oxy)-5-(7H-pyrrolo[2,3-d]pyrimidin-4-yl)benzonitrile To a stirred solution of (S)-tert-butyl (1-(2-cyano-4-(7H-pyrrolo[2,3-d]pyrimidin-4-yl)phenoxy)-2,4-dimethylpentan-2-yl)carbamate (40 mg, 0.089 mmol) in DCM (2 mL) at 0° C., 4N HCl in 1,4-dioxane (2 mL, 65.8 mmol) was added and stirred for 30 min. The reaction mixture was concentrated under reduced pressure. The crude material was purified by prep HPLC (method B) to afford to afford (S)-2-((2-amino-2,4-dimethylpentyl)oxy)-5-(7H-pyrrolo[2,3-d]pyrimidin-4-yl)benzonitrile (5.8 mg, 0.017 mmol, 19% yield) as a pale yellow solid. LCMS (ESI) m/e 350.0 [(M+H)⁺, calcd for $C_{20}H_{24}N_5O$ 350.2]; LC/MS retention time (method D): $t_R$=1.11 min. ¹H NMR (400 MHz, METHANOL-d₄): δ 8.82 (s, 1H), 8.42-8.49 (m, 2H), 7.60 (d, J=3.58 Hz, 1H), 7.45 (d, J=9.60 Hz, 1H), 6.92 (d, J=3.64 Hz, 1H), 4.17 (d, J=2.26 Hz, 2H), 1.86-1.98 (m, 1H), 1.72-1.80 (m, 1H), 1.61-1.69 (m, 1H), 1.41 (s, 3H), 1.07-1.09 (m, 6H) ppm.

Example 363

(S)-1-(4-(7H-pyrrolo[2,3-d]pyrimidin-4-yl)-2-(trifluoromethyl)phenoxy)-2,4-dimethylpentan-2-amine

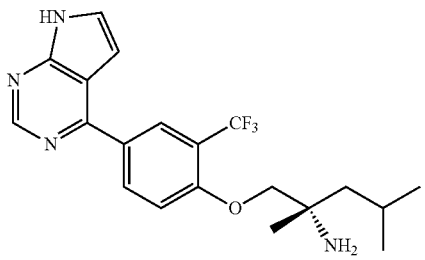

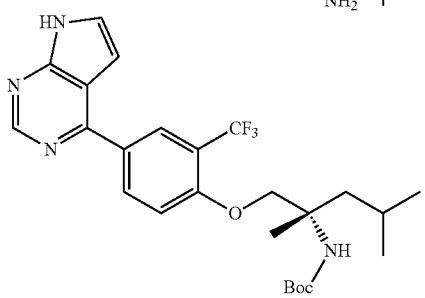

Part A: (S)-tert-but(1-(4-(7H-pyrrolo[2,3-d]pyrimidin-4-yl)-2-(trifluoromethyl)phenoxy)-2,4-dimethylpentan-2-yl)carbamate A mixture of (S)-tert-butyl (2,4-dimethyl-1-(4-(4,4,5,5-tetramethyl-1,3,2-dioxaborolan-2-yl)-2-(trifluoromethyl)

phenoxy)pentan-2-yl)carbamate (prepared as described in Example 255, Parts A and B) (126 mg, 0.251 mmol), 4-chloro-7H-pyrrolo[2,3-d]pyrimidine (35 mg, 0.228 mmol), Pd(Ph₃P)₄ (13.17 mg, 0.011 mmol) and 2M aq. potassium phosphate (0.342 mL, 0.684 mmol) in 1,4-dioxane (4 mL) was purged with nitrogen and heated at 100° C. and stirred for 12 h. The reaction mixture was diluted with ethyl acetate (25 mL) and filtered through diatomaceous earth. The filtrate was concentrated under reduced pressure to afford a blackish residue. The residue was purified by silica gel chromatography (10% ethyl acetate-hexane) to afford (S)-tert-butyl (1-(4-(7H-pyrrolo[2,3-d]pyrimidin-4-yl)-2-(trifluoromethyl)phenoxy)-2,4-dimethylpentan-2-yl)carbamate (80 mg, 0.071 mmol, 31% yield) as a black gummy solid. LCMS (ESI) m/e 493.3 [(M+H)⁺, calcd for $C_{25}H_{32}F_3N_4O_3$ 493.2]; LC/MS retention time (method B): $t_R$=1.02 min.

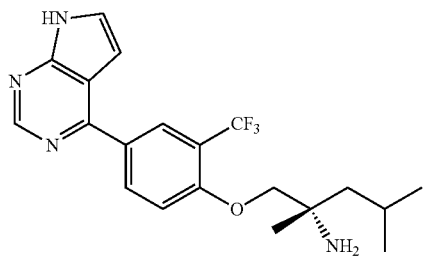

Part B: (S)-1-(4-(7H-pyrrolo[2,3-d]pyrimidin-4-yl)-2-(trifluoromethyl)phenoxy)-2,4-dimethylpentan-2-amine To a stirred solution of (S)-tert-butyl (1-(4-(7H-pyrrolo[2,3-d]pyrimidin-4-yl)-2-(trifluoromethyl)phenoxy)-2,4-dimethylpentan-2-yl)carbamate (80 mg, 0.162 mmol) in DCM (4 mL) at 0° C. was added 4N HCl in 1,4-dioxane (2 mL, 8.00 mmol). The solution was stirred for 30 min. The reaction mixture was concentrated under reduced pressure. The crude material was purified by prep HPLC (method B) to afford (S)-1-(4-(7H-pyrrolo[2,3-d]pyrimidin-4-yl)-2-(trifluoromethyl)phenoxy)-2,4-dimethylpentan-2-amine (41.8 mg, 0.102 mmol, 63% yield) as a pale yellow solid. LCMS (ESI) m/e 393.0 [(M+H)⁺, calcd for $C_{20}H_{24}F_3N_4O$ 393.2]; LC/MS retention time (method D): $t_R$=1.40 min. ¹H NMR (400 MHz, METHANOL-d₄): δ 8.81 (s, 1H), 8.38-8.44 (m, 2H), 7.59 (d, J=3.64 Hz, 1H), 7.44 (d, J=8.41 Hz, 1H), 6.89 (d, J=3.64 Hz, 1H), 4.05-4.13 (m, 2H), 1.81-1.91 (m, 1H), 1.55-1.71 (m, 2H), 1.35 (s, 3H), 1.03 (m, 6H) ppm.

Example 364

(S)-2-((2-amino-2,4-dimethylpentyl)oxy)-5-(7-methyl-7H-pyrrolo[2,3-d]pyrimidin-4-yl)benzonitrile

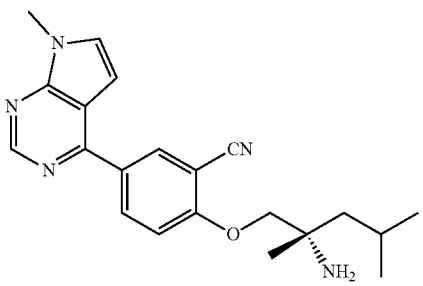 [SMILES: CC(C)C[C@](C)(N)COc1ccc(-c2ncnc3c2ccn3C)cc1C#N]

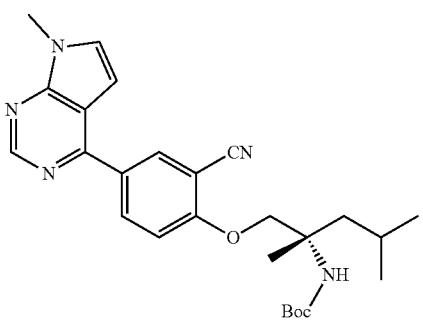 [SMILES: CC(C)C[C@@](C)(COc1ccc(-c2ncnc3c2ccn3C)cc1C#N)NC(=O)OC(C)(C)C]

Part A: (S)-tert-butyl (1-(2-cyano-4-(7-methyl-7H-pyrrolo[2,3-d]pyrimidin-4-yl)phenoxy)-2,4-dimethylpentan-2-yl)carbamate A mixture of (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (120 mg, 0.263 mmol), 4-chloro-7-methyl-7H-pyrrolo[2,3-d]pyrimidine (synthesis previously described *J. Med. Chem.*, 2012, 55, 7193) (40 mg, 0.239 mmol), Pd(Ph₃P)₄ (13.79 mg, 0.012 mmol) and 2M aq. potassium phosphate (0.358 mL, 0.716 mmol) in 1,4-dioxane (4 mL) was purged with nitrogen and heated at 100° C. for 12 h. The reaction mixture was diluted with ethyl acetate (25 mL) and filtered through diatomaceous earth. The filtrate was concentrated under reduced pressure to afford a blackish residue. The residue was purified by silica gel chromatography (10% ethyl acetate-hexane) to afford (S)-tert-butyl (1-(2-cyano-4-(7-methyl-7H-pyrrolo[2,3-d]pyrimidin-4-yl)phenoxy)-2,4-dimethylpentan-2-yl)carbamate (85 mg, 0.145 mmol, 61% yield) as a brown gummy solid. LCMS (ESI) m/e 464.2 [(M+H)⁺, calcd for $C_{26}H_{34}N_5O_3$ 464.3]; LC/MS retention time (Method C): $t_R$=1.14 min.

137

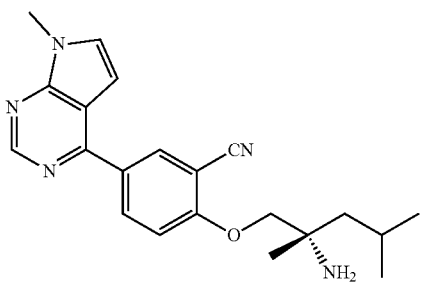 [SMILES: CC(C)C[C@](C)(N)COc1ccc(-c2ncnc3c2ccn3C)cc1C#N]

Part B: (S)-2-((2-amino-2,4-dimethylpentyl)oxy)-5-(7-methyl-7H-pyrrolo[2,3-d]pyrimidin-4-yl)benzonitrile To a stirred solution of (S)-tert-butyl (1-(2-cyano-4-(7-methyl-7H-pyrrolo[2,3-d]pyrimidin-4-yl)phenoxy)-2,4-dimethylpentan-2-yl)carbamate (85 mg, 0.145 mmol) in DCM (3 mL) at 0° C. was added 4N HCl in 1,4-dioxane (4 mL, 132 mmol) and the mixture stirred for 30 min. The reaction mixture was concentrated under reduced pressure. The crude material was purified by prep HPLC (method B) to afford (S)-2-((2-amino-2,4-dimethylpentyl)oxy)-5-(7-methyl-7H-pyrrolo[2,3-d]pyrimidin-4-yl)benzonitrile (20 mg, 0.053 mmol, 36% yield) as a pale yellow solid. LCMS (ESI) m/e 364.2 [(M+H)+, calcd for $C_{21}H_{26}N_5O$ 364.3]; LC/MS retention time (method D): $t_R$=1.25 min. $^1$H NMR (400 MHz, METHANOL-$d_4$): δ 8.86 (s, 1H), 8.41-8.46 (m, 2H), 7.59 (d, J=3.64 Hz, 1H), 7.44 (d, J=9.54 Hz, 1H), 6.92 (d, J=3.64 Hz, 1H), 4.15 (d, J=2.45 Hz, 2H), 3.95 (s, 3H), 1.85-1.96 (m, 1H), 1.71-1.79 (m, 1H), 1.60-1.67 (m, 1H), 1.39 (s, 3H), 1.02-1.07 (m, 6H), ppm.

Example 365

(S)-1-(2-fluoro-4-(7-methyl-7H-pyrrolo[2,3-d]pyrimidin-4-yl)phenoxy)-2,4-dimethylpentan-2-amine

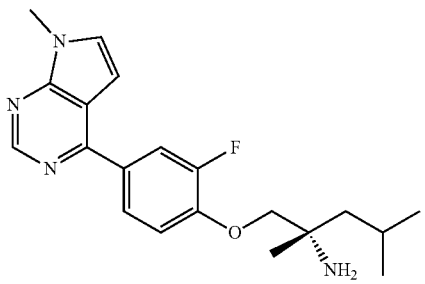 [SMILES: CC(C)C[C@](C)(N)COc1ccc(-c2ncnc3c2ccn3C)cc1F]

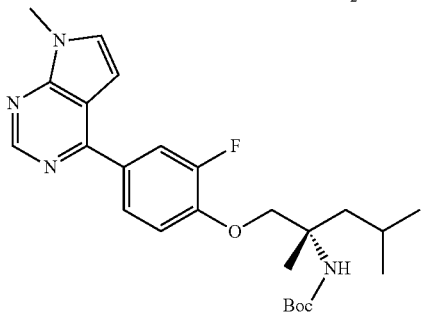

138

Part A: (S)-tert-butyl (1-(2-fluoro-4-(7-methyl-7H-pyrrolo[2,3-d]pyrimidin-4-yl)phenoxy)-2,4-dimethylpentan-2-yl)carbamate A mixture of (S)-tert-butyl (1-(2-fluoro-4-(4,4,5,5-tetramethyl-1,3,2-dioxaborolan-2-yl)phenoxy)-2,4-dimethylpentan-2-yl)carbamate (prepared as in Example 253, Part B) (119 mg, 0.263 mmol), 4-chloro-7-methyl-7H-pyrrolo[2,3-d]pyrimidine (40 mg, 0.239 mmol) (synthesis previously described J. Med. Chem., 2012, 55, 7193), Pd(Ph$_3$P)$_4$ (13.79 mg, 0.012 mmol) and 2M aq. potassium phosphate (0.358 mL, 0.716 mmol) in 1,4-dioxane (4 mL) was purged with nitrogen and heated at 100° C. for 12h. The reaction mixture was diluted with ethyl acetate (25 mL) and filtered through diatomaceous earth. The filtrate was concentrated under reduced pressure to afford a blackish residue. The residue was purified by silica gel chromatography (10% ethyl acetate-hexane) to afford (S)-tert-butyl (1-(2-fluoro-4-(7-methyl-7H-pyrrolo[2,3-d]pyrimidin-4-yl)phenoxy)-2,4-dimethylpentan-2 yl)carbamate (80 mg, 0.116 mmol, 49% yield) as a brown gummy solid. LCMS (ESI) m/e 457.2 [(M+H)+, calcd for $C_{25}H_{34}FN_4O_3$ 457.2]; LC/MS retention time (Method C): $t_R$=1.18 min.

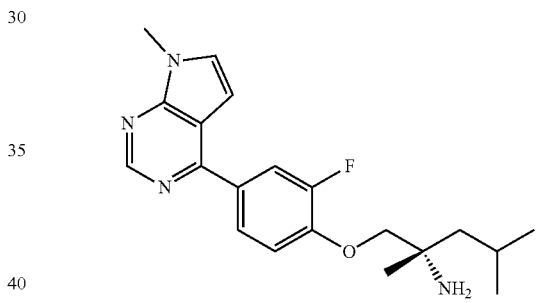

Part B: (S)-1-(2-fluoro-4-(7-methyl-7H-pyrrolo[2,3-d]pyrimidin-4-yl)phenoxy)-2,4-dimethylpentan-2-amine To a stirred solution of (S)-tert-butyl (1-(2-fluoro-4-(7-methyl-7H-pyrrolo[2,3-d]pyrimidin-4-yl)phenoxy)-2,4-dimethylpentan-2-yl)carbamate (80 mg, 0.175 mmol) in DCM (3 mL) at 0° C. was added 4N HCl in 1,4-dioxane (4 mL, 132 mmol) and the solution stirred for 1 h. The reaction mixture was concentrated under reduced pressure. The crude material was purified by prep HPLC (method B) to afford (S)-1-(2-fluoro-4-(7-methyl-7H-pyrrolo[2,3-d]pyrimidin-4-yl)phenoxy)-2,4-dimethylpentan-2-amine (6.5 mg, 0.018 mmol, 10% yield) as a pale yellow solid. LCMS (ESI) m/e 357.0 [(M+H)+, calcd for $C_{20}H_{26}FN_4O$ 357.2]; LC/MS retention time (Method E): $t_R$=0.83 min. $^1$H NMR (400 MHz, METHANOL-$d_4$): δ 8.84 (s, 1H), 7.92-8.00 (m, 2H), 7.57 (d, J=3.64 Hz, 1H), 7.40 (t, J=8.63 Hz, 1H), 6.91 (d, J=3.64 Hz, 1H), 4.13-4.25 (m, 2H), 3.94 (s, 3H), 1.79-1.92 (m, 2H), 1.65-1.72 (m, 1H), 1.47 (s, 3H), 1.05-1.09 (m, 6H) ppm.

Example 366

(S)-2,4-dimethyl-1-(4-(7-methyl-7H-pyrrolo[2,3-d]pyrimidin-4-yl)-2-(trifluoromethyl)phenoxy)pentan-2-amine

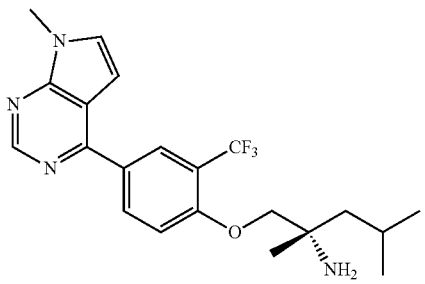 [SMILES: CC(C)C[C@](C)(N)COc1ccc(-c2ncnc3c2ccn3C)cc1C(F)(F)F]

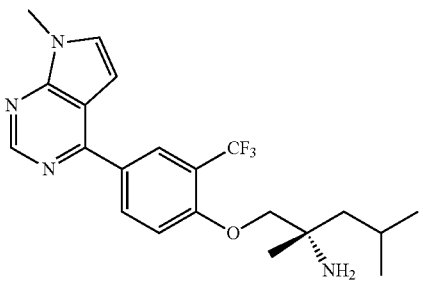

Part B: (S)-2,4-dimethyl-1-(4-(7-methyl-7H-pyrrolo[2,3-d]pyrimidin-4-yl)-2 (trifluoromethyl)phenoxy)pentan-2-amine To a stirred solution of (S)-tert-butyl (2,4-dimethyl-1-(4-(7-methyl-7H-pyrrolo[2,3-d]pyrimidin-4-yl)-2-(trifluoromethyl)phenoxy)pentan-2-yl)carbamate (80 mg, 0.111 mmol) in DCM (3 mL) at 0° C. was added 4M HCl in 1,4-dioxane (4 mL, 132 mmol) and the solution stirred for 2 h. The reaction mixture was concentrated under reduced pressure. The crude material was purified by prep HPLC (method B) to afford (S)-2,4-dimethyl-1-(4-(7-methyl-7H-pyrrolo[2,3-d]pyrimidin-4-yl)-2-(trifluoromethyl)phenoxy)pentan-2-amine (13.2 mg, 0.032 mmol, 29% yield) as a pale yellow solid. LCMS (ESI) m/e 407.2 [(M+H)$^+$, calcd for $C_{21}H_{26}F_3N_4O$ 407.2]; LC/MS retention time (method D): $t_R$=1.70 min. $^1$H NMR (400 MHz, METHANOL-d$_4$): δ 8.86 (s, 1H), 8.37-8.45 (m, 2H), 7.58 (d, J=3.70 Hz, 1H), 7.44 (d, J=8.47 Hz, 1H), 6.89 (d, J=3.64 Hz, 1H), 4.07-4.22 (m, 2H), 3.95 (s, 3H), 1.83-1.93 (m, 1H), 1.57-1.75 (m, 2H), 1.38 (s, 3H), 1.03 (m, 6H) ppm.

Example 368

(S)—N-(4-(4-((2-amino-2,4-dimethylpentyl)oxy)-3-methylphenyl)pyrimidin-2-yl)thiazol-2-amine

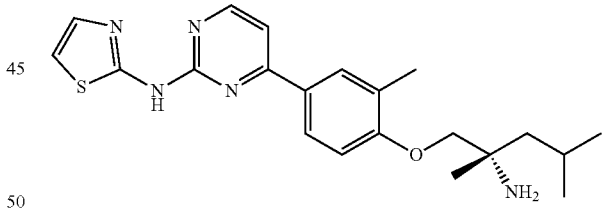

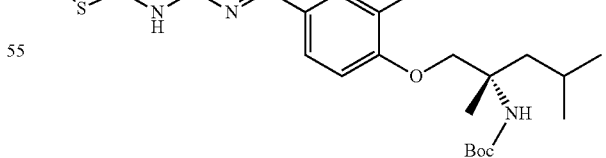

Part A: (S)-tert-butyl (2,4-dimethyl-1-(2-methyl-4-(2-(thiazol-2-ylamino)pyrimidin-4-yl)phenoxy)pentan-2-yl)carbamate Part A: (S)-tert-butyl (2,4-dimethyl-1-(4-(7-methyl-7H-pyrrolo[2,3-d]pyrimidin-4-yl)-2-(trifluoromethyl)phenoxy)pentan-2-yl)carbamate A mixture of (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (99 mg, 0.197 mmol), 4-chloro-7-methyl-7H-pyrrolo[2,3-d]pyrimidine (synthesis previously described J. Med. Chem., 2012, 55, 7193) (30 mg, 0.179 mmol), Pd(Ph$_3$P)$_4$ (10.34 mg, 8.95 μmol) and 2M aq. solution of potassium phosphate (0.269 mL, 0.537 mmol) in 1,4-dioxane (4 mL) was purged with nitrogen and heated at 100° C. for 12h. The reaction mixture was diluted with ethyl acetate (25 mL) and filtered through diatomaceous earth. The filtrate was concentrated under reduced pressure to obtain crude residue. The residue was purified by silica gel chromatography (5-10% ethyl acetate in hexanes) to afford (S)-tert-butyl (2,4-dimethyl-1-(4-(7-methyl-7H-pyrrolo[2,3-d]pyrimidin-4-yl)-2 (trifluoromethyl)phenoxy)pentan-2-yl)carbamate (80 mg, 0.115 mmol, 64% yield) as a brown gummy solid. LCMS (ESI) m/e 507.3 [(M+H)$^+$, calcd for $C_{26}H_{33}F_3N_4O_3$ 507.2]; LC/MS retention time (method B): $t_R$=1.06 min.

To a stirred solution of (S)-tert-butyl (1-(4-(2-chloropyrimidin-4-yl)-2-methylphenoxy)-2,4-dimethylpentan-2-yl)

carbamate (prepared as described in Example 367) (30 mg, 0.069 mmol) in 1,4-dioxane (2 mL), thiazol-2-amine (9.00 mg, 0.090 mmol), XANTPHOS (16.00 mg, 0.028 mmol), Cs$_2$CO$_3$ (45.0 mg, 0.138 mmol) and Pd$_2$dba$_3$ (12.66 mg, 0.014 mmol) were added. The mixture was heated to 90° C. for 12 h. The reaction mixture was cooled to room temperature, concentrated, diluted with water and extracted with ethyl acetate. The ethyl acetate layer was collected, dried over Na$_2$SO$_4$, filtered, and concentrated under reduced pressure to afford (S)-tert-butyl (2,4-dimethyl-1-(2-methyl-4-(2-(thiazol-2-ylamino)pyrimidin-4-yl)phenoxy)pentan-2-yl) carbamate (30 mg, 0.039 mmol, 57% yield) as a brown semi-solid. LCMS (ESI) m/e 498.3 [(M+H)$^+$, calcd for C$_{26}$H$_{36}$N$_5$O$_3$S 498.2]; LC/MS retention time (method B): t$_R$=1.05 min.

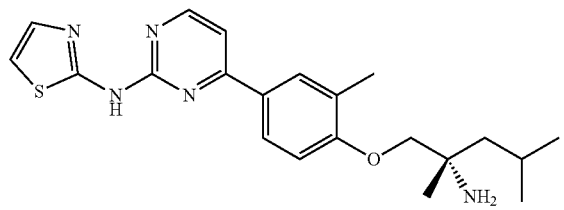 [SMILES: Cc1cc(-c2ccnc(Nc3nccs3)n2)ccc1OC[C@@](C)(N)CC(C)C]

Part B: (S)—N-(4-(4-((2-amino-2,4-dimethylpentyl) oxy)-3-methylphenyl)pyrimidin-2-yl) thiazol-2-amine To a stirred solution of (S)-tert-butyl (2,4-dimethyl-1-(2-methyl-4-(2-(thiazol-2-ylamino)pyrimidin-4-yl)phenoxy) pentan-2-yl)carbamate (30 mg, 0.039 mmol) in DCM (2 mL) at 0° C. was added 4N HCl in 1,4-dioxane (5 mL, 20.00 mmol) and the solution stirred for 1 h. The reaction mixture was concentrated under reduced pressure. The crude material was purified by prep HPLC (method B) to afford (S)—N-(4-(4-((2-amino-2,4-dimethylpentyl)oxy)-3-methylphenyl)pyrimidin-2-yl)thiazol-2-amine (6.3 mg, 0.015 mmol, 39% yield) as a pale yellow solid. LCMS (ESI) m/e 398.0 [(M+H)$^+$, calcd for C$_{21}$H$_{28}$N$_5$OS 398.2]; LC/MS retention time (method D): t$_R$=1.07 min. $^1$H NMR (400 MHz, METHANOL-d$_4$): δ 8.56 (d, J=5.77 Hz, 1H), 8.26 (dd, J=8.53, 2.07 Hz, 1H), 7.55 (d, J=5.77 Hz, 1H), 7.49 (d, J=4.02 Hz, 1H), 7.15-7.23 (m, 2H), 4.16-4.27 (m, 2H), 2.46 (s, 3H), 1.85-1.98 (m, 2H), 1.69-1.79 (m, 1H), 1.56 (s, 3H), 1.06-1.09 (m, 6H) ppm.

Example 369

(S)-4-(4-((2-amino-2,4-dimethylpentyl)oxy)-3-methylphenyl)-N-cyclopropylpyrimidin-2-amine

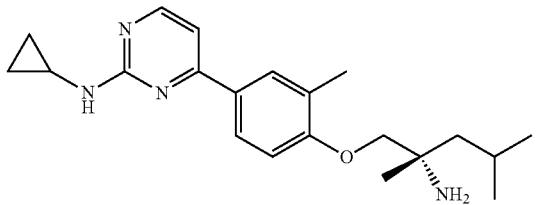

-continued

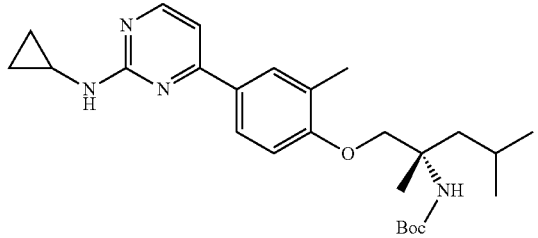

Part A: (S)-tert-butyl (1-(4-(2-(cyclopropylamino) pyrimidin-4-yl)-2-methylphenoxy)-2,4-dimethylpentan-2-yl) carbamate To a stirred solution of (S)-tert-butyl (1-(4-(2-chloropyrimidin-4-yl)-2-methylphenoxy)-2,4-dimethylpentan-2-yl) carbamate (prepared as described in Example 367) (20 mg, 0.046 mmol) in 1,4-dioxane (2 mL), cyclopropanamine (5.26 mg, 0.092 mmol), XANTPHOS (10.67 mg, 0.018 mmol), Cs$_2$CO$_3$ (30.0 mg, 0.092 mmol) and Pd$_2$dba$_3$ (8.44 mg, 9.22 μmol) were added. The mixture was heated at 90° C. for 12 h. The reaction mixture was cooled to room temperature, concentrated, diluted with water and extracted with ethyl acetate. The ethyl acetate layer was collected, dried over Na$_2$SO$_4$, filtered, and concentrated under reduced pressure to afford (S)-tert-butyl (1-(4-(2-(cyclopropylamino) pyrimidin-4-yl)-2-methylphenoxy)-2,4-dimethylpentan-2-yl)carbamate (10 mg, 0.016 mmol, 35% yield) as a brown semi-solid. LCMS (ESI) m/e 455.3 [(M+H)$^+$, calcd for C$_{26}$H$_{39}$N$_4$O$_3$ 455.3]; LC/MS retention time (method B): t$_R$=1.01 min.

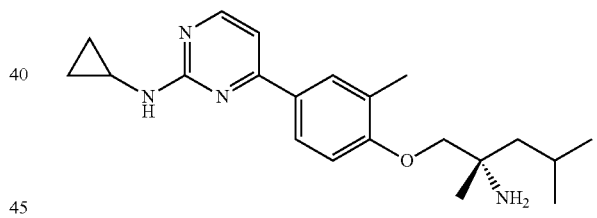

Part B: (S)-4-(4-((2-amino-2,4-dimethylpentyl)oxy)-3-methylphenyl)-N-cyclopropylpyrimidin-2-amine To a stirred solution of (S)-tert-butyl (1-(4-(2-(cyclopropylamino)pyrimidin-4-yl)-2-methylphenoxy)-2,4-dimethylpentan-2-yl)carbamate (10 mg, 0.022 mmol) in DCM (2 mL) at 0° C., 4N HCl in 1,4-dioxane (2 mL, 8.00 mmol) was added and stirred for 1 h at RT. The reaction mixture was concentrated under reduced pressure. The crude material was purified by prep HPLC (method B) to afford (S)-4-(4-((2-amino-2,4-dimethylpentyl)oxy)-3-methylphenyl)-N-cyclopropylpyrimidin-2-amine (3 mg, 8.38 μmol, 38% yield) as a pale yellow solid. LCMS (ESI) m/e 355.2 [(M+H)$^+$, calcd for C$_{21}$H$_{31}$N$_4$O 355.2]; LC/MS retention time (method D): t$_R$=1.55 min. $^1$H NMR (400 MHz, METHANOL-d$_4$): δ 8.28 (d, J=5.40 Hz, 1H), 7.96-8.01 (m, 2H), 7.05-7.13 (m, 2H), 4.06-4.15 (m, 2H), 2.77 (s, 1H), 2.39 (s, 3H), 1.84-1.91 (m, 2H), 1.66-1.72 (m, 1H), 1.49 (s, 3H), 1.06-1.09 (m, 6H), 0.84-0.86 (m, 2H), 0.55-0.60 (m, 2H) ppm.

Example 371

(S)—N-(4-(4-((2-amino-2,4-dimethylpentyl)oxy)-3-(trifluoromethyl)phenyl)pyrimidin-2-yl)thiazol-2-amine

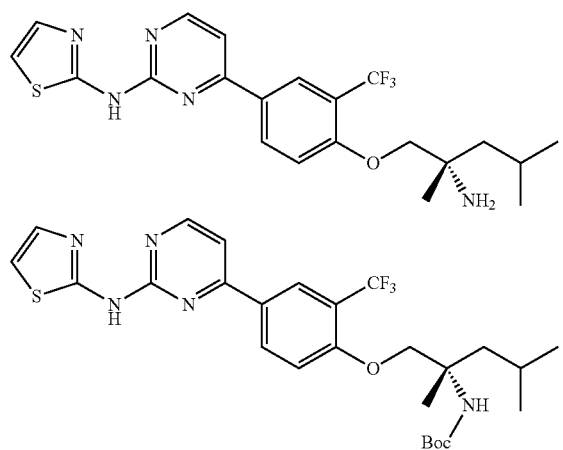

Part A: (S)-tert-butyl (2,4-dimethyl-1-(4-(2-(thiazol-2-ylamino)pyrimidin-4-yl)-2-(trifluoromethyl)phenoxy)pentan-2-yl)carbamate To a stirred solution of (S)-tert-butyl (1-(4-(2-chloropyrimidin-4-yl)-2(trifluoromethyl)phenoxy)-2,4-dimethylpentan-2-yl)carbamate (prepared as described in Example 367) (35 mg, 0.072 mmol) in 1,4-dioxane (3 mL), thiazol-2-amine (9.34 mg, 0.093 mmol), XANTPHOS (16.60 mg, 0.029 mmol), Cs$_2$CO$_3$ (46.7 mg, 0.143 mmol) and Pd$_2$dba$_3$ (13.14 mg, 0.014 mmol) were added and heated at 90° C. for 12 h. The reaction mixture was cooled to room temperature, concentrated, diluted with water and extracted with ethyl acetate. The ethyl acetate layer was collected, dried over Na$_2$SO$_4$, filtered, and concentrated under reduced pressure to afford (S)-tert-butyl (2,4-dimethyl-1-(4-(2-(thiazol-2-ylamino)pyrimidin-4-yl)-2-(trifluoromethyl)phenoxy)pentan-2-yl)carbamate (60 mg, 0.049 mmol, 68% yield) as a brown semi-solid. LCMS (ESI) m/e 552.2 [(M+H)$^+$, calcd for C$_{26}$H$_{33}$F$_3$N$_5$O$_3$S 552.2]; LC/MS retention time (method B): t$_R$=1.19 min.

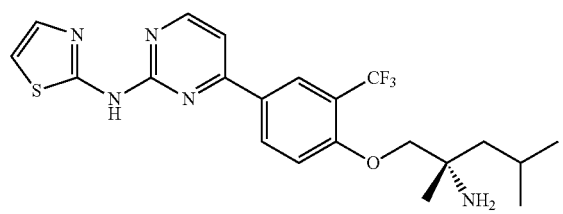 [SMILES: CC(C)C[C@](C)(N)COc1ccc(-c2ccnc(Nc3nccs3)n2)cc1C(F)(F)F]

Part B: (S)—N-(4-(4-((2-amino-2,4-dimethylpentyl)oxy)-3-(trifluoromethyl)phenyl)pyrimidin-2-yl)thiazol-2-amine To a stirred solution of (S)-tert-butyl (2,4-dimethyl-1-(4-(2-(thiazol-2-ylamino)pyrimidin-4-yl)-2-(trifluoromethyl)phenoxy)pentan-2-yl)carbamate (60 mg, 0.109 mmol) in DCM (4 mL) at 0° C., 4N HCl in 1,4-dioxane (5 mL, 20.00 mmol) was added and stirring was continued for 1 h at RT. The reaction mixture was concentrated under reduced pressure. The crude material was purified by prep HPLC (method B) to afford (S)—N-(4-(4-((2-amino-2,4-dimethylpentyl)oxy)-3-(trifluoromethyl)phenyl)pyrimidin-2-yl)thiazol-2-amine (12 mg, 0.026 mmol, 24% yield) as a pale yellow solid. LCMS (ESI) m/e 452.2 [(M+H)$^+$, calcd for C$_{21}$H$_{25}$F$_3$N$_5$OS 452.2]; LC/MS retention time (method D): t$_R$=2.56 min. $^1$H NMR (400 MHz, METHANOL-d$_4$): δ 8.68 (d, J=2.07 Hz, 1H), 8.64 (d, J=5.33 Hz, 1H), 8.52 (dd, J=8.72, 2.20 Hz, 1H), 7.52 (d, J=5.33 Hz, 1H), 7.46 (d, J=3.70 Hz, 1H), 7.37 (d, J=8.78 Hz, 1H), 7.09 (d, J=3.64 Hz, 1H), 4.02-4.10 (m, 2H), 1.79-1.91 (m, 1H), 1.55-1.67 (m, 2H), 1.32 (s, 3H), 1.02 (m, 6H) ppm.

Example 376

(S)—N-(4-(4-((2-amino-2,4-dimethylpentyl)oxy)-3-(trifluoromethyl)phenyl)pyrimidin-2-yl)-4-methylthiazol-2-amine

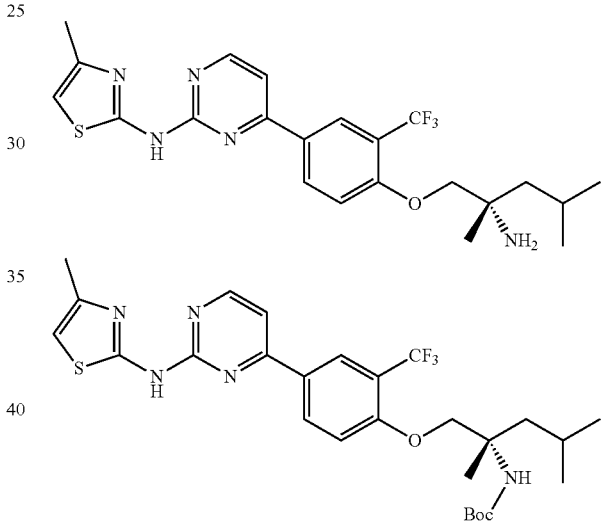

Part A: (S)-tert-butyl (2,4-dimethyl-1-(4-(2-((4-methylthiazol-2-yl)amino)pyrimidin-4-yl)-2-(trifluoromethyl)phenoxy)pentan-2-yl)carbamate To a stirred solution of (S)-tert-butyl (1-(4-(2-chloropyrimidin-4-yl)-2(trifluoromethyl)phenoxy)-2,4-dimethylpentan-2-yl)carbamate (prepared as described in Example 367) (50 mg, 0.102 mmol) in 1,4-dioxane (3 mL), 4-methylthiazol-2-amine (12.87 mg, 0.113 mmol), XANTPHOS (23.72 mg, 0.041 mmol), Cs$_2$CO$_3$ (66.8 mg, 0.205 mmol) and Pd$_2$dba$_3$ (18.77 mg, 0.020 mmol) were added and the mixture heated at 90° C. for 16 h. The reaction mixture was diluted with ethyl acetate (25 mL) and filtered through diatomaceous earth. The filtrate was concentrated under reduced pressure to afford a brown residue. The residue was purified by silica gel chromatography (20% ethyl acetate in hexanes) to afford (S)-tert-butyl (2,4-dimethyl-1-(4-(2-((4-methylthiazol-2-yl)amino)pyrimidin-4-yl)-2-(trifluoromethyl)phenoxy)pentan-2-yl)carbamate (25 mg, 0.044 mmol, 43% yield) as a yellow semi-solid. LCMS (ESI) m/e 566.2

[(M+H)$^+$, calcd for C$_{27}$H$_{35}$F$_3$N$_5$O$_3$S 566.2]; LC/MS retention time (Method C): $t_R$=1.32 min.

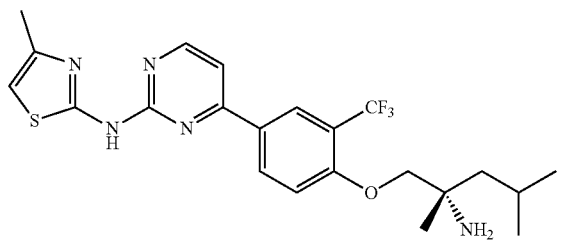

Part B. (S)—N-(4-(4-((2-amino-2,4-dimethylpentyl)oxy)-3-(trifluoromethyl)phenyl)pyrimidin-2-yl)-4-methylthiazol-2-amine To a stirred solution of (S)-tert-butyl (2,4-dimethyl-1-(4-(2-((4-methylthiazol-2-yl)amino)pyrimidin-4-yl)-2-(trifluoromethyl)phenoxy)pentan-2-yl)carbamate (25 mg, 0.044 mmol) in DCM (2 mL) at 0° C., 4N HCl in 1,4-dioxane (5 mL, 20.00 mmol) was added and stirred for 1 h. The mixture was then was cooled to 0° C., diluted with water (10 mL) and extracted with ethyl acetate (2×20 mL). The EtOAc layer was collected, dried over Na$_2$SO$_4$, filtered, and concentrated under reduced pressure. The crude material was purified by prep HPLC (method B) to afford (S)—N-(4-(4-((2-amino-2,4-dimethylpentyl)oxy)-3-(trifluoromethyl)phenyl)pyrimidin-2-yl)-4-methylthiazol-2-amine (11 mg, 0.022 mmol, 49% yield) as a pale yellow solid. LCMS (ESI) m/e 466.2 [(M+H)$^+$, calcd for C$_{22}$H$_{27}$F$_3$N$_5$OS 466.2]; LC/MS retention time (Method C1): $t_R$=2.77 min. $^1$H NMR (400 MHz, METHANOL-d$_4$): δ 8.69 (d, J=2.13 Hz, 1H), 8.63 (d, J=5.33 Hz, 1H), 8.52 (dd, J=8.82, 2.35 Hz, 1H), 7.52 (d, J=5.33 Hz, 1H), 7.38 (d, J=8.78 Hz, 1H), 6.64 (d, J=1.07 Hz, 1H), 3.98-4.12 (m, 2H), 2.35 (d, J=1.00 Hz, 3H), 1.81-1.91 (m, 1H), 1.54-1.70 (m, 2H), 1.33 (s, 3H), 1.02 (m, 6H) ppm.

Example 377

(S)-4-(4-((2-amino-2,4-dimethylpentyl)oxy)-3-(trifluoromethyl)phenyl)-N-cyclopentylpyrimidin-2-amine

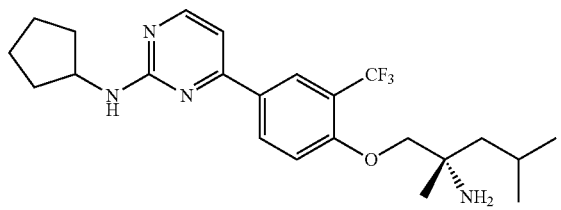 [SMILES: CC(C)C[C@](C)(N)COc1ccc(-c2ccnc(NC3CCCC3)n2)cc1C(F)(F)F]

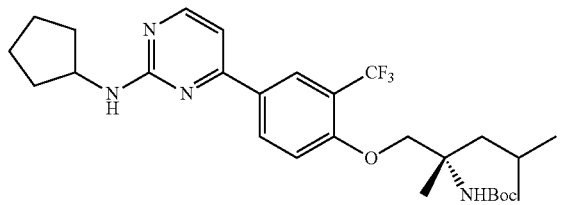

Part A: (S)-tert-butyl (1-(4-(2-(cyclopentylamino)pyrimidin-4-yl)-2-(trifluoromethyl)phenoxy)-2,4-dimethylpentan-2-yl)carbamate To a stirred solution of (S)-tert-butyl (1-(4-(2-chloropyrimidin-4-yl)-2(trifluoromethyl)phenoxy)-2,4-dimethylpentan-2-yl)carbamate (prepared as described in Example 367) (50 mg, 0.102 mmol) in 1,4-dioxane (3 mL), cyclopentanamine (9.60 mg, 0.113 mmol), XANTPHOS (23.72 mg, 0.041 mmol), Cs$_2$CO$_3$ (66.8 mg, 0.205 mmol) and Pd$_2$dba$_3$ (18.77 mg, 0.020 mmol) were added and heated at 90° C. for 16 h. The reaction mixture was diluted with ethyl acetate (25 mL) and filtered through diatomaceous earth. The filtrate was concentrated under reduced pressure to afford brown residue. The residue was purified by silica gel chromatography (7% ethyl acetate in hexanes) to afford (S)-tert-butyl (1-(4-(2-(cyclopentylamino)pyrimidin-4-yl)-2-(trifluoromethyl)phenoxy)-2,4-dimethylpentan-2-yl)carbamate (10 mg, 0.018 mmol, 18% yield) as a yellow semi-solid. LCMS (ESI) m/e 537.3 [(M+H)$^+$, calcd for C$_{28}$H$_{40}$F$_3$N$_4$O$_3$ 537.3]; LC/MS retention time (Method C): $t_R$=1.45 min.

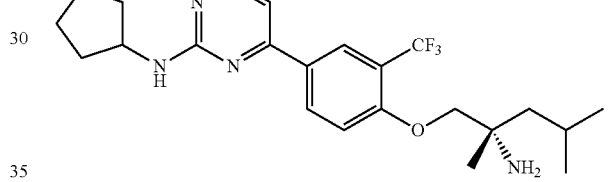

Part B: (S)-4-(4-((2-amino-2,4-dimethylpentyl)oxy)-3-(trifluoromethyl)phenyl)-N-cyclopentylpyrimidin-2-amine To a stirred solution of (S)-tert-butyl (1-(4-(2-(cyclopentylamino)pyrimidin-4-yl)-2-(trifluoromethyl)phenoxy)-2,4-dimethylpentan-2-yl)carbamate (10 mg, 0.019 mmol) in DCM (2 mL) at 0° C., 4N HCl in 1,4-dioxane (5 mL, 20.00 mmol) was added and stirred for 1 h. The mixture was then was cooled to 0° C., diluted with water (10 mL) and extracted with ethyl acetate (2×50 mL). The EtOAc layer was collected, dried over Na$_2$SO$_4$, filtered, and concentrated under reduced pressure. The crude material was purified by prep HPLC (method B) to afford (S)-4-(4-((2-amino-2,4-dimethylpentyl)oxy)-3-(trifluoromethyl)phenyl)-N-cyclopentylpyrimidin-2-amine (4 mg, 8.89 mmol, 48% yield) as a pale yellow solid. LCMS (ESI) m/e 437.2 [(M+H)$^+$, calcd for C$_{23}$H$_{32}$F$_3$N$_4$O 437.2]; LC/MS retention time (method D): $t_R$=3.14 min. $^1$H NMR (400 MHz, METHANOL-d$_4$): δ8.45 (d, J=2.01 Hz, 1H), 8.33-8.38 (m, 1H), 8.29 (d, J=5.27 Hz, 1H), 7.34 (d, J=8.78 Hz, 1H), 7.10 (d, J=5.40 Hz, 1H), 4.29-4.38 (m, 1H), 4.14 (q, J=9.58 Hz, 2H), 2.04-2.14 (m, 2H), 1.54-1.89 (m, 9H), 1.41 (s, 3H), 1.03-1.05 (m, 6H) ppm.

Example 380

(S)-2-((2-amino-2,4-dimethylpentyl)oxy)-5-(2-((4-methylthiazol-2-yl)amino)pyrimidin-4-yl)benzonitrile

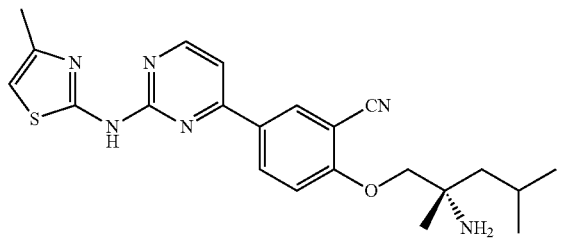 [SMILES: Cc1csc(Nc2nccc(-c3ccc(OC[C@@](C)(N)CC(C)C)c(C#N)c3)n2)n1]

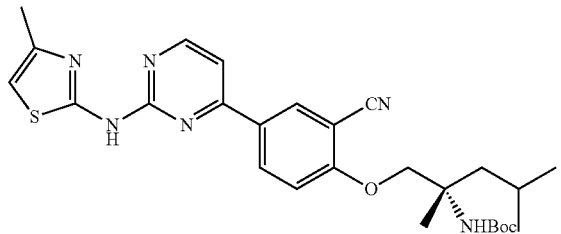

Part A. (S)-tert-butyl (1-(2-cyano-4-(2-((4-methylthiazol-2-yl)amino)pyrimidin-4-yl)phenoxy)-2,4-dimethylpentan-2-yl)carbamate To a stirred solution of (S)-tert-butyl (1-(4-(2-chloropyrimidin-4-yl)-2-cyanophenoxy)-2,4-dimethylpentan-2-yl)carbamate (prepared as described in Example 367) (50 mg, 0.112 mmol) in 1,4-dioxane (3 mL) was added 4-methylthiazol-2-amine (14.11 mg, 0.124 mmol), XANTPHOS (13.00 mg, 0.022 mmol), $Cs_2CO_3$ (73.2 mg, 0.225 mmol) and $Pd_2dba_3$ (10.29 mg, 0.011 mmol). The mixture was heated at 90° C. for 12 h. The reaction mixture was cooled to room temperature and diluted with ethyl acetate (25 mL) then filtered through diatomaceous earth. The filtrate was concentrated under reduced pressure to afford brown residue. The residue was purified by silica gel chromatography (5% ethyl acetate in hexanes) to afford (S)-tert-butyl (1-(2-cyano-4-(2-((4-methylthiazol-2-yl)amino)pyrimidin-4-yl)phenoxy)-2,4-dimethylpentan-2-yl)carbamate (25 mg, 0.040 mmol, 36% yield) as a brown semi-solid. LCMS (ESI) m/e 523.6 [(M+H)$^+$, calcd for $C_{27}H_{35}N_6O_3S$ 523.2]; LC/MS retention time (method B): $t_R$=1.09 min.

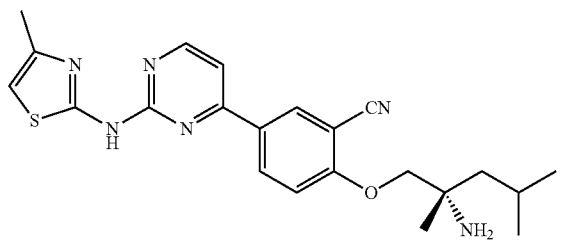

Part B. (S)-2-((2-amino-2,4-dimethylpentyl)oxy)-5-(2-((4-methylthiazol-2-yl)amino)pyrimidin-4-yl)benzonitrile To a stirred solution of (S)-tert-butyl (1-(2-cyano-4-(2-((4-methylthiazol-2-yl)amino)pyrimidin-4-yl)phenoxy)-2,4-dimethylpentan-2-yl)carbamate (25 mg, 0.048 mmol) in DCM at 0° C. was added 4N HCl in 1,4-dioxane (2 mL, 8.00 mmol) and the mixture stirred for 1 h. The mixture was diluted with water (10 mL) and extracted with ethyl acetate (2×50 mL). The EtOAc layer was collected, dried over $Na_2SO_4$, filtered, and concentrated under reduced pressure. The crude material was purified by prep HPLC (method A) to afford (S)-2-((2-amino-2,4-dimethylpentyl)oxy)-5-(2-((4-methylthiazol-2-yl)amino)pyrimidin-4 yl)benzonitrile (10 mg, 0.023 mmol, 48% yield) as a pale yellow solid. LCMS (ESI) m/e 423.2 [(M+H)$^+$, calcd for $C_{22}H_{27}N_6OS$ 423.2]; LC/MS retention time (method D): $t_R$=2.46 min. $^1$H NMR (400 MHz, METHANOL-$d_4$): δ 8.57-8.67 (m, 3H), 7.51 (d, J=5.27 Hz, 1H), 7.40 (d, J=8.85 Hz, 1H), 6.65 (d, J=1.13 Hz, 1H), 4.10 (d, J=1.95 Hz, 2H), 2.35 (s, 3H), 1.84-1.97 (m, 1H), 1.66-1.72 (m, 1H), 1.58-1.65 (m, 1H), 1.35 (s, 3H), 1.02-1.06 (m, 6H) ppm.

Example 381

(S)—N-(4-(4-((2-amino-2,4-dimethylpentyl)oxy)-3-methylphenyl)pyrimidin-2-yl)-4-methylthiazol-2-amine

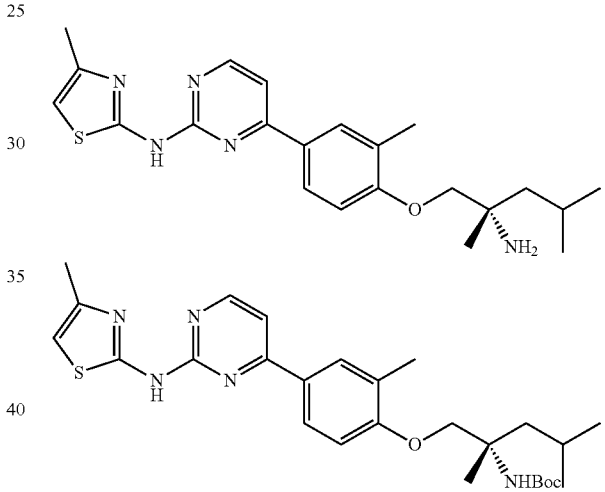

Part A. (S)-tert-butyl (2,4-dimethyl-1-(2-methyl-4-(2-((4-methylthiazol-2-yl)amino)pyrimidin-4-yl)phenoxy)pentan-2-yl)carbamate To a stirred solution of (S)-tert-butyl (1-(4-(2-chloropyrimidin-4-yl)-2-methylphenoxy)-2,4-dimethylpentan-2-yl)carbamate (prepared as described in Example 367) (50 mg, 0.115 mmol) in 1,4-dioxane (3 mL) was added 4-methylthiazol-2-amine (14.47 mg, 0.127 mmol), XANTPHOS (13.33 mg, 0.023 mmol), $Cs_2CO_3$ (75 mg, 0.230 mmol) and $Pd_2dba_3$ (10.55 mg, 0.012 mmol) and the mixture was heated at 90° C. for 12 h. The reaction mixture was diluted with ethyl acetate (25 mL) and filtered through diatomaceous earth. The filtrate was concentrated under reduced pressure to afford a brown residue. The residue was purified by silica gel chromatography (25% ethyl acetate in hexanes) to afford (S)-tert-butyl (2,4-dimethyl-1-(2-methyl-4-(2-((4-methylthiazol-2-yl)amino)pyrimidin-4-yl)phenoxy)pentan-2-yl)carbamate (25 mg, 0.039 mmol, 34% yield) as a brown semi-solid. LCMS (ESI) m/e 512.6 [(M+H)$^+$, calcd for $C_{27}H_{38}N_5O_3S$ 512.3]; LC/MS retention time (method B): $t_R$=1.15 min.

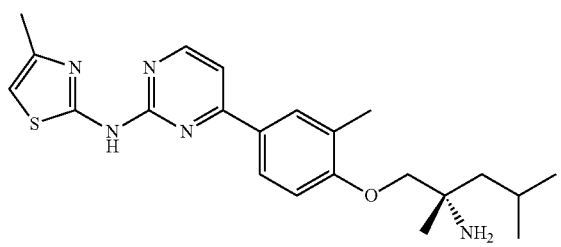 [SMILES: Cc1csc(Nc2nccc(-c3ccc(OC[C@@](C)(N)CC(C)C)c(C)c3)n2)n1]

Part B. (S)—N-(4-(4-((2-amino-2,4-dimethylpentyl)oxy)-3-methylphenyl)pyrimidin-2-yl)-4-methylthiazol-2-amine To a stirred solution of (S)-tert-butyl (2,4-dimethyl-1-(2-methyl-4-(2-((4-methylthiazol-2-yl)amino)pyrimidin-4-yl)phenoxy)pentan-2-yl)carbamate (25 mg, 0.049 mmol) in DCM at 0° C. was added 4N HCl in 1,4-dioxane (2 mL, 8.00 mmol) and the mixture stirred for 1 h. The mixture was diluted with water (10 mL) and extracted with ethyl acetate (2×25 mL). The EtOAc layer was collected, dried over Na$_2$SO$_4$, filtered, and concentrated under reduced pressure. The crude material was purified by prep HPLC (method A) to afford (S)—N-(4-(4-((2-amino-2,4-dimethylpentyl)oxy)-3-methylphenyl)pyrimidin-2-yl)-4-methylthiazol-2-amine (4 mg, 0.0943 mmol, 19% yield) as a pale yellow solid. LCMS (ESI) m/e 412.2 [(M+H)$^+$, calcd for C$_{22}$H$_{30}$N$_5$OS 412.2]; LC/MS retention time (method D): t$_R$=2.38 min. $^1$H NMR (400 MHz, METHANOL-d$_4$): δ 8.53-8.58 (m, 1H), 8.12-8.22 (m, 2H), 7.37-7.49 (m, 1H), 7.06-7.14 (m, 1H), 6.61-6.66 (m, 1H), 3.95-3.99 (m, 2H), 2.40 (s, 3H), 2.35 (s, 3H), 1.82-1.95 (m, 1H), 1.53-1.76 (m, 2H), 1.35 (s, 3H), 1.01-1.05 (m, 6H) ppm.

Example 389

(S)—N-(4-(4-((2-amino-2,4-dimethylpentyl)oxy)-3-(trifluoromethyl)phenyl)pyridin-2-yl)cyclopropanecarboxamide

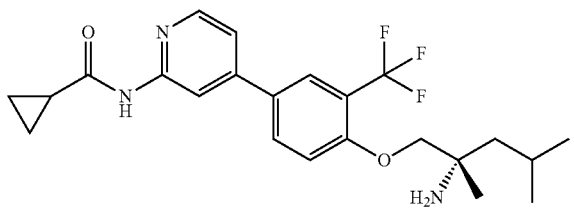 [SMILES: CC(C)C[C@](C)(N)COc1ccc(-c2ccnc(NC(=O)C3CC3)c2)cc1C(F)(F)F]

To a flask containing (S)-tert-butyl (1-(4-(2-aminopyridin-4-yl)-2-(trifluoromethyl)phenoxy)-2,4-dimethylpentan-2-yl)carbamate (20 mg, 0.043 mmol) (prepared as described in Example 290) was added cyclopropanecarboxylic acid (0.051 mmol, 1.2 equiv.), HATU (24.40 mg, 0.064 mmol), DIPEA (0.022 mL, 0.128 mmol) and DMF (1 mL). The reaction mixture was heated at 60° C. overnight. The reaction mixture was cooled to room temperature and concentrated under reduced pressure. To the residue at 0° C. was added 30% TFA in DCM (1 mL) and the mixture stirred for 30 min. The solvent was removed and the crude material was purified by reverse phase prep HPLC (Method E) to afford (S)—N-(4-(4-((2-amino-2,4-dimethylpentyl)oxy)-3-(trifluoromethyl)phenyl)pyridin-2-yl)cyclopropanecarboxamide (13.4 mg, 0.030 mmol, 72% yield) as a pale yellow solid. LCMS (ESI) m/e 436.2 [(M+H)$^+$, calcd for C$_{23}$H$_{29}$F$_3$N$_3$O$_2$ 436.2]; LC/MS retention time (method H): t$_R$=2.54 min. $^1$H NMR (400 MHz, DMSO-d$_6$) δ 10.93 (s, 1H), 8.40-8.37 (m, 2H), 8.06-8.01 (m, 1H), 7.93 (d, J=2.3 Hz, 1H), 7.49-7.45 (m, 2H), 4.20 (s, 2H), 2.08-2.00 (m, 1H), 1.87-1.77 (m, 1H), 1.76-1.69 (m, 1H), 1.63-1.57 (m, 1H), 1.38 (s, 3H), 0.95-0.91 (m, 6H), 0.86-0.81 (m, 4H) ppm.

Example 390

(S)—N-(4-(4-((2-amino-2,4-dimethylpentyl)oxy)-3-(trifluoromethyl)phenyl)pyridin-2-yl)cyclobutanecarboxamide

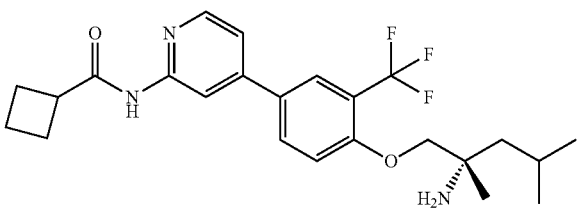 [SMILES: CC(C)C[C@](C)(N)COc1ccc(-c2ccnc(NC(=O)C3CCC3)c2)cc1C(F)(F)F]

Prepared as described in Example 389 to afford (S)—N-(4-(4-((2-amino-2,4-dimethylpentyl)oxy)-3-(trifluoromethyl)phenyl)pyridin-2-yl)cyclobutanecarboxamide (18 mg, 0.040 mmol, 93% yield for two steps) as a pale yellow solid. LCMS (ESI) m/e 450.2 [(M+H)$^+$, calcd for C$_{24}$H$_{31}$F$_3$N$_3$O$_2$ 450.2]; LC/MS retention time (method H): t$_R$=2.73 min. $^1$H NMR (400 MHz, DMSO-d$_6$) δ 10.45 (s, 1H), 8.43 (s, 1H), 8.37 (d, J=5.3 Hz, 1H), 8.09-7.99 (m, 1H), 7.95 (d, J=2.0 Hz, 1H), 7.51-7.45 (m, 2H), 4.21 (s, 2H), 3.40 (dt, J=16.9, 8.3 Hz, 1H), 2.28-2.18 (m, 2H), 2.16-2.07 (m, 2H), 1.98-1.90 (m, 1H), 1.82 (dt, J=12.2, 6.0 Hz, 2H), 1.76-1.70 (m, 1H), 1.64-1.57 (m, 1H), 1.38 (s, 3H), 0.95-0.92 (m, 6H) ppm.

Example 391

(S)—N-(4-(4-((2-amino-2,4-dimethylpentyl)oxy)-3-(trifluoromethyl)phenyl)pyridin-2-yl)cyclopentanecarboxamide

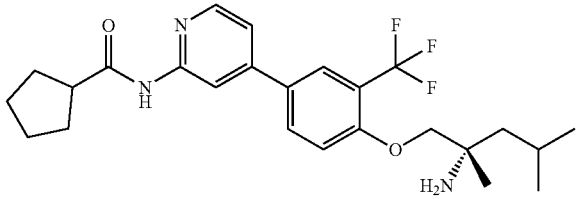 [SMILES: CC(C)C[C@](C)(N)COc1ccc(-c2ccnc(NC(=O)C3CCCC3)c2)cc1C(F)(F)F]

Prepared as described in Example 389 to afford (S)—N-(4-(4-((2-amino-2,4-dimethylpentyl)oxy)-3-(trifluoromethyl)phenyl)pyridin-2-yl)cyclopentanecarboxamide (3.5 mg, 7.55 μmol, 18% yield for two steps) as a pale yellow solid. LCMS (ESI) m/e 464.2 [(M+H)$^+$, calcd for C$_{25}$H$_{33}$F$_3$N$_3$O$_2$ 464.2]; LC/MS retention time (method H): t$_R$=2.90 min. $^1$H NMR (400 MHz, DMSO-d$_6$) δ 10.52 (s, 1H), 8.41 (d, J=1.0 Hz, 1H), 8.36 (dd, J=5.3, 1 Hz, 1H), 8.00 (dd, J=8.5, 2.3 Hz, 1H), 7.90 (d, J=2.3 Hz, 1H), 7.44 (dd, J=5.3, 1.8 Hz, 1H), 7.38 (d, J=8.5 Hz, 1H), 3.92-3.85 (m, 2H), 2.97 (quin, J=7.8 Hz, 1H), 1.90-1.62 (m, 7H), 1.59-1.52 (m, 2H), 1.43-1.39 (m, 2H), 1.14 (s, 3H), 0.94-0.90 (m, 6H) ppm.

Example 392

(S)—N-(4-(4-((2-amino-2,4-dimethylpentyl)oxy)-3-(trifluoromethyl)phenyl)pyridin-2-yl)-2-cyclopentylacetamide

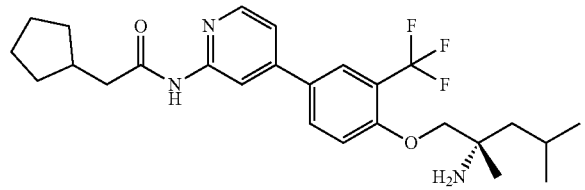 [SMILES: CC(C)C[C@](C)(N)COc1ccc(-c2ccnc(NC(=O)CC3CCCC3)c2)cc1C(F)(F)F]

Prepared as described in Example 389 to afford (S)—N-(4-(4-((2-amino-2,4-dimethylpentyl)oxy)-3-(trifluoromethyl)phenyl)pyridin-2-yl)-2-cyclopentylacetamide (3.3 mg, 6.91 μmol, 16% yield for two steps) as a pale yellow solid. LCMS (ESI) m/e 478.2 [(M+H)$^+$, calcd for $C_{26}H_{35}F_3N_3O_2$ 478.2]; LC/MS retention time (method H): $t_R$=3.08 min. $^1$H NMR (400 MHz, DMSO-$d_6$) δ 10.50 (s, 1H), 8.40-8.34 (m, 2H), 7.99 (dd, J=8.8, 2.3 Hz, 1H), 7.89 (d, J=2.0 Hz, 1H), 7.45-7.37 (m, 2H), 3.93-3.86 (m, 2H), 2.42 (d, J=7.3 Hz, 2H), 2.24 (dt, J=15.2, 7.7 Hz, 1H), 1.84-1.71 (m, 3H), 1.65-1.39 (m, 6H), 1.24-1.13 (m, 5H), 0.92-0.90 (dd, J=6.5, 2.5 Hz, 6H) ppm.

Example 393

(S)—N-(4-(4-((2-amino-2,4-dimethylpentyl)oxy)-3-(trifluoromethyl)phenyl)pyridin-2-yl)-3-cyclopentylpropanamide

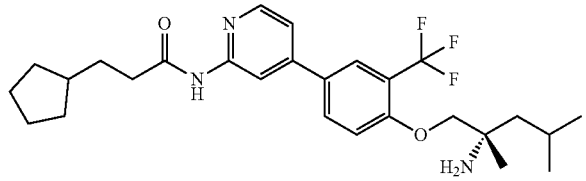 [SMILES: CC(C)C[C@](C)(N)COc1ccc(-c2ccnc(NC(=O)CCC3CCCC3)c2)cc1C(F)(F)F]

Prepared as described in Example 389 to afford (S)—N-(4-(4-((2-amino-2,4-dimethylpentyl)oxy)-3-(trifluoromethyl)phenyl)pyridin-2-yl)-3-cyclopentylpropanamide (6.7 mg, 0.014 mmol, 32% yield for two steps) as a pale yellow solid. LCMS (ESI) m/e 492.2 [(M+H)$^+$, calcd for $C_{27}H_{37}F_3N_3O_2$ 492.3]; LC/MS retention time (method H): $t_R$=3.23 min. $^1$H NMR (400 MHz, DMSO-$d_6$) δ 10.55 (s, 1H), 8.40 (s, 1H), 8.36 (d, J=6.0 Hz, 1H), 8.00 (dd, J=8.8, 2.3 Hz, 1H), 7.90 (d, J=2.5 Hz, 1H), 7.46-7.43 (m, 1H), 7.40 (d, J=9.0 Hz, 1H), 3.94-3.87 (m, 2H), 2.46-2.40 (m, 2H), 1.85-1.70 (m, 4H), 1.60 (d, J=4.0 Hz, 4H), 1.53-1.45 (m, 2H), 1.44-1.39 (m, 2H), 1.15 (s, 3H), 1.10 (dd, J=11.8, 6.8 Hz, 2H), 0.94-0.89 (m, 6H) ppm.

Example 394

(S)—N-(4-(4-((2-amino-2,4-dimethylpentyl)oxy)-3-(trifluoromethyl)phenyl)pyridin-2-yl)-2-cyclohexylacetamide

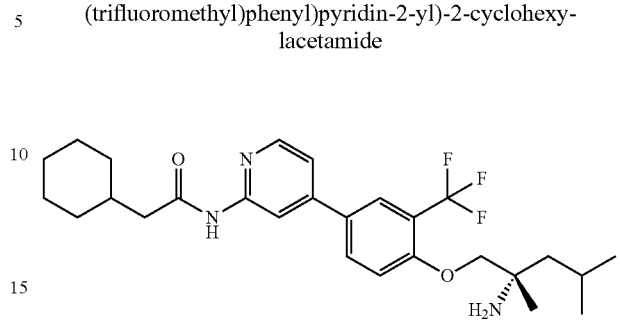

Prepared as described in Example 389 to afford (S)—N-(4-(4-((2-amino-2,4-dimethylpentyl)oxy)-3-(trifluoromethyl)phenyl)pyridin-2-yl)-2-cyclohexylacetamide (7.6 mg, 0.015 mmol, 36% yield for two steps) as a pale yellow solid. LCMS (ESI) m/e 492.2 [(M+H)$^+$, calcd for $C_{27}H_{37}F_3N_3O_2$ 492.3]; LC/MS retention time (method H): $t_R$=3.13 min. $^1$H NMR (400 MHz, DMSO-$d_6$) δ 10.52 (s, 1H), 8.41 (d, J=1.0 Hz, 1H), 8.36 (d, J=6.0 Hz, 1H), 8.01 (d, J=2.5 Hz, 1H), 7.90 (d, J=2.5 Hz, 1H), 7.46-7.43 (m, 1H), 7.39 (d, J=9.0 Hz, 1H), 3.94-3.86 (m, 2H), 2.31 (d, J=7.0 Hz, 2H), 1.86-1.75 (m, 2H), 1.74-1.58 (m, 5H), 1.42 (dd, J=5.5, 2.0 Hz, 2H), 1.28-1.17 (m, 3H), 1.15 (s, 3H), 1.04-0.95 (m, 2H), 0.94-0.89 (m, 6H) ppm.

Example 398

N-(4-(4-(((S)-2-amino-2,4-dimethylpentyl)oxy)-3-(trifluoromethyl)phenyl)pyridin-2-yl)tetrahydrofuran-2-carboxamide

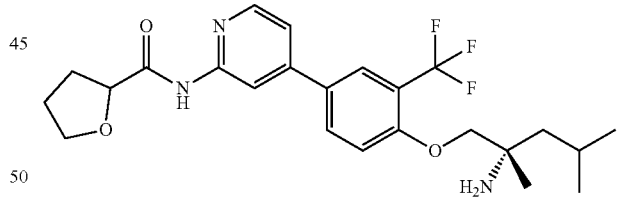

Prepared as described in Example 389 to afford N-(4-(4-(((S)-2-amino-2,4-dimethylpentyl)oxy)-3-(trifluoromethyl)phenyl)pyridin-2-yl)tetrahydrofuran-2-carboxamide (8.0 mg, 0.017 mmol, 40% yield for two steps) as a pale yellow solid.

LCMS (ESI) m/e 466.3 [(M+H)$^+$, calcd for $C_{24}H_{31}F_3N_3O_3$ 466.22]; LC/MS retention time (method H): $t_R$=1.87 min. $^1$H NMR (400 MHz, DMSO-$d_6$) δ 9.88 (s, 1H), 8.42-8.35 (m, 2H), 8.01 (dd, J=8.5, 2.0 Hz, 1H), 7.92 (d, J=2.5 Hz, 1H), 7.54-7.49 (m, 1H), 7.39 (d, J=9.0 Hz, 1H), 4.52 (dd, J=8.5, 5.5 Hz, 1H), 4.00 (dt, J=8.0, 6.8 Hz, 1H), 3.91-3.82 (m, 3H), 2.28-2.17 (m, 1H), 2.06-1.96 (m, 1H), 1.95-1.74 (m, 3H), 1.40 (d, J=5.5 Hz, 2H), 1.13 (s, 3H), 0.93-0.91 (m, 6H) ppm.

Example 399

(S)—N-(4-(4-((2-amino-2,4-dimethylpentyl)oxy)-3-(trifluoromethyl)phenyl)pyridin-2-yl)-2-cycloheptylacetamide

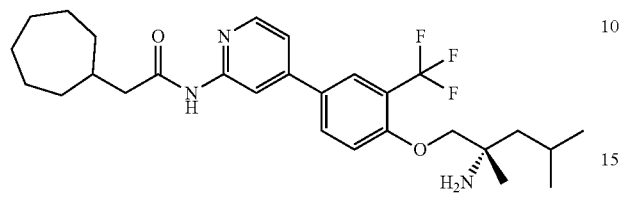

Prepared as described in Example 389 to afford (S)—N-(4-(4-((2-amino-2,4-dimethylpentyl)oxy)-3-(trifluoromethyl)phenyl)pyridin-2-yl)-2-cycloheptylacetamide (2.7 mg, 5.34 μmol, 12% yield for two steps) as a pale yellow solid. LCMS (ESI) m/e 506.2 [(M+H)$^+$, calcd for $C_{28}H_{39}F_3N_3O_2$ 506.29]; LC/MS retention time (method H): $t_R$=3.31 min. $^1$H NMR (400 MHz, DMSO-$d_6$) δ 10.50 (s, 1H), 8.40 (s, 1H), 8.35 (d, J=5.3 Hz, 1H), 7.98 (dd, J=8.9, 2.4 Hz, 1H), 7.89 (d, J=2.3 Hz, 1H), 7.43 (dd, J=5.3, 1.5 Hz, 1H), 7.37 (d, J=8.8 Hz, 1H), 3.88-3.81 (m, 2H), 2.34 (d, J=7.3 Hz, 2H), 2.05-1.94 (m, 1H), 1.87-1.75 (m, 1H), 1.74-1.65 (m, 2H), 1.64-1.35 (m, 10H), 1.28-1.13 (m, 2H), 1.11 (s, 3H), 0.92-0.90 (m, 6H) ppm.

Example 400

(S)—N-(4-(4-((2-amino-2,4-dimethylpentyl)oxy)-3-(trifluoromethyl)phenyl)pyridin-2-yl)furan-2-carboxamide

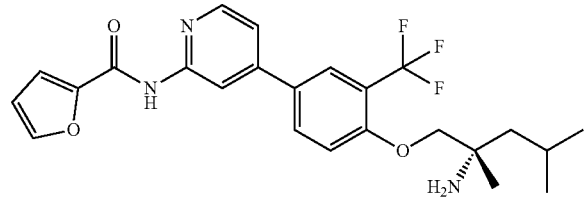 [SMILES: CC(C)C[C@](C)(N)COc1ccc(-c2ccnc(NC(=O)c3ccco3)c2)cc1C(F)(F)F]

Prepared as described in Example 389 to afford (S)—N-(4-(4-((2-amino-2,4-dimethylpentyl)oxy)-3-(trifluoromethyl)phenyl)pyridin-2-yl)furan-2-carboxamide (10.4 mg, 0.023 mmol, 52% yield for two steps) as a pale yellow solid. LCMS (ESI) m/e 462.2 [(M+H)$^+$, calcd for $C_{24}H_{27}F_3N_3O_3$ 462.2]; LC/MS retention time (method H): $t_R$=2.67 min. $^1$H NMR (400 MHz, DMSO-$d_6$) δ 10.69 (br. s., 1H), 8.47-8.41 (m, 2H), 8.04 (dd, J=8.8, 2.3 Hz, 1H), 8.01-7.94 (m, 2H), 7.64 (d, J=3.5 Hz, 1H), 7.53 (dd, J=5.3, 1.8 Hz, 1H), 7.42 (d, J=8.5 Hz, 1H), 6.75-6.70 (m, 1H), 3.94-3.86 (m, 2H), 1.87-1.75 (m, 1H), 1.47-1.36 (m, 2H), 1.15 (s, 3H), 0.93-0.91 (m, 6H) ppm.

Example 401

(S)—N-(4-(4-((2-amino-2,4-dimethylpentyl)oxy)-3-(trifluoromethyl)phenyl)pyridin-2-yl)-5-bromofuran-2-carboxamide

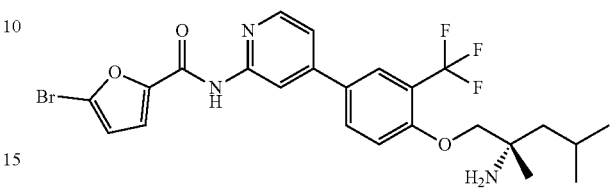

Prepared as described in Example 389 to afford (S)—N-(4-(4-((2-amino-2,4-dimethylpentyl)oxy)-3-(trifluoromethyl)phenyl)pyridin-2-yl)-5-bromofuran-2-carboxamide (2.5 mg, 4.63 μmol, 11% yield for two steps) as a pale yellow solid. LCMS (ESI) m/e 540.0 [(M+H)$^+$, calcd for $C_{24}H_{26}BrF_3N_3O_3$ 540.1]; LC/MS retention time (method H): $t_R$=2.95 min. $^1$H NMR (400 MHz, DMSO-$d_6$) δ 10.86 (br. s., 1H), 8.45 (s, 1H), 8.39 (s, 1H), 8.05 (dd, J=8.8, 2.3 Hz, 1H), 7.96 (d, J=2.0 Hz, 1H), 7.68 (d, J=4.0 Hz, 1H), 7.55 (dd, J=5.0, 1.5 Hz, 1H), 7.44 (d, J=8.5 Hz, 1H), 6.86 (d, J=3.5 Hz, 1H), 4.01-3.93 (m, 2H), 1.81 (dt, J=12.8, 6.1 Hz, 1H), 1.54-1.40 (m, 2H), 1.20 (s, 3H), 0.94-0.91 (dd, J=6.8, 3.8 Hz, 4H) ppm.

Example 402

(S)-2-acetamido-N-(4-(4-((2-amino-2,4-dimethylpentyl)oxy)-3-(trifluoromethyl)phenyl)pyridin-2-yl)acetamide

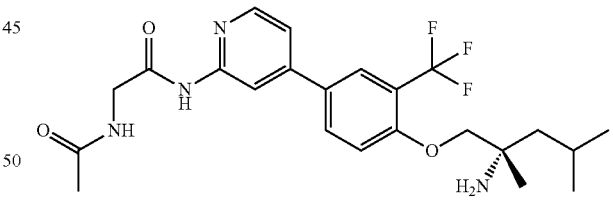

Prepared as described in Example 389 to afford (S)-2-acetamido-N-(4-(4-((2-amino-2,4-dimethylpentyl)oxy)-3-(trifluoromethyl)phenyl)pyridin-2-yl)acetamide (7.7 mg, 0.017 mmol, 38% yield for two steps) as a pale yellow solid. LCMS (ESI) m/e 467.2 [(M+H)$^+$, calcd for $C_{23}H_{30}F_3N_4O_3$ 467.2]; LC/MS retention time (method H): $t_R$=2.03 min. $^1$H NMR (400 MHz, DMSO-$d_6$) δ 10.59 (s, 1H), 8.42-8.33 (m, 2H), 8.20 (t, J=5.8 Hz, 1H), 8.01 (dd, J=8.8, 2.3 Hz, 1H), 7.91 (d, J=2.0 Hz, 1H), 7.47 (dd, J=5.3, 1.8 Hz, 1H), 7.40 (d, J=8.5 Hz, 1H), 4.00-3.88 (m, 4H), 1.92-1.86 (m, 3H), 1.86-1.72 (m, 1H), 1.51-1.38 (m, 2H), 1.17 (s, 3H), 0.92-0.90 (m, 6H) ppm.

Example 403

(S)—N-(4-(4-((2-amino-2,4-dimethylpentyl)oxy)-3-(trifluoromethyl)phenyl)pyridin-2-yl)thiophene-2-carboxamide

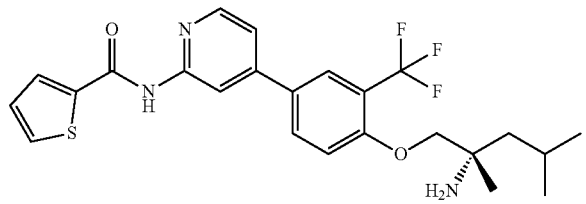

Prepared as described in Example 389 to afford (S)—N-(4-(4-((2-amino-2,4-dimethylpentyl)oxy)-3-(trifluoromethyl)phenyl)pyridin-2-yl)thiophene-2-carboxamide (5.6 mg, 0.012 mmol, 27% yield for two steps) as a pale yellow solid. LCMS (ESI) m/e 478.0 [(M+H)$^+$, calcd for $C_{24}H_{27}F_3N_3O_2S$ 478.1]; LC/MS retention time (method H): $t_R$=2.77 min. $^1$H NMR (400 MHz, DMSO-d$_6$) δ 11.03 (s, 1H), 8.47-8.43 (m, 2H), 8.28 (dd, J=3.8, 1.0 Hz, 1H), 8.05 (dd, J=8.8, 2.3 Hz, 1H), 7.96 (d, J=2.3 Hz, 1H), 7.91 (dd, J=4.9, 1.1 Hz, 1H), 7.54 (dd, J=5.3, 1.8 Hz, 1H), 7.42 (d, J=8.8 Hz, 1H), 7.23 (dd, J=4.9, 3.9 Hz, 1H), 3.98-3.91 (m, 2H), 1.86-1.75 (m, 1H), 1.51-1.40 (m, 2H), 1.18 (s, 3H), 0.95-0.89 (m, 6H) ppm.

Example 404

(S)—N-(4-(4-((2-amino-2,4-dimethylpentyl)oxy)-3-(trifluoromethyl)phenyl)pyridin-2-yl)pyrazine-2-carboxamide

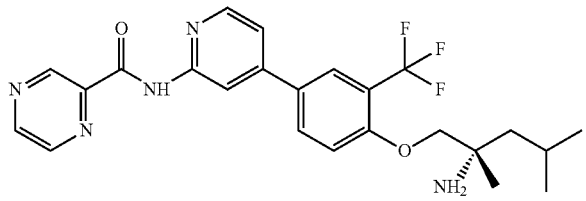 [SMILES: CC(C)C[C@](C)(N)COc1ccc(-c2ccnc(NC(=O)c3cnccn3)c2)cc1C(F)(F)F]

Prepared as described in Example 389 to afford (S)—N-(4-(4-((2-amino-2,4-dimethylpentyl)oxy)-3-(trifluoromethyl)phenyl)pyridin-2-yl)pyrazine-2-carboxamide (8.7 mg, 0.018 mmol, 43% yield for two steps) as a pale yellow solid. LCMS (ESI) m/e 474.2 [(M+H)$^+$, calcd for $C_{24}H_{27}F_3N_5O_2$ 474.2]; LC/MS retention time (method H): $t_R$=2.65 min. $^1$H NMR (400 MHz, DMSO-d$_6$) δ 10.45 (br. s., 1H), 9.38 (d, J=1.5 Hz, 1H), 9.00 (d, J=2.5 Hz, 1H), 8.87 (dd, J=2.5, 1.5 Hz, 1H), 8.55 (d, J=1.0 Hz, 1H), 8.48 (d, J=5.5 Hz, 1H), 8.09 (dd, J=8.8, 2.3 Hz, 1H), 8.00 (d, J=2.5 Hz, 1H), 7.65-7.60 (m, 1H), 7.44 (d, J=8.5 Hz, 1H), 3.98-3.89 (m, 2H), 1.81 (tt, J=12.4, 6.1 Hz, 1H), 1.50-1.39 (m, 2H), 1.17 (s, 3H), 0.95-0.90 (m, 6H) ppm.

Example 405

(S)—N-(4-(4-((2-amino-2,4-dimethylpentyl)oxy)-3-(trifluoromethyl)phenyl)pyridin-2-yl)-2-methylnicotinamide

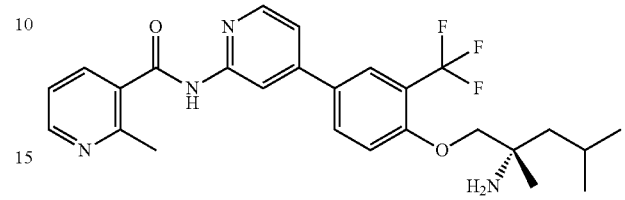

Prepared as described in Example 389 to afford (S)—N-(4-(4-((2-amino-2,4-dimethylpentyl)oxy)-3-(trifluoromethyl)phenyl)pyridin-2-yl)-2-methylnicotinamide (9.0 mg, 0.018 mmol, 43% yield for two steps) as a pale yellow solid. LCMS (ESI) m/e 487.2 [(M+H)$^+$, calcd for $C_{26}H_{30}F_3N_4O_2$ 487.2]; LC/MS retention time (method H): $t_R$=2.39 min. $^1$H NMR (400 MHz, DMSO-d$_6$) δ 11.10 (s, 1H), 8.55 (dd, J=5.0, 1.5 Hz, 1H), 8.48 (s, 1H), 8.43 (d, J=5.0 Hz, 1H), 8.06 (dd, J=8.5, 2.5 Hz, 1H), 7.96 (d, J=2.0 Hz, 1H), 7.88 (dd, J=7.8, 1.8 Hz, 1H), 7.57-7.53 (m, 1H), 7.43 (d, J=9.0 Hz, 1H), 7.33 (dd, J=8.0, 4.5 Hz, 1H), 3.97-3.90 (m, 2H), 2.59 (s, 3H), 1.85-1.76 (m, 1H), 1.47-1.42 (m, 2H), 1.17 (s, 3H), 0.93-0.91 (m, 6H) ppm.

Example 406

(S)—N-(4-(4-((2-amino-2,4-dimethylpentyl)oxy)-3-(trifluoromethyl)phenyl)pyridin-2-yl)-1H-1,2,3-triazole-5-carboxamide

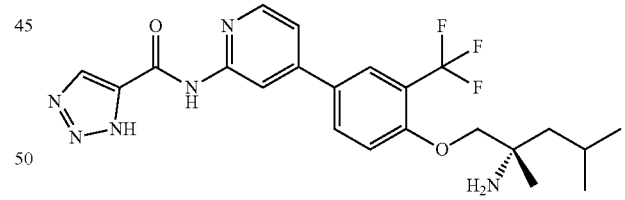

Prepared as described in Example 389 to afford (S)—N-(4-(4-((2-amino-2,4-dimethylpentyl)oxy)-3-(trifluoromethyl)phenyl)pyridin-2-yl)-1H-1,2,3-triazole-5-carboxamide (4.7 mg, 10.16 μmol, 24% yield for two steps) as a pale yellow solid. LCMS (ESI) m/e 463.3 [(M+H)$^+$, calcd for $C_{22}H_{26}F_3N_6O_2$ 463.2]; LC/MS retention time (method H): $t_R$=1.44 min. $^1$H NMR (400 MHz, DMSO-d$_6$) δ 10.14 (br. s., 1H), 8.50-8.47 (m, 2H), 8.45-8.42 (m, 1H), 8.07 (dd, J=8.5, 2.0 Hz, 1H), 7.98 (d, J=2.5 Hz, 1H), 7.54 (dd, J=5.3, 1.8 Hz, 1H), 7.45 (d, J=9.0 Hz, 1H), 4.02-3.95 (m, 2H), 1.86-1.77 (m, 1H), 1.54-1.42 (m, 2H), 1.21 (s, 3H), 0.95-0.92 (m, 6H) ppm.

Example 407

(S)—N-(4-(4-((2-amino-2,4-dimethylpentyl)oxy)-3-(trifluoromethyl)phenyl)pyridin-2-yl)-6-oxo-1,4,5,6-tetrahydropyridazine-3-carboxamide

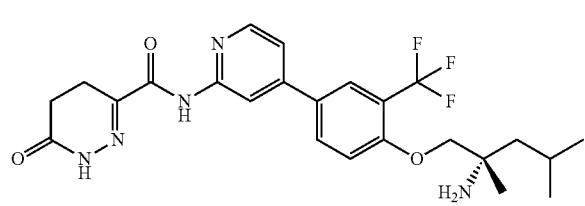 [SMILES: CC(C)C[C@](C)(N)COc1ccc(-c2ccnc(NC(=O)C3=NNC(=O)CC3)c2)cc1C(F)(F)F]

Prepared as described in Example 389 to afford (S)—N-(4-(4-((2-amino-2,4-dimethylpentyl)oxy)-3-(trifluoromethyl)phenyl)pyridin-2-yl)-6-oxo-1,4,5,6-tetrahydropyridazine-3-carboxamide (4.9 mg, 9.97 μmol, 23% yield for two steps) as a pale yellow solid. LCMS (ESI) m/e 492.3 [(M+H)$^+$, calcd for $C_{24}H_{29}F_3N_5O_3$ 492.2]; LC/MS retention time (method H): $t_R$=1.58 min. $^1$H NMR (400 MHz, DMSO-$d_6$) δ 11.38 (s, 1H), 9.66 (s, 1H), 8.43 (d, J=5.0 Hz, 1H), 8.39 (s, 1H), 8.10 (dd, J=8.8, 2.3 Hz, 1H), 8.05-7.97 (m, 1H), 7.57 (dd, J=5.3, 1.8 Hz, 1H), 7.51 (d, J=9.0 Hz, 1H), 4.22 (s, 2H), 2.86 (t, J=8.5 Hz, 2H), 2.50 (t, J=8.5 Hz, 2H), 1.85-1.80 (m, 1H), 1.77-1.70 (m, 1H), 1.63-1.58 (m, 1H), 1.39 (s, 3H), 0.96-0.92 (m, 6H) ppm.

Example 408

(S)—N-(4-(4-((2-amino-2,4-dimethylpentyl)oxy)-3-(trifluoromethyl)phenyl)pyridin-2-yl)-5-methylisoxazole-3-carboxamide

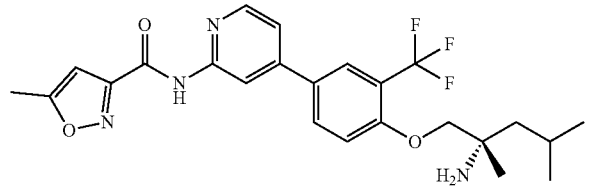 [SMILES: Cc1cc(C(=O)Nc2cc(-c3ccc(OC[C@@](C)(N)CC(C)C)c(C(F)(F)F)c3)ccn2)no1]

Prepared as described in Example 389 to afford (S)—N-(4-(4-((2-amino-2,4-dimethylpentyl)oxy)-3-(trifluoromethyl)phenyl)pyridin-2-yl)-5-methylisoxazole-3-carboxamide (8.3 mg, 0.017 mmol, 41% yield for two steps) as a pale yellow solid.

LCMS (ESI) m/e 477.2 [(M+H)$^+$, calcd for $C_{24}H_{28}F_3N_4O_3$ 477.2]; LC/MS retention time (method H): $t_R$=2.82 min. $^1$H NMR (400 MHz, DMSO-$d_6$) δ 11.12-10.00 (m, 1H), 8.47-8.44 (m, 1H), 8.36 (d, J=1.0 Hz, 1H), 8.05 (dd, J=8.5, 2.5 Hz, 1H), 7.96 (d, J=2.5 Hz, 1H), 7.58 (dd, J=5.3, 1.8 Hz, 1H), 7.41 (d, J=8.5 Hz, 1H), 6.76 (d, J=1.0 Hz, 1H), 3.96-3.86 (m, 2H), 2.50 (s, 3H), 1.79 (tt, J=12.6, 6.2 Hz, 1H), 1.47-1.36 (m, 2H), 1.15 (s, 3H), 0.92-0.89 (m, 6H) ppm.

Example 409

(S)—N-(4-(4-((2-amino-2,4-dimethylpentyl)oxy)-3-(trifluoromethyl)phenyl)pyridin-2-yl)-5-isopropyl-1H-pyrazole-3-carboxamide

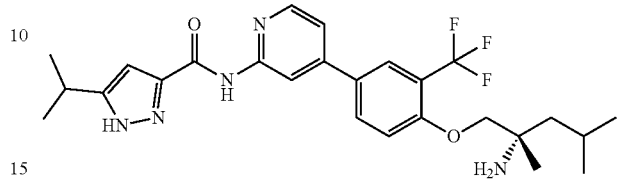

Prepared as described in Example 389 to afford (S)—N-(4-(4-((2-amino-2,4-dimethylpentyl)oxy)-3-(trifluoromethyl)phenyl)pyridin-2-yl)-5-isopropyl-1H-pyrazole-3-carboxamide (4.5 mg, 8.94 μmol, 21% yield for two steps) as a pale yellow solid. LCMS (ESI) m/e 504.2 [(M+H)$^+$, calcd for $C_{26}H_{33}F_3N_5O_2$ 504.2]; LC/MS retention time (method H): $t_R$=2.76 min. $^1$H NMR (400 MHz, DMSO-$d_6$) δ 13.30 (br. s., 1H), 9.60 (br. s., 1H), 8.47 (d, J=1.0 Hz, 1H), 8.41 (d, J=5.5 Hz, 1H), 8.05 (dd, J=8.8, 2.3 Hz, 1H), 7.95 (d, J=2.5 Hz, 1H), 7.54-7.51 (m, 1H), 7.42 (d, J=8.5 Hz, 1H), 6.63 (br. s., 1H), 3.96-3.87 (m, 2H), 3.07-2.97 (m, 1H), 1.84-1.76 (m, 1H), 1.43-1.41 (m, 2H), 1.26 (d, J=7.0 Hz, 6H), 1.15 (s, 3H), 0.94-0.91 (m, 6H) ppm.

Example 410

(S)-4-(4-((2-amino-2,4-dimethylpentyl)oxy)-3-(trifluoromethyl)phenyl)-N-(pyridin-3-ylmethyl)pyridin-2-amine

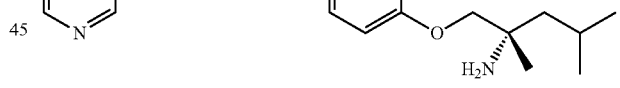

To a vial was added zinc chloride (5.83 mg, 0.043 mmol), sodium cyanoborohydride (8.06 mg, 0.128 mmol) and methanol (1 mL). The reaction mixture was stirred at RT for 1 h and to this solution was added (S)-tert-butyl (1-(4-(2-aminopyridin-4-yl)-2-(trifluoromethyl)phenoxy)-2,4-dimethylpentan-2-yl)carbamate (prepared as described in Example 290) (20 mg, 0.043 mmol) and nicotinaldehyde (5.0 mg, 0.047 mmol). The reaction mixture was stirred at 60° C. overnight. The reaction mixture was cooled to room temperature and concentrated under reduced pressure. The crude product was used for the next step without further purification.

To the crude intermediate cooled to at 0° C. was added 30% TFA in DCM (1 mL) and the mixture was stirred for 30 min. The solvent was removed under reduced pressure and the crude material was purified by reverse phase prep HPLC (Method E) to afford (S)-4-(4-((2-amino-2,4-dimethylpentyl)oxy)-3-(trifluoromethyl)phenyl)-N-(pyridin-3-ylmethyl)pyridin-2-amine as a pale yellow solid. LCMS (ESI) m/e 459.3 [(M+H)+, calcd for $C_{25}H_{30}F_3N_4O$ 459.23]; LC/MS retention time (method H): $t_R$=1.70 min. $^1$H NMR (400 MHz, DMSO-$d_6$) δ 8.05 (d, J=5.0 Hz, 1H), 7.93 (dd, J=8.8, 2.3 Hz, 1H), 7.84 (d, J=2.0 Hz, 1H), 7.57-7.55 (m, 1H), 7.37 (d, J=8.5 Hz, 1H), 6.97 (t, J=6.0 Hz, 1H), 6.85 (dd, J=5.3, 1.8 Hz, 1H), 6.81 (s, 1H), 6.39-6.37 (m, 1H), 6.28-6.25 (m, 1H), 4.51 (d, J=6.0 Hz, 2H), 4.00-3.93 (m, 2H), 1.80 (dt, J=12.8, 6.1 Hz, 1H), 1.54-1.41 (m, 2H), 1.20 (s, 3H), 0.93-0.90 (m, 6H) ppm.

Example 411

(S)-4-(4-((2-amino-2,4-dimethylpentyl)oxy)-3-(trifluoromethyl)phenyl)-N-(furan-2-ylmethyl)pyridin-2-amine

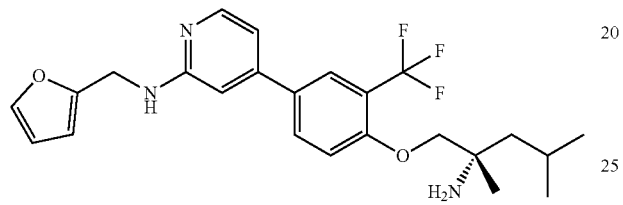

Prepared as described in Example 412 to afford (S)-4-(4-((2-amino-2,4-dimethylpentyl)oxy)-3-(trifluoromethyl)phenyl)-N-(furan-2-ylmethyl)pyridin-2-amine (4.7 mg, 10.50 µmol, 24% yield for two steps) as a pale yellow solid. LCMS (ESI) m/e 448.2 [(M+H)+, calcd for $C_{24}H_{29}F_3N_3O_2$ 448.2]; LC/MS retention time (method H): $t_R$=2.76 min. $^1$H NMR (400 MHz, DMSO-$d_6$) δ 8.57 (d, J=2.0 Hz, 1H), 8.43 (dd, J=4.5, 1.5 Hz, 1H), 8.03 (d, J=5.5 Hz, 1H), 7.93 (dd, J=8.8, 2.3 Hz, 1H), 7.83 (d, J=2.5 Hz, 1H), 7.76-7.71 (m, 1H), 7.21-7.16 (m, 1H), 6.84 (dd, J=5.5, 1.5 Hz, 1H), 6.80 (s, 1H), 4.55 (d, J=6.0 Hz, 2H), 3.96-3.89 (m, 2H), 1.83-1.75 (m, 1H), 1.51-1.39 (m, 2H), 1.18 (s, 3H), 0.92-0.90 (m, 6H) ppm.

Example 412

(S)-4-(4-((2-amino-2,4-dimethylpentyl)oxy)-3-(trifluoromethyl)phenyl)-N-(benzo[d][1,3]dioxol-5-yl)pyridin-2-amine

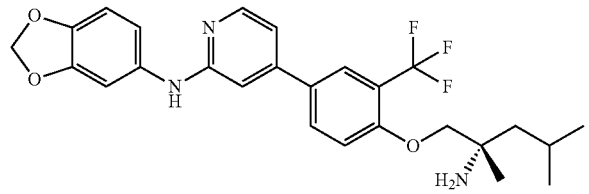 [SMILES: CC(C)C[C@](C)(N)COc1ccc(-c2ccnc(Nc3ccc4c(c3)OCO4)c2)cc1C(F)(F)F]

To a microwave vial was added (S)-tert-butyl (1-(4-(2-aminopyridin-4-yl)-2-(trifluoromethyl)phenoxy)-2,4-dimethylpentan-2-yl)carbamate (20 mg, 0.043 mmol), 5-bromobenzo[d][1,3]dioxole (0.043 mmol, 1 eq), cesium carbonate (27.9 mg, 0.086 mmol), XANTPHOS (12.38 mg, 0.021 mmol) and 1,4-dioxane (1 mL). The reaction mixture was purged with nitrogen and Pd$_2$(dba)3 (19.59 mg, 0.021 mmol) was added. Then reaction mixture was irradiated in a microwave at 100° C. for 1 h. The reaction mixture was cooled to room temperature and concentrated under reduced pressure. The crude product was used for the next step without further purification. To the crude intermediate at 0° C. was added 30% TFA in DCM (1 mL) and the mixture was stirred for 30 min. The solvent was removed and the crude material was purified by reverse phase prep HPLC (Method E) to afford (S)-4-(4-((2-amino-2,4-dimethylpentyl)oxy)-3-(trifluoromethyl)phenyl)-N-(benzo[d][1,3]dioxol-5-yl)pyridin-2-amine as a pale yellow solid. LCMS (ESI) m/e 488.2 [(M+H)+, calcd for $C_{26}H_{29}F_3N_3O_3$ 488.2]; LC/MS retention time (method H): $t_R$=2.88 min. $^1$H NMR (400 MHz, DMSO-$d_6$) δ=9.25 (br. s., 1H), 8.16 (d, J=5.5 Hz, 1H), 8.07-8.02 (m, 1H), 7.95 (d, J=2.0 Hz, 1H), 7.51-7.41 (m, 2H), 7.24-7.06 (m, 2H), 7.02-6.96 (m, 1H), 6.88 (d, J=8.5 Hz, 1H), 5.99 (s, 2H), 4.21 (s, 2H), 1.86-1.80 (m, 1H), 1.76-1.69 (m, 1H), 1.65-1.57 (m, 1H), 1.39 (s, 3H), 0.98-0.90 (m, 6H) ppm.

Example 413

(S)-4-(4-((2-amino-2,4-dimethylpentyl)oxy)-3-fluorophenyl)-6-methyl-6,7-dihydro-5H-pyrrolo [3,4-b]pyridin-5-one

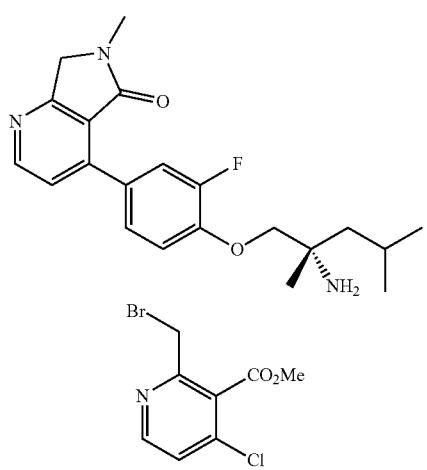

Part A. methyl 2-(bromomethyl)-4-chloronicotinate

To a solution of methyl 4-chloro-2-methylnicotinate (0.5 g, 2.69 mmol) in CCl$_4$ (10 mL) was added NBS (0.623 g, 3.50 mmol) followed by AIBN (0.044 g, 0.269 mmol). The reaction mixture was heated at 90° C. for 16 h. The reaction mixture was cooled to room temperature and concentrated under reduced pressure. The residue was purified by silica gel chromatography (10% ethyl acetate in pet ether) to afford methyl 2-(bromomethyl)-4-chloronicotinate (0.3 g, 1.090 mmol, 40% yield) as wine red oil. LCMS (ESI) m/e 264.0 (bromo pattern) [(M+H)+, calcd for $C_8H_8BrClNO_2$ 264.0]; LC/MS retention time (Method A1): $t_R$=2.13 min.

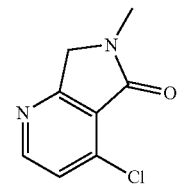

Part B. 4-chloro-6-methyl-6,7-dihydro-5H-pyrrolo[3,4-b]pyridin-5-one

A solution of methyl 2-(bromomethyl)-4-chloronicotinate (0.075 g, 0.284 mmol) in 2M methylamine in THF (0.709 mL, 1.418 mmol) was heated at 70° C. for 30 min in a pressure tube. The mixture was cooled to room temperature, concentrated under reduced pressure, diluted with water (20 mL) and extracted with dichloromethane (80 mL). The organic layer was separated, dried over $Na_2SO_4$, filtered, and concentrated under reduced pressure to afford 4-chloro-6-methyl-6,7-dihydro-5H-pyrrolo[3,4-b]pyridin-5-one (0.03 g, 0.164 mmol, 58% yield) as a pale yellow solid. LCMS (ESI) m/e 183.0 [(M+H)$^+$, calcd for $C_8H_8ClN_2O$ 183.0]; LC/MS retention time (Method F): $t_R$=1.43 min.

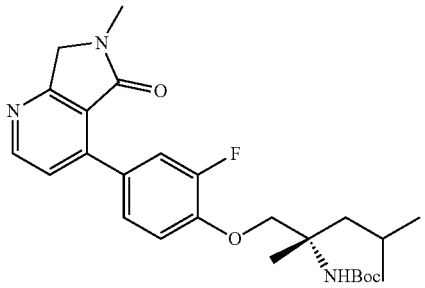 [SMILES: CC(C)C[C@@](C)(COc1ccc(-c2ccnc3c2C(=O)N(C)C3)cc1F)NC(=O)OC(C)(C)C]

Part C. (S)-tert-butyl (1-(2-fluoro-4-(6-methyl-5-oxo-6,7-dihydro-5H-pyrrolo[3,4-b]pyridin-4-yl)phenoxy)-2,4-dimethylpentan-2-yl)carbamate A mixture of 4-chloro-6-methyl-6,7-dihydro-5H-pyrrolo [3,4-b]pyridin-5-one (0.03 g, 0.164 mmol), (S)-tert-butyl (1-(2-fluoro-4-(4,4,5,5-tetramethyl-1,3,2-dioxaborolan-2-yl)phenoxy)-2,4-dimethylpentan-2-yl)carbamate (prepared as in Example 253, Part B) (0.074 g, 0.164 mmol), $PdCl_2$ (dppf)-$CH_2Cl_2$ adduct (0.013 g, 0.016 mmol) and potassium phosphate, dibasic (0.057 g, 0.329 mmol) in 1,4-dioxane (6 mL)-water (2 mL) was heated at 100° C. for 3 h. The solution cooled to room temperature and was concentrated under reduced pressure. Water (20 mL) was added and the solution was extracted with EtOAc (2×20 mL). The combined organic extracts were washed with water (20 mL) and brine (20 mL), dried over sodium sulfate, filtered, and concentrated under reduced pressure. The residue was purified by silica gel chromatography (EtOAc in hexanes) to afford (S)-tert-butyl (1-(2-fluoro-4-(6-methyl-5-oxo-6,7-dihydro-5H-pyrrolo[3,4-b]pyridin-4-yl)phenoxy)-2,4-dimethylpentan-2-yl)carbamate (0.015 g, 0.024 mmol, 15% yield) as a gummy liquid. LCMS (ESI) m/e 472.2 [(M+H)$^+$, calcd for $C_{26}H_{35}FN_3O_4$ 472.2]; LC/MS retention time (Method F): $t_R$=2.29 min.

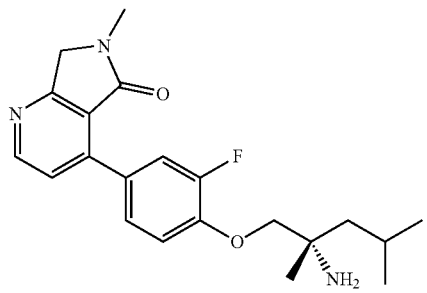 [SMILES: CC(C)C[C@](C)(N)COc1ccc(-c2ccnc3c2C(=O)N(C)C3)cc1F]

Part D. (S)-4-(4-((2-amino-2,4-dimethylpentyl)oxy)-3-fluorophenyl)-6-methyl-6,7-dihydro-5H-pyrrolo[3,4-b]pyridin-5-one To a stirred solution of (S)-tert-butyl (1-(2-fluoro-4-(6-methyl-5-oxo-6,7-dihydro-5H-pyrrolo [3,4-b]pyridin-4-yl)phenoxy)-2,4-dimethylpentan-2-yl)carbamate (0.012 g, 0.025 mmol) in DCM (3 mL) at 0° C. was added 4N HCl in 1,4-dioxane (0.127 mL, 0.509 mmol) and the mixture stirred for 2 h at RT. The reaction mixture was concentrated under reduced pressure and was purified by prep HPLC (method B) to afford (S)-4-(4-((2-amino-2,4-dimethylpentyl)oxy)-3-fluorophenyl)-6-methyl-6,7-dihydro-5H-pyrrolo[3,4-b]pyridin-5-one (0.007 g, 0.019 mmol, 74% yield) as a yellow solid. LCMS (ESI) m/e 372.0 [(M+H)$^+$, calcd for $C_{21}H_{27}FN_3O_2$ 372.2]; LC/MS retention time (Method E): $t_R$=0.95 min; LCMS retention time (method F): $t_R$=1.13 min. $^1$H NMR (400 MHz, METHANOL-$d_4$): δ 8.72 (d, J=5.52 Hz, 1H), 7.62 (dd, J=12.30, 2.26 Hz, 1H), 7.48-7.56 (m, 2H), 7.31 (t, J=8.53 Hz, 1H), 4.58 (s, 2H), 4.15-4.31 (m, 2H), 3.23 (s, 3H), 1.83-1.95 (m, 2H), 1.72 (d, J=9.04 Hz, 1H), 1.53 (s, 3H), 1.02-1.14 (m, 6H) ppm.

Example 414

(S)-2-((2-amino-2,4-dimethylpentyl)oxy)-5-(6-methyl-5-oxo-6,7-dihydro-5H-pyrrolo[3,4-b]pyridin-4-yl)benzonitrile

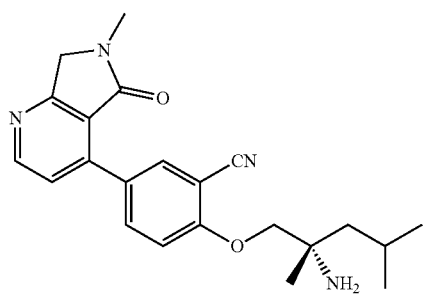 [SMILES: CC(C)C[C@](C)(N)COc1ccc(-c2ccnc3c2C(=O)N(C)C3)cc1C#N]

Prepared in a similar fashion as described in Example 413 using (S)-tert-butyl (1-(2-cyano-4-(6-methyl-5-oxo-6,7-dihydro-5H-pyrrolo[3,4-b]pyridin-4-yl)phenoxy)-2,4-dimethylpentan-2-yl)carbamate (0.05 g, 0.042 mmol) in the final step to afford (S)-2-((2-amino-2,4-dimethylpentyl)oxy)-5-(6-methyl-5-oxo-6,7-dihydro-5H-pyrrolo[3,4-b]pyridin-4-yl)benzonitrile (0.005 g, 0.013 mmol, 30% yield) as a yellow solid. LCMS (ESI) m/e 379.0 [(M+H)$^+$, calcd for $C_{22}H_{27}N_4O_2$ 379.2]; LC/MS retention time (Method E):

$t_R$=0.96 min; LCMS retention time (method F): $t_R$=1.12 min. $^1$H NMR (400 MHz, METHANOL-$d_4$): δ 8.75 (d, J=5.52 Hz, 1H), 8.11 (d, J=2.51 Hz, 1H), 8.00-8.06 (m, 1H), 7.52 (d, J=5.02 Hz, 1H), 7.39 (d, J=8.53 Hz, 1H), 4.59 (s, 2H), 4.33 (d, J=2.51 Hz, 2H), 3.23 (s, 3H), 1.85-2.02 (m, 2H), 1.74 (m, 1H), 1.57 (s, 3H), 1.09 (m, 6H) ppm.

Example 415

(S)-2-((2-amino-2,4-dimethylpentyl)oxy)-5-(5-oxo-6,7-dihydro-5H-pyrrolo[3,4-b]pyridin-4-yl)benzonitrile

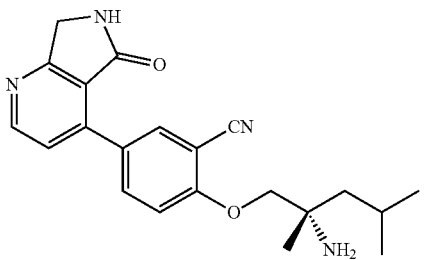 [SMILES: CC(C)C[C@](C)(N)COc1ccc(-c2ccnc3c2C(=O)NC3)cc1C#N]

Prepared in a similar fashion as described in Example 413 using (S)-tert-butyl (1-(2-cyano-4-(5-oxo-6,7-dihydro-5H-pyrrolo[3,4-b]pyridin-4-yl)phenoxy)-2,4-dimethylpentan-2-yl)carbamate (0.05 g, 0.108 mmol) in the final step to afford (S)-2-((2-amino-2,4-dimethylpentyl)oxy)-5-(5-oxo-6,7-dihydro-5H-pyrrolo[3,4-b]pyridin-4-yl)benzonitrile (0.03 g, 0.082 mmol, 76% yield) as a yellow solid. LCMS (ESI) m/e 365.0 [(M+H)$^+$, calcd for $C_{21}H_{25}N_4O_2$ 365.2]; LC/MS retention time (Method E): $t_R$=0.89 min; LCMS retention time (method F): $t_R$=0.99 min. $^1$H NMR (400 MHz, METHANOL-$d_4$): δ 8.79 (d, J=5.52 Hz, 1H), 8.01-8.14 (m, 2H), 7.53 (d, J=5.02 Hz, 1H), 7.39 (d, J=9.04 Hz, 1H), 4.55 (s, 2H), 4.28-4.37 (m, 2H), 3.23 (s, 3H), 1.85-2.03 (m, 2H), 1.71-1.79 (m, 1H), 1.57 (s, 3H), 1.09 (m, 6H) ppm.

Example 416

(S)-4-(4-((2-amino-2,4-dimethylpentyl)oxy)-3-fluorophenyl)-6,7-dihydro-5H-pyrrolo[3,4-b]pyridin-5-one

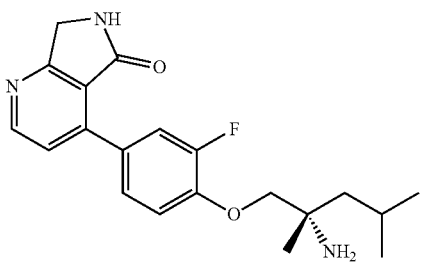

Prepared in a similar fashion as described in Example 413 using (S)-tert-butyl (1-(2-fluoro-4-(5-oxo-6,7-dihydro-5H-pyrrolo[3,4-b]pyridin-4-yl)phenoxy)-2,4-dimethylpentan-2-yl)carbamate (prepared as described in Example 285) (0.05 g, 0.109 mmol) in the final step to afford (S)-4-(4-((2-amino-2,4-dimethylpentyl)oxy)-3-fluorophenyl)-6,7-dihydro-5H-pyrrolo[3,4-b]pyridin-5-one (0.025 g, 0.068 mmol, 63% yield) as a yellow solid. LCMS (ESI) m/e 358.0 [(M+H)$^+$, calcd for $C_{20}H_{25}FN_3O_2$ 358.2]; LC/MS retention time (Method E): $t_R$=0.90 min; LCMS retention time (method F): $t_R$=1.01 min. $^1$H NMR (400 MHz, METHANOL-$d_4$): δ 8.74 (d, J=5.02 Hz, 1H), 7.58-7.65 (m, 1H), 7.47-7.55 (m, 2H), 7.26 (t, J=8.53 Hz, 1H), 4.52 (s, 2H), 3.99-4.12 (m, 2H), 1.82-1.94 (m, 1H), 1.68-1.77 (m, 1H), 1.55-1.64 (m, 1H), 1.37 (s, 3H), 1.04 (m, 6H) ppm.

Example 417

(S)-4-(4-((2-amino-2,4-dimethylpentyl)oxy)-3-chlorophenyl)-6,7-dihydro-5H-pyrrolo[3,4-b]pyridin-5-one

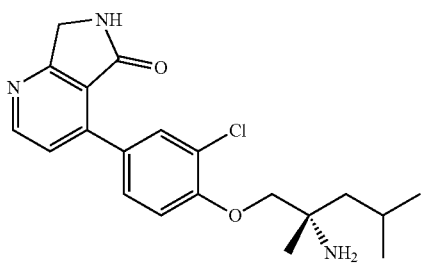

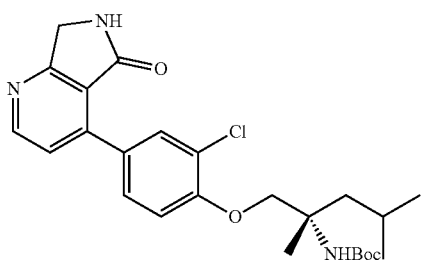

Part A. (S)-tert-butyl (1-(2-chloro-4-(5-oxo-6,7-dihydro-5H-pyrrolo[3,4-b]pyridin-4-yl)phenoxy)-2,4-dimethylpentan-2-yl)carbamate A mixture of 4-chloro-6,7-dihydro-5H-pyrrolo[3,4-b]pyridin-5-one (0.05 g, 0.297 mmol), (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (0.139 g, 0.297 mmol), Pd(Ph$_3$P)$_4$ (0.034 g, 0.030 mmol), KBr (0.046 g, 0.386 mmol) and potassium phosphate (0.445 mL, 0.890 mmol) in 1,4-dioxane (5 mL) was heated at 100° C. for 3 h. The reaction mixture was cooled to room temperature, concentrated under reduced pressure, diluted with brine and extracted with ethyl acetate (20 mL). The organic layer was separated, dried over Na$_2$SO$_4$, filtered, and concentrated to afford (S)-tert-butyl (1-(2-chloro-4-(5-oxo-6,7-dihydro-5H-pyrrolo[3,4-b]pyridin-4-yl)phenoxy)-2,4-dimethylpentan-2-yl)carbamate (0.06 g, 0.124 mmol, 42% yield) as a yellowish semi-solid. LCMS (ESI) m/e 474.2 [(M+H)$^+$, calcd for $C_{25}H_{32}ClN_3O_4$ 474.2]; LC/MS retention time (Method F): $t_R$=2.30 min.

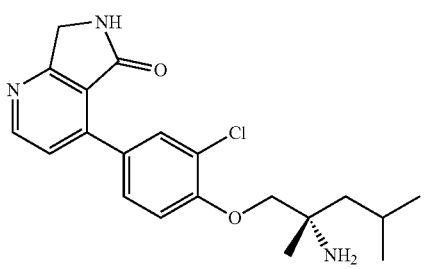 [SMILES: CC(C)C[C@](C)(N)COc1ccc(-c2ccnc3c2C(=O)NC3)cc1F]

Part B. (S)-4-(4-((2-amino-2,4-dimethylpentyl)oxy)-3-chlorophenyl)-6,7-dihydro-5H-pyrrolo[3,4-b]pyridin-5-one A stirred solution of (S)-tert-butyl (1-(2-chloro-4-(5-oxo-6,7-dihydro-5H-pyrrolo[3,4-b]pyridin-4-yl)phenoxy)-2,4-dimethylpentan-2-yl)carbamate (0.05 g, 0.105 mmol) in DCM (3 mL) at 0° C. was treated with 4N HCl in 1,4-dioxane (0.527 mL, 2.110 mmol) and the mixture stirred for 2 h at RT. The reaction mixture was concentrated under reduced pressure and was purified by prep HPLC (method B) to afford (S)-4-(4-((2-amino-2,4-dimethylpentyl)oxy)-3-chlorophenyl)-6,7-dihydro-5H-pyrrolo[3,4-b]pyridin-5-one (28 mg, 0.073 mmol, 69% yield) as a yellow solid. LCMS (ESI) m/e 374.0 [(M+H)$^+$, calcd for $C_{20}H_{25}ClN_3O_2$ 374.2]; LCMS retention time (method F): $t_R$=1.13 min. $^1$H NMR (400 MHz, METHANOL-d$_4$): δ 8.74 (d, J=5.02 Hz, 1H), 7.84 (d, J=2.01 Hz, 1H), 7.67 (dd, J=8.53, 2.01 Hz, 1H), 7.50 (d, J=5.02 Hz, 1H), 7.22 (d, J=8.53 Hz, 1H), 4.53 (s, 2H), 4.01-4.12 (m, 2H), 1.82-1.95 (m, 1H), 1.71-1.81 (m, 1H), 1.58-1.66 (m, 1H), 1.40 (s, 3H), 1.04 (m, 6H) ppm.

Example 418

(S)-4-(4-((2-amino-2,4-dimethylpentyl)oxy)-3-(trifluoromethyl)phenyl)-6-ethyl-6,7-dihydro-5H-pyrrolo[3,4-b]pyridin-5-one

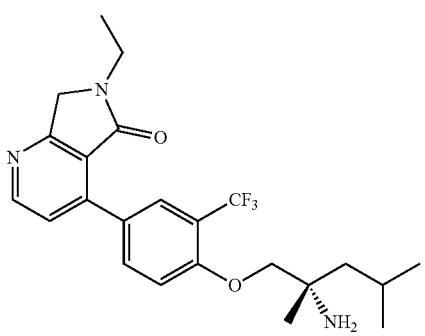

Part A. 4-chloro-6-ethyl-6,7-dihydro-5H-pyrrolo[3,4-b]pyridin-5-one

Methyl 2-(bromomethyl)-4-chloronicotinate (0.5 g, 1.890 mmol) was treated with 2M ethylamine in THF (4.73 mL, 9.45 mmol) and heated at 70° C. for 30 min in a sealed-tube. The reaction mixture was cooled to room temperature then diluted with water (150 mL) and extracted with dichloromethane (280 mL). The organic layer was separated and washed with brine, dried over sodium sulfate, filtered and concentrated under reduced pressure to afford 4-chloro-6-ethyl-6,7-dihydro-5H-pyrrolo[3,4-b]pyridin-5-one (0.35 g, 1.304 mmol, 69% yield) as yellow semi-solid. LCMS (ESI) m/e 197.0 [(M+H)$^+$, calcd for $C_9H_{10}ClN_2O$ 197.0]; LC/MS retention time (Method F): $t_R$=1.56 min.

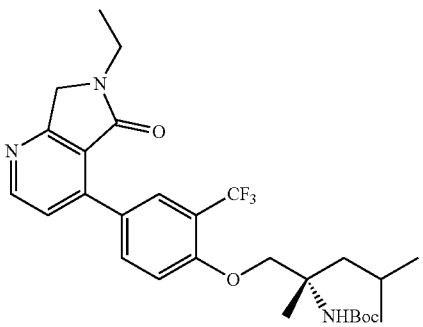 [SMILES: CCN1Cc2nccc(-c3ccc(OC[C@](C)(CC(C)C)NC(=O)OC(C)(C)C)c(C(F)(F)F)c3)c2C1=O]

Part B. (S)-tert-butyl (1-(4-(6-ethyl-5-oxo-6,7-dihydro-5H-pyrrolo[3,4-b]pyridin-4-yl)-2-(trifluoromethyl)phenoxy)-2,4-dimethylpentan-2-yl)carbamate A mixture of 4-chloro-6-ethyl-6,7-dihydro-5H-pyrrolo[3,4-b]pyridin-5-one (0.05 g, 0.186 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.093 g, 0.186 mmol), Pd(Ph$_3$P)$_4$ (0.022 g, 0.019 mmol), KBr (0.029 g, 0.242 mmol) and potassium phosphate (0.279 mL, 0.559 mmol) in 1,4-dioxane (5 mL) was heated at 100° C. for 3 h. The reaction mixture was cooled to room temperature, concentrated under reduced pressure, diluted with brine and extracted with ethyl acetate (20 mL). The organic layer was separated, dried over Na$_2$SO$_4$, filtered, and concentrated to afford (S)-tert-butyl (1-(4-(6-ethyl-5-oxo-6,7-dihydro-5H-pyrrolo[3,4-b]pyridin-4-yl)-2-(trifluoromethyl)phenoxy)-2,4-dimethylpentan-2-yl)carbamate (0.22 g, 0.166 mmol, 89% yield) as a pale semi-solid. LCMS (ESI) m/e 480.2 [(M+H-$^t$Bu)$^+$, calcd for $C_{28}H_{37}F_3N_3O_4$ 536.2]; LC/MS retention time (Method A1): $t_R$=2.66 min.

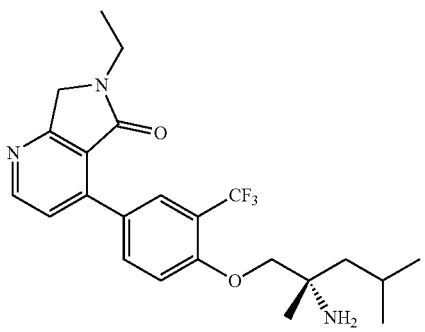 [SMILES: CCN1Cc2nccc(-c3ccc(OC[C@@](C)(N)CC(C)C)c(F)c3)c2C1=O]

Part C. (S)-4-(4-((2-amino-2,4-dimethylpentyl)oxy)-3-(trifluoromethyl)phenyl)-6-ethyl-6,7-dihydro-5H-pyrrolo[3,4-b]pyridin-5-one A stirred solution of (S)-tert-butyl (1-(4-(6-ethyl-5-oxo-6,7-dihydro-5H-pyrrolo[3,4-b]pyridin-4-yl)-2-(trifluoromethyl)phenoxy)-2,4-dimethylpentan-2-yl)carbamate (0.22 g, 0.166 mmol) in DCM (5 mL) at 0° C. was treated with 4M HCl in 1,4-dioxane (0.829 mL, 3.32 mmol) and the mixture stirred for 2 h at RT. The reaction mixture was concentrated under reduced pressure and was purified by prep HPLC (method B) to afford (S)-4-(4-((2-amino-2,4-dimethylpentyl)oxy)-3-(trifluoromethyl)phenyl)-6-ethyl-6,7-dihydro-5H-pyrrolo[3,4-b]pyridin-5-one (0.07 g, 0.159 mmol, 96% yield) as a yellow solid. LCMS (ESI) m/e 436.0 [(M+H)$^+$, calcd for $C_{23}H_{29}F_3N_3O_2$ 436.2]; LC/MS retention time (Method E): $t_R$=1.36 min; LCMS retention time (method F): $t_R$=1.48 min. $^1$H NMR (400 MHz, METHANOL-d$_4$): δ=8.75 (d, J=5.5 Hz, 1H), 8.05 (d, J=2.5 Hz, 1H), 7.99 (dd, J=8.5, 2.5 Hz, 1H), 7.52 (d, J=5.0 Hz, 1H), 7.39 (d, J=9.0 Hz, 1H), 4.34-4.22 (m, 2H), 3.71 (q, J=7.5 Hz, 2H), 3.3 (s, 2H), 1.94-1.84 (m, 2H), 1.77-1.70 (m, 1H), 1.55 (s, 3H), 1.34-1.30 (m, 3H), 1.11-1.01 (m, 6H) ppm.

Example 419

(S)-4-(4-((2-amino-2,4-dimethylpentyl)oxy)-3-fluorophenyl)-6-ethyl-6,7-dihydro-5H-pyrrolo [3,4-b]pyridin-5-one

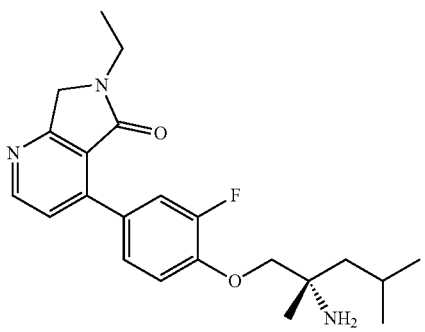

Part A. (S)-tert-butyl (1-(4-(6-ethyl-5-oxo-6,7-dihydro-5H-pyrrolo[3,4-b]pyridin-4-yl)-2-fluorophenoxy)-2,4-dimethylpentan-2-yl)carbamate A mixture of 4-chloro-6-ethyl-6,7-dihydro-5H-pyrrolo[3,4-b]pyridin-5-one (prepared as described in Example 418) (0.05 g, 0.186 mmol), (S)-tert-butyl (1-(2-fluoro-4-(4,4,5,5-tetramethyl-1,3,2-dioxaborolan-2-yl)phenoxy)-2,4-dimethylpentan-2-yl)carbamate (prepared as in Example 253, Part B) (0.084 g, 0.186 mmol), Pd(Ph$_3$P)$_4$ (0.022 g, 0.019 mmol), KBr (0.029 g, 0.242 mmol) and potassium phosphate (0.279 mL, 0.559 mmol) in 1,4-dioxane (5 mL) was heated at 100° C. for 3 h. The reaction mixture was cooled to room temperature, concentrated under reduced pressure, diluted with brine and extracted with ethyl acetate (20 mL). The organic layer was separated, dried over Na$_2$SO$_4$, filtered, and concentrated to afford (S)-tert-butyl (1-(4-(6-ethyl-5-oxo-6,7-dihydro-5H-pyrrolo[3,4-b]pyridin-4-yl)-2-fluorophenoxy)-2,4-dimethylpentan-2-yl)carbamate (0.16 g, 0.113 mmol, 61% yield) as a pale semi-solid. LCMS (ESI) m/e 486.2 [(M+H)$^+$, calcd for $C_{27}H_{37}FN_3O_4$ 486.3]; LC/MS retention time (Method A1): $t_R$=2.58 min.

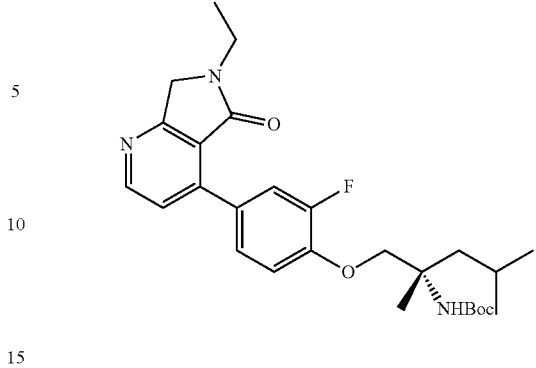

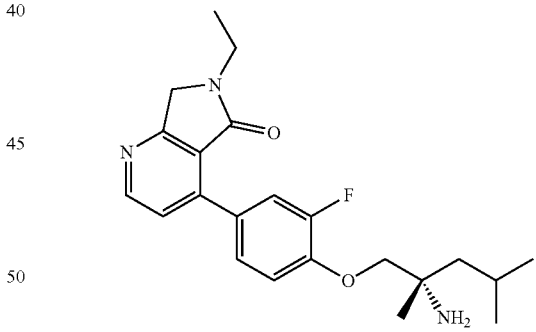

Part B. (S)-4-(4-((2-amino-2,4-dimethylpentyl)oxy)-3-fluorophenyl)-6-ethyl-6,7-dihydro-5H-pyrrolo[3,4-b]pyridin-5-one A stirred solution of (S)-tert-butyl (1-(4-(6-ethyl-5-oxo-6,7-dihydro-5H-pyrrolo[3,4-b]pyridin-4-yl)-2-fluorophenoxy)-2,4-dimethylpentan-2-yl)carbamate (0.16 g, 0.113 mmol) in DCM (5 mL) at 0° C. was treated with 4M HCl in 1,4-dioxane (0.564 mL, 2.257 mmol) and the mixture stirred for 2 h at RT. The reaction mixture was concentrated under reduced pressure and was purified by prep HPLC (method B) to afford (S)-4-(4-((2-amino-2,4-dimethylpentyl)oxy)-3-fluorophenyl)-6-ethyl-6,7-dihydro-5H-pyrrolo[3,4-b]pyridin-5-one (0.025 g, 0.065 mmol, 58% yield) as a yellow solid. LCMS (ESI) m/e 386.0 [(M+H)+, calcd for $C_{22}H_{29}FN_3O_2$ 386.2]; LC/MS retention time (Method E): $t_R$=1.21 min; LCMS retention time (method F): $t_R$=1.13 min. $^1$H NMR (400 MHz, CD3OD): δ 8.69 (d, J=5.60 Hz, 1H), 7.47-7.65 (m, 3H), 7.26 (m, 1H), 4.57 (s, 2H), 4.06-4.16 (m, 2H), 3.62-3.72 (m, 2H), 1.75-1.88 (m, 2H), 1.61-1.66 (m, 1H), 1.42 (s, 3H), 1.28-1.31 (m, 3H), 1.01-1.06 (m, 6H) ppm.

Example 420

(S)-1-(2-fluoro-4-(1H-pyrrolo[3,2-b]pyridin-7-yl)phenoxy)-2,4-dimethylpentan-2-amine

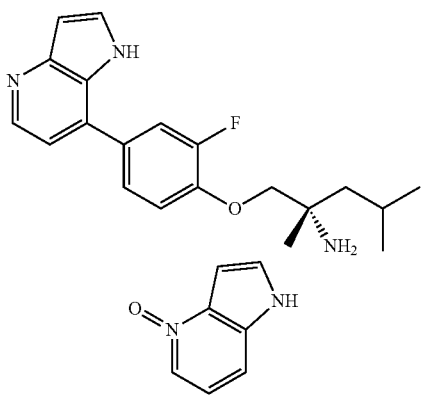

Part A. 1H-pyrrolo[3,2-b]pyridine 4-oxide

To a solution of 1H-pyrrolo[3,2-b]pyridine (0.85 g, 7.20 mmol) in DCM (20 mL) at 0° C., was added m-CPBA (2.71 g, 8.63 mmol) and the mixture was stirred overnight at RT. The solution was warmed to room temperature and concentrated under reduced pressure. The residue was purified by silica gel chromatography (10% methanol in dichloromethane) to afford 1H-pyrrolo[3,2-b]pyridine 4-oxide (0.85 g, 6.34 mmol, 88% yield) as a yellow solid, $^1$H NMR (300 MHz, DMSO-$d_6$): δ 11.79 (bs, 1H), 8.03 (dd, J=6.04, 0.76 Hz, 1H), 7.55-7.62 (m, 1H), 7.45 (d, J=7.93 Hz, 1H), 7.08 (dd, J=8.31, 6.04 Hz, 1H), 6.63-6.69 (m, 1H), ppm.

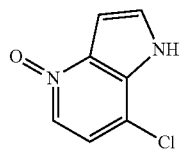 [SMILES: [O-][n+]1ccc(Cl)c2[nH]ccc21]

Part B. 7-chloro-1H-pyrrolo[3,2-b]pyridine

A solution of 1H-pyrrolo[3,2-b]pyridine 4-oxide (0.85 g, 6.34 mmol) in POCl$_3$ (11.81 mL, 127 mmol) was heated at reflux for 6 h. The reaction mixture was concentrated under reduced pressure, quenched with saturated aqueous sodium bicarbonate and extracted with dichloromethane (50 mL). The organic layer was separated, dried over sodium sulfate and concentrated under reduced pressure to afford 7-chloro-1H-pyrrolo[3,2-b]pyridine (0.85 g, 4.90 mmol, 77% yield) as a yellow solid. LCMS (ESI) m/e 153.2 [(M+H)+, calcd for $C_7H_6ClN_2$ 153.0]; LC/MS retention time (Method A1): $t_R$=1.80 min.

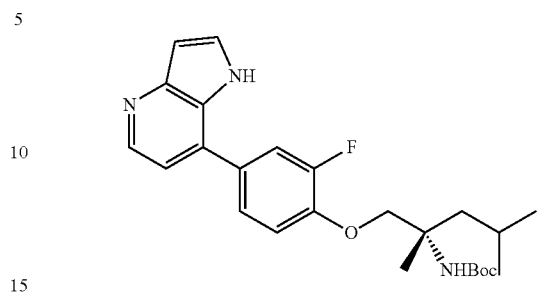

Part C. (S)-tert-butyl (1-(2-fluoro-4-(1H-pyrrolo[3,2-b]pyridin-7-yl)phenoxy)-2,4-dimethylpentan-2-yl)carbamate A mixture of 7-chloro-1H-pyrrolo[3,2-b]pyridine (0.05 g, 0.328 mmol), (S)-tert-butyl (1-(2-fluoro-4-(4,4,5,5-tetramethyl-1,3,2-dioxaborolan-2-yl)phenoxy)-2,4-dimethylpentan-2-yl)carbamate (prepared as in Example 253, Part B) (0.148 g, 0.328 mmol), Pd(Ph$_3$P)$_4$ (0.019 g, 0.016 mmol), KBr (0.051 g, 0.426 mmol) and potassium phosphate (0.492 mL, 0.983 mmol) in 1,4-dioxane (5 mL) was heated at 100° C. for 3 h. The reaction mixture was cooled to room temperature, concentrated under reduced pressure, diluted with brine and extracted with ethyl acetate (20 mL). The organic layer was separated, dried over Na$_2$SO$_4$, filtered, and concentrated to afford (S)-tert-butyl (1-(2-fluoro-4-(1H-pyrrolo[3,2-b]pyridin-7-yl)phenoxy)-2,4-dimethylpentan-2-yl)carbamate (0.25 g, 0.125 mmol, 38% yield) as a brownish semi-solid. LCMS (ESI) m/e 440.2 [(M−H)−, calcd for $C_{25}H_{31}FN_3O_3$ 440.2]; LC/MS retention time (Method A1): $t_R$=1.79 min.

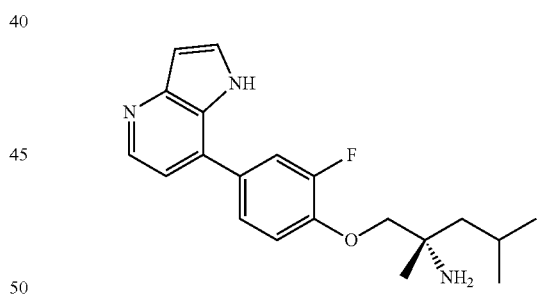

Part D. (S)-1-(2-fluoro-4-(1H-pyrrolo[3,2-b]pyridin-7-yl)phenoxy)-2,4-dimethylpentan-2-amine A solution of (S)-tert-butyl (1-(2-fluoro-4-(1H-pyrrolo[3,2-b]pyridin-7-yl)phenoxy)-2,4-dimethylpentan-2-yl)carbamate (0.25 g, 0.136 mmol) in DCM (5 mL) at 0° C., was treated with 4M HCl in 1,4-dioxane (0.679 mL, 2.72 mmol) and the mixture stirred for 2 h at RT. The reaction mixture was concentrated under reduced pressure and was purified by prep HPLC (method B) to afford (S)-1-(2-fluoro-4-(1H-pyrrolo[3,2-b]pyridin-7-yl)phenoxy)-2,4-dimethylpentan-2-amine (0.01 g, 0.029 mmol, 21% yield) as a yellow solid. LCMS (ESI) m/e 342.0 [(M+H)+, calcd for $C_{20}H_{25}FN_3O$ 342.2]; LC/MS retention time (Method E): $t_R$=075; LCMS retention time (method F): $t_R$=1.17 min. $^1$H NMR (400

MHz, DMSO-d$_6$): δ 11.38 (bs, 1H), 8.37 (d, J=4.52 Hz, 1H), 7.57-7.69 (m, 2H), 7.49-7.55 (m, 1H), 7.35 (t, J=8.78 Hz, 1H), 7.16 (d, J=5.02 Hz, 1H), 6.61-6.68 (m, 1H), 3.88 (s, 2H), 1.84 (s, 1H), 1.45 (m, 2H), 1.18 (s, 3H), 0.89-1.02 (m, 6H) ppm.

Example 421

(S)-2-((2-amino-2,4-dimethylpentyl)oxy)-5-(1H-pyrrolo[3,2-b]pyridin-7-yl)benzonitrile

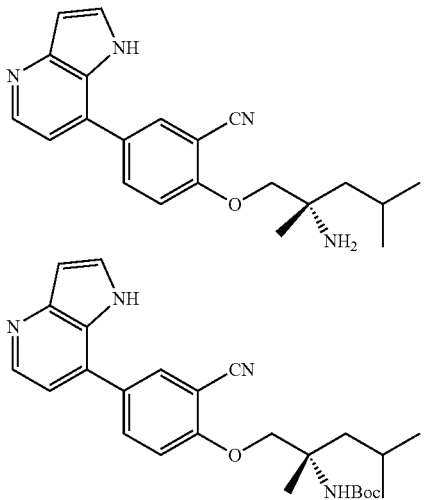

Part A. (S)-tert-butyl (1-(2-cyano-4-(1H-pyrrolo[3,2-b]pyridin-7-yl)phenoxy)-2,4-dimethylpentan-2-yl)carbamate A mixture of 7-chloro-1H-pyrrolo[3,2-b]pyridine (prepared as described in Example 420) (0.05 g, 0.328 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (0.150 g, 0.328 mmol), Pd(Ph$_3$P)$_4$ (0.038 g, 0.033 mmol), KBr (0.051 g, 0.426 mmol) and potassium phosphate (0.492 mL, 0.983 mmol) in 1,4-dioxane (5 mL) was heated at 100° C. for 3 h. The reaction mixture was cooled to room temperature, concentrated under reduced pressure, diluted with brine and extracted with ethyl acetate (20 mL). The organic layer was separated, dried over Na$_2$SO$_4$, filtered, and concentrated to afford (S)-tert-butyl (1-(2-cyano-4-(1H-pyrrolo[3,2-b]pyridin-7-yl)phenoxy)-2,4-dimethylpentan-2-yl)carbamate (0.25 g, 0.128 mmol, 39% yield) as a brownish semi-solid. LCMS (ESI) m/e 449.2 [(M+H)$^+$, calcd for C$_{26}$H$_{33}$N$_4$O$_3$ 449.2]; LC/MS retention time (Method A1): t$_R$=2.49 min.

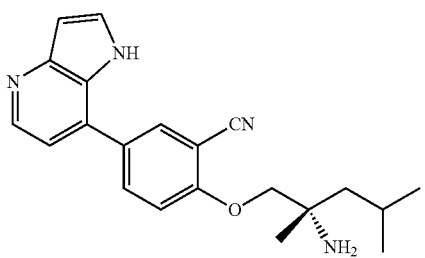 [SMILES: CC(C)C[C@](C)(N)COc1ccc(-c2ccnc3cc[nH]c23)cc1C#N]

Part B. (S)-2-((2-amino-2,4-dimethylpentyl)oxy)-5-(1H-pyrrolo[3,2-b]pyridin-7-yl)benzonitrile A stirred solution of (S)-tert-butyl (1-(2-cyano-4-(1H-pyrrolo[3,2-b]pyridin-7-yl)phenoxy)-2,4-dimethylpentan-2-yl)carbamate (0.25 g, 0.557 mmol) in DCM (5 mL) at 0° C., was treated with 4N HCl in 1,4-dioxane (2.79 mL, 11.15 mmol) and the mixture stirred for 2 h at RT. The reaction mixture was concentrated under reduced pressure and was purified by prep HPLC (method A) to afford (S)-2-((2-amino-2,4-dimethylpentyl)oxy)-5-(1H-pyrrolo[3,2-b]pyridin-7-yl)benzonitrile (0.01 g, 0.027 mmol, 5% yield) as a yellow solid. LCMS (ESI) m/e 349.0 [(M+H)$^+$, calcd for C$_{21}$H$_{25}$N$_4$O 349.2]; LC/MS retention time (Method E): t$_R$=0.73 min; LCMS retention time (method F): t$_R$=1.17 min. $^1$H NMR (400 MHz, DMSO-d$_6$): δ 11.46 (bs, 1H), 8.40 (d, J=5.02 Hz, 1H), 8.11 (d, J=2.01 Hz, 1H), 8.01 (dd, J=8.78, 2.26 Hz, 1H), 7.69 (t, J=3.26 Hz, 1H), 7.44 (d, J=8.53 Hz, 1H), 7.19 (d, J=5.02 Hz, 1H), 6.67 (dd, J=3.26, 1.76 Hz, 1H), 4.01 (bs, 2H), 1.78-1.93 (m, 1H), 1.50 (m, 2H), 1.23 (s, 3H), 1.01-0.96 (m, 6H) ppm.

Example 423

(S)-2-((2-amino-2,4-dimethylpentyl)oxy)-5-(1-methyl-1H-pyrrolo[3,2-b]pyridin-7-yl)benzonitrile

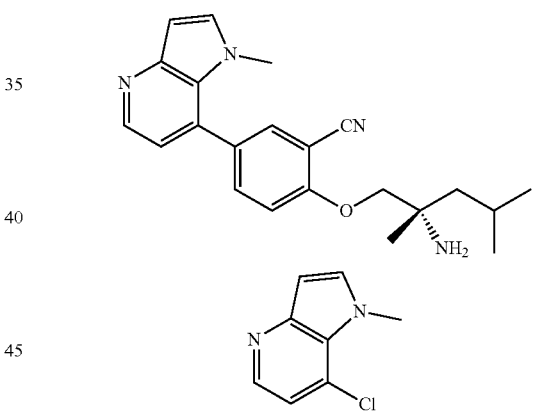

Part A. 7-chloro-1-methyl-1H-pyrrolo[3,2-b]pyridine

To a solution of 7-chloro-1H-pyrrolo[3,2-b]pyridine (prepared as described in Example 420) (0.3 g, 1.612 mmol) in DMF (5 mL) at 0° C. was added NaH (0.129 g, 3.22 mmol). The mixture was stirred for 30 min at RT and then methyl iodide (0.302 mL, 4.84 mmol) was added and mixture was stirred overnight. The mixture was quenched with water (20 mL) and extracted with ethyl acetate (30 mL). The organic layer separated, dried over Na$_2$SO$_4$, filtered, and concentrated under reduced pressure to afford 7-chloro-1-methyl-1H-pyrrolo[3,2-b]pyridine (0.16 g, 0.463 mmol, 29% yield) as a brownish semi-solid. LCMS (ESI) m/e 167.0 [(M+H)$^+$, calcd for C$_8$H$_8$ClN$_2$ 167.0]; LC/MS retention time (Method A1): t$_R$=2.65 min.

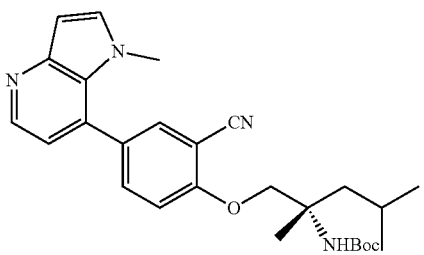 [SMILES: CC(C)C[C@@](C)(COc1ccc(-c2ccnc3ccn(C)c23)cc1C#N)NC(=O)OC(C)(C)C]

Part B. (S)-tert-butyl (1-(2-cyano-4-(1-methyl-1H-pyrrolo[3,2-b]pyridin-7-yl)phenoxy)-2,4-dimethyl-pentan-2-yl)carbamate A mixture of 7-chloro-1-methyl-1H-pyrrolo[3,2-b]pyridine (0.06 g, 0.174 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (0.08 g, 0.176 mmol), KBr (0.027 g, 0.226 mmol), Pd(Ph$_3$P)$_4$ (0.020 g, 0.017 mmol), and potassium phosphate (0.261 mL, 0.521 mmol) in 1,4-dioxane (5 mL) was heated at 100° C. overnight. The reaction mixture was cooled to room temperature, concentrated under reduced pressure, diluted with brine and extracted with ethyl acetate (30 mL). The organic layer was separated, dried over Na$_2$SO$_4$, filtered, and concentrated to afford (S)-tert-butyl (1-(2-cyano-4-(1-methyl-1H-pyrrolo[3,2-b]pyridin-7-yl)phenoxy)-2,4-dimethylpentan-2-yl)carbamate (0.02 g, 0.031 mmol, 18% yield) as a brownish semi-solid. LCMS (ESI) m/e 463.2 [(M+H)$^+$, calcd for C$_{27}$H$_{35}$N$_4$O$_3$ 463.2]; LC/MS retention time (Method F): t$_R$=2.21 min.

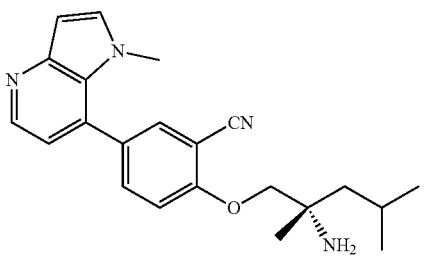

Part C. (S)-2-((2-amino-2,4-dimethylpentyl)oxy)-5-(1-methyl-1H-pyrrolo[3,2-b]pyridin-7-yl)benzonitrile A solution of (S)-tert-butyl (1-(2-cyano-4-(1-methyl-1H-pyrrolo[3,2-b]pyridin-7-yl)phenoxy)-2,4-dimethylpentan-2-yl)carbamate (0.03 g, 0.065 mmol) in DCM (5 mL) at 0° C. was treated with 4N HCl in 1,4-dioxane (0.324 mL, 1.297 mmol) and the mixture stirred for 2 h at RT. The reaction mixture was concentrated under reduced pressure and was purified by prep HPLC (method A) to afford (S)-2-((2-amino-2,4-dimethylpentyl)oxy)-5-(1-methyl-1H-pyrrolo[3,2-b]pyridin-7-yl)benzonitrile (0.005 g, 0.014 mmol, 21% yield) as a yellow solid. LCMS (ESI) m/e 363.0 [(M+H)$^+$, calcd for C$_{22}$H$_{27}$N$_4$O 363.2]; LC/MS retention time (Method E): t$_R$=0.82 min; LCMS retention time (method F): t$_R$=1.44 min. $^1$H NMR (400 MHz, METHANOL-d$_4$): δ 8.27-8.33 (m, 2H), 7.98 (dd, J=8.53, 1.00 Hz, 1H), 7.68 (d, J=8.53 Hz, 1H), 7.58 (d, J=3.51 Hz, 1H), 7.40 (d, J=9.04 Hz, 1H), 6.66-6.71 (m, 1H), 4.29 (d, J=4.52 Hz, 2H), 3.92 (s, 3H), 1.93 (s, 2H), 1.73 (d, J=8.53 Hz, 1H), 1.50-1.59 (m, 3H), 1.09 (m, 6.53 Hz, 6H) ppm.

Example 424

(S)-1-(4-(1H-pyrrolo[3,2-b]pyridin-7-yl)-2-(trifluoromethyl)phenoxy)-2,4-dimethylpentan-2-amine

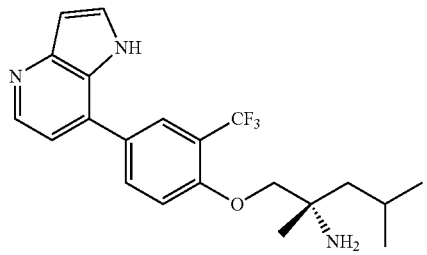 [SMILES: CC(C)C[C@](C)(N)COc1ccc(-c2ccnc3cc[nH]c23)cc1C(F)(F)F]

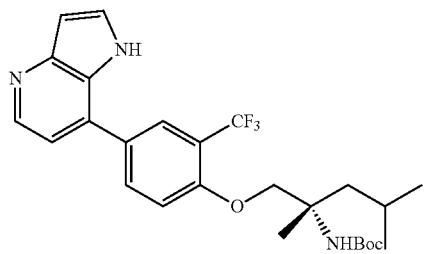 [SMILES: CC(C)C[C@@](C)(COc1ccc(-c2ccnc3cc[nH]c23)cc1C(F)(F)F)NC(=O)OC(C)(C)C]

Part A. (S)-tert-butyl (1-(4-(1H-pyrrolo[3,2-b]pyridin-7-yl)-2-(trifluoromethyl)phenoxy)-2,4-dimethylpentan-2-yl)carbamate A mixture of 7-chloro-1H-pyrrolo[3,2-b]pyridine (prepared as described in Example 420) (0.03 g, 0.197 mmol, (S)-tert-butyl(2,4-dimethyl-1-(4-(4,4,5,5-tetramethyl-1,3,2-dioxaborolan-2-yl)-2-(trifluoromethyl)phenoxy)pentan-2-yl)carbamate (0.337 g, 0.671 mmol), KBr (0.02 g, 0.197 mmol), Pd(Ph$_3$P)$_4$ (0.023 g, 0.020 mmol) and potassium phosphate (0.295 mL, 0.590 mmol) in 1,4-dioxane (5 mL) was heated at 100° C. overnight. The reaction mixture was cooled to room temperature, concentrated under reduced pressure, diluted with brine and extracted with ethyl acetate (20 mL). The organic layer was separated, dried over Na$_2$SO$_4$, filtered, and concentrated under reduced pressure to afford (S)-tert-butyl (1-(4-(1H-pyrrolo[3,2-b]pyridin-7-yl)-2-(trifluoromethyl)phenoxy)-2,4-dimethylpentan-2-yl)carbamate (0.03 g, 0.059 mmol, 30% yield) as a brown semi-solid. LCMS (ESI) m/e 492.2 [(M+H)$^+$, calcd for C$_{26}$H$_{33}$F$_3$N$_3$O$_3$ 492.2]; LC/MS retention time (Method F): t$_R$=2.10 min.

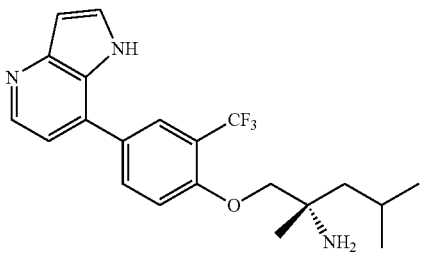 [SMILES: CC(C)C[C@](C)(N)COc1ccc(-c2ccnc3cc[nH]c23)cc1C(F)(F)F]

Part B. (S)-1-(4-(1H-pyrrolo[3,2-b]pyridin-7-yl)-2-(trifluoromethyl)phenoxy)-2,4-dimethylpentan-2-amine A solution of (S)-tert-butyl (1-(4-(1H-pyrrolo[3,2-b]pyridin-7-yl)-2-(trifluoromethyl)phenoxy)-2,4-dimethylpentan-2-yl)carbamate (0.03 g, 0.061 mmol) in DCM (5 mL) at 0° C., was treated with 4N HCl in 1,4-dioxane (0.305 mL, 1.221 mmol) and the mixture stirred for 2 h at RT. The reaction mixture was concentrated under reduced pressure and was purified by prep HPLC (method A) to afford (S)-1-(4-(1H-pyrrolo[3,2-b]pyridin-7-yl)-2-(trifluoromethyl)phenoxy)-2,4-dimethylpentan-2-amine (0.005 g, 0.013 mmol, 21% yield) as a yellow solid. LCMS (ESI) m/e 392.0 [(M+H)$^+$, calcd for $C_{21}H_{25}F_3N_3O$ 392.2]; LC/MS retention time (Method E): $t_R$=0.89 min; LCMS retention time (method F): $t_R$=1.55 min. $^1$H NMR (400 MHz, METHANOL-$d_4$): δ 8.42 (d, J=5.02 Hz, 1H), 8.01-8.07 (m, 2H), 7.69 (d, J=3.51 Hz, 1H), 7.50 (d, J=9.04 Hz, 1H), 7.28 (d, J=5.02 Hz, 1H), 6.75 (d, J=3.51 Hz, 1H), 4.25-4.35 (m, 2H), 1.87-1.97 (m, 2H), 1.75 (d, J=8.53 Hz, 1H), 1.56 (s, 3H), 1.07 (m, 6H) ppm.

Example 425

(S)-4-(4-((2-amino-2,4-dimethylpentyl)oxy)-3-(trifluoromethyl)phenyl)-6,7-dihydro-5H-pyrrolo [3,4-b]pyridin-5-one

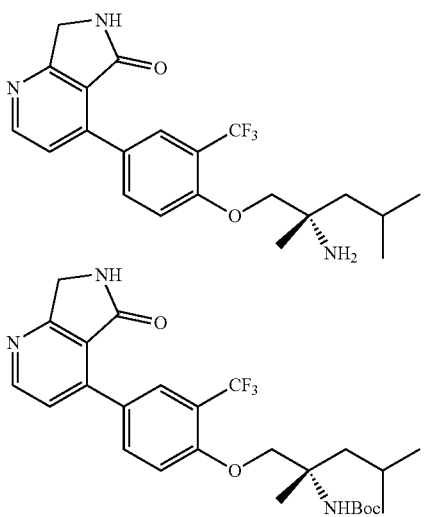

Part A. (S)-tert-butyl (2,4-dimethyl-1-(4-(5-oxo-6,7-dihydro-5H-pyrrolo[3,4-b]pyridin-4-yl)-2-(trifluoromethyl)phenoxy)pentan-2-yl)carbamate A mixture of 4-chloro-6,7-dihydro-5H-pyrrolo[3,4-b]pyridin-5-one (prepared as described in Example 415) (0.03 g, 0.178 mmol), (S)-tert-butyl(2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 290) (0.034 g, 0.178 mmol), KBr (0.028 g, 0.231 mmol), Pd(Ph$_3$P)$_4$ (0.021 g, 0.018 mmol) and potassium phosphate, dibasic (0.267 mL, 0.534 mmol) in 1,4-dioxane (3 mL) was heated at 100° C. for 3 h.

The reaction mixture was cooled to room temperature, concentrated under reduced pressure, diluted with brine and extracted with ethyl acetate (15 mL). The organic layer was separated, dried over Na$_2$SO$_4$, filtered, and concentrated under reduced pressure to afford (S)-tert-butyl(2,4-dimethyl-1-(4-(5-oxo-6,7-dihydro-5H-pyrrolo[3,4-b]pyridin-4-yl)-2-(trifluoromethyl)phenoxy)pentan-2-yl)carbamate (0.03 g, 0.057 mmol, 32% yield) as a brownish semi-solid. LCMS (ESI) m/e 508.2 [(M+H)$^+$, calcd for $C_{26}H_{33}F_3N_3O_4$ 508.2]; LC/MS retention time (Method F): $t_R$=2.40 min.

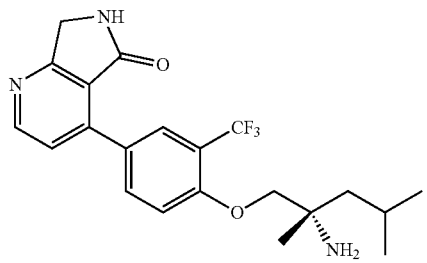 [SMILES: CC(C)C[C@](C)(N)COc1ccc(-c2ccnc3c2C(=O)NC3)cc1C(F)(F)F]

Part B. (S)-4-(4-((2-amino-2,4-dimethylpentyl)oxy)-3-(trifluoromethyl)phenyl)-6,7-dihydro-5H-pyrrolo [3,4-b]pyridin-5-one A solution of (S)-tert-butyl (2,4-dimethyl-1-(4-(5-oxo-6,7-dihydro-5H-pyrrolo[3,4-b]pyridin-4-yl)-2-(trifluoromethyl)phenoxy)pentan-2-yl)carbamate (0.025 g, 0.049 mmol) in DCM (5 mL) at 0° C., was treated with 4N HCl in 1,4-dioxane (0.246 mL, 0.985 mmol) and stirred for 4 h. The reaction mixture was concentrated under reduced pressure and was purified by prep HPLC (method A) to afford (S)-4-(4-((2-amino-2,4-dimethylpentyl)oxy)-3-(trifluoromethyl)phenyl)-6,7-dihydro-5H-pyrrolo[3,4-b]pyridin-5-one (0.005 g, 0.012 mmol, 24% yield) as a yellow solid. LCMS (ESI) m/e 408.0 [(M+H)$^+$, calcd for $C_{21}H_{24}F_3N_3O_2$ 408.2]; LC/MS retention time (Method E): $t_R$=1.07 min; LCMS retention time (method F): $t_R$=1.30 min. $^1$H NMR (400 MHz, METHANOL-$d_4$): δ 8.77 (d, J=5.02 Hz, 1H) 8.04 (d, J=2.51 Hz, 1H), 7.97 (dd, J=8.53, 2.51 Hz, 1H), 7.53 (d, J=5.02 Hz, 1H), 7.33 (d, J=9.04 Hz, 1H), 4.52-4.61 (m, 2H), 4.01-4.13 (m, 2H), 1.94 (s, 1H), 1.81-1.90 (m, 1H), 1.56-1.74 (m, 2H), 1.36 (s, 3H), 1.03 (m, 6H) ppm.

Example 426

(S)-4-(4-((2-amino-2,4-dimethylpentyl)oxy)-3-(trifluoromethyl)phenyl)-6-methyl-6,7-dihydro-5H-pyrrolo[3,4-b]pyridin-5-one

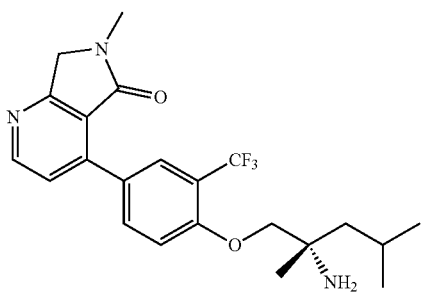 [SMILES: CC(C)C[C@](C)(N)COc1ccc(-c2ccnc3c2C(=O)N(C)C3)cc1C(F)(F)F]

Part A. (S)-tert-butyl (2,4-dimethyl-1-(4-(6-methyl-5-oxo-6,7-dihydro-5H-pyrrolo[3,4-b]pyridin-4-yl)-2-(trifluoromethyl)phenoxy)pentan-2-yl)carbamate A solution of 4-chloro-6-methyl-6,7-dihydro-5H-pyrrolo[3,4-b]pyridin-5-one (prepared as described in Example 413) (0.04 g, 0.219 mmol), (S)-tert-butyl(2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 290) (0.045 g, 0.219 mmol), KBr (0.034 g, 0.285 mmol), Pd(Ph$_3$P)$_4$ (0.025 g, 0.022 mmol) and potassium phosphate (0.329 mL, 0.657 mmol) in 1,4-dioxane (4 mL) was heated at 100° C. overnight. The reaction mixture was cooled to room temperature, concentrated under reduced pressure, diluted with brine and extracted with ethyl acetate (20 mL). The organic layer was separated, dried over Na$_2$SO$_4$, filtered, and concentrated under reduced pressure to afford (S)-tert-butyl (2,4-dimethyl-1-(4-(6-methyl-5-oxo-6,7-dihydro-5H-pyrrolo[3,4-b]pyridin-4-yl)-2-(trifluoromethyl)phenoxy)pentan-2-yl)carbamate (0.03 g, 0.055 mmol, 25% yield) as a brownish semi-solid. LCMS (ESI) m/e 522.2 [(M+H)$^+$, calcd for C$_{27}$H$_{35}$F$_3$N$_3$O$_4$ 522.2]; LC/MS retention time (Method F): t$_R$=2.49 min.

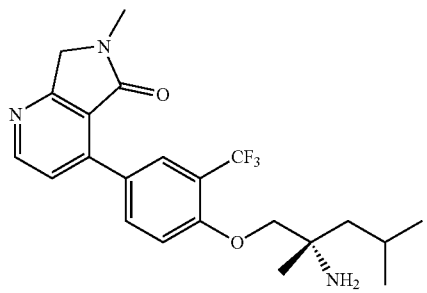 [SMILES: CC(C)C[C@](C)(N)COc1ccc(-c2ccnc3c2C(=O)N(C)C3)cc1C(F)(F)F]

Part B. (S)-4-(4-((2-amino-2,4-dimethylpentyl)oxy)-3-(trifluoromethyl)phenyl)-6-methyl-6,7-dihydro-5H-pyrrolo[3,4-b]pyridin-5-one A solution of (S)-tert-butyl (2,4-dimethyl-1-(4-(6-methyl-5-oxo-6,7-dihydro-5H-pyrrolo[3,4-b]pyridin-4-yl)-2-(trifluoromethyl)phenoxy)pentan-2-yl)carbamate (0.025 g, 0.048 mmol) in DCM (5 mL) at 0° C. was treated with 4N HCl in 1,4-dioxane (0.240 mL, 0.959 mmol) and stirred for 4 h. The reaction mixture was concentrated under reduced pressure and was purified by prep HPLC (method A) to afford (S)-4-(4-((2-amino-2,4-dimethylpentyl)oxy)-3-(trifluoromethyl)phenyl)-6-methyl-6,7-dihydro-5H-pyrrolo[3,4-b]pyridin-5-one (0.005 g, 0.012 mmol, 24% yield) as a yellow solid. LCMS (ESI) m/e 422.0 [(M+H)$^+$, calcd for C$_{22}$H$_{27}$F$_3$N$_3$O$_2$ 422.2]; LC/MS retention time (method D): t$_R$=1.43 min. $^1$H NMR (400 MHz, METHANOL-d$_4$): δ 8.74 (d, J=5.52 Hz, 1H), 8.04 (d, J=2.01 Hz, 1H), 7.97 (dd, J=8.78, 2.26 Hz, 1H), 7.52 (d, J=5.02 Hz, 1H), 7.35 (d, J=8.53 Hz, 1H), 4.58 (s, 2H), 4.15 (q, J=9.54 Hz, 2H), 3.23 (s, 3H), 1.88 (s, 1H), 1.76 (d, J=5.52 Hz, H), 1.67 (d, J=5.52 Hz, 1H), 1.43 (s, 3H), 1.04 (m, 6H) ppm.

Example 427

(S)-2,4-dimethyl-1-(2-methyl-4-(1-methyl-1H-pyrrolo[3,2-b]pyridin-7-yl)phenoxy)pentan-2-amine

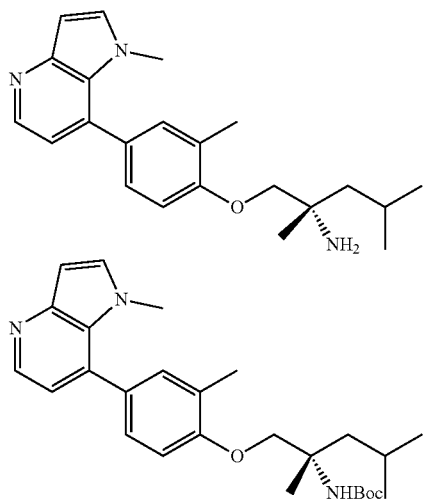

Part A. (S)-tert-butyl (2,4-dimethyl-1-(2-methyl-4-(1-methyl-1H-pyrrolo[3,2-b]pyridin-7-yl)phenoxy)pentan-2-yl) carbamate A mixture of 7-chloro-1-methyl-1H-pyrrolo[3,2-b]pyridine (prepared as described in Example 423) (0.06 g, 0.174 mmol), (S)-tert-butyl (2,4-dimethyl-1-(2-methyl-4-(4,4,5,5-tetramethyl-1,3,2-dioxaborolan-2-yl)phenoxy)pentan-2-yl) carbamate (prepared as described in Example 259, Part A and B) (80 mg, 0.176 mmol), KBr (0.027 g, 0.226 mmol), Pd(Ph$_3$P)$_4$ (0.020 g, 0.017 mmol) and potassium phosphate (0.261 mL, 0.521 mmol)) in 1,4-dioxane (5 mL) was heated at 100° C. overnight. The reaction mixture was cooled to room temperature, concentrated under reduced pressure, diluted with brine and extracted with ethyl acetate (20 mL). The organic layer was separated, dried over Na$_2$SO$_4$, filtered, and concentrated under reduced pressure to afford (S)-tert-butyl (2,4-dimethyl-1-(2-methyl-4-(1-methyl-1H-pyrrolo[3,2-b]pyridin-7-yl)phenoxy)pentan-2-yl)carbamate (0.025 g, 0.046 mmol, 26% yield) as a brownish semi-solid. LCMS (ESI) m/e 452.2 [(M+H)$^+$, calcd for C$_{27}$H$_{38}$N$_3$O$_3$ 452.3]; LC/MS retention time (Method F): t$_R$=2.13 min.

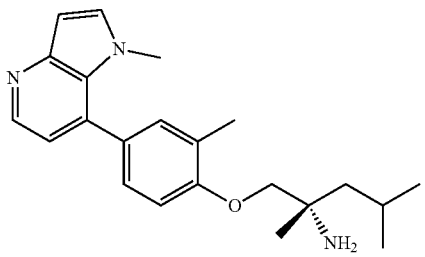 [SMILES: Cc1cc(-c2ccnc3ccn(C)c23)ccc1OC[C@@](C)(N)CC(C)C]

Part B. (S)-2,4-dimethyl-1-(2-methyl-4-(1-methyl-1H-pyrrolo[3,2-b]pyridin-7-yl)phenoxy)pentan-2-amine A solution of (S)-tert-butyl (2,4-dimethyl-1-(2-methyl-4-(1-methyl-1H-pyrrolo[3,2-b]pyridin-7-yl)phenoxy)pentan-2-yl)carbamate (0.03 g, 0.066 mmol) in DCM (5 mL) at 0° C. was treated with 4N HCl in 1,4-dioxane (0.332 mL, 1.329 mmol) and stirred for 3 h. The reaction mixture was concentrated under reduced pressure and was purified by prep HPLC (method B) to afford (S)-2,4-dimethyl-1-(2-methyl-4-(1-methyl-1H-pyrrolo[3,2-b]pyridin-7-yl)phenoxy)pentan-2-amine (0.005 g, 0.014 mmol, 21% yield) as a yellow solid. LCMS (ESI) m/e 352.2 [(M+H)$^+$, calcd for C$_{22}$H$_{30}$N$_3$O 352.2]; LC/MS retention time (Method E): t$_R$=0.90 min; LCMS retention time (method F): t$_R$=1.46 min. $^1$H NMR (400 MHz, DMSO-d$_6$): δ 7.89 (d, J 8.8 Hz, 1H), 7.76-7.72 (m, 2H), 7.57 (d, J=8.8 Hz, 1H), 7.50 (d, J=3.2 Hz, 1H), 7.06 (d, J=8.8 Hz, 1H), 6.62 (m, 1H), 4.02-4.12 (m, 2H), 3.90 (bs, 3H), 2.37 (s, 3H), 1.73-1.87 (m, 2H), 1.57-1.66 (m, 1H), 1.40 (s, 3H), 0.96 (m, 6H) ppm.

Example 428

(S)-4-(4-((2-amino-2,4-dimethylpentyl)oxy)-3-methylphenyl)-6,7-dihydro-5H-pyrrolo[3,4-b]pyridin-5-one

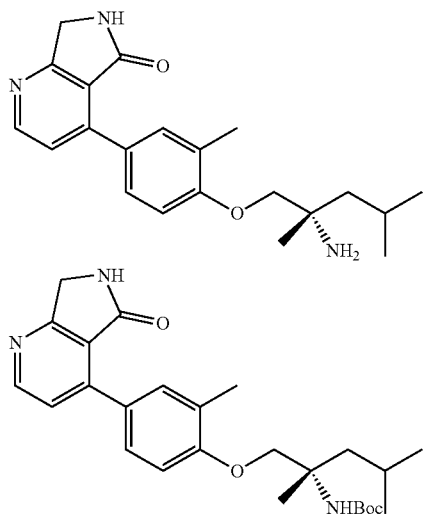

Part A. (S)-tert-butyl (2,4-dimethyl-1-(2-methyl-4-(5-oxo-6,7-dihydro-5H-pyrrolo[3,4-b]pyridin-4-yl)phenoxy)pentan-2-yl)carbamate A mixture of 4-chloro-6,7-dihydro-5H-pyrrolo[3,4-b]pyridin-5-one (prepared as described in Example 415) (0.03 g, 0.178 mmol), (S)-tert-butyl (2,4-dimethyl-1-(2-methyl-4-(4,4,5,5-tetramethyl-1,3,2-dioxaborolan-2-yl)phenoxy)pentan-2-yl)carbamate (prepared as described in Example 259, Part A and B) (80 mg, 0.178 mmol), KBr (0.028 g, 0.231 mmol), Pd(Ph$_3$P)$_4$ (0.021 g, 0.018 mmol) and potassium phosphate (0.267 mL, 0.534 mmol) in 1,4-dioxane (3 mL) was heated at 100° C. for 3 h. The reaction mixture was cooled to room temperature, concentrated under reduced pressure, diluted with brine and extracted with ethyl acetate (20 mL). The organic layer was separated, dried over Na$_2$SO$_4$, filtered, and concentrated under reduced pressure to afford (S)-tert-butyl (2,4-dimethyl-1-(2-methyl-4-(5-oxo-6,7-dihydro-5H-pyrrolo[3,4-b]pyridin-4-yl)phenoxy)pentan-2-yl)carbamate (0.025 g, 0.037 mmol, 21% yield) as a brownish semi-solid. LCMS (ESI) m/e 454.2 [(M+H)$^+$, calcd for C$_{26}$H$_{36}$N$_3$O$_4$, 454.2]; LC/MS retention time (Method F): t$_R$=2.34 min.

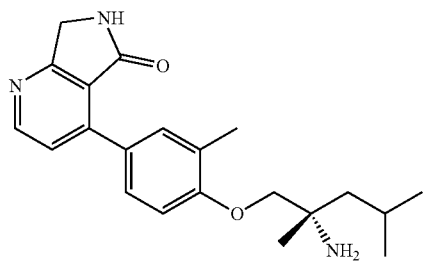 [SMILES: Cc1cc(-c2ccnc3c2C(=O)NC3)ccc1OC[C@@](C)(N)CC(C)C]

Part B. (S)-4-(4-((2-amino-2,4-dimethylpentyl)oxy)-3-methylphenyl)-6,7-dihydro-5H-pyrrolo[3,4-b]pyridin-5-one A solution of (S)-tert-butyl (2,4-dimethyl-1-(2-methyl-4-(5-oxo-6,7-dihydro-5H-pyrrolo[3,4-b]pyridin-4-yl)phenoxy)pentan-2-yl)carbamate (0.025 g, 0.055 mmol) in DCM (5 mL) at 0° C. was treated with 4N HCl in 1,4-dioxane (0.276 mL, 1.102 mmol) and stirred for 3 h. The reaction mixture was concentrated under reduced pressure and was purified by prep HPLC (method A) to afford (S)-4-(4-((2-amino-2,4-dimethylpentyl)oxy)-3-methylphenyl)-6,7-dihydro-5H-pyrrolo[3,4-b]pyridin-5-one (0.005 g, 0.014 mmol, 25% yield) as a yellow solid. LCMS (ESI) m/e 354.0 [(M+H)$^+$, calcd for $C_{21}H_{28}N_3O_2$ 354.2]; LC/MS retention time (Method E): $t_R$=0.97 min; LCMS retention time (method F): $t_R$=1.06 min. $^1$H NMR (400 MHz, METHANOL-$d_4$): δ 8.70 (d, J=5.52 Hz, 1H), 7.55-7.60 (m, 2H), 7.48 (d, J=5.02 Hz, 1H), 7.05 (d, J=9.04 Hz, 1H), 4.51 (s, 2H), 4.03 (q, J=9.54 Hz, 2H), 2.38 (s, 3H), 1.74-1.91 (m, 1H), 1.64 (dd, J=14.06, 5.52 Hz, 2H), 1.42 (s, 3H), 1.04 (m, 6H) ppm.

Example 429

(S)-4-(4-((2-amino-2,4-dimethylpentyl)oxy)-3-chlorophenyl)-6-methyl-6,7-dihydro-5H-pyrrolo[3,4-b]pyridin-5-one

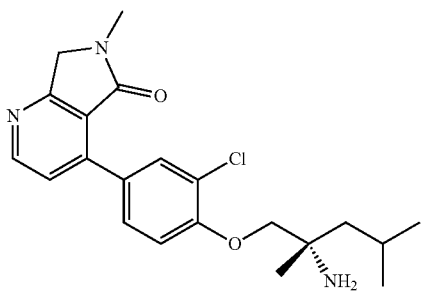

Part A. (S)-tert-butyl (1-(2-chloro-4-(6-methyl-5-oxo-6,7-dihydro-5H-pyrrolo[3,4-b]pyridin-4-yl)phenoxy)-2,4-dimethylpentan-2-yl)carbamate A mixture of 4-chloro-6-methyl-6,7-dihydro-5H-pyrrolo[3,4-b]pyridin-5-one (prepared as described in Example 413) (0.03 g, 0.164 mmol), (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 285) (0.121 g, 0.260 mmol), Pd(Ph$_3$P)$_4$ (0.019 g, 0.016 mmol), KBr (0.020 g, 0.164 mmol) and potassium phosphate, dibasic (0.029 g, 0.164 mmol) in 1,4-1,4-dioxane (5 mL) was heated at 100° C. for 3 h. The reaction mixture was cooled to room temperature, concentrated under reduced pressure, diluted with brine and extracted with ethyl acetate (20 mL). The organic layer was separated, dried over Na$_2$SO$_4$, filtered, and concentrated under reduced pressure to afford (S)-tert-butyl (1-(2-chloro-4-(6-methyl-5-oxo-6,7-dihydro-5H-pyrrolo[3,4-b]pyridin-4-yl)phenoxy)-2,4-dimethylpentan-2-yl)carbamate (0.06 g, 0.074 mmol, 45% yield) as a brownish semi-solid. LCMS (ESI) m/e 488.2 [(M+H)$^+$, calcd for $C_{26}H_{35}ClN_3O_4$ 488.2]; LC/MS retention time (Method A1): $t_R$=2.87 min.

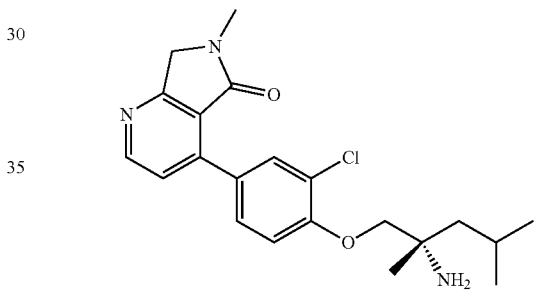

Part B. (S)-4-(4-((2-amino-2,4-dimethylpentyl)oxy)-3-chlorophenyl)-6-methyl-6,7-dihydro-5H-pyrrolo[3,4-b]pyridin-5-one A solution of (S)-tert-butyl (1-(2-chloro-4-(6-methyl-5-oxo-6,7-dihydro-5H-pyrrolo[3,4-b]pyridin-4-yl)phenoxy)-2,4-dimethylpentan-2-yl)carbamate (0.05 g, 0.102 mmol) in DCM (5 mL) at 0° C. was treated with 4N HCl in 1,4-dioxane (0.512 mL, 2.049 mmol) and stirred for 4 h. The reaction mixture was concentrated under reduced pressure and was purified by prep HPLC (method A) to afford (S)-4-(4-((2-amino-2,4-dimethylpentyl)oxy)-3-chlorophenyl)-6-methyl-6,7-dihydro-5H-pyrrolo[3,4-b]pyridin-5-one (0.03 g, 0.077 mmol, 75% yield) as a yellow solid. LCMS (ESI) m/e 388.0 [(M+H)$^+$, calcd for $C_{21}H_{27}ClN_3O_2$ 388.2]; LC/MS retention time (Method E): $t_R$=1.14; LCMS retention time (method F): $t_R$=1.20 min. $^1$H NMR (400 MHz, METHANOL-$d_4$): δ 8.71 (d, J=5.52 Hz, 1H), 7.84 (d, J=2.01 Hz, 1H), 7.66 (dd, J=8.53, 2.51 Hz, 1H), 7.49 (d, J=5.52 Hz, 1H), 7.24 (d, J=8.53 Hz, 1H), 4.57 (s, 2H), 4.05-4.21 (m, 2H), 3.22 (s, 3H), 1.76-1.91 (m, 2H), 1.58-1.73 (m, 1H), 1.43 (s, 3H), 1.05 (m, 6H) ppm.

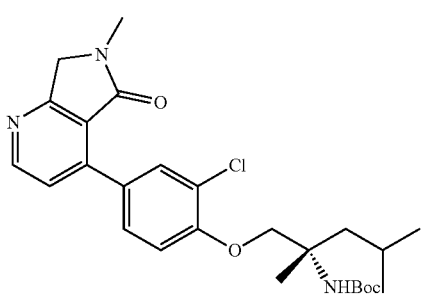 [SMILES: CC(C)C[C@@](C)(COc1ccc(-c2ccnc3c2C(=O)N(C)C3)cc1Cl)NC(=O)OC(C)(C)C]

Example 430

(S)-4-(4-((2-amino-2,4-dimethylpentyl)oxy)-3-methylphenyl)-6-methyl-6,7-dihydro-5H-pyrrolo[3,4-b]pyridin-5-one

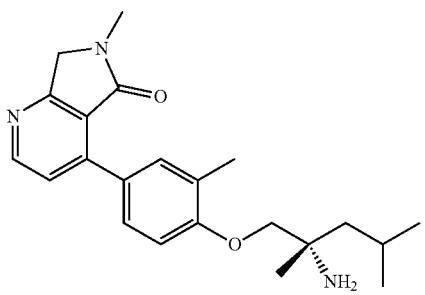

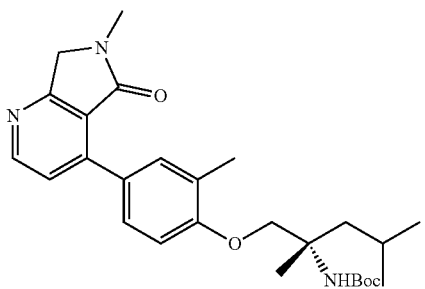

Part A. (S)-tert-butyl (2,4-dimethyl-1-(2-methyl-4-(6-methyl-5-oxo-6,7-dihydro-5H-pyrrolo[3,4-b]pyridin-4-yl)phenoxy)pentan-2-yl)carbamate A mixture of 4-chloro-6-methyl-6,7-dihydro-5H-pyrrolo[3,4-b]pyridin-5-one (prepared as described in Example 413) (0.03 g, 0.164 mmol), (S)-tert-butyl (2,4-dimethyl-1-(2-methyl-4-(4,4,5,5-tetramethyl-1,3,2-dioxaborolan-2-yl)phenoxy)pentan-2-yl)carbamate (prepared as described in Example 259, Part A and B) (80 mg, 0.176 mmol), KBr (0.025 g, 0.214 mmol), Pd(Ph$_3$P)$_4$ (0.019 g, 0.016 mmol) and potassium phosphate (0.246 mL, 0.493 mmol) in 1,4-dioxane (5 mL) was heated at 100° C. for 3 h. The reaction mixture was cooled to room temperature, concentrated under reduced pressure, diluted with brine and extracted with ethyl acetate (20 mL). The organic layer was separated, dried over Na$_2$SO$_4$, filtered, and concentrated under reduced pressure to afford (S)-tert-butyl (2,4-dimethyl-1-(2-methyl-4-(6-methyl-5-oxo-6,7-dihydro-5H-pyrrolo [3,4-b]pyridin-4-yl)phenoxy)pentan-2-yl)carbamate (0.06 g, 0.054 mmol, 33% yield) as a brown semi-solid. LCMS (ESI) m/e 412.2 (M+H-$^t$Bu)$^+$, calcd for C$_{27}$H$_{38}$N$_3$O$_4$ 468.3]; LC/MS retention time (Method A1): t$_R$=2.73 min.

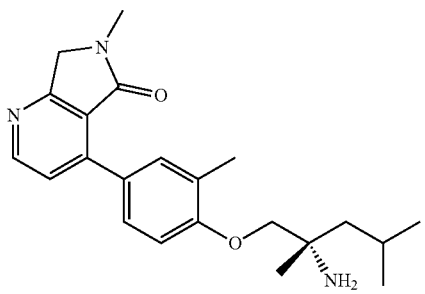 [SMILES: Cc1cc(-c2ccnc3c2C(=O)N(C)C3)ccc1OC[C@@](C)(N)CC(C)C]

Part B. (S)-4-(4-((2-amino-2,4-dimethylpentyl)oxy)-3-methylphenyl)-6-methyl-6,7-dihydro-5H-pyrrolo[3,4-b]pyridin-5-one A solution of (S)-tert-butyl (2,4-dimethyl-1-(2-methyl-4-(6-methyl-5-oxo-6,7-dihydro-5H-pyrrolo[3,4-b]pyridin-4-yl)phenoxy)pentan-2-yl)carbamate (0.05 g, 0.107 mmol) in DCM (5 mL) at 0° C., was treated with 4N HCl in 1,4-dioxane (0.535 mL, 2.139 mmol) and the mixture stirred for 4 h. The reaction mixture was concentrated under reduced pressure and was purified by prep HPLC (method A) to afford (S)-4-(4-((2-amino-2,4-dimethylpentyl)oxy)-3-methylphenyl)-6-methyl-6,7-dihydro-5H-pyrrolo[3,4-b]pyridin-5-one (0.025 g, 0.067 mmol, 62% yield) as a yellow solid. LCMS (ESI) m/e 368.0 [(M+H)$^+$, calcd for C$_{22}$H$_{30}$N$_3$O$_2$ 368.2]; LC/MS retention time (Method E): t$_R$=1.13 min; LCMS retention time (method F): t$_R$=1.13 min. $^1$H NMR (400 MHz, METHANOL-d$_4$): δ 8.67 (d, J=5.02 Hz, 1H) 7.53-7.58 (m, 2H), 7.47 (d, J=5.02 Hz, 1H), 7.07 (d, J=9.04 Hz, 1H), 4.56 (s, 2H), 4.01-4.14 (m, 2H), 3.22 (s, 3H), 2.39 (s, 3H), 1.81-1.91 (m, 2H), 1.61-1.76 (m, 1H), 1.47 (s, 3H), 1.05 (m, 6H) ppm.

Example 448

6-(4-(((S)-2-amino-2,4-dimethylpentyl)oxy)-3-(trifluoromethyl)phenyl)-N-(tetrahydrofuran-3-yl)pyrimidin-4-amine

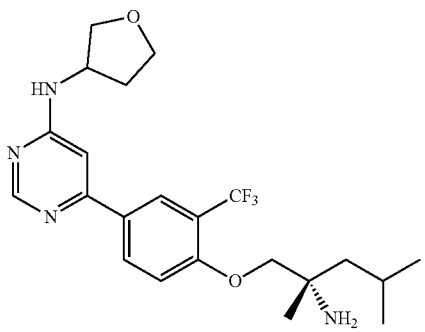

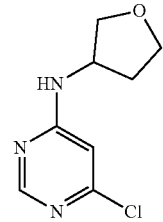

Part A.
6-chloro-N-(tetrahydrofuran-3-yl)pyrimidin-4-amine

To a stirred solution of 4,6-dichloropyrimidine (0.3 g, 2.014 mmol) in DMF (10 mL) at 0° C., was added NaH (0.242 g, 6.04 mmol). After stirred for 5 min, tetrahydrofuran-3-amine (0.175 g, 2.014 mmol) was added and stirred overnight at to RT The reaction mixture was cooled to room temperature and concentrated under reduced pressure. The residue was diluted with water (50 mL) and extracted with DCM (80 mL). The organic layer was washed with brine (40 mL), dried over sodium sulfate, filtered and concentrated under reduced pressure to afford 6-chloro-N-(tetrahydrofuran-3-yl)pyrimidin-4-amine (0.3 g, 0.872 mmol, 43% yield) as a yellowish semi-solid. LCMS (ESI) m/e 200.4 [(M+H)$^+$, calcd for $C_8H_{11}ClN_3O$, 200.1]; LC/MS retention time (method B): $t_R$=0.60 min.

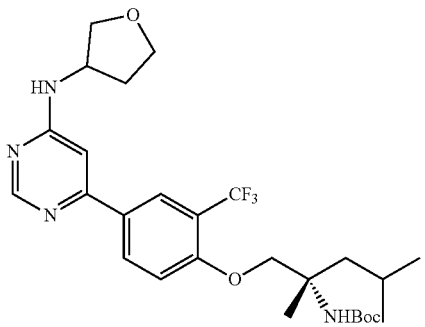 [SMILES: CC(C)C[C@@](C)(COc1ccc(-c2cc(NC3CCOC3)ncn2)cc1C(F)(F)F)NC(=O)OC(C)(C)C]

Part B. tert-butyl ((2S)-2,4-dimethyl-1-(4-(6-((tetrahydrofuran-3-yl)amino)pyrimidin-4-yl)-2-(trifluoromethyl)phenoxy)pentan-2-yl)carbamate A mixture of 6-chloro-N-(tetrahydrofuran-3-yl)pyrimidin-4-amine (0.05 g, 0.140 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.070 g, 0.140 mmol), PdCl$_2$(dppf)-CH$_2$Cl$_2$-adduct (0.011 g, 0.014 mmol), and Cs$_2$CO$_3$ (0.137 g, 0.421 mmol)) in 1,4-dioxane (2 mL) was heated at 80° C. overnight. The reaction mixture was cooled to room temperature then filtered through diatomaceous earth, washing the diatomaceous earth bed with ethyl acetate (100 mL). The filtrate was concentrated under reduced pressure and the residue was purified by silica gel chromatography (20% ethyl acetate in hexane) to afford tert-butyl ((2S)-2,4-dimethyl-1-(4-(6-((tetrahydrofuran-3-yl)amino)pyrimidin-4-yl)-2-(trifluoromethyl)phenoxy)pentan-2-yl)carbamate (0.12 g, 0.118 mmol, 84% yield) as a yellowish semi-solid. LCMS (ESI) m/e 539.2 [(M+H)$^+$, calcd for $C_{27}H_{38}F_3N_4O_4$ 539.3]; LC/MS retention time (Method A1): $t_R$=3.05 min.

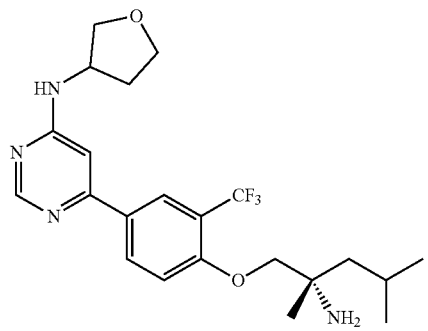

Part C. 6-(4-(((S)-2-amino-2,4-dimethylpentyl)oxy)-3-(trifluoromethyl)phenyl)-N-(tetrahydrofuran-3-yl)pyrimidin-4-amine To a stirred solution of tert-butyl ((2S)-2,4-dimethyl-1-(4-(6-((tetrahydrofuran-3-yl)amino)pyrimidin-4-yl)-2-(trifluoromethyl)phenoxy)pentan-2-yl)carbamate (0.12 g, 0.223 mmol) in DCM (2 mL) at 0° C. was added TFA (0.172 mL, 2.228 mmol) and the reaction mixture was allowed to stir for 2 h at room temperature The reaction mixture was diluted with saturated aqueous sodium bicarbonate (20 mL) and extracted with ethyl acetate (30 mL). The organic layer was separated, dried over anhydrous sodium sulfate, and concentrated under reduced pressure. The residue was purified by preparative LC/MS (Method A) to afford 6-(4-(((S)-2-amino-2,4-dimethylpentyl)oxy)-3-(trifluoromethyl)phenyl)-N-(tetrahydrofuran-3-yl)pyrimidin-4-amine (0.008 g, 0.017 mmol, 7% yield) as a yellow solid. LCMS (ESI) m/e 439.2 [(M+H)$^+$, calcd for $C_{22}H_{30}F_3N_4O_2$ 439.2]; LC/MS retention time (Method E): $t_R$=1.78 min; LCMS retention time (method F): $t_R$=2.39 min. $^1$H NMR (400 MHz, METHANOL-d$_4$): δ 8.50 (d, J=1.00 Hz, 1H), 8.24 (d, J=2.01 Hz, 1H), 8.18 (dd, J=8.78, 2.26 Hz, 1H), 7.33 (d, J=9.04 Hz, 1H), 6.91 (d, J=1.51 Hz, 1H), 4.58 (bs, 2H), 3.96-4.11 (m, 4H), 3.88 (td, J=8.53, 5.52 Hz, 1H), 3.73 (dd, J=9.04, 3.51 Hz, 1H), 2.30-2.40 (m, 1H), 1.95-2.01 (m, 1H), 1.79-1.91 (m, 1H), 1.54-1.73 (m, 1H), 1.34 (s, 3H), 0.97-1.07 (m, 6H) ppm.

Example 449

6-(6-(((S)-2-amino-2,4-dimethylpentyl)oxy)-5-chloropyridin-3-yl)-N-(tetrahydrofuran-3-yl)pyrimidin-4-amine

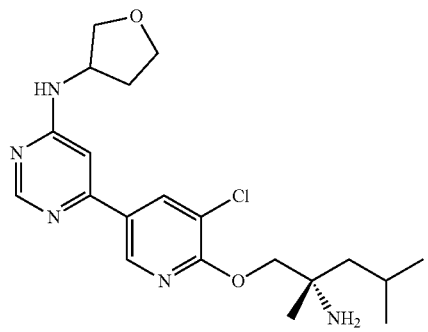 [SMILES: CC(C)C[C@](C)(N)COc1ccc(-c2cc(NC3CCOC3)ncn2)cc1C(F)(F)F]

-continued

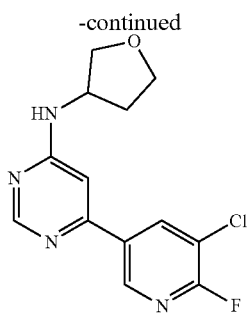

Part A. 6-(5-chloro-6-fluoropyridin-3-yl)-N-(tetrahydrofuran-3-yl)pyrimidin-4-amine A mixture of (5-chloro-6-fluoropyridin-3-yl)boronic acid (0.035 g, 0.200 mmol), 6-chloro-N-(tetrahydrofuran-3-yl)pyrimidin-4-amine (0.04 g, 0.200 mmol), PdCl$_2$(dppf)-CH$_2$Cl$_2$-adduct (0.016 g, 0.020 mmol), and Cs$_2$CO$_3$ (0.196 g, 0.601 mmol) in 1,4-dioxane (3 mL) was heated at 80° C. for 3 h. The reaction mixture was cooled to room temperature and concentrated under reduced pressure. The residue was diluted with water (50 mL) and extracted with DCM (80 mL). The organic layer was washed with brine (40 mL), dried over sodium sulfate, filtered and concentrated under reduced pressure to afford 6-(5-chloro-6-fluoropyridin-3-yl)-N-(tetrahydrofuran-3-yl)pyrimidin-4-amine (0.07 g, 0.088 mmol, 44% yield) as a yellowish semi-solid. LCMS (ESI) m/e 293.0 [(M−H)$^-$, calcd for C$_{13}$H$_{13}$ClFN$_4$O 293.1]; LC/MS retention time (method D): t$_R$=2.24 min.

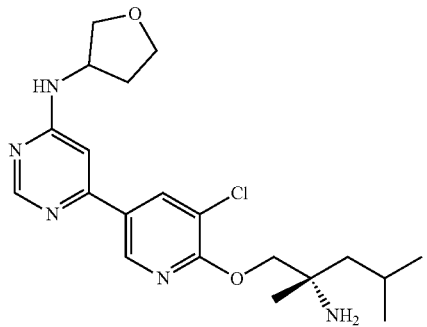 [SMILES: CC(C)C[C@](C)(N)COc1ncc(-c2cc(NC3CCOC3)ncn2)cc1Cl]

Part B. 6-(6-(((S)-2-amino-2,4-dimethylpentyl)oxy)-5-chloropyridin-3-yl)-N-(tetrahydrofuran-3-yl)pyrimidin-4-amine A mixture of 6-(5-chloro-6-fluoropyridin-3-yl)-N-(tetrahydrofuran-3-yl)pyrimidin-4-amine (0.04 g, 0.136 mmol), (S)-2-amino-2,4-dimethylpentan-1-ol (0.018 g, 0.136 mmol), and NaH (15 mg, 0.625 mmol) in tetrahydrofuran (3 mL) was stirred at RT overnight. The reaction mixture was cooled to room temperature and filtered through diatomaceous earth. The diatomaceous earth bed was washed with ethyl acetate (100 mL). The filtrate was concentrated under reduced pressure and purified by preparative LC/MS (Method A) to afford 6-(6-(((S)-2-amino-2,4-dimethylpentyl)oxy)-5-chloropyridin-3-yl)-N-(tetrahydrofuran-3-yl)pyrimidin-4-amine (0.005 g, 0.012 mmol, 8% yield) as a yellow solid. LCMS (ESI) m/e 406.2 [(M+H)$^+$, calcd for C$_{20}$H$_{29}$ClN$_5$O$_2$ 406.2]; LC/MS retention time (Method E): t$_R$=1.68 min; LCMS retention time (method F): t$_R$=2.14 min. $^1$H NMR (400 MHz, METHANOL-d$_4$): δ 8.68 (d, J=2.01 Hz, 1H), 8.51 (d, J=1.00 Hz, 1H), 8.38 (d, J=2.01 Hz, 1H), 6.90 (d, J=1.00 Hz, 1H), 4.48 (s, 2H), 3.97-4.03 (m, 2H), 3.84-3.94 (m, 1H), 3.73 (dd, J=9.04, 3.51 Hz, 1H), 2.29-2.42 (m, 1H), 1.85-2.00 (m, 3H), 1.76-1.82 (m, 1H), 1.59-1.70 (m, 1H), 1.44 (s, 3H), 1.05 (m, 6H) ppm.

Example 452

(S)-2,4-dimethyl-1-((2-methyl-6-(2-methylimidazo[1,2-b]pyridazin-8-yl)pyridin-3-yl)oxy)pentan-2-amine

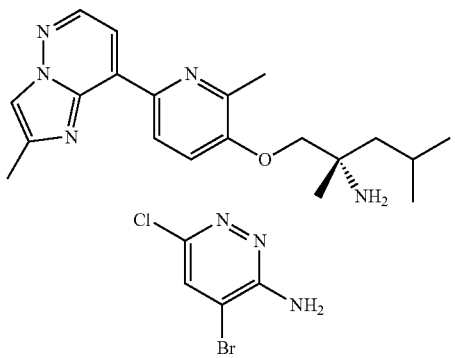

Part A. 4-bromo-6-chloropyridazin-3-amine

To a solution of 6-chloropyridazin-3-amine (5.0 g, 38.6 mmol) in MeOH (200 mL) sodium bicarbonate (6.48 g, 77 mmol) was added and stirred at room temperature for 10 min. Bromine (1.988 mL, 38.6 mmol) was added dropwise to the reaction mixture and the reaction mixture was stirred at room temperature for 16 h. The reaction mixture was concentrated under reduced pressure at 30° C. To the residue was added water (150 mL) and the mixture stirred for 10 min. The brown solid that precipitated out was collected by vacuum filtration and dried under vacuum overnight to afford 4-bromo-6-chloropyridazin-3-amine (3.75 g, 13.85 mmol, 36% yield). LCMS (ESI) m/e 208.4; 210.4 (bromo pattern) [(M+H)$^+$, calcd for C$_4$H$_4$BrClN$_3$ 208.0]; LC/MS retention time (method B): t$_R$=0.58 min.

Part B. 6,8-dichloro-2-methylimidazo[1,2-b]pyridazine

To 4-bromo-6-chloropyridazin-3-amine (2.5 g, 11.99 mmol) in a sealed tube was added 1-chloropropan-2-one (7.77 g, 84 mmol) and the reaction mixture was heated to 90° C. for 16 h. The reaction mixture was cooled to room temperature and ether (100 mL) was added. The solid that precipitated was collected by vacuum filtration and dried under vacuum. Water (10 mL) was added to the solid and saturated aqueous sodium bicarbonate solution was added to adjust the pH of the solution to 9. A pale brown solid precipitated which was collected by vacuum filtration and dried under vacuum overnight to afford 6,8-dichloro-2-methylimidazo[1,2-b]pyridazine (1.0 g, 4.21 mmol, 35% yield). LCMS (ESI) m/e 201.9 [(M+H)$^+$, calcd for $C_7H_6C_{12}N_3$ 201.9]; LC/MS retention time (Method C): $t_R$=0.75 min.

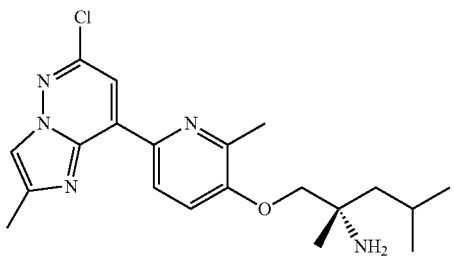 [SMILES: Cc1cn2nc(Cl)cc(-c3ccc(OC[C@@](C)(N)CC(C)C)c(C)n3)c2n1]

Part C. (S)-tert-butyl (1-((6-(6-chloro-2-methylimidazo[1,2-b]pyridazin-8-yl)-2-methylpyridin-3-yl)oxy)-2,4-dimethylpentan-2-yl)carbamate A solution of 6,8-dichloro-2-methylimidazo[1,2-b]pyridazine (0.3 g, 1.485 mmol), (S)-tert-butyl (1-((6-iodo-2-methylpyridin-3-yl)oxy)-2,4-dimethylpentan-2-yl)carbamate (prepared in similar fashion as described for 343) (0.666 g, 1.485 mmol), and hexamethylditin (0.308 mL, 1.485 mmol) in 1,4-dioxane (10 mL) was flushed with nitrogen for 5 min. Pd(Ph$_3$P)$_4$ (0.086 g, 0.074 mmol) was added and the solution again flushed for a further 5 min with nitrogen. The reaction mixture was heated in a microwave at 150° C. for 90 min. The reaction mixture was then filtered through diatomaceous earth and the diatomaceous earth bed was washed with ethyl acetate (100 mL). The filtrate was concentrated under reduced pressure and the crude product was purified by silica gel chromatography (60% ethyl acetate in hexane) to afford (S)-tert-butyl (1-((6-(6-chloro-2-methylimidazo[1,2-b]pyridazin-8-yl)-2-methylpyridin-3-yl)oxy)-2,4-dimethylpentan-2-yl)carbamate (0.28 g, 0.252 mmol, 17% yield). LCMS (ESI) m/e 488.7 [(M+H)$^+$, calcd for $C_{25}H_{35}ClN_5O_3$ 488.2]; LC/MS retention time (method B): $t_R$=1.04 min.

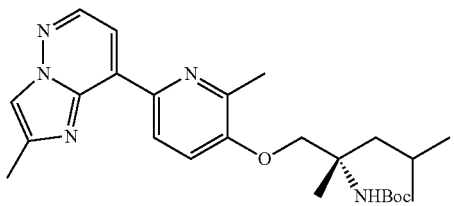

Part D. (S)-tert-butyl (2,4-dimethyl-1-((2-methyl-6-(2-methylimidazo[1,2-b]pyridazin-8-yl)pyridin-3-yl)oxy)pentan-2-yl)carbamate To a solution of (S)-tert-butyl (1-((6-(6-chloro-2-methylimidazo[1,2-b]pyridazin-8-yl)-2-methylpyridin-3-yl)oxy)-2,4-dimethylpentan-2-yl)carbamate (0.28 g, 0.255 mmol) in methanol (5 mL) was added palladium on carbon (0.043 g, 0.041 mmol) and the mixture was stirred at room temperature overnight under 1 atm H$_2$. The reaction mixture filtered through diatomaceous earth and the diatomaceous earth bed was washed with methanol (10 mL). The filtrate was concentrated under reduced pressure to afford (S)-tert-butyl (2,4-dimethyl-1-((2-methyl-6-(2-methylimidazo[1,2-b]pyridazin-8-yl)pyridin-3-yl)oxy)pentan-2-yl)carbamate (0.25 g, 0.228 mmol, 89% yield). LCMS (ESI) m/e 454.2 [(M+H)$^+$, calcd for $C_{25}H_{36}N_5O_3$ 454.2]; LC/MS retention time (Method G): $t_R$=1.62 min.

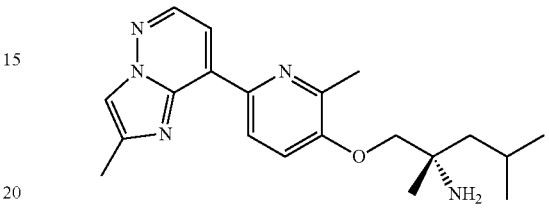

Part E. (S)-2,4-dimethyl-1-((2-methyl-6-(2-methylimidazo[1,2-b]pyridazin-8-yl)pyridin-3-yl)oxy)pentan-2-amine A solution of (S)-tert-butyl (2,4-dimethyl-1-((2-methyl-6-(2-methylimidazo[1,2-b]pyridazin-8-yl)pyridin-3-yl)oxy)pentan-2-yl)carbamate (0.25 g, 0.243 mmol) in MeOH (2 mL) was cooled to 0° C., 4M HCl in 1,4-dioxane (0.606 mL, 2.425 mmol) was added and stirred at room temperature. The reaction mixture diluted with saturated sodium bicarbonate solution (20 mL), extracted with ethyl acetate (30 mL), dried over anhydrous Na$_2$SO$_4$, and concentrated under reduced pressure. The crude material was purified by prep LC/MS (method A) to afford (S)-2,4-dimethyl-1-((2-methyl-6-(2-methylimidazo[1,2-b]pyridazin-8-yl)pyridin-3-yl)oxy)pentan-2-amine (0.038 g, 0.107 mmol, 44% yield) as a pale yellow solid. LCMS (ESI) m/e 354.3 [(M+H)$^+$, calcd for $C_{20}H_{28}N_5O$ 354.2]; LC/MS retention time (method H): $t_R$=1.48 min; LC/MS retention time (method I): $t_R$=0.79 min. $^1$H NMR (400 MHz, methanol-d$_4$): δ 8.70 (d, J=8.40 Hz, 1H), 8.42 (d, J=4.80 Hz, 1H), 7.94 (s, 1H), 7.79 (d, J=4.80 Hz, 1H), 7.47 (d, J=8.40 Hz, 1H), 4.04 (d, J 26.40 Hz, 2H), 2.61 (s, 3H), 2.51 (s, 3H), 1.83-1.90 (m, 1H), 1.71-1.76 (m, 1H), 1.60-1.64 (m, 1H), 1.39 (s, 3H), 1.02-1.04 (m, 6H) ppm.

Example 453

(S)-1-((2-(difluoromethyl)-6-(2-methylimidazo[1,2-b]pyridazin-8-yl)pyridin-3-yl)oxy)-2,4-dimethylpentan-2-amine

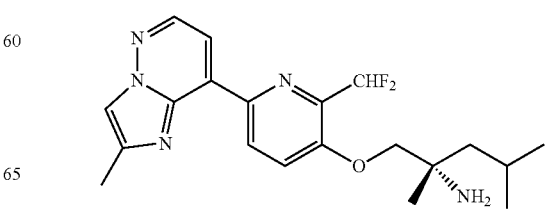

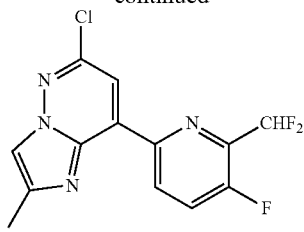

Part A. 6-chloro-8-(6-(difluoromethyl)-5-fluoropyridin-2-yl)-2-methylimidazo[1,2-b]pyridazine A solution of 6,8-dichloro-2-methylimidazo[1,2-b]pyridazine (prepared as described in Example 452) (0.12 g, 0.594 mmol), 6-bromo-2-(difluoromethyl)-3-fluoropyridine (prepared as described in Example 322) (0.134 g, 0.594 mmol), and hexamethylditin (0.123 mL, 0.594 mmol) in 1,4-dioxane (5 mL) was flushed with nitrogen for 5 min. Pd(Ph$_3$P)$_4$ (0.034 g, 0.030 mmol) was added and the reaction mixture was heated in a microwave at 150° C. for 90 min. The reaction mixture was then filtered through diatomaceous earth and the diatomaceous earth bed and washed with ethyl acetate (100 mL). The filtrate was concentrated under reduced pressure and the crude product was purified by silica gel chromatography (60% ethyl acetate in hexane) to afford 6-chloro-8-(6-(difluoromethyl)-5-fluoropyridin-2-yl)-2-methylimidazo[1,2-b]pyridazine (0.04 g, 0.125 mmol, 21% yield) as a brown solid. LCMS (ESI) m/e 313.0 [(M+H)$^+$, calcd for C$_{13}$H$_9$ClF$_3$N$_4$ 313.0]; LC/MS retention time (Method C): t$_R$=1.09 min.

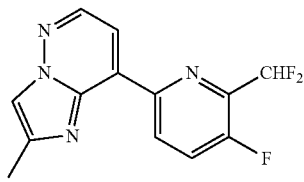 [SMILES: Cc1cn2nccc(-c3ccc(F)c(C(F)F)n3)c2n1]

Part B. 8-(6-(difluoromethyl)-5-fluoropyridin-2-yl)-2-methylimidazo[1,2-b]pyridazine To a solution of 6-chloro-8-(6-(difluoromethyl)-5-fluoropyridin-2-yl)-2-methylimidazo[1,2-b]pyridazine (0.04 g, 0.128 mmol) in MeOH (5 mL) was added palladium on carbon (0.022 g, 0.020 mmol). The mixture was then stirred at room temperature overnight under 1 atm H$_2$. The reaction mixture was filtered through diatomaceous earth and the diatomaceous earth bed was washed with methanol (20 mL) The filtrate was concentrated under reduced pressure to afford 8-(6-(difluoromethyl)-5-fluoropyridin-2-yl)-2-methylimidazo[1,2-b]pyridazine (0.03 g, 0.075 mmol, 58% yield) as a brown solid. LCMS (ESI) m/e 279.2 [(M+H)$^+$, calcd for C$_{13}$H$_{10}$F$_3$N$_4$ 279.1]; LC/MS retention time (Method G): t$_R$=2.51 min.

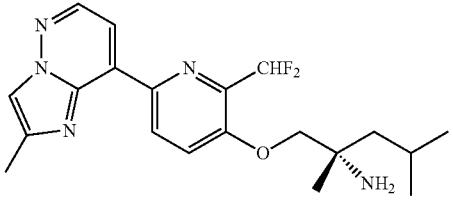 [SMILES: Cc1cn2nccc(-c3ccc(OC[C@@](C)(N)CC(C)C)c(C(F)F)n3)c2n1]

Part C. (S)-1-((2-(difluoromethyl)-6-(2-methylimidazo[1,2-b]pyridazin-8-yl)pyridin-3-yl)oxy)-2,4-dimethylpentan-2-amine A solution of 8-(6-(difluoromethyl)-5-fluoropyridin-2-yl)-2-methylimidazo[1,2-b]pyridazine (0.03 g, 0.075 mmol), (S)-2-amino-2,4-dimethylpentan-1-ol (9.79 mg, 0.075 mmol), and NaH (5.97 mg, 0.149 mmol) in DMF (3 mL) was stirred at room temperature overnight. The reaction mixture was then filtered through diatomaceous earth and the diatomaceous earth bed and washed with ethyl acetate (20 mL). The filtrate was concentrated under reduced pressure. The crude material was purified by prep LC/MS (method B) to afford (S)-1-((2-(difluoromethyl)-6-(2-methylimidazo[1,2-b]pyridazin-8-yl)pyridin-3-yl)oxy)-2,4-dimethylpentan-2-amine (0.008 g, 0.020 mmol, 27% yield) as a pale yellow solid. LCMS (ESI) m/e 390.3 [(M+H)$^+$, calcd for C$_{20}$H$_{26}$F$_2$N$_5$O 390.2]; LC/MS retention time (method H): t$_R$=1.65 min; LC/MS retention time (method I): t$_R$=0.84 min. $^1$H NMR (400 MHz, CD3OD)-d4: δ 9.17 (d, J=8.00 Hz, 1H), 8.47 (d, J=4.80 Hz, 1H), 7.93-7.98 (m, 2H), 7.77 (d, J=9.20 Hz, 1H), 7.07 (t, J=108.00 Hz, 1H), 4.07-4.18 (m, 2H), 2.53 (s, 3H), 1.82-1.88 (m, 1H), 1.67-1.72 (m, 1H), 1.57-1.62 (m, 1H), 1.40 (s, 3H), 0.99-1.04 (m, 6H) ppm.

Example 455

(S)-7-(4-((2-amino-2,4-dimethylpentyl)oxy)-2-fluorophenyl)pyrazolo[1,5-a]pyrimidin-5-amine

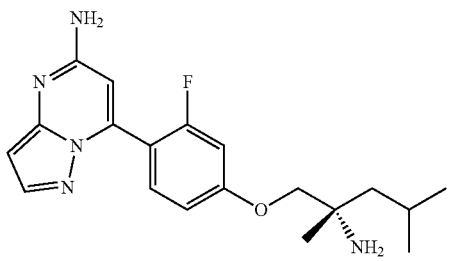

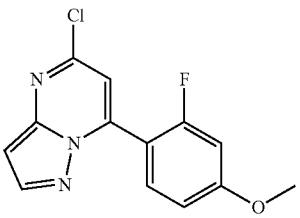

Part A: 5-chloro-7-(2-fluoro-4-methoxyphenyl)pyrazolo[1,5-a]pyrimidine

A solution of 5,7-dichloropyrazolo[1,5-a]pyrimidine (0.5 g, 2.66 mmol), (2-fluoro-4-methoxyphenyl)boronic acid (0.452 g, 2.66 mmol), and Cs₂CO₃ (1.733 g, 5.32 mmol) in 1,4-dioxane (10 mL) and water (1 mL) was purged with nitrogen gas for 30 min. PdCl₂(dppf)-CH₂Cl₂ adduct (0.217 g, 0.266 mmol) was added to the reaction mixture and the solution was purged with nitrogen gas again for 10 min. The reaction mixture was heated at 80° C. for 6 h. The reaction mixture was concentrated and the residue obtained was dissolved in ethyl acetate (50 mL) and water (30 mL). The biphasic mixture was filtered through diatomaceous earth. The diatomaceous earth was washed with ethyl acetate (50 mL). The organic layer was separated, dried over Na₂SO₄, filtered, and concentrated under reduced pressure to afford crude product as a brown solid which was purified by silica gel-column chromatography (EtOAc in pet ether) to afford 5-chloro-7-(2-fluoro-4-methoxyphenyl) pyrazolo [1,5-a]pyrimidine (0.52 g, 1.873 mmol, 70% yield) as a off-white color solid. LCMS (ESI) m/e 278.0 [(M+H)⁺, calcd for C₁₃H₁₀ClFN₃O 278.0]; LC/MS retention time (Method C): $t_R$=1.05 min.

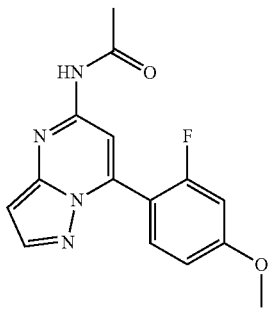 [SMILES: COc1ccc(-c2cc(NC(C)=O)nc3ccnn23)c(F)c1]

Part B: N-(7-(2-fluoro-4-methoxyphenyl)pyrazolo [1,5-a]pyrimidin-5-yl)acetamide

A solution of 5-chloro-7-(2-fluoro-4-methoxyphenyl) pyrazolo[1,5-a]pyrimidine (0.3 g, 1.080 mmol), acetamide (0.077 g, 1.296 mmol), and Cs₂CO₃ (0.704 g, 2.161 mmol) in 1,4-dioxane (10 mL) and water (1 mL) was purged with nitrogen gas for 30 min. PdOAc₂ (0.012 g, 0.054 mmol) was added to the reaction mixture and the solution was purged with nitrogen gas again for 10 min. The reaction mixture was heated at 100° C. for 4 h. The reaction mixture was concentrated and the residue obtained was dissolved in ethyl acetate (25 mL) and water (20 mL). The biphasic mixture was filtered through diatomaceous earth. The diatomaceous earth was washed with ethyl acetate (50 mL). The organic layer was separated, dried over Na₂SO₄, filtered, and concentrated under reduced pressure to afford crude product as a brown solid which was purified by silica gel-column chromatography (EtOAc in petroleum ether) to afford N-(7-(2-fluoro-4-methoxyphenyl) pyrazolo [1,5-a]pyrimidin-5-yl) acetamide (0.22 g, 0.667 mmol, 62% yield) as an off-white color solid. LCMS (ESI) m/e 301.2 [(M+H)⁺, calcd for C₁₅H₁₄FN₄O₂ 301.1]; LC/MS retention time (Method A1): $t_R$=2.21 min.

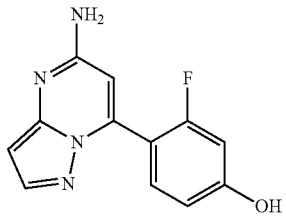 [SMILES: Nc1cc(-c2ccc(O)cc2F)n2nccc2n1]

Part C: 4-(5-aminopyrazolo [1,5-a]pyrimidin-7-yl)-3-fluorophenol

HBr in AcOH (34%) (5 mL, 92 mmol) was added to a round bottomed flask containing of N-(7-(2-fluoro-4-methoxyphenyl) pyrazolo [1,5-a]pyrimidin-5-yl) acetamide (0.15 g, 0.500 mmol) at 0° C. The reaction mixture was heated at 105° C. for 12 h. The reaction mixture was concentrated under reduced pressure. The residue was reconstituted with ethyl acetate/pet ether (5:5 mL), filtered and dried to afford 4-(5-aminopyrazolo[1,5-a]pyrimidin-7-yl)-3-fluorophenol (0.13 g, 0.335 mmol, 67% yield) as an off-white solid which was carried forward without further purification. LCMS (ESI) m/e 245.0 [(M+H)⁺, calcd for C₁₂H₁₀FN₄O 245.1]; LC/MS retention time (method B): $t_R$=0.50 min.

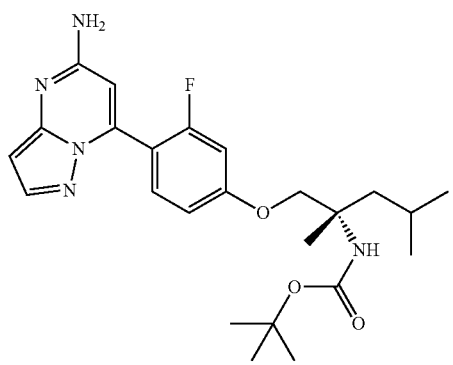 [SMILES: CC(C)C[C@@](C)(COc1ccc(-c2cc(N)nc3ccnn23)c(F)c1)NC(=O)OC(C)(C)C]

Part D: (S)-tert-butyl (1-(4-(5-aminopyrazolo [1,5-a]pyrimidin-7-yl)-3-fluorophenoxy)-2,4-dimethylpentan-2-yl)carbamate A solution of ethyl 4-(5-aminopyrazolo [1,5-a]pyrimidin-7-yl)-3-fluorophenol (0.13 g, 0.532 mmol) in DMF (5 mL) was cooled to 0° C. K₂CO₃ (0.221 g, 1.597 mmol) was added in portions to the reaction mixture followed by slow addition of (S)-tert-butyl 4-isobutyl-4-methyl-1,2,3-oxathiazolidine-3-carboxylate 2,2-dioxide (prepared as described in Example 251, Parts A-E) (0.187 g, 0.639 mmol) in 1 mL DMF at 0° C. The reaction mixture was then heated at 88° C. for 12 h. The reaction mixture was cooled to 0° C. and quenched with aqueous ammonium chloride solution (10 mL). The reaction mixture was extracted with ethyl acetate (2×20 mL). The ethyl acetate layer was washed with water (2×20 mL), brine (10 mL), dried over Na₂SO₄, filtered, and concentrated under reduced pressure to afford (S)-tert-butyl (1-(4-(5-aminopyrazolo[1,5-a]pyrimidin-7-yl)-3-fluorophenoxy)-2,4-dimethylpentan-2-yl)carbamate (80 mg, 0.175 mmol, 33% yield) as a brown color semi-solid which was taken for next step without purification. LCMS (ESI) m/e 458.2 [(M+H)$^+$, calcd for $C_{24}H_{33}FN_5O_3$ 458.2]; LC/MS retention time (method B): $t_R$=2.42 min.

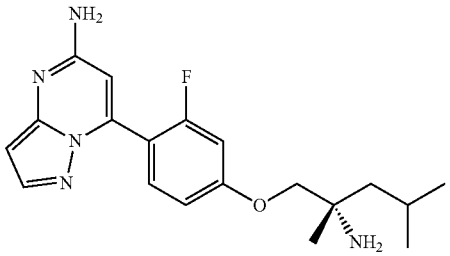 [SMILES: CC(C)C[C@](C)(N)COc1ccc(-c2cc(N)nc3ccnn23)c(F)c1]

Part E: (S)-7-(4-((2-amino-2,4-dimethylpentyl)oxy)-2-fluorophenyl)pyrazolo[1,5-a]pyrimidin-5-amine To a solution of (S)-tert-butyl (1-(4-(5-aminopyrazolo[1,5-a]pyrimidin-7-yl)-3-fluorophenoxy)-2,4-dimethylpentan-2-yl)carbamate (20 mg, 0.044 mmol) in DCM (2 mL) at 0° C. was added TFA (0.067 mL, 0.874 mmol) and the solution stirred for 5 min at 0° C. The reaction mixture was allowed to stir for 4 h at room temperature, then was concentrated under reduced pressure. The crude material was purified by prep LC/MS (method A) to afford (S)-7-(4-((2-amino-2,4-dimethylpentyl)oxy)-2-fluorophenyl)pyrazolo[1,5-a]pyrimidin-5-amine (8 mg. 0.022 mmol, 50% yield) as a pale yellow solid. LCMS (ESI) m/e 358.4 [(M+H)$^+$, calcd for $C_{19}H_{25}FN_5O$ 358.2]; LC/MS retention time (method H): $t_R$=1.00 min; LC/MS retention time (method I): $t_R$=0.78 min. $^1$H NMR (400 MHz, Methanol-d$_4$): δ 7.80 (d, J=2.40 Hz, 1H), 7.68 (t, J=16.80 Hz, 1H), 7.02-7.07 (m, 2H), 6.34 (s, 1H), 6.10 (d, J=2.40 Hz, 1H), 4.08-4.19 (m, 2H), 1.79-1.89 (m, 2H), 1.65-1.70 (m, 1H), 1.48 (s, 3H), 1.04-1.09 (m, 6H) ppm.

Example 456

(S)-1-(2-chloro-4-(pyrazolo [1,5-a]pyrimidin-7-yl)phenoxy)-2,4-dimethylpentan-2-amine

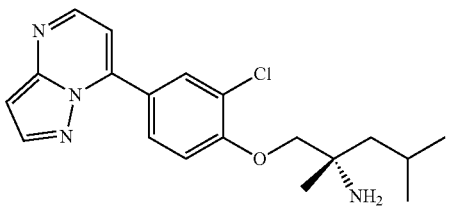 [SMILES: CC(C)C[C@](C)(N)COc1ccc(-c2ccnc3ccnn23)cc1Cl]

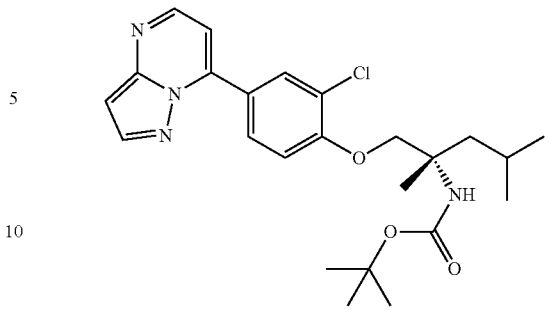

Part A: (S)-Tert-butyl (1-(2-chloro-4-(pyrazolo [1,5-a]pyrimidin-7-yl)phenoxy)-2,4-dimethylpentan-2-yl)carbamate A solution of 7-chloropyrazolo[1,5-a]pyrimidine (0.05 g, 0.326 mmol), (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (0.152 g, 0.326 mmol), $Cs_2CO_3$ (0.212 g, 0.651 mmol), and KBr (0.039 g, 0.326 mmol) in 1,4-dioxane (10 mL) and water (1 mL) was purged with nitrogen gas for 30 min. $PdCl_2$ (dppf)-$CH_2Cl_2$ adduct (0.027 g, 0.033 mmol) was added to the reaction mixture and the solution was purged with nitrogen gas again for 10 min. The reaction mixture was heated at 80° C. for 12 h. The reaction mixture was concentrated and the residue obtained was dissolved in ethyl acetate (30 mL) and water (30 mL). The biphasic mixture was filtered through diatomaceous earth. The diatomaceous earth was washed with ethyl acetate (50 mL). The organic layer was separated, dried over $Na_2SO_4$, filtered, and concentrated under reduced pressure to afford crude product as a brown solid which was purified by silica-gel column chromatography (pet ether/ethyl acetate) to afford (S)-tert-butyl (1-(2-chloro-4-(pyrazolo[1,5-a]pyrimidin-7-yl)phenoxy)-2,4-dimethylpentan-2-yl)carbamate (0.08 g, 0.174 mmol, 54% yield) as an off-white solid. LCMS (ESI) m/e 459.2 [(M+H)$^+$, calcd for $C_{24}H_{32}ClN_4O_3$ 459.2]; LC/MS retention time (Method A1): $t_R$=3.28 min.

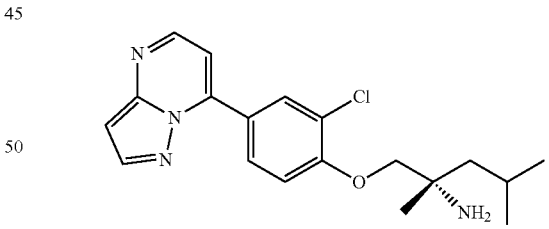

Part B: (S)-1-(2-chloro-4-(pyrazolo[1,5-a]pyrimidin-7-yl)phenoxy)-2,4-dimethylpentan-2-amine To a solution of (S)-tert-butyl (1-(2-chloro-4-(pyrazolo[1,5-a]pyrimidin-7-yl)phenoxy)-2,4-dimethylpentan-2-yl)carbamate (0.08 g, 0.174 mmol) in DCM (2 mL) at 0° C. was added TFA (0.269 mL, 3.49 mmol) and the mixture stirred for 5 min at 0° C. The reaction mixture was allowed to stir for 4 h at room temperature, then was concentrated under reduced pressure. The crude material was purified by prep LC/MS (method C) to afford (S)-1-(2-chloro-4-(pyrazolo[1,5-a]pyrimidin-7-yl)phenoxy)-2,4-dimethylpentan-2-amine, TFA (73.1 mg. 0.153 mmol, 88% yield) as a pale yellow solid. LCMS (ESI) m/e 359.0 [(M+H)$^+$, calcd for $C_{19}H_{24}ClN_4O$ 359.2]; LC/MS retention time (method I): $t_R$=1.22 min. $^1$H NMR (400 MHz, DMSO-$d_6$): δ 8.59 (d, J=4.40 Hz, 1H), 8.40 (d, J=2.40 Hz, 1H), 8.30 (d, J=2.40 Hz, 1H), 8.15-8.18 (m, 1H), 7.30-7.37 (m, 2H), 6.83 (d, J=2.40 Hz, 1H), 3.89-3.92 (m, 2H), 1.79-1.86 (m, 1H), 1.41-1.50 (m, 2H), 1.18 (s, 3H), 0.92-0.95 (m, 6H) ppm.

Example 457

(S)-7-(4-((2-amino-2,4-dimethylpentyl) oxy)-3-fluorophenyl)pyrazolo[1,5-a]pyrimidin-5-amine

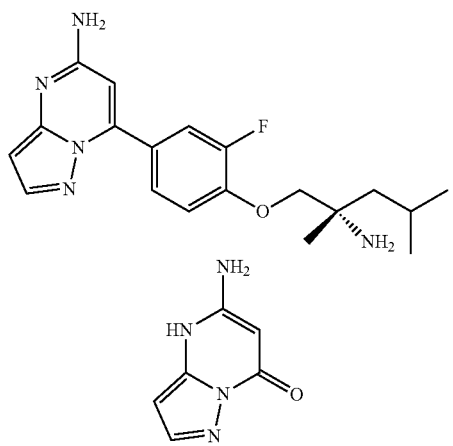

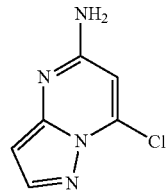 [SMILES: Nc1cc(Cl)n2nccc2n1]

Part A: 5-aminopyrazolo[1,5-a]pyrimidin-7(4H)-one

A solution of ethyl 3-ethoxy-3-iminopropanoate hydrochloride (5 g, 25.6 mmol) in ethanol (50 mL) cooled at 0° C. was added TEA (3.56 mL, 25.6 mmol) dropwise and the reaction mixture was stirred at room temperature for 30 min. 1H-pyrazol-5-amine (2.336 g, 28.1 mmol) in ethanol (10 mL) was added dropwise to the reaction mixture and the mixture was heated 80° C. for 16 h. The reaction mixture was cooled to room temperature and the white colored precipitate that formed was collected by vacuum filtration, washed with an excess of cold ethanol (10 mL), and dried to give 5-aminopyrazolo[1,5-a]pyrimidin-7(4H)-one (2 g, 13.32 mmol, 52% yield) as an off-white solid which was carried forward without further purification. LCMS (ESI) m/e 149.0 [(M–H)$^-$, calcd for $C_6H_5N_4O$ 149.1]; LC/MS retention time (Method A1): $t_R$=0.21 min.

Part B: 7-chloropyrazolo [1,5-a]pyrimidin-5-amine

To 5-aminopyrazolo [1,5-a]pyrimidin-7(4H)-one (2 g, 13.32 mmol) cooled at 0° C. was added POCl$_3$ (1.242 mL, 13.32 mmol) dropwise. The reaction mixture and stirred for 5 min at 0° C. then at 105° C. for 12 h. The reaction mixture was concentrated under reduced pressure to afford white colored residue. The residue was basified with 10% aqueous sodium hydroxide solution (pH~12) and extracted with ethyl acetate (3×25 mL). The ethyl acetate layer was dried over Na$_2$SO$_4$, filtered, and concentrated under reduced pressure to afford 7-chloropyrazolo[1,5-a]pyrimidin-5-amine (1.5 g, 8.90 mmol, 67% yield) as an off-white solid. LCMS (ESI) m/e 167.0 [(M–H)$^-$, calcd for $C_6H_5ClN_4$ 167.0]; LC/MS retention time (method A2): $t_R$=0.26 min.

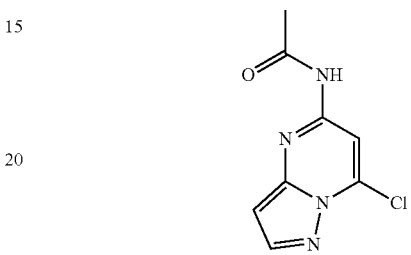

Part C: N-(7-chloropyrazolo[1,5-a]pyrimidin-5-yl) acetamide

A solution of 7-chloropyrazolo[1,5-a]pyrimidin-5-amine (0.6 g, 3.56 mmol) in DCM (10 mL) was cooled to 0° C. DIPEA (0.622 mL, 3.56 mmol) was added followed by slow addition of AcCl (0.253 mL, 3.56 mmol) and the mixture stirred for 10 min at 0° C. The reaction mixture stirred at room temperature for 12 h. The reaction mixture was concentrated under reduced pressure to afford a brown colored residue. The residue was washed with ethyl acetate/petroleum ether (5 mL/15 mL) then dried to afford N-(7-chloropyrazolo[1,5-a]pyrimidin-5-yl)acetamide (0.7 g, 3.10 mmol, 87% yield) as a brown color semi-solid which was used for next step without purification. $^1$H NMR (400 MHz, DMSO-$d_6$): δ 11.94 (s, 1H), 8.31 (s, 1H), 7.88 (d, J=2.40 Hz, 1H), 6.98 (d, J=2.40 Hz, 1H), 2.49 (s, 3H) ppm.

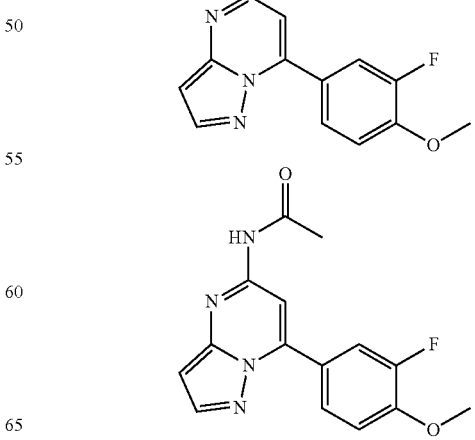

Part D: N-(7-(3-fluoro-4-methoxyphenyl)pyrazolo [1,5-a]pyrimidin-5-yl)acetamide and 7-(3-fluoro-4-methoxyphenyl)pyrazolo [1,5-a]pyrimidin-5-amine A solution of N-(7-chloropyrazolo[1,5-a]pyrimidin-5-yl) acetamide (0.4 g, 1.899 mmol), (3-fluoro-4-methoxyphenyl) boronic acid (0.323 g, 1.899 mmol), and $Cs_2CO_3$ (1.238 g, 3.80 mmol) in 1,4-dioxane (10 mL) and water (3 mL) was purged with nitrogen gas for 30 min. $PdCl_2(dppf)$-$CH_2Cl_2$ adduct (0.155 g, 0.190 mmol) was added to the reaction mixture and the solution was purged with nitrogen gas again for 10 min. The reaction mixture was heated at 80° C. for 6 h. The reaction mixture was concentrated and the residue obtained was dissolved in ethyl acetate (50 mL) and water (40 mL). The biphasic mixture was filtered through diatomaceous earth. The diatomaceous earth was washed with ethyl acetate (50 mL). The organic layer was separated, dried over $Na_2SO_4$, filtered, and concentrated under reduced pressure. The residue was purified by silica gel chromatography (EtOAc in pet ether) to afford two products N-(7-(3-fluoro-4-methoxyphenyl)pyrazolo[1,5-a]pyrimidin-5-yl)acetamide (0.28 g, 0.932 mmol, 49% yield) as a light yellow solid LCMS (ESI) m/e 301.2 [(M+H)+, calcd for $C_{15}H_{14}FN_4O_2$ 301.1]; LC/MS retention time (Method A1): $t_R$=2.02 min and 7-(3-fluoro-4-methoxyphenyl)pyrazolo[1, 5-a]pyrimidin-5-amine (0.12 g, 0.465 mmol, 24% yield) as a brown solid. LCMS (ESI) m/e 259.2 [(M+H)+, calcd for $C_{13}H_{12}FN_4O$ 259.1]; LC/MS retention time (Method A1): $t_R$=1.90 min.

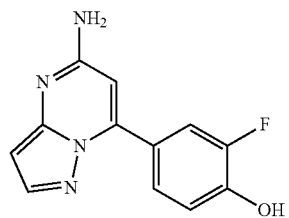 [SMILES: Nc1cc(-c2ccc(O)c(F)c2)n2nccc2n1]

Part E: 4-(5-aminopyrazolo[1,5-a]pyrimidin-7-yl)-2-fluorophenol

To a solution of N-(7-(3-fluoro-4-methoxyphenyl) pyrazolo [1,5-a]pyrimidin-5-yl) acetamide (0.28 g, 0.932 mmol) cooled to 0° C. was added HBr in AcOH (34%) (5 mL, 92 mmol). The reaction mixture was heated at 105° C. for 12 h. The reaction mixture was concentrated under reduced pressure. The residue was reconstituted with ethyl acetate/pet ether(5:5 mL), filtered and dried to afford 4-(5-aminopyrazolo[1,5-a]pyrimidin-7-yl)-2-fluorophenol (0.34 g, 0.390 mmol, 42% yield) as an off-white solid which was carried forward without further purification. LCMS (ESI) m/e 245.2 [(M+H)+, calcd for $C_{12}H_{10}FN_4O$ 245.1]; LC/MS retention time (Method A1): $t_R$=1.69 min.

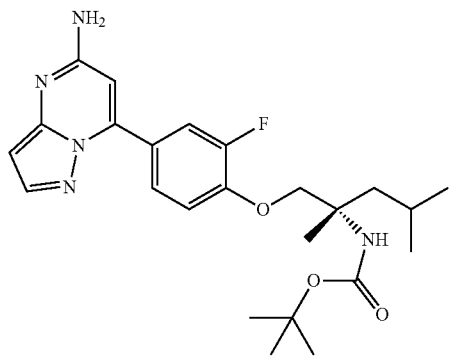 [SMILES: CC(C)C[C@@](C)(COc1ccc(-c2cc(N)nc3ccnn23)cc1F)NC(=O)OC(C)(C)C]

Part F: (S)-tert-butyl (1-(4-(5-aminopyrazolo[1,5-a] pyrimidin-7-yl)-2-fluorophenoxy)-2,4-dimethylpentan-2-yl)carbamate A solution of ethyl 4-(5-aminopyrazolo [1,5-a]pyrimidin-7-yl)-2-fluorophenol (0.34 g, 0.418 mmol) in DMF (5 mL) was cooled to 0° C. $K_2CO_3$ (0.173 g, 1.253 mmol) was added in portions followed by slow addition of (S)-tert-butyl 4-isobutyl-4-methyl-1,2,3-oxathiazolidine-3-carboxylate 2,2-dioxide (prepared as described in Example 251, Parts A-E) (0.147 g, 0.501 mmol) in 1 mL DMF. The reaction mixture was heated at 88° C. for 12 h. The reaction mixture was cooled to 0° C. and quenched with aqueous ammonium chloride solution (10 mL). The reaction mixture extracted with ethyl acetate (2×20 mL). The ethyl acetate layer was washed with water (2×20 mL) and brine(10 mL), dried over $Na_2SO_4$, filtered, and concentrated under reduced pressure to afford (S)-tert-butyl (1-(4-(5-aminopyrazolo[1,5-a]pyrimidin-7-yl)-2-fluorophenoxy)-2,4-dimethylpentan-2-yl) carbamate (0.092 g, 0.201 mmol, 48% yield) as a brown color semi-solid. The residue was taken for next step without further purification. LCMS (ESI) m/e 458.0 [(M+H)+, calcd for $C_{24}H_{33}FN_5O_3$ 458.2]; LC/MS retention time (Method A1): $t_R$=2.09 min.

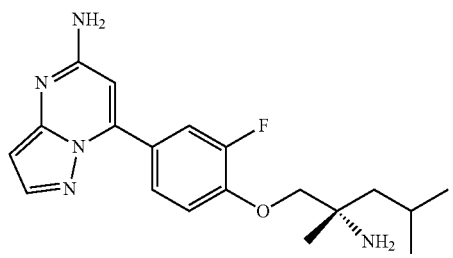 [SMILES: CC(C)C[C@](C)(N)COc1ccc(-c2cc(N)nc3ccnn23)cc1F]

Part G: (S)-7-(4-((2-amino-2,4-dimethylpentyl)oxy)-3-fluorophenyl)pyrazolo[1,5-a]pyrimidin-5-amine To a solution of (S)-tert-butyl (1-(4-(5-aminopyrazolo[1, 5-a]pyrimidin-7-yl)-2-fluorophenoxy)-2,4-dimethylpentan-2-yl)carbamate (20 mg, 0.044 mmol) in DCM (2 mL) at 0° C. was added TFA (0.067 mL, 0.874 mmol) and the mixture stirred for 5 min at 0° C. The reaction mixture was allowed to stir for 4 h at room temperature, then was concentrated under reduced pressure. The crude material was purified by prep LC/MS (method A) to afford (S)-7-(4-((2-amino-2,4-dimethylpentyl)oxy)-3-fluorophenyl)pyrazolo[1,5-a]pyrimidin-5-amine (2.75 mg. 7.69 μmol, 18% yield) as a pale yellow solid. LCMS (ESI) m/e 358.2 [(M+H)+, calcd for $C_{19}H_{25}FN_5O$ 358.2]; LC/MS retention time (method H): $t_R$=1.05 min. $^1$H NMR (400 MHz, Methanol-$d_4$): δ 7.85-7.89 (m, 2H), 7.74-7.77 (m, 1H), 7.36 (t, J=17.20 Hz, 1H), 6.39 (s, 1H), 6.11 (s, 1H), 4.16-4.25 (m, 2H), 1.82-1.87 (m, 2H), 1.68-1.71 (m, 1H), 1.49 (s, 3H), 1.04-1.09 (m, 6H) ppm.

Example 459

(S)-1-(2-chloro-4-(2,5-dimethylpyrazolo[1,5-a]pyrimidin-7-yl)phenoxy)-2,4-dimethylpentan-2-amine

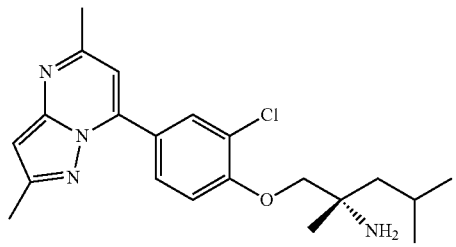 [SMILES: Cc1cc(-c2ccc(OC[C@@](C)(N)CC(C)C)c(Cl)c2)n2nc(C)cc2n1]

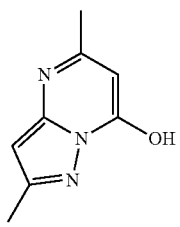

Part A: 2,5-dimethylpyrazolo [1,5-a]pyrimidin-7-ol

To a solution of 5-methyl-1H-pyrazol-3-amine (10 g, 103 mmol) in 1,4-dioxane (100 mL) was added ethyl 3-oxobutanoate (16.08 g, 124 mmol) dropwise followed by slow addition of AcOH (5.89 mL, 103 mmol). The reaction mixture was heated at 80° C. for 14 h. The reaction mixture was concentrated under reduced pressure. The residue was mixed with ice-water. A solid formed that was collected by vacuum filtration to afford 2,5-dimethylpyrazolo [1,5-a]pyrimidin-7-ol (7.5 g, 45.5 mmol, 44% yield) as an off-white color solid. LCMS (ESI) m/e 164.2 [(M+H)+, calcd for $C_8H_{10}N_3O$ 164.1]; LC/MS retention time (Method A1): $t_R$=0.58 min.

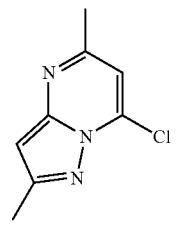

Part B: 7-chloro-2,5-dimethylpyrazolo[1,5-a]pyrimidine 2,5-Dimethylpyrazolo[1,5-a]pyrimidin-7-ol (3 g, 18.38 mmol) was taken in a 100 mL round bottom and cooled to 0° C. POCl$_3$ (10 mL, 107 mmol) was added dropwise and the reaction mixture stirred for 5 min at 0° C. The reaction mixture was heated at 105° C. for 12 h. The reaction mixture was concentrated under reduced pressure to afford a white colored residue. The residue was basified with 10% aqueous sodium hydroxide solution (pH~12) and extracted with ethyl acetate (3×25 mL). The ethyl acetate layer was dried over Na$_2$SO$_4$, filtered, and concentrated under reduced pressure to afford 7-chloro-2,5-dimethylpyrazolo [1,5-a]pyrimidine (1.8 g, 9.91 mmol, 54% yield) as an off-white solid. LCMS (ESI) m/e 182.2 [(M+H)+, calcd for $C_8H_9ClN_3$ 182.0]; LC/MS retention time (Method A1): $t_R$=1.77 min.

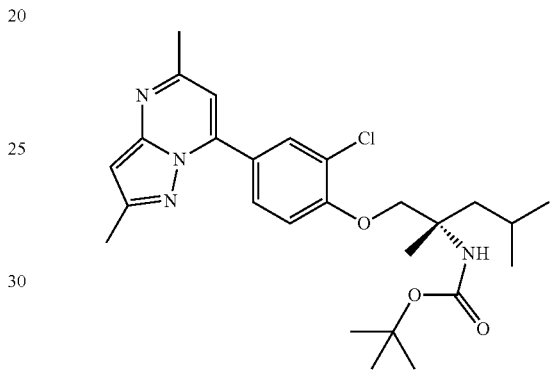

Part C: (S)-tert-butyl (1-(2-chloro-4-(2,5-dimethylpyrazolo[1,5-a]pyrimidin-7-yl)phenoxy)-2,4-dimethylpentan-2-yl)carbamate A solution of 7-chloro-2,5-dimethylpyrazolo[1,5-a]pyrimidine (0.04 g, 0.220 mmol), (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (0.103 g, 0.220 mmol), potassium phosphate, tribasic (0.038 g, 0.220 mmol), and KBr (0.026 g, 0.220 mmol) in 1,4-dioxane (5 mL) was purged with nitrogen gas for 30 min. PdCl$_2$(dppf)-CH$_2$Cl$_2$ adduct (0.018 g, 0.022 mmol) was added to the reaction mixture and the solution was purged with nitrogen gas again for 10 min. The reaction mixture was heated at 100° C. for 6 h. The reaction mixture was concentrated and the residue obtained was dissolved in ethyl acetate (25 mL) and water (20 mL). The biphasic mixture was filtered through diatomaceous earth. The diatomaceous earth was washed with ethyl acetate (30 mL). The organic layer was separated, dried over Na$_2$SO$_4$, filtered, and concentrated under reduced pressure to afford (S)-tert-butyl (1-(2-chloro-4-(2,5-dimethylpyrazolo[1,5-a]pyrimidin-7-yl)phenoxy)-2,4-dimethylpentan-2-yl)carbamate (crude yield) (0.064 g, 0.131 mmol, 60% yield) as a brown solid which was used for next step without further purification. LCMS (ESI) m/e 487.2 [(M+2H)+, calcd for $C_{26}H_{36}ClN_4O_3$ 487.2]; LC/MS retention time (Method A1): $t_R$=2.91 min.

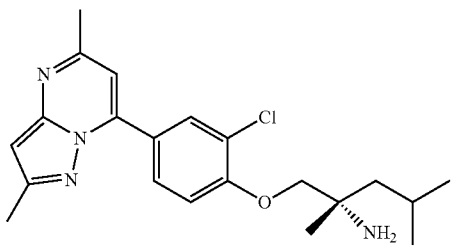 [SMILES: Cc1cc(-c2ccc(OC[C@@](C)(N)CC(C)C)c(Cl)c2)n2nc(C)cc2n1]

Part D: (S)-1-(2-chloro-4-(2,5-dimethylpyrazolo[1,5-a]pyrimidin-7-yl)phenoxy)-2,4-dimethylpentan-2-amine To a solution of (S)-tert-butyl (1-(2-chloro-4-(2,5-dimethylpyrazolo[1,5-a]pyrimidin-7-yl)phenoxy)-2,4-dimethylpentan-2-yl)carbamate (0.084 g, 0.172 mmol) in DCM (2 mL) at 0° C. was added TFA (0.266 mL, 3.45 mmol) and the mixture stirred for 5 min at 0° C. The reaction mixture was allowed to stir for 4 h at room temperature, then was concentrated under reduced pressure. The crude material was purified by prep LC/MS (method A) to afford (S)-1-(2-chloro-4-(2,5-dimethylpyrazolo[1,5-a]pyrimidin-7-yl)phenoxy)-2,4-dimethylpentan-2-amine (52.5 mg. 0.134 mmol, 78% yield) as a pale yellow solid. LCMS (ESI) m/e 387.0 [(M+2H)$^+$, calcd for $C_{21}H_{28}ClN_4O$ 387.2]; LC/MS retention time (method H): $t_R$=1.68 min; LC/MS retention time (method I)): $t_R$=1.29 min. $^1$H NMR (400 MHz, Methanol-d$_4$): δ 8.27 (d, J=2.00 Hz, 1H), 8.07-8.09 (m, 1H), 7.35 (d, J=8.80 Hz, 1H), 6.97 (s, 1H), 6.44 (s, 1H), 4.16-4.22 (m, 2H), 2.62 (s, 3H), 2.49 (s, 3H), 1.85-1.90 (m, 2H), 1.67-1.72 (m, 1H), 1.48 (s, 3H), 1.04-1.08 (m, 6H) ppm.

Example 460

(S)-2-((2-amino-2,4-dimethylpentyl)oxy)-5-(pyrazolo[1,5-a]pyrimidin-7-yl)benzonitrile

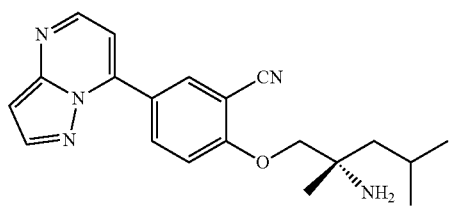

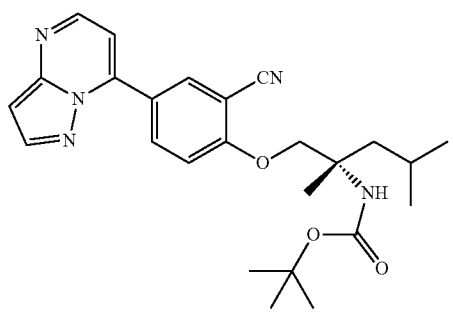

Part A: (S)-Tert-butyl (1-(2-cyano-4-(pyrazolo[1,5-a]pyrimidin-7-yl)phenoxy)-2,4-dimethylpentan-2-yl)carbamate A solution of 7-chloropyrazolo[1,5-a]pyrimidine (0.04 g, 0.260 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (0.119 g, 0.260 mmol), KBr (0.031 g, 0.260 mmol), and potassium phosphate, tribasic (0.045 g, 0.260 mmol) in 1,4-dioxane (5 mL) was purged with nitrogen gas for 30 min. PdCl$_2$(dppf)-CH$_2$Cl$_2$ adduct (0.021 g, 0.026 mmol) was added to the reaction mixture and the solution was purged with nitrogen gas again for 10 min. The reaction mixture was heated at 100° C. for 12 h. The reaction mixture was concentrated and the residue obtained was dissolved in ethyl acetate (30 mL) and water (30 mL). The biphasic mixture was filtered through diatomaceous earth. The diatomaceous earth was washed with ethyl acetate (25 mL). The organic layer was separated, dried over Na$_2$SO$_4$, filtered, and concentrated under reduced pressure to afford (S)-tert-butyl (1-(2-cyano-4-(pyrazolo[1,5-a]pyrimidin-7-yl)phenoxy)-2,4-dimethylpentan-2-yl)carbamate (crude yield) (62 mg, 0.138 mmol, 53% yield) as a brown solid which was carried forward without further purification. LCMS (ESI) m/e 451.2 [(M+H)$^+$, calcd for $C_{25}H_{32}N_5O_3$ 450.2]; LC/MS retention time (method B): $t_R$=1.09 min.

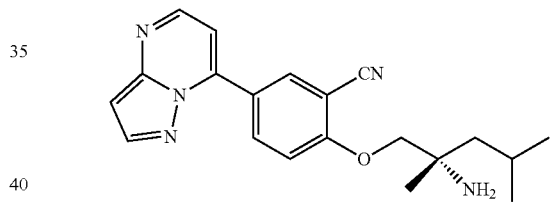

Part B: (S)-2-((2-amino-2,4-dimethylpentyl)oxy)-5-(pyrazolo [1,5-a]pyrimidin-7-yl)benzonitrile To a solution of (S)-tert-butyl (1-(2-cyano-4-(pyrazolo[1,5-a]pyrimidin-7-yl)phenoxy)-2,4-dimethylpentan-2-yl)carbamate (prepared as described in Example 285) (0.06 g, 0.133 mmol) in DCM (2 mL) at 0° C. was added TFA (0.206 mL, 2.67 mmol) and the mixture stirred for 5 min at 0° C. The reaction mixture was allowed to stir for 4 h at room temperature, then was concentrated under reduced pressure. The crude material was purified by prep LC/MS (method B) to afford (S)-2-((2-amino-2,4-dimethylpentyl)oxy)-5-(pyrazolo[1,5-a]pyrimidin-7-yl)benzonitrile (41.5 mg. 0.119 mmol, 89% yield) as a pale yellow solid. LCMS (ESI) m/e 350.0 [(M+H)$^+$, calcd for $C_{20}H_{24}N_5O$ 350.2]; LC/MS retention time (method H): $t_R$=1.28 min; LC/MS retention time (method I): $t_R$=1.05 min. $^1$H NMR (400 MHz, Methanol-d4: δ 8.59-8.63 (m, 2H), 8.49-8.51 (m, 1H), 8.25-8.28 (m, 1H), 7.50 (d, J=8.80 Hz, 1H), 7.22 (d, J=4.40 Hz, 1H), 6.82-6.85 (m, 1H), 4.35-4.47 (m, 2H), 1.88-1.98 (m, 2H), 1.73-1.77 (m, 1H), 1.56 (s, 3H), 1.06-1.11 (m, 6H) ppm.

Example 461

(S)-1-(2-fluoro-4-(pyrazolo [1,5-a]pyrimidin-7-yl) phenoxy)-2,4-dimethylpentan-2-amine

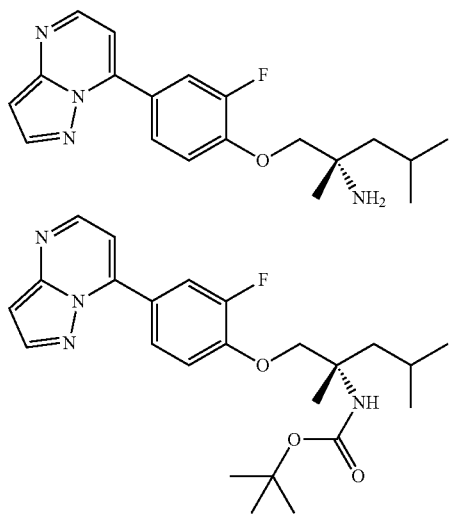

Part A: (S)-tert-butyl (1-(2-fluoro-4-(pyrazolo [1,5-a]pyrimidin-7-yl) phenoxy)-2,4-dimethylpentan-2-yl) carbamate A solution of 7-chloropyrazolo[1,5-a]pyrimidine (0.04 g, 0.260 mmol), (S)-tert-butyl (1-(2-fluoro-4-(4,4,5,5-tetramethyl-1,3,2-dioxaborolan-2-yl)phenoxy)-2,4-dimethylpentan-2-yl)carbamate (prepared as in Example 253, Part B) (0.118 g, 0.260 mmol), KBr (0.031 g, 0.260 mmol), and potassium phosphate, tribasic (0.045 g, 0.260 mmol) in 1,4-dioxane (5 mL) was purged with nitrogen gas for 10 min. PdCl$_2$ (dppf)-CH$_2$Cl$_2$ adduct (0.021 g, 0.026 mmol) was added to the reaction mixture and the solution was purged with nitrogen gas again for 10 min. The reaction mixture was heated at 88° C. for 12 h. The reaction mixture was concentrated then dissolved in ethyl acetate (30 mL) and water (30 mL). The biphasic mixture was filtered through diatomaceous earth. The diatomaceous earth was washed with ethyl acetate (30 mL). The organic layer was separated, dried over Na$_2$SO$_4$, filtered, and concentrated under reduced pressure to afford the crude product (S)-tert-butyl (1-(2-fluoro-4-(pyrazolo[1,5-a]pyrimidin-7-yl)phenoxy)-2,4-dimethylpentan-2-yl)carbamate (62 mg, 0.098 mmol, 38% yield) as an off-white solid which was carried forward without further purification. LCMS (ESI) m/e 443.2 [(M+H)$^+$, calcd for C$_{24}$H$_{32}$FN$_4$O$_3$ 443.2]; LC/MS retention time (Method A1): t$_R$=2.33 min.

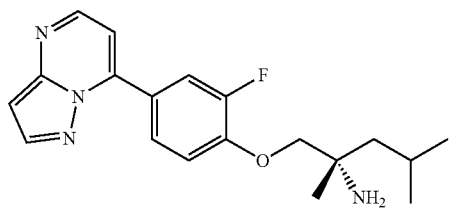 [SMILES: CC(C)C[C@](C)(N)COc1ccc(-c2ccnc3ccnn23)cc1F]

Part B: (S)-1-(2-fluoro-4-(pyrazolo [1,5-a]pyrimidin-7-yl) phenoxy)-2,4-dimethylpentan-2-amine To a solution (S)-tert-butyl (1-(2-fluoro-4-(pyrazolo[1,5-a]pyrimidin-7-yl)phenoxy)-2,4-dimethylpentan-2-yl)carbamate (50 mg, 0.113 mmol) in DCM (2 mL) at 0° C. was added TFA (0.174 mL, 2.260 mmol) and the mixture stirred for 5 min at 0° C. The reaction mixture was allowed to stir for 4 h at room temperature, then was concentrated under reduced pressure. The crude material was purified by preparative LC/MS (method A) to afford (S)-1-(2-fluoro-4-(pyrazolo [1,5-a]pyrimidin-7-yl) phenoxy)-2,4-dimethylpentan-2-amine (15.3 mg, 0.044, 39% yield) as a pale yellow solid. LCMS (ESI) m/e 343.0 [(M+H)$^+$, calcd for C$_{19}$H$_{24}$FN$_4$O 343.2]; LC/MS retention time (method H): t$_R$=1.29 min; LC/MS retention time (method I): t$_R$=1.09 min. $^1$H NMR (400 MHz, Methanol)-d4: δ 8.55 (d, J=4.40 Hz, 1H), 8.22 (d, J=2.40 Hz, 1H), 8.11-8.15 (m, 1H), 7.97-8.00 (m, 1H), 7.38 (t, J=17.60 Hz, 1H), 7.16 (d, J=4.80 Hz, 1H), 6.79 (d, J=2.40 Hz, 1H), 4.15-4.25 (m, 2H), 1.80-1.89 (m, 2H), 1.65-1.69 (m, 1H), 1.46 (s, 3H), 1.02-1.07 (m, 6H) ppm.

Example 463

(S)—N-(7-(4-((2-amino-2,4-dimethylpentyl) oxy)-3-fluorophenyl) pyrazolo [1,5-a]pyrimidin-5-yl) acetamide

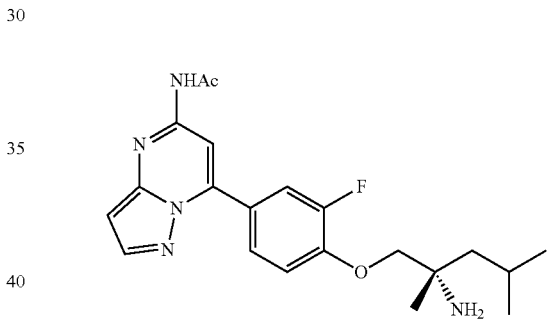

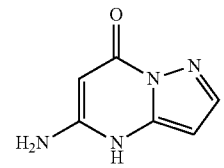 [SMILES: Nc1cc(=O)n2nccc2[nH]1]

Part A: 5-aminopyrazolo [1,5-a]pyrimidin-7(4H)-one

A solution of ethyl 3-ethoxy-3-iminopropanoate hydrochloride (5 g, 25.6 mmol) in ethanol (50 mL) was to at 0° C. TEA (3.56 mL, 25.6 mmol) was added dropwise and the reaction mixture was stirred at room temperature for 30 min. 1H-pyrazol-5-amine (2.336 g, 28.1 mmol) in ethanol (10 mL) was added dropwise to the reaction mixture and was the mixture heated to reflux for 16 h. The reaction mixture was allowed to cool to room temperature and the white colored precipitate formed was collected by vacuum filtration. The white solid was washed with an excess of cold ethanol (10 mL) and dried to give 5-aminopyrazolo [1,5-a]pyrimidin-7

(4H)-one (2 g, 13.32 mmol, 52% yield) as an off-white solid which was carried forward without further purification. LCMS (ESI) m/e 149.0 [(M−H)−, calcd for C₆H₅N₄O 149.1]; LC/MS retention time (Method A1): t_R=0.21 min.

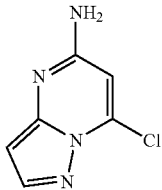 [SMILES: Nc1cc(Cl)n2nccc2n1]

Part B: 7-chloropyrazolo[1, 5-a]pyrimidin-5-amine

5-Aminopyrazolo [1,5-a]pyrimidin-7(4H)-one (2 g, 13.32 mmol) was taken in a 100 mL round bottom flask and cooled to 0° C. POCl₃ (1.242 mL, 13.32 mmol) was added dropwise and the reaction mixture was stirred for 5 min at 0° C., then heated at 105° C. for 12 h. The reaction mixture was concentrated under reduced pressure to afford a white colored residue. The residue was basified with 10% aqueous sodium hydroxide solution (pH~12) and extracted with ethyl acetate (3×25 mL). The ethyl acetate layer was dried over Na₂SO₄, filtered, and concentrated under reduced pressure to afford 7-chloropyrazolo[1,5-a]pyrimidin-5-amine (1.5 g, 8.90 mmol, 67% yield) as an off-white solid. LCMS (ESI) m/e 167.0 [(M−H)−, calcd for C₆H₅ClN₄ 167.0]; LC/MS retention time (method A2): t_R=0.6 min.

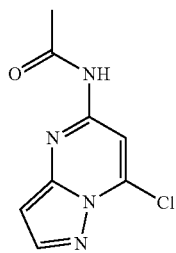

Part C: N-(7-chloropyrazolo[1,5-a]pyrimidin-5-yl) acetamide

A solution of 7-chloropyrazolo[1,5-a]pyrimidin-5-amine (0.6 g, 3.56 mmol) in DCM (10 mL) was cooled to 0° C. DIPEA (0.622 mL, 3.56 mmol) was added followed by slow addition of AcCl (0.253 mL, 3.56 mmol) and the mixture stirred for 10 min at 0° C., then at room temperature for 12 h. The reaction mixture was concentrated under reduced pressure to afford a brown colored residue. The solid residue was washed with ethyl acetate/petroleum ether (5 mL/15 mL), dried to afford N-(7-chloropyrazolo[1,5-a]pyrimidin-5-yl)acetamide (0.7 g, 3.10 mmol, 87% yield) as a brown color semi-solid which carried forward without further purification. 400 MHz, DMSO-d₆: δ 11.94 (s, 1H), 8.31 (s, 1H), 7.88 (d, J=2.40 Hz, 1H), 6.98 (d, J=2.40 Hz, 1H), 2.49 (s, 3H) ppm.

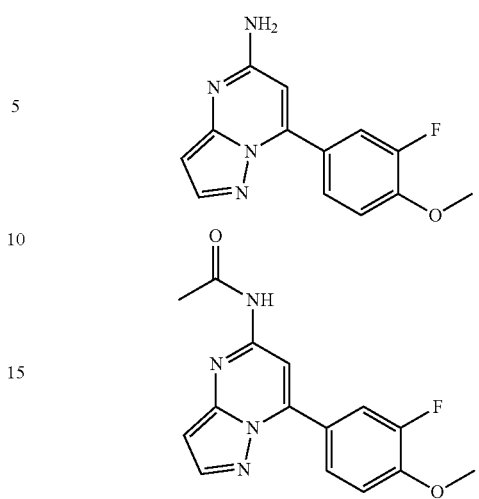

Part D: N-(7-(3-fluoro-4-methoxyphenyl)pyrazolo [1,5-a]pyrimidin-5-yl)acetamide and 7-(3-fluoro-4-methoxyphenyl)pyrazolo [1,5-a]pyrimidin-5-amine A solution of N-(7-chloropyrazolo[1,5-a]pyrimidin-5-yl) acetamide (0.4 g, 1.899 mmol), (3-fluoro-4-methoxyphenyl) boronic acid (0.323 g, 1.899 mmol), and Cs₂CO₃ (1.238 g, 3.80 mmol) in 1,4-dioxane (10 mL) and water (3 mL) was purged with nitrogen gas for 30 min. PdCl₂(dppf)-CH₂Cl₂ adduct (0.155 g, 0.190 mmol) was added to the reaction mixture and the solution was purged with nitrogen gas again for 10 min. The reaction mixture was heated at 80° C. for 6 h. The reaction mixture was concentrated and the residue obtained was dissolved in ethyl acetate (50 mL) and water (40 mL). The biphasic mixture was filtered through diatomaceous earth. The diatomaceous earth was washed with ethyl acetate (50 mL). The organic layer was separated, dried over Na₂SO₄, filtered, and concentrated under reduced pressure. The residue was purified by silica gel chromatography (EtOAc in pet ether) to afford two products N-(7-(3-fluoro-4-methoxyphenyl)pyrazolo[1,5-a]pyrimidin-5-yl)acetamide (0.28 g, 0.932 mmol, 49% yield) as a light yellow solid LCMS (ESI) m/e 301.2 [(M+H)+, calcd for C₁₅H₁₄FN₄O₂ 301.1]; LC/MS retention time (Method A1): t_R=2.02 min and 7-(3-fluoro-4-methoxyphenyl)pyrazolo[1,5-a]pyrimidin-5-amine (0.12 g, 0.465 mmol, 24% yield) as a brown solid. LCMS (ESI) m/e 259.2 [(M+H)+, calcd for C₁₃H₁₂FN₄O 259.1]; LC/MS retention time (Method A1): t_R=1.90 min.

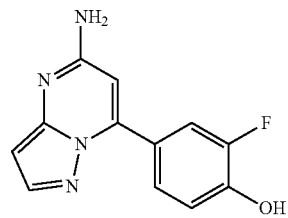 [SMILES: Nc1cc(-c2ccc(O)c(F)c2)n2nccc2n1]

Part E: 4-(5-aminopyrazolo[1,5-a]pyrimidin-7-yl)-2-fluorophenol

N-(7-(3-fluoro-4-methoxyphenyl) pyrazolo [1,5-a]pyrimidin-5-yl) acetamide (0.28 g, 0.932 mmol) was taken in a 100 mL round bottom flask, cooled to 0° C. and HBr in AcOH (34%) (5 mL, 92 mmol) was added. The reaction mixture was heated at 105° C. for 12 h. The reaction mixture was concentrated under reduced pressure. The residue was reconstituted with ethyl acetate/pet ether (5 mL/5 mL), filtered and dried to afford 4-(5-aminopyrazolo[1,5-a]pyrimidin-7-yl)-2-fluorophenol (0.34 g, 0.390 mmol, 42% yield) as an off-white solid which was taken forward without further purification. LCMS (ESI) m/e 245.2 [(M+H)$^+$, calcd for $C_{12}H_{10}FN_4O$ 245.1]; LC/MS retention time (Method A1): $t_R$=1.69 min.

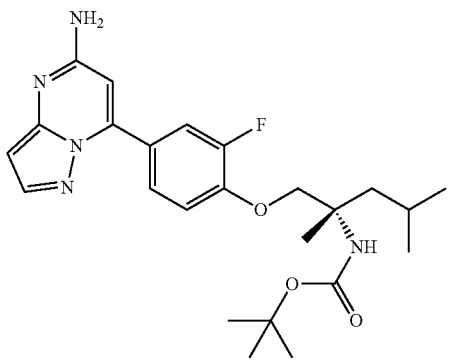 [SMILES: CC(C)C[C@@](C)(COc1ccc(-c2cc(N)nc3ccnn23)cc1F)NC(=O)OC(C)(C)C]

Part F: (S)-tert-butyl (1-(4-(5-aminopyrazolo[1,5-a]pyrimidin-7-yl)-2-fluorophenoxy)-2,4-dimethylpentan-2-yl)carbamate A solution of ethyl 4-(5-aminopyrazolo [1,5-a]pyrimidin-7-yl)-2-fluorophenol (0.34 g, 0.418 mmol) in DMF (5 mL) was cooled to 0° C. $K_2CO_3$ (0.173 g, 1.253 mmol) was added in portions followed by slow addition of a solution of (S)-tert-butyl 4-isobutyl-4-methyl-1,2,3-oxathiazolidine-3-carboxylate 2,2-dioxide (prepared as described in Example 251, Parts A-E) (0.147 g, 0.501 mmol) in 1 mL DMF. The reaction mixture was heated at 88° C. for 12 h. The reaction mixture was cooled to 0° C. and quenched with aqueous ammonium chloride solution (10 mL). The reaction mixture extracted with ethyl acetate (2×20 mL). The ethyl acetate layer was washed with water (2×20 mL) and brine (10 mL), dried over $Na_2SO_4$, filtered, and concentrated under reduced pressure to afford (S)-tert-butyl (1-(4-(5-aminopyrazolo[1,5-a]pyrimidin-7-yl)-2-fluorophenoxy)-2,4-dimethylpentan-2-yl)carbamate (0.092 g, 0.201 mmol, 48% yield) as a brown color semi-solid. The residue was taken forward without further purification. LCMS (ESI) m/e 458.0 [(M+H)$^+$, calcd for $C_{24}H_{33}FN_5O_3$ 458.2]; LC/MS retention time (Method A1): $t_R$=2.09 min.

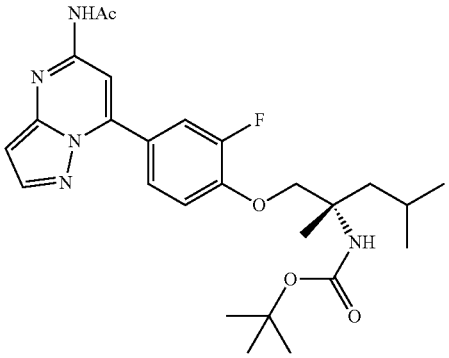 [SMILES: CC(=O)Nc1cc(-c2ccc(OC[C@](C)(CC(C)C)NC(=O)OC(C)(C)C)c(F)c2)n2nccc2n1]

Part G: (S)-tert-butyl (1-(4-(5-acetamidopyrazolo[1,5-a]pyrimidin-7-yl)-2-fluorophenoxy)-2,4-dimethylpentan-2-yl)carbamate A solution of (S)-tert-butyl (1-(4-(5-aminopyrazolo [1,5-a]pyrimidin-7-yl)-2-fluorophenoxy)-2,4-dimethylpentan-2-yl) carbamate (0.05 g, 0.109 mmol) in pyridine (2 mL) was cooled to 0° C. and AcCl (7.77 µl, 0.109 mmol) was added dropwise. The reaction mixture was allowed to stir at 0° C. for 10 min then at room temperature for 4 h. The reaction mixture was concentrated under reduced pressure to afford a brown colored residue. The residue was dissolved in ethyl acetate (20 mL) and water (20 mL). The ethyl acetate layer was separated, dried over $Na_2SO_4$, filtered, and concentrated under reduced pressure to afford (S)-tert-butyl (1-(4-(5-acetamidopyrazolo[1,5-a]pyrimidin-7-yl)-2-fluorophenoxy)-2,4-dimethylpentan-2-yl)carbamate (0.06 g, 0.055 mmol, 510% yield) as an off-white solid which was carried forward without further purification. LCMS (ESI) m/e 500.2 [(M+H)$^+$, calcd for $C_{26}H_{35}FN_5O_4$ 500.2]; LC/MS retention time (Method A1): $t_R$=2.54 min.

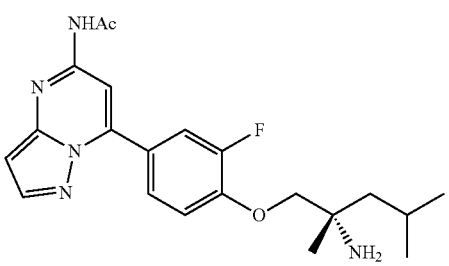 [SMILES: CC(=O)Nc1cc(-c2ccc(OC[C@@](C)(N)CC(C)C)c(F)c2)n2nccc2n1]

Part H: (S)—N-(7-(4-((2-amino-2,4-dimethylpentyl)oxy)-3-fluorophenyl) pyrazolo [1,5-a]pyrimidin-5-yl) acetamide To a solution of (S)-tert-butyl (1-(4-(5-acetamidopyrazolo [1,5-a]pyrimidin-7-yl)-2-fluorophenoxy)-2,4-dimethylpentan-2-yl)carbamate (52 mg, 0.048 mmol) in DCM (2 mL) at 0° C. was added TFA (0.074 mL, 0.958 mmol) and the mixture stirred for 5 min at 0° C. The reaction mixture was allowed to stir for 4 h at room temperature, then was concentrated under reduced pressure. The crude material was purified by prep LC/MS (method A) to afford (S)—N-(7-(4-((2-amino-2,4-dimethylpentyl) oxy)-3-fluorophenyl) pyrazolo [1,5-a]pyrimidin-5-yl) acetamide (2 mg. 5.01 µmol, 10% yield) as a pale yellow solid. LCMS (ESI) m/e 400.0 [(M+H)$^+$, calcd for C$_{21}$H$_{27}$FN$_5$O$_2$ 400.2]; LC/MS retention time (method H): $t_R$=1.14 min; LC/MS retention time (method I): $t_R$=1.11 min. $^1$H NMR (400 MHz, Methanol-d$_4$): δ 8.09 (d, J=2.40 Hz, 1H), 8.02-8.05 (m, 1H), 7.98 (s, 1H), 7.85-7.89 (m, 1H), 7.38 (t, J=17.20 Hz, 1H), 6.50 (d, J=2.00 Hz, 1H), 4.14-4.24 (m, 2H), 2.23 (s, 3H), 1.79-1.88 (m, 2H), 1.64-1.69 (m, 1H), 1.46 (s, 3H), 1.02-1.07 (m, 6H) ppm.

Example 464

(S)-2-((2-amino-2,4-dimethylpentyl)oxy)-5-(2,5-dimethylpyrazolo[1,5-a]pyrimidin-7-yl)benzonitrile

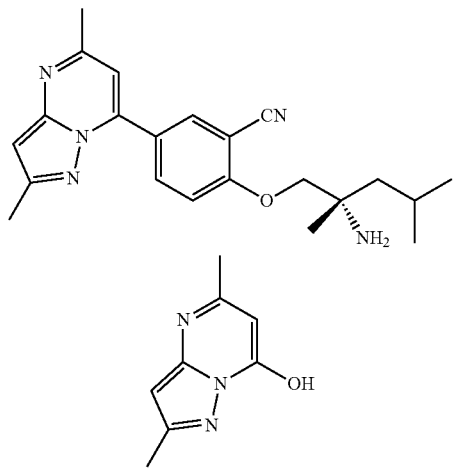

Part A: 2,5-dimethylpyrazolo [1,5-a]pyrimidin-7-ol

To a solution of 5-methyl-1H-pyrazol-3-amine (10 g, 103 mmol) in 1,4-dioxane (100 mL) was added ethyl 3-oxobutanoate (16.08 g, 124 mmol) dropwise followed by slow addition of AcOH (5.89 mL, 103 mmol). The reaction mixture was heated at 80° C. for 14 h. The reaction mixture was cooled to room temperature and concentrated under reduced pressure. The residue was mixed with ice-water to afford an off-white colored solid which was collected by vacuum filtration and dried to give 2,5-dimethylpyrazolo [1,5-a]pyrimidin-7-ol (7.5 g, 45.5 mmol, 44% yield). LCMS (ESI) m/e 164.2 [(M+H)$^+$, calcd for C$_8$H$_{10}$N$_3$O 164.1]; LC/MS retention time (Method A1): $t_R$=0.58 min.

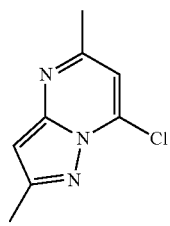

Part B: 7-chloro-2,5-dimethylpyrazolo[1,5-a]pyrimidine 2,5-Dimethylpyrazolo[1,5-a]pyrimidin-7-ol (3 g, 18.38 mmol) was taken in a 100 mL round bottom and cooled to 0° C. POCl$_3$ (10 mL, 107 mmol) was added dropwise and the reaction mixture stirred for 5 min at 0° C. The reaction mixture was heated at 105° C. for 12 h. The reaction mixture was concentrated under reduced pressure to afford a white colored residue. The residue was basified with 10% aqueous sodium hydroxide solution (pH~12) and extracted with ethyl acetate (3×25 mL). The ethyl acetate layer was dried over Na$_2$SO$_4$, filtered, and concentrated under reduced pressure to afford 7-chloro-2,5-dimethylpyrazolo [1,5-a]pyrimidine (1.8 g, 9.91 mmol, 54% yield) as an off-white solid. LCMS (ESI) m/e 182.2 [(M+H)$^+$, calcd for C$_8$H$_9$ClN$_3$ 182.0]; LC/MS retention time (Method A1): $t_R$=1.77 min.

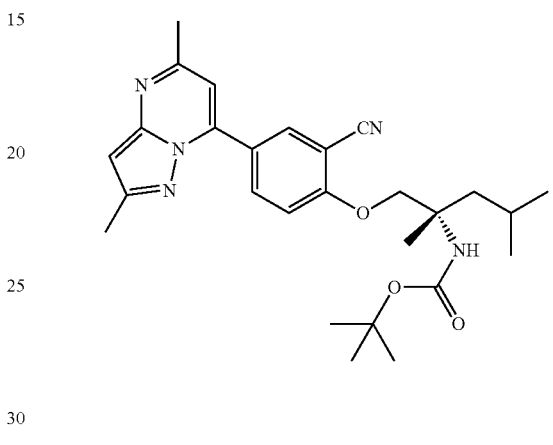

Part C: (S)-tert-butyl (1-(2-cyano-4-(2,5-dimethylpyrazolo[1,5-a]pyrimidin-7-yl)phenoxy)-2,4-dimethylpentan-2-yl)carbamate A solution of 7-chloro-2,5-dimethylpyrazolo[1,5-a]pyrimidine (0.04 g, 0.220 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (0.101 g, 0.220 mmol), potassium phosphate, tribasic (0.038 g, 0.220 mmol), and KBr (0.026 g, 0.220 mmol) in 1,4-dioxane (5 mL) was purged with nitrogen gas for 30 min. PdCl$_2$(dppf)-CH$_2$Cl$_2$ adduct (0.018 g, 0.022 mmol) was added to the reaction mixture and the solution was purged with nitrogen gas again for 10 min. The reaction mixture was heated at 100° C. for 6 h. The reaction mixture was concentrated and the residue obtained was dissolved in ethyl acetate (20 mL) and water (20 mL). The biphasic mixture was filtered through diatomaceous earth. The diatomaceous earth was washed with ethyl acetate (30 mL). The ethyl acetate layer was separated, dried over Na$_2$SO$_4$, filtered, and concentrated under reduced pressure to afford a brown solid which was purified by silica gel chromatography (EtOAc in pet ether) to afford (S)-tert-butyl (1-(2-cyano-4-(2,5-dimethylpyrazolo[1,5-a]pyrimidin-7-yl)phenoxy)-2,4-dimethylpentan-2-yl)carbamate (52 mg, 0.109 mmol, 49% yield). LCMS (ESI) m/e 478.2 [(M+H)$^+$, calcd for C$_{27}$H$_{36}$N$_5$O$_3$ 478.2]; LC/MS retention time (Method A1): $t_R$=2.66 min.

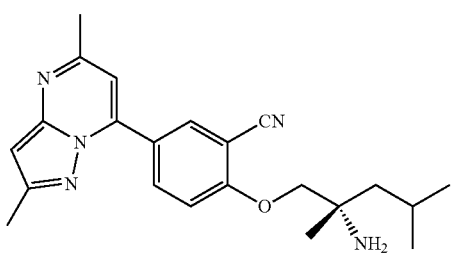 [SMILES: Cc1cc(-c2ccc(OC[C@@](C)(N)CC(C)C)c(C#N)c2)n2nc(C)cc2n1]

Part D: (S)-2-((2-amino-2,4-dimethylpentyl)oxy)-5-(2,5-dimethylpyrazolo[1,5-a]pyrimidin-7-yl)benzonitrile To a solution of (S)-tert-butyl (1-(2-cyano-4-(2,5-dimethylpyrazolo[1,5-a]pyrimidin-7-yl)phenoxy)-2,4-dimethylpentan-2-yl)carbamate (52 mg, 0.109 mmol) in DCM (2 mL) at 0° C. was added TFA (0.168 mL, 2.178 mmol) and the mixture stirred for 5 min at 0° C. The reaction mixture was allowed to stir for 4 h at room temperature, then was concentrated under reduced pressure. The crude material was purified by prep LC/MS (method A) to afford (S)-2-((2-amino-2,4-dimethylpentyl)oxy)-5-(2,5-dimethylpyrazolo[1,5-a]pyrimidin-7-yl)benzonitrile (12.3 mg, 0.032 mmol, 30% yield) as a pale yellow solid. LCMS (ESI) m/e 378.0 [(M+H)$^+$, calcd for $C_{22}H_{28}N_5O$ 378.0]; LC/MS retention time (method H): $t_R$=1.38 min; LC/MS retention time (method I)): $t_R$=1.31 min. $^1$H NMR (400 MHz, Methanol-d4): δ 8.52 (d, J=2.00 Hz, 1H), 8.40-8.43 (m, 1H), 7.44 (d, J=9.20 Hz, 1H), 7.02 (s, 1H), 6.45 (s, 1H), 4.16-4.22 (m, 2H), 2.63 (s, 3H), 2.50 (s, 3H), 1.76-1.89 (m, 2H), 1.63-1.68 (m, 1H), 1.42 (s, 3H), 1.04-1.07 (m, 6H) ppm.

Example 466

(S)-2-(2-amino-2,4-dimethylpentyloxy)-5-(2-(piperidin-4-ylamino) pyridin-4-yl) benzonitrile

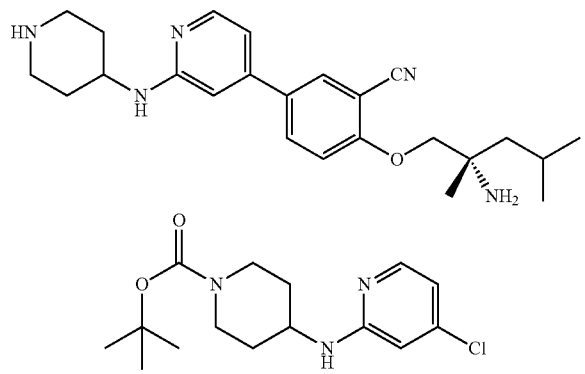

Part A: Tert-butyl 4-((4-chloropyridin-2-yl) amino) piperidine-1-carboxylate

A mixture of 2-bromo-4-chloropyridine (0.05 g, 0.260 mmol), tert-butyl 4-aminopiperidine-1-carboxylate (0.062 g, 0.312 mmol), tert-butyl 4-aminopiperidine-1-carboxylate (0.062 g, 0.312 mmol), Cs$_2$CO$_3$ (0.169 g, 0.520 mmol), and BINAP (0.162 g, 0.260 mmol) in toluene (5 mL) was solution was purged with nitrogen gas for 30 min. PdOAc$_2$ (0.058 g, 0.260 mmol) was added to the reaction mixture and again the solution was purged with nitrogen gas for 10 min the mixture was heated at 80° C. for 12 h. The reaction mixture was concentrated, dissolved in ethyl acetate (25 mL) and water (20 mL) and biphasic mixture was filtered through diatomaceous earth. The diatomaceous earth was washed with ethyl acetate (50 mL). The ethyl acetate layer was separated and dried over Na$_2$SO$_4$, filtered, and concentrated under reduced pressure. The residue was purified by silica gel chromatography (0-20% EtOAc in pet ether) to afford, tert-butyl 4-((4-chloropyridin-2-yl) amino) piperidine-1-carboxylate (32 mg, 0.103 mmol, 40% yield) as an off-white solid. LCMS (ESI) m/e 312.2 [(M+H)$^+$, calcd for $C_{15}H_{22}ClN_3O_2$ 312.1]; LC/MS retention time (Method A1): $t_R$=2.63 min.

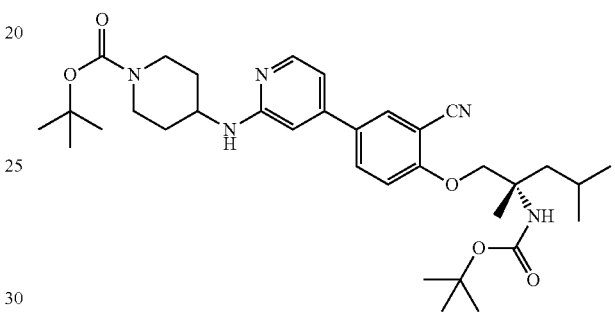

Part B: (S)-Tert-butyl 4-((4-(4-((2-((tert-butoxycarbonyl) amino)-2,4-dimethylpentyl) oxy)-3-cyanophenyl) pyridin-2-yl) amino) piperidine-1-carboxylate A mixture of tert-butyl 4-((4-chloropyridin-2-yl)amino) piperidine-1-carboxylate (0.05 g, 0.160 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (0.088 g, 0.192 mmol), and potassium phosphate tribasic (0.085 g, 0.401 mmol) in THF (5 mL) and water (0.5 mL) was purged with nitrogen gas for 30 min. XPhos 2$^{nd}$ generation precatalyst (7.43 mg, 0.024 mmol) was added to the reaction mixture and the solution was again purged with nitrogen gas for another 10 min. The reaction mixture was heated at 70° C. for 2 h. The reaction mixture was concentrated and the residue dissolved in ethyl acetate (30 mL) and water (30 mL). The biphasic mixture was filtered through diatomaceous earth. The diatomaceous earth was washed with ethyl acetate (50 mL). The ethyl acetate layer was separated and dried over Na$_2$SO$_4$, filtered, and concentrated under reduced pressure to afford (S)-tert-butyl 4-((4-(4-((2-((tert-butoxycarbonyl)amino)-2,4-dimethylpentyl)oxy)-3-cyanophenyl) pyridin-2-yl)amino)piperidine-1-carboxylate (80 mg, 0.026 mmol, 16% yield) as a brown solid which was carried forward without further purification. LCMS (ESI) m/e 608.4 [(M+H)$^+$, calcd for $C_{34}H_{50}N_5O_5$ 608.4]; LC/MS retention time (method B): $t_R$=3.51 min.

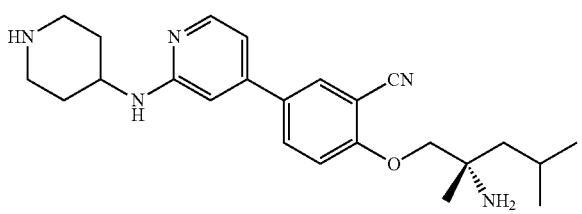 [SMILES: CC(C)C[C@](C)(N)COc1ccc(-c2ccnc(NC3CCNCC3)c2)cc1C#N]

Part C: (S)-2-(2-amino-2,4-dimethylpentyloxy)-5-(2-(piperidin-4-ylamino)pyridin-4-yl)benzonitrile To a solution of (S)-tert-butyl4-((4-(4-((2-((tert-butoxycarbonyl)amino)-2,4-dimethylpentyl)oxy)-3-cyanophenyl) pyridin-2-yl)amino)piperidine-1-carboxylate (60 mg, 0.099 mmol) in DCM (2 mL) at 0° C. was added TFA (0.152 mL, 1.974 mmol) and the mixture stirred for 5 min at 0° C. The reaction mixture was allowed to stir for 4 h at room temperature, then was concentrated under reduced pressure. The crude material was purified by prep LC/MS (method A) to afford (S)-2-(2-amino-2,4-dimethylpentyloxy)-5-(2-(piperidin-4-ylamino) pyridin-4-yl) benzonitrile (17 mg, 0.023 mmol, 23% yield) a pale yellow solid. LCMS (ESI) m/e 408.2 [(M+H)$^+$, calcd for $C_{24}H_{34}N_5O$ 408.3]; LC/MS retention time (method H): $t_R$=0.95 min; LC/MS retention time (method I): $t_R$=0.66 min. $^1$H NMR (400 MHz, Methanol-d$_4$): δ 8.02-8.05 (m, 2H), 7.96-7.99 (m, 1H), 7.37 (d, J=8.80 Hz, 1H), 6.85-6.87 (m, 1H), 6.78 (s, 1H), 4.25-4.30 (m, 2H), 3.45-3.51 (m, 2H), 3.13-3.20 (m, 2H), 2.24-2.29 (m, 2H), 1.86-1.99 (m, 3H), 1.69-1.78 (m, 3H), 1.53 (s, 3H), 1.03-1.08 (m, 6H) ppm.

Example 467

(S)-2,4-dimethyl-1-(4-(pyrazolo[1,5-a]pyrimidin-7-yl)-2-(trifluoromethyl)phenoxy)pentan-2-amine

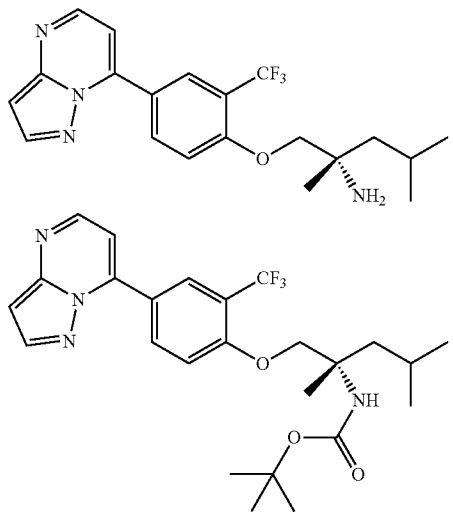

Part A: (S)-Tert-butyl(2,4-dimethyl-1-(4-(pyrazolo [1,5-a]pyrimidin-7-yl)-2-(trifluoromethyl)phenoxy) pentan-2-yl)carbamate A solution of 7-chloropyrazolo[1,5-a]pyrimidine (0.15 g, 0.977 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.588 g, 1.172 mmol), Cs$_2$CO$_3$ (0.955 g, 2.93 mmol), and KBr (0.116 g, 0.977 mmol) in 1,4-dioxane (5 mL) was purged with nitrogen gas for 30 min. PdCl$_2$(dppf)-CH$_2$Cl$_2$ adduct (0.080 g, 0.098 mmol) was added to the reaction mixture and the solution was purged with nitrogen gas again for 10 min. The reaction mixture was heated at 80° C. for 12 h. The reaction mixture was concentrated and the residue obtained was dissolved in ethyl acetate (50 mL) and water (40 mL). The biphasic mixture was filtered through diatomaceous earth and the diatomaceous earth was washed with ethyl acetate (50 mL). The ethyl acetate layer was separated, dried over Na$_2$SO$_4$, filtered, and concentrated under reduced pressure to afford a brown solid which was purified by silica gel column chromatography (0-30% ethyl acetate in pet ether) to afford (S)-tert-butyl (2,4-dimethyl-1-(4-(pyrazolo[1,5-a]pyrimidin-7-yl)-2-(trifluoromethyl)phenoxy)pentan-2-yl)carbamate (0.13 g, 0.264 mmol, 27% yield) as a off-white semi-solid. LCMS (ESI) m/e 493.2 [(M+H)$^+$, calcd for $C_{25}H_{32}F_3N_4O_3$ 493.2]; LC/MS retention time (method B): $t_R$=1.27 min.

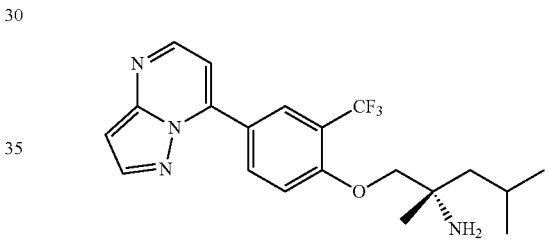

Part B: (S)-2,4-dimethyl-1-(4-(pyrazolo[1,5-a]pyrimidin-7-yl)-2-(trifluoromethyl)phenoxy)pentan-2-amine To a solution of (S)-tert-butyl (2,4-dimethyl-1-(4-(pyrazolo[1,5-a]pyrimidin-7-yl)-2-(trifluoromethyl)phenoxy) pentan-2-yl)carbamate (0.06 g, 0.122 mmol) in DCM (2 mL) at 0° C. was added TFA (0.188 mL, 2.436 mmol) and the mixture stirred for 5 min at 0° C. The reaction mixture was allowed to stir for 4 h at room temperature, then was concentrated under reduced pressure. The crude material was purified by prep LC/MS (method A) to afford (S)-2,4-dimethyl-1-(4-(pyrazolo[1,5-a]pyrimidin-7-yl)-2-(trifluoromethyl)phenoxy)pentan-2-amine, TFA (9 mg. 0.018 mmol, 15% yield) as a pale yellow solid. LCMS (ESI) m/e 393.0 [(M+H)$^+$, calcd for $C_{20}H_{24}F_3N_4O$ 393.2]; LC/MS retention time (method H): $t_R$=1.67 min; LC/MS retention time (method I): $t_R$=1.27 min. $^1$H NMR (400 MHz, DMSO-d$_6$): δ 8.54-8.57 (m, 2H), 8.40-8.42 (m, 1H), 8.23 (d, J=2.40 Hz, 1H), 7.43 (d, J=9.20 Hz, 1H), 7.19 (d, J=4.40 Hz, 1H), 6.79 (d, J=2.40 Hz, 1H), 4.10-4.17 (m, 2H), 1.82-1.88 (m, 1H), 1.58-1.76 (m, 2H), 1.38 (s, 3H), 0.99-1.03 (m, 6H) ppm.

Example 468

(S)-2-(2-amino-2,4-dimethylpentyloxy)-5-(2-(tetrahydro-2H-pyran-4-ylamino)pyridin-4yl)benzonitrile

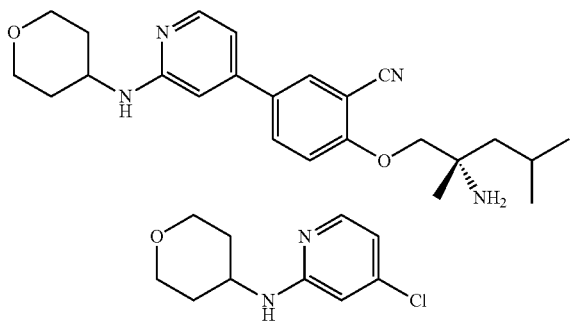

Part A: 4-chloro-N-(tetrahydro-2H-pyran-4-yl) pyridin-2-amine

A mixture of 2-bromo-4-chloropyridine (0.5 g, 2.60 mmol), tetrahydro-2H-pyran-4-amine (0.315 g, 3.12 mmol), $Cs_2CO_3$ (1.693 g, 5.20 mmol), and BINAP (1.618 g, 2.60 mmol) in toluene (30 mL) was purged with nitrogen gas for 30 min and $PdOAc_2$ (0.583 g, 2.60 mmol) was added. The reaction mixture was again purged with nitrogen gas for another 10 min and heated at 80° C. for 12 h. The reaction mixture was cooled to room temperature and was concentrated under reduced pressure. The residue was diluted with water (25 mL) and ethyl acetate (20 mL). The biphasic mixture was filtered through diatomaceous earth. The diatomaceous earth was washed with ethyl acetate (50 mL). The ethyl acetate layer was separated, dried over $Na_2SO_4$, filtered, and concentrated under reduced pressure. The residue was purified by silica gel chromatography (0-30% ethyl acetate in pet ether) to afford 4-chloro-N-(tetrahydro-2H-pyran-4-yl) pyridin-2-amine (150 mg, 0.705 mmol, 27% yield) as colorless oil. LCMS (ESI) m/e 213.2 [(M+H)$^+$, calcd for $C_{10}H_{14}ClN_2O$ 213.1]; LC/MS retention time (Method A1): $t_R$=2.48 min.

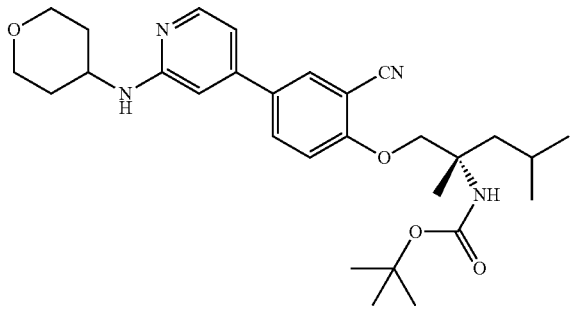 [SMILES: CC(C)C[C@@](C)(COc1ccc(-c2ccnc(NC3CCOCC3)c2)cc1C#N)NC(=O)OC(C)(C)C]

Part B: (S)-tert-butyl (1-(2-cyano-4-(2-((tetrahydro-2H-pyran-4-yl)amino)pyridin-4-yl)phenoxy)-2,4-dimethylpentan-2-yl)carbamate A solution of 4-chloro-N-(tetrahydro-2H-pyran-4-yl)pyridin-2-amine (0.04 g, 0.188 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (0.103 g, 0.226 mmol), and potassium phosphate, tribasic (0.033 g, 0.188 mmol) in THF (5 mL) and water (3 mL) was purged with nitrogen for 5 min. XPhos 2$^{nd}$ generation precatalyst (8.72 mg, 0.028 mmol) was added to the reaction mixture under nitrogen. The reaction mixture was again purged with nitrogen gas for 10 min and was heated at 70° C. for 12 h. The reaction mixture was concentrated and the residue obtained was diluted with water (30 mL) and ethyl acetate (30 mL). The biphasic layer was filtered through diatomaceous earth and the diatomaceous earth bed was washed with ethyl acetate (50 mL). The organic layer was separated, dried over $Na_2SO_4$, filtered, and concentrated to afford (S)-tert-butyl (1-(2-cyano-4-(2-((tetrahydro-2H-pyran-4-yl)amino)pyridin-4-yl)phenoxy)-2,4-dimethylpentan-2-yl)carbamate (60 mg, 0.118 mmol, 63% yield) as a brown solid which was carried forward without further purification. LCMS (ESI) m/e 509.2 [(M+H)$^+$, calcd for $C_{29}H_{41}N_4O_4$ 509.3]; LC/MS retention time (Method C): $t_R$=1.28 min.

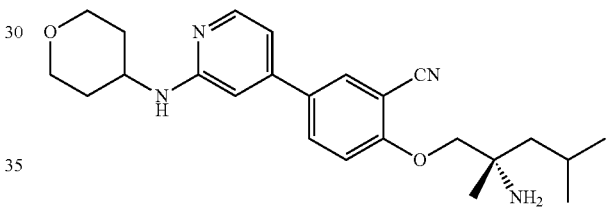

Part C: (S)-2-(2-amino-2,4-dimethylpentyloxy)-5-(2-(tetrahydro-2H-pyran-4-ylamino)pyridine-4yl)benzonitrile To a solution of (S)-tert-butyl (1-(2-cyano-4-(2-((tetrahydro-2H-pyran-4-yl)amino)pyridin-4-yl)phenoxy)-2,4-dimethylpentan-2-yl)carbamate (60 mg, 0.118 mmol) in dichloromethane (2 mL) at 0° C. was added TFA (0.182 mL, 2.359 mmol) and the mixture stirred for 5 min at 0° C. The reaction mixture was allowed to stir for 4 h at room temperature, then was concentrated under reduced pressure. The crude material was purified by prep LC/MS (method A) to afford (S)-2-(2-amino-2,4-dimethylpentyloxy)-5-(2-(tetrahydro-2H-pyran-4-ylamino)pyridine-4yl)benzonitrile (64.1 mg, 0.099 mmol, 84% yield) as a pale yellow solid. LCMS (ESI) m/e 409.2 [(M+H)$^+$, calcd for $C_{24}H_{33}N_4O_2$ 409.2]; LC/MS retention time (method H): $t_R$=1.35 min; LC/MS retention time (method I): $t_R$=0.82 min. $^1$H NMR (400 MHz, DMSO-d$_6$): δ 8.19 (d, J=2.40 Hz, 1H), 8.09-8.11 (m, 1H), 7.92 (d, J=6.40 Hz, 1H), 7.45 (d, J=8.80 Hz, 1H), 7.16-7.20 (m, 2H), 4.33 (s, 2H), 3.98-4.03 (m, 2H), 3.90-3.96 (m, 1H), 3.54-3.60 (m, 2H), 1.86-2.04 (m, 4H), 1.65-1.75 (m, 3H), 1.54 (s, 3H), 1.03-1.08 (m, 6H) ppm.

Example 470

(S)-4-(4-(2-amino-2,4-dimethylpentyloxy)-3-(trifluoromethyl)phenyl)-N-(piperidin-4-yl)pyridin-2-amine

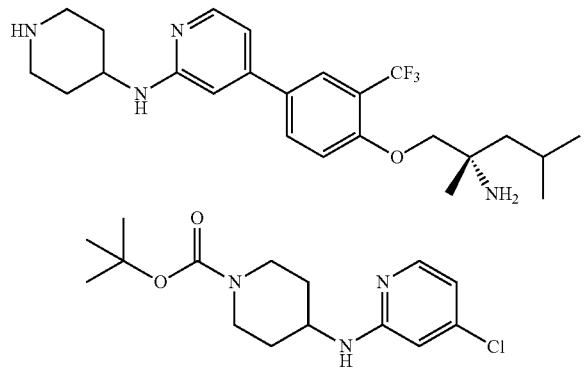

Part A: tert-butyl 4-((4-chloropyridin-2-yl) amino) piperidine-1-carboxylate A mixture of 2-bromo-4-chloropyridine (0.05 g, 0.260 mmol), tert-butyl 4-aminopiperidine-1-carboxylate (0.062 g, 0.312 mmol), tert-butyl 4-aminopiperidine-1-carboxylate (0.062 g, 0.312 mmol), $Cs_2CO_3$ (0.169 g, 0.520 mmol), and BINAP (0.162 g, 0.260 mmol) in toluene (5 mL) was purged with nitrogen gas for 30 min. $PdOAc_2$ (0.058 g, 0.260 mmol) was added to the reaction mixture and again the solution was purged with nitrogen gas for another 10 min. The reaction mixture was heated at 80° C. for 12 h. The reaction mixture was cooled to room temperature and was concentrated under reduced pressure. The residue was diluted with water (20 mL) and ethyl acetate (25 mL). The biphasic mixture was filtered through diatomaceous earth. The diatomaceous earth was washed with ethyl acetate (50 mL). The ethyl acetate layer was separated, dried over $Na_2SO_4$, filtered, and concentrated under reduced pressure to get a brown residue which was purified by silica gel column chromatography (0-30% petroleum ether/ethyl acetate) to afford tert-butyl 4-((4-chloropyridin-2-yl) amino) piperidine-1-carboxylate (32 mg, 0.103 mmol, 40% yield) as an off-white solid. LCMS (ESI) m/e 312.2 [(M+H)$^+$, calcd for $C_{15}H_{23}ClN_3O_2$ 312.1]; LC/MS retention time (Method A1): $t_R$=2.63 min.

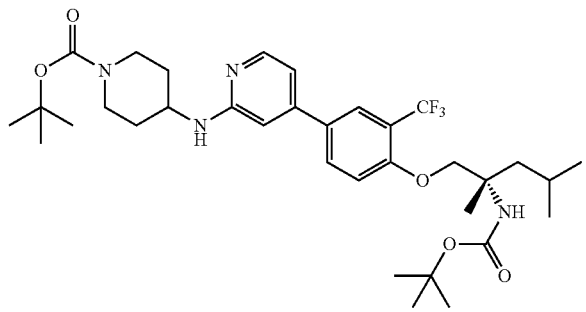 [SMILES: CC(C)C[C@@](C)(COc1ccc(-c2ccnc(NC3CCN(C(=O)OC(C)(C)C)CC3)c2)cc1C(F)(F)F)NC(=O)OC(C)(C)C]

Part B: (S)-tert-butyl 4-((4-(4-((2-((tert-butoxycarbonyl)amino)-2,4-dimethylpentyl) oxy)-3-(trifluoromethyl)phenyl)pyridin-2-yl)amino)piperidine-1-carboxylate A solution of tert-butyl 4-(4-chloropyridin-2-ylamino) piperidine-1-carboxylate (0.035 g, 0.112 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl) carbamate (prepared as described in Example 255, Parts A and B) (0.067 g, 0.134 mmol), and potassium phosphate, tribasic (0.112 mL, 0.559 mmol) in THF (5 mL) was purged with nitrogen gas for 30 min. XPhos $2^{nd}$ generation precatalyst (15 mg, 0.049 mmol) was added to the reaction mixture and again the solution was purged with nitrogen gas for another 10 min. The reaction mixture was heated at 70° C. for 12 h. The reaction mixture was cooled to room temperature and was concentrated under reduced pressure. The residue was diluted with water (20 mL) and ethyl acetate (20 mL). The biphasic mixture was filtered through diatomaceous earth. The diatomaceous earth was washed with ethyl acetate (50 mL). The ethyl acetate layer was separated, dried over $Na_2SO_4$, filtered, and concentrated under reduced pressure to afford the crude product (S)-tert-butyl 4-((4-(4-((2-((tert-butoxycarbonyl)amino)-2,4-dimethylpentyl)oxy)-3-(trifluoromethyl)phenyl)pyridin-2-yl)amino)piperidine-1-carboxylate (60 mg, 0.092 mmol, 82% yield) as a brown solid which was carried forward without further purification. LCMS (ESI) m/e 651.4 [(M+H)$^+$, calcd for $C_{34}H_{50}F_3N_4O_5$ 651.4]; LC/MS retention time (Method C): $t_R$=1.42 min.

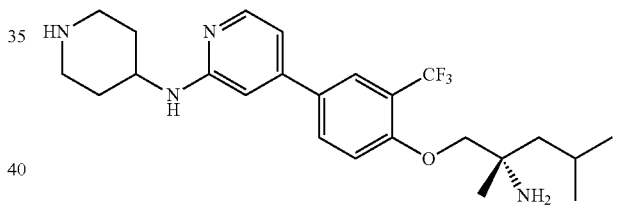

Part C: (S)-4-(4-(2-amino-2,4-dimethylpentyloxy)-3-(trifluoromethyl) phenyl)-N-(piperidin-4-yl) pyridin-2-amine To a solution of (S)-tert-butyl 4-((4-(4-((2-((tert-butoxycarbonyl)amino)-2,4-dimethylpentyl)oxy)-3-(trifluoromethyl)phenyl)pyridin-2-yl)amino)piperidine-1-carboxylate (30 mg, 0.046 mmol) in dichloromethane (2 mL) at 0° C. was added TFA (0.071 mL, 0.922 mmol) and the mixture stirred for 5 min at 0° C. The reaction mixture was allowed to stir for 4 h at room temperature, then was concentrated under reduced pressure. The crude material was purified by preparative LC/MS (method B) to afford (S)-4-(4-(2-amino-2,4-dimethylpentyloxy)-3-(trifluoromethyl)phenyl)-N-(piperidin-4-yl)pyridin-2-amine (1.5 mg, 1.94 umol, 4% yield) as a pale yellow solid. LCMS (ESI) m/e 451.2 [(M+H)$^+$, calcd for $C_{24}H_{34}F_3N_4O$ 451.2]; LC/MS retention time (method H): $t_R$=1.21 min; LC/MS retention time (method I): $t_R$=0.93 min. $^1$H NMR (400 MHz, Methanol-$d_4$): δ 8.02-8.08 (m, 3H), 7.47 (d, J=8.80 Hz, 1H), 7.14-7.18 (m, 2H), 4.26-4.34 (m, 2H), 4.09-4.13 (m, 1H), 3.50-3.56 (m, 2H), 3.15-3.24 (m, 2H), 2.30-2.34 (m, 2H), 1.85-1.93 (m, 4H), 1.72-1.77 (m, 1H), 1.55 (s, 3H), 1.03-1.08 (m, 6H) ppm.

Example 471

(S)-1-(4-(6,7-difluoroquinazolin-4-yl)-2-(trifluoromethyl)phenoxy)-2,4-dimethylpentan-2-amine

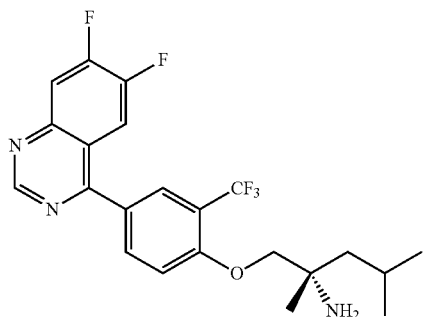

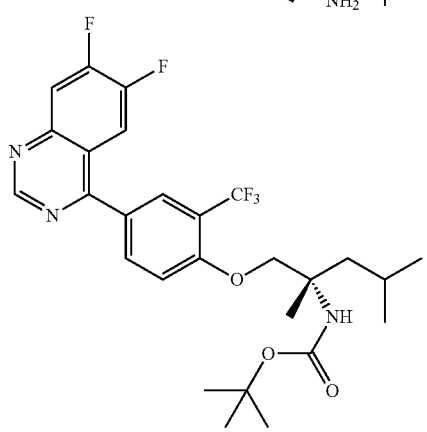

Part A: (S)-tert-butyl 1-(4-(6,7-difluoroquinazolin-4-yl)-2-(trifluoromethyl)phenoxy)-2,4-dimethylpentan-2-ylcarbamate A mixture of 4-chloro-6,7-difluoroquinazoline (0.04 g, 0.199 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.120 g, 0.239 mmol), potassium phosphate, tribasic (0.127 g, 0.598 mmol), and 2-dicyclohexylphosphino-2',6'-dimethoxybiphenyl (0.041 g, 0.100 mmol) in toluene (4 mL) was purged with nitrogen gas for 30 min and $Pd_2(dba)_3$ (0.046 g, 0.050 mmol) was added. The reaction mixture was again purged with nitrogen gas for 10 min and heated in a microwave at 110° C. for 1.5 h. The reaction mixture was cooled to room temperature and was concentrated under reduced pressure. The residue was diluted with water (20 mL) and ethyl acetate (20 mL). The biphasic mixture was filtered through diatomaceous earth. The diatomaceous earth was washed with ethyl acetate (50 mL). The ethyl acetate layer was separated, dried over $Na_2SO_4$, filtered, and concentrated under reduced pressure to afford (S)-tert-butyl 1-(4-(6,7-difluoroquinazolin-4-yl)-2-(trifluoromethyl)phenoxy)-2,4-dimethylpentan-2-ylcarbamate (52 mg, 0.096 mmol, 48% yield) as a brown solid. The solid was carried forward without further purification. LCMS (ESI) m/e 540.2 [(M+H)$^+$, calcd for $C_{27}H_{31}F_5N_3O_3$ 540.2]; LC/MS retention time (Method A1): $t_R$=3.11 min.

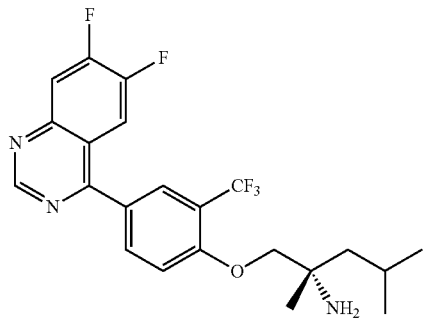 [SMILES: CC(C)C[C@](C)(N)COc1ccc(-c2ncnc3cc(F)c(F)cc23)cc1C(F)(F)F]

Part B: (S)-1-(4-(6,7-difluoroquinazolin-4-yl)-2-(trifluoromethyl)phenoxy)-2,4-dimethylpentan-2-amine To a solution of (S)-tert-butyl (1-(4-(6,7-difluoroquinazolin-4-yl)-2-(trifluoromethyl)phenoxy)-2,4-dimethylpentan-2-yl)carbamate (52 mg, 0.096 mmol) in dichloromethane (2 mL) at 0° C. was added TFA (0.149 mL, 1.928 mmol) and the mixture stirred for 5 min at 0° C. The reaction mixture was allowed to stir for 4 h at room temperature, then was concentrated under reduced pressure. The crude material was purified by prep LC/MS (method C) to afford (S)-1-(4-(6,7-difluoroquinazolin-4-yl)-2-(trifluoromethyl)phenoxy)-2,4-dimethylpentan-2-amine (1.5 mg, 0.003 mmol, 3% yield) as a pale yellow solid. LCMS (ESI) m/e 440.0 [(M+H)$^+$, calcd for $C_{22}H_{23}F_5N_3O$ 440.2]; LC/MS retention time (method H): $t_R$=2.02 min; LC/MS retention time (method I): $t_R$=1.46 min. $^1$H NMR (400 MHz, Methanol-d4): δ 9.29 (s, 1H), 8.08-8.14 (m, 2H), 7.96-8.01 (m, 2H), 7.49 (d, J=8.80 Hz, 1H), 4.18-4.25 (m, 2H), 1.76-1.89 (m, 2H), 1.64-1.69 (m, 1H), 1.45 (s, 3H), 1.05-1.08 (m, 6H) ppm.

Example 472

(S)-2,4-dimethyl-1-(2-methyl-4-(pyrazolo[1,5-a]pyrimidin-7-yl)phenoxy)pentan-2-amine

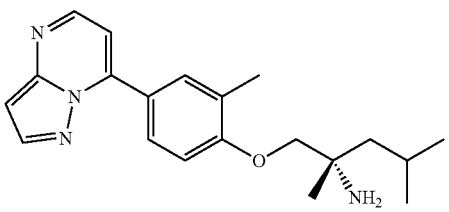

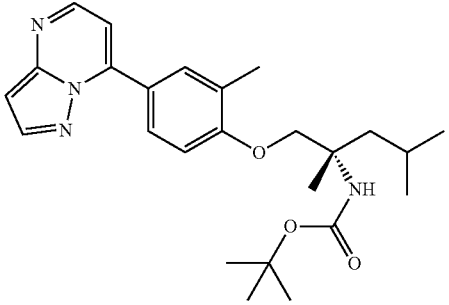

Part A: (S)-Tert-butyl (2,4-dimethyl-1-(2-methyl-4-(pyrazolo[1,5-a]pyrimidin-7-yl)phenoxy)pentan-2-yl)carbamate A solution of 7-chloropyrazolo[1,5-a]pyrimidine (0.05 g, 0.326 mmol), (S)-tert-butyl (2,4-dimethyl-1-(2-methyl-4-(4,4,5,5-tetramethyl-1,3,2-dioxaborolan-2-yl)phenoxy)pentan-2-yl)carbamate (prepared as described in Example 259, Part A and B) (0.146 g, 0.326 mmol), Cs$_2$CO$_3$ (0.212 g, 0.651 mmol), and KBr (0.039 g, 0.326 mmol) in 1,4-dioxane (10 mL) was purged with nitrogen gas for 30 min. PdCl$_2$(dppf)-CH$_2$Cl$_2$ adduct (0.027 g, 0.033 mmol) was added to the reaction mixture and the solution was purged with nitrogen gas again for 10 min. The reaction mixture was heated at 80° C. for 12 h. The reaction mixture was concentrated and the residue obtained was dissolved in ethyl acetate (30 mL) and water (30 mL). The biphasic mixture was filtered through diatomaceous earth. The diatomaceous earth was washed with ethyl acetate (50 mL). The ethyl acetate layer was separated, dried over Na$_2$SO$_4$, filtered, and concentrated under reduced pressure to afford a brown solid which was purified by silica-gel column chromatography (0-40% EtOAc in pet ether) to afford (S)-tert-butyl (2,4-dimethyl-1-(2-methyl-4-(pyrazolo[1,5-a]pyrimidin-7-yl)phenoxy)pentan-2-yl)carbamate (40 mg, 0.091 mmol, 28% yield) as a light yellow semi-solid. LCMS (ESI) m/e 439.4 [(M+H)$^+$, calcd for C$_{25}$H$_{35}$N$_4$O$_3$ 439.3]; LC/MS retention time (Method A1): t$_R$=2.60 min.

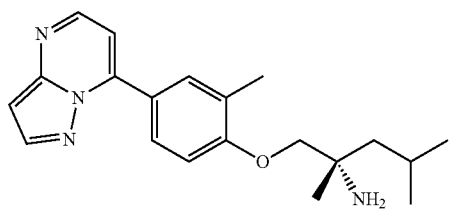

Part B: (S)-2,4-dimethyl-1-(2-methyl-4-(pyrazolo[1,5-a]pyrimidin-7-yl)phenoxy)pentan-2-amine To a solution of (S)-tert-butyl (2,4-dimethyl-1-(2-methyl-4-(pyrazolo[1,5-a]pyrimidin-7-yl)phenoxy)pentan-2-yl)carbamate (35 mg, 0.080 mmol) in DCM (2 mL) at 0° C. was added TFA (0.123 mL, 1.596 mmol) and the mixture stirred for 5 min at 0° C. The reaction mixture was allowed to stir for 4 h at room temperature, then was concentrated under reduced pressure. The crude material was purified by prep LC/MS (method C) to afford (S)-2,4-dimethyl-1-(2-methyl-4-(pyrazolo[1,5-a]pyrimidin-7-yl)phenoxy)pentan-2-amine, TFA (11 mg. 0.024 mmol, 30% yield) as a pale yellow solid. LCMS (ESI) m/e 339.2 [(M+H)$^+$, calcd for C$_{20}$H$_{27}$N$_4$O 339.2]; LC/MS retention time (method H): t$_R$=2.03 min. $^1$H NMR (400 MHz, Methanol-d4): δ 8.52 (d, J=4.40 Hz, 1H), 8.19 (d, J=2.40 Hz, 1H), 7.99-8.04 (m, 2H), 7.09-7.16 (m, 2H), 6.76 (d, J=2.40 Hz, 1H), 4.02-4.09 (m, 2H), 2.40 (s, 3H), 1.75-1.88 (m, 2H), 1.61-1.66 (m, 1H), 1.42 (s, 3H), 1.00-1.05 (m, 6H) ppm.

Example 473

(S)-2,4-dimethyl-1-(4-(pyrazolo[1,5-a]pyrimidin-3-yl)-2-(trifluoromethyl)phenoxy)pentan-2-amine

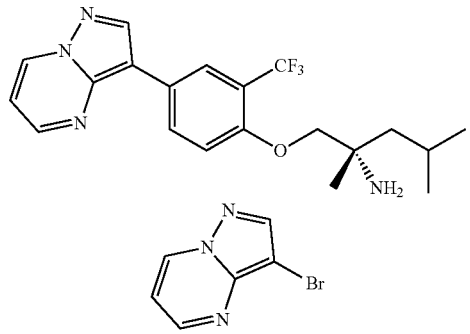

Part A: 3-bromopyrazolo[1,5-a]pyrimidine

To a solution of pyrazolo[1,5-a]pyrimidine (1 g, 8.39 mmol) in acetonitrile (5 mL) was added NBS (1.494 g, 8.39 mmol) and the reaction mixture stirred at room temperature for 8 h. The reaction mixture was concentrated under reduced pressure and the residue purified by silica gel chromatography (0-30% petroleum ether/EtOAc) to afford 3-bromopyrazolo[1,5-a]pyrimidine (1.2 g, 6.06 mmol, 72% yield) as a brown solid. LCMS (ESI) m/e 198.0 [(M+H)$^+$, calcd for C$_6$H$_5$BrN$_3$ 198.0]; LC/MS retention time (method A2): t$_R$=1.43 min.

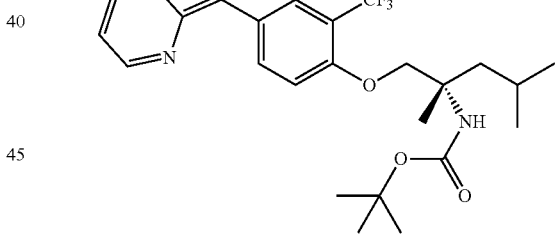

Part B: (S)-Tert-butyl (2,4-dimethyl-1-(4-(pyrazolo[1,5-a]pyrimidin-3-yl)-2-(trifluoromethyl)phenoxy)pentan-2-yl)carbamate A solution of 3-bromopyrazolo[1,5-a]pyrimidine (0.04 g, 0.202 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.122 g, 0.242 mmol), and potassium phosphate tribasic (0.106 g, 0.606 mmol) in THF (5 mL) and water (0.5 mL) was purged with nitrogen gas for 30 min. XPhos 2$^{nd}$ generation precatalyst (9.37 mg, 0.030 mmol) was added to the reaction mixture and the solution was purged with nitrogen gas again for 10 min. The reaction mixture was heated at 80° C. for 12 h. The reaction mixture was concentrated and the residue obtained was dissolved in ethyl acetate (30 mL) and water (30 mL). The biphasic mixture was filtered through diatomaceous earth and the diatomaceous earth was washed with ethyl acetate (50 mL). The ethyl acetate layer was separated, dried over Na$_2$SO$_4$, filtered, and concentrated under reduced pressure to afford (S)-tert-butyl (2,4-dimethyl-1-(4-(pyrazolo[1,5-a]pyrimidin-3-yl)-2-(trifluoromethyl)phenoxy)pentan-2-yl)carbamate (50 mg, 0.102 mmol, 50% yield) as a brown solid which was carried forward without further purification. LCMS (ESI) m/e 493.3 [(M+H)$^+$, calcd for C$_{25}$H$_{32}$F$_3$N$_4$O$_3$ 493.2]; LC/MS retention time (Method A1): t$_R$=1.83 min.

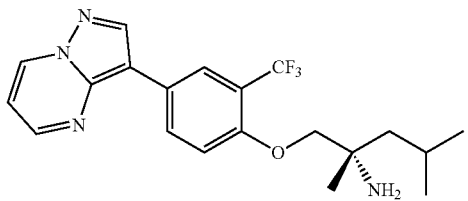 [SMILES: CC(C)C[C@](C)(N)COc1ccc(-c2cnn3cccnc23)cc1C(F)(F)F]

Part C: (S)-2,4-dimethyl-1-(4-(pyrazolo[1,5-a]pyrimidin-3-yl)-2-(trifluoromethyl)phenoxy)pentan-2-amine To a solution of (S)-tert-butyl (2,4-dimethyl-1-(4-(pyrazolo[1,5-a]pyrimidin-3-yl)-2-(trifluoromethyl)phenoxy)pentan-2-yl)carbamate (40 mg, 0.081 mmol) in DCM (2 mL) at 0° C. was added TFA (6.26 μl, 0.081 mmol) and the mixture stirred for 5 min at 0° C. The reaction mixture was allowed to stir for 4 h at room temperature, then was concentrated under reduced pressure. The crude material was purified by prep LC/MS (method B) to afford (S)-2,4-dimethyl-1-(4-(pyrazolo[1,5-a]pyrimidin-3-yl)-2-(trifluoromethyl)phenoxy)pentan-2-amine (10 mg. 0.024 mmol, 30% yield) as a pale yellow solid. LCMS (ESI) m/e 393.2 [(M+H)$^+$, calcd for C$_{20}$H$_{24}$F$_3$N$_4$O 393.2]; LC/MS retention time (method H): t$_R$=1.63 min. $^1$H NMR (400 MHz, Methanol-d4): δ 8.95-8.98 (m, 1H), 8.67-8.68 (m, 1H), 8.62 (s, 1H), 8.51 (d, J=2.00 Hz, 1H), 8.33-8.36 (m, 1H), 7.36 (d, J=8.80 Hz, 1H), 7.07-7.10 (m, 1H), 4.19-4.28 (m, 2H), 1.88-1.93 (m, 2H), 1.70-1.76 (m, 1H), 1.55 (s, 3H), 1.04-1.09 (m, 6H) ppm.

Example 475

4-(4-((S)-2-amino-2,4-dimethylpentyloxy)-3-(trifluoromethyl)phenyl)-N-(tetrahydro-2H-pyran-3-yl)pyridin-2-amine

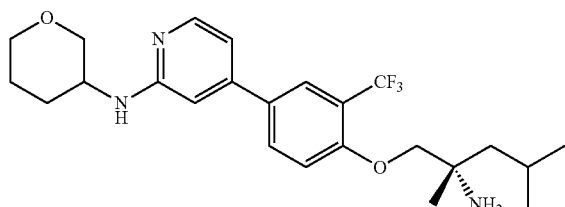

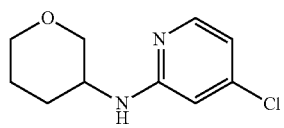

Part A: 4-chloro-N-(tetrahydro-2H-pyran-3-yl)pyridin-2-amine

To a solution of 4-chloro-2-fluoropyridine (0.5 g, 3.80 mmol), tetrahydro-2H-pyran-3-amine (0.461 g, 4.56 mmol) in DMSO (5 mL) was added Cs$_2$CO$_3$ (2.477 g, 7.60 mmol) and the reaction mixture was heated in a microwave at 90° C. for 2 h. The reaction mixture was allowed to cool to 0° C. and quenched with ice-water then extracted with ethyl acetate (30 mL). The aqueous layer was again extracted with ethyl acetate (2×30 mL). The combined organic layers were washed with water (20 mL) and brine (20 mL), dried over Na$_2$SO$_4$, and concentrated under reduced pressure. The residue was purified by silica gel chromatography (0-30% ethyl acetate in pet ether) to afford 4-chloro-N-(tetrahydro-2H-pyran-3-yl)pyridin-2-amine (0.35, 1.646 mmol, 43% yield) as a light yellow oil. $^1$H NMR (400 MHz, DMSO-d$_6$): δ 7.92 (d, J=7.20 Hz, 1H), 6.74 (d, J=9.60 Hz, 1H), 6.52-6.56 (m, 2H), 3.81-3.88 (m, 2H), 3.66-3.73 (m, 1H), 3.31-3.39 (m, 1H), 3.08-3.15 (m, 1H), 1.85-1.95 (m, 1H), 1.67-1.74 (m, 1H), 1.45-1.60 (m, 2H) ppm.

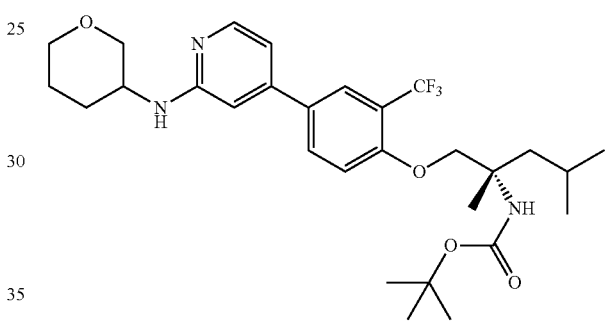

Part B: Tert-butyl ((2S)-2,4-dimethyl-1-(4-(2-((tetrahydro-2H-pyran-3-yl) amino)pyridin-4-yl)-2-(trifluoromethyl)phenoxy)pentan-2-yl)carbamate A mixture of 4-chloro-N-(tetrahydro-2H-pyran-3-yl)pyridin-2-amine (0.04 g, 0.188 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl) (prepared as described in Example 255, Parts A and B) (0.113 g, 0.226 mmol), and potassium phosphate, tribasic (0.033 g, 0.188 mmol) in 1,4-dioxane (8 mL) and water (2 mL) was purged with nitrogen gas for 30 min. XPhos 2$^{nd}$ generation precatalyst (8.72 mg, 0.028 mmol) was added to the reaction mixture and again the solution was purged with nitrogen gas for 10 min and heated at 100° C. for 2 h. The reaction mixture was concentrated under reduced pressure and the residue was dissolved in ethyl acetate (30 mL) and water (30 mL). The biphasic mixture was filtered through diatomaceous earth. The diatomaceous earth was washed with ethyl acetate (50 mL). The ethyl acetate layer was separated and dried over Na$_2$SO$_4$, filtered, and concentrated under reduced pressure to afford tert-butyl ((2S)-2,4-dimethyl-1-(4-(2-((tetrahydro-2H-pyran-3-yl)amino)pyridin-4-yl)-2-(trifluoromethyl)phenoxy)pentan-2-yl)carbamate (68 mg, 0.123 mmol, 66% yield) as a brown solid which was carried forward without further purification. LCMS (ESI) m/e 552.2 [(M+H)$^+$, calcd for C$_{29}$H$_{41}$F$_3$N$_3$O$_4$ 552.3]; LC/MS retention time (Method A1): t$_R$=2.86 min.

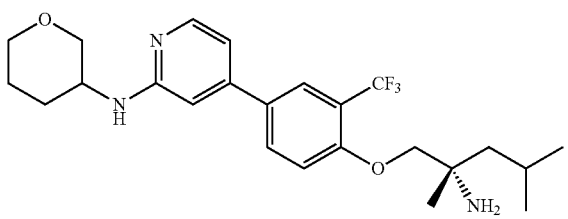 [SMILES: CC(C)C[C@](C)(N)COc1ccc(-c2ccnc(NC3CCCOC3)c2)cc1C(F)(F)F]

Part C: 4-(4-((S)-2-amino-2,4-dimethylpentyloxy)-3-(trifluoromethyl)phenyl)-N-(tetrahydro-2H-pyran-3-yl)pyridin-2-amine To a solution of tert-butyl((2S)-2,4-dimethyl-1-(4-(2-((tetrahydro-2H-pyran-3-yl)amino)pyridin-4-yl)-2-(trifluoromethyl)phenoxy)pentan-2-yl)carbamate (50 mg, 0.091 mmol) in DCM (2 mL) at 0° C. was added TFA (0.140 mL, 1.813 mmol) and the mixture stirred for 5 min at 0° C. The reaction mixture was allowed to stir for 4 h at room temperature, then was concentrated under reduced pressure. The crude material was purified by prep LC/MS (method C) to afford 4-(4-((S)-2-amino-2,4-dimethylpentyloxy)-3-(trifluoromethyl)phenyl)-N-(tetrahydro-2H-pyran-3-yl)pyridin-2-amine (20 mg, 0.044 mmol, 48% yield) as a pale yellow solid. LCMS (ESI) m/e 452.2 [(M+H)$^+$, calcd for $C_{24}H_{33}F_3N_3O_2$ 452.2]; LC/MS retention time (method H): $t_R$=1.87 min. $^1$H NMR (400 MHz, Methanol-d4): δ 7.87-7.99 (m, 3H), 7.31 (d, J=8.40 Hz, 1H), 6.77-6.82 (m, 2H), 3.92-4.12 (m, 4H), 3.77-3.81 (m, 1H), 3.51-3.54 (m, 1H), 1.98-2.07 (m, 3H), 1.58-1.85 (m, 5H), 1.38 (s, 3H), 0.98-1.03 (m, 6H) ppm.

Examples 476 and 477

4-(4-(((S)-2-amino-2,4-dimethylpentyl)oxy)-3-(trifluoromethyl)phenyl)-N-(tetrahydro-2H-pyran-3-yl)pyridin-2-amine and 4-(4-(((S)-2-amino-2,4-dimethylpentyl)oxy)-3-(trifluoromethyl)phenyl)-N-(tetrahydro-2H-pyran-3-yl)pyridin-2-amine Dia 1

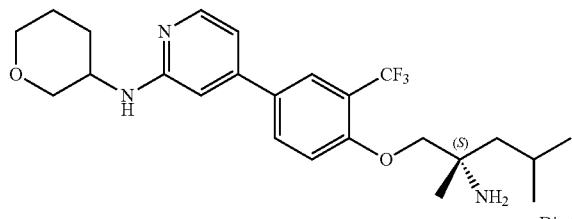

Dia 2

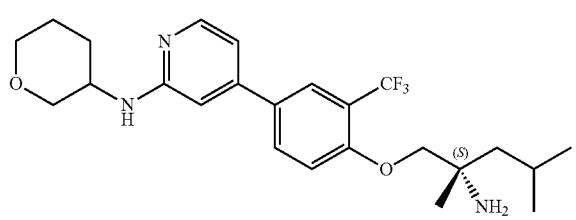

Racemic 4-(4-(((S)-2-amino-2,4-dimethylpentyl)oxy)-3-(trifluoromethyl)phenyl)-N-(tetrahydro-2H-pyran-3-yl)pyridin-2-amine (12 mg. 0.026 mmol) prepared in Example 475 was resolved by Chiral HPLC (Method A) to afford two diastereomers. The absolute stereochemistry of the pyran linkage was not determined.

Diastereomer: 1

Part B: 4-(4-(((S)-2-amino-2,4-dimethylpentyl)oxy)-3-(trifluoromethyl)phenyl)-N-(tetrahydro-2H-pyran-3-yl)pyridin-2-amine (1 mg. 2.148 µmol, 8% yield) as a pale yellow solid. LCMS (ESI) m/e 452.2 [(M+H)$^+$, calcd for $C_{24}H_{33}F_3N_3O_2$ 452.2]; LC/MS retention time (method A1): $t_R$=1.95 min. HPLC purity: 98%; HPLC retention time (method A): $t_R$=5.49 min. $^1$H NMR (400 MHz, Methanol-d4): δ 7.90-8.00 (m, 1H), 7.86-7.90 (m, 2H), 7.30 (d, J=8.40 Hz, 1H), 6.76-6.82 (m, 2H), 3.94-4.07 (m, 4H), 3.48-3.81 (m, 2H), 2.03-2.11 (m, 1H), 1.80-1.85 (m, 2H), 1.55-1.69 (m, 5H), 1.34 (s, 3H), 0.88-0.99 (m, 6H) ppm.

Diastereomer: 2

4-(4-(((S)-2-amino-2,4-dimethylpentyl)oxy)-3-(trifluoromethyl)phenyl)-N-(tetrahydro-2H-pyran-3-yl)pyridin-2-amine (4 mg. 8.59 mmol, 33% yield) as a pale yellow solid. LCMS (ESI) m/e 452.2 [(M+H)$^+$, calcd for $C_{24}H_{33}F_3N_3O_2$ 452.2]; LC/MS retention time (method A1): $t_R$=1.95 min. HPLC purity: 98%; HPLC retention time (method A): $t_R$=5.49 min. $^1$H NMR (400 MHz, Methanol-d4): δ 7.96-8.00 (m, 1H), 7.85-7.89 (m, 1H), 7.28 (d, J=8.00 Hz, 1H), 6.96 (s, 1H), 6.76-6.81 (m, 2H), 3.94-4.05 (m, 4H), 3.47-3.81 (m, 2H), 2.01-2.09 (m, 1H), 1.76-1.85 (m, 2H), 1.55-1.75 (m, 5H), 1.41 (s, 3H), 0.92-1.01 (m, 6H) ppm.

Example 478

(S)-3-(5-((2-amino-2,4-dimethylpentyl)oxy)-6-methylpyridin-2-yl)pyrazolo[1,5-a]pyrimidine-6-carbonitrile

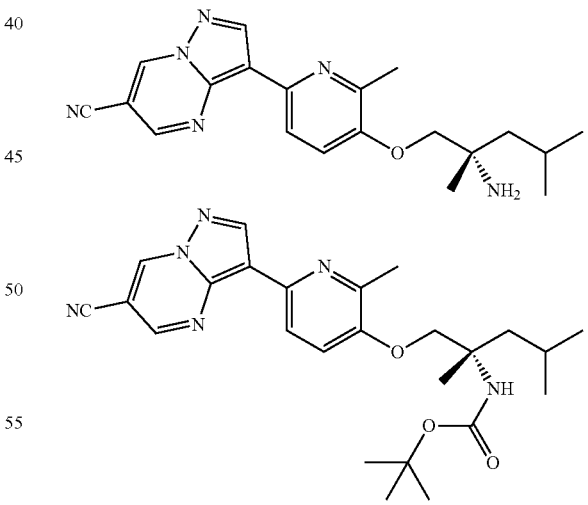

Part A: (S)-Tert-butyl (1-((6-(6-cyanopyrazolo[1,5-a]pyrimidin-3-yl)-2-methylpyridin-3-yl) oxy)-2,4-dimethylpentan-2-yl)carbamate A solution of 3-(4,4,5,5-tetramethyl-1,3,2-dioxaborolan-2-yl)pyrazolo[1,5-a]pyrimidine-6-carbonitrile (0.04 g, 0.148 mmol), (S)-tert-butyl (1-((6-iodo-2-methylpyridin-3-yl)

oxy)-2,4-dimethylpentan-2-yl)carbamate (prepared as described in Example 343) (0.080 g, 0.178 mmol), and Cs$_2$CO$_3$ (0.04 g, 0.148 mmol) in 1,4-dioxane (5 mL) and water (0.5 mL) was purged with nitrogen gas for 30 min. PdCl$_2$ (dppf)-CH$_2$Cl$_2$ adduct (0.121 g, 0.148 mmol) was added to the reaction mixture and the solution was purged with nitrogen gas again for 10 min. The reaction mixture was heated at 100° C. for 12 h. The reaction mixture was concentrated and the residue obtained was dissolved in ethyl acetate (30 mL) and water (30 mL). The biphasic mixture was filtered through diatomaceous earth and the diatomaceous earth was washed with ethyl acetate (50 mL). The ethyl acetate layer was separated, dried over Na$_2$SO$_4$, filtered, and concentrated under reduced pressure to afford as a brown solid which was purified by silica gel chromatography (0-30% ethyl acetate in pet ether) to afford (S)-tert-butyl (1-((6-(6-cyanopyrazolo[1,5-a]pyrimidin-3-yl)-2-methylpyridin-3-yl)oxy)-2,4-dimethylpentan-2-yl) carbamate (10 mg, 0.022 mmol, 15% yield) as a light yellow solid. LCMS (ESI) m/e 465.2 [(M+H)$^+$, calcd for C$_{25}$H$_{33}$N$_6$O$_3$ 465.2]; LC/MS retention time (Method A1): t$_R$=2.70 min.

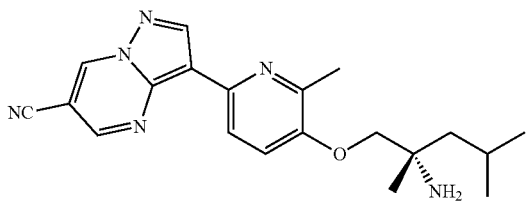 [SMILES: Cc1nc(-c2cnn3cc(C#N)cnc23)ccc1OC[C@@](C)(N)CC(C)C]

Part B: (S)-3-(5-((2-amino-2,4-dimethylpentyl)oxy)-6-methylpyridin-2-yl)pyrazolo[1,5-a]pyrimidine-6-carbonitrile To a solution of (S)-tert-butyl (1-((6-(6-cyanopyrazolo[1,5-a]pyrimidin-3-yl)-2-methylpyridin-3-yl)oxy)-2,4-dimethylpentan-2-yl)carbamate (40 mg, 0.086 mmol) in DCM (2 mL) at 0° C. was added TFA (6.63 µl, 0.086 mmol) and the mixture stirred for 5 min at 0° C. The reaction mixture was allowed to stir for 4 h at room temperature, then was concentrated under reduced pressure. The crude material was purified by prep LC/MS (method A) to afford (S)-3-(5-((2-amino-2,4-dimethylpentyl)oxy)-6-methylpyridin-2-yl)pyrazolo[1,5-a]pyrimidine-6-carbonitrile (1 mg. 2.74 µmol, 3% yield) as a pale yellow solid. LCMS (ESI) m/e 365.2 [(M+H)$^+$, calcd for C$_{20}$H$_{25}$N$_6$O 365.2]; LC/MS retention time (method H): t$_R$=1.27 min; LC/MS retention time (method I): t$_R$=0.80 min. $^1$H NMR (400 MHz, Methanol-d4): δ 9.67 (d, J=2.40 Hz, 1H), 8.95 (s, 1H), 8.79 (s, 1H), 8.31 (d, J=8.40 Hz, 1H), 7.48 (d, J=8.40 Hz, 1H), 4.03-4.11 (m, 2H), 2.61 (s, 3H), 1.79-1.90 (m, 2H), 1.65-1.70 (m, 1H), 1.46 (s, 3H), 1.03-1.08 (m, 6H) ppm.

Example 481

(S)-2,4-dimethyl-1-(4-(2-methylthieno[2,3-d]pyrimidin-4-yl)-2-(trifluoromethyl)phenoxy)pentan-2-amine

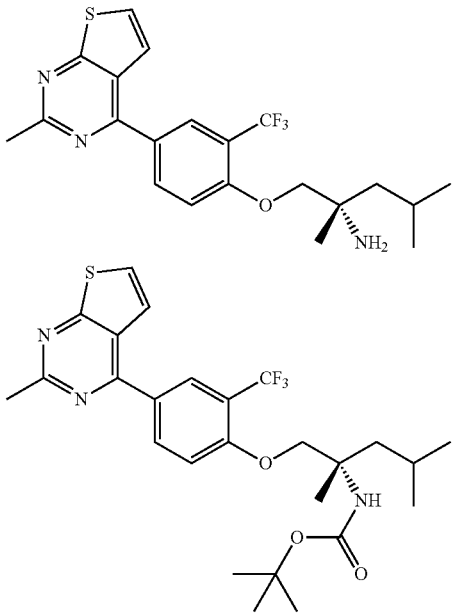

Part A: (S)-tert-butyl (2,4-dimethyl-1-(4-(2-methylthieno[2,3-d]pyrimidin-4-yl)-2-(trifluoromethyl)phenoxy)pentan-2-yl)carbamate A solution of 4-chloro-2-methylthieno[2,3-d]pyrimidine (0.03 g, 0.162 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl)carbamate (prepared as described in Example 255, Parts A and B) (0.090 g, 0.179 mmol), Cs$_2$CO$_3$ (0.159 g, 0.487 mmol), and KBr (0.019 g, 0.162 mmol) in 1,4-dioxane (10 mL) was purged with nitrogen gas for 30 min. PdCl$_2$ (dppf)-CH$_2$Cl$_2$ adduct (0.013 g, 0.016 mmol) was added to the reaction mixture and the solution was purged with nitrogen gas again for 10 min. The reaction mixture was heated at 80° C. for 12 h. The reaction mixture was concentrated and the residue obtained was dissolved in ethyl acetate (20 mL) and water (20 mL). The biphasic mixture was filtered through diatomaceous earth (Diatomaceous Earth®) and the bed was washed with ethyl acetate (25 mL). The ethyl acetate layer was separated, dried over Na$_2$SO$_4$, filtered, and concentrated under reduced pressure to afford (S)-tert-butyl (2,4-dimethyl-1-(4-(2-methylthieno[2,3-d]pyrimidin-4-yl)-2-(trifluoromethyl)phenoxy)pentan-2-yl)carbamate (crude yield) (0.06 g, 0.115 mmol, 71% yield) as a brown solid which was carried forward without further purification. LCMS (ESI) m/e 524.2 [(M+H)$^+$, calcd for C$_{26}$H$_{33}$F$_3$N$_3$O$_3$S 524.2]; LC/MS retention time (Method C): t$_R$=1.60 min.

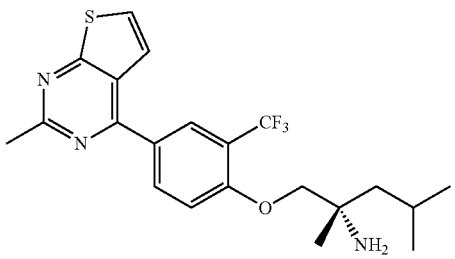 [SMILES: Cc1nc(-c2ccc(OC[C@@](C)(N)CC(C)C)c(C(F)(F)F)c2)c2ccsc2n1]

Part B: (S)-2,4-dimethyl-1-(4-(2-methylthieno[2,3-d]pyrimidin-4-yl)-2-(trifluoromethyl)phenoxy)pentan-2-amine To a solution of (S)-tert-butyl (2,4-dimethyl-1-(4-(2-methylthieno[2,3-d]pyrimidin-4-yl)-2-(trifluoromethyl)phenoxy)pentan-2-yl)carbamate (0.03 g, 0.057 mmol) in DCM (2 mL) at 0° C. was added TFA (0.088 mL, 1.146 mmol) and the mixture stirred for 5 min at 0° C. The reaction mixture was allowed to stir for 4 h at room temperature, then was concentrated under reduced pressure. The crude material was purified by prep LC/MS (method C) to afford (S)-2,4-dimethyl-1-(4-(2-methylthieno[2,3-d]pyrimidin-4-yl)-2-(trifluoromethyl)phenoxy)pentan-2-amine (6 mg. 0.014 mmol, 24% yield) as a pale yellow solid. LCMS (ESI) m/e 424.2 [(M+H)$^+$, calcd for $C_{21}H_{25}F_3N_3OS$ 424.2]; LC/MS retention time (method H): $t_R$=2.83 min; LC/MS retention time (method I): $t_R$=2.08 min. $^1$H NMR (400 MHz, Methanol-d4: δ 8.26-8.29 (m, 2H), 7.80 (d, J=6.00 Hz, 1H), 7.63 (d, J=6.00 Hz, 1H), 7.46 (d, J=8.00 Hz, 1H), 4.14-4.21 (m, 2H), 2.86 (s, 3H), 1.85-1.91 (m, 1H), 1.62-1.78 (m, 2H), 1.42 (s, 3H), 1.02-1.06 (m, 6H) ppm.

Example 482

(S)-1-(2-chloro-4-(2-cyclopropylpyrazolo[1,5-a]pyrimidin-7-yl)phenoxy)-2,4-dimethylpentan-2-amine

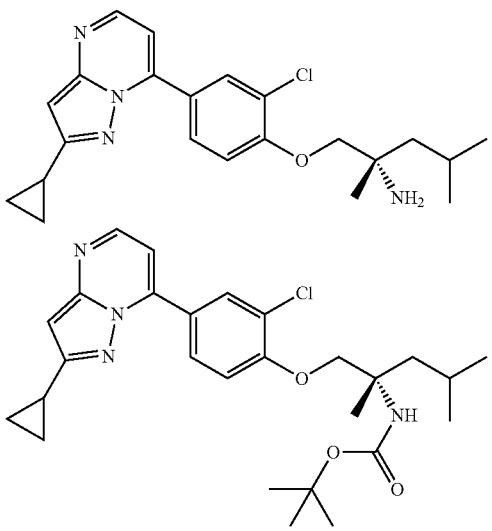

Part D: (S)-tert-butyl (1-(2-chloro-4-(2-cyclopropylpyrazolo[1,5-a]pyrimidin-7-yl)phenoxy)-2,4-dimethylpentan-2-yl)carbamate A solution of 7-chloro-2-cyclopropylpyrazolo[1,5-a]pyrimidine (prepared as described in Example 266, Parts A-C) (40 mg, 0.207 mmol), (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (97 mg, 0.207 mmol), $Cs_2CO_3$ (135 mg, 0.413 mmol), and KBr (24.58 mg, 0.207 mmol) in 1,4-dioxane (10 mL) was purged with nitrogen gas for 30 min. $PdCl_2$ (dppf)-$CH_2Cl_2$ adduct (16.87 mg, 0.021 mmol) was added to the reaction mixture and the solution was purged with nitrogen gas again for 10 min. The reaction mixture was heated at 100° C. for 12 h. The reaction mixture was concentrated and the residue obtained was dissolved in ethyl acetate (30 mL) and water (30 mL). The biphasic mixture was filtered through diatomaceous earth (Diatomaceous Earth®) and the bed was washed with ethyl acetate (50 mL). The ethyl acetate layer was separated, dried over $Na_2SO_4$, filtered, and concentrated under reduced pressure to afford (S)-tert-butyl (1-(2-chloro-4-(2-cyclopropylpyrazolo[1,5-a]pyrimidin-7-yl)phenoxy)-2,4-dimethylpentan-2-yl)carbamate (60 mg, 0.064 mmol, 31% yield) as a brown solid which was carried forward without further purification. LCMS (ESI) m/e 499.2 [(M+H)$^+$, calcd for $C_{27}H_{36}ClN_4O_3$ 499.2]; LC/MS retention time (Method A1): $t_R$=2.85 min.

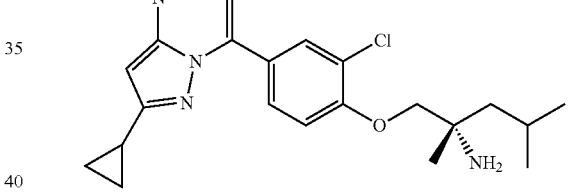

Part E: (S)-1-(2-chloro-4-(2-cyclopropylpyrazolo[1,5-a]pyrimidin-7-yl)phenoxy)-2,4-dimethylpentan-2-amine To a solution of (S)-tert-butyl (1-(2-chloro-4-(2-cyclopropylpyrazolo[1,5-a]pyrimidin-7-yl)phenoxy)-2,4-dimethylpentan-2-yl)carbamate (0.05 g, 0.100 mmol) in DCM (2 mL) at 0° C. was added TFA (0.154 mL, 2.004 mmol) and the mixture stirred for 5 min at 0° C. The reaction mixture was allowed to stir for 4 h at room temperature, then was concentrated under reduced pressure. The crude material was purified by prep LC/MS (method C) which afforded (S)-1-(2-chloro-4-(2-cyclopropylpyrazolo[1,5-4]pyrimidin-7-yl)phenoxy)-2,4-dimethylpentan-2-amine, TFA (21 mg. 0.040 mmol, 40% yield) as a pale yellow solid. LCMS (ESI) m/e 399.2 [(M+H)$^+$, calcd for $C_{22}H_{28}ClN_4O$. TFA 399.2]; LC/MS retention time (method H): $t_R$=2.62 min; LC/MS retention time (method I): $t_R$=2.07 min. $^1$H NMR (400 MHz, Methanol-d4): δ 8.45 (d, J=4.80 Hz, 1H), 8.35 (d, J=2.40 Hz, 1H), 8.14-8.16 (m, 1H), 7.34 (d, J=8.80 Hz, 1H), 7.05 (d, J=4.40 Hz, 1H), 6.45 (s, 1H), 4.05-4.15 (m, 2H), 2.15-2.20 (m, 1H), 1.79-1.93 (m, 2H), 1.64-1.69 (m, 1H), 1.44 (s, 3H), 1.03-1.11 (m, 8H), 0.94-0.95 (m, 2H) ppm.

Example 483

(S)-1-(4-(2-Cyclopropylpyrazolo[1,5-a]pyrimidin-7-yl)-2-(trifluoromethyl)phenoxy)-2,4-dimethylpentan-2-amine

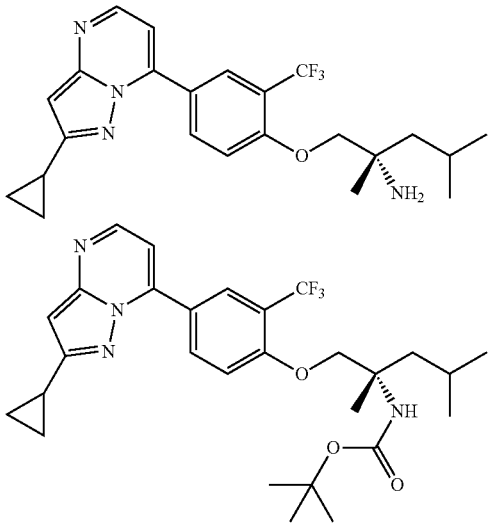

Part A: (S)-Tert-butyl(1-(4-(2-cyclopropylpyrazolo[1,5-a]pyrimidin-7-yl)-2-(trifluoromethyl)phenoxy)-2,4-dimethylpentan-2-yl)carbamate A solution of 7-chloro-2-cyclopropylpyrazolo[1,5-a]pyrimidine (prepared as described in Example 266, Parts A-C) (40 mg, 0.207 mmol), (S)-tert-butyl (2,4-dimethyl-1-(4-(4,4,5,5-tetramethyl-1,3,2-dioxaborolan-2-yl)-2-(trifluoromethyl)phenoxy)pentan-2-yl) (prepared as described in Example 255, Parts A and B) (104 mg, 0.207 mmol), $Cs_2CO_3$ (135 mg, 0.413 mmol), and KBr (24.58 mg, 0.207 mmol) in 1,4-dioxane (10 mL) was purged with nitrogen gas for 30 min. $PdCl_2$ (dppf)-$CH_2Cl_2$ adduct (16.87 mg, 0.021 mmol) was added to the reaction mixture and the solution was purged with nitrogen gas again for 10 min. The reaction mixture was heated at 100° C. for 12 h. The reaction mixture was concentrated and the residue obtained was dissolved in ethyl acetate (30 mL) and water (30 mL). The biphasic mixture was filtered through diatomaceous earth (Diatomaceous Earth®) and the bed was washed with ethyl acetate (50 mL). The ethyl acetate layer was separated, dried over $Na_2SO_4$, filtered, and concentrated under reduced pressure to afford ((S)-tert-butyl (1-(4-(2-cyclopropylpyrazolo[1,5-a]pyrimidin-7-yl)-2-(trifluoromethyl)phenoxy)-2,4-dimethylpentan-2-yl)carbamate (80 mg, 0.033 mmol, 16% yield) as a brown solid which was carried forward without further purification. LCMS (ESI) m/e 533.2 [(M+H)$^+$, calcd for $C_{28}H_{36}F_3N_4O_3$ 533.3]; LC/MS retention time (Method A1): $t_R$=3.23 min.

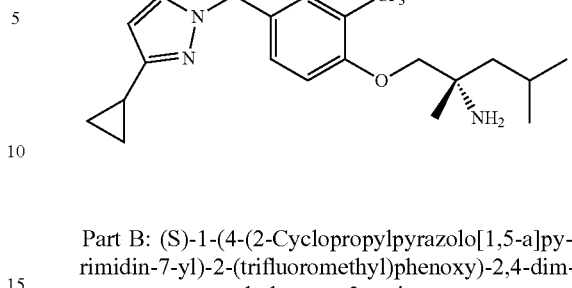

Part B: (S)-1-(4-(2-Cyclopropylpyrazolo[1,5-a]pyrimidin-7-yl)-2-(trifluoromethyl)phenoxy)-2,4-dimethylpentan-2-amine To a solution of (S)-tert-butyl (1-(4-(2-cyclopropylpyrazolo[1,5-a]pyrimidin-7-yl)-2-(trifluoromethyl)phenoxy)-2,4-dimethylpentan-2-yl)carbamate (80 mg, 0.033 mmol) in DCM (2 mL) at 0° C. was added TFA (0.051 mL, 0.661 mmol) and the mixture stirred for 5 min at 0° C. The reaction mixture was allowed to stir for 4 h at room temperature, then was concentrated under reduced pressure. The crude material was purified by prep LC/MS (method A) which afforded (S)-1-(4-(2-cyclopropylpyrazolo[1,5-a]pyrimidin-7-yl)-2-(trifluoromethyl)phenoxy)-2,4-dimethylpentan-2-amine (3 mg. 6.94 µmol, 21% yield) as a pale yellow solid. LCMS (ESI) m/e 433.3 [(M+H)$^+$, calcd for $C_{23}H_{28}F_3N_4O$ 433.3]; LC/MS retention time (method H): $t_R$=2.08 min; LC/MS retention time (method I): $t_R$=1.47 min. $^1$H NMR (400 MHz, Methanol-d4): δ 8.59 (d, J=2.00 Hz, 1H), 8.39-8.45 (m, 2H), 7.41 (d, J=8.80 Hz, 1H), 7.08 (d, J=4.80 Hz, 1H), 6.46 (s, 1H), 4.06-4.12 (m, 2H), 2.11-2.17 (m, 1H), 1.81-1.88 (m, 1H), 1.56-1.69 (m, 2H), 1.34 (s, 3H), 0.98-1.10 (m, 8H), 0.90-0.95 (m, 2H) ppm.

Example 485

(S)-2-((2-amino-2,4-dimethylpentyl)oxy)-5-(2-(trifluoromethyl)pyrazolo[1,5-a]pyrimidin-7-yl)benzonitrile

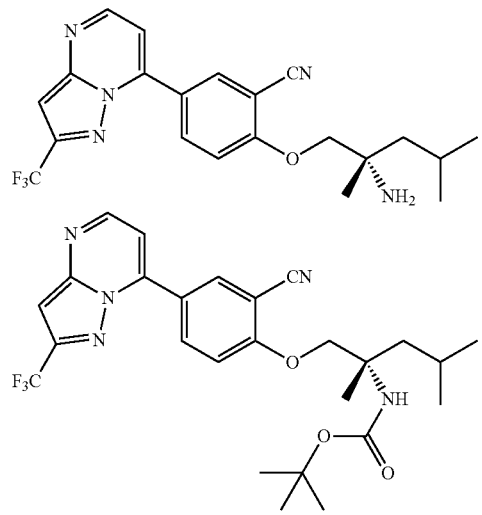

Part A: (S)-Tert-butyl (1-(2-cyano-4-(2-(trifluoromethyl)pyrazolo[1,5-a]pyrimidin-7-yl)phenoxy)-2,4-dimethylpentan-2-yl)carbamate A solution of 7-chloro-2-(trifluoromethyl)pyrazolo[1,5-a]pyrimidine (25 mg, 0.113 mmol), (S)-tert-butyl (1-(2-cyano-4-(4,4,5,5-tetramethyl-1,3,2-dioxaborolan-2-yl)phenoxy)-2,4-dimethylpentan-2-yl)carbamate (prepared as in Example 254, Part B-G) (56.9 mg, 0.124 mmol), and potassium phosphate, tribasic (71.9 mg, 0.338 mmol in 1,4-dioxane (10 mL) was purged with nitrogen gas for 30 min. (2-Dicyclohexylphosphino-2',4',6'-triisopropyl-1,1'-biphenyl)[2-(2-aminoethyl) phenyl]palladium(II) chloride (16.67 mg, 0.023 mmol) was added to the reaction mixture and the solution was purged with nitrogen gas again for 10 min. The reaction mixture was heated at 80° C. for 4 h. The reaction mixture was concentrated and the residue obtained was dissolved in ethyl acetate (30 mL) and water (30 mL). The biphasic mixture was filtered through diatomaceous earth (Diatomaceous Earth®) and the bed was washed with ethyl acetate (50 mL). The ethyl acetate layer was separated, dried over Na$_2$SO$_4$, filtered, and concentrated under reduced pressure to afford (S)-tert-butyl (1-(2-cyano-4-(2-(trifluoromethyl)pyrazolo[1,5-a]pyrimidin-7-yl)phenoxy)-2,4-dimethylpentan-2-yl)carbamate (crude yield) (40 mg, 0.077 mmol, 69% yield) as a brown solid which was carried forward without further purification. $^1$H NMR (400 MHz, DMSO-d$_6$): δ 8.80 (d, J=2.80 Hz, 1H), 8.43-8.50 (m, 2H), 7.17-7.56 (m, 3H), 6.94 (s, 1H), 4.03-4.18 (m, 2H), 1.56-1.83 (m, 2H), 1.46-1.53 (m, 1H), 1.43 (s, 3H), 1.28-1.35 (m, 9H), 0.89-0.96 (m, 6H) ppm.

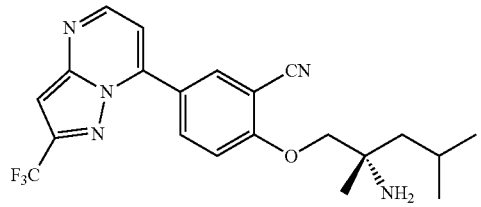 [SMILES: CC(C)C[C@](C)(N)COc1ccc(-c2ccnc3cc(C(F)(F)F)nn23)cc1C#N]

Part B: (S)-2-((2-amino-2,4-dimethylpentyl)oxy)-5-(2-(trifluoromethyl)pyrazolo[1,5-a]pyrimidin-7-yl)benzonitrile To a solution of (S)-tert-butyl (1-(2-cyano-4-(2-(trifluoromethyl)pyrazolo[1,5-a]pyrimidin-7-yl)phenoxy)-2,4-dimethylpentan-2-yl)carbamate (0.04 g, 0.077 mmol) in DCM (2 mL) at 0° C. was added TFA (0.119 mL, 1.546 mmol) and the mixture stirred for 5 min at 0° C. The reaction mixture was allowed to stir for 4 h at room temperature, then was concentrated under reduced pressure. The crude material was purified by prep LC/MS (method B) which afforded (S)-2-((2-amino-2,4-dimethylpentyl)oxy)-5-(2-(trifluoromethyl)pyrazolo[1,5-a]pyrimidin-7-yl)benzonitrile, 2 TFA (9 mg. 0.015 mmol, 19% yield) as a pale yellow solid. LCMS (ESI) m/e 418.2 [(M+H)$^+$, calcd for C$_{21}$H$_{23}$F$_3$N$_5$O 418.2]; LC/MS retention time (method H): t$_R$=1.78 min; LC/MS retention time (method I): t$_R$=1.37 min. $^1$H NMR (400 MHz, Methanol): δ 8.74 (d, J=4.40 Hz, 1H), 8.52-8.56 (m, 2H), 7.53 (d, J=8.80 Hz, 1H), 7.42 (d, J=4.40 Hz, 1H), 7.16 (s, 1H), 4.36-4.42 (m, 2H), 1.90-2.01 (m, 2H), 1.73-1.78 (m, 1H), 1.58 (s, 3H), 1.07-1.11 (m, 6H) ppm.

Example 486

(S)-5-((2-amino-2,4-dimethylpentyl)oxy)-2-(pyrazolo[1,5-a]pyrimidin-7-yl)isonicotinonitrile

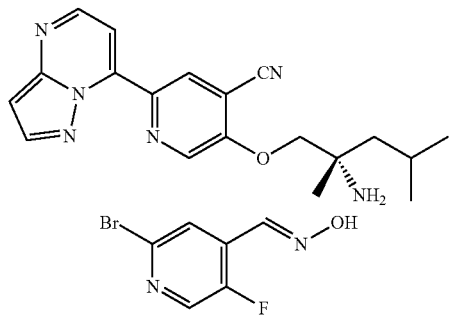

Part A: 2-bromo-5-fluoroisonicotinaldehyde oxime

2-Bromo-5-fluoroisonicotinaldehyde (2 g, 9.80 mmol) and hydroxylamine hydrochloride (1.022 g, 14.71 mmol) were dissolved in methanol (20 mL) and water (20 mL). The reaction mixture was heated at 60° C. for 5 h. The reaction mixture was concentrated under reduced pressure. The residue was diluted with saturated aqueous sodium bicarbonate and the solution was extracted with ethyl acetate. The ethyl acetate layer was dried over magnesium sulfate and concentrated under reduced pressure to obtain 2-bromo-5-fluoroisonicotinaldehyde oxime (1.8 g, 8.22 mmol, 84% yield) as an off-white solid which was carried forward without further purification. LCMS (ESI) m/e 219.0 [(M+H)$^+$, calcd for C$_6$H$_5$BrFN$_2$O 219.0]; LC/MS retention time (method A1): t$_R$=1.63 min.

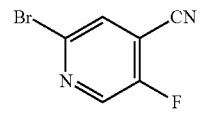

Part B: 2-bromo-5-fluoroisonicotinonitrile

2-Bromo-5-fluoroisonicotinaldehyde oxime (1 g, 4.57 mmol) in chloroform (20 mL) was cooled to 0° C. POCl$_3$ (2.128 mL, 22.83 mmol) was added dropwise and the reaction mixture stirred for 5 min at 0° C. The reaction mixture was heated at 65° C. for 12 h. The reaction mixture was concentrated under reduced pressure to afford a brown colored residue. The residue was diluted with ice-water, basified with saturated aqueous sodium carbonate and extracted with ethyl acetate (3×25 mL). The ethyl acetate layer was dried over Na$_2$SO$_4$ and evaporated to afford 2-bromo-5-fluoroisonicotinonitrile (0.8 g, 3.98 mmol, 87% yield) as a brown solid that was taken for next step without further purification. $^1$H NMR 400 MHz, DMSO-d6: δ 8.81 (d, J=4.40 Hz, 1H), 8.41-8.43 (m, 1H) ppm.

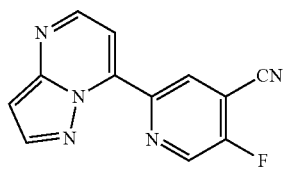 [SMILES: N#Cc1cc(-c2ccnc3ccnn23)ncc1F]

Part C: 5-fluoro-2-(pyrazolo[1,5-a]pyrimidin-7-yl)isonicotinonitrile

A solution of 7-chloropyrazolo[1,5-a]pyrimidine (0.05 g, 0.326 mmol), 2-bromo-5-fluoroisonicotinonitrile (0.065 g, 0.326 mmol) and 1,1,1,2,2,2-hexamethyldistannane (0.107 g, 0.326 mmol) in 1,4-dioxane (2 mL) was purged with nitrogen gas for 10 min. Pd(Ph$_3$P)$_4$ (0.038 g, 0.033 mmol) was added and the solution was purged with nitrogen gas again for 10 min. The reaction mixture was heated in a microwave at 150° C. for 2 h. The reaction mixture was concentrated and the residue obtained was dissolved in ethyl acetate (20 mL) and water (20 mL). The biphasic mixture was filtered through diatomaceous earth (Diatomaceous Earth®) and the bed was washed with ethyl acetate (25 mL). The ethyl acetate layer was separated, dried over Na$_2$SO$_4$, filtered, and concentrated under reduced pressure to afford a brown colored solid. The solid was purified by silica gel chromatography (0-40% EtOAc in pet ether) to afford 5-fluoro-2-(pyrazolo[1,5-a]pyrimidin-7-yl)isonicotinonitrile (30 mg, 0.125 mmol, 39% yield) as a light yellow solid. LCMS (ESI) m/e 240.0 [(M+H)$^+$, calcd for C$_{12}$H$_7$FN$_5$ 240.1]; LC/MS retention time (Method A1): t$_R$=1.97 min.

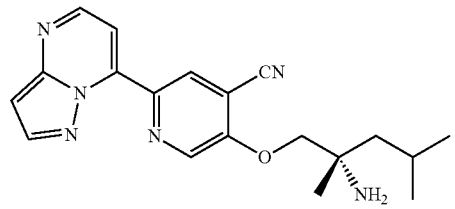 [SMILES: CC(C)C[C@](C)(N)COc1cnc(-c2ccnc3ccnn23)cc1C#N]

Part D: (S)-5-((2-amino-2,4-dimethylpentyl)oxy)-2-(pyrazolo[1,5-a]pyrimidin-7-yl)isonicotinonitrile A solution of (S)-2-amino-2,4-dimethylpentan-1-ol (0.016 g, 0.125 mmol) in DMF (4 mL) was cooled to 0° C. and 5-fluoro-2-(pyrazolo[1,5-a]pyrimidin-7-yl)isonicotinonitrile (0.030 g, 0.125 mmol) was added followed by portionwise addition of NaH (9.03 mg, 0.376 mmol) and the mixture stirred for 5 min at 0° C. The reaction mixture was stirred at 25° C. for 4 h. The reaction mixture was cooled to 0° C., quenched with water (20 mL) and extracted with ethyl acetate (20 mL). The ethyl acetate layer was separated out, dried over Na$_2$SO$_4$, filtered, and concentrated under reduced pressure. The crude material was purified by prep LC/MS (method A) which afforded (S)-5-((2-amino-2,4-dimethylpentyl)oxy)-2-(pyrazolo[1,5-a]pyrimidin-7-yl)isonicotinonitrile (5 mg, 0.014 mmol, 95% yield) as a pale yellow solid. LCMS (ESI) m/e 351.2 [(M+H)$^+$, calcd for C$_{19}$H$_{23}$N$_6$O 351.2]; LC/MS retention time (method H): t$_R$=2.50 min; LC/MS retention time (method I): t$_R$=2.50 min. $^1$H NMR (400 MHz, Methanol-d4): δ 9.46 (s, 1H), 8.77 (s, 1H), 8.58 (d, J=4.80 Hz, 1H), 8.31 (d, J=2.40 Hz, 1H), 7.82 (d, J=4.40 Hz, 1H), 6.79 (d, J=2.40 Hz, 1H), 3.58-3.82 (m, 2H), 1.85-1.92 (m, 2H), 1.77-1.82 (m, 1H), 1.52 (s, 3H), 0.98-1.02 (m, 6H) ppm.

Example 488

(S)-2,4-dimethyl-1-((2-methyl-6-(pyrazolo[1,5-a]pyrimidin-7-yl)pyridin-3-yl)oxy)pentan-2-amine

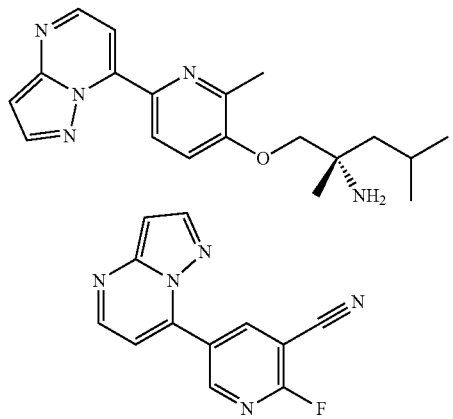

Part A: 2-fluoro-5-(pyrazolo[1,5-a]pyrimidin-7-yl)nicotinonitrile

A solution of 7-chloropyrazolo[1,5-a]pyrimidine (0.1 g, 0.651 mmol), 5-bromo-2-fluoronicotinonitrile (prepared as described in Example 487) (0.131 g, 0.651 mmol) and 1,1,1,2,2,2-hexamethyldistannane (0.213 g, 0.651 mmol) in 1,4-dioxane (2 mL) was purged with nitrogen gas for 10 min. Pd (Ph$_3$P)$_4$ (0.075 g, 0.065 mmol) was added to the reaction mixture and the solution was purged with nitrogen gas again for 10 min. The reaction mixture was heated in a microwave at 150° C. for 2 h. The reaction mixture was concentrated and the residue obtained was dissolved in ethyl acetate (20 mL) and water (20 mL). The biphasic mixture was filtered through diatomaceous earth (Diatomaceous Earth®) and the bed was washed with ethyl acetate (25 mL). The ethyl acetate layer was separated, dried over Na$_2$SO$_4$, filtered, and concentrated under reduced pressure to afford a brown colored solid. The solid was purified by silica gel chromatography (0-40% EtOAc in pet ether) to afford 2-fluoro-5-(pyrazolo[1,5-a]pyrimidin-7-yl)nicotinonitrile (0.032 g, 0.134 mmol, 21% yield) as a light-yellow color solid. LCMS (ESI) m/e 239.0 [(M)$^+$, calcd for C$_{12}$H$_6$FN$_5$ 239.1]; LC/MS retention time (Method A1): t$_R$=2.33 min.

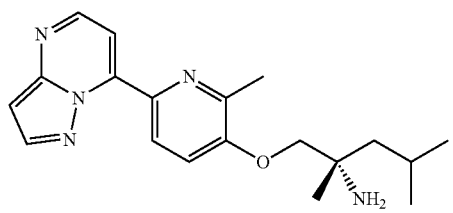 [SMILES: Cc1nc(-c2ccnc3ccnn23)ccc1OC[C@@](C)(N)CC(C)C]

Part B: (S)-2,4-dimethyl-1-((2-methyl-6-(pyrazolo [1,5-a]pyrimidin-7-yl)pyridin-3-yl)oxy)pentan-2-amine A solution of (S)-2-amino-2,4-dimethylpentan-1-ol (0.019 g, 0.145 mmol) in DMF (4 mL) was cooled to 0° C. NaH (3.47 mg, 0.145 mmol) was added followed by slow addition of 7-(5-fluoro-6-methylpyridin-2-yl)pyrazolo[1,5-a]pyrimidine (0.033 g, 0.145 mmol) and the mixture stirred for 5 min at 0° C. The reaction mixture was allowed to warm to room temperature and stirred at 60° C. for 4 h. The reaction mixture was cooled to room temperature, quenched with water (20 mL), and extracted with ethyl acetate (20 mL). The ethyl acetate layer was separated out, dried over $Na_2SO_4$, and concentrated under reduced pressure. The crude material was purified by prep LC/MS (method A) to afford (S)-2,4-dimethyl-1-((2-methyl-6-(pyrazolo [1,5-a]pyrimidin-7-yl)pyridin-3-yl)oxy)pentan-2-amine (23 mg. 0.068 mmol, 47% yield) as a pale yellow solid. LCMS (ESI) m/e 340.2 [(M+H)$^+$, calcd for $C_{19}H_{26}N_5O$ 340.2]; LC/MS retention time (method H): $t_R$=1.99 min; LC/MS retention time (method I): $t_R$=1.66 min. $^1$H NMR (400 MHz, Methanol-d4: δ 9.03 (d, J 8.40 Hz, 1H), 8.61 (d, J=4.40 Hz, 1H), 8.27 (d, J=2.40 Hz, 1H), 7.76 (d, J=4.40 Hz, 1H), 7.55 (d, J=8.80 Hz, 1H), 6.81 (d, J=2.40 Hz, 1H), 4.12-4.20 (m, 2H), 2.65 (s, 3H), 1.80-1.90 (m, 2H), 1.66-1.70 (m, 1H), 1.47 (s, 3H), 1.02-1.07 (m, 6H) ppm.

Example 489

(S)-1-(2,5-difluoro-4-(pyrazolo[1,5-a]pyrimidin-7-yl)phenoxy)-2,4-dimethylpentan-2-amine

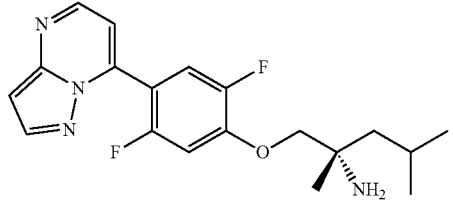 [SMILES: CC(C)C[C@](C)(N)COc1cc(F)c(-c2ccnc3ccnn23)cc1F]

Part A: (S)-tert-butyl (1-(2,5-difluoro-4-(pyrazolo[1,5-a]pyrimidin-7-yl)phenoxy)-2,4-dimethylpentan-2-yl)carbamate A solution of 7-chloropyrazolo[1,5-a]pyrimidine (25 mg, 0.163 mmol), (S)-tert-butyl (1-(2,5-difluoro-4-(4,4,5,5-tetramethyl-1,3,2-dioxaborolan-2-yl)phenoxy)-2,4-dimethylpentan-2-yl)carbamate (prepared as described in Example 285) (76 mg, 0.163 mmol), $Cs_2CO_3$ (106 mg, 0.326 mmol), and KBr (19.37 mg, 0.163 mmol) in 1,4-dioxane (10 mL) was purged with nitrogen gas for 30 min. $PdCl_2$ (dppf)-$CH_2Cl_2$ adduct (13.29 mg, 0.016 mmol) was added to the reaction mixture and the solution was purged with nitrogen gas again for 10 min. The reaction mixture was heated in a microwave at 88° C. for 2 h. The reaction mixture was concentrated and the residue obtained was dissolved in ethyl acetate (30 mL) and water (30 mL). The biphasic mixture was filtered through diatomaceous earth (Diatomaceous Earth®) and the bed was washed with ethyl acetate (50 mL). The ethyl acetate layer was separated, dried over $Na_2SO_4$, filtered, and concentrated under reduced pressure to afford (S)-tert-butyl (1-(2,5-difluoro-4-(pyrazolo [1,5-a]pyrimidin-7-yl)phenoxy)-2,4-dimethylpentan-2-yl)carbamate (40 mg, 0.087 mmol, 53% yield) as a brown solid which was carried forward without further purification. LCMS (ESI) m/e 461.2 [(M+H)$^+$, calcd for $C_{24}H_{31}F_2N_4O_3$ 461.2]; LC/MS retention time (Method A1): $t_R$=2.73 min.

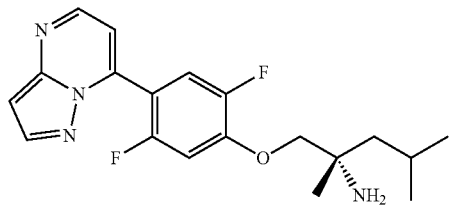 [SMILES: CC(C)C[C@](C)(N)COc1cc(F)c(-c2ccnc3ccnn23)cc1F]

Part B: (S)-1-(2,5-difluoro-4-(pyrazolo[1,5-a]pyrimidin-7-yl)phenoxy)-2,4-dimethylpentan-2-amine To a solution of (S)-tert-butyl (1-(2,5-difluoro-4-(pyrazolo[1,5-a]pyrimidin-7-yl)phenoxy)-2,4-dimethylpentan-2-yl)carbamate (0.04 g, 0.087 mmol) in DCM (2 mL) at 0° C. was added TFA (0.134 mL, 1.737 mmol) and the mixture stirred for 5 min at 0° C. The reaction mixture was allowed to stir for 4 h at room temperature, then was concentrated under reduced pressure. The crude material was purified by prep LC/MS (method A) to afford ((S)-1-(2,5-difluoro-4-(pyrazolo[1,5-a]pyrimidin-7-yl)phenoxy)-2,4-dimethylpentan-2-amine, TFA (7 mg. 0.015 mmol, 17% yield) as a pale yellow solid. LCMS (ESI) m/e 361.2 [(M+H)$^+$, calcd for $C_{19}H_{23}F_2N_4O$ 361.2]; LC/MS retention time (method H): $t_R$=2.04 min; LC/MS retention time (method I): $t_R$=1.71 min. $^1$H NMR (400 MHz, Methanol-d$_4$): δ 8.59 (d, J=4.40 Hz, 1H), 8.20 (d, J=2.40 Hz, 1H), 7.76-7.81 (m, 1H), 7.27-7.32 (m, 1H), 7.11-7.13 (m, 1H), 6.83 (d, J=2.40 Hz, 1H), 4.15-4.25 (m, 2H), 1.79-1.92 (m, 2H), 1.65-1.70 (m, 1H), 1.47 (s, 3H), 1.04-1.08 (m, 6H)

Example 490

1,1,1-trifluoro-4-methyl-2-(((2-methyl-6-(pyrazolo [1,5-a]pyrimidin-7-yl)pyridin-3-yl)oxy)methyl)pentan-2-amine

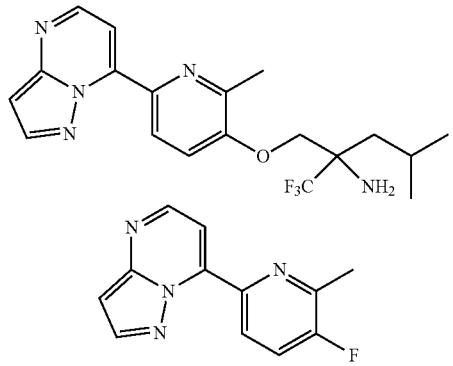

Part A: 7-(5-fluoro-6-methylpyridin-2-yl)pyrazolo [1,5-a]pyrimidine

A solution of 7-chloropyrazolo[1,5-a]pyrimidine (0.1 g, 0.651 mmol), 6-bromo-3-fluoro-2-methylpyridine (0.124 g, 0.651 mmol) and 1,1,1,2,2,2-hexamethyldistannane (0.213 g, 0.651 mmol) in 1,4-dioxane (2 mL) was purged with nitrogen gas for 10 min. Pd(Ph₃P)₄ (0.075 g, 0.065 mmol) was added to the reaction mixture and the solution was purged with nitrogen gas again for 10 min. The reaction mixture was heated in a microwave at 150° C. for 2 h. The reaction mixture was concentrated and the residue obtained was dissolved in ethyl acetate (20 mL) and water (20 mL). The biphasic mixture was filtered through diatomaceous earth (Diatomaceous Earth®) and the bed was washed with ethyl acetate (25 mL). The ethyl acetate layer was separated, dried over Na₂SO₄, filtered, and concentrated under reduced pressure to afford a brown colored solid. The solid was purified by silica gel chromatography (0-40% EtOAc in pet ether) to afford 7-(5-fluoro-6-methylpyridin-3-yl)pyrazolo[1,5-a]pyrimidine (0.06 g, 0.263 mmol, 40% yield) as a light yellow solid. LCMS (ESI) m/e 228.22 [(M+H)⁺, calcd for C₁₂H₉FN₄ 229.2]; LC/MS retention time (Method A1): $t_R$=2.20 min.

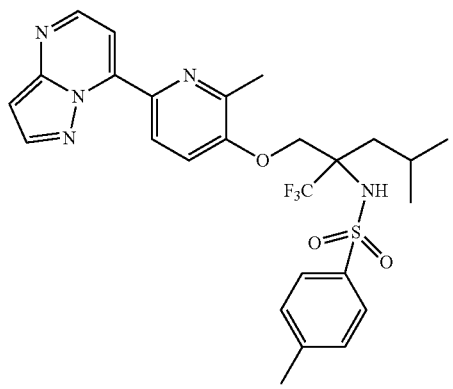 [SMILES: Cc1ccc(S(=O)(=O)NC(COc2ccc(-c3ccnc4ccnn34)nc2C)(CC(C)C)C(F)(F)F)cc1]

Part B: 4-methyl-N-(1,1,1-trifluoro-4-methyl-2-(((2-methyl-6-(pyrazolo[1,5-a]pyrimidin-7-yl)pyridin-3-yl)oxy)methyl)pentan-2-yl)benzenesulfonamide A solution of 4-methyl-N-(1,1,1-trifluoro-2-(hydroxymethyl)-4-methylpentan-2-yl)benzenesulfonamide (53.5 mg, 0.158 mmol) (prepared as described in Example 273) (53.5 mg, 0.158 mmol in DMF (4 mL) was cooled to 0° C. NaH (3.15 mg, 0.131 mmol) was added followed by slow addition of 7-(5-fluoro-6-methylpyridin-2-yl)pyrazolo[1,5-a]pyrimidine (30 mg, 0.131 mmol) and the mixture stirred for 5 min at 0° C. The reaction mixture was heated at 80° C. for 4 h. The reaction mixture was cooled to 0° C., quenched with water (20 mL), and extracted with ethyl acetate (20 mL). The ethyl acetate layer was separated out, dried over Na₂SO₄, filtered, and concentrated under reduced pressure to afford 4-methyl-N-(1,1,1-trifluoro-4-methyl-2-(((2-methyl-6-(pyrazolo[1,5-a]pyrimidin-7-yl)pyridin-3-yl)oxy)methyl)pentan-2-yl)benzenesulfonamide (45 mg, 0.082 mmol, 63% yield) as an off-white semi-solid which was carried to next step without further purification. LCMS (ESI) m/e 547.59 [(M+H)⁺, calcd for C₂₆H₂₈F₃N₅O₃S 548.2]; LC/MS retention time (Method A1): $t_R$=1.22 min.

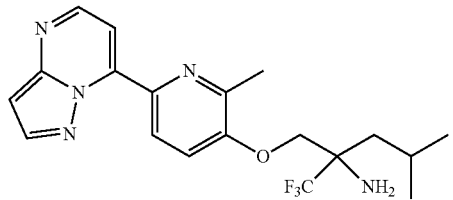 [SMILES: Cc1nc(-c2ccnc3ccnn23)ccc1OCC(N)(CC(C)C)C(F)(F)F]

Part C: 1,1,1-trifluoro-4-methyl-2-(((2-methyl-6-(pyrazolo[1,5-a]pyrimidin-7-yl)pyridin-3-yl)oxy)methyl)pentan-2-amine 4-Methyl-N-(1,1,1-trifluoro-4-methyl-2-(((2-methyl-6-(pyrazolo[1,5-a]pyrimidin-7-yl)pyridin-3-yl)oxy)methyl)pentan-2-yl)benzenesulfonamide (45 mg, 0.082 mmol) was cooled to 0° C. and sulfuric acid (2 mL, 37.5 mmol) was added dropwise then the mixture was stirred for 2 h at 0° C. The reaction mixture was basified with cold saturated aqueous sodium bicarbonate solution (pH-8-9). The reaction mixture was extracted with ethyl acetate(3×20 mL). The ethyl acetate layer was dried over Na₂SO₄, and concentrated under reduced pressure. The crude material was purified by prep LC/MS (method A) to afford 1,1,1-trifluoro-4-methyl-2-(((2-methyl-6-(pyrazolo[1,5-a]pyrimidin-7-yl)pyridin-3-yl)oxy)methyl)pentan-2-amine (11 mg. 0.028 mmol, 95% yield) as a pale yellow solid. LCMS (ESI) m/e 393.40 [(M+H)⁺, calcd for C₁₉H₂₂F₃N₅O 394.3]; LC/MS retention time (method H): $t_R$=2.04 min; LC/MS retention time (method I): $t_R$=1.45 min. ¹H NMR (400 MHz, Methanol-d4): δ 9.03 (d, J=8.80 Hz, 1H), 8.60 (d, J=4.40 Hz, 1H), 8.26 (d, J=2.40 Hz, 1H), 7.76 (d, J=4.40 Hz, 1H), 7.54 (d, J=8.80 Hz, 1H), 6.80 (d, J=2.40 Hz, 1H), 4.25-4.31 (m, 2H), 2.59-0.00 (m, 3H), 1.98-2.04 (m, 1H), 1.71-1.92 (m, 2H), 1.01-1.09 (m, 6H) ppm.

Example 492

(S)-2-((2-amino-2,4-dimethylpentyl)oxy)-5-(2-methylimidazo[1,2-b]pyridazin-8-yl)benzonitrile

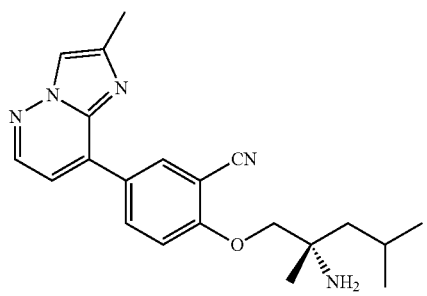 [SMILES: Cc1cn2nccc(-c3ccc(OC[C@@](C)(N)CC(C)C)c(C#N)c3)c2n1]

Prepared in a similar fashion as described in Example 452 to give (S)-2-((2-amino-2,4-dimethylpentyl)oxy)-5-(2-methylimidazo[1,2-b]pyridazin-8-yl)benzonitrile (16.6 mg, 0.045 mmol, 64% yield) as a pale yellow solid. LCMS (ESI) m/e 364.2 [(M+H)⁺, calcd for C₂₁H₂₆N₅O, 364.2]; LC/MS retention time (method D): $t_R$=1.34 min; LC/MS retention time (Method E): $t_R$=1.01 min. ¹H NMR (400 MHz, METHANOL-d₄): δ 8.50 (d, J=2.00 Hz, 1H), 8.37-8.41 (m, 2H), 7.97 (d, J=0.80 Hz, 1H), 7.37 (d, J=9.20 Hz, 1H), 7.31

(d, J=4.80 Hz, 1H), 4.05-4.10 (m, 2H), 2.50 (s, 3H), 1.83-1.90 (m, 1H), 1.56-1.70 (m, 2H), 1.33 (s, 3H), 1.00-1.03 (m, 6H) ppm.

Example 493

(S)-1-(4-(2-cyclopropylimidazo[1,2-b]pyridazin-8-yl)-2-fluorophenoxy)-2,4-dimethylpentan-2-amine

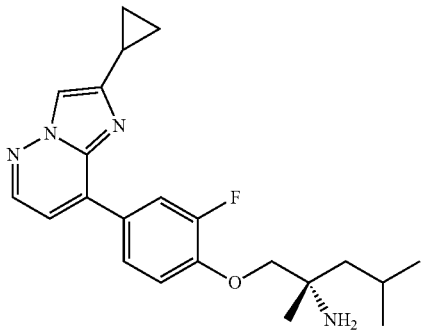 [SMILES: CC(C)C[C@](C)(N)COc1ccc(-c2ccnn3cc(C4CC4)nc23)cc1F]

Prepared in a similar fashion as described in Example 452 to give (S)-1-(4-(2-cyclopropylimidazo[1,2-b]pyridazin-8-yl)-2-fluorophenoxy)-2,4-dimethylpentan-2-amine (37 mg, 0.091 mmol, 88% yield) as a pale yellow solid. LCMS (ESI) m/e 383.2 [(M+H)$^+$, calcd for $C_{22}H_{28}FN_4O$, 383.2]; LC/MS retention time (method D): $t_R$=1.65 min; LC/MS retention time (Method E): $t_R$=1.20 min. $^1$H NMR (400 MHz, METHANOL-d$_4$): δ 8.37 (d, J=5.20 Hz, 1H), 8.11-8.15 (m, 1H), 8.00-8.03 (m, 1H), 7.93 (s, 1H), 7.29-7.34 (m, 2H), 4.03-4.10 (m, 2H), 2.14-2.21 (m, 1H), 1.86-1.88 (m, 1H), 1.58-1.70 (m, 2H), 1.37 (s, 3H), 1.02-1.08 (m, 8H), 0.95-0.98 (m, 2H) ppm.

Example 494

(5)-2-((2-amino-2,4-dimethylpentyl)oxy)-5-(6-chloro-2-cyclopropylimidazo[1,2-b]pyridazin-8-yl)benzonitrile

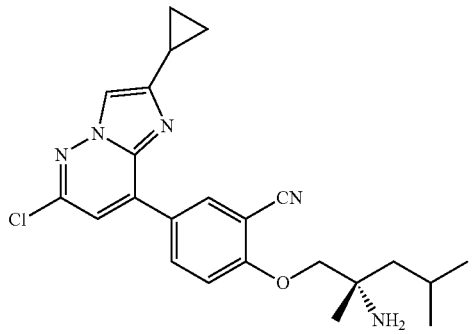 [SMILES: CC(C)C[C@](C)(N)COc1ccc(-c2cc(Cl)nn3cc(C4CC4)nc23)cc1C#N]

Prepared in a similar fashion as described in Example 452 to give (S)-2-((2-amino-2,4-dimethylpentyl)oxy)-5-(6-chloro-2-cyclopropylimidazo[1,2-b]pyridazin-8-yl)benzonitrile (11 mg, 0.026 mmol, 67% yield) as a pale yellow solid. LCMS (ESI) m/e 424.0 [(M+H)$^+$, calcd for $C_{23}H_{27}ClN_5O$, 424.2] LC/MS retention time (method D): $t_R$=2.00 min; LC/MS retention time (Method E): $t_R$=1.59 min. $^1$H NMR (400 MHz; DMSO-d$_6$): δ 8.80-8.84 (m, 2H), 8.21 (s, 1H), 7.75 (s, 1H), 7.46 (d, J 8.80 Hz, 1H), 3.98-3.99 (m, 2H), 2.09-2.15 (m, 1H), 1.80-1.84 (m, 1H), 1.40-1.50 (m, 2H), 1.17 (s, 3H), 0.99-1.06 (m, 2H), 0.88-0.95 (m, 8H) ppm.

Example 495

(S)-1-(4-(6-chloro-2-methylimidazo [1,2-b] pyridazin-8-yl)-2-(trifluoromethyl)phenoxy)-2,4-dimethylpentan-2-amine

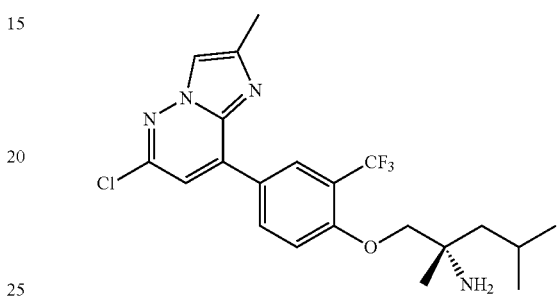

Prepared in a similar fashion as described in Example 452 to give (S)-1-(4-(6-chloro-2-methylimidazo[1,2-b]pyridazin-8-yl)-2-(trifluoromethyl)phenoxy)-2,4-dimethylpentan-2-amine (14 mg, 0.031 mmol, 57% yield) as a pale yellow solid. LCMS (ESI) m/e 441.0 [(M+H)$^+$, calcd for $C_{21}H_{25}ClF_3N_4O$, 441.2]; LC/MS retention time (method D): $t_R$=2.15 min; LC/MS retention time (Method E): $t_R$=1.49 min. $^1$H NMR (400 MHz, METHANOL-d$_4$): δ 8.55 (d, J=2.00 Hz, 1H), 8.42-8.44 (m, 1H), 7.99 (s, 1H), 7.44-7.46 (m, 2H), 4.20-4.27 (m, 2H), 2.52 (s, 3H), 1.82-1.89 (m, 2H), 1.68-1.72 (m, 1H), 1.49 (s, 3H), 1.03-1.08 (m, 6H) ppm

Example 496

(S)-1-(4-(6-chloro-2-cyclopropylimidazo [1,2-b] pyridazin-8-yl)-2-(trifluoromethyl)phenoxy)-2,4-dimethylpentan-2-amine

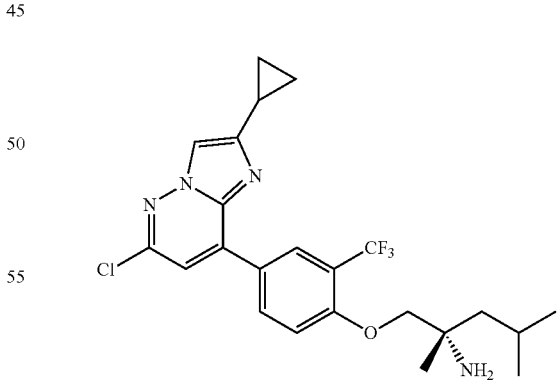

Prepared in a similar fashion as described in Example 452 to give (S)-1-(4-(6-chloro-2-cyclopropylimidazo[1,2-b]pyridazin-8-yl)-2-(trifluoromethyl)phenoxy)-2,4-dimethylpentan-2-amine (6.1 mg, 0.013 mmol, 29% yield) as a pale yellow solid. LCMS (ESI) m/e 467.0 [(M+H)$^+$, calcd for $C_{23}H_{27}ClF_3N_4O$, 467.2]; LC/MS retention time (method D): $t_R$=2.44 min; LC/MS retention time (Method E): $t_R$=1.75 min. $^1$H NMR (400 MHz; DMSO-$d_6$): δ 8.94 (d, J=2.00 Hz, 1H), 8.69-8.72 (m, 1H), 8.23 (s, 1H), 7.77 (s, 1H), 7.50-7.52 (m, 1H), 4.18 (s, 2H), 2.09-2.15 (m, 1H), 1.81-1.84 (m, 1H), 1.57-1.65 (m, 2H), 1.33 (s, 3H), 1.02-1.04 (m, 2H), 0.96-1.02 (m, 8H) ppm.

Example 497

(S)-1-(2-fluoro-4-(2-methylimidazo [1,2-b] pyridazin-8-yl)phenoxy)-2,4-dimethylpentan-2-amine

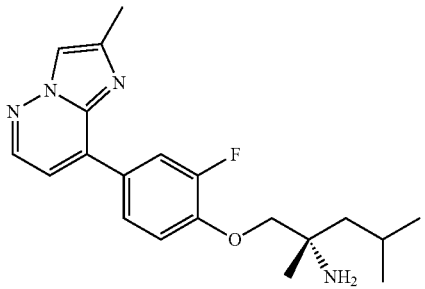 [SMILES: Cc1cn2nccc(-c3ccc(OC[C@@](C)(N)CC(C)C)c(F)c3)c2n1]

To a solution of (S)-tert-butyl (1-(2-fluoro-4-(2-methylimidazo[1,2-b]pyridazin-8-yl)phenoxy)-2,4-dimethylpentan-2-yl)carbamate (prepared in a similar fashion as described in Example 452) (40 mg, 0.088 mmol) in DCM (1 mL) at 0° C. was added 4N HCl in 1,4-dioxane (0.219 mL, 0.876 mmol). The mixture was warmed to room temperature and stirred for 5 h. The reaction mixture diluted with saturated sodium bicarbonate solution (20 mL) and extracted with ethyl acetate (30 mL). The organic layer was dried over anhydrous $Na_2SO_4$, concentrated under reduced pressure. The crude material was purified by prep LC/MS (method C) to afford (S)-1-(2-fluoro-4-(2-methylimidazo [1,2-b] pyridazin-8-yl)phenoxy)-2,4-dimethylpentan-2-amine (3.8 mg, 9.81 μmol, 11% yield) as a pale yellow solid. LCMS (ESI) m/e 357.2 [(M+H)$^+$, calcd for $C_{20}H_{26}FN_4O$, 357.2]; LC/MS retention time (method D): $t_R$=1.43 min; LC/MS retention time (Method E): $t_R$=0.78 min. $^1$H NMR (400 MHz, METHANOL-$d_4$): δ 8.40 (d, J=5.20 Hz, 1H), 8.02-8.06 (m, 1H), 7.92-7.97 (m, 2H), 7.29-7.34 (m, 2H), 4.00-4.07 (m, 2H), 2.51 (s, 3H), 1.86-1.92 (m, 1H), 1.66-1.71 (m, 2H), 1.34 (s, 3H), 1.01-1.05 (m, 6H) ppm.

Example 498

(S)-2,4-dimethyl-1-(4-(2-methylimidazo[1,2-b] pyridazin-8-yl)-2-(trifluoromethyl)phenoxy)pentan-2-amine

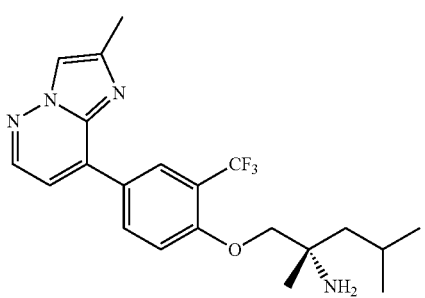

Prepared in a similar fashion as described in Example 452 to give (S)-2,4-dimethyl-1-(4-(2-methylimidazo [1,2-b] pyridazin-8-yl)-2-(trifluoromethyl)phenoxy)pentan-2-amine (11.2 mg, 0.027 mmol, 35% yield) as a pale yellow solid. LCMS (ESI) m/e 407.2 [(M+H)$^+$, calcd for $C_{21}H_{26}F_3N_4O$, 407.2]; LC/MS retention time (method D): $t_R$=1.78 min; LC/MS retention time (Method E): $t_R$=0.97 min. $^1$H NMR (400 MHz, METHANOL-$d_4$): δ 8.34-8.43 (m, 3H), 7.96 (d, J=0.80 Hz, 1H), 7.38 (d, J=8.80 Hz, 1H), 7.30 (d, J=4.80 Hz, 1H), 4.04-4.10 (m, 2H), 2.49 (d, J=0.80 Hz, 3H), 1.81-1.86 (m, 1H), 1.55-1.69 (m, 2H), 1.34 (s, 3H), 0.98-1.02 (m, 6H) ppm.

Example 499

(S)-2-((2-amino-2,4-dimethylpentyl)oxy)-5-(2-cyclopropylimidazo[1,2-b]pyridazin-8-yl)benzonitrile

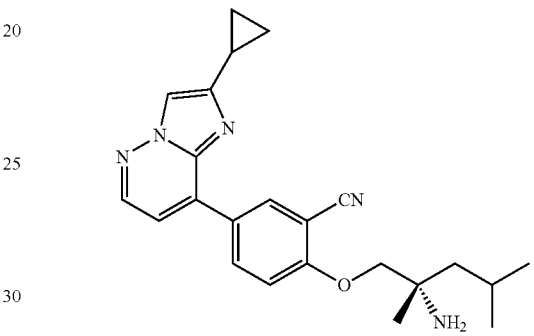

Prepared in a similar fashion as described in Example 452 to give (S)-2-((2-amino-2,4-dimethylpentyl)oxy)-5-(2-cyclopropylimidazo[1,2-b]pyridazin-8-yl)benzonitrile (4.9 mg, 0.012 mmol, 25% yield) as a pale yellow solid. LCMS (ESI) m/e 390.2 [(M+H)$^+$, calcd for $C_{23}H_{28}N_5O$, 390.2]; LC/MS retention time (method D): $t_R$=1.70 min; LC/MS retention time (Method E): $t_R$=1.08 min. $^1$H NMR (400 MHz, METHANOL-$d_4$): δ 8.61 (d, J=2.5 Hz, 1H), 8.53-8.49 (m, 1H), 8.40 (d, J=4.5 Hz, 1H), 7.95 (s, 1H), 7.41 (d, J=9.0 Hz, 1H), 7.34 (d, J=4.5 Hz, 1H), 4.15 (d, J=2.5 Hz, 2H), 2.19-2.11 (m, 1H), 1.93-1.86 (m, 1H), 1.79-1.73 (m, 1H), 1.67-1.61 (m, 1H), 1.40 (s, 3H), 1.09-1.02 (m, 8H), 0.98-0.94 (m, 2H) ppm.

Example 500

(S)-2,4-dimethyl-1-(2-methyl-4-(2-(trifluoromethyl) imidazo[1,2-b]pyridazin-8-yl)phenoxy)pentan-2-amine

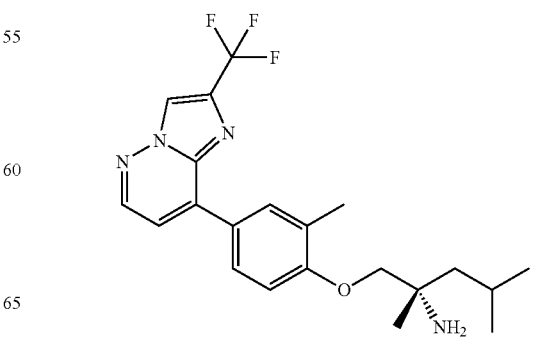

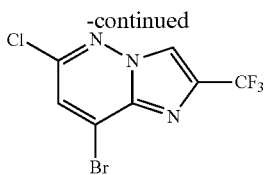

Part A: 8-bromo-6-chloro-2-(trifluoromethyl)imidazo[1,2-b]pyridazine

A mixture of 4-bromo-6-chloropyridazin-3-amine (1 g, 4.80 mmol) and 3-bromo-1,1,1-trifluoropropan-2-one (2.75 g, 14.39 mmol) was heated at 90° C. for 16 h in a pressure tube. The reaction mixture was cooled to room temperature and concentrated under reduced pressure. The residue was purified by silica gel chromatography (0-20% EtOAc in pet ether) to afford 8-bromo-6-chloro-2-(trifluoromethyl)imidazo[1,2-b]pyridazine (600 mg, 1.917 mmol, 40% yield) as a pale yellow solid. LCMS (ESI) m/e 300.0 (bromo pattern) [(M+H)+, calcd for $C_7H_3BrClF_3N_3$, 300.0]; LC/MS retention time (method A2): $t_R$=2.05 min.

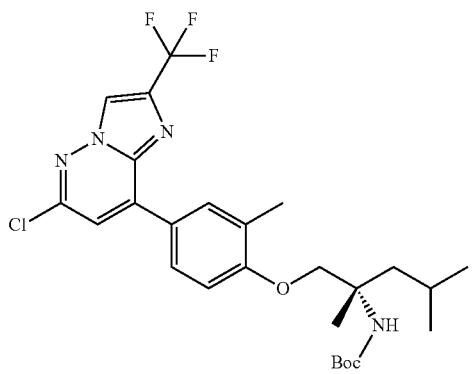 [SMILES: Cc1cc(-c2cc(Cl)nn3cc(C(F)(F)F)nc23)ccc1OC[C@](C)(CC(C)C)NC(=O)OC(C)(C)C]

Part B: (S)-tert-butyl (1-(4-(6-chloro-2-(trifluoromethyl)imidazo [1,2-b]pyridazin-8-yl)-2-methylphenoxy)-2,4-dimethylpentan-2-yl)carbamate To a stirred solution of 8-bromo-6-chloro-2-(trifluoromethyl)imidazo[1,2-b]pyridazine (50 mg, 0.166 mmol) and (S)-tert-butyl (2,4-dimethyl-1-(2-methyl-4-(4,4,5,5-tetramethyl-1,3,2-dioxaborolan-2-yl)phenoxy)pentan-2-yl)carbamate (74.5 mg, 0.166 mmol) in 1,4-dioxane (1 mL) was added tripotassium phosphate 3M in water (0.166 mL, 0.499 mmol). The mixture was purged with argon for 5 min and Pd(Ph$_3$P)$_4$ (19.23 mg, 0.017 mmol) was added. The reaction mixture was heated to 100° C. for 16 h. The reaction mixture was cooled to room temperature and diluted with ethyl acetate (10 mL). The mixture was filtered through diatomaceous earth (Diatomaceous Earth®), washing the bed with ethyl acetate (10 mL) and the filtrate was concentrated under reduced pressure. The residue was purified via silica gel chromatography (0-20% EtOAc in pet ether) to afford (S)-tert-butyl (1-(4-(6-chloro-2-(trifluoromethyl)imidazo[1,2-b]pyridazin-8-yl)-2-methylphenoxy)-2,4-dimethylpentan-2-yl)carbamate (50 mg, 0.091 mmol, 55% yield) as a yellow semi-solid. LCMS (ESI) m/e 541.2 [(M+H)+, calcd for $C_{26}H_{33}ClF_3N_4O_3$, 541.2]; LC/MS retention time (Method C): $t_R$=1.71 min.

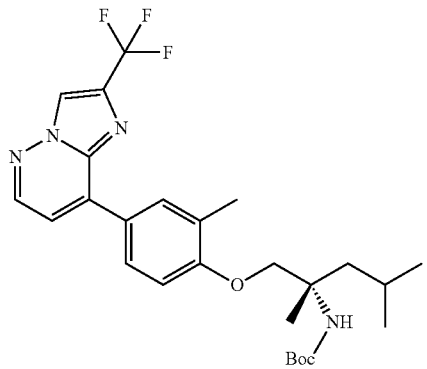 [SMILES: Cc1cc(-c2ccnn3cc(C(F)(F)F)nc23)ccc1OC[C@](C)(CC(C)C)NC(=O)OC(C)(C)C]

Part C: (S)-tert-butyl (2,4-dimethyl-1-(2-methyl-4-(2-(trifluoromethyl)imidazo[1,2-b]pyridazin-8-yl)phenoxy)pentan-2-yl)carbamate To a stirred solution of (S)-tert-butyl (1-(4-(6-chloro-2-(trifluoromethyl)imidazo[1,2-b]pyridazin-8-yl)-2-methylphenoxy)-2,4-dimethylpentan-2-yl)carbamate (50 mg, 0.092 mmol) in MeOH (2 mL) was added ammonium formate (23.31 mg, 0.370 mmol) followed by palladium on carbon (19.67 mg, 0.018 mmol). The reaction mixture was heated to 70° C. for 8 h under 1 atm H$_2$ gas. The reaction mixture was cooled to room temperature and filtered through diatomaceous earth (Diatomaceous Earth®), washing with bed with ethyl acetate (20 mL). The filtrate was concentrated under reduced pressure and the residue was dissolved in ethyl acetate (25 mL). The ethyl acetate layer was washed with water (10 mL). The organic layer was separated, dried over sodium sulfate and concentrated under reduced pressure to afford (S)-tert-butyl (2,4-dimethyl-1-(2-methyl-4-(2-(trifluoromethyl)imidazo[1,2-b]pyridazin-8-yl)phenoxy)pentan-2-yl)carbamate (40 mg, 0.060 mmol, 65% yield) as yellow semi-solid. LCMS (ESI) m/e 507.3 [(M+H)+, calcd for $C_{26}H_{34}F_3N_4O_3$, 507.3]; LC/MS retention time (method B): $t_R$=1.34 min.

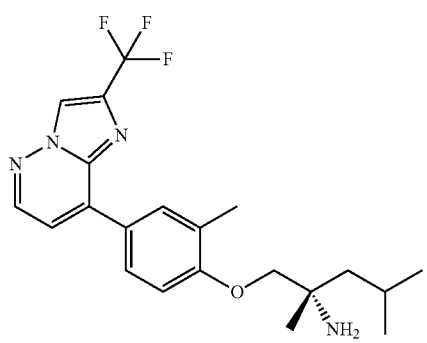 [SMILES: Cc1cc(-c2ccnn3cc(C(F)(F)F)nc23)ccc1OC[C@@](C)(N)CC(C)C]

Part D: (S)-2,4-dimethyl-1-(2-methyl-4-(2-(trifluoromethyl)imidazo [1,2-b]pyridazin-8-yl)phenoxy)pentan-2-amine To a solution of (S)-tert-butyl (2,4-dimethyl-1-(2-methyl-4-(2-(trifluoromethyl)imidazo[1,2-b]pyridazin-8-yl)phenoxy)pentan-2-yl)carbamate (35 mg, 0.053 mmol) in MeOH (1 mL) at 0° C. was added HCl 4M in 1,4-dioxane (0.263 mL, 1.050 mmol). The mixture was warmed to room temperature and stirred for 6 h. The reaction mixture diluted with saturated sodium bicarbonate solution (20 mL) and extracted with ethyl acetate (30 mL). The organic layer was dried over anhydrous $Na_2SO_4$, concentrated under reduced pressure. The crude material was purified by prep LC/MS (Method A) to afford (S)-2,4-dimethyl-1-(2-methyl-4-(2-(trifluoromethyl)imidazo[1,2-b]pyridazin-8-yl)phenoxy)pentan-2-amine (14.2 mg, 0.034 mmol, 64% yield) as a pale yellow solid. LCMS (ESI) m/e 407.0 [(M+H)$^+$, calcd for $C_{21}H_{26}F_3N_4O$, 407.2]; LC/MS retention time (method D): $t_R$=1.85 min; LC/MS retention time (Method E): $t_R$=1.58 min. $^1$H NMR (400 MHz, METHANOL-$d_4$): δ 8.57 (d, J=0.80 Hz, 1H), 8.52 (d, J=4.80 Hz, 1H), 8.18-8.21 (m, 1H), 8.07 (d, J=2.00 Hz, 1H), 7.47 (d, J=5.20 Hz, 1H), 7.10 (d, J=8.40 Hz, 1H), 3.92-3.98 (m, 2H), 2.38 (s, 3H), 1.81-1.90 (m, 1H), 1.65-1.70 (m, 1H), 1.55-1.60 (m, 1H), 1.33 (s, 3H), 1.01-1.02 (m, 6H) ppm.

Example 501

(S)-2,4-dimethyl-1-(4-(2-(trifluoromethyl)imidazo[1,2-b]pyridazin-8-yl)phenoxy)pentan-2-amine

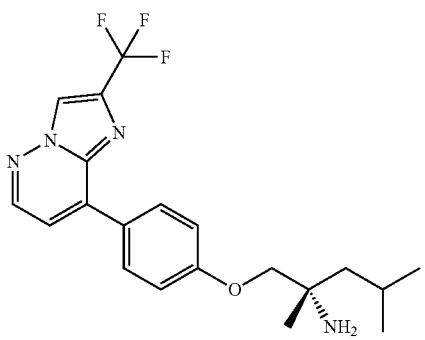 [SMILES: CC(C)C[C@](C)(N)COc1ccc(-c2ccnn3cc(C(F)(F)F)nc23)cc1]

Prepared in a similar fashion as described in Example 500 to afford (S)-2,4-dimethyl-1-(4-(2-(trifluoromethyl)imidazo[1,2-b]pyridazin-8-yl)phenoxy)pentan-2-amine (23.5 mg, 0.059 mmol, 96% yield) as a pale yellow solid. LCMS (ESI) m/e 393.0 [(M+H)$^+$, calcd for $C_{20}H_{24}F_3N_4O$, 393.1]; LC/MS retention time (method D): $t_R$=1.71 min; LC/MS retention time (Method E): $t_R$=1.44 min. $^1$H NMR (400 MHz, METHANOL-$d_4$): δ 8.54-8.59 (m, 2H), 8.30-8.32 (m, 2H), 7.50 (d, J=4.80 Hz, 1H), 7.20-7.22 (m, 2H), 4.02-4.12 (m, 2H), 1.70-1.90 (m, 2H), 1.60-1.65 (m, 1H), 1.41 (s, 3H), 1.00-1.05 (m, 6H) ppm.

Example 502

(S)-1-(4-(imidazo[1,2-b]pyridazin-3-yl)-2-methylphenoxy)-2,4-dimethylpentan-2-amine

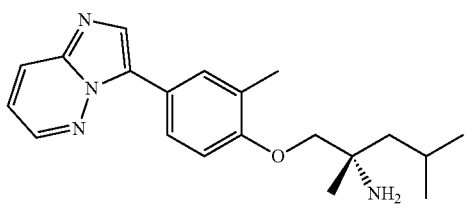 [SMILES: Cc1cc(-c2cnc3cccnn23)ccc1OC[C@@](C)(N)CC(C)C]

Prepared in a similar fashion as described in Example 473 to give (S)-1-(4-(imidazo[1,2-b]pyridazin-3-yl)-2-methylphenoxy)-2,4-dimethylpentan-2-amine (3 mg, 8.78 μmol, 10% yield) as a pale yellow solid. LCMS (ESI) m/e 339.3 [(M+H)$^+$, calcd for $C_{20}H_{27}N_4O$, 339.2]; LC/MS retention time (method D): $t_R$=1.36 min; LC/MS retention time (Method E): $t_R$=0.95 min. $^1$H NMR (400 MHz, METHANOL-$d_4$): δ 8.56-8.57 (m, 1H), 8.09 (d, J=1.60 Hz, 1H), 8.06 (d, J=1.60 Hz, 1H), 8.03 (s, 1H), 7.99 (d, J=2.00 Hz, 1H), 7.26-7.30 (m, 1H), 7.09 (d, J=8.80 Hz, 1H), 3.98-4.05 (m, 2H), 2.39 (s, 3H), 1.76-1.93 (m, 2H), 1.62-1.67 (m, 1H), 1.42 (s, 3H), 1.02-1.07 (m, 6H) ppm.

Example 503

(S)-1-(2-chloro-4-(imidazo[1,2-b]pyridazin-3-yl)phenoxy)-2,4-dimethylpentan-2-amine

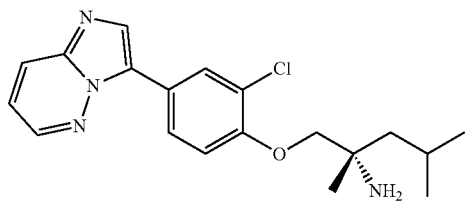 [SMILES: CC(C)C[C@](C)(N)COc1ccc(-c2cnc3cccnn23)cc1Cl]

Prepared in a similar fashion as described in Example 473 to give (S)-1-(2-chloro-4-(imidazo[1,2-b]pyridazin-3-yl)phenoxy)-2,4-dimethylpentan-2-amine (6 mg, 0.016 mmol, 21% yield) as a pale yellow solid. LCMS (ESI) m/e 359.2 [(M+H)$^+$, calcd for $C_{19}H_{24}ClN_4O$, 359.1]; LC/MS retention time (method D): $t_R$=2.02 min; LC/MS retention time (Method E): $t_R$=1.42 min. $^1$H NMR (400 MHz, METHANOL-$d_4$): δ 8.58-8.59 (m, 1H), 8.28 (d, J=2.00 Hz, 1H), 8.03-8.10 (m, 3H), 7.28-7.31 (m, 1H), 7.24 (d, J=8.80 Hz, 1H), 4.00-4.06 (m, 2H), 1.83-1.91 (m, 1H), 1.71-1.76 (m, 1H), 1.58-1.63 (m, 1H), 1.37 (s, 3H), 1.00-1.03 (m, 6H) ppm.

Example 504

(R)-2,4-dimethyl-1-((3-methyl-5-(2-(trifluoromethyl)imidazo[1,2-b]pyridazin-8-yl)pyridin-2-yl)oxy)pentan-2-amine

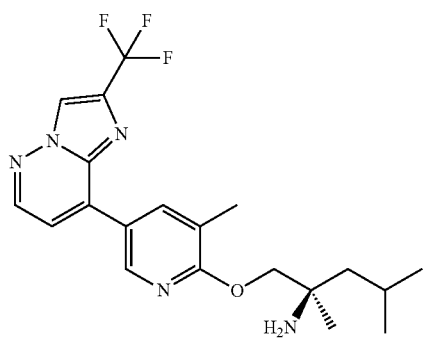 [SMILES: Cc1cc(-c2ccnn3cc(C(F)(F)F)nc23)cnc1OC[C@](C)(N)CC(C)C]

Prepared in a similar fashion as described in Example 500 to afford (R)-2,4-dimethyl-1-((3-methyl-5-(2-(trifluoromethyl)imidazo[1,2-b]pyridazin-8-yl)pyridin-2-yl)oxy)pentan-2-amine (11 mg, 0.026 mmol, 17% yield) as a pale yellow solid. LCMS (ESI) m/e 408.2 [(M+H)+, calcd for $C_{20}H_{25}F_3N_5O$, 408.2]; LC/MS retention time (method D): $t_R$=2.51 min; LC/MS retention time (Method E): $t_R$=2.16 min. $^1$H NMR (400 MHz, METHANOL-$d_4$): δ 9.00-9.01 (m, 1H), 8.63 (d, J=1.20 Hz, 1H), 8.58 (d, J=4.80 Hz, 1H), 8.39-8.40 (m, 1H), 8.55 (d, J=4.80 Hz, 1H), 4.47 (s, 2H), 2.40 (s, 3H), 1.86-1.91 (m, 1H), 1.77-1.82 (m, 1H), 1.62-1.67 (m, 1H), 1.45 (s, 3H), 1.02-1.07 (m, 6H) ppm.

Example 509

(S)-6-(4-((2-amino-2,4-dimethylpentyl)oxy)-3-chlorophenyl)pyrimidin-4(3H)-one

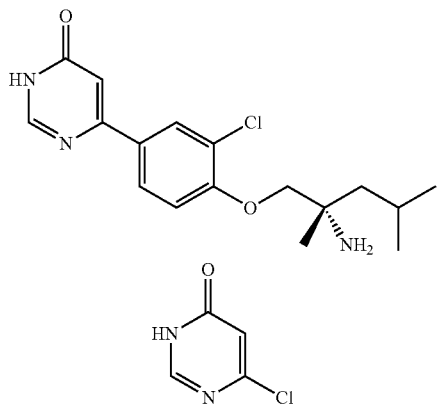

Part A: 6-chloropyrimidin-4(3H)-one

A solution of 4,6-dichloropyrimidine (2 g, 13.42 mmol) in a mixture of 4N HCl (10.49 mL, 121 mmol)-1,4-dioxane (10 mL)-water (10 mL) was heated to 70° C. for 6 h. The reaction mixture was cooled to room temperature and concentrated under reduced pressure to afford a pink solid. Ethanol (25 mL) was added to the solid and the mixture was heated at 50° C. until the solid dissolved. The resulting pink solution was left overnight at room temperature and the precipitation formed was filtered and dried under vacuum to afford 6-chloropyrimidin-4(3H)-one (1 g, 7.51 mmol, 56% yield) as an off-white solid. LCMS (ESI) m/e 130.8 [(M+H)+, calcd for $C_4H_4ClN_2O$, 130.9]; LC/MS retention time (Method C): $t_R$=0.51 min.

Part B: (S)-tert-butyl (1-(2-chloro-4-(6-oxo-1,6-dihydropyrimidin-4-yl)phenoxy)-2,4-dimethylpentan-2-yl)carbamate A mixture of 6-chloropyrimidin-4(3H)-one (25 mg, 0.192 mmol), (S)-tert-butyl (1-(2-chloro-4-(4,4,5,5-tetramethyl-1,3,2-dioxaborolan-2-yl)phenoxy)-2,4-dimethylpentan-2-yl)carbamate (prepared as described in Example 260, Part A and B) (90 mg, 0.192 mmol), $K_2CO_3$ (79 mg, 0.575 mmol) and Pd(Ph$_3$P)$_4$ (11.07 mg, 9.58 μmol) in 1,4-dioxane (1 mL)-water (0.1 mL) was heated at 100° C. for 16 h. The reaction mixture was cooled to RT and acidified with 1.5N HCl until the pH reached 4. The solution was extracted with ethyl acetate and the layers were separated. The organic layer was dried over sodium sulfate and concentrated under reduced pressure to afford (S)-tert-butyl (1-(2-chloro-4-(6-oxo-1,6-dihydropyrimidin-4-yl)phenoxy)-2,4-dimethylpentan-2-yl)carbamate (120 mg, 0.066 mmol, 35% yield) as a yellow solid which was carried forward without further purification. LCMS (ESI) m/e 436.2 [(M+H)+, calcd for $C_{22}H_{31}ClN_3O_4$, 436.2]; LC/MS retention time(method E): $t_R$=1.13 min.

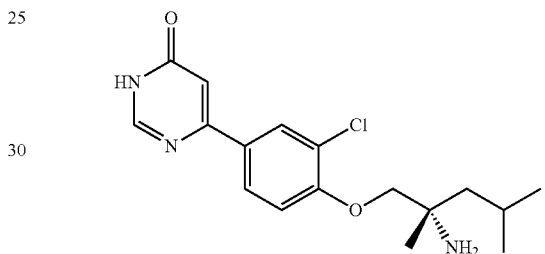

Part C: (S)-6-(4-((2-amino-2,4-dimethylpentyl)oxy)-3-chlorophenyl)pyrimidin-4(3H)-one To a stirred solution of (S)-tert-butyl (1-(2-chloro-4-(6-oxo-1,6-dihydropyrimidin-4-yl)phenoxy)-2,4-dimethylpentan-2-yl)carbamate (30 mg, 0.069 mmol) in MeOH (1 mL) was added HCl 1 M in 1,4-dioxane (0.172 mL, 0.688 mmol) and the reaction mixture was stirred at RT for 8 h. The mixture was concentrated under reduced pressure. The crude material was purified by prep LC/MS (method C) to afford (S)-6-(4-((2-amino-2,4-dimethylpentyl)oxy)-3-chlorophenyl)pyrimidin-4(3H)-one (2 mg, 5.42 μmol, 8% yield) as a pale yellow solid. LCMS (ESI) m/e 336.2 [(M+H)+, calcd for $C_{17}H_{23}ClN_3O_2$, 336.1]; LC/MS retention time (method D): $t_R$=1.66 min: LC/MS retention time (Method E): $t_R$=1.47 min. $^1$H NMR (400 MHz, METHANOL-$d_4$): δ 7.25 (d, J=0.80 Hz, 1H), 8.16 (d, J=2.40 Hz, 1H), 7.98-8.01 (m, 1H), 7.26 (d, J=8.40 Hz, 1H), 7.85 (d, J=3.20 Hz, 1H), 4.17-4.25 (m, 2H), 1.85-1.95 (m, 2H), 1.68-1.73 (m, 1H), 1.52 (s, 3H), 1.01-1.07 (m, 6H) ppm.

Biological Data

Methods

AAK1 Kinase Assay

The assays were performed in U-bottom 384-well plates. The final assay volume was 30 μl prepared from 15 μl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM MgCl$_2$, 0.01% Tween-20 and 1.0 mM DTT).

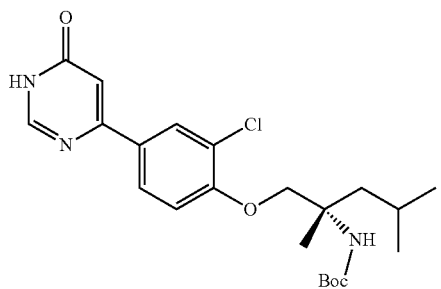 [SMILES: CC(C)C[C@@](C)(COc1ccc(-c2cc(=O)[nH]cn2)cc1Cl)NC(=O)OC(C)(C)C]

The reactions were initiated by the combination of bacterially expressed, GST-Xa-hAAK1 with substrates and test compounds. The reactions were incubated at room temperature for 3 hours and terminated by adding 60 μl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 μM; (5-FAM)-Aha-KEEQSQITSQVTGQIGWR-NH2, 1.5 μM; GST-Xa-hAAK1, 3.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis. Results are shown in Table 1.

TABLE 1

| Example | AAK1 $IC_{50}$ (nM) |
|---|---|
| 251 | 310 |
| 252 | 285 |
| 253 | 537 |
| 254 | 22 |
| 255 | 42 |
| 256 | 0.82 |
| 257 | 0.45 |
| 258 | 0.47 |
| 259 | 229 |
| 260 | 0.48 |
| 261 | 0.36 |
| 262 | 1.9 |
| 264 | 79 |
| 265 | 55 |
| 266 | 265 |
| 267 | 362 |
| 269 | 3.4 |
| 270 | 8.4 |
| 271 | 4.1 |
| 272 | 0.8 |
| 275 | 2.2 |
| 276 | 0.9 |
| 277 | 1.8 |
| 281 | 3.4 |
| 282 | 36 |
| 283 | 0.4 |
| 284 | 0.6 |
| 286 | 47 |
| 287 | 0.5 |
| 288 | 0.9 |
| 289 | 58 |
| 291 | 34 |
| 292 | 0.4 |
| 293 | 14 |
| 294 | 120 |
| 295 | 22 |
| 296 | 132 |
| 302 | 5.3 |
| 303 | 0.6 |
| 321 | 162 |
| 322 | 0.4 |
| 332 | 94 |
| 333 | 99 |
| 334 | 15 |
| 335 | 262 |
| 336 | 15 |
| 338 | 35 |
| 339 | 17 |
| 340 | 110 |
| 341 | 212 |
| 342 | 39 |
| 345 | 5.2 |
| 346 | 23 |
| 347 | 964 |
| 351 | 0.40 |
| 353 | 0.20 |
| 358 | 385 |
| 361 | 1.7 |
| 362 | 1.0 |
| 363 | 0.40 |
| 364 | 24 |
| 365 | 98 |
| 366 | 60 |
| 368 | 0.30 |
| 369 | 1.7 |
| 371 | 0.20 |
| 376 | 0.8 |
| 377 | 7.4 |
| 380 | 1.0 |
| 381 | 1.5 |
| 389 | 0.3 |
| 390 | 0.5 |
| 391 | 0.5 |
| 392 | 0.7 |
| 393 | 7.3 |
| 394 | 2.0 |
| 395 | 0.7 |
| 396 | 1.6 |
| 397 | 0.7 |
| 398 | 1.0 |
| 399 | 5.9 |
| 400 | 0.3 |
| 401 | 0.6 |
| 402 | 0.5 |
| 403 | 0.5 |
| 404 | 0.7 |
| 405 | 2.0 |
| 406 | 0.3 |
| 407 | 0.8 |
| 408 | 0.5 |
| 409 | 0.7 |
| 410 | 3.6 |
| 411 | 1.1 |
| 412 | 6.4 |
| 413 | 765 |
| 414 | 47 |
| 415 | 3.1 |
| 416 | 94 |
| 417 | 3.6 |
| 418 | 29 |
| 419 | 1138 |
| 420 | 1.1 |
| 421 | 0.5 |
| 423 | 862 |
| 424 | 1.2 |
| 425 | 1.4 |
| 426 | 7.2 |
| 427 | 1738 |
| 428 | 13 |
| 429 | 36 |
| 430 | 67 |
| 448 | 399 |
| 449 | 352 |
| 452 | 11 |
| 453 | 0.4 |
| 455 | 391 |
| 456 | 1.0 |
| 457 | 160 |
| 459 | 1271 |
| 460 | 0.6 |
| 461 | 2.9 |
| 463 | 184 |
| 464 | 495 |
| 466 | 64 |
| 467 | 0.4 |
| 468 | 54 |
| 470 | 138 |
| 471 | 6.3 |
| 472 | 0.5 |

TABLE 1-continued

| Example | AAK1 IC$_{50}$ (nM) |
|---|---|
| 473 | 112 |
| 475 | 15 |
| 476 | 125 |
| 477 | 50 |
| 478 | 11 |
| 481 | 52 |
| 482 | 1.4 |
| 483 | 2.7 |
| 485 | 4.5 |
| 486 | 1370 |
| 488 | 4.0 |
| 489 | 278 |
| 490 | 37 |
| 492 | 1.8 |
| 493 | 15 |
| 494 | 222 |
| 495 | 66 |
| 496 | 297 |
| 497 | 11 |
| 498 | 0.5 |
| 499 | 1.2 |
| 500 | 30 |
| 501 | 69 |
| 502 | 144 |
| 503 | 62 |
| 504 | 606 |
| 509 | 6.1 |

AAK1 Knockout Mice

Mice homozygous (−/−) for the disruption of the AAK1 gene were prepared by two methods: gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 µl of 5% formalin is subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. *An automated flinch detecting system for use in the formalin nociceptive bioassay. J Appl Physiol.*, 2001; 90:2386-402. As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

It will be evident to one skilled in the art that the present disclosure is not limited to the foregoing illustrative Examples, and that it can be embodied in other specific forms without departing from the essential attributes thereof. It is therefore desired that the Examples be considered in all respects as illustrative and not restrictive, reference being made to the appended claims, rather than to the foregoing Examples, and all changes which come within the meaning and range of equivalency of the claims are therefore intended to be embraced therein.

The invention claimed is:
1. A compound of formula (I)
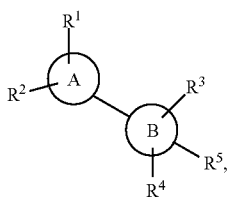
or a pharmaceutically acceptable salt thereof, wherein:
A is selected from
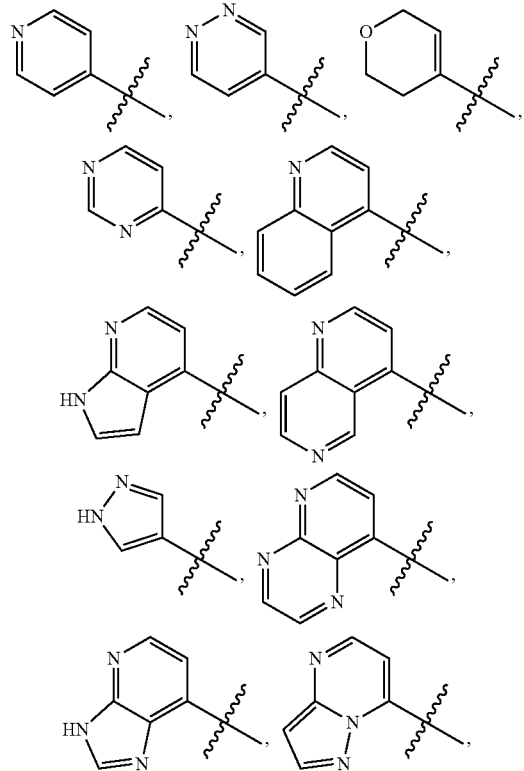
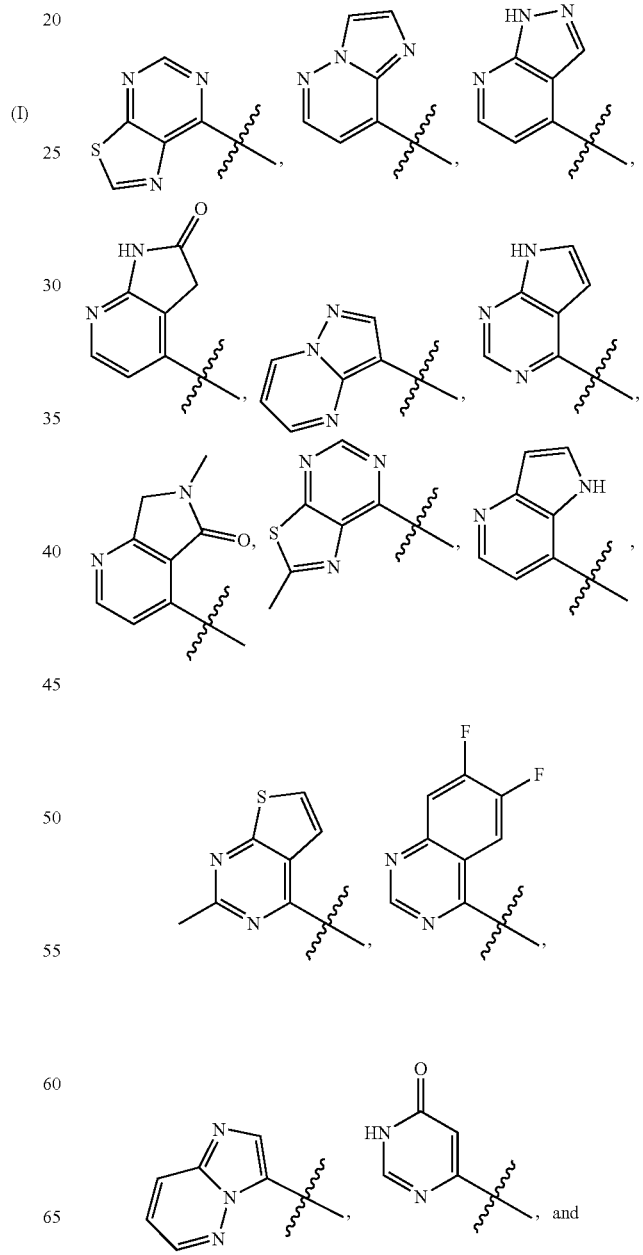
and -continued

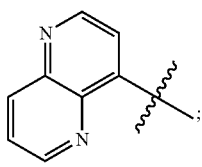

wherein "⌇" denotes the point of attachment to B;

B is selected from

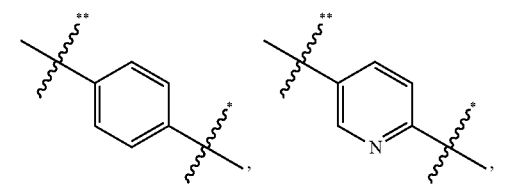

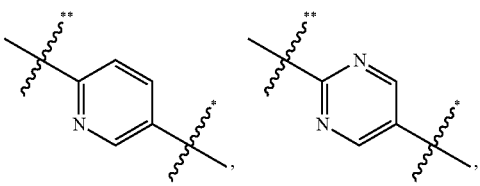

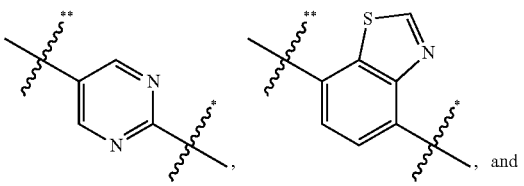

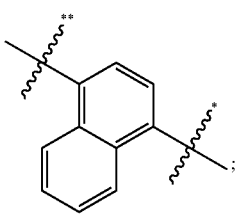

wherein "*" indicates the point of attachment to R⁵ and "**" indicates the point of attachment to ring A;

R$^1$ is selected from hydrogen, amino, —CO$_2$H, cyclopropyl, difluoromethyl, ethyl, halo, hydroxymethyl, methoxy, methoxymethyl, methyl, —NHC(O)CH$_3$, —NHCO$_2$CH$_3$, trifluoromethoxy, trifluoromethyl,

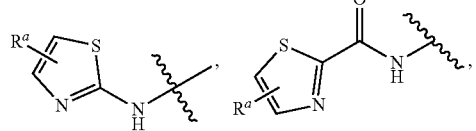

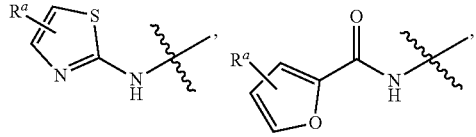

-continued

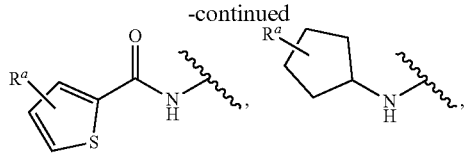

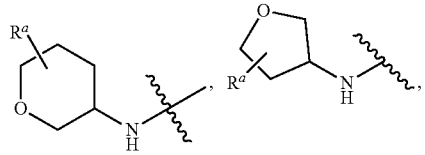

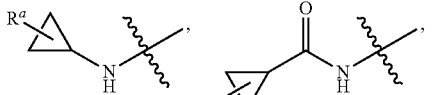

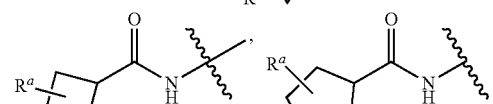

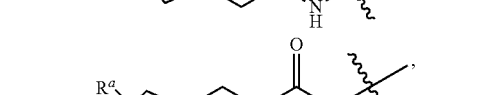

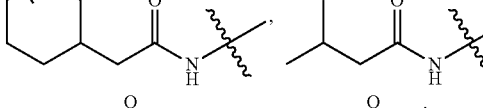

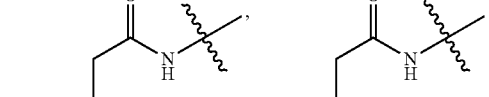

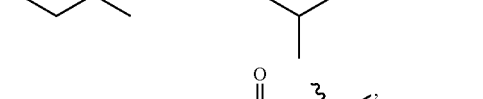

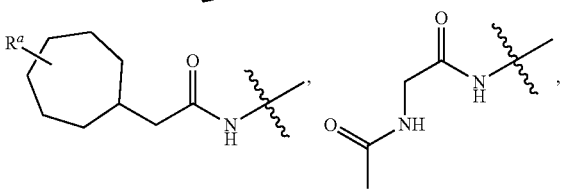

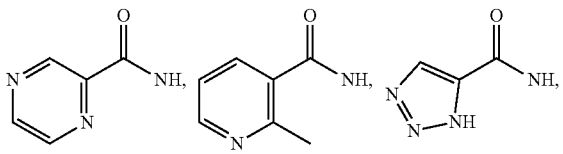

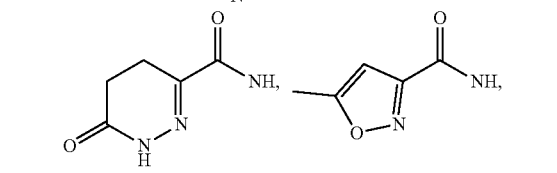

-continued

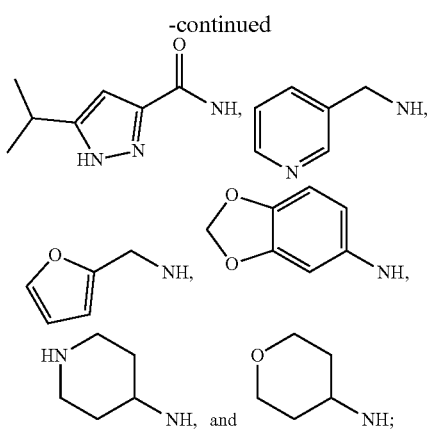

wherein R$^a$ is selected from hydrogen, halo and methyl;
R$^2$ is selected from hydrogen, cyano, —CH$_2$OH, halo, and methyl;
R$^3$ is selected from hydrogen, cyano, cyclopropyl, difluoromethyl, fluoromethyl, halo, hydroxymethyl, methoxy, methyl, methylsulfonyl, trifluoromethoxy, trifluoromethyl, —CH$_2$N(CH$_3$)$_2$, and a five-membered aromatic ring containing one, two, or three heteroatoms selected from nitrogen, oxygen, and sulfur;
R$^4$ is selected from hydrogen, halo, and methyl;
R$^5$ is selected from

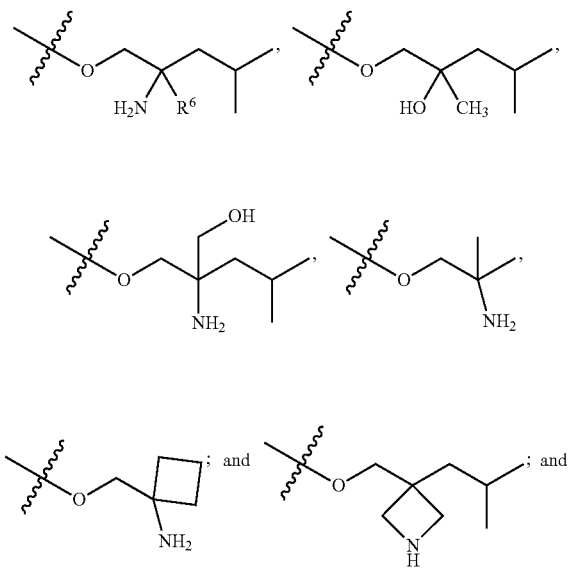

R$^6$ is selected from hydrogen, ethyl, fluoromethyl, difluoromethyl, methyl, and trifluoromethyl;
provided that when A is

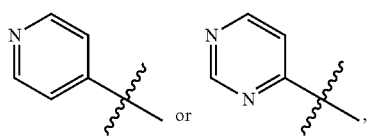 [SMILES: *c1ccncc1 ; *c1ccncn1]

then B is

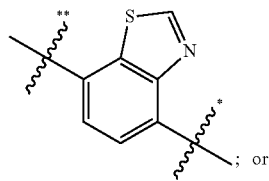 [SMILES: *c1ccc(*)c2scnc12]

; or

R$^1$ is selected from cyclopropyl, methoxymethyl,

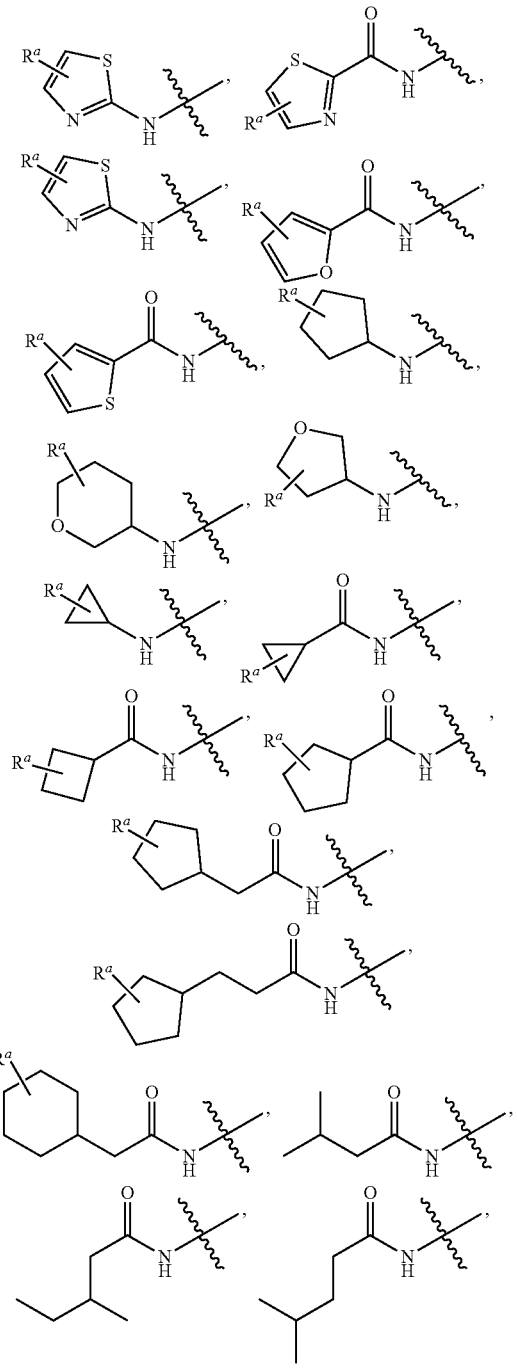

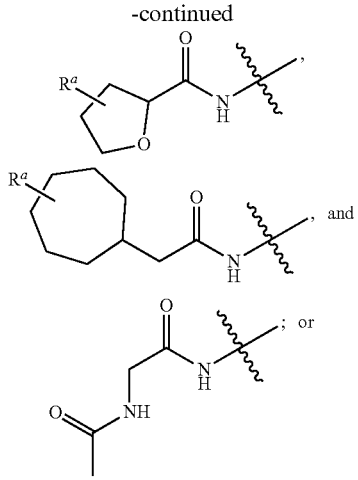

$R^5$ is selected from

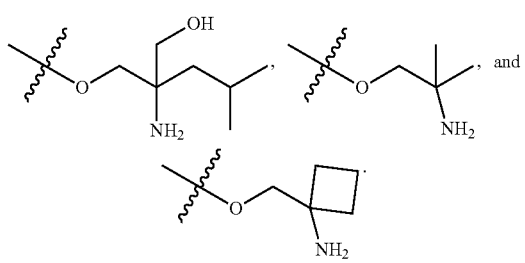

2. A compound of claim 1, or a pharmaceutically acceptable salt thereof, wherein A is selected from

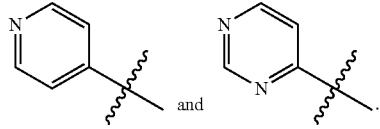 [SMILES: *c1ccncc1 ; *c1ccncn1]

3. A compound of claim 2, or a pharmaceutically acceptable salt thereof, wherein B is selected from

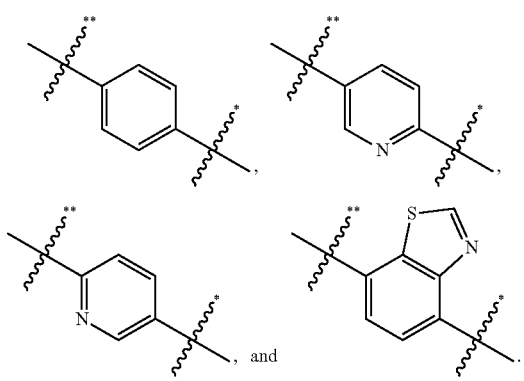

4. A compound of claim 1, or a pharmaceutically acceptable salt thereof, wherein A is selected from

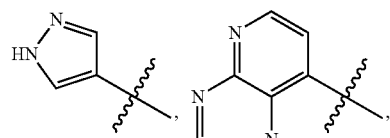
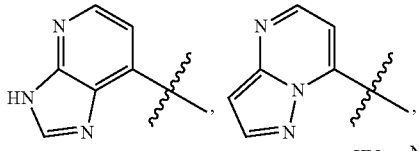
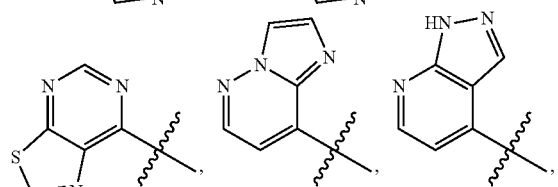
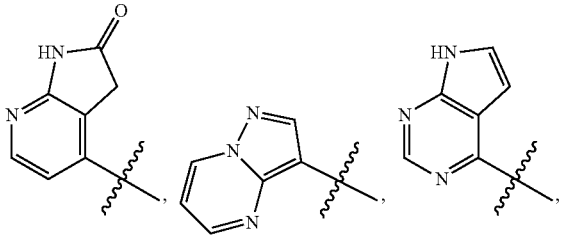
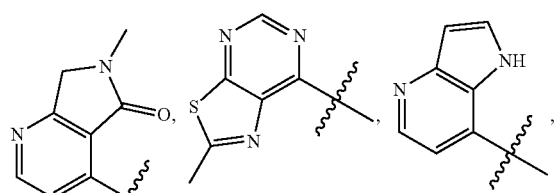
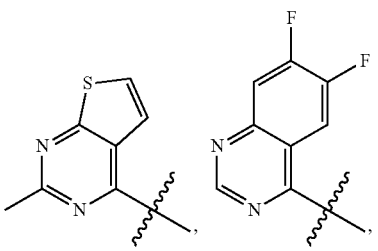
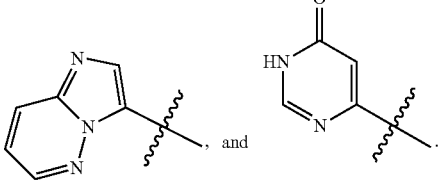

5. A compound of claim 3, or a pharmaceutically acceptable salt thereof, wherein B is selected from

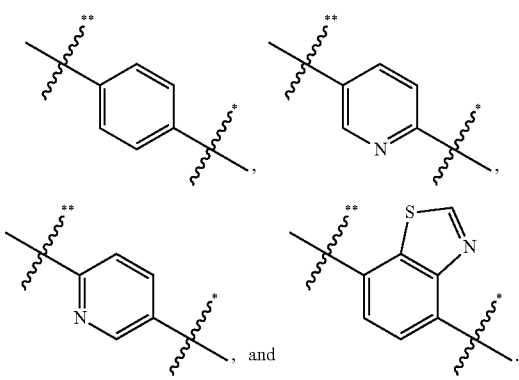

6. A compound selected from
(S)-1-(4-(3,5-dimethyl-1H-pyrazol-4-yl)-2-fluorophenoxy)-2,4-dimethylpentan-2-amine;
(S)-2-((2-amino-2,4-dimethylpentyl)oxy)-5-(2,3-dimethylpyrido[2,3-b]pyrazin-8-yl)benzonitrile;
(S)-1-(2-fluoro-4-(pyrido[2,3-b]pyrazin-8-yl)phenoxy)-2,4-dimethylpentan-2-amine
(S)-2-((2-amino-2,4-dimethylpentyl)oxy)-5-(2-amino-3H-imidazo [4,5-b]pyridin-7-yl)benzonitrile;
(S)-7-(4-((2-amino-2,4-dimethylpentyl)oxy)-3-(trifluoromethyl)phenyl)-3H-imidazo[4,5-b]pyridin-2-amine;
(S)—N-(4-(4-((2-amino-2,4-dimethylpentyl)oxy)-3-(trifluoromethyl)phenyl)pyridin-2-yl)thiazol-2-amine;
(S)—N-(4-(4-((2-amino-2,4-dimethylpentyl)oxy)-3-chlorophenyl)pyridin-2-yl)thiazol-2-amine;
(S)—N-(4-(4-((2-amino-2,4-dimethylpentyl)oxy)-3-(trifluoromethyl)phenyl)pyridin-2-yl)thiazole-2-carboxamide;
(S)-7-(4-((2-amino-2,4-dimethylpentyl)oxy)-3-methylphenyl)-3H-imidazo [4,5-b]pyridin-2-amine;
(S)—N-(4-(4-((2-amino-2,4-dimethylpentyl)oxy)-3-chlorophenyl)pyridin-2-yl)thiazole-2-carboxamide;
(S)—N-(4-(4-((2-amino-2,4-dimethylpentyl)oxy)-3-cyanophenyl)pyridin-2-yl)thiazole-2-carboxamide;
(S)—N-(4-(4-((2-amino-2,4-dimethylpentyl)oxy)-3-chlorophenyl)pyridin-2-yl)-4-methylthiazol-2-amine;
(R)-2,4-dimethyl-1-((3-methyl-5-(pyrazolo[1,5-a]pyrimidin-7-yl)pyridin-2-yl)oxy)pentan-2-amine;
(R)-1-((3-chloro-5-(pyrazolo[1,5-a]pyrimidin-7-yl)pyridin-2-yl)oxy)-2,4-dimethylpentan-2-amine;
(R)-1-((5-(2-cyclopropylpyrazolo[1,5-a]pyrimidin-7-yl)-3-methylpyridin-2-yl)oxy)-2,4-dimethylpentan-2-amine;
(S)-2,4-dimethyl-1-((7-(2-methylpyridin-4-yl)benzo[d]thiazol-4-yl)oxy)pentan-2-amine;
(S)-methyl (4-(4-((2-amino-2,4-dimethylpentyl)oxy)benzo [d]thiazol-7-yl)pyridin-2-yl)carbamate;
(S)-2,4-dimethyl-1-(4-(2-methylthiazolo [5,4-d]pyrimidin-7-yl)-2-(trifluoromethyl)phenoxy)pentan-2-amine;
(S)-2-((2-amino-2,4-dimethylpentyl)oxy)-5-(2-methylthiazolo[5,4-d]pyrimidin-7-yl)benzonitrile;
(S)-1-((3-chloro-5-(pyrazolo[1,5-a]pyrimidin-7-yl)pyridin-2-yl)oxy)-2,4-dimethylpentan-2-amine;
(S)-2,4-dimethyl-1-((3-methyl-5-(pyrazolo[1,5-a]pyrimidin-7-yl)pyridin-2-yl)oxy)pentan-2-amine;
(S)-1-((2-(fluoromethyl)-6-(pyrazolo[1,5-a]pyrimidin-7-yl)pyridin-3-yl)oxy)-2,4-dimethylpentan-2-amine
2-amino-2-(((2',4-bis(difluoromethyl)-[2,4'-bipyridin]-5-yl)oxy)methyl)-4-methylpentan-1-ol;
(S)-1-(4-(imidazo[1,2-b]pyridazin-8-yl)phenoxy)-2,4-dimethylpentan-2-amine;
(S)-1-(2-chloro-4-(2-methyl-3H-imidazo[4,5-b]pyridin-7-yl)phenoxy)-2,4-dimethylpentan-2-amine;
(S)-1-(4-(imidazo[1,2-b]pyridazin-8-yl)-2-(trifluoromethyl)phenoxy)-2,4-dimethylpentan-2-amine;
(S)-1-(2-chloro-4-(1H-pyrazolo[3,4-b]pyridin-4-yl)phenoxy)-2,4-dimethylpentan-2-amine;
(S)-2-((2-amino-2,4-dimethylpentyl)oxy)-5-(6-chloroimidazo[1,2-b]pyridazin-8-yl)benzonitrile;
(S)-2-((2-amino-2,4-dimethylpentyl)oxy)-5-(imidazo[1,2-b]pyridazin-8-yl)benzonitrile;
(S)-1-(2-fluoro-4-(1H-pyrazolo[3,4-b]pyridin-4-yl)phenoxy)-2,4-dimethylpentan-2-amine;
(S)-1-(2-fluoro-4-(1-methyl-1H-pyrazolo[3,4-b]pyridin-4-yl)phenoxy)-2,4-dimethylpentan-2-amine
2,4-dimethyl-1-(4-(2-methyl-3H-imidazo[4,5-b]pyridin-7-yl)-2-(trifluoromethyl)phenoxy)pentan-2-amine;
(S)-1-(4-(1H-pyrazolo[3,4-b]pyridin-4-yl)-2-(trifluoromethyl)phenoxy)-2,4-dimethylpentan-2-amine;
(S)-2-((2-amino-2,4-dimethylpentyl)oxy)-5-(2-methyl-3H-imidazo [4,5-b]pyridin-7-yl)benzonitrile;
(S)-2,4-dimethyl-1-(2-methyl-4-(2-methyl-3H-imidazo [4,5-b]pyridin-7-yl)phenoxy)pentan-2-amine;
(S)-1-(4-(2-(methoxymethyl)-3H-imidazo [4,5-b]pyridin-7-yl)-2-(trifluoromethyl)phenoxy)-2,4-dimethylpentan-2-amine;
(S)-1-(4-(2-(methoxymethyl)-3H-imidazo[4,5-b]pyridin-7-yl)-2-methylphenoxy)-2,4-dimethylpentan-2-amine;
(S)-2-((2-amino-2,4-dimethylpentyl)oxy)-5-(2-oxo-2,3-dihydro-1H-pyrrolo [2,3-b]pyridin-4-yl)benzonitrile;
(S)-4-(4-((2-amino-2,4-dimethylpentyl)oxy)-3-(trifluoromethyl)phenyl)-1H-pyrrolo[2,3-b]pyridin-2(3H)-one
2-methyl-1-((2-methyl-6-(2-methylpyrimidin-4-yl)pyridin-3-yl)oxy)propan-2-amine;
(S)-1-((2-(difluoromethyl)-6-(pyrazolo[1,5-a]pyrimidin-7-yl)pyridin-3-yl)oxy)-2,4-dimethylpentan-2-amine;
(S)-1-(2-chloro-4-(pyrazolo [,5-a]pyridin-3-yl)phenoxy)-2,4-dimethylpentan-2-amine (S)-2,4-dimethyl-1-(2-methyl-4-(pyrazolo[1,5-a]pyridin-3-yl)phenoxy)pentan-2-amine 4-(4-(((S)-2-amino-2,4-dimethylpentyl)oxy)-3-chlorophenyl)-N-(3-fluorocyclopentyl)pyridin-2-amine;
(S)-1-(2-fluoro-4-(2-(trifluoromethyl) pyrazolo[1,5-a]pyrimidin-7-yl)phenoxy)-2,4-dimethylpentan-2-amine;
(S)-1-(2-chloro-4-(2-(trifluoromethyl)pyrazolo[1,5-a]pyrimidin-7-yl)phenoxy)-2,4-dimethylpentan-2-amine
4-(4-(((S)-2-amino-2,4-dimethylpentyl)oxy)-3-chlorophenyl)-N-(tetrahydro-2H-pyran-3-yl)pyridin-2-amine
4-(4-(((S)-2-amino-2,4-dimethylpentyl)oxy)-3-chlorophenyl)-N-(tetrahydro-2H-pyran-3-yl)pyridin-2-amine
4-(4-(((S)-2-amino-2,4-dimethylpentyl)oxy)-3-chlorophenyl)-N-(tetrahydro-2H-pyran-3-yl)pyridin-2-amine;
(S)-2,4-dimethyl-1-((7-(pyrazolo[1,5-a]pyrimidin-7-yl)benzo [d]thiazol-4-yl)oxy)pentan-2-amine;
(S)-2,4-dimethyl-1-((7-(2-methylpyrimidin-4-yl)benzo[d]thiazol-4-yl)oxy)pentan-2-amine
4-(4-(((S)-2-amino-2,4-dimethylpentyl)oxy)-3-chlorophenyl)-N-(tetrahydrofuran-3-yl)pyridin-2-amine
4-(4-(((S)-2-amino-2,4-dimethylpentyl)oxy)-3-methylphenyl)-N-(tetrahydrofuran-3-yl)pyridin-2-amine
1-(((3-methyl-5-(2-methylpyrimidin-4-yl)pyridin-2-yl)oxy)methyl)cyclobutanamine;
(S)-1-(2-(difluoromethyl)-4-(pyrazolo[1,5-a]pyrimidin-7-yl)phenoxy)-2,4-dimethylpentan-2-amine;

(S)-1-(2-(fluoromethyl)-4-(pyrazolo[1,5-a]pyrimidin-7-yl)phenoxy)-2,4-dimethylpentan-2amine;
(S)-2,4-dimethyl-1-(5-methyl-2-(pyridin-4-yl)thiazol-4-yloxy)pentan-2-amine
6-(4-(((S)-2-amino-2,4-dimethylpentyl)oxy)-3-(trifluoromethyl)phenyl)-N-(tetrahydro-2H-pyran-3-yl)pyrimidin-4-amine;
(S)-1-(2-chloro-4-(7H-pyrrolo [2,3-d]pyrimidin-4-yl)phenoxy)-2,4-dimethylpentan-2-amine;
(S)-2-((2-amino-2,4-dimethylpentyl)oxy)-5-(7H-pyrrolo[2,3-d]pyrimidin-4-yl)benzonitrile;
(S)-1-(4-(7H-pyrrolo [2,3-d]pyrimidin-4-yl)-2-(trifluoromethyl)phenoxy)-2,4-dimethylpentan-2-amine;
(S)-2-((2-amino-2,4-dimethylpentyl)oxy)-5-(7-methyl-7H-pyrrolo [2,3-d]pyrimidin-4-yl)benzonitrile;
(S)-1-(2-fluoro-4-(7-methyl-7H-pyrrolo [2,3-d]pyrimidin-4-yl)phenoxy)-2,4-dimethylpentan-2-amine;
(S)-2,4-dimethyl-1-(4-(7-methyl-7H-pyrrolo [2,3-d]pyrimidin-4-yl)-2-(trifluoromethyl)phenoxy)pentan-2-amine;
(S)—N-(4-(4-((2-amino-2,4-dimethylpentyl)oxy)-3-methylphenyl)pyrimidin-2-yl)thiazol-2-amine;
(S)-4-(4-((2-amino-2,4-dimethylpentyl)oxy)-3-methylphenyl)-N-cyclopropylpyrimidin-2-amine;
(S)—N-(4-(4-((2-amino-2,4-dimethylpentyl)oxy)-3-(trifluoromethyl)phenyl)pyrimidin-2-yl)thiazol-2-amine;
(S)—N-(4-(4-((2-amino-2,4-dimethylpentyl)oxy)-3-(trifluoromethyl)phenyl)pyrimidin-2-yl)-4-methylthiazol-2-amine;
(S)-4-(4-((2-amino-2,4-dimethylpentyl)oxy)-3-(trifluoromethyl)phenyl)-N-cyclopentylpyrimidin-2-amine;
(S)-2-((2-amino-2,4-dimethylpentyl)oxy)-5-(2-((4-methylthiazol-2-yl)amino)pyrimidin-4-yl)benzonitrile;
(S)—N-(4-(4-((2-amino-2,4-dimethylpentyl)oxy)-3-methylphenyl)pyrimidin-2-yl)-4-methylthiazol-2-
(S)—N-(4-(4-((2-amino-2,4-dimethylpentyl)oxy)-3-(trifluoromethyl)phenyl)pyridin-2-yl)cyclopropanecarboxamide;
(S)—N-(4-(4-((2-amino-2,4-dimethylpentyl)oxy)-3-(trifluoromethyl)phenyl)pyridin-2-yl)cyclobutanecarboxamide
(S)—N-(4-(4-((2-amino-2,4-dimethylpentyl)oxy)-3-(trifluoromethyl)phenyl)pyridin-2-yl)cyclopentanecarboxamide
(S)—N-(4-(4-((2-amino-2,4-dimethylpentyl)oxy)-3-(trifluoromethyl)phenyl)pyridin-2-yl)-2-cyclopentylacetamide;
(S)—N-(4-(4-((2-amino-2,4-dimethylpentyl)oxy)-3-(trifluoromethyl)phenyl)pyridin-2-yl)-3-cyclopentylpropanamide;
(S)—N-(4-(4-((2-amino-2,4-dimethylpentyl)oxy)-3-(trifluoromethyl)phenyl)pyridin-2-yl)-2-cyclohexylacetamide
N-(4-(4-(((S)-2-amino-2,4-dimethylpentyl)oxy)-3-(trifluoromethyl)phenyl)pyridin-2-yl)tetrahydrofuran-2-carboxamide;
(S)—N-(4-(4-((2-amino-2,4-dimethylpentyl)oxy)-3-(trifluoromethyl)phenyl)pyridin-2-yl)-2-cycloheptylacetamide
(S)—N-(4-(4-((2-amino-2,4-dimethylpentyl)oxy)-3-(trifluoromethyl)phenyl)pyridin-2-yl)furan-2-carboxamide
(S)—N-(4-(4-((2-amino-2,4-dimethylpentyl)oxy)-3-(trifluoromethyl)phenyl)pyridin-2-yl)-5-bromofuran-2-carboxamide;
(S)-2-acetamido-N-(4-(4-((2-amino-2,4-dimethylpentyl)oxy)-3-(trifluoromethyl)phenyl)pyridin-2-yl)acetamide;
(S)—N-(4-(4-((2-amino-2,4-dimethylpentyl)oxy)-3-(trifluoromethyl)phenyl)pyridin-2-yl)thiophene-2-carboxamide;
(S)—N-(4-(4-((2-amino-2,4-dimethylpentyl)oxy)-3-(trifluoromethyl)phenyl)pyridin-2-yl)pyrazine-2-carboxamide;
(S)—N-(4-(4-((2-amino-2,4-dimethylpentyl)oxy)-3-(trifluoromethyl)phenyl)pyridin-2-yl)-2-methylnicotinamide;
(S)—N-(4-(4-((2-amino-2,4-dimethylpentyl)oxy)-3-(trifluoromethyl)phenyl)pyridin-2-yl)-1H-1,2,3-triazole-5-carboxamide
(S)—N-(4-(4-((2-amino-2,4-dimethylpentyl)oxy)-3-(trifluoromethyl)phenyl)pyridin-2-yl)-6-oxo-1,4,5,6-tetrahydropyridazine-3-carboxamide
(S)—N-(4-(4-((2-amino-2,4-dimethylpentyl)oxy)-3-(trifluoromethyl)phenyl)pyridin-2-yl)-5-methylisoxazole-3-carboxamide
(S)—N-(4-(4-((2-amino-2,4-dimethylpentyl)oxy)-3-(trifluoromethyl)phenyl)pyridin-2-yl)-5-isopropyl-1H-pyrazole-3-carboxamide
(S)-4-(4-((2-amino-2,4-dimethylpentyl)oxy)-3-(trifluoromethyl)phenyl)-N-(pyridin-3-ylmethyl)pyridin-2-amine;
(S)-4-(4-((2-amino-2,4-dimethylpentyl)oxy)-3-(trifluoromethyl)phenyl)-N-(furan-2-ylmethyl)pyridin-2-amine;
(S)-4-(4-((2-amino-2,4-dimethylpentyl)oxy)-3-(trifluoromethyl)phenyl)-N-(benzo[d][1,3]dioxol-5-yl)pyridin-2-amine;
(S)-4-(4-((2-amino-2,4-dimethylpentyl)oxy)-3-fluorophenyl)-6-methyl-6,7-dihydro-5H-pyrrolo [3,4-b]pyridin-5-one;
(S)-2-((2-amino-2,4-dimethylpentyl)oxy)-5-(6-methyl-5-oxo-6,7-dihydro-5H-pyrrolo[3,4-b]pyridin-4-yl)benzonitrile;
(S)-2-((2-amino-2,4-dimethylpentyl)oxy)-5-(5-oxo-6,7-dihydro-5H-pyrrolo[3,4-b]pyridin-4-yl)benzonitrile;
(S)-4-(4-((2-amino-2,4-dimethylpentyl)oxy)-3-fluorophenyl)-6,7-dihydro-5H-pyrrolo [3,4-b]pyridin-5-one;
(S)-4-(4-((2-amino-2,4-dimethylpentyl)oxy)-3-chlorophenyl)-6,7-dihydro-5H-pyrrolo [3,4-b]pyridin-5-one;
(S)-4-(4-((2-amino-2,4-dimethylpentyl)oxy)-3-(trifluoromethyl)phenyl)-6-ethyl-6,7-dihydro-5H-pyrrolo [3,4-b]pyridin-5-one;
(S)-4-(4-((2-amino-2,4-dimethylpentyl)oxy)-3-fluorophenyl)-6-ethyl-6,7-dihydro-5H-pyrrolo [3,4-b]pyridin-5-one;
(S)-1-(2-fluoro-4-(1H-pyrrolo[3,2-b]pyridin-7-yl)phenoxy)-2,4-dimethylpentan-2-amine;
(S)-2-((2-amino-2,4-dimethylpentyl)oxy)-5-(1H-pyrrolo[3,2-b]pyridin-7-yl)benzonitrile;
(S)-2-((2-amino-2,4-dimethylpentyl)oxy)-5-(1-methyl-1H-pyrrolo[3,2-b]pyridin-7-yl)benzonitrile;
(S)-1-(4-(1H-pyrrolo[3,2-b]pyridin-7-yl)-2-(trifluoromethyl)phenoxy)-2,4-dimethylpentan-2-amine;
(S)-4-(4-((2-amino-2,4-dimethylpentyl)oxy)-3-(trifluoromethyl)phenyl)-6,7-dihydro-5H-pyrrolo [3,4-b]pyridin-5-one;
(S)-4-(4-((2-amino-2,4-dimethylpentyl)oxy)-3-(trifluoromethyl)phenyl)-6-methyl-6,7-dihydro-5H-pyrrolo [3,4-b]pyridin-5-one;
(S)-2,4-dimethyl-1-(2-methyl-4-(1-methyl-1H-pyrrolo[3,2-b]pyridin-7-yl)phenoxy)pentan-2-amine;
(S)-4-(4-((2-amino-2,4-dimethylpentyl)oxy)-3-methylphenyl)-6,7-dihydro-5H-pyrrolo [3,4-b]pyridin-5-one;

(S)-4-(4-((2-amino-2,4-dimethylpentyl)oxy)-3-chlorophenyl)-6-methyl-6,7-dihydro-5H-pyrrolo [3,4-b]pyridin-5-one;

(S)-4-(4-((2-amino-2,4-dimethylpentyl)oxy)-3-methylphenyl)-6-methyl-6,7-dihydro-5H-pyrrolo[3,4-b]pyridin-5-one 6-(4-(((S)-2-amino-2,4-dimethylpentyl)oxy)-3-(trifluoromethyl)phenyl)-N-(tetrahydrofuran-3-yl)pyrimidin-4-amine 6-(6-(((S)-2-amino-2,4-dimethylpentyl)oxy)-5-chloropyridin-3-yl)-N-(tetrahydrofuran-3-yl)pyrimidin-4-amine;

(S)-2,4-dimethyl-1-((2-methyl-6-(2-methylimidazo [1,2-b]pyridazin-8-yl)pyridin-3-yl)oxy)pentan-2-amine;

(S)-1-((2-(difluoromethyl)-6-(2-methylimidazo[1,2-b]pyridazin-8-yl)pyridin-3-yl)oxy)-2,4-dimethylpentan-2-amine;

(S)-7-(4-((2-amino-2,4-dimethylpentyl)oxy)-2-fluorophenyl)pyrazolo[1,5-a]pyrimidin-5-amine;

(S)-1-(2-chloro-4-(pyrazolo [1,5-a]pyrimidin-7-yl)phenoxy)-2,4-dimethylpentan-2-amine;

(S)-7-(4-((2-amino-2,4-dimethylpentyl) oxy)-3-fluorophenyl)pyrazolo[1,5-a]pyrimidin-5-amine;

(S)-1-(2-chloro-4-(2,5-dimethylpyrazolo[1,5-a]pyrimidin-7-yl)phenoxy)-2,4-dimethylpentan-2-amine;

(S)-2-((2-amino-2,4-dimethylpentyl)oxy)-5-(pyrazolo[1,5-a]pyrimidin-7-yl)benzonitrile;

(S)-1-(2-fluoro-4-(pyrazolo [1,5-a]pyrimidin-7-yl)phenoxy)-2,4-dimethylpentan-2-amine;

(S)—N-(7-(4-((2-amino-2,4-dimethylpentyl) oxy)-3-fluorophenyl) pyrazolo [1,5-a]pyrimidin-5-yl) acetamide;

(S)-2-((2-amino-2,4-dimethylpentyl)oxy)-5-(2,5-dimethylpyrazolo[1,5-a]pyrimidin-7-yl)benzonitrile;

(S)-2-(2-amino-2,4-dimethylpentyloxy)-5-(2-(piperidin-4-ylamino) pyridin-4-yl) benzonitrile;

(S)-2,4-dimethyl-1-(4-(pyrazolo[1,5-a]pyrimidin-7-yl)-2-(trifluoromethyl)phenoxy)pentan-2-amine;

(S)-2-(2-amino-2,4-dimethylpentyloxy)-5-(2-(tetrahydro-2H-pyran-4-ylamino)pyridin-4yl)benzonitrile;

(S)-4-(4-(2-amino-2,4-dimethylpentyloxy)-3-(trifluoromethyl)phenyl)-N-(piperidin-4-yl)pyridin-2-amine;

(S)-1-(4-(6,7-difluoroquinazolin-4-yl)-2-(trifluoromethyl)phenoxy)-2,4-dimethylpentan-2-amine;

(S)-2,4-dimethyl-1-(2-methyl-4-(pyrazolo [1,5-a]pyrimidin-7-yl)phenoxy)pentan-2-amine;

(S)-2,4-dimethyl-1-(4-(pyrazolo[1,5-a]pyrimidin-3-yl)-2-(trifluoromethyl)phenoxy)pentan-2-amine 4-(4-((5)-2-amino-2,4-dimethylpentyloxy)-3-(trifluoromethyl)phenyl)-N-(tetrahydro-2H-pyran-3-yl)pyridin-2-amine 4-(4-(((5)-2-amino-2,4-dimethylpentyl)oxy)-3-(trifluoromethyl)phenyl)-N-(tetrahydro-2H-pyran-3-yl)pyridin-2-amine 4-(4-(((5)-2-amino-2,4-dimethylpentyl)oxy)-3-(trifluoromethyl)phenyl)-N-(tetrahydro-2H-pyran-3-yl)pyridin-2-amine;

(S)-3-(5-((2-amino-2,4-dimethylpentyl)oxy)-6-methylpyridin-2-yl)pyrazolo [1,5-a]pyrimidine-6-carbonitrile;

(S)-2,4-dimethyl-1-(4-(2-methylthieno [2,3-d]pyrimidin-4-yl)-2-(trifluoromethyl)phenoxy)pentan-2-amine;

(S)-1-(2-chloro-4-(2-cyclopropylpyrazolo [1,5-a]pyrimidin-7-yl)phenoxy)-2,4-dimethylpentan-2-amine;

(S)-1-(4-(2-Cyclopropylpyrazolo [1,5-a]pyrimidin-7-yl)-2-(trifluoromethyl)phenoxy)-2,4-dimethylpentan-2-amine;

(S)-2-((2-amino-2,4-dimethylpentyl)oxy)-5-(2-(trifluoromethyl)pyrazolo [1,5-a]pyrimidin-7-yl)benzonitrile;

(S)-5-((2-amino-2,4-dimethylpentyl)oxy)-2-(pyrazolo [1,5-a]pyrimidin-7-yl)isonicotinonitrile;

(S)-2,4-dimethyl-1-((2-methyl-6-(pyrazolo [1,5-a]pyrimidin-7-yl)pyridin-3-yl)oxy)pentan-2-amine;

(S)-1-(2,5-difluoro-4-(pyrazolo[1,5-a]pyrimidin-7-yl)phenoxy)-2,4-dimethylpentan-2-amine 1,1,1-trifluoro-4-methyl-2-(((2-methyl-6-(pyrazolo [1,5-a]pyrimidin-7-yl)pyridin-3-yl)oxy)methyl)pentan-2-amine;

(S)-2-((2-amino-2,4-dimethylpentyl)oxy)-5-(2-methylimidazo [1,2-b]pyridazin-8-yl)benzonitrile (S)-1-(4-(2-cyclopropylimidazo [1,2-b]pyridazin-8-yl)-2-fluorophenoxy)-2,4-dimethylpentan-2-amine;

(S)-2-((2-amino-2,4-dimethylpentyl)oxy)-5-(6-chloro-2-cyclopropylimidazo[1,2-b]pyridazin-8-yl)benzonitrile;

(S)-1-(4-(6-chloro-2-methylimidazo [1,2-b]pyridazin-8-yl)-2-(trifluoromethyl)phenoxy)-2,4-dimethylpentan-2-amine;

(S)-1-(4-(6-chloro-2-cyclopropylimidazo [1,2-b]pyridazin-8-yl)-2-(trifluoromethyl)phenoxy)-2,4-dimethylpentan-2-amine;

(S)-1-(2-fluoro-4-(2-methylimidazo[1,2-b]pyridazin-8-yl)phenoxy)-2,4-dimethylpentan-2-amine;

(S)-2,4-dimethyl-1-(4-(2-methylimidazo [1,2-b]pyridazin-8-yl)-2-(trifluoromethyl)phenoxy)pentan-2-amine;

(S)-2-((2-amino-2,4-dimethylpentyl)oxy)-5-(2-cyclopropylimidazo[1,2-b]pyridazin-8-yl)benzonitrile;

(S)-2,4-dimethyl-1-(2-methyl-4-(2-(trifluoromethyl)imidazo [1,2-b]pyridazin-8-yl)phenoxy)pentan-2-amine;

(S)-2,4-dimethyl-1-(4-(2-(trifluoromethyl)imidazo [1,2-b]pyridazin-8-yl)phenoxy)pentan-2-amine;

(S)-1-(4-(imidazo[1,2-b]pyridazin-3-yl)-2-methylphenoxy)-2,4-dimethylpentan-2-amine;

(S)-1-(2-chloro-4-(imidazo [1,2-b]pyridazin-3-yl)phenoxy)-2,4-dimethylpentan-2-amine;

(R)-2,4-dimethyl-1-((3-methyl-5-(2-(trifluoromethyl)imidazo[1,2-b]pyridazin-8-yl)pyridin-2-yl)oxy)pentan-2-amine; and (S)-6-(4-((2-amino-2,4-dimethylpentyl)oxy)-3-chlorophenyl)pyrimidin-4(3H)-one;

or a pharmaceutically acceptable salt thereof.

7. A composition comprising a pharmaceutically acceptable amount of a compound of claim 1, or a pharmaceutically acceptable salt thereof, and a pharmaceutically acceptable carrier.

8. A method of inhibiting adaptor associated kinase 1 (AAK1) activity, comprising contacting AAK1 with a compound of claim 1, or a pharmaceutically acceptable salt thereof.

* * * * *

SEQUENCE LISTING
<160> NUMBER OF SEQ ID NOS: 1
<210> SEQ ID NO 1
<211> LENGTH: 18
<212> TYPE: PRT
<213> ORGANISM: Artificial Sequence
<220> FEATURE:
<223> OTHER INFORMATION: fluoresceinated peptide
<400> SEQUENCE: 1
Lys Glu Glu Gln Ser Gln Ile Thr Ser Gln Val Thr Gly Gln Ile Gly
1               5                   10                  15
Trp Arg